US009233115B2

(12) United States Patent
Bernardini et al.

(10) Patent No.: US 9,233,115 B2
(45) Date of Patent: Jan. 12, 2016

(54) PROTEASOME INHIBITORS AND METHODS OF USING THE SAME

(71) Applicant: Cephalon, Inc., Frazer, PA (US)

(72) Inventors: Raffaella Bernardini, Calci (IT); Alberto Bernareggi, Concorezzo (IT); Paolo G. Cassara, Monza (IT); Sankar Chatterjee, Wynnewood, PA (US); Germano D'Arasmo, Novate Milanese (IT); Sergio De Munari, Milan (IT); Edmondo Ferretti, Ravenna (IT); Mohamed Iqbal, Malvern, PA (US); Ernesto Menta, Cemusco sul Naviglio (IT); Patricia A. Messina McLaughlin, Glen Mills, PA (US); Ambrogio Oliva, Saronno (IT)

(73) Assignee: Millennium Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 13/949,346

(22) Filed: Jul. 24, 2013

(65) Prior Publication Data

US 2014/0088042 A1 Mar. 27, 2014

Related U.S. Application Data

(60) Continuation of application No. 13/249,738, filed on Sep. 30, 2011, now Pat. No. 8,546,608, which is a continuation of application No. 13/020,425, filed on Feb. 3, 2011, now Pat. No. 8,058,262, which is a continuation of application No. 12/496,359, filed on Jul. 1, 2009, now Pat. No. 7,915,236, which is a division of application No. 10/918,664, filed on Aug. 12, 2004, now Pat. No. 7,576,206.

(60) Provisional application No. 60/495,764, filed on Aug. 14, 2003.

(51) Int. Cl.
*A61K 31/69* (2006.01)
*A61K 45/06* (2006.01)
*C07F 5/02* (2006.01)

(52) U.S. Cl.
CPC ................ *A61K 31/69* (2013.01); *A61K 45/06* (2013.01); *C07F 5/025* (2013.01)

(58) Field of Classification Search
CPC ........ C07F 5/022; C07F 5/025; C07F 7/0812; C07F 7/1856; C07D 473/00
See application file for complete search history.

(56) References Cited

U.S. PATENT DOCUMENTS

| | | | | |
|---|---|---|---|---|
| 4,499,082 | A * | 2/1985 | Shenvi et al. | ................ 514/20.4 |
| 4,537,773 | A | 8/1985 | Shenvi | |
| 4,963,655 | A | 10/1990 | Klnder et al. | |
| 5,023,236 | A | 6/1991 | Edsinston et al. | |
| 5,106,948 | A | 4/1992 | Kinder et al. | |
| 5,159,060 | A | 10/1992 | Kinder et al. | |
| 5,169,841 | A | 12/1992 | Kleeman et al. | |
| 5,187,157 | A | 2/1993 | Kettner et al. | |
| 5,242,904 | A | 9/1993 | Kettner et al. | |
| 5,250,720 | A | 10/1993 | Kettner et al. | |
| 5,470,864 | A | 11/1995 | Dufloes et al. | |
| 5,550,262 | A | 8/1996 | Iqbal et al. | |
| 5,580,486 | A | 12/1996 | Labeque et al. | |
| 5,585,390 | A | 12/1996 | Dufloes et al. | |
| 5,614,649 | A | 3/1997 | Iqbal et al. | |
| 5,658,885 | A | 8/1997 | Lee et al. | |
| 5,693,617 | A | 12/1997 | Stein et al. | |
| 5,780,454 | A | 7/1998 | Adams et al. | |
| 5,830,870 | A | 11/1998 | Iqbal et al. | |
| 5,834,487 | A | 11/1998 | Lum et al. | |
| 5,990,083 | A | 11/1999 | Iqbal et al. | |
| 6,066,730 | A | 5/2000 | Adams et al. | |
| 6,075,150 | A | 6/2000 | Wang et al. | |
| 6,083,903 | A | 7/2000 | Adams et al. | |
| 6,096,778 | A | 8/2000 | Chatterjee et al. | |
| 6,297,217 | B1 | 10/2001 | Adams et al. | |
| 6,310,057 | B1 | 10/2001 | Chatterjee et al. | |
| 6,372,883 | B1 | 4/2002 | Attwood et al. | |
| 6,465,433 | B1 | 10/2002 | Adams et al. | |
| 6,548,668 | B2 | 4/2003 | Adams et al. | |
| 7,442,830 | B1 | 10/2008 | Olhava et al. | |
| 2001/0012854 | A1 | 8/2001 | Siman et al. | |
| 2002/0173488 | A1 | 11/2002 | Adams et al. | |
| 2002/0188100 | A1 | 12/2002 | Plamondon et al. | |

(Continued)

FOREIGN PATENT DOCUMENTS

| | | |
|---|---|---|
| DE | 1991 4 474 | 10/1999 |
| EP | 293881 | 12/1988 |

(Continued)

OTHER PUBLICATIONS

Hideshima, The role of tumor necrosis factor a in the pathophysiology of human multiple myeloma: therapeutic applications, Oncogene, 2001, 20, pp. 4519-4527.*
Simone, Oncology: Introduction, Cecil Textbook of Medicine, 20th Edition, 1996 vol. 1, pp. 1004-1010.*
Adams et al., "Potent and Selective Inhibitors of the Proteasome: Dipeptidyl Boronic Acids," *Bioorganic & Medicinal Chemistry Letters*, 1998, 8(4), 333-338.
Andersen et aL, Chemische Berichte, 122, 1989, pp. 1777-1782.
Aoyagi et al., "Structures and Activities of Protease Inhibitors of Microbial Origin,"*Proteases and Biological Control*,1975, 429-454.
Armstrong et al., "Central Nervous System Toxicity from Cancer Treatment" Current Oncology Reports, Jan. 2004, 6(1), 11-19.
Attwood et al, The Design and Synthesis of Potent Inhibitors of Hepatitis C Virus NS3-4A Proteinase, Antiviral Chemistry & Chemotherapy, 1999, 10(5), 259-273.

(Continued)

*Primary Examiner* — San-Ming Hui
*Assistant Examiner* — Andrew Lee
(74) *Attorney, Agent, or Firm* — Baker & Hostetler LLP

(57) ABSTRACT

The present invention provides boronic acid compounds, boronic esters, and compositions thereof that can modulate apoptosis such as by inhibition of proteasome activity. The compounds and compositions can be used in methods of inducing apoptosis and treating diseases such as cancer and other disorders associated directly of indirectly with proteasome activity.

10 Claims, No Drawings

(56) References Cited

U.S. PATENT DOCUMENTS

| | | | |
|---|---|---|---|
| 2003/0008828 A1 | 1/2003 | Priestly et al. |
| 2005/0101781 A1 | 5/2005 | Agoulnik et al. |

FOREIGN PATENT DOCUMENTS

| | | |
|---|---|---|
| EP | 315574 | 5/1989 |
| EP | 354522 | 2/1990 |
| EP | 632026 | 6/1994 |
| EP | 0 995 757 | 4/2000 |
| EP | 0 116 6781 | 2/2002 |
| WO | WO 89/09225 | 10/1989 |
| WO | WO 91/13904 A1 | 9/1991 |
| WO | WO 94/04653 | 3/1994 |
| WO | WO 94/17816 A1 | 8/1994 |
| WO | WO 94/25049 | 11/1994 |
| WO | WO 94/25051 | 11/1994 |
| WO | WO 95/09634 | 4/1995 |
| WO | WO 95/09838 | 4/1995 |
| WO | WO 95/20603 | 8/1995 |
| WO | WO 95/25533 A1 | 9/1995 |
| WO | WO 96/11697 | 4/1996 |
| WO | WO 96/12499 | 5/1996 |
| WO | WO 96/13266 | 5/1996 |
| WO | WO 96/14857 | 5/1996 |
| WO | WO 98/17679 | 4/1998 |
| WO | WO 98/22496 | 5/1998 |
| WO | WO 99/30707 | 6/1999 |
| WO | WO 00/02548 | 1/2000 |
| WO | WO 00/23614 | 4/2000 |
| WO | WO 00/64467 | 11/2000 |
| WO | WO 00/64863 A1 | 11/2000 |
| WO | WO 00/66557 | 11/2000 |
| WO | WO 01/02424 | 1/2001 |
| WO | WO 01/20995 | 3/2001 |
| WO | WO 01/28579 | 4/2001 |
| WO | WO 02/08187 | 1/2002 |
| WO | WO 02/30455 | 4/2002 |
| WO | WO 02/059130 | 8/2002 |
| WO | WO 02/059131 | 8/2002 |
| WO | WO 02/082091 | 10/2002 |
| WO | WO 02/094857 | 11/2002 |
| WO | WO 02/096933 | 12/2002 |
| WO | WO 03/015706 | 2/2003 |
| WO | WO 03/033507 | 4/2003 |
| WO | WO 03/059898 | 7/2003 |
| WO | WO 2005/016859 | 2/2005 |
| WO | 2009/020448 | 2/2009 |
| WO | WO 2009/020448 | 2/2009 |

OTHER PUBLICATIONS

Christie et al, "Alzheimer's Disease: Correlation of the Suppression of P-Amyloid Peptide Secretion From Cultured Cells With Inhibition of the Chymotrypsin-Like Activity of the Proteasome," J. of Neurochemistry, 1999, 73(1), 195-204.

Dick et al., "Degradation of Oxidized Insulin B Chain by the Multi Proteinase Complex Macropain (proteasome)," *Biochemistry*, Mar. 12, 1991; 30(10):2725-34.

Dudson et al., "Solid Phase Synthesis of Aminoboronic Acids: Potent Inhibitors of the Hepatitis C Virus NS3 Proteinase," *Bioorganic & Medicinal Chemistry Letters*, 2000, 10(14), 1577-1579.

European Opposition—Proprietor First Auxiliary Request, Apr. 24, 2012.

European Opposition—Hearing Minutes, Nov. 2, 2011.

European Opposition—Opposition Division Opposition Decision, Dec. 14, 2011.

European Opposition—Text Approved by Opposition Division, Dec. 14, 2011.

European Opposition—Proprietors Amended Claims, Jan. 17, 2011.

European Opposition—Proprietors Response 1 to Opponent's Reply, Sep. 21, 2011.

European Opposition—Main Request Replacement Page, Sep. 21, 2011.

European Opposition—Auxiliary Request 1 Replacement Page, Sep. 21, 2011.

European Opposition—Auxiliary Request 2 Replacement Page, Sep. 21, 2011.

European Opposition—Proprietor's Response 2 to Opponent's Reply, Sep. 21, 2011.

European Opposition—Opposition Division Decision on Hearing Minutes, Dec. 5, 2011.

European Opposition—Proprietor Response to Opponent Request to Correct Hearing Minutes, Nov. 29, 2011.

European Opposition—Opponent Request to Correct Hearing Minutes, Nov. 10, 2011.

European Opposition—Opponent Response to Proprietor Response to Opponent Request, Dec. 7, 2011.

European Opposition—Opponent's Reply, Sep. 19, 2011.

European Opposition—Proprietor Second Auxiliary Request, Apr. 24, 2012.

European Opposition—Proprietor's Submissions, Sep. 5, 2011.

European Opposition—Auxiliary Request 2, Sep. 5, 2011.

European Opposition—Auxiliary Request 1, Sep. 5, 2011.

European Opposition—Main Request, Sep. 5, 2011.

European Opposition—Notices of Appeal, Feb. 23, 2012.

European Opposition—Opponent Grounds of Appeal, Apr. 23, 2012.

European Opposition—Proprietor Main Request, Apr. 24, 2012.

European Opposition—Proprietor's Response to Notice of Opposition, Jan. 17, 2011.

Evrard-Todeschi et al Conformations in Soluation and Bound to Bacterial Ribonsomes of Ketolides, HMR 3647 (Telithromycin) and RU 72366: A New Class of Highly Potent Antibacterials; *Bioorg. Med. Chem.*, Jul. 2000, 8(7):1579-97.

Fenteany et al., "A Beta-Lactone Related to Lactacystin Induces Neurite Outgrowth in a Neuroblastoma Cell Line and Inhibits Cell Cycle progression in an Osteosarcoma Cell Line,"*Proc. Nail Acad. Sci*, Apr. 12 1994,91(8):3358-62.

Fenteany et al., "Inhibition of Proteasome Activities and Subunit-Specific Amino-Terminal Threonine Modification by Lactacystin," *Science*, May 5, 1995, 268(5211):726-31.

Garcia et al., "A New Structural Class of Selective and Non-Covalent Inhibitors Chymotrypsin-Like Activity of the 20s Proteasome," Bioorg. Med. Chem. *Lett*., May 2001, 11(10):1317-9.

Gardner et al., "Characterization of Peptidyl Boronic Acid Inhibitors of Mammalian 20 S and 26 S Proteasomes and Their Inhibition of Proteasomes in Cultured Cells," Biochem. J., Mar. 2000, 346(Pt2):447-54.

Goldberg et al., "Proteolysis, Proteasomes and Antigen Presentation," Nature, Jun. 1992, 4;357(6377):375-9.

Goldberg et al., "The Mechanism and Functions of ATP-Dependent Proteases in Bacterial and Animal Cells," Eur. F. Biochem. Jan. 1992, 203(1-2):9-23.

Hoffmann et aL, Chemische Berichte, 123, 1990, pp. 2387-2394.

Iqbal el al., "Potent α-Ketocarbonyl and Boronic Ester Derived Inhibitors of Proteasome." Bioorg. Med. Chem. Lett., 1996, 6, 287-290.

Iqbal et al., "Potent Inhibitors of Proteasome," J. Med. Chem., Jun. 1995, 38(13):2276-7.

Kettner et al., "Inhibition of the serine proteases leukocyte elastase, pancreatic elastase, cathepsin G, and chymotrypsin by peptide boronic acids," J. Biol. Chem. Dec. 1984, 259(24):15106-14.

Kisselev et al., "Proteasome Inhibitors: From Research Tools to Drug Candidates," Chem, Biol., Aug. 2001, 8(8):739-58.

Kupperman et al., "Evaluation of the Proteasome Inhibitor MLN9708 in Preclinical Models of Human Cancer," Cancer Research 2010, 70(5), 1970-80.

Li et al. "Isolation and Characterization of a Novel Endogenous Inhibitor of the Proteasome." Biochemistry, Oct. 1991, 30(40):9709-15.

Matteson et al., "99% Chirally Selective Synthesis Via Pinanediol Boronic Esters: Insect Pheromones, Diols, and an Amino Alcohol." J. Am. Chem. Soc. 1986, 108, 810-819.

Murakami et al., "Endogenous Inhibitor of Non Lysosomal High Molecular Weight Protease and Calcium-Dependent Protease," Proc. Nat. Acad. Sci., Oct. 1986, 83(20):7588-92.

(56) References Cited

OTHER PUBLICATIONS

Nkemgu-Njinkeng et al., "Antitrypanosomal Activities of Proteasome Inhibitors." Antimicrob. Agents Chemother., Jun. 2002, 46(6):2038-40.

Notice of Opposition against European Patent EP1660507 B9 (corresponding to instant application), May 4, 2010.

Orlowski et al., "The Multicatalytic Proteinase Complex, A Major Extra Lysosomal Proteolytic System," Biochemistry, Nov. 1990, 29(45):10289-97.

Protective Groups in Organic Synthesis, 3rd Edition. Edited by Greene and Wuts. pp. 531-537, published in 1999.

Purandare et al., "Identification of a Potent and Rapidly Reversible Inhibitor of the 20S-Proteasome," Bioorganic & Medicinal Chemistry Letters, 2004, pp. 1-4.

Rivett et al., "The Multicatalytic Proteinase of Mammalian Cells," Arch. Biochem. Biophys., Jan. 1989,268(1):1-8.

Rivett et al., "The Multicatalytic Proteinase. Multiple Proteolytic Activities," J. Biol. Chem., Jul. 1989, 264(21):122.15-9.

Rock et al., "Inhibitors of the Proteasome Block the Degradation of Most Cell Proteins and the Generation of Peptides Presented on MHC Class I Molecules," Cell. Sep. 1994, 78(5):761-71.

Simov, Biljana Peric, et al., ChiralCarbanions. Part 4: Borylation or (Trimethylsiiyl)methylN,N-Dialkyl-carbamates-Diastereoselectivity and Structural Studies, Synthesis 2004,16, 2704-2710.

Tanaka et at., "Proteasomes: Protein and Gene Structures," New Biol., 1992, 4(3):173-187.

Tsubuki et al., "Purification and Characterization of a Z-Leu-Leu-Leu-MCA Degrading Protease Expected to Regulate Neurite Formation: A Novel Catalytic Activity in Protcasorne," Biochem. BioJrilys Res Commutt., Nov. 1993, 196(3):1195-201.

Vinitsky et al., "Inhibition of the Chymotrypsin-like Activity of the Pituitary Multicatalytic Oteinase Complex," Biochemistry, Oct. 1992,31(39):9421-8.

Wallace and Zong, Tetrahedron Letters 33(46), 1992, pp. 6941-6944.

Wu et al., "Proteasorne Inhibitors Stimulate Activator Protein-1 Pathway Via Reactive Oxygen Species Production," FEBS Letters, 2002, 526(I0,101-105.

Zembower et al., "Versatile Synthetic Ligands for Affinity Chromatography of Serine Proteinases," Int'l J. of Peptide & Protein Research, 1996, 47(5), 405-413.

Zenk et al., "Organic Boronic A cids and Boronic A cid Esters in Industrial Synthesis" Chimica Oggi, May 2003, 21(5), 70-73.

Almond et al., "The Proteasome: A Novel Target for Cancer Chemotherapy", Nature Publishing Group, Leukemia, pp. 433-443, 2002.

Boccadoro et al., "New Developments and Treatment in Multiple Myeloma: New Drugs in the Treatment of Multiple Myeloma", European Society for Medical Oncology, pp. 55-58, 2002.

Mitsiades et al., "The Proteasome Inhibitor PS-341 Potentiates Sensitivity of Multiple Myeloma Cells to Conventional Chemotherapeutic Agents: Therapeutics Applications", The American Society of Hematology, Blood, vol. 101, No. 6, pp. 2377-2380, Mar. 2003.

Orlowski et al., The Role of the Ubiquitination-Proteasome Pathway in Breast Cancer Applying Drugs That Affect the Ubiquitin-Proteasome Pathway to the Therapy of Breast Cancer, Breast Cancer Research Cancer, vol. 5 No. 1, pp. 1-7, 2003.

* cited by examiner

PROTEASOME INHIBITORS AND METHODS OF USING THE SAME

CROSS REFERENCE TO RELATED APPLICATIONS

This application is a continuation of U.S. application Ser. No. 13/249,738, filed Sep. 30, 2011, which is a continuation of U.S. application Ser. No. 13/020,425, filed Feb. 3, 2011, (now U.S. Pat. No. 8,058,262, issued Nov. 15, 2011), which is a continuation of U.S. application Ser. No. 12/496,359, filed Jul. 1, 2009 (now U.S. Pat. No. 7,915,236, issued Mar. 29, 2011), which is a divisional of U.S. application Ser. No. 10/918,664, filed Aug. 12, 2004 (now U.S. Pat. No. 7,576, 206, issued Aug. 18, 2009), which claims the benefit of U.S. Provisional Application No. 60/495,764, filed Aug. 14, 2003, the disclosures of which are incorporated herein by reference in their entireties.

FIELD OF THE INVENTION

The present invention relates to boronic acid and boronic ester compounds useful as proteasome inhibitors and modulation of apoptosis.

BACKGROUND OF THE INVENTION

The proteasome, (also referred to as multicatalytic protease (MCP), multicatalytic proteinase, multicatalytic proteinase complex, multicatalytic endopeptidase complex, 20S, 26S, or ingensin) is a large, multiprotein complex present in both the cytoplasm and the nucleus of all eukaryotic cells. It is a highly conserved cellular structure that is responsible for the ATP-dependent proteolysis of most cellular proteins (Tanaka, *Biochem Biophy. Res. Commun.,* 1998, 247, 537). The 26S proteasome consists of a 20S core catalytic complex that is capped at each end by a 19S regulatory subunit. The archaebacterial 20S proteasome contains fourteen copies of two distinct types of subunits, α and β, which form a cylindrical structure consisting of four stacked rings. The top and bottom rings contain seven α-subunits each, while the inner rings contain seven β-subunits. The more complex eukaryotic 20S proteasome is composed of about 15 distinct 20-30 kDa subunits and is characterized by three major activities with respect to peptide substrates. For example, the proteasome displays tryptic-, chymotryptic-, and peptidylglutamyl peptide-hydrolytic activities (Rivett, *Biochem. J.,* 1993, 291, 1 and Orlowski, *Biochemistry,* 1990, 29, 10289). Further, the proteasome has a unique active site mechanism which is believed to utilize a threonine residue as the catalytic nucleophile (Seemuller, et al., *Science,* 1995, 268, 579).

The 26S proteasome is able to degrade proteins that have been marked by the addition of ubiquitin molecules. Typically, ubiquitin is attached to the ϵ-amino groups of lysines in a multistep process utilizing ATP and E1 (ubiquitin activating) and E2 (ubiquitin-conjugating) enzymes. Multi-ubiquitinated substrate proteins are recognized by the 26S proteasome and are degraded. The multi-ubiquitin chains are generally released from the complex and ubiquitin is recycled (Goldberg, et al., *Nature,* 1992, 357, 375).

Numerous regulatory proteins are substrates for ubiquitin dependent proteolysis. Many of these proteins function as regulators of physiological as well as pathophysiological cellular processes. Alterations in proteasome activity have been implicated in a number of pathologies including neurodegenerative diseases such as Parkinson's disease, Alzheimer's disease, as well as occlusion/ischaemia reperfusion injuries, and aging of the central nervous system.

The ubiquitin-proteasome pathway also plays a role in neoplastic growth. The regulated degradation of proteins such as cyclins, CDK2 inhibitors, and tumor suppressors is believed to be important in cell cycle progression and mitosis. A known substrate of the proteasome is the tumor suppressor p53 which is involved in several cellular processes (see, e.g., Ko, L. J. *Genes Dev.,* 1996, 10, 1054). Tumor suppressor p53 has been shown to induce apoptosis in several haematopoietic cell lines (Oren, M., *Semin. Cancer Biol.,* 1994, 5, 221). Induction of p53 leads to cell growth arrest in the G1 phase of the cell cycle as well as cell death by apoptosis. Tumor suppressor p53 degradation is known to be carried out via the ubiquitin-proteasome pathway, and disrupting p53 degradation by inhibition of the proteasome is a possible mode of inducing apoptosis.

The proteasome is also required for activation of the transcription factor NF-κB by degradation of its inhibitory protein, IκB (Palombella, et al., *Cell,* 1994, 78, 773). NF-κB has a role in maintaining cell viability through the transcription of inhibitors of apoptosis. Blockade of NF-κB activity has been demonstrated to make cells more susceptible to apoptosis.

Several inhibitors of the proteolytic activity of the proteasome have been reported. See, for example, Kisselev, et al., *Chemistry & Biology,* 2001, 8, 739. Lactacystin is a *Streptomyces* metabolite that specifically inhibits the proteolytic activity of the proteasome complex (Fenteany, et al., *Science,* 1995, 268, 726). This molecule is capable of inhibiting the proliferation of several cell types (Fenteany, et al., *Proc. Natl. Acad. Sci. USA,* 1994, 91, 3358). It has been shown that lactacystin binds irreversibly, through its β-lactone moiety, to a threonine residue located at the amino terminus of the β-subunit of the proteasome.

Peptide aldehydes have been reported to inhibit the chymotrypsin-like activity associated with the proteasome (Vinitsky, et al., *Biochemistry,* 1992, 31, 9421; Tsubuki, et al., *Biochem. Biophys. Res. Commun.,* 1993, 196, 1195; and Rock, et al., *Cell,* 1994, 78, 761). Dipeptidyl aldehyde inhibitors that have $IC_{50}$ values in the 10-100 nM range in vitro (Iqbal, M., et al., *J. Med. Chem.,* 1995, 38, 2276) have also been reported. A series of similarly potent in vitro inhibitors from α.-ketocarbonyl and boronic ester derived dipeptides has also been reported (Iqbal, et al., *Bioorg. Med. Chem. Lett.,* 1996, 6, 287, U.S. Pat. Nos. 5,614,649; 5,830,870; 5,990,083; 6,096,778; 6,310,057; U.S. Pat. App. Pub. No. 2001/0012854, and WO 99/30707).

N-terminal peptidyl boronic ester and acid compounds have been reported previously (U.S. Pat. Nos. 4,499,082 and 4,537,773; WO 91/13904; Kettner, et al., *J. Biol. Chem.,* 1984, 259(24), 15106). These compounds are reported to be inhibitors of certain proteolytic enzymes. N-terminal tri-peptide boronic ester and acid compounds have been shown to inhibit the growth of cancer cells (U.S. Pat. No. 5,106,948). A broad class of N-terminal tri-peptide boronic ester and acid compounds and analogs thereof has been shown to inhibit renin (U.S. Pat. No. 5,169,841).

Various inhibitors of the peptidase activities of the proteasome have also been reported. See, e.g., Dick, et al., *Biochemistry,* 1991, 30, 2725; Goldberg, et al., *Nature,* 1992, 357, 375; Goldberg, *Eur. J. Biochem.,* 1992, 203, 9; Orlowski, *Biochemistry,* 1990, 29, 10289; Rivett, et al., *Archs. Biochem. Biophys.,* 1989, 218, 1; Rivett, et al., *J. Biol. Chem.,* 1989, 264, 12215; Tanaka, et al., *New Biol.,* 1992, 4, 1; Murakami, et al., *Proc. Natl. Acad. Sci. USA,* 1986, 83, 7588; Li et al., *Biochemistry,* 1991, 30, 9709; Goldberg, *Eur. J. Biochem.,*

1992, 203, 9; and Aoyagi, et al., *Proteases and Biological Control*, Cold Spring Harbor Laboratory Press (1975), pp. 429-454.

Stein et al., U.S. patent application Ser. No. 08/212,909, filed Mar. 15, 1994, report peptide aldehydes useful for reducing in an animal both the rate of loss of muscle mass and the rate of intracellular protein breakdown. The compounds are also said to reduce the rate of degradation of p53 protein in an animal. Palombella, et al., WO 95/25533, report the use of peptide aldehydes to reduce the cellular content and activity of NF-κB in an animal by contacting cells of the animal with a peptide aldehyde inhibitor of proteasome function or ubiquitin conjugation. Goldberg and Rock, WO 94/17816, report the use of proteasome inhibitors to inhibit MHC-I antigen presentation. Stein, et al., U.S. Pat. No. 5,693,617 report peptidyl aldehyde compounds as proteasome inhibitors useful for reducing the rate of degradation of protein in an animal Inhibition of the 26S and 20S proteasome by indanone derivatives and a method for inhibiting cell proliferation using indanone derivatives are reported by Lum et al., U.S. Pat. No. 5,834,487. Alpha-ketoamide compounds useful for treating disorders mediated by 20S proteasome in mammals are reported in Wang et al., U.S. Pat. No. 6,075,150. France, et al., WO 00/64863, report the use of 2,4-diamino-3-hydroxycarboxylic acid derivatives as proteasome inhibitors. Carboxylic acid derivatives as proteasome inhibitors are reported by Yamaguchi et al., EP 1166781. Ditzel, et al., EP 0 995 757 report bivalent inhibitors of the proteasome. 2-Aminobenzylstatine derivatives that inhibit non-covalently the chymotrypsin-like activity of the 20S proteasome have been reported by Garcia-Echeverria, et al., *Bioorg. Med. Chem. Lett.*, 2001, 11, 1317.

Some further proteasome inhibitors can contain boron moieties. For example, Drexler et al., WO 00/64467, report a method of selectively inducing apoptosis in activated endothelial cells or leukemic cells having a high expression level of c-myc by using tetrapeptidic boronate containing proteasome inhibitors. Furet et al., WO 02/096933 report 2-[[N-(2-amino-3-(heteroaryl or aryl)propionyl)aminoacyl]amino] alkylboronic acids and esters for the therapeutic treatment of proliferative diseases in warm-blooded animals. U.S. Pat. Nos. 6,083,903; 6,297,217; 5,780454; 6,066,730; 6,297,217; 6,548,668; U.S. Patent Application Pub. No. 2002/0173488; and WO 96/13266 report boronic ester and acid compounds and a method for reducing the rate of degradation of proteins. A method for inhibiting viral replication using certain boronic acids and esters is also reported in U.S. Pat. No. 6,465,433 and WO 01/02424. Pharmaceutically acceptable compositions of boronic acids and novel boronic acid anhydrides and boronate ester compounds are reported by Plamondon, et al., U.S. Patent Application Pub. No. 2002/0188100. A series of di- and tripeptidyl boronic acids are shown to be inhibitors of 20S and 26S proteasome in Gardner, et al., *Biochem. J.,* 2000, 346, 447.

Other boron-containing peptidyl and related compounds are reported in U.S. Pat. Nos. 5,250,720; 5,242,904; 5,187,157; 5,159,060; 5,106,948; 4,963,655; 4,499,082; and WO 89/09225, WO/98/17679, WO 98/22496, WO 00/66557, WO 02/059130, WO 03/15706, WO 96/12499, WO 95/20603, WO 95/09838, WO 94/25051, WO 94/25049, WO 94/04653, WO 02/08187, EP 632026, and EP 354522.

A great interest exists, as evidenced by the above references, in drugs which can modulate proteasome activity. For example, molecules capable of inhibiting proteasome activity can arrest or delay cancer progression by interfering with the ordered degradation of cell cycle proteins or tumor suppressors. Accordingly, there is an ongoing need for new and/or improved inhibitors of proteasome.

SUMMARY OF THE INVENTION

The present invention is directed to novel boronic acid and boronic ester compounds useful as proteasome inhibitors and modulation of apoptosis. The subject invention also comprises methods for inhibition of multicatalytic protease ("MCP") associated with certain disorders, including the treatment of muscle wasting disorders.

In one embodiment are provided compounds having Formula (I):

(I)

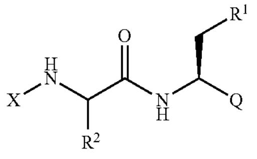

wherein constituent members are defined infra, as well as preferred constituent members.

In another embodiment the present invention provides a pharmaceutical composition comprising a compound of Formula (I) and a pharmaceutically acceptable carrier.

In another embodiment the present invention provides a method of inhibiting activity of proteasome comprising contacting a compound of Formula (I) with said proteasome.

In another embodiment the present invention provides a method of treating cancer comprising administering to a mammal having or predisposed to said cancer a therapeutically effective amount of a compound of Formula (I).

In another embodiment the present invention provides a method of treating cancer treating cancer comprising administering to a mammal having or predisposed to said cancer a therapeutically effective amount of a compound of Formula (I), and wherein said cancer is selected from skin, prostate, colorectal, pancreas, kidney, ovary, mammary, liver, tongue, lung, and smooth muscle tissue.

In another embodiment the present invention provides a method of treating cancer comprising administering to a mammal having or predisposed to said cancer a therapeutically effective amount of a compound of Formula (I), and wherein said cancer is selected from leukemia, lymphoma, non-Hodgkin lymphoma, myeloma, and multiple myeloma.

In another embodiment the present invention provides a method of treating cancer comprising administering to a mammal having or predisposed to said cancer a therapeutically effective amount of a compound of Formula (I) in combination with one or more antitumor or anticancer agent and/or radiotherapy.

In another embodiment the present invention provides a method of inhibiting activity of transcription factor NF-κB comprising contacting IκB, the inhibitor of transcription factor NF-κB, with a compound of Formula (I).

In another embodiment, the present invention provides processes for preparing a compound of Formula (II):

(II)

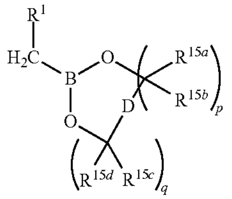

wherein constituent members are defined herein, by reacting a diol of Formula (II-b):

(II-b)

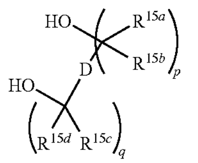

with an appropriate trialkoxyborane of Formula (II-a):

(II-a)

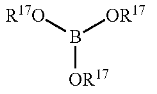

wherein constituent members are defined herein; for a time and under conditions suitable for forming an intermediate of Formula (II-c):

(II-c)

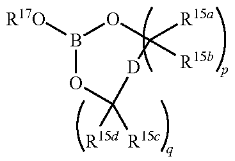

and reacting the intermediate of Formula (II-c) with either i) a reagent of formula $R^1CH_2MX^{hal}$, wherein M is a metal and $X^{hal}$ is a halogen atom, or ii) a reagent of formula $R^1CH_2Li$, for a time and under conditions suitable for forming the compound of Formula (II).

These and other features of the compounds will be set forth in expanded form as the disclosure continues.

DESCRIPTION OF EMBODIMENTS OF THE INVENTION

The present invention provides, inter alia, compounds that can inhibit proteasome activity and be used for the treatment of diseases or disorders related to proteasome activity. Compounds of the invention include compounds of Formula (I)

(I)

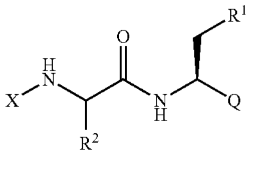

or pharmaceutically acceptable salt, stereoisomeric or tautomeric form thereof, wherein:

$R^1$ is $C_1$-$C_8$ alkyl, $C_2$-$C_8$ alkenyl, $C_2$-$C_8$ alkynyl, or $C_3$-$C_7$ cycloalkyl;

$R^2$ is H, $—(CH_2)_aCH_2NHC(=NR^4)NH—Y$, $—(CH_2)_bCH_2CONR^5R^6$, $—(CH_2)_cCH_2N(R^4)CONH_2$, $—(CH_2)_dCH(R^7)NR^9R^{10}$, or $—(CH_2)_eCH(R^7)ZR^8$;

a, b, and c are each, independently, 0, 1, 2, 3, 4, 5, or 6;

d and e are each, independently, 0, 1, 2, 3, or 4;

$R^4$ is H or $C_1$-$C_{10}$ alkyl;

$R^5$ and $R^6$ are each, independently, H, $C_1$-$C_{10}$ alkyl, carbocyclyl, heterocarbocyclyl, or an amino protecting group;

alternatively, $R^5$ and $R^6$ together with the N atom to which they are attached form a heterocarbocyclyl group;

$R^7$ is H or $C_1$-$C_{10}$ alkyl;

$R^8$ is H, $C_1$-$C_{10}$ alkyl, alkyl-$S(=O)_2$—, aryl-$S(=O)_2$—, $H_2NS(=O)_2$—, $—SO_3H$, or a protecting group;

$R^9$ is H, $C_1$-$C_{10}$ alkyl, carbocyclyl, or heterocarbocyclyl;

$R^{10}$ is H, $C_1$-$C_{10}$ alkyl, carbocyclyl, heterocarbocyclyl, $C_1$-$C_{10}$ alkyl-C(=O)—, $C_2$-$C_{10}$ alkenyl-C(=O)—, $C_2$-$C_{10}$ alkynyl-C(=O)—, carbocyclyl-C(=O)—, heterocarbocyclyl-C(=O)—, carbocyclylalkyl-C(=O)—, heterocarbocyclylalkyl-C(=O)—, $C_1$-$C_{10}$ alkyl-$S(=O)_2$—, carbocyclyl-$S(=O)_2$—, heterocarbocyclyl-$S(=O)_2$—, carbocyclylalkyl-$S(=O)_2$—, heterocarbocyclylalkyl-S$(=O)_2$—, $C_1$-$C_{10}$ alkyl-NHC(=O)—, carbocyclyl-NHC(=O)—, heterocarbocyclyl-NHC(=O)—, carbocyclylalkyl-NHC(=O)—, heterocarbocyclylalkyl-NHC(=O)—, $C_1$-$C_{10}$ alkyl-OC(=O)—, carbocyclyl-OC(=O)—, heterocarbocyclyl-OC(=O)—, carbocyclylalkyl-OC(=O)—, heterocarbocyclylalkyl-OC(=O)—, $C_1$-$C_{10}$ alkyl-NH—C(=O)—NHS$(=O)_2$—, carbocyclyl-NH—C(=O)—NHS$(=O)_2$—, heterocarbocyclyl-NH—C(=O)—NHS$(=O)_2$—, $C_1$-$C_{10}$ alkyl-$S(=O)_2$—NH—C(=O)—, carbocyclyl-$S(=O)_2$—NH—C(=O)—, heterocarbocyclyl-$S(=O)_2$—NH—C(=O)—, or an amino protecting group; wherein $R^{10}$ is optionally substituted with 1, 2 or 3, $R^{23}$;

alternatively, $R^9$ and $R^{10}$ together with the N atom to which they are attached form a heterocarbocyclyl group optionally substituted with 1, 2 or 3 $R^{23}$;

Y is H, —CN, $—NO_2$, $—S(=O)_2R^{11}$, or a guanidino protecting group;

$R^{11}$ is $C_1$-$C_6$ alkyl, aryl, or $NR^{12}R^{13}$;

$R^{12}$ and $R^{13}$ are, independently, H, $C_1$-$C_{10}$ alkyl, carbocyclyl, heterocarbocyclyl, or an amino protecting group;

alternatively, $R^{12}$ and $R^{13}$ together with the N atom to which they are attached form a heterocarbocyclyl group;

Z is O, S, Se, or Te;

Q is $—B(OH)_2$, $—B(OR^{14})_2$, or a cyclic boronic ester wherein said cyclic boronic ester contains from 2 to 20 carbon atoms, and, optionally, a heteroatom which can be N, S, or O;

$R^{14}$ is H, $C_1$-$C_4$ alkyl, cycloalkyl, cycloalkylalkyl, aryl, or aralkyl;

X is $R^AC(=O)$—, $R^ANHC(=O)$—, $R^AS(=O)_2$—, $R^AC(=O)$—, $R^ASC(=O)$—, or $R^A$;

$R^A$ is $C_1$-$C_{20}$ alkyl optionally substituted with $R^{20}$; $C_2$-$C_{20}$ alkenyl optionally substituted with $R^{20}$; $C_2$-$C_{20}$ alkynyl optionally substituted with $R^{20}$; carbocyclyl optionally substituted with 1-5 $R^{21}$; or heterocarbocyclyl optionally substituted with 1-5 $R^{21}$;

$R^{20}$ is selected from the group consisting of:

—CN, halo, haloalkyl-, $C_1$-$C_4$ alkyl, $C_2$-$C_4$ alkenyl, $C_2$-$C_4$ alkynyl, $—CO_2H$, $—C(=O)CO_2H$, $—C(=O)NH_2$, —C(=O)H, $—S(=O)NH_2$, $—S(=O)_2NH_2$, —OH, —SH, $—NH_2$, —NH(alkyl), $—N(alkyl)_2$, $—NHC(=O)NH_2$, $—NHC(=O)R^{20a}$, $—NHC(=O)OR^{20a}$, $—OR^{20a}$, $—SR^{20a}$, $—(=O)R^{20a}$, $—S(=O)_2R^{20a}$, $—S(=O)_2—NHR^{20a}$, $—SC(=O)R^{20a}$, $—C(=O)R^{20a}$, $—C(=O)NHR^{20a}$, $—C(=O)O—R^{20a}$, $—NHS(=O)_2R^{20a}$, $—NHR^{20b}$, phthalimido, $—(O\text{-alkyl})_r$-OH, $—(O\text{-alkyl})_r$-(O-alkyl), $—OR^{20c}$, $—SR^{20c}$, —O-alkyl-$R^{20c}$, —S-alkyl-$R^{20c}$, $—S(=o)—R^{20c}$, $—S(=O)_2—R^{20c}$, $—S(=O)_2—NHR^{20c}$, —SC(=O)

$R^{20c}$, —C(=O)$R^{20c}$, —(=O)O$R^{20c}$, —C(=O)NH$R^{20c}$, carbocyclyl optionally substituted with 1-5 $R^{21}$; and heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, OH, CN, $C_1$-$C_4$ alkyl, $C_1$-$C_4$ alkoxy, $C_2$-$C_8$ alkoxyalkoxy, aryl, heteroaryl or —NH$R^{20b}$;

$R^{20b}$ is an amino protecting group;

$R^{20c}$ is carbocyclyl optionally substituted with 1-5 $R^{22}$; or heterocarbocyclyl optionally substituted with 1-5 $R^{22}$;

$R^{21}$ is selected from the group consisting of:

$C_1$-$C_{20}$ alkyl, $C_2$-$C_{20}$ alkenyl, $C_2$-$C_{20}$ alkynyl, —O$R^{21a}$, —S$R^{21a}$, —CN, halo, haloalkyl, —$NH_2$, —NH(alkyl), —N$(alkyl)_2$, —NHC(=O)O-alkyl, —NHC(=O)alkyl, —COOH, —C(=O)O-alkyl, —C(=O)alkyl, —C(O)H, —S(=O)-alkyl, —S$(=O)_2$-alkyl, —S(=O)-aryl, —S$(=O)_2$-aryl, carbocyclyl optionally substituted with 1-5 $R^{22}$, and heterocarbocyclyl optionally substituted with 1-5 $R^{22}$;

$R^{21a}$ is H, $C_1$-$C_{20}$ alkyl, $C_2$-$C_{20}$ alkenyl, $C_2$-$C_{20}$ alkynyl, carbocyclyl or heterocarbocyclyl;

$R^{22}$ is selected from the group consisting of:

$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(=O)—, alkyl-C(=O)—, aryl-OC(=O)—, alkyl-OC(=O)NH—, aryl-OC(=O)NH—, alkyl-C(=O)NH—, alkyl-C(=O)O—, (alkyl-O)$_r$-alkyl, HO-(alkyl-O)$_r$-alkyl-, —OH, —SH, —CN, —$N_3$, —CNO, —CNS, alkyl-S(=O)—, alkyl-S$(=O)_2$—, $H_2$NS(=O)—, and $H_2$NS$(=O)_2$—;

$R^{23}$ is selected from the group consisting of:

$C_1$-$C_6$ alkyl, $C_2$-$C_6$ alkenyl, $C_2$-$C_6$ alkynyl, F, Cl, Br, I, haloalkyl, —$NH_2$, —NH$R^{23a}$, —N$(R^{23a})_2$, —$N_3$, —$NO_2$, —CN, —CNO, —CNS, —C(=O)O$R^{23a}$, —C(=O)$R^{23a}$, —OC(=O)$R^{23a}$, N($R^{23a}$)C(=O)$R^{23a}$, —N($R^{23a}$)C(O)O$R^{23a}$, —C(=O)N$(R^{23a})_2$, ureido, —O$R^{23a}$, —S$R^{23a}$, —S(=O)—($C_1$-$C_6$ alkyl), —S$(=O)_2$—($C_1$-$C_6$ alkyl), —S(=O)-aryl, —S$(=O)_2$-aryl, —S$(=O)_2$—N$(R^{23a})_2$;

carbocyclyl optionally substituted with 1-5 $R^{24}$; and heterocarbocyclyl optionally substituted with 1-5 $R^{24}$;

$R^{23a}$ is H or $C_1$-$C_6$ alkyl;

alternatively, two $R^{23a}$ may be combined, together with the N atom to which they are attached, to form a 5 to 7 membered heterocyclic group; and $R^{24}$ is selected from the group consisting of:

$C_1$-$C_4$ alkyl, $C_2$-$C_4$ alkenyl, $C_2$-$C_4$ alkynyl, phenyl, halo, haloalkyl, alkoxy, thialkoxy, amino, alkylamino, dialkylamino, carboxyl, alkyl-OC(=O)—, alkyl-C(=O)—, aryl-OC(=O)—, alkyl-OC(=O)NH—, aryl-OC(=O)NH—, alkyl-C(=O)NH—, alkyl-C(=O)O—, (alkyl-O)$_r$-alkyl, HO-(alkyl-O)$_r$-alkyl-, —OH, —SH, —CN, —$N_3$, —CNO, —CNS, alkyl-S(=O)—, alkyl-S$(=O)_2$—, $H_2$NS(=O)—, and $H_2$NS$(=O)_2$—; and r is 1, 2, 3, 4, 5, 6, 7, 8, 9, or 10;

with the proviso that when Q is a 1,1,2,2-tetramethylethanediol boronic ester, then X is not aralkyloxycarbonyl;

with the proviso that when Q is a 1,1,2,2-tetramethylethanediol boronic ester, and $R^1$ is cycloalkyl, then $R^2$ is not —$CH_2CONH_2$; and with the proviso that when X is $R^A$C(=O)—, $R^A$ is a $C_4$-$C_{15}$ straight-chained alkyl substituted with $R^{20}$, and $R^{20}$ is —CN, —$CO_2$H, —C(=O)O—$R^{20a}$, —NHS$(=O)_2R^{20a}$, —NHC(=O)$R^{20a}$, —NH$R^{20b}$, or phthalimido; then $R^2$ is not —$(CH_2)_a$$CH_2$NHC(=N$R^4$)NH—Y, wherein Y is H, —CN, —$NO_2$, or a guanidino protecting group.

In further embodiments, when $R^2$ is —$(CH_2)_e$CH($R^7$)Z$R^8$, e is 0, $R^7$ is H, $R^8$ is $C_1$-$C_{10}$ alkyl and X is $R^A$C(=O)—, then $R^A$ is not aminoalkyl-, alkylaminoalkyl-, dialkylaminoalkyl-, or ureidoalkyl-.

In some embodiments, $R^1$ can be $C_1$-$C_4$ alkyl, and in further embodiments, $R^1$ can be propyl, such as 2-propyl.

In some embodiments, $R^2$ can be —$(CH_2)_a$$CH_2$NHC(=N$R^4$)NH—Y, —$(CH_2)_b$$CH_2$CON$R^5R^6$, —$(CH_2)_c$$CH_2$N($R^4$)CON$H_2$, —$(CH_2)_d$CH($R^7$)N$R^9R^{10}$, or —$(CH_2)_e$CH($R^7$)Z$R^8$.

In some embodiments, $R^2$ is —$(CH_2)_a$$CH_2$NHC(=N$R^4$)NH—Y and a is 1, 2, 3, 4, or 5.

In some embodiments, $R^2$ is —$(CH_2)_a$$CH_2$NHC(=N$R^4$)NH—Y and a is 2.

In some embodiments, $R^2$ is —$CH_2CH_2CH_2$NHC(=N$R^4$)NH—Y.

In some embodiments, $R^2$ is —$(CH_2)_d$CH($R^7$)N$R^9R^{10}$ and d is 0, 1, or 2.

In some embodiments, $R^2$ is —$(CH_2)_d$CH($R^7$)N$R^9R^{10}$ and d is 0.

In some embodiments, $R^2$ is —$(CH_2)_d$CH($R^7$)N$R^9R^{10}$ and $R^9$ is H.

In some embodiments, $R^2$ is —$(CH_2)_d$CH($R^7$)N$R^9R^{10}$.

In some embodiments, $R^2$ is —CH($R^7$)N$R^9R^{10}$.

In some embodiments, $R^2$ is —$CH_2$NH—C(=O)O$CH_2$($C_6H_5$).

In some embodiments, $R^2$ is —$(CH_2)_e$CH($R^7$)Z$R^8$ and e is 0, 1, or 2.

In some embodiments, $R^2$ is —$(CH_2)_e$CH($R^7$)Z$R^8$ and e is 0.

In some embodiments, $R^2$ is —$(CH_2)_e$CH($R^7$)Z$R^8$.

In some embodiments, $R^2$ is —CH($R^7$)Z$R^8$.

In further embodiments, Z is O.

In further embodiments, Q has Formula (II-a):

(II-a)

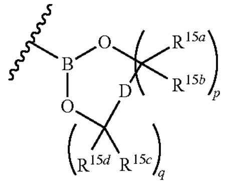

wherein D, $R^{15a}$, $R^{15b}$, $R^{15c}$, $R^{15d}$, p and q are defined herein below.

In further embodiments, Q is $B(OH)_2$ or a cyclic boronic ester wherein said cyclic boronic ester contains from 6 to 10 carbon atoms and contains at least one cycloalkyl moiety.

In further embodiments Q is $B(OH)_2$.

In further embodiments Q is pinanediol boronic ester.

In further embodiments Q is bicyclohexyl-1,1'-diol boronic ester.

In further embodiments, Q is 1,2-dicyclohexyl-ethane-1,2-diol boronic ester.

Alternatively, in some embodiments, Q is —$B(OH)_2$, —B$(OR^{14})_2$,

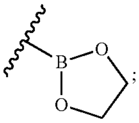;
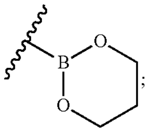;
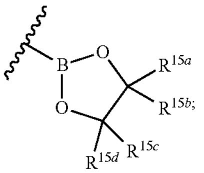

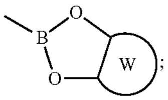;
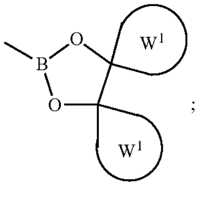; and

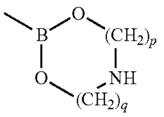

wherein:

$R^{14}$, $R^{15a}$, $R^{15b}$, $R^{15c}$, $R^{15d}$, W, $W^1$, p and q are as defined hereinbelow.

In further embodiments Q is:

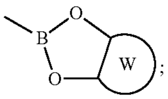;

and

W is a substituted or unsubstituted $C_4$-$C_{10}$ cycloalkyl ring.

In some embodiments, X is $R^AC(=O)$—.

In some embodiments, X is $R^ANHC(=O)$—.

In some embodiments, X is $R^AS(O)_2$—.

In some embodiments, $R^A$ is $C_1$-$C_{14}$ alkyl substituted by —(O-alkyl)$_r$-OH or —(O-alkyl)$_r$-(O-alkyl), wherein r is 1, 2, 3, 4, or 5.

In some embodiments, $R^A$ is $C_1$-$C_{14}$ alkyl substituted by —(O-alkyl)$_r$-OH or —(O-alkyl)$_r$-(O-alkyl), wherein r is 1, 2 or 3.

In some embodiments, $R^A$ comprises at least one —$CH_2CH_2O$— group.

In some embodiments, $R^A$ is —$CH_2(OCH_2CH_2)_rOCH_3$.

In some embodiments, $R^A$ is —$CH_2OCH_2CH_2OCH_2CH_2OCH_3$ or —$CH_2OCH_2CH_2OCH_3$.

In some embodiments, $R^A$ is aryl or heteroaryl each optionally substituted with 1-5 $R^{21}$.

In some embodiments, $R^A$ is cycloalkyl or heterocycloalkyl each optionally substituted with 1-5 $R^{21}$.

In some embodiments, $R^A$ is $C_1$-$C_{20}$ alkyl; $C_2$-$C_{20}$ alkenyl; or $C_2$-$C_{20}$ alkynyl, each optionally substituted with $R^{20}$.

In some embodiments, $R^A$ is $C_1$-$C_{20}$ alkyl; $C_2$-$C_{20}$ alkenyl; or $C_2$-$C_{20}$ alkynyl, each substituted with a carbocyclyl group or a heterocarbocyclyl group wherein said carbocyclyl group or heterocarbocyclyl group is optionally substituted with 1, 2 or 3 $R^{21}$.

In some embodiments, $R^A$ is $C_1$-$C_{20}$ alkyl; $C_2$-$C_{20}$ alkenyl; or $C_2$-$C_{20}$ alkynyl, each substituted with an aryl group wherein said aryl group is optionally substituted with 1, 2 or 3 $R^{21}$.

In some embodiments, $R^A$ is $C_1$-$C_{20}$ alkyl; $C_2$-$C_{20}$ alkenyl; or $C_2$-$C_{20}$ alkynyl, each substituted with an heteroaryl group wherein said heteroaryl group is optionally substituted with 1, 2 or 3 $R^{21}$.

In some embodiments, $R^A$ is $C_1$-$C_{20}$ alkyl; $C_2$-$C_{20}$ alkenyl; or $C_2$-$C_{20}$ alkynyl, each substituted with an cycloalkyl group wherein said cycloalkyl group is optionally substituted with 1, 2 or 3 $R^{21}$.

In some embodiments, $R^A$ is $C_1$-$C_{20}$ alkyl; $C_2$-$C_{20}$ alkenyl; or $C_2$-$C_{20}$ alkynyl, each substituted with an heterocycloalkyl group wherein said heterocycloalkyl group is optionally substituted with 1, 2 or 3 $R^{21}$.

In some embodiments, $R^A$ is $C_1$-$C_{20}$ alkyl; $C_2$-$C_{20}$ alkenyl; or $C_2$-$C_{20}$ alkynyl, each optionally substituted with $R^{20}$, wherein $R^{20}$ is selected from CN, halo, haloalkyl, —$CO_2H$, —$C(=O)CO_2H$, —$C(=O)NH_2$, —$C(=O)H$, —$S(O)NH_2$, —$S(O)_2NH_2$, —OH, —SH, —$NH_2$, —NH(alkyl), —$N(alkyl)_2$, —$NHC(=O)NH_2$, —$NHC(=O)R^{20a}$, —$NHC(=O)OR^{20a}$, —$OR^{20a}$, —$SR^{20a}$, —$S(O)R^{20a}$, —$S(O)_2$—$NHR^{20a}$, —$S(O)_2$—$NHR^{20a}$, —$SC(=O)R^{20a}$, —$C(=O)R^{20a}$, —$C(=O)NHR^{20a}$, —$C(=O)O$—$R^{20a}$, —$NHS(O)_2R^{20a}$, —$NHR^{20b}$, phthalimido, —(O-alkyl), —(O-alkyl)$_r$-OH, —(O-alkyl)$_r$-(O-alkyl), —$OR^{20c}$, —$SR^{20c}$, —O-alkyl-$R^{20c}$, —S-alkyl-$R^{20c}$, —S(O)—$R^{20c}$, —$S(O)_2$—$R^{20c}$, —$S(O)_2$—$NHR^{20c}$, —$SC(=O)R^{20c}$, —$C(=O)R^{20c}$, —$C(=O)OR^{20c}$, and —$C(=O)NHR^{20c}$.

In some embodiments, $R^2$ is H and X is (O-alkyl)-(O-alkyl)$_r$-($C_1$-$C_{14}$ alkyl)-C(=O)— or HO-(alkyl-O)$_r$—($C_1$-$C_{14}$ alkyl)-C(=O)—.

In some embodiments X is $R^AC(=O)$— and $R^A$ is $C_4$-$C_{16}$ alkyl.

In some embodiments X is $R^AC(=O)$— and $R^A$ is aryl optionally substituted with 1-3 $R^{21}$.

In some embodiments X is $R^AC(=O)$— and $R^A$ is heterocarbocyclyl group optionally substituted with 1-3 $R^{21}$.

In some embodiments X is $R^AC(=O)$—; $R^A$ is phenyl substituted with one $R^{21}$; and $R^{21}$ is phenoxy.

In some embodiments X is $R^AC(=O)$—, $R^A$ is $C_1$-$C_4$ alkyl substituted with $R^{20}$, and $R^{20}$ is aryl optionally substituted with 1-3 $R^{21}$; and in yet further embodiments aryl is substituted by at least one halo.

In some embodiments X is $R^AC(=O)$—; $R^A$ is $C_1$-$C_{14}$ alkyl substituted with $R^{20}$; and $R^{20}$ is —$OR^{20a}$ or —$OR^{20c}$.

In some embodiments X is $R^AC(=O)$—; $R^A$ is $C_1$-$C_{14}$ alkyl substituted with $R^{20}$; and $R^{20}$ is heterocarbocyclyl optionally substituted with 1-3 $R^{21}$.

In some embodiments X is $R^AS(O)_2$— and $R^A$ is $C_3$-$C_{16}$ alkyl.

In some embodiments the present invention provides compounds of Formula (I) wherein the stereochemistry is of Formula (I-s):

(I-s)

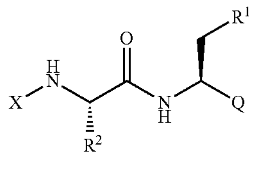

or pharmaceutically acceptable salt form thereof.

In some embodiments, the present invention provides compounds of Formula (I)

(I)

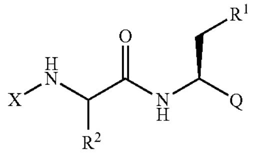

or pharmaceutically acceptable salt, stereoisomeric or tautomeric form thereof, wherein:

$R^1$ is $C_1$-$C_8$ alkyl, $C_2$-$C_8$ alkenyl, $C_2$-$C_8$ alkynyl, or $C_3$-$C_7$ cycloalkyl;

$R^2$ is H, $—(CH_2)_aCH_2NHC(═NR^4)NH—Y$, $—(CH_2)_bCH_2CONR^5R^6$, $—(CH_2)_cCH_2N(R^4)CONH_2$, $—(CH_2)_dCH(R^7)NR^9R^{10}$, or $—(CH_2)_eCH(R^7)ZR^8$;

a, b, and c are each, independently, 0, 1, 2, 3, 4, 5, or 6;

d and e are each, independently, 0, 1, 2, 3, or 4;

$R^4$ is H or $C_1$-$C_{10}$ alkyl;

$R^5$ and $R^6$ are each, independently, H, $C_1$-$C_{10}$ alkyl, carbocyclyl, heterocarbocyclyl, or an amino protecting group;

alternatively, $R^5$ and $R^6$ together with the N atom to which they are attached form a heterocarbocyclyl group;

$R^7$ is H or $C_1$-$C_{10}$ alkyl;

$R^8$ is H, $C_1$-$C_{10}$ alkyl, alkyl-S(═O)$_2$—, aryl-S(═O)$_2$—, $H_2NS(═O)_2$—, —$SO_3H$, or a protecting group;

$R^9$ is H, $C_1$-$C_{10}$ alkyl, carbocyclyl, or heterocarbocyclyl;

$R^{10}$ is H, $C_1$-$C_{10}$ alkyl, carbocyclyl, heterocarbocyclyl, $C_1$-$C_{10}$ alkyl-C(═O)—, carbocyclyl-C(═O)—, heterocarbocyclyl-C(═O)—, carbocyclylalkyl-C(═O)—, heterocarbocyclylalkyl-C(═O)—, $C_1$-$C_{10}$ alkyl-S(═O)$_2$—, carbocyclyl-S(═O)$_2$—, heterocarbocyclyl-S(═O)$_2$—, carbocyclylalkyl-S(═O)$_2$—, heterocarbocyclylalkyl-S(═O)$_2$—, $C_1$-$C_{10}$ alkyl-NHC(═O)—, carbocyclyl-NHC(═O)—, heterocarbocyclyl-NHC(═O)—, carbocyclylalkyl-NHC(═O)—, heterocarbocyclylalkyl-NHC(═O)—, $C_1$-$C_{10}$ alkyl-OC(═O)—, carbocyclyl-OC(═O)—, heterocarbocyclyl-OC(═O)—, carbocyclylalkyl-OC(═O)—, heterocarbocyclylalkyl-OC(═O)—, or an amino protecting group; wherein $R^{10}$ is optionally substituted with 1, 2, or 3 $R^{23}$;

alternatively, $R^9$ and $R^{10}$ together with the N atom to which they are attached form a heterocarbocyclyl group;

Y is —H, —CN, —$NO_2$, —S(═O)$_2R^{11}$, or a guanidino protecting group;

$R^{11}$ is $C_1$-$C_6$ alkyl, aryl, or $NR^{12}R^{13}$;

$R^{12}$ and $R^{13}$ are, independently, H, $C_1$-$C_{10}$ alkyl, carbocyclyl, heterocarbocyclyl, or an amino protecting group;

alternatively, $R^{12}$ and $R^{13}$ together with the N atom to which they are attached form a heterocarbocyclyl group;

Z is O, S, Se, or Te;

Q is —B(OH)$_2$, —B(OR$^{14}$)$_2$, or a cyclic boronic ester wherein said cyclic boronic ester contains from 2 to 20 carbon atoms, and, optionally, a heteroatom which can be N, S, or O;

$R^{14}$ is H, $C_1$-$C_4$ alkyl, cycloalkyl, cycloalkylalkyl, aryl, or aralkyl;

X is $R^AC$(═O)—, $R^A$NHC(═O)—, $R^AS$(═O)$_2$—, $R^AC$(═O)—, $R^A$SC(═O)—, or $R^A$;

$R^A$ is $C_1$-$C_{20}$ alkyl optionally substituted with $R^{20}$;

$C_2$-$C_{20}$ alkenyl optionally substituted with $R^{20}$;

$C_2$-$C_{20}$ alkynyl optionally substituted with $R^{20}$;

carbocyclyl optionally substituted with 1-5 $R^{21}$; or heterocarbocyclyl optionally substituted with 1-5 $R^{21}$;

$R^{20}$ is selected from the group consisting of:

—CN, halo, haloalkyl-, $C_1$-$C_4$ alkyl, $C_2$-$C_4$ alkenyl, $C_2$-$C_4$ alkynyl, —$CO_2H$, —C(═O)$CO_2H$, —C(═O)$NH_2$, —C(═O)H, —S(═O)$NH_2$, —S(═O)$_2NH_2$, —OH, —SH, —$NH_2$, —NH(alkyl), —N(alkyl)$_2$, —NHC(═O)$NH_2$, —NHC(═O)$R^{20a}$, —NHC(═O)O$R^{20a}$, —O$R^{20a}$, —S$R^{20a}$, —S(═O)$R^{20a}$, —S(═)$_2R^{20a}$, —S(═O)$_2$—NH$R^{20a}$, —SC(═O)$R^{20a}$, —C(═O)$R^{20a}$, —C(═O)NH$R^{20a}$, —C(═O)O—$R^{20a}$, —NHS(═O)$_2R^{20a}$, —NH$R^{20b}$, phthalimido, -(—O-alkyl)$_r$, —O-alkyl-OH, —(O-alkyl)$_r$-OH, —O$R^{20c}$, —S$R^{20c}$, —O-alkyl-$R^{20c}$, —S-alkyl-$R^{20c}$, —S(═O)—$R^{20c}$, —S(═O)$_2$—$R^{20c}$, —S(═O)$_2$—NH$R^{20c}$, —SC(═O)$R^{20c}$, —C(═O)$R^{20c}$, —C(═O)O$R^{20c}$, —C(═O)NH$R^{20c}$, carbocyclyl optionally substituted with 1-5 $R^{21}$; and heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —NH$R^{20b}$;

$R^{20b}$ is an amino protecting group;

$R^{20a}$ is carbocyclyl optionally substituted with 1-5 $R^{22}$; or heterocarbocyclyl optionally substituted with 1-5 $R^{22}$;

$R^{21}$ is selected from the group consisting of:

$C_1$-$C_{20}$ alkyl, $C_2$-$C_{20}$ alkenyl, $C_2$-$C_{20}$ alkynyl, $C_1$-$C_{20}$ alkoxy, $C_1$-$C_{20}$ thialkoxy, —OH, —CN, halo, haloalkyl, —$NH_2$, —NH(alkyl), —N(alkyl)$_2$, —NHC(═O)O-alkyl, —NHC(═O)alkyl, —C(═O)O-alkyl, —C(═O)alkyl, —S(═O)-alkyl, —S(═O)$_2$-alkyl, —S(═O)-aryl, —S(═O)$_2$-aryl, carbocyclyl optionally substituted with 1-5 $R^{22}$; and heterocarbocyclyl optionally substituted with 1-5 $R^{22}$;

$R^{22}$ is selected from the group consisting of:

$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, (alkyl-O)$_r$-alkyl, HO-(alkyl-O)$_r$-alkyl-, —OH, —SH, —CN, —$N_3$, —CNO, —CNS, alkyl-S(═O)—, alkyl-S(═O)$_2$—, $H_2NS$(═O)—, and $H_2NS$(═O)$_2$—;

$R^{23}$ is selected from the group consisting of:

$C_1$-$C_6$ alkyl, $C_2$-$C_6$ alkenyl, $C_2$-$C_6$ alkynyl, F, Cl, Br, I, haloalkyl, —$NH_2$, —NH$R^{23a}$, N($R^{23a}$)$_2$, —$N_3$, —$NO_2$, —CN, —CNO, —CNS, —C(═O)O$R^{23a}$, —C(═O)$R^{23a}$, —OC(═O)$R^{23a}$, —N($R^{23a}$)C(═O)$R^{23a}$, —C(═O)N($R^{23a}$)$_2$, ureido, —O$R^{23a}$, —S$R^{23a}$, —S(═O)$_2$—($C_1$-$C_6$ alkyl), —S(═O)$_2$-aryl, and —S(═O)$_2$—N($R^{23a}$)$_2$;

$R^{23a}$ is H or $C_1$-$C_6$ alkyl;

alternatively, two $R^{23a}$ may be combined, together with the N atom to which they are attached, to form a 5 to 7 membered heterocyclic group; and r is 2, 3, 4, 5, 6, 7, 8, 9, or 10; and with the proviso that when Q is a 1,1,2,2-tetramethylethanediol boronic ester, then X is not aralkyloxycarbonyl;

with the proviso that when when Q is a 1,1,2,2-tetramethylethanediol boronic ester, and $R^1$ is cycloalkyl, then $R^2$ is not —$CH_2CONH_2$; and with the proviso that when X is $R^AC$(═O)—, $R^A$ is a $C_4$-$C_{15}$ straight-chained alkyl substituted with $R^{20}$, and $R^{20}$ is —CN, —$CO_2H$, —C(═O)O—$R^{20a}$, —NHS(═O)$_2R^{20a}$, —NHC(═O)$R^{20a}$, —NH$R^{20b}$, or phthalimido; then $R^2$ is not —$(CH_2)_aCH_2NHC(═NR^4)NH$—Y, wherein Y is H, —CN, —$NO_2$, or a guanidino protecting group.

In some embodiments, $R^1$ is 2-propyl; $R^2$ is H, $—(CH_2)_aCH_2NHC(═NR^4)NH—Y$, $—(CH_2)_bCH_2CONR^5R^6$, $—(CH_2)_cCH_2N(R^4)CONH_2$, $—(CH_2)_dCH(R^7)NR^9R^{10}$, or $—(CH_2)_eCH(R^7)ZR^8$; Q is $—B(OH)_2$ or pinanediol boronic ester; X is $R^AC(═O)—$; and $R^A$ is $C_4$-$C_{16}$ alkyl; aryl optionally substituted with 1-3 $R^{21}$; or heterocarbocyclyl group optionally substituted with 1-3 $R^{21}$.

In some embodiments, the present invention provides compounds of Formula (I)

(I)

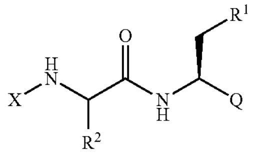

or pharmaceutically acceptable salt, stereoisomeric or tautomeric form thereof, wherein:

$R^1$ is $C_1$-$C_8$ alkyl;

$R^2$ is $—(CH_2)_aCH_2NHC(═NH)NH—Y$, $—(CH_2)_cCH_2NHCONH_2$, $—(CH_2)_dCH(R^7)NR^9R^{10}$, or $—(CH_2)_eCH(R^7)ZR^8$;

a is 1, 2, 3, 4, or 5;

c is 1, 2, 3, 4, or 5;

d is 0, 1, or 2;

e is 0, 1, or 2;

$R^7$ is H or methyl;

$R^8$ is H, $C_1$-$C_{10}$ alkyl, $—S(═O)_2$-alkyl, $—S(═O)_2$-aryl, $—S(═O)_2—NH_2$, $—SO_3H$, or a protecting group;

Y is —H, —CN, $—NO_2$, $—S(═O)_2R^{11}$, or a guanidino protecting group;

$R^9$ is H, $C_1$-$C_{10}$ alkyl, carbocyclyl, or heterocarbocyclyl;

$R^{10}$ is H, $C_1$-$C_{10}$ alkyl, carbocyclyl, heterocarbocyclyl, $C_1$-$C_{10}$ alkyl-C(═O)—, carbocyclyl-C(═O)—, heterocarbocyclyl-C(═O)—, carbocyclylalkyl-C(═O)—, heterocarbocyclylalkyl-C(═O)—, $C_1$-$C_{10}$ alkyl-$S(═O)_2$—, carbocyclyl-$S(═O)_2$—, heterocarbocyclyl-$S(═O)_2$—, carbocyclylalkyl-$S(═O)_2$—, heterocarbocyclylalkyl-$S(═O)_2$—, $C_1$-$C_{10}$ alkyl-NHC(═O)—, carbocyclyl-NHC(═O)—, heterocarbocyclyl-NHC(═O)—, carbocyclylalkyl-NHC(═O)—, heterocarbocyclylalkyl-NHC(═O)—, $C_1$-$C_{10}$ alkyl-OC(═O)—, carbocyclyl-OC(═O)—, heterocarbocyclyl-OC(═O)—, carbocyclylalkyl-OC(═O)—, heterocarbocyclylalkyl-OC(═O)—, or an amino protecting group; wherein $R^{10}$ is optionally substituted with 1, 2 or 3 $R^{23}$;

alternatively, $R^9$ and $R^{10}$ together with the N atom to which they are attached form a heterocarbocyclyl group;

$R^{11}$ is $C_1$-$C_6$ alkyl, aryl, or $NR^{12}R^{13}$;

$R^{12}$ and $R^{13}$ are, independently, H, $C_1$-$C_{10}$ alkyl, carbocyclyl, heterocarbocyclyl, or an amino protecting group;

alternatively, $R^{12}$ and $R^{13}$ together with the N atom to which they are attached form a heterocarbocyclyl group;

Z is O or S;

Q is $—B(OH)_2$, $—B(OR^{14})_2$, or a cyclic boronic ester wherein said cyclic boronic ester contains from 6 to 20 carbon atoms and contains at least one cycloalkyl moiety;

$R^{14}$ is H, $C_1$-$C_4$ alkyl, or cycloalkyl;

X is $R^AC(═O)—$, $R^ANHC(═O)—$, $R^AS(═O)_2—$, $R^AC(═O)—$, $R^ASC(═O)—$, or $R^A$;

$R^A$ is $C_1$-$C_{20}$ alkyl optionally substituted with $R^{20}$;
$C_2$-$C_{20}$ alkenyl optionally substituted with $R^{20}$;
$C_2$-$C_{20}$ alkynyl optionally substituted with $R^{20}$;
carbocyclyl optionally substituted with 1-5 $R^{21}$; or
heterocarbocyclyl optionally substituted with 1-5 $R^{21}$;

$R^{20}$ is selected from the group consisting of:

—CN, halo, haloalkyl-, $C_1$-$C_4$ alkyl, $C_2$-$C_4$ alkenyl, $C_2$-$C_4$ alkynyl, $—CO_2H$, $—C(═O)CO_2H$, $—C(═O)NH_2$, —C(═O)H, $—S(═O)NH_2$, $—S(═O)_2NH_2$, —OH, —SH, $—NH_2$, —NH(alkyl), $—N(alkyl)_2$, $—NHC(═O)NH_2$, $—NHC(═O)R^{20a}$, $—NHC(═O)OR^{20a}$, $—OR^{20a}$, $—SR^{20a}$, $—(═O)R^{20a}$, $—S(═O)_2R^{20a}$, $—S(═O)_2—NHR^{20a}$, $—SC(═O)R^{20a}$, $—C(═O)R^{20a}$, $—C(═O)NHR^{20a}$, $—C(═O)O—R^{20a}$, $—NHS(═O)_2R^{20a}$, $—NHR^{20b}$, phthalimido, $—(O\text{-alkyl})_r$, —O-alkyl-OH, $—(O\text{-alkyl})_r$-OH, $—OR^{20c}$, $—SR^{20c}$, —O-alkyl-$R^{20c}$, —S-alkyl-$R^{20c}$, $—S(═O)—R^{20c}$, $—S(═O)_2—R^{20c}$, $—S(═O)_2—NHR^{20c}$, $—SC(═O)R^{20c}$, $—C(═O)R^{20c}$, $—C(═O)OR^{20c}$, $—C(═O)NHR^{20c}$, carbocyclyl optionally substituted with 1-5 $R^{21}$; and heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or $—NHR^{20b}$;

$R^{20b}$ is an amino protecting group;

$R^{20b}$ is carbocyclyl optionally substituted with 1-5 $R^{22}$; or heterocarbocyclyl optionally substituted with 1-5 $R^{22}$;

$R^{21}$ is selected from the group consisting of:

$C_1$-$C_{20}$ alkyl, $C_2$-$C_{20}$ alkenyl, $C_2$-$C_{20}$ alkynyl, $C_1$-$C_{20}$ alkoxy, $C_1$-$C_{20}$ thialkoxy, —OH, —CN, halo, haloalkyl, $—NH_2$, —NH(alkyl), $—N(alkyl)_2$, —NHC(═O)O-alkyl, —NHC(═O)alkyl, —C(═O)O-alkyl, —C(═O)alkyl, —S(═O)-alkyl, $—S(═O)_2$-alkyl, —S(═O)-aryl, $—S(═O)_2$-aryl, carbocyclyl optionally substituted with 1-5 $R^{22}$, and heterocarbocyclyl optionally substituted with 1-5 $R^{22}$;

$R^{22}$ is selected from the group consisting of:

$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, $(\text{alkyl-O})_r$-alkyl, HO-$(\text{alkyl-O})_r$-alkyl-, —OH, —SH, —CN, $—N_3$, —CNO, —CNS, alkyl-S(═O)—, alkyl-$S(═O)_2$—, $H_2NS(═O)—$, and $H_2NS(═O)_2—$;

$R^{23}$ is selected from the group consisting of:

$C_1$-$C_6$ alkyl, $C_2$-$C_6$ alkenyl, $C_2$-$C_6$ alkynyl, F, Cl, Br, I, haloalkyl, $—NH_2$, $—NHR^{23a}$, $—N(R^{23a})_2$, $—N_3$, $—NO_2$, —CN, —CNO, —CNS, $—C(═O)OR^{23a}$, $—C(═O)R^{23a}$, $—OC(═O)R^{23a}$, $—N(R^{23a})C(═O)R^{23a}$, $—C(═O)N(R^{23a})_2$, ureido, $—OR^{23a}$, $—SR^{23a}$, $—S(═O)_2—(C_1\text{-}C_6\ \text{alkyl})$, $—S(═O)_2$-aryl, and $—S(═O)_2—N(R^{23a})_2$;

$R^{23a}$ is H or $C_1$-$C_6$ alkyl;

alternatively, two $R^{23a}$ may be combined, together with the N atom to which they are attached, to form a 5 to 7 membered heterocyclic group; and r is 2, 3, 4, 5, 6, 7, 8, 9, or 10;

with the proviso that when X is $R^AC(═O)—$, $R^A$ is a $C_4$-$C_{15}$ straight-chained alkyl substituted with $R^{20}$, and $R^{20}$ is —CN, $—CO_2H$, $—C(═O)O—R^{20a}$, $—NHS(═O)_2R^{20a}$, $—NHC(═O)R^{20a}$, $—NHR^{20b}$, or phthalimido; then $R^2$ is not $—(CH_2)_aCH_2NHC(═NR^4)NH—Y$, wherein Y is H, —CN, $—NO_2$, or a guanidino protecting group.

In further embodiments, the present invention provides compounds of Formula (I)

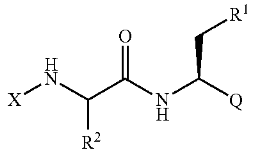

(I)

or pharmaceutically acceptable salt, stereoisomeric or tautomeric form thereof, wherein:

$R^1$ is $C_1$-$C_4$ alkyl;

$R^2$ is —$(CH_2)_a CH_2NHC(=NH)NH$—Y, —$(CH_2)_c CH_2NHCONH_2$, or —$(CH_2)_d CH(R^7)NR^9R^{10}$;

a is 1, 2, or 3;

c is 1, 2, or 3;

d is 0 or 1;

$R^7$ is H or methyl;

$R^9$ is H or $C_1$-$C_{10}$ alkyl;

$R^{10}$ is H, $C_1$-$C_{10}$ alkyl, or an amino protecting group;

Y is H, CN, or $NO_2$;

Q is —$B(OH)_2$, pinanediol boronic ester, bicyclohexyl-1,1'-diol boronic ester, or 1,2-dicyclohexyl-ethane-1,2-diol boronic ester;

X is $R^AC(=O)$—, $R^ANHC(=O)$—, $R^AS(=O)_2$—, $R^AC(=O)$—, $R^ASC(=O)$—, or $R^A$;

$R^A$ is $C_1$-$C_{20}$ alkyl optionally substituted with $R^{20}$;
$C_2$-$C_{20}$ alkenyl optionally substituted with $R^{20}$;
$C_2$-$C_{20}$ alkynyl optionally substituted with $R^{20}$;
carbocyclyl optionally substituted with 1-5 $R^{21}$; or
heterocarbocyclyl optionally substituted with 1-5 $R^{21}$;

$R^{20}$ is selected from the group consisting of:
—CN, halo, haloalkyl-, $C_1$-$C_4$ alkyl, $C_2$-$C_4$ alkenyl, $C_2$-$C_4$ alkynyl, —$CO_2H$, —$C(=O)CO_2H$, —$C(=O)NH_2$, —$C(=O)H$, —$S(=O)NH_2$, —$S(=O)_2NH_2$, —OH, —SH, —$NH_2$, —NH(alkyl), —$N(alkyl)_2$, —$NHC(=O)NH_2$, —$NHC(=O)R^{20a}$, —$NHC(=O)OR^{20a}$, —$OR^{20a}$, —$SR^{20a}$, —$S(=O)_2R^{20a}$, —$S(=O)_2R^{20a}$, —$S(=O)_2$—$NHR^{20a}$, —$SC(=O)R^{20a}$, —$C(=O)R^{20a}$, —$C(=O)NHR^{20a}$, —$C(=O)O$—$R^{20a}$, —$NHS(=O)_2R^{20a}$, —$NHR^{20b}$, phthalimido, —$(O\text{-alkyl})_r$, —O-alkyl-OH, —$(O\text{-alkyl})_r$-OH, —$OR^{20c}$, —$SR^{20c}$, —O-alkyl-$R^{20c}$, —S-alkyl-$R^{20c}$, —$S(=O)$—$R^{20c}$, —$S(=O)_2$—$R^{20c}$, —$S(=O)_2$—$NHR^{20c}$, —$SC(=O)R^{20c}$, —$C(=O)R^{20c}$, —$C(=O)OR^{20c}$, —$C(=O)NHR^{20c}$, carbocyclyl optionally substituted with 1-5 $R^{21}$; and
heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —$NHR^{20b}$;

$R^{20b}$ is an amino protecting group;

$R^{20c}$ is carbocyclyl optionally substituted with 1-5 $R^{22}$; or heterocarbocyclyl optionally substituted with 1-5 $R^{22}$;

$R^{21}$ is selected from the group consisting of:
$C_1$-$C_{20}$ alkyl, $C_2$-$C_{20}$ alkenyl, $C_2$-$C_{20}$ alkynyl, $C_1$-$C_{20}$ alkoxy, $C_1$-$C_{20}$ thialkoxy, —OH—CN, halo, haloalkyl, —$NH_2$, —NH(alkyl), —$N(alkyl)_2$, —$NHC(=O)O$-alkyl, —$NHC(=O)$alkyl, —$C(=O)O$-alkyl, —$C(=O)$alkyl, —$S(=O)$-alkyl, —$S(=O)_2$-alkyl, —$S(=O)$-aryl, —$S(=O)_2$-aryl, carbocyclyl optionally substituted with 1-5 $R^{22}$, and
heterocarbocyclyl optionally substituted with 1-5 $R^{22}$;

$R^{22}$ is selected from the group consisting of:
$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-$OC(=O)$—, alkyl-$C(=O)$—, aryl-$OC(=O)$—, alkyl-$OC(=O)NH$—, aryl-$OC(=O)NH$—, alkyl-$C(=O)NH$—, alkyl-$C(=O)O$—, $(\text{alkyl-O})_r$-alkyl, HO-$(\text{alkyl-O})_r$-alkyl-, —OH, —SH, —CN, —$N_3$, —CNO, —CNS, alkyl-$S(=O)$—, alkyl-$S(=O)_2$—, $H_2NS(=O)$—, and $H_2NS(=O)_2$—; and r is 2, 3, 4, or 5;

with the proviso that when X is $R^AC(=O)$—, $R^A$ is a $C_4$-$C_{15}$ straight-chained alkyl substituted with $R^{20}$, and $R^{20}$ is —CN, —$CO_2H$, —$C(=O)O$—$R^{20a}$, —$NHS(=O)_2R^{20a}$, —$NHC(=O)R^{20a}$, —$NHR^{20b}$, or phthalimido; then $R^2$ is not —$(CH_2)_a CH_2NHC(=NR^4)NH$—Y, wherein Y is H, —CN, or —$NO_2$.

In yet further embodiments, the present invention provides compound of Formula (I) or pharmaceutically acceptable salt, stereoisomeric or tautomeric form thereof, wherein:

$R^1$ is $C_1$-$C_6$ alkyl, $C_2$-$C_6$ alkenyl, $C_2$-$C_6$ alkynyl, or $C_3$-$C_7$ cycloalkyl;

$R^2$ is —$CH_2NH_2$ or —$CH_2NR^9R^{10}$;

$R^9$ is H or $C_1$-$C_{10}$ alkyl;

$R^{10}$ is H, $C_1$-$C_{10}$ alkyl, carbocyclyl, heterocarbocyclyl, $C_1$-$C_{10}$ alkyl-$C(=O)$—, carbocyclyl-$C(=O)$—, heterocarbocyclyl-$C(=O)$—, carbocyclylalkyl-$C(=O)$—, heterocarbocyclylalkyl-$C(=O)$—, $C_1$-$C_{10}$ alkyl-$S(=O)_2$—, carbocyclyl-$S(=O)_2$—, heterocarbocyclyl-$S(=O)_2$—, carbocyclylalkyl-$S(=O)_2$—, heterocarbocyclylalkyl-$S(=O)_2$—, $C_1$-$C_{10}$ alkyl-$NHC(=O)$—, carbocyclyl-$NHC(=O)$—, heterocarbocyclyl-$NHC(=O)$—, carbocyclylalkyl-$NHC(=O)$—, heterocarbocyclylalkyl-$NHC(=O)$—, $C_1$-$C_{10}$ alkyl-$OC(=O)$—, carbocyclyl-$OC(=O)$—, heterocarbocyclyl-$OC(=O)$—, carbocyclylalkyl-$OC(=O)$—, heterocarbocyclylalkyl-$OC(=O)$—, or an amino protecting group; wherein $R^{10}$ is optionally substituted with 1, 2 or 3, $R^{23}$;

alternatively, $R^9$ and $R^{10}$ together with the N atom to which they are attached form a heterocarbocyclyl group;

Q is —$B(OH)_2$, —$B(OR^{14})_2$, or a cyclic boronic ester wherein said cyclic boronic ester contains from 2 to 20 carbon atoms, and, optionally, a heteroatom which can be N, S, or O;

$R^{14}$ is H, $C_1$-$C_4$ alkyl, cycloalkyl, cycloalkylalkyl, aryl, or aralkyl;

X is $R^AC(=O)$—, $R^ANHC(=O)$—, $R^AS(=O)_2$—, $R^AC(=O)$—, $R^ASC(=O)$—, or $R^A$;

$R^A$ is $C_1$-$C_{20}$ alkyl optionally substituted with $R^{20}$; $C_2$-$C_{20}$ alkenyl optionally substituted with $R^{20}$;
$C_2$-$C_{20}$ alkynyl optionally substituted with $R^{20}$;
carbocyclyl optionally substituted with 1-5 $R^{21}$; or
heterocarbocyclyl optionally substituted with 1-5 $R^{21}$;

$R^{20}$ is selected from the group consisting of:
—CN, halo, haloalkyl-, $C_1$-$C_4$ alkyl, $C_2$-$C_4$ alkenyl, $C_2$-$C_4$ alkynyl, —$CO_2H$, —$C(=O)CO_2H$, —$C(=O)NH_2$, —$C(=O)H$, —$S(=O)NH_2$, —$S(=O)_2NH_2$, —OH, —SH, —$NH_2$, —NH(alkyl), —$N(alkyl)_2$, —$NHC(=O)NH_2$, —$NHC(=O)R^{20a}$, —$NHC(=O)OR^{20a}$, —$OR^{20a}$, —$SR^{20a}$, —$S(=O)R^{20a}$, —$S(=O)_2R^{20a}$, —$S(=O)_2$—$NHR^{20a}$, —$SC(=O)R^{20c}$, —$C(=O)R^{20c}$, —$C(=O)OR^{20c}$, —$C(=O)NHR^{20a}$, —$C(=O)OR^{20a}$, —$NHS(=O)_2R^{20a}$, —$NHR^{20b}$, phthalimido, —$(O\text{-alkyl})_r$, —O-alkyl-OH, —$(O\text{-alkyl})_r$-OH, —$OR^{20c}$, —$SR^{20c}$, —O-alkyl-$R^{20c}$, —S-alkyl-$R^{20c}$, —$S(=O)$—$R^{20c}$, —$S(=O)_2R^{20c}$, —$S(=O)_2$—$NHR^{20c}$, —$SC(=O)R^{20c}$, —$C(=O)R^{20c}$, —$C(=O)NHR^{20c}$, carbocyclyl optionally substituted with 1-5 $R^{21}$; and
heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —$NHR^{20b}$;

$R^{20b}$ is an amino protecting group;

$R^{20c}$ is carbocyclyl optionally substituted with 1-5 $R^{22}$; or heterocarbocyclyl optionally substituted with 1-5 $R^{22}$;

$R^{21}$ is selected from the group consisting of:

$C_1$-$C_{20}$ alkyl, $C_2$-$C_{20}$ alkenyl, $C_2$-$C_{20}$ alkynyl, $C_1$-$C_{20}$ alkoxy, $C_1$-$C_{20}$ thialkoxy, —OH—CN, halo, haloalkyl, —$NH_2$, —NH(alkyl), —N$(alkyl)_2$, —NHC(═O)O-alkyl, —NHC(═O)alkyl, —C(═O)O-alkyl, —C(═O)alkyl, —S(═O)-alkyl, —S$(═O)_2$-alkyl, —S(═O)-aryl, —S$(═O)_2$-aryl, carbocyclyl optionally substituted with 1-5 $R^{22}$, and heterocarbocyclyl optionally substituted with 1-5 $R^{22}$;

$R^{22}$ is selected from the group consisting of:

$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, (alkyl-O)$_r$-alkyl, HO-(alkyl-O)$_r$-alkyl-, —OH, —SH, —CN, —$N_3$, —CNO, —CNS, alkyl-S(═O)—, alkyl-S$(═O)_2$—, $H_2$NS(═O)—, and $H_2$NS$(═O)_2$—;

$R^{23}$ is selected from the group consisting of:

$C_1$-$C_6$ alkyl, $C_2$-$C_6$ alkenyl, $C_2$-$C_6$ alkynyl, F, Cl, Br, I, haloalkyl, —$NH_2$, —$NHR^{23a}$, —N$(R^{23a})_2$, —$N_3$, —$NO_2$, —CN, —CNO, —CNS, —C(═O)$OR^{23a}$, —C(═O)$R^{23a}$, —OC(═O)$R^{23a}$, —N$(R^{23a})$C(═O)$R^{23a}$, —C(═O)N$(R^{23a})_2$, ureido, —$OR^{23a}$, —$SR^{23a}$, —S$(═O)_2$—($C_1$-$C_6$ alkyl), —S$(═O)_2$-aryl, and —S$(═O)_2$—N$(R^{23a})_2$;

$R^{23a}$ is H or $C_1$-$C_6$ alkyl;

alternatively, two $R^{23a}$ may be combined, together with the N atom to which they are attached, to form a 5 to 7 membered heterocyclic group; and r is 2, 3, 4, or 5.

In yet further embodiments, the present invention provides compounds of Formula (I) or pharmaceutically acceptable salt, stereoisomeric or tautomeric form thereof, wherein:

$R^1$ is $C_1$-$C_8$ alkyl, $C_2$-$C_8$ alkenyl, $C_2$-$C_8$ alkynyl, or $C_3$-$C_7$ cycloalkyl;

$R^2$ is H;

Q is —B$(OH)_2$, —B$(OR^{14})_2$, or a cyclic boronic ester wherein said cyclic boronic ester contains from 2 to 20 carbon atoms, and, optionally, a heteroatom which can be N, S, or O;

$R^{14}$ is H, $C_1$-$C_4$ alkyl, cycloalkyl, cycloalkylalkyl, aryl, or aralkyl;

X is $R^A$C(═O)—, $R^A$NHC(═O)—, $R^A$S$(═O)_2$—, $R^A$C(═O)—, $R^A$SC(═O)—, or $R^A$;

$R^A$ is $C_1$-$C_{20}$ alkyl optionally substituted with $R^{20}$;

$C_2$-$C_{20}$ alkenyl optionally substituted with $R^{20}$;

$C_2$-$C_{20}$ alkynyl optionally substituted with $R^{20}$;

carbocyclyl optionally substituted with 1-5 $R^{22}$; or heterocarbocyclyl optionally substituted with 1-5 $R^{22}$;

$R^{20}$ is selected from the group consisting of:

—$OR^{20a}$, —$SR^{20a}$, —S(═O)$R^{20a}$, —S$(═O)_2R^{20a}$, —S$(═O)_2$—$NHR^{20a}$, —SC(═O)$R^{20a}$, —C(═O)$NHR^{20a}$C(═O)O—$R^{20a}$, phthalimido, —(O-alkyl)$_r$, —O-alkyl-OH, —(O-alkyl)$_r$-OH, —$OR^{20c}$, —$SR^{20c}$, —O-alkyl-$R^{20c}$, —S-alkyl-$R^{20c}$, —S(═O)—$R^{20c}$, —S$(═O)_2$—$R^{20c}$, —S$(═O)_2$—$NHR^{20c}$, —SC(═O)$R^{20c}$, —C(═O)$R^{20c}$, —C(═O)$OR^{20c}$, —C(═O)$NHR^{20c}$, carbocyclyl optionally substituted with 1-5 $R^{22}$; and heterocarbocyclyl optionally substituted with 1-5 $R^{22}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —$NHR^{20b}$;

$R^{20c}$ is carbocyclyl optionally substituted with 1-5 $R^{22}$; or heterocarbocyclyl optionally substituted with 1-5 $R^{22}$;

$R^{22}$ is selected from the group consisting of:

$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, (alkyl-O)$_r$-alkyl, HO-(alkyl-O)$_r$-alkyl-, —OH, —SH, —CN, —$N_3$, —CNO, —CNS, alkyl-S(═O)—, alkyl-S$(═O)_2$—, $H_2$NS(═O)—, and $H_2$NS$(═O)_2$—; and r is 2, 3, 4, 5, 6, 7, 8, 9, or 10.

In yet further embodiments:

X is $R^A$C(═O)—, $R^A$NHC(═O)—, $R^A$S$(O)_2$—, or $R^A$; $R^A$ is $C_1$-$C_{14}$ alkyl optionally substituted with $R^{20}$; $R^{20}$ is —(O-alkyl)$_r$-OH or —(O-alkyl)$_r$-(O-alkyl); and r is 1, 2, 3, 4, or 5. In further embodiments, the O-alkyl is methoxy, ethoxy, or propoxy.

In yet further embodiments, the present invention provides compounds of Formula (I) or pharmaceutically acceptable salts, stereoisomeric or tautomeric forms thereof, wherein:

$R^1$ is 2-propyl;

$R^2$ is —$CH_2CH_2CH_2$NHC(═NH)NH—$NO_2$, —$CH_2CH_2CH_2$NHC(═O)$NH_2$, —CH$(CH_3)$OH, —$CH_2CONH_2$, —$CH_2NH_2$, or —$CH_2NR^9R^{10}$;

$R^9$ is H;

$R^{10}$ is methyl-C(═O)—, ethyl-C(═O)—, propyl-C(═O)—, butyl-C(═O)—, pentyl-C(═O)—, 2-(ethoxycarbonyl)ethyl-C(═O)—, 4-methyl-phenyl-C(═O)—, cyclopropyl-C(═O)—, 4-fluoro-phenyl-C(═O)—, 4-$H_2NSO_2$-phenyl-C(═O)—, 4-$H_3CSO_2$-phenyl-C(═O)—, 4-phenyl-phenyl-C(═O)—, 3,4-dimethoxy-benzyl-C(═O)—, 3-pyridinyl-C(═O)—, 2-(hydroxy)-pyridin-3-yl-C(═O)—, 6-(morpholino)-pyridin-3-yl-C(═O)—, 2-(pyridin-4-yl)thiazol-4-yl-C(═O)—, 2-pyrazinyl-C(═O)—, 2,5-dimethyl-pyrazolyl-C(═O)—, N-methyl-2-pyrrolyl-C(═O)—, 2-pyrrolidinyl-C(═O)—, 2-thiophenyl-C(═O)—, 5-isoxazolyl-C(═O)—, 4-(tetrazol-5-yl)phenyl-C(═O)—, (5-tetrazolyl)$CH_2$—C(═O)—, N—$H_3CSO_2$-piperidinyl-C(═O)—, butyl-OC(═O)—, (benzyl)-OC(═O)—, (9-fluorenylmethyl)-OC(═O)—, pentyl-NHC(═O)—, propyl-NHC(═O)—, phenyl-NHC(═O)—, 4-methyl-phenyl-NHC(═O)—, methyl-S$(═O)_2$—, 4-fluoro-phenyl-S$(═O)_2$—, 4-cyano-phenyl-S$(═O)_2$—, 1-methyl-imidazol-4-yl-S$(═O)_2$—, 2-thiophenyl-S$(═O)_2$—, (4-methyl-phenyl)-NHC(═O)NH—S$(═O)_2$—, and (4-methyl-phenyl)-S$(═O)_2$NHC(═O)—, alternatively, $R^9$ and $R^{10}$ together with the N atom to which they are attached form pyrrolyl or pyrazolyl;

Q is —B$(OH)_2$, pinanediol boronic ester, bicyclohexyl-1,1'-diol boronic ester, or 1,2-dicyclohexyl-ethane-1,2-diol boronic ester;

X is $R^A$C(═O)—, $R^A$NHC(═O)—, $R^A$S$(═O)_2$—, or $R^A$C(═O)—;

$R^A$ is $CH_3$—, $C_2H_5$—, $C_3H_7$—, $C_4H_9$—, $C_5H_{11}$—, $C_6H_{13}$—, $C_7H_{15}$—, $C_8H_{17}$—, $C_9H_{19}$—, $C_{10}H_{21}$—, $C_{11}H_{23}$—, $C_{12}H_{25}$—, $C_{13}H_{27}$—, adamantyl-, bicycloheptanyl-, $C_{1-3}$ alkyl substituted with $R^{20}$;

$C_{2-10}$ alkenyl substituted with $R^{20}$;

cyclopropyl substituted with 0-3 $R^{21}$;

cyclopentyl substituted with 0-2 $R^{21}$;

cyclohexyl substituted with 0-2 $R^{21}$;

phenyl substituted with 0-3 $R^{21}$;
naphthyl-substituted with 0-2 $R^{21}$;
pyrazinyl substituted with 0-1 $R^{21}$;
quinolinyl substituted with 0-1 $R^{21}$;
imidazolyl substituted with 0-1 $R^{21}$;
tetrahydrofuranyl substituted with 0-1 $R^{21}$;
oxothiazolidinyl substituted with 0-1 $R^{21}$;
benzothiazolyl substituted with 0-1 $R^{21}$;
thiazolyl substituted with 0-2 $R^{21}$;
furanyl substituted with 0-2 $R^{21}$;
pyrrolidinyl substituted with 0-1 $R^{21}$;
piperidinyl substituted with 0-1 $R^{21}$;
piperazinyl substituted with 0-1 $R^{21}$; or
pyridinyl substituted with 0-1 $R^{21}$;

$R^{20}$ is selected from the group consisting of:

hydroxy-, methoxy-, ethoxy-, propoxy-, butoxy-, pentoxy-, hexyloxy-, heptyloxy-, octyloxy-, methoxyethoxy-, methoxyethoxyethoxy-, methyl-S—, ethyl-S—, octyl-S—, methyl-C(═O)S—, (acetylamino) methyl-S—, amino-, methylamino-, dimethylamino-, methyl-C(═O)—, phenyl-C(═O)—, $(H_3CSO_2)$phenyl-C(═O)—, thiophenyl-C(═O)—, methyl-OC(═O)—, ethyl-OC(═O)—, butyl-OC(═O)NH—, methyl-C(═O)NH—, methoxyethoxy-methyl-C(═O)NH—, $H_2NC$(═O)—, methyl-NHC(═O)—, ethyl-NHC(═O)—, propyl-NHC(═O)—, phenyl-NHC(═O)—, $H_2NC$(═O)NH—, $H_2NS(═O)_2$—, octyl-S(═O)$_2$—, phenyl-S(═O)$_2$—, methylphenyl-S(═O)$_2$—, thiophenyl-S(═O)$_2$—, cyclopentyl-, cyclohexyl-, cycloheptyl-, adamantyl-, bicycloheptanyl-, cyclopentenyl-, phenyl-, methoxy-phenyl-, methyl-phenyl-, dimethyl-phenyl-, ethyl-phenyl-, propyl-phenyl-, butyl-phenyl-, fluoro-phenyl-, difluoro-phenyl-, chloro-phenyl-, bromo-phenyl-, iodo-phenyl-, dimethylamino-phenyl-, cyclohexyloxy-, 2-isopropyl-5-methyl-cyclohexyloxy-, naphthyl-, methoxynaphthyl-, naphthyloxy-, phenoxy-, (methyl-phenyl)oxy-, (ethyl-phenyl)oxy-, (propyl-phenyl)oxy-, (butyl-phenyl)oxy-, (fluoro-phenyl)oxy-, (chloro-phenyl)oxy-, (bromo-phenyl)oxy-, naphthyl-S—, benzyl-S—, (methyl-phenyl)methyl-S—, pyrimidinyl-S—, piperidinyl-, N-methyl-piperidinyl-, N-propyl-piperidinyl-, phthalimido-, thiophenyl-, methyl-thiophenyl-, imidazolyl-, furnayl-, tetrazolyl-, oxopyrrolidinyl-, indolyl-, and methyl-indolyl-; and $R^{21}$ is selected from the group consisting of:

methyl-, ethyl-, propyl-, butyl-, pentyl-, hexyl-, heptyl-, ethenyl-, propenyl-, butenyl-, methoxy-, ethoxy-, propoxy-, phenoxy-, fluoro-, chloro-, bromo-, methyl-C(═O)—, butyl-OC(═O)—, butyl-OC(═O)NH—, phenyl-, methoxyphenyl-, fluorophenyl-, chlorophenyl-, bromophenyl-, pyrrolyl-, and pyridinyl-.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, the phrase "boronic acid" refers to a compound containing a $B(OH)_2$ moiety. In some embodiments, boronic acid compounds can form oligomeric anhydrides by dehydration of the boronic moiety. For example, Snyder, et al., *J. Am. Chem. Soc.,* 1958, 80, 3611 report oligomeric arylboronic acids. Thus, unless otherwise indicated, "boronic acid", or a chemical formula containing a —$B(OH)_2$ moiety, is intended to encompass free boronic acids, oligomeric anhydrides, including but not limited to, dimers, trimers, tetramers, and mixtures thereof.

As used herein, "boronic acid anhydride" or "boronic anhydride" refers to a compound formed by the combination of two or more molecules of a boronic acid compound of Formula (I), with loss of one or more water molecules from the boronic acid moieties. When contacted with water, the boronic acid anhydride compound can be hydrated to release free boronic acid compound. In some embodiments, the boronic acid anhydride structure can contain two, three, four, or more boronic acid units and can have a cyclic or linear configuration. In some embodiments, the boronic acid anhydride compound exists substantially in a single oligomeric form; however, boronic acid anhydrides also encompass mixtures of different oligomeric boronic acid anhydride as well as free boronic acids.

Non-limiting examples of boronic acid anhydrides of the invention include compounds of Formula (II) and (III) where G is a moiety of Formula (IV) and t is 0 to 10 or 1, 2, 3, or 4.

(II)

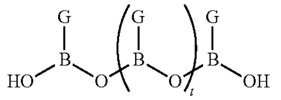

(III)

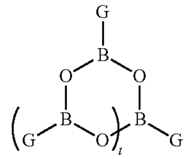

(IV)

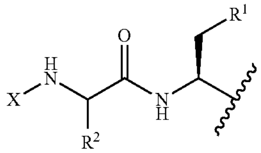

In some embodiments, at least about 80% of boronic acid present in a boronic acid anhydride compound exists in a single oligomeric anhydride form. In further embodiments, at least about 85, about 90, about 95, or about 99% of the boronic acid present in the boronic acid anhydride exists in a single oligomeric anhydride form. In some embodiments, the boronic acid anhydride compound consists essentially of a single oligomeric boronic acid anhydride. In yet further embodiments, the boronic acid anhydride compound consists of a single oligomeric boronic acid anhydride. In further embodiments, the boronic acid anhydride compound contains a boroxine of Formula (III), wherein t is 1.

Boronic acid anhydride compounds can be prepared from the corresponding boronic acid compound by exposure to dehydrating conditions, including, for example, crystallization, lyophilization, exposure to heat, and/or exposure to a drying agent. Some suitable crystallization solvents include ethyl acetate, dichloromethane, hexanes, ether, benzene, acetonitrile, ethanol, and mixtures thereof.

As used herein, the phrase "boronic ester" or "boronic acid ester" refers to an ester derivative of a boronic acid compound. As used herein, "cyclic boronic ester" is intended to mean a stable cyclic boronic moiety of general formula —B(OR)(OR) wherein the two R substituents are linked together forming a cyclic moiety (e.g., 3- to 10-membered cycloalkyl group) optionally further substituted with one or more substituents or fused with (sharing at least one bond) one or more further carbocyclyl or heterocarbocyclyl groups. The cyclic boronic ester can contain from 2 to 20 carbon atoms, and optionally, a heteroatom which can be N, S, or O. Cyclic boronic esters are well known in the art. Examples of cyclic boronic esters include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 1,1,2,2-tetramethylethanediol boronic ester, 1,2-diisopropylethanediol boronic ester, 5,6-decanediol boronic ester, 1,2-dicyclohexylethanediol boronic ester, bicyclohexyl-1,1'-diol, diethanolamine boronic ester, and 1,2-diphenyl-1,2-ethanediol boronic ester.

In some embodiments, the "cyclic boronic ester" has Formula (II-a):

(II-a)

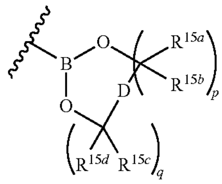

wherein:

D is absent, O, S, $NR^{16}$, or $CR^{15e}R^{15f}$;

$R^{15a}$, $R^{15b}$, $R^{15c}$, $R^{15d}$, $R^{15e}$, $R^{15f}$ are each, independently, H, $C_1$-$C_{10}$ alkyl, $C_3$-$C_7$ cycloalkyl, aryl or heteroaryl, wherein said $C_1$-$C_{10}$ alkyl, $C_3$-$C_{10}$ cycloalkyl, aryl or heteroaryl are each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl;

or $R^{15a}$ and $R^{15b}$ together with the C atoms to which they are attached form $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl;

or $R^{15c}$ and $R^{15d}$ together with the C atoms to which they are attached form $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl;

or $R^{15b}$ and $R^{15c}$ together with the C atoms to which they are attached and the intervening D moiety form aryl, heteroaryl, $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl;

$R^{16}$ is H or $C_1$-$C_6$ alkyl; and p and q are each, independently, 1, 2 or 3.

In some embodiments, D is absent.

In some embodiments, D is $NR^{16}$.

In some embodiments, D is NH.

In some embodiments, D is $CH_2$.

In some embodiments, $R^{15a}$ and $R^{15b}$ together with the C atoms to which they are attached form $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl; and $R^{15c}$ and $R^{15d}$ together with the C atoms to which they are attached form $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl.

In some embodiments, $R^{15a}$ and $R^{15b}$ together with the C atoms to which they are attached form cyclopropyl, cyclobutyl, cyclopenytyl, cyclohexyl or cycloheptyl; and $R^{15c}$ and $R^{15d}$ together with the C atoms to which they are attached form cyclopropyl, cyclobutyl, cyclopenytyl, cyclohexyl or cycloheptyl.

In some embodiments, D is absent and $R^{15b}$ and $R^{15c}$ together with the C atoms to which they are attached form aryl, heteroaryl, $C_3$-$C_{10}$ cycloalkyl or a 3- to 10-membered heterocycloalkyl group, each optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl.

In some embodiments, D is absent and $R^{15b}$ and $R^{15c}$ together with the C atoms to which they are attached form $C_3$-$C_{10}$ cycloalkyl optionally substituted by 1, 2, 3 or 4 halo, $C_1$-$C_4$ alkyl, $C_1$-$C_4$ alkoxy, $C_1$-$C_4$ haloalkoxy, OH, amino, alkylamino, dialkylamino, aryl, or heteroaryl.

In some embodiments, D is absent and $R^{15b}$ and $R^{15c}$ together with the C atoms to which they are attached form $C_3$-$C_{10}$ cycloalkyl optionally substituted by 1, 2, 3 or 4 halo or $C_1$-$C_4$ alkyl.

In some embodiments, D is absent and $R^{15b}$ and $R^{15c}$ together with the C atoms to which they are attached form a $C_7$-$C_{10}$ bicyclic cycloalkyl group optionally substituted by 1, 2, 3 or 4 halo or $C_1$-$C_4$ alkyl.

In some embodiments, p and q are each 1.

In some embodiments, at least one of $R^{15a}$, $R^{15b}$, $R^{15c}$, $R^{15d}$ is other than H.

Further examples of "cyclic boronic esters", as defined herein, include, boronic esters with the following structures:

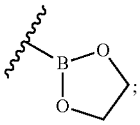 ; 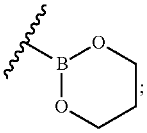 ;

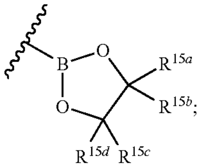 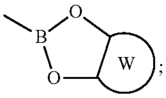 ;

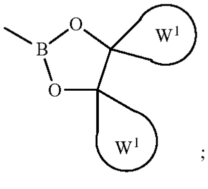 ; and 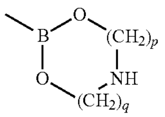

wherein: W is a substituted or unsubstituted $C_4$-$C_{10}$ cycloalkyl ring or a substituted or unsubstituted phenyl ring; $W^1$ is, independently at each occurrence, a substituted or unsubstituted $C_3$-$C_6$ cycloalkyl ring. Groups $R^{15a}$, $R^{15b}$, $R^{15c}$, $R^{15d}$, $R^{15e}$, $R^{15f}$, p and q are, defined as provided above.

As used herein, the term "alkyl" or "alkylene" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include ethynyl, propynyl, butynyl, pentynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl." Examples perhaloalkyl groups include $CF_3$ and $C_2F_5$.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from 3 to about 20, 3 to about 10, or 3 to about 7 carbon atoms.

As used herein, "aryl" refers to aromatic carbocyclyl groups including monocyclic or polycyclic aromatic hydrocarbons such as, for example, phenyl, naphthyl, anthracenyl, phenanthrenyl, indanyl, indenyl, and the like. In some embodiments, aryl groups have from 6 to about 18 ring-forming carbon atoms.

As used herein, "cycloalkyl" refers to non-aromatic carbocyclyl groups including cyclized alkyl, alkenyl, and alkynyl groups. Cycloalkyl groups can include bi- or poly-cyclic ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like. In some embodiments, cycloalkyl groups can have 3, 4, 5, 6, or 7 ring forming carbon atoms. In some embodiments, cycloalkyl groups can have 0, 1, or 2 double or triple ring-forming bonds.

As used herein, "heterocarbocyclyl" groups can be saturated or unsaturated carbocyclyl groups wherein one or more of the ring-forming carbon atoms of the carbocyclyl group is replaced with a heteroatom such as O, S, or N. Heterocarbocyclyl groups can be aromatic (e.g., "heteroaryl") or non-aromatic (e.g., "heterocycloalkyl"). Heterocarbocyclyl groups can correspond to hydrogenated and partially hydrogenated heteroaryl groups. Heterocarbocyclyl groups can contain, in addition to at least one heteroatom, from about 1 to about 20, about 2 to about 10, or about 2 to about 7 carbon atoms and can be attached through a carbon atom or heteroatom. Examples of heterocarbocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, is oxazolidinyl, isothiazolidinyl, pyrazolidinyl, oxazolidinyl, thiazolidinyl, imidazolidinyl, and the like.

As used herein, "heteroaryl" groups are aromatic heterocarbocyclyl groups and include monocyclic and polycyclic aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, and the like. In some embodiments, heteroaryl groups can have from 3 to about 20 ring-forming carbon atoms, and in further embodiments from about 3 to about 12 ring forming carbon atoms. In some embodiments, heteroaryl groups have 1 to about 4, 1 to about 3, or 1 to 2 heteroatoms.

As used herein, "heterocycloalkyl" refers to a non-aromatic heterocarbocyclyl group including cyclized alkyl, alkenyl, and alkynyl groups where one or more of the ring-forming carbon atoms is replaced by a heteroatom such as an O, N, or S atom. Ring-forming carbon and heteroatoms such as S and N can further be oxidized in a heterocycloalkyl moeity. For example, the ring-forming carbon or heteroatom can bear one or two oxo or sufido moieties (e.g., >C═O, >S═O, >S(═O)$_2$, N→O, etc.). Also included in the definition of heterocycloalkyl are moieties that have one or more aromatic rings fused (i.e., having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups. In some embodiments, heterocycloalkyl groups have 3 to about 20 ring-forming atoms. In some embodiments, heterocycloalkyl groups have 3, 4, 5, 6, or 7 ring-forming atoms. In some embodiments, heterocycloalkyl groups have 0, 1, or 2 double or triple ring-forming bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like. In some embodiments, alkoxy groups have from 1 to 20, 1 to 12, 1 to 8, 1 to 6, 1 to 4 or 1 to 3 carbon atoms.

As used herein, "alkoxyalkoxy" refers to an —O-alkyl-O-alkyl group.

As used herein, "thioalkoxy" refers to an alkoxy group in which the O atom is replaced by an S atom.

As used herein, "aryloxy" refers to an —O-aryl group. An example aryloxy group is phenoxy.

As used herein, "thioaryloxy" refers to an aryloxy group in which the O atom is replaced by an S atom.

As used herein, "aralkyl" refers to an alkyl moiety substituted by an aryl group. Example aralkyl groups include benzyl and naphthylmethyl groups. In some embodiments, aralkyl groups have from 7 to 11 carbon atoms.

As used herein, "amino" refers to an —$NH_2$ group. "Alkylamino" refers to an amino group substituted by an alkyl group and "dialkylamino" refers to an amino group substituted by two alkyl groups. On the contrary, "aminoalkyl" refers to an alkyl group substituted by an amino group.

As used herein, "carbonyl" refers to >C═O.

As used herein, "carboxy" or "carboxyl" refers to —COOH.

As used herein, "hydroxy" refers to —OH.

As used herein, "mercapto" refers to —SH.

As used herein, "ureido" refers to —$NHCONH_2$.

As used herein, "sulfinyl" refers to >SO.

As used herein, "sulfonyl" refers to $>SO_2$.

As used herein, "oxy" refers to —O—.

The above chemical terms can be combined to refer to moieties containing a combination of chemical groups. This combination term is generally read such that a recited term is understood to be a substituent of a following term. For example, "alkylcarbonylalkenyl" refers to an alkenyl group substituted by a carbonyl group which in turn is substituted by an alkyl group. The following terms can also exemplify such combinations.

As used herein, "carbocyclylalkyl" refers to an alkyl moiety substituted by a carbocyclyl group. Example carbocyclylalkyl groups include "aralkyl" (alkyl substituted by aryl) and "cycloalkylalkyl" (alkyl substituted by cycloalkyl).

As used herein, "carbocyclylalkenyl" refers to an alkenyl moiety substituted by a carbocyclyl group. Example carbocyclylalkenyl groups include "aralkenyl" (alkenyl substituted by aryl) and "cycloalkylalkenyl" (alkenyl substituted by cycloalkyl).

As used herein, "carbocyclylalkynyl" refers to an alkynyl moiety substituted by a carbocyclyl group. Example carbocyclylalkynyl groups include "aralkynyl" (alkynyl substituted by aryl) and "cycloalkylalkynyl" (alkynyl substituted by cycloalkyl).

As used herein, "heterocarbocyclylalkyl" refers to an alkyl moiety substituted by a heterocarbocyclyl group. Example heterocarbocyclylalkyl groups include "heteroarylalkyl" (alkyl substituted by heteroaryl) and "heterocycloalkylalkyl" (alkyl substituted by heterocycloalkyl).

As used herein, "heterocarbocyclylalkenyl" refers to an alkenyl moiety substituted by a heterocarbocyclyl group. Example heterocarbocyclylalkenyl groups include "heteroarylalkenyl" (alkenyl substituted by heteroaryl) and "heterocycloalkylalkenyl" (alkenyl substituted by heterocycloalkyl).

As used herein, "heterocarbocyclylalkynyl" refers to an alkynyl moiety substituted by a heterocarbocyclyl group. Example heterocarbocyclylalkynyl groups include "heteroarylalkynyl" (alkynyl substituted by heteroaryl) and "heterocycloalkynylalkyl" (alkynyl substituted by heterocycloalkyl).

As used herein, the phrase "protecting group" refers to a chemical functional group that can be selectively appended to and removed from functionalities, such as hydroxyl groups, amino groups, and carboxyl groups. Protecting groups are usually introduced into a chemical compound to render such functionality inert to chemical reaction conditions to which the compound is exposed. Any of a variety of protecting groups can be employed with the present invention. A protecting group of an amino moiety can be referred to as an "amino protecting group" and a protecting group of a guanidino moiety can be referred to as a "guanidino protecting group." Amino and guanidino protecting groups can have the formulas aryl-$SO_2$—, alkyl-$SO_2$—, aryl-C(═O)—, aralkyl-C(═O)—, alkyl-C(═O)—, aryl-OC(═O)—, aralkyl-OC(═O)—, alkyl-OC(═O)—, aryl-NHC(═O)—, alkyl-NHC(═O)—, and the like, wherein said alkyl, aryl and aralkyl groups may be substituted or unsubstituted. Example amino and guanidino protecting groups can also include t-butyloxycarbonyl (BOC), fluorenylmethoxycarbonyl (Fmoc), benzyloxycarbonyl (Cbz), and a phthalimido group. Other protecting groups include the following moieties:

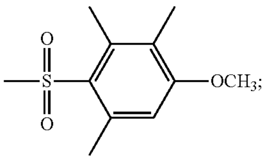

MTR

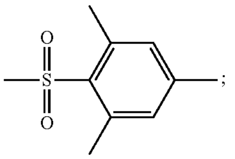

MTS

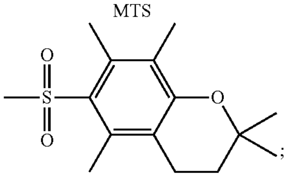

and

PMC

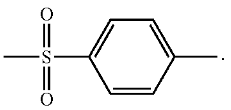

TOS

Further representative protecting groups can be found in T. W. Green and P. G. M. Wuts, *Protective Groups in Organic Synthesis,* 3rd. Ed., Wiley & Sons, Inc., New York (1999), which is incorporated herein by reference in its entirety.

As used herein, "substituted" indicates that at least one hydrogen atom of a chemical group is replaced by a non-hydrogen moiety. Example substituents include F, Cl, Br, I, $C_1$-$C_6$ alkyl, $C_1$-$C_6$ alkenyl, $C_1$-$C_6$, alkynyl, haloalkyl, $NR^ER^F$, $N_3$, $NO_2$, CN, CNO, CNS, C(═O)$OR^E$, $R^E$CO, $R^E$C(O)O, $R^E$CON$R^E$, $R^ER^F$NCO, ureido, $OR^E$, $SR^E$, $SO_2$-alkyl, $SO_2$-aryl, and $SO_2$—$NR^ER^F$, wherein $R^E$ and $R^F$ are each, independently, H or $C_1$-$C_6$ alkyl. Alternatively, $R^E$ and $R^F$ may be combined, with the nitrogen to which they are attached, to form a 5 to 7 membered heterocyclic ring, for example pyrrolidinyl, piperidinyl, morpholinyl, piperazinyl, and N-methylpiperazinyl. When a chemical group herein is "substituted" it may have up to the full valance of substitution, provided the resulting compound is a stable compound or stable structure; for example, a methyl group may be substituted by 1, 2, or 3 substituents, a methylene group may be substituted by 1 or 2 substituents, a phenyl group may be substituted by 1, 2, 3, 4, or 5 substituents, and the like.

As used herein, "leaving group" refers to any group that can be replaced by a nucleophile upon nucleophilic substitution. Example leaving groups include, halo (F, Cl, Br, I), hydroxyl, alkoxy, mercapto, thioalkoxy, triflate, alkylsulfonyl, substituted alkylsulfonate, arylsulfonate, substituted arylsulfonate, heterocyclosulfonate or trichloroacetimidate. Representative examples include p-(2,4-dinitroanilino)benzenesulfonate, benzenesulfonate, methylsulfonate, p-methylbenzenesulfonate, p-bromobenzenesulfonate, trichloroacetimidate, acyloxy, 2,2,2-trifluoroethanesulfonate, imidazolesulfonyl and 2,4,6-trichlorophenyl.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In addition to the above, the compounds herein described may have asymmetric centers which result in one enantiomer of a compound of Formula (I) demonstrating superior biological activity over the opposite enantiomer. Both of the configurations are considered part of the invention. For example, the R2 substituent of a compound of Formula (I) may exist in either an S or R configuration. An example of a preferred enantiomeric configuration of the invention is a compound of Formula (I-s):

(I-s)

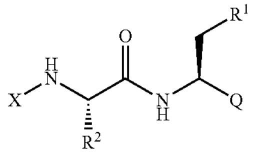

but is not intended to be limited to this example. When required, separation of the racemic material can be achieved by methods known in the art.

Compounds of the invention can also include tautomeric forms, such as keto-enol tautomers. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and in the *Journal of Pharmaceutical Science,* 66, 2 (1977), the disclosures of each of which are hereby incorporated by reference.

Synthesis

Compounds of the invention, including salts and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

Compounds of the invention can be prepared according to methods for preparing aminoboronic acids, esters thereof, and related compounds described in the art, such as in U.S. Pat. No. 4,537,773, and in U.S. Pat. No. 5,614,649, each of which is incorporated herein by reference in its entirety. In some embodiments, the present compounds can be prepared by the sequential coupling of three fragment components (F1, F2, and F3).

F1 Fragment

Synthesis of compounds of the invention can involve a boron-containing fragment (F1) having a structure indicated by Formula (A).

(A)

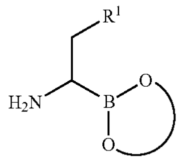

The boronic ester moiety of F1 can include, for example, a diol ester such as is indicated by the loop connecting oxygen atoms in Formula (A).

Stereochemistry at the carbon atom alpha to the boron atom in Formula (A) can be controlled using an asymmetric boronic ester group in the preparation of F1. For example, pinanediol esters of boronic acid can facilitate the preparation or stereochemically pure, or substantially stereochemically pure, F1 fragment. As an example, the F1 fragment can be prepared by reacting a compound of Formula (B) (showing a pinanediol boronic ester obtained from (+)-pinanediol) with a strong base (e.g., lithium diisopropylamide or lithium dicyclohexylamide) in the presence of dichloromethane or dibromomethane, followed by addition of a Lewis acid, (e.g., $ZnCl_2$, $ZnBr_2$, or $FeCl_3$) to yield a compound of Formula (C) (where L is halo) having a newly introduced stereocenter at the carbon alpha to the boron.

(B)

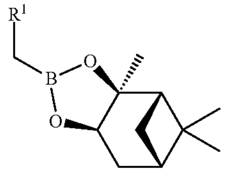

(C)

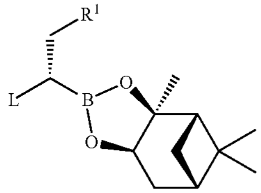

The compound of Formula (C) can, in turn, be reacted with an alkali amide (e.g., lithium bis(trimethylsilyl)amide, sodium bis(trimethylsilyl)amide, and potassium bis(trimethylsilyl)amide) or other nucleophile that effectively inverts the newly formed stereocenter (such as by an SN2 type mechanism) and introduces an amine group ($NR_2$) in place of the halo group (e.g., chloro), forming a compound of Formula (D) (where R can be, e.g., alkyl, $Si(alkyl)_3$, aryl, or aralkyl).

(D)

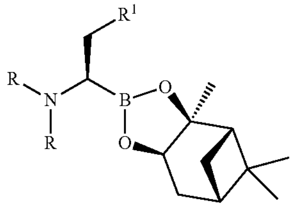

The compound of Formula (D) can be further reacted with an agent capable of converting the $NR_2$ group to $NH_2$, or salt thereof, to form an F1 fragment substantially capable of coupling with a further fragment through the amine. A suitable agent for converting the $NR_2$ group to $NH_2$ can be a protic acid such as HCl such as when R is a silyl group (e.g., trimethylsilyl).

The compound of Formula (B) can also be prepared according to a two step procedure involving reaction of a trialkoxyborane, preferably triisopropoxyborane, with (1S,2S,3R,5S)-(+) pinanediol, to give a mono-alkoxy[(1S,2S,3R,5S)-(+) pinanediol] borane intermediate wherein two of the alkoxy groups of the trialkoxy borane have been replaced by (1S,2S,3R,5S)-(+) pinanediol. This mixed pinanediol alkoxy borane, upon reaction with the appropriate organometallic derivative, e.g. the Grignard reagent $R^1CH_2MgBr$ or the alkyl lithium $R^1CH_2Li$, gives compound (B) in good yields and purities. The process starting from triisopropoxyborane to give the intermediate mixed pinanediol isopropoxy borane (F) and the compounds of formula (B) is depicted in the following scheme:

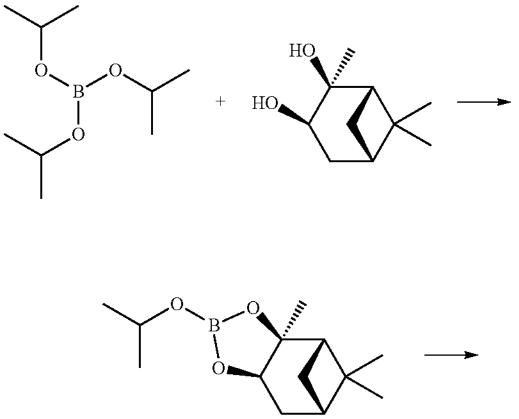

(F)

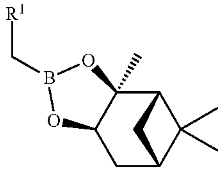

(B)

and exemplified in Example A.2, herein.

Accordingly, the present invention is further directed to methods of preparing compounds of Formula (II):

(II)

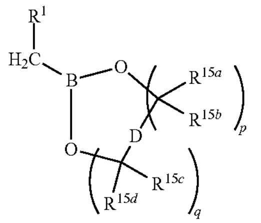

wherein the variable constituents are defined hereinabove, by the process of a) reacting a diol of Formula (II-b):

(II-b)

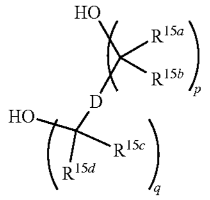

with an appropriate trialkoxyborane of Formula (II-a):

(II-a)

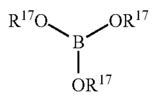

wherein each $R^{17}$ is, independently, $C_1$-$C_{10}$ alkyl or $C_3$-$C_{10}$ cycloalkyl; for a time and under conditions suitable for forming a mixed trialkoxyborane intermediate of Formula (II-c):

(II-c)

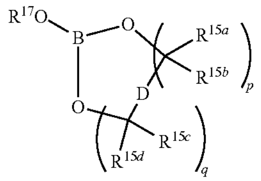

and reacting the intermediate of Formula (II-c) with either i) a reagent of formula $R^1CH_2MX^{hal}$, wherein M is a metal and $X^{hal}$ is a halogen atom, or ii) a reagent of formula $R^1CH_2Li$, for a time and under conditions suitable for forming the compound of Formula (II).

In some embodiments, $R^{17}$ is $C_1$-$C_4$ alkyl.

In some embodiments, $R^{17}$ is isopropyl.

In some embodiments, the diol of Formula (H-b) is pinanediol, pinacol, bicyclohexyl-1,1'-diol, 1,2-ethanediol, 1,3-propanediol, 1,2-propanediol, 2,3-butanediol, 1, 1,2,2-tetramethylethanediol, 1,2-diisopropylethanediol, 5,6-decanediol, 1,2-dicyclohexylethanediol, bicyclohexyl-1,1'-diol, diethanolamine, or 1,2-diphenyl-1,2-ethanediol.

In some embodiments, the diol of Formula (II-b) is pinanediol.

In some embodiments, the Formula $R^1CH_2MX^{hal}$ is a Grignard reagent.

In some embodiments, the Formula $R^1CH_2MX^{hal}$ is $R^1CH_2MgBr$.

In some embodiments, $R^1$ is isopropyl.

In some embodiments, the present invention provides a process for preparing a compound of Formula (II-i):

(II-i)

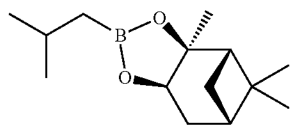

comprising:

a) reacting (1S,2S,3R,5S)-(+)-pinanediol with triisopropoxy borane for a time and under conditions suitable for forming an intermediate of Formula (II-ii):

(II-ii)

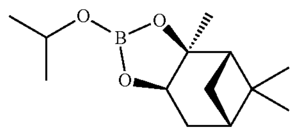

and b) reacting the intermediate of Formula (II-ii) with isobutyl magnesium bromide for a time and under conditions suitable for forming the compound of Formula (II-0.

In some embodiments, the present invention provides a compound of Formula (II-ii):

(II-ii)

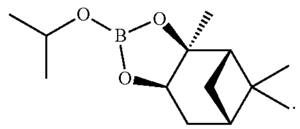

The reacting steps can be carried out in any suitable solvent that is non-reactive with the reagents and products and allows combining of reagents at lowered temperatures (e.g., temperatures colder than room temperature). Suitable solvents include ethers such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether. In some embodiments, the ether solvent contains tetrahydrofuran and/or diethyl ether.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.) and "reduced temperature" refers to temperatures below room temperature.

In some embodiments, suitable temperatures are reduced temperatures. The reaction of the trialkoxyborane and diol to prepare a mixed trialkoxyborane intermediate can be carried out, for example, at a temperature of about −20 to about 10° C. In some embodiments, the reaction of the trialkoxyborane and diol can be carried out at about 0° C. The reaction of the mixed trialkoxyborane intermediate with the organometallic reagent $R^1CH_2MX^{hal}$ or the alkyl lithium reagent $R^1CH_2Li$ can be carried out, for example, at temperature from about −100 to about −20° C. In some embodiments, the reaction of the mixed trialkoxyborane intermediate and $R^1CH_2MX^{hal}$ is carried out at about −78° C.

The reactions of the processes described herein can be carried out in air or under an inert atomosphere. Typically, reactions containing reagents or products that are substantially reactive with air can be carried out using air-sensitive synthetic techniques that are well known to the skilled artisan.

B. F2 Fragment

The mid-section of compounds of the present invention can be represented by fragment F2 which couples to fragment F1 by peptide bond formation for form an F2-F 1 intermediate. Methods for coupling compounds through peptide bonds, or amide bonds, are well known in the art and described, for example, in *The Peptides: Analysis, Synthesis, Biology*, Vol. I., eds. Gross, et al., Academic Press, 1979. An example F2 fragment is provided in Formula (E) (Pg is an amino protecting group, $R^2$ is defined herein). Additionally, protection of the amino group of aminoacids using Boc or other amino protecting groups is well known in the art.

(E)

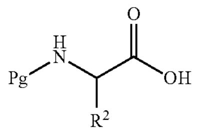

Compounds of Formula (E) that are aminoacids or amino acid derivatives are available commercially or prepared by routine methods. For example, aza-serines can be prepared generally by the Hoffman Rearrangement (Hoffman's Reaction) using, for example, asparagine where the amide of the asparagine side chain is converted to an amine (which can be subsequently protected). Methods for carrying out Hoffman Rearrangements, such as for aminoacids, are known in the art and also provided in the Examples below. Additionally aza-serines can be prepared as disclosed in Zhang, et al. *J. Org. Chem.*, 1997, 62, 6918-6920. Boc-cyanoarginine derivatives can be prepared as disclosed in Wagenaar et al., *J. Org. Chem.* 1993, 58, 4331-4338. Synthesis of F2 fragments wherein $R^2$ is $—CH_2CH_2CH_2NHC(=NR^4)NH—Y$, $—CH_2CONR^5R^6$, $—CH_2NHCONR^5R^6$, $—CH_2NR^9R^{10}$, or $—CH(R^7)ZR^8$ are further disclosed herein. F2 fragments can be obtained from commercial sources or made by methods known to one skilled in the art.

C. F3 Fragments

A further fragment (F3) can be coupled to the F2 fragment of the F2-F1 intermediate by any of various means such as by nucleophilic substitution or addition reactions where, for example, F2 contains a nucleophile (e.g., amine) and F3 contains an electrophile (e.g., CO, $SO_2$, and the like) and optionally a leaving group (e.g., halo, hydroxy, alkoxy, alkylsulfonyl, arylsulfonyl, and the like). Example F3 fragments can have the formula $R^XCOX^L$, $R^XSO_2X^L$, $R^XNCO$, or $R^XHCO$, (e.g., $R^X$ can be $R^A$, $R^B$, or $R^C$ as defined herein and $X^L$ can be a leaving group). Coupling of $R^XCOX^L$ (such as when $X^L$ is OH) to the F2-F1 intermediate can be carried out according to standard procedures for peptide bond formation to prepare compounds having the formula F3-F2-F1 where the F3 and F2 fragments are coupled via an amide bond. In other embodiments, F3 and F2 can be coupled by a sulfonylamino linkage prepared by reacting $R^XSO_2X^L$ with the F2-F1 intermediate in which an amino moiety on the F2-F1 intermediate displaces the $X^L$ leaving group of $R^XSO_2X^L$. Additionally, reaction of $R^XNCO$ with an amino moiety of the F2-F1 intermediate can result in a urea linkage (—HNCONH—), while reaction of $R^XHCO$ with an amino moiety of the F2-F1 intermediate followed by reduction of the resulting imine moiety can form an amine linkage. Other coupling means are known in the art and are also suitable. F3 fragments can be obtained from commercial sources or made by methods known in the art.

Certain compounds of the invention wherein $R^2$ is $—(CH_2)_dCH(R^7)NR^9R^{10}$ can be prepared by removal of an $R^{10}$ amino protecting group to form the corresponding deprotected compound wherein $R^{10}$ is H. This deprotected compound can be reacted with a reagent having the formula $R^{10a}X^L$, wherein $R^{10a}$ has the same meaning as $R^{10}$ with the exception of H and $X^L$ is a leaving group such as halo or a sulfonic acid derivative, or wherein $R^{10a}$ and $X^L$ taken together represent, for example, a reactive alkyl, carbocyclyl or heterocarbocyclyl isocyanate, or an alkyl, carbocyclyl, heterocarbocyclyl sulphonylisocyanate. For example, the compound of Example D.26 can be prepared by the deprotection of the benzyloxycarbonyl group of Example D.16.6 to give Example D.17, from which the azaserine nitrogen can be subsequently acylated.

The present invention further provides methods for preparing azaserine (e.g., where $R^2$ is $—CH_2NH_2$) compounds of Formula I. In general, the azaserine group can be generated by removal of a benzyloxycarbonyl group ($—C(=O)OCH_2(C_6H_5)$) which is attached to one of the nitrogens of the azaserine group (e.g., compounds of Formula I where $R^2$ is $—CH_2NR^9R^{10}$ and $R^9$ is H and $R^{10}$ is $—C(=O)OCH_2(C_6H_5)$). Removal of the benzyloxycarbonyl group can be carried out by treatment with a reducing agent, such as a hydrogenation reagent. In some embodiments, the hydrogenation reagent contains $H_2$ which is optionally used in the presence of a metal catalyst (e.g., Pd/C 10%). Hydrogenation can be further carried out in the presence of a protic acid such as HCl and in a suitable hydrogenation solvent containing, for example, an alcohol and/or an ether solvent. In some embodiments, the hydrogenation solvent contains an ether such as 1,4-dioxane. In further embodiments, the hydrogenation solvent contains an alcohol such as methanol. In further embodiments, the hydrogenation solvent contains a mixture of alcohol and ether. An example preparation of an azaserine compound according to this process is provided, for example, in Example D.17. Reaction parameters including temperature, pressure, atomosphere and the like are readily determined by one skilled in the art of chemical synthesis and reaction progress can be monitored by routine methods including, e.g., NMR.

Accordingly, the present invention provides a process for the preparation of compounds of Formula (I):

(I)

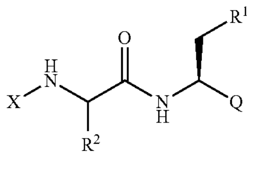

wherein:

$R^1$ is $C_1$-$C_6$ alkyl, $C_2$-$C_6$ alkenyl, $C_2$-$C_6$ alkynyl, or $C_3$-$C_7$ cycloalkyl;

$R^2$ is —$CH_2NH_2$;

Q is —$B(OR^{14})_2$, or a cyclic boronic ester wherein said cyclic boronic ester contains from 2 to 20 carbon atoms, and, optionally, a heteroatom which can be N, S, or O;

$R^{14}$ is $C_1$-$C_4$ alkyl, cycloalkyl, cycloalkylalkyl, aryl, or aralkyl;

X is $R^4C$(═O)—;

$R^4$ is $C_1$-$C_{20}$ alkyl optionally substituted with $R^{20}$;
$C_2$-$C_{20}$ alkenyl optionally substituted with $R^{20}$;
$C_2$-$C_{20}$ alkynyl optionally substituted with $R^{20}$;
carbocyclyl optionally substituted with 1-5 $R^{21}$; or
heterocarbocyclyl optionally substituted with 1-5 $R^{21}$;

$R^{20}$ is selected from the group consisting of:
—CN, halo, haloalkyl-, $C_1$-$C_4$ alkyl, $C_2$-$C_4$ alkenyl, $C_2$-$C_4$ alkynyl, —$CO_2H$, —C(═O)$CO_2H$, —C(═O)$NH_2$, —C(═O)H, —S(═O)$NH_2$, —S(═O)$_2NH_2$, —OH, —SH, —$NH_2$, —NH(alkyl), —N(alkyl)$_2$, —NHC(═O)$NH_2$, —NHC(═O)$R^{20a}$, NHC(═O)O$R^{20a}$, —O$R^{20a}$, —S$R^{20a}$, —S(═O)$R^{20a}$, —S(═O)$_2R^{20a}$, —S(═O)$_2$—NH$R^{20a}$, —SC(═O)$R^{20a}$, —C(═O)$R^{20a}$, —C(═O)NH$R^{20a}$, —C(═O)O$R^{20a}$, —NHS(═O)$_2$ $R^{20a}$, NH$R^{20b}$, phthalimido, —(O-alkyl)$_r$, —O-alkyl-OH, —(O-alkyl)$_r$-OH, —O$R^{20c}$, —S$R^{20c}$, —O-alkyl-$R^{20c}$, —S-alkyl-$R^{20c}$, —S(═O)—$R^{20c}$, —S(═O)$_2$—$R^{20c}$, —S(═O)$_2$—NH$R^{20c}$, —SC(═O)$R^{20c}$, —C(═O)O$R^{20c}$, —C(═O)O$R^{20c}$, C(═O)NH$R^{20c}$, carbocyclyl optionally substituted with 1-5 $R^{21}$; and
heterocarbocyclyl optionally substituted with 1-5 $R^{21}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —NH$R^{20b}$;

$R^{20b}$ is an amino protecting group;

$R^{20c}$ is carbocyclyl optionally substituted with 1-5 $R^{22}$; or heterocarbocyclyl optionally substituted with 1-5 $R^{22}$;

$R^{21}$ is selected from the group consisting of:
$C_1$-$C_{20}$ alkyl, $C_2$-$C_{20}$ alkenyl, $C_2$-$C_{20}$ alkynyl, $C_1$-$C_{20}$ alkoxy, $C_1$-$C_{20}$ thialkoxy, —OH —CN, halo, haloalkyl, —$NH_2$, —NH(alkyl), —N(alkyl)$_2$, —NHC(═O)O-alkyl, —NHC(═O)alkyl, —C(═O)O-alkyl, —C(═O)alkyl, —S(═O)-alkyl, —S(═O)$_2$-alkyl, —S(═O)-aryl, —S(═O)$_2$-aryl, carbocyclyl optionally substituted with 1-5 $R^{22}$, and
heterocarbocyclyl optionally substituted with 1-5 $R^{22}$;

$R^{22}$ is selected from the group consisting of:
$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, (alkyl-O)$_r$-alkyl, HO-(alkyl-O)$_r$-alkyl-, —OH, —SH, —CN, —$N_3$, —CNO, —CNS, alkyl-S(═O)—, alkyl-S(═O)$_2$—, $H_2NS$(═O)—, and $H_2NS$(═O)$_2$—; and r is 2, 3, 4, or 5;

comprising:

reacting a compound of Formula (I) wherein $R^2$ is —$CH_2NH$—C(═O)$OCH_2(C_6H_5)$; with a suitable hydrogenation reagent for a time and under conditions suitable for forming the compound of Formula (I) wherein $R^2$ is —$CH_2NH_2$, provided the hydrogenation agent is selective for the benzyloxycarbonyl group of $R^2$.

In some embodiments, the hydrogenation agent is $H_2$ in the presence of Pd/C 10% and HCl in 1,4-dioxane.

Boronic Ester/Boronic Acid Conversion

Compounds of the invention containing boronic esters, such as pinanediol esters, can be hydrolyzed by any suitable means to prepare corresponding boronic acid (—$B(OH)_2$) derivatives. Hydrolysis conditions can include contacting a boronic ester with excess acid, such as a protic acid like HCl.

Conversely, boronic acids can be esterified by contacting the acid compound (—$B(OH)_2$) with an alcohol such as a diol for sufficient time to produce the corresponding ester. The esterification reaction can be acid or base catalyzed.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example A.1

Synthesis of (1R)-1-[(3aS,4S,6S,7aR)-hexahydro-3a,5,5-trimethyl-4,6-methano-1,3,2-benzodioxaborol-2-yl]-3-methylbutylamine hydrochloride salt

Step 1: 2-(2-methylpropyl)-(3aS,4S,6S,7aR)-hexahydro-3a,5,5-trimethyl-4,6-methano-1,3,2-benzodioxaborole

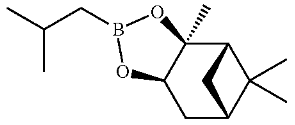 [SMILES: CC(C)CB1O[C@@H]2C[C@@H]3C[C@@H](C3(C)C)[C@]2(C)O1]

A mixture of (+)-pinanediol (23.9 g, 0.140 mol) and 2-methylpropylboronic acid (15 g, 0.147 mol) in diethyl ether (300 ml) was stirred at room temperature for 24 h. The mixture was dried over anhydrous sodium sulfate and purified by column chromatography (Silica gel 230-400 mesh), eluting with hexane:ethyl acetate 90:10 mixture. The product was obtained as a clear oil (32.6 g, 94% yield).

$^1$H NMR (DMSO-$d_6$): 4.28 (1H, dd, J=8.8 Hz, 2.0); 2.30 (1H, m); 2.18 (1H, m); 1.96 (1H, t, J=5.3); 1.86 (1H, m); 1.78 (1H, set, J=6.8); 1.68 (1H, m); 1.30 (3H, s); 1.25 (3H, s); 1.01 (1H, d); 0.9 (6H, d, J=6.6); 0.81 (3H, s); 0.69 (2H, m).

Step 2: 2-[(1S)-1-chloro-3-methylbutyl]-(3aS,4S,6S,7aR)-hexahydro-3a,5,5-trimethyl-4,6-methano-1,3,2-benzodioxaborole

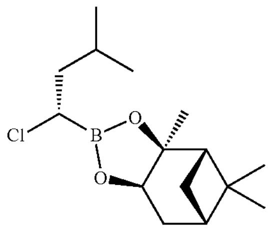 [SMILES: CC(C)C[C@@H](Cl)B1O[C@@H]2C[C@@H]3C[C@@H](C3(C)C)[C@]2(C)O1]

A solution of lithium diisopropylamide was prepared by addition of 10.0 M butyl lithium solution in hexane (25.4 ml, 0.254 mol) to a solution of diisopropylamine (35.7 ml, 0.254 mol) in dry tetrahydrofuran (60 ml), at −50° C., and allowing the temperature to rise to −30° C. This solution was transferred via canula into a solution of 2-(2-methylpropyl)-(3aS,4S,6S,7aR)-hexahydro-3a,5,5-trimethyl-4,6-methano-1,3,2-benzodioxaborole of Step 1 (50 g, 0.212 mol) and $CH_2Cl_2$ (50 ml, 0.848 mol) in dry tetrahydrofuran (700 ml), while keeping the temperature below −70° C. A 1.0 M solution of dry zinc chloride in diethyl ether (339 ml, 0.339 mol) was then added over a 30 minutes period while keeping the internal temperature below −70° C. The reaction mixture was stirred at −78° C. for 3 hours, then allowed to warm to room temperature. After removal of the solvents by rotary evaporation the residue was partitioned between petroleum ether (1000 ml) and a 10% aqueous solution of ammonium chloride (800 ml). The aqueous layer was further extracted with petroleum ether (300 ml). The combined organic phases were dried over anhydrous sodium sulfate and concentrated. The product was obtained as a brown oil (59.0 g, 98% yield) containing about 9% mol/mol of starting material ($^1$H-NMR), and was used in the subsequent step without further purification.

$^1$H NMR (DMSO-$d_6$): 4.43 (1H, dd, J=8.8, 1.8); 3.59 (1H, m); 2.33 (1H, m); 2.21 (1H, m); 2.01 (1H, m); 1.88 (1H, m); 1.84-1.55 (5H, m); 1.34 (3H, s); 1.26 (3H, s); 1.09 (1H, J=10.1); 0.9 (3H, d, J=6.8); 0.87 (3H, d, J=6.4); 0.82 (3H, s).

Step 3: N,N-Bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine

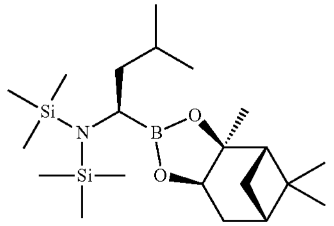

A 1.0 M solution of lithium bis(trimethylsilyl)amide in tetrahydrofuran (189 ml, 0.189 mol) was added, over 30 minutes, to a solution of crude 2-[(1S)-1-chloro-3-methylbutyl]-(3aS,4S,6S,7aR)-hexahydro-3a,5,5-trimethyl-4,6-methano-1,3,2-benzodioxaborole of Step 2 (59.0 g, 91% purity, 0.189 mol) in tetrahydrofuran (580 ml) while cooling at −78° C. The reaction mixture was allowed to slowly warm to room temperature overnight. The solvent was removed by rotary evaporation and the residue taken up with dry hexane (800 ml). The resulting suspension was stirred at room temperature for 2 hours, then the solid was removed by filtration on a celite cake, which was washed with dry hexane (3×100 ml). The filtrate was concentrated giving a satisfactorily pure product as a brown oil (79 g) in practically quantitative yield. The product was used for the subsequent step without further purification.

$^1$H NMR (DMSO-$d_6$): 4.33 (1H, dd, J=1.5 Hz, 8.6); 2.58 (1H, m); 2.29 (1H, m); 2.18 (1H, m); 1.95 (1H, t, J=5.9); 1.85 (1H, m); 1.9-1.55 (3H, m); 1.31 (3H, s); 1.24 (3H, s); 1.17 (1H, m); 1.01 (1H, d, J=10.6); 0.85 (3H, d, J=6.6), 0.83 (3H, d, J=6.6); 0.80 (3H, s); 0.08 (18H, s).

Step 4: (1R)-1-[(3aS,4S,6S,7aR)-hexahydro-3a,5,5-trimethyl-4,6-methano-1,3,2-benzodioxaborol-2-yl]-3-methylbutylamine hydrochloride salt

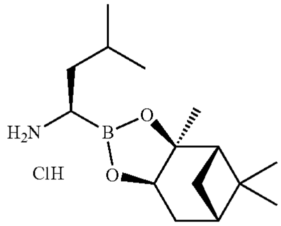 [SMILES: CC(C)C[C@H](N)B1O[C@@H]2C[C@@H]3C[C@@H](C3(C)C)[C@]2(C)O1 ; Cl]

To a solution of crude N,N-Bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine of Step 3 (79 g, 0.193 mol) in a mixture of dioxane (100 ml) and diethyl ether (200 ml), a 4 N solution of hydrogen chloride in dioxane (193 ml, 0.772 mol) was added, while cooling at 0° C. The mixture was then stirred at room temperature for 4 hours and concentrated. The residue was taken up with anhydrous hexane (500 ml) and a 2 M solution of hydrogen chloride in diethyl ether (48 ml, 0.096 mol) was added. The mixture was stirred at 0° C. for 1 hour, then concentrated. The residue was taken up with anhydrous hexane and the resulting suspension was stirred at room temperature overnight. The solid was collected by filtration and dried under vacuum affording 38.1 g of product (66% yield). A second crop (4.13 g, 7% yield) was obtained from the mother liquors.

$^1$H NMR (DMSO-$d_6$): 7.85 (3H, br); 4.45 (1H, dd, J=9.2 Hz); 2.78 (1H, m); 2.34 (1H, m); 2.21 (1H, m); 2.01 (1H, t, J=5.3); 1.89 (1H, m); 1.82-1.65 (2H, m); 1.49 (1H, m); 1.38 (3H, s); 1.27 (3H, s); 1.12 (1H, d, J=1.12); 0.87 (6H, d, J=6.6); 0.83 (3H, s).

Example A.2

Alternate synthesis of 2-(2-methylpropyl)-(3aS,4S,6S,7aR)-hexahydro-3a,5,5-trimethyl-4,6-methano-1,3,2-benzodioxaborole Step 1: 2-(1-methylethoxy)-(3aS,4S,6S,7aR)-hexahydro-3a,5,5-trimethyl-4,6-methano-1,3,2-benzodioxaborole

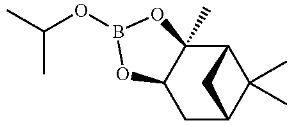 [SMILES: CC(C)OB1O[C@@H]2C[C@@H]3C[C@@H](C3(C)C)[C@]2(C)O1]

To a solution of (1S,2S,3R,5S)-(+)-Pinanediol (50.0 g, 0.293 mol) in anhydrous tetrahydrofuran (350 ml) triisopropoxy borane was slowly added while stirring at 0° C. under nitrogen. After 2 h the solvent was removed by rotary evaporation. The oily residue was redissolved in hexane (150 ml) and the solution was filtered to remove a very small amount of a white solid. The filtrate was concentrated by rotary evaporation affording the product as a clear oil (62.6 g, 90% yield).

$^1$H NMR (DMSO-$d_6$): 4.31-4.20 (2H, m); 2.34-2.16 (2H, m); 1.96 (1H, t, J=5.5); 1.90-1.85 (1H, m); 1.74-1.67 (1H, m); 1.32 (3H, s); 1.31 (1H, d, J=7.6); 1.25 (3H, s); 1.14 (3H, d, J=6.1); 1.13 (3H, d, J=6.1); 0.81 (3H, s).

Step 2: 2-(2-methylpropyl)-(3aS,4S,6S,7aR)-hexahydro-3a,5,5-trimethyl-4,6-methano-1,3,2-benzodioxaborole

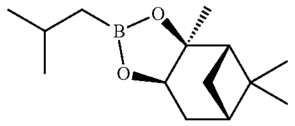 [SMILES: CC(C)CB1O[C@@H]2C[C@@H]3C[C@@H](C3(C)C)[C@]2(C)O1]

A 2M solution of isobutyl magnesium bromide in diethyl ether (131.5 ml, 0.263 mol) was added dropwise, in 1 hour, to a solution of 2-(1-methylethoxy)-(3aS,4S,6S,7aR)-hexahydro-3a,5,5-trimethyl-4,6-methano-1,3,2-benzodioxaborole obtained in Step 1 (62.6 g, 0.263 mol), in anhydrous tetrahydrofuran (330 ml) while stirring at −78° C., under nitrogen. The mixture was then allowed to warm to room temperature, then transferred in a mixture of 2N sulfuric acid (150 ml) and diisopropyl ether (250 ml). After stirring for 10 minutes, a saturated solution of NaCl was added (100 ml) and the layers were separated. The organic phase was washed with brine (100 ml), dried over sodium sulfate and concentrated. The residue was purified by column chromatography (silica gel) eluting with 5% diethyl ether in hexane. The product was obtained as a clear oil (38.45 g, 62% yield).

Example B.1

Carbamic acid 1,1-dimethylethyl ester, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]

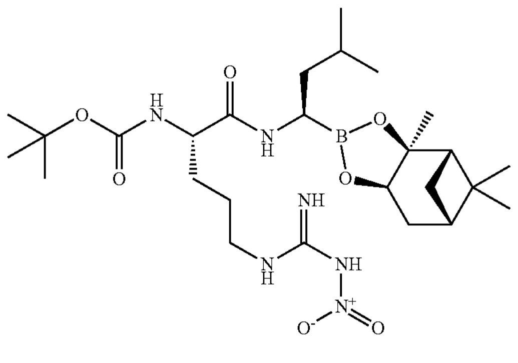 [SMILES: CC(C)C[C@H](NC(=O)[C@H](CCCNC(=N)N[N+](=O)[O-])NC(=O)OC(C)(C)C)B1O[C@@H]2C[C@@H]3C[C@@H](C3(C)C)[C@]2(C)O1]

Method A: HOAt/HATU

To a solution of BocNH($NO_2$)ArgOH (15.7 g, 49.3 mmol) in anhydrous DMF (100 ml), HATU (O-(7-azabenzotriazol-1-yl)-1, 1,3,3-tetramethyluronium hexafluorophosphate; 18.7 g, 49.3 mmol) and HOAt (1-hydroxy-7-azabenzotriazole; 6.71 g, 49.3 mmol) were added. The mixture was cooled to 0° C. and N-methylmorpholine was added (13.6 ml, 0.123 mol). After 10 minutes (1R)-1-[(3aS,4S,6S,7aR)-hexahydro-3a,5,5-trimethyl-4,6-methano-1,3,2-benzodioxaborol-2-yl]-3-methylbutylamine hydrochloride salt of Example A.1 (12.4 g, 41.1 mmol) was added. The cooling bath was removed and the mixture was stirred at r.t. for 4.5 hours. The mixture was diluted with ethyl acetate (800 ml), washed with a 2% solution of citric acid (2×150 ml), 2% solution of $NaHCO_3$ (2×150 ml) and 2% solution of NaCl (2×150 ml). The aqueous phases were further extracted with ethyl acetate (150 ml). The combined organic phases were dried over sodium sulfate and concentrated. The resulting oily residue was redissolved in ethyl acetate (500 ml) and the solution was washed with cold water (200 ml). The aqueous phases were further extracted with ethyl acetate (500 ml). The combined organic phases were dried over sodium sulfate and concentrated. The residue was dissolved in diethyl ether (100 ml) an the solution was slowly added to hexane (600 ml) while stirring. The white solid was collected by filtration (43.4 g) and purified by column chromatography eluting initially with 50:50 hexane: ethyl acetate mixture and then with ethyl acetate. The fractions containing the product were concentrated, the residue was dissolved in diethyl ether (100 ml) and the resulting solution was slowly added to hexane (600 ml) while stirring. The white solid was collected by filtration (15.2 g, 66% yield).

Method B: IBCF

To a suspension of BocNH($NO_2$)ArgOH (5.82 g, 18.2 mmol) in anhydrous dichloromethane (100 ml) N-methylmorpholine (2.0 ml, 18.2 mmol) was added. The mixture was cooled to −15° C. then isobutyl chloroformate was added (2.37 ml, 18.2 mmol). The mixture was stirred at −15° C. for 10 minutes then (1R)-1-[(3aS,4S,6S,7aR)-hexahydro-3a,5,5-trimethyl-4,6-methano-1,3,2-benzodioxaborol-2-yl]-3-methylbutylamine hydrochloride salt obtained as in Example A.1 was added (5.0 g, 16.6 mmol), immediately followed by further N-methylmorpholine (2.0 ml, 18.2 mmol). The reaction mixture was stirred for 1.5 hours at −15° C., then allowed to warm to room temperature and partitioned between ethyl acetate (150 ml), water (150 ml) and 0.1N hydrochloric acid (10 ml). The organic phase was washed with a saturated solution of $NaHCO_3$, dried over anhydrous sodium sulphate and concentrated. The oily residue (9.25 g) was purified by crystallization from ethyl acetate affording three crops of satisfactorily pure product (5.03 g, 54% yield).

$^1$H NMR (DMSO-$d_6$): 8.80 (1H, br); 8.50 (1H, br), 7.87 (2H, br); 7.01 (1H, d, J=7.9), 4.07 (1H, dd, J=7.9); 4.0 (1H, m); 3.12 (2H, m); 2.55 (1H, m); 2.2 (1H, m); 2.01 (1H, m); 1.83 (1H, t, J=5.1); 1.78 (1H, m); 1.74-1.44 (7H, m); 1.38 (9H, s); 1.33 (1H, d, J=10.3); 1.24 (5H, s); 1.22 (3H, s); 0.84 (6H, d, J=6.6); 0.81 (3H, s)

Example B.2

Carbamic acid 1,1-dimethylethyl ester, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]-

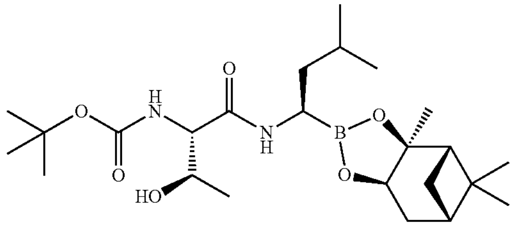 [SMILES: CC(C)C[C@H](NC(=O)[C@@H](NC(=O)OC(C)(C)C)[C@@H](C)O)B1O[C@@H]2C[C@@H]3C[C@@H](C3(C)C)[C@]2(C)O1]

Boc-L-threonine (870 mg, 3.97 mmol, 1.2 eq.) was dissolved in DMF dry (30 ml) at r.t. To this solution, TBTU (N,N,N',N'-tetramethyl-O-(benzotriazol-1-yl)uronium tetrafluoroborate; 1270 mg, 3.97 mmol, 1.2 eq.) was added and the mixture was cooled at 0°-5° C. Then NMM (0.9 ml, 8.27 mmol, 2.5 eq.) and (1R)-1-[(3aS,4S,6S,7aR)-hexahydro-3a, 5,5-trimethyl-4,6-methano-1,3,2-benzodioxaborol-2-yl]-3-methylbutylamine hydrochloride salt of Example A.1 (1000 mg, 3.3 mmol, 1 eq.) were added. The mixture was stirred at r.t. for 16 h, then was extracted with ethyl acetate (100 ml) washed with the following solutions: citric acid 2% (50 ml), sodium bicarbonate 2% (50 ml), NaCl 2% (50 ml). The organic solution was dried over sodium sulphate anhydrous, filtered and evaporated under reduced pressure to give 1290 mg of glassy solid. Yield 84.3%.

M.p. 25°-30° C.

$^1$H NMR (DMSO-$d_6$): 8.88 (1H, br); 6.49 (1H, d, J=8.4 Hz); 4.88 (1H, d, J=5.8); 4.05 (1H, dd); 3.93 (1H, m); (1H, m); 2.51 (1H, m); 2.19 (1H, m); 2.01 (1H, m); 1.83 (1H, t, J=5.9), 1.78 (1H, m); 1.68 (1H, m); 1.62 (1H, m); 1.39 (9H, s); 1.34 (1H, d, J=10.0); 1.24 (3H, s); 1.22 (3H, s); 1.06 (3H, d, J=6.4); 0.85 (6H, d, J=6.4); 0.80 (3H, s)

Example B.3

Further Intermediate Compounds

Starting from the appropriate intermediate and following either of the procedures described in the Example B.1 and B.2, the intermediates reported below were prepared.

(2S)-2-[(1,1-dimethylethoxycarbonyl)amino]-5-ureidopentanamide, N-[(1R)-1-[(3aS,4S,6S,7aR)-hexahydro-3a,5,5-trimethyl-4,6-methano-1,3,2-benzodioxaborol-2-yl]-3-methylbutyl]

Chiral

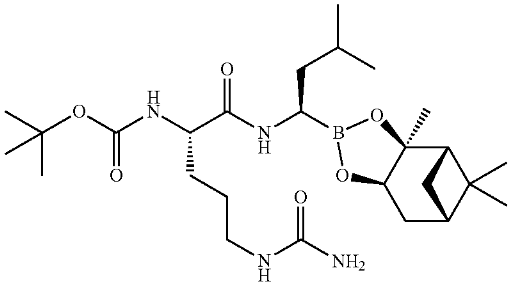

$^1$H NMR (DMSO-$d_6$): 8.85 (1H, br); 7.01 (1H, d, J=8.0 Hz); 5.9 (1H, t, J=5.7); 5.36 (2H, br); 4.03 (2H, m); 2.93 (2H, m); 2.19 (1H, m); 2.0 (1H, m); 1.83 (1H, t, J=5.3); 1.78 (1H, m); 1.68 (1H, m); 1.62 (1H, m); 1.52 (2H, m); 1.38 (9H, s); 1.33 (1H, d, J=9.9); 1.24 (3H, s); 1.22 (2H, s); 0.86 (3H, d, J=6.6); 0.84 (3H, d, J=6.6); 0.80 (3H, s).

(2S)-3-(Aminocarbonyl)-2-[(1,1-dimethylethoxycarbonyl)amino]propanamide, N-[(1R)-1-[(3aS,4S,6S,7aR)-hexahydro-3a, 5,5-trimethyl-4,6-methano-1,3,2-benzodioxaborol-2-yl]-3-methylbutyl]

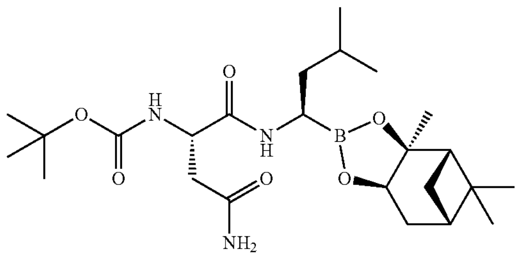 [SMILES: CC(C)C[C@H](NC(=O)[C@H](CC(N)=O)NC(=O)OC(C)(C)C)B1O[C@@H]2C[C@@H]3C[C@@H](C3(C)C)[C@]2(C)O1]

$^1$H NMR (DMSO-$d_6$): 8.74 (1H, br); 7.28 (1H, br); 6.95 (2H, m); 4.36 (1H, m); 4.07 (1H, m); 2.55 (1H, m); 2.38 (2H, m); 2.2 (1H, m); 2.02 (2H, m); 1.84 (1H, t, J=5.5); (1H, m); 1.79 (1H, m); 1.68 (1H, m); 1.63 (1H, m); 1.38 (9H, s); 1.33 (1H, d, J=10); 1.24 (3H, s); 1.22 (2H, s); 0.85 (3H, d, J=6.4); 0.83 (3H, d, J=6.4); 0.81 (3H, s).

Carbamic acid benzyl ester, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]

Chiral

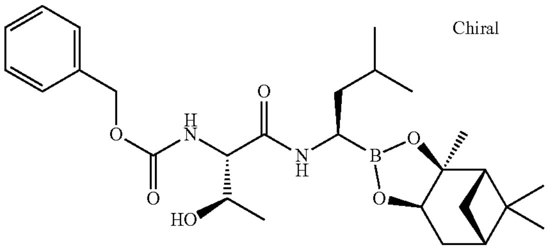 [SMILES: CC(C)C[C@H](NC(=O)[C@@H](NC(=O)OCc1ccccc1)[C@@H](C)O)B1O[C@@H]2C[C@@H]3C[C@@H](C3(C)C)[C@]2(C)O1]

M.p. 57-60° C. $^1$H NMR (DMSO-d6): 8.66 (1H, s); 7.40-7.29 (5H, m); 7.09 (1H, d, J=8.75); 5.06 (2H, s); 4.90 (1H, J=5.68); 4.11-3.99 (2H, m); 3.91-3.77 (1H, m); 2.58-2.53 (1H, m); 2.26-2.14 (1H, m); 2.07-1.97 (1H, s); 1.84 (1H, t, J=5.52); 1.81-1.75 (1H, m); 1.73-1.58 (2H, m); 1.33 (2H, d, J=10.1); 1.27-1.20 (7H, m); 1.06 (3H, t, J=6.27); 0.91-0.79 (9H, m).

Example B.4

(2S)-2-[(1,1-Dimethylethoxycarbonyl)amino]-3-[(4-methylbenzoyl)amino]propanamide, N-[(1R)-1-[(3aS,4S,6S,7aR)-hexahydro-3a,5,5-trimethyl-4,6-methano-1,3,2-benzodioxaborol-2-yl]-3-methylbutyl]-

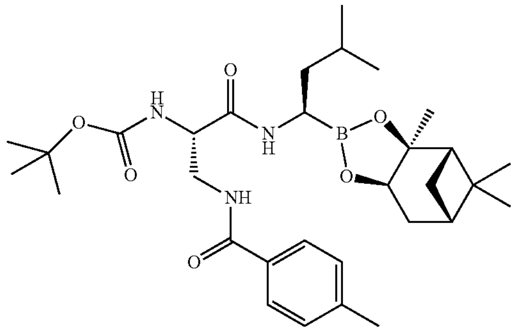 [SMILES: Cc1ccc(C(=O)NC[C@H](NC(=O)OC(C)(C)C)C(=O)N[C@@H](CC(C)C)B2O[C@@H]3C[C@@H]4C[C@@H](C4(C)C)[C@]3(C)O2)cc1]

(2S)-2-[(1,1-Dimethylethoxycarbonyl)amino]-3-[(4-methylbenzoyl)amino]-propanoic acid, (650 mg, 2 mmol, 1.2 eq.) of Example G.6, was dissolved in DMF dry (15 ml), under nitrogen, and TBTU (640 mg, 2 mmol, 1.2 eq.) was added at r.t. The mixture was cooled at 0°-5° C. with ice bath and NMM (0.55 ml, 5 mmol, 2.5 eq.) and (1R)-1-[(3aS,4S,6S,7aR)-hexahydro-3a,5,5-trimethyl-4,6-methano-1,3,2-benzodioxaborol-2-yl]-3-methylbutylamine hydrochloride salt, (500 mg, 1.65 mmol, 1 eq.) of Example A.1, were added. The mixture was stirred overnight, poured in water (200 ml) and extracted with ethyl acetate (100 ml). The organic layer was washed with the following solutions: citric acid 2% (20 mL), sodium bicarbonate 2% (20 ml), NaCl 2% (20 ml). The organic solution was dried over sodium sulphate anhydrous, filtered and evaporated to give 740 mg of glassy solid (quantitative yield).

$^1$H NMR (DMSO-$d_6$) 8.76 (1H, br); 8.28 (1H, t, J=5.31 Hz); 7.71 (2H, d, J=7.9); 7.26 (2H, d, J=7.9); 6.97 (1H, d, J=8.0); 4.27 (1H, m); 4.07 (1H, dd, J=8.2, 1.5); 3.48 (2H, m), 2.58 (1H, m); 2.35 (3H, s); 2.19 (1H, m); 2.02 (1H, m); 1.83 (1H, t, J=4.9); 1.78 (1H, m); 1.62 (2H, m); 1.35 (12H, m); 1.24 (3H, s); 1.23 (3H, s); 0.82 (3H, d); 0.80 (3H, d); 0.78 (3H, s).

Example B.5

2-S-[(1,1-Dimethylethoxycarbonyl)amino]-3-(hexanoylamino)-propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

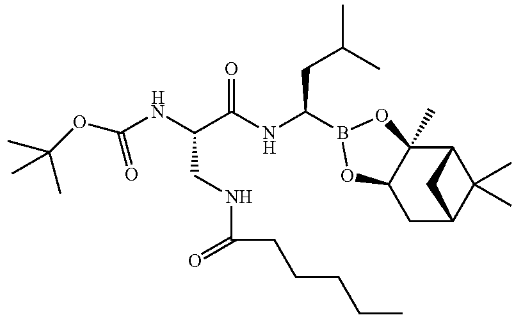 [SMILES: CCCCCC(=O)NC[C@H](NC(=O)OC(C)(C)C)C(=O)N[C@@H](CC(C)C)B1O[C@@H]2C[C@@H]3C[C@@H](C3(C)C)[C@]2(C)O1]

2-S-[(1,1-dimethylethoxycarbonyl)amino]-3-(hexanoylamino)propionic acid, (300 mg, 1 mmol, 1.2 eq.) of Example G.7 was dissolved in DMF dry (25 ml), under nitrogen, and TBTU (318 mg, 1 mmol, 1.2 eq.) was added at r.t. The mixture was cooled at 0°-5° C. with ice bath and NMM (0.27 ml, 2.47 mmol, 2.47 eq.) and (1R)-1-[(3aS,4S,6S,7aR)-hexahydro-3a,5,5-trimethyl-4,6-methano-1,3,2-benzodioxaborol-2-yl]-3-methylbutylamine hydrochloride salt, (250 mg, 0.82 mmol, 1 eq.) of Example A.1, were added. The mixture was stirred 3 h, poured in water (150 ml) and extracted with ethyl acetate (100 ml). The organic layer was washed with the following solutions: citric acid 2% (50 mL), sodium bicarbonate 2% (50 ml), NaCl 2% (50 ml). The organic solution was dried over sodium sulphate anhydrous, filtered and evaporated to give 450 mg of glassy solid. Yield quantitative.

Analytical data:

$^1$H NMR (DMSO-$d_6$).

$\delta_H$: 8.71 (1H, br d, J=2.6 Hz); 7.73 (1H, br t, J=5.9 Hz); 6.81 (1H, d, J=8.2); 4.10 (2H, m); 3.24 (2H, m); 2.56 (1H, m); 2.19 (1H, m); 2.03 (3H, m); 1.83 (1H, t, J=5.5); 1.78 (1H, m); 1.64 (2H, m); 1.47 (2H, m); 1.36 (9H, s); 1.4-1.15 (9H, m); 1.24 (3H, s); 1.21 (3H); 0.83 (9H, m); 0.79 (3H, s)

Example B.6

2-S-[(1,1-Dimethylethoxycarbonyl)amino]-3-(4-fluorosulfonylamino)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

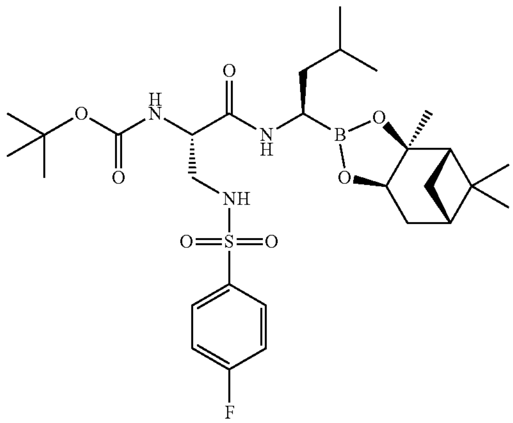 [SMILES: CC(C)C[C@H](NC(=O)[C@H](CNS(=O)(=O)c1ccc(F)cc1)NC(=O)OC(C)(C)C)B1O[C@@H]2C[C@@H]3C[C@@H](C3(C)C)[C@]2(C)O1]

2-S-[(1,1-dimethylethoxycarbonyl)amino]-3-(4-fluorosulfonylamino)propionic acid, (1.39 g, 3.83 mmol, 1.2 eq.) of Example G.8, was dissolved in DMF dry (20 ml), under nitrogen, and TBTU (1.23 g, 3.83 mmol, 1.2 eq.) was added at r.t. The mixture was cooled at 0°-5° C. with ice bath and NMM (1 ml, 9.57 mmol, 3 eq.) and (1R)-1-[(3aS,4S,6S,7aR)-hexahydro-3a,5,5-trimethyl-4,6-methano-1,3,2-benzodioxaborol-2-yl]-3-methylbutylamine hydrochloride salt, (0.96 g, 3.19 mmol, 1 eq.) of Example A.1, were added. The mixture was stirred 2 h, poured in water (200 ml) and extracted with ethyl acetate (100 ml). The organic layer was washed with the following solutions: citric acid 2% (50 mL), sodium bicarbonate 2% (50 ml), NaCl 2% (50 ml). The organic solution was dried over sodium sulphate anhydrous, filtered and evaporated with diethyl ether to give 1.5 g of white solid. Yield 77%.

Analytical data:

$^1$H NMR (DMSO-$d_6$).

$\delta_H$, 8.54 (1H, d, J=2.9 Hz); 7.91 (2H, m); 7.75 (1H, t, J=5.9); 7.50 (2H, t, J=8.8); 6.83 (1H, d, J=8.4); 4.19 (1H, br d, J=8.2); 4.14 (1H, m); 3.01 (2H, m); 2.69 (1H, m); 2.25 (1H, m); 2.09 (1H, m); 1.90 (1H, t, J=5.7); 1.85 (1H, m); 1.8-1.6 (2H, m); 1.5-1.2 (5H, m); 1.43 (9H, s); 1.29 (6H, s); 0.89 (6H, d, J=6.4); 0.86 (3H, s).

Example B.7

2-S-[(1,1-Dimethylethoxycarbonyl)amino]-3-(3,4-dimethoxyphenylacetamido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

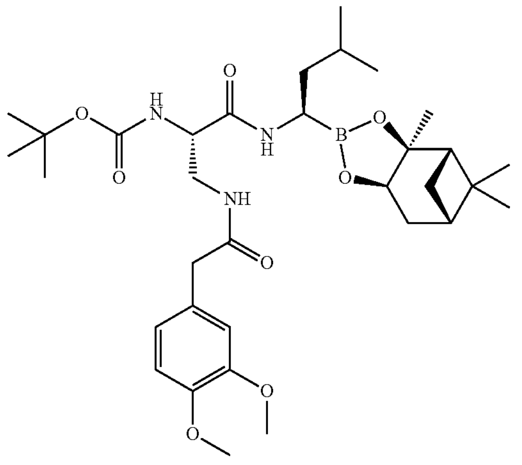 [SMILES: COc1ccc(CC(=O)NC[C@H](NC(=O)OC(C)(C)C)C(=O)N[C@@H](CC(C)C)B2O[C@@H]3C[C@@H]4C[C@@H](C4(C)C)[C@]3(C)O2)cc1OC]

2-S-[(1,1-dimethylethoxycarbonyl)amino]-3-(3,4-dimethoxyphenylacetamido)-propionic acid, (0.73 g, 1.90 mmol, 1.2 eq.) of Example G.9, was dissolved in DMF dry (20 ml), under nitrogen, and TBTU (0.61 g, 1.90 mmol, 1.2 eq.) was added at r.t. The mixture was cooled at 0°-5° C. with ice bath and NMM (0.52 ml, 4.7 mmol, 2.5 eq.) and (1R)-1-[(3aS,4S,6S,7aR)-hexahydro-3a,5,5-trimethyl-4,6-methano-1,3,2-benzodioxaborol-2-yl]-3-methylbutylamine hydrochloride salt, (0.47 g, 1.6 mmol, 1 eq.) of Example A.1, were added. The mixture was stirred 2 h, poured in water (200 ml) and extracted with ethyl acetate (100 ml). The organic layer was washed with the following solutions: citric acid 2% (50 mL), sodium bicarbonate 2% (50 ml), NaCl 2% (50 ml). The organic solution was dried over sodium sulphate anhydrous, filtered and evaporated with diethyl ether to give 0.95 g of crude that was purified by silica gel chromatography (eluent ethyl acetate) to give 0.3 g of white foam. Yield 30%.

Analytical data: TLC silica gel (eluent ethyl acetate 100%, R.f.=0.50)

$^1$H NMR (DMSO-$d_6$).

$\delta_H$, 8.69 (1H, d, J=2.6 Hz); 7.90 (1H, t, J=5.7); 6.85 (2H, m); 6.74 (1H, dd, J=1.5, 8.1); 6.85 (3H, m); 4.12 (2H, m); 3.73 (3H, s); 3.72 (3H, s); 3.34 (2H, s); 3.31 (2H, m); 2.58 (1H, m); 2.20 (1H, m); 2.03 (1H, m); 1.85 (1H, t, J=5.3); 1.79 (1H, m); 1.66 (2H, m); 1.38 (9H, s); 1.40-1.15 (3H, m); 1.25 (3H, s); 1.23 (3H, s); 0.83 (6H, d, J=6.6); 0.81 (3H, s).

Example B.8

2-S-[(1,1-Dimethylethoxycarbonyl)amino]-3-(3-phenylureido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

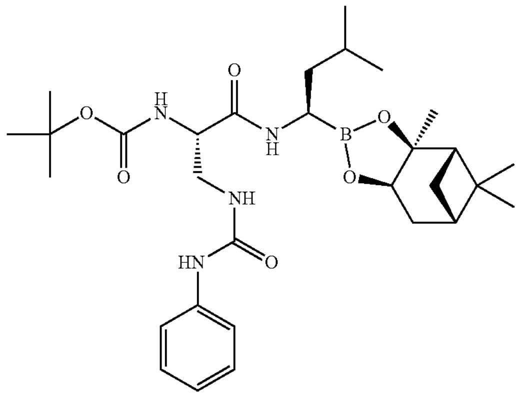 [SMILES: CC(C)C[C@H](NC(=O)[C@H](CNC(=O)Nc1ccccc1)NC(=O)OC(C)(C)C)B1O[C@@H]2C[C@@H]3C[C@@H](C3(C)C)[C@]2(C)O1]

2-S-[(1,1-dimethylethoxycarbonyl)amino]-3-(3-phenylureido)propionic acid, (0.41 g, 1.26 mmol, 1.2 eq.) of Example G.10, was dissolved in DMF dry (20 ml), under nitrogen, and TBTU (0.40 g, 1.26 mmol, 1.2 eq.) was added at r.t. The mixture was cooled at 0°-5° C. with ice bath and NMM (0.346 ml, 3.15 mmol, 2.5 eq.) and (1R)-1-[(3aS,4S,6S,7aR)-hexahydro-3a,5,5-trimethyl-4,6-methano-1,3,2-benzodioxaborol-2-yl]-3-methylbutylamine hydrochloride salt, (0.31 g, 1 mmol, 1 eq.) of Example A.1, were added. The mixture was stirred 2 h, poured in water (200 ml) and extracted with ethyl acetate (100 ml). The organic layer was washed with the following solutions: citric acid 2% (50 mL), sodium bicarbonate 2% (50 ml), NaCl 2% (50 ml). The organic solution was dried over sodium sulphate anhydrous, filtered and evaporated with diethyl ether (50 ml) to give 0.58 g of white solid. Yield 96.6%.

Analytical data: TLC silica gel (eluent ethyl acetate 100%, R.f.=0.47), m.p. 128°-130° C.

$^1$H NMR (DMSO-$d_6$).

$\delta_H$: 8.79 (1H, d, J=2.7 Hz); 8.69 (1H, s); 7.38 (2H, d, J=7.9); 7.22 (2H, t, J=8.1); 7.00 (1H, d, J=8.1); 6.90 (1H, t, J=7.3); 6.16 (1H, t, J=5.7); 4.12 (2H, m); 3.45 (1H, m); 3.17 (1H, m); 2.60 (1H, m); 2.21 (1H, m); 2.04 (1H, m); 1.85 (1H, t, J=5.3); 1.79 (1H, m); 1.66 (2H, m); 1.38 (9H, s); 1.40-1.15 (3H, m); 1.26 (3H, s); 1.23 (3H, s); 0.84 (6H, d, J=6.6); 0.81 (3H, s).

Example B.9

Synthesis of Further Compounds

Following the procedures of Examples B.4-B.8, the following compounds can be prepared by reaction of (1R)-1-[(3aS,4S,6S,7aR)-hexahydro-3a,5,5-trimethyl-4,6-methano-1,3,2-benzodioxaborol-2-yl]-3-methylbutylamine hydrochloride salt of Example A.1 and intermediates of Examples G.11, G.12 and G.13.

B.9.1 2-S-[(1,1-dimethylethoxycarbonyl)amino]-3-(acetamido-)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl].

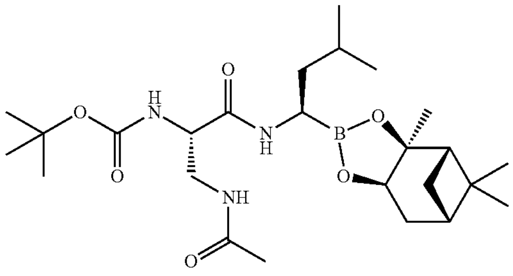 [SMILES: CC(=O)NC[C@H](NC(=O)OC(C)(C)C)C(=O)N[C@@H](CC(C)C)B1O[C@@H]2C[C@@H]3C[C@@H](C3(C)C)[C@]2(C)O1]

B.9.2 2-S-[(1,1-dimethylethoxycarbonyl)amino]-3-(9-fluorenylmethyloxycarbamoyl)ethyl]-propionamide,N-[(1S)-1-[[(1R)-1-R3aS,4S,6S,7aR)-hexahydro-3a,5,5-trimethyl-4,6-methano-1,3,2-benzodioxaborol-2-yl]-3-methylbutyl]amino]carbonyl].

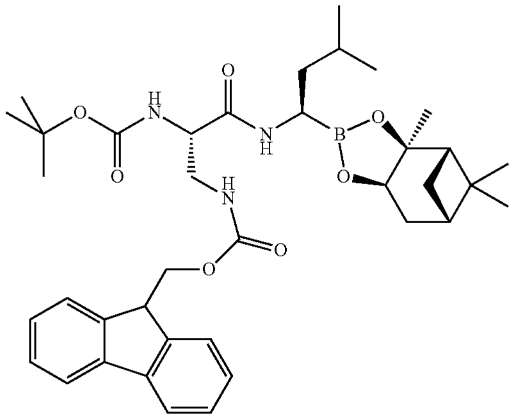

B.9.3 2-S-[(1,1-dimethylethoxycarbonyl)amino]-2-[(pentylureido)ethyl]-N-(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-

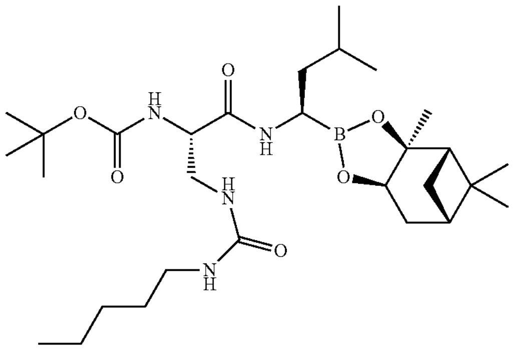 [SMILES: CCCCCNC(=O)NC[C@H](NC(=O)OC(C)(C)C)C(=O)N[C@@H](CC(C)C)B1O[C@@H]2C[C@@H]3C[C@@H](C3(C)C)[C@]2(C)O1]

B.9.4 2-S-[(1,1-dimethylethoxycarbonyl)amino]-2-(methanesolfonamido)ethyl]-N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-

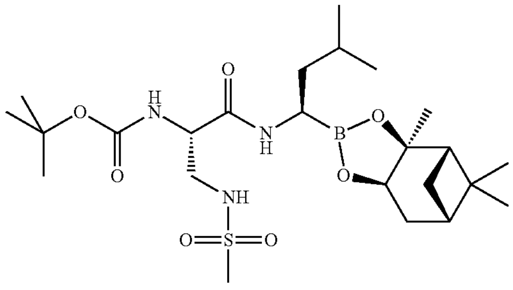 [SMILES: CC(C)C[C@H](NC(=O)[C@H](CNS(C)(=O)=O)NC(=O)OC(C)(C)C)B1O[C@@H]2C[C@@H]3C[C@@H](C3(C)C)[C@]2(C)O1]

-continued

B.9.5 2-S-[(1,1-dimethylethoxycarbonyl)amino]-2-[(ethoxcarbonylsuccinyl]-amide)ethyl]-N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-

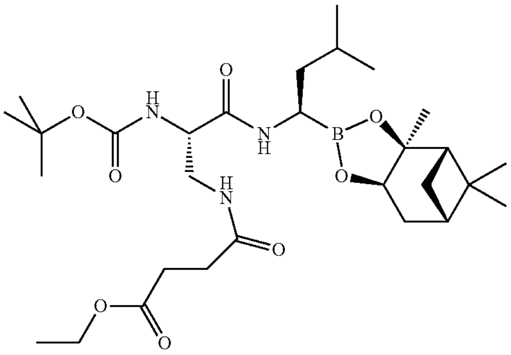 [SMILES: CCOC(=O)CCC(=O)NC[C@H](NC(=O)OC(C)(C)C)C(=O)N[C@@H](CC(C)C)B1O[C@@H]2C[C@@H]3C[C@@H](C3(C)C)[C@]2(C)O1]

B.9.6 2-S-[(1,1-dimethylethoxycarbonyl)amino]-3-(benzyloxycarbamoyl)ethyl]-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl].

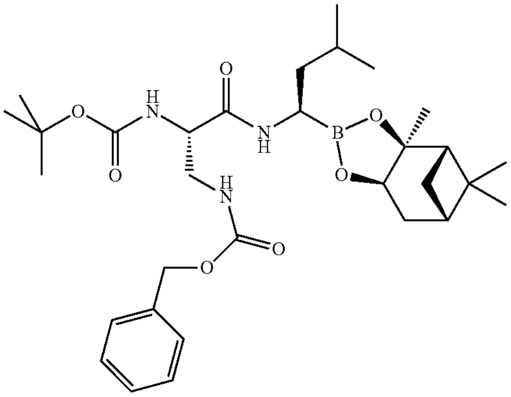 [SMILES: CC(C)C[C@H](NC(=O)[C@H](CNC(=O)OCc1ccccc1)NC(=O)OC(C)(C)C)B1O[C@@H]2C[C@@H]3C[C@@H](C3(C)C)[C@]2(C)O1]

B.9.7 2-S-[(1,1-dimethylethoxycarbonyl)amino]-3-[2-(1H-pyrazol)ethyl]-N-[(1S)-1-[[[(1R)-1-[(3aS,aS,6S,7aR)-hexahydro-3a5,5-trimethyl-4,6-methano-1,3,2 benzodioxaborol-2-yl-]-3-methylbutyl]amino]carbonyl]

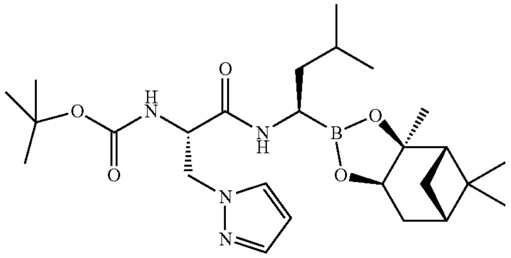 [SMILES: CC(C)C[C@H](NC(=O)[C@H](Cn1cccn1)NC(=O)OC(C)(C)C)B1O[C@@H]2C[C@@H]3C[C@@H](C3(C)C)[C@]2(C)O1]

Example B.10

Carbamic acid 1,1-dimethylethyl ester, N-[(1S,2R)-1-[[[(1R)-1-[(3aS,4S,6S,7aR)-hexahydro-3a,5,5-trimethyl-4,6-methano-1,3,2-benzodioxaborol-2-yl]-1-methylbutyl]amino]carbonyl]-methyl

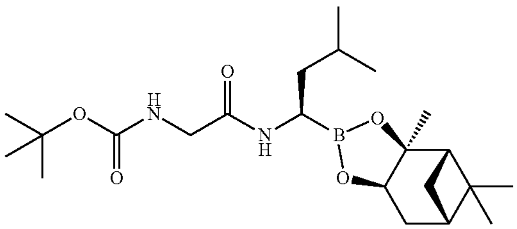 [SMILES: CC(C)C[C@H](NC(=O)CNC(=O)OC(C)(C)C)B1O[C@@H]2C[C@@H]3C[C@@H](C3(C)C)[C@]2(C)O1]

This compound has been prepared following the procedure of Example B.1 Method B starting from (1R)-1-[(3aS,4S,6S,7aR)-hexahydro-3a,5,5-trimethyl-4,6-methano-1,3,2-benzodioxaborol-2-yl]-3-methylbutylamine hydrochloride salt of Example A.1 and commercially available N-(1,1-dimethylethoxycarbonyl)glycine.

$^{1}$H-NMR (DMSO-d6): 8.84 (1H, s); 7.08 (1H, t, J=5.93 Hz); 4.06 (1H, d, J=7.48 Hz); 3.67 (2H, t, J=5.32 Hz); 2.60-2.48 (1H, m); 2.24-2.16 (1H, m); 2.06-1.96 (1H, m); 1.84 (1H, t, J=5.50 Hz); 1.82-1.76 (1H, m); 1.74-1.58 (2H, m); 1.39 (10H, bs); 1.23 (9H, d, J=8.18 Hz); 0.87-0.83 (6H, m); 0.82 (3H, bs).

Example C.1

(2S)-2-amino-5-[[imino(nitroamino)methyl]amino] pentanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt

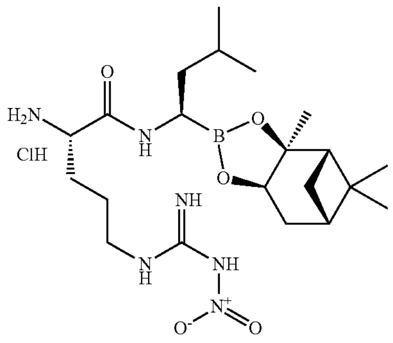 [SMILES: Cl ; CC(C)C[C@H](NC(=O)[C@@H](N)CCCNC(=N)N[N+](=O)[O-])B1O[C@@H]2C[C@@H]3C[C@@H](C3(C)C)[C@]2(C)O1]

Method A

A 4 N solution of hydrogen chloride in dioxane (15 ml) was added to a solution of carbamic acid 1,1-dimethylethyl ester, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl] amino]butyl]- of Example B.1, (4.04 g, 7.06 mmol) in a mixture of dioxane (40 ml) and diethyl ether (7 ml), while cooling at 0° C. The reaction mixture was allowed to warm to room temperature and stirred for further 4 hours. The solvent was removed by rotary evaporation, the residue was treated with diethyl ether (50 ml) and the mixture was stirred at r.t. for three days. The resulting solid was collected by filtration affording 3.18 g of pure product (90% yield)

Method B

Carbamic acid 1,1-dimethyl ethyl ester, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]-amino]-carbonyl]-4-[[imino(nitroamino)-methyl]-amino] butyl]- of Example B.1, (3 g, 5.3 mmol) was dissolved in $Et_2O$ (40 mL) and a solution of about 10% HCl in $Et_2O$ (20 mL) was added dropwise at 0° C. under nitrogen. The reaction mixture was allowed to warm to room temperature and to stir for further 5 hours. The solvent was decanted and the residue, washed twice with $Et_2O$ (20 mL), was dried in vacuo to give the title compound as a white powder (2.43 g, yield 91%).

$^{1}$H NMR (DMSO-$d_6$): 8.56 (2H, br); 8.22 (3H, br); 7.97 (2H, br); 4.28 (1H, dd, J=8.6 Hz, 2.01); 3.77 (1H, m); 3.04 (1H, m); 2.28 (1H, m); 2.11 (2H, m), 1.92 (1H, t, J=5.5); 1.83 (1H, m); 1.79-1.59 (4H, m); 1.59-1.37 (3H, m); 1.31 (4H, s); 1.24 (3H, s); 1.19 (1H, d, J=10.4); 0.88 (3H, d, J=6.0); 0.86 (3H, d, J=6.0); 0.81 (3H, s).

Example C.2

Boronic acid, [(1R)-1-[[(2S)-2-amino-5-[[imino(nitroamino)methyl]amino]-1-oxopentyl]amino]-3-methylbutyl], hydrochloride salt

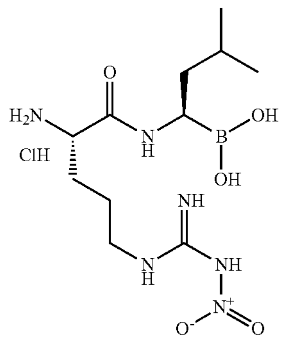 [SMILES: Cl ; CC(C)C[C@H](NC(=O)[C@@H](N)CCCNC(=N)N[N+](=O)[O-])B(O)O]

Carbamic acid 1,1-dimethyl ethyl ester, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl] amino]carbonyl]-4-[[imino(nitroamino)methyl]amino] butyl]- of Example B.1, (3.1 g, 5.48 mmol) was carefully dissolved, under nitrogen at 0° C., in 20 mL of HCl 37%; the resultant mixture was allowed to warm to room temperature and to stir overnight. The reaction mixture was washed with $Et_2O$ until complete removal of pinanediol; the aqueous solution was concentrated to dryness and dried in vacuo to afford 1.82 g (4.93 mmol, yield 90%) of the title compound, used without further purification.

$^{1}$H NMR (DMSO+$D_2O$+TFA): 3.78 (m, 1H); 3.19 (m, 2H); 3.09 (m, 1H); 1.71 (m, 2H); 1.70-1.48 (m, 3H); 1.49-1.23 (m, 2H); 0.89 (d, J=5.8 Hz, 3H); 0.88 (d, J=5.8 Hz, 3H).

Example C.3

Synthesis of Further Intermediates

Starting from the appropriate intermediate and following either the procedures described in the Example C.1 the intermediates reported below were prepared:

(2S,3R)-2-Amino-3-hydroxybutanamide, N-[(1R)-1-[(3aS,4S,6S,7aR)-hexahydro-3a, 5,5-trimethyl-4,6-methano-1,3,2-benzodioxaborol-2-yl]-3-methylbutyl]-, hydrochloride salt

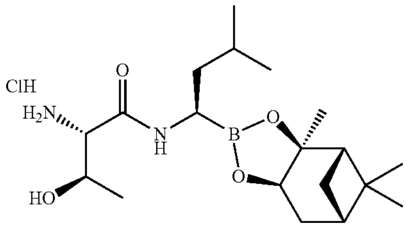 [SMILES: Cl ; CC(C)C[C@H](NC(=O)[C@@H](N)[C@@H](C)O)B1O[C@@H]2C[C@@H]3C[C@@H](C3(C)C)[C@]2(C)O1]

$^1$H NMR (DMSO-$d_6$) $\delta_H$: 8.62 (1H, d, J=5.0 Hz); 8.17 (3H, d, J=3.5); 4.28 (1H, dd, J=8.8, 1.8); 3.78 (1H, m); 3.52 (1H, m); 3.00 (1H, m); 2.28 (1H, m); 2.10 (1H, m); 1.92 (1H, t, J=5.7); 1.84 (1H, m); 1.75-1.62 (2H, m); 1.43 (1H, m); 1.31 (3H, s); 1.25 (3H, s); 1.22 (1H, d, J=10.6); 1.14 (3H, d, J=6.2); 0.88 (3H, d, J=6.4); 0.86 (3H, d, J=6.4); 0.81 (3H, s)

(2S)-2-Amino-5-ureidopentanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt Chiral

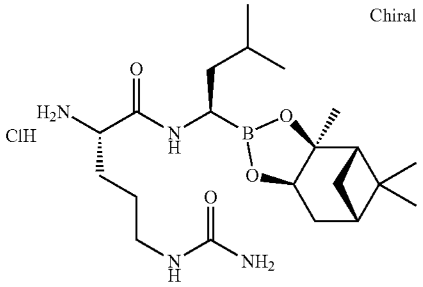 [SMILES: Cl ; CC(C)C[C@H](NC(=O)[C@@H](N)CCCNC(N)=O)B1O[C@@H]2C[C@@H]3C[C@@H](C3(C)C)[C@]2(C)O1]

$^1$H NMR (DMSO-$d_6$) 8.51 (1H, d, J=5.1 Hz); 8.17 (3H, br); 6.1 (1H, br); 4.27 (1H, dd, J=8.6 Hz, 1.8); 3.73 (1H, m); 2.99 (1H, m); 2.94 (2H, t); 2.27 (1H, m); 2.10 (1H, m), 1.92 (1H, t, J=5.5); 1.82 (1H, m); 1.75-1.15 (9H, m); 1.30 (3H, s); 1.23 (3H, m); 0.87 (3H, d, J=6.0); 0.85 (3H, d, J=6.0); 0.80 (3H, s).

(2S)-2-Amino-3-carbamoylpropanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt Chiral

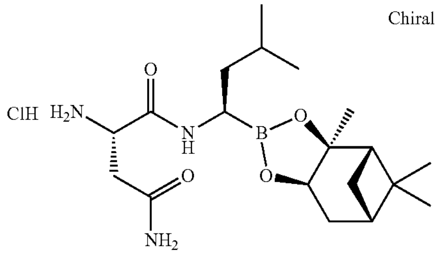 [SMILES: Cl ; CC(C)C[C@H](NC(=O)[C@@H](N)CC(N)=O)B1O[C@@H]2C[C@@H]3C[C@@H](C3(C)C)[C@]2(C)O1]

$^1$H-NMR (DMSO-d6): 8.46-8.41 (1H, m); 8.06 (3H, bs); 7.67 (1H, s); 7.26 (1H, s); 4.30-4.25 (1H, m); 4.08-4.02 (1H, m); 2.96 (1H, m); 2.60-2.52 (1H, m); 2.36-2.24 (1H, m); 2.20-2.10 (1H, m); 1.95 (1H, t, J=5.5); 1.88-1.83 (1H, m); 1.75-1.60 (2H, m); 1.46-1.36 (1H, m); 1.32 (3H, s); 1.30-1.18 (6H, m); 0.86 (6H, t, J=6.7); 0.82 (3H, s).

2-Aminoacetamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-1-methylbutyl]; Hydrochloride salt Chiral

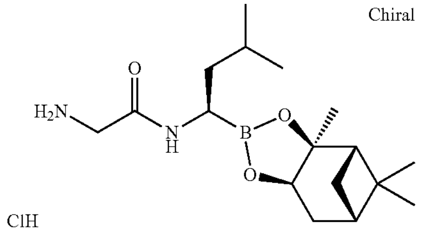 [SMILES: Cl ; CC(C)C[C@H](NC(=O)CN)B1O[C@@H]2C[C@@H]3C[C@@H](C3(C)C)[C@]2(C)O1]

$^1$H-NMR (DMSO-d6): 8.50 (1H, s); 8.20 (3H, bs); 4.29 (1H, d, J=7.70 Hz); 3.15 (2H, bs); 3.05 (1H, s); 2.36-2.24 (1H, m); 2.20-2.10 (1H, m); 1.95 (1H, t, J=5.38 Hz); 1.85 (1H, s); 1.75-1.60 (2H, m); 1.50-1.38 (1H, m); 1.35-1.30 (3H, m); 1.28-1.25 (4H, m); 1.24-1.17 (1H, m); 0.86 (6H, t, J=5.94 Hz); 0.84 (3H, s).

Example C.4

(2S)-2-Amino-3-[(4-methylbenzoyl)amino]propanamide, N-[(1R)-1-[(3aS,4S,6S,7aR)-hexahydro-3a,5,5-trimethyl-4,6-methano-1,3,2-benzodioxaborol-2-yl]-3-methylbutyl]-, hydrochloride salt

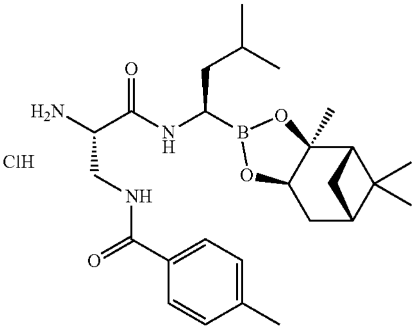 [SMILES: Cl ; Cc1ccc(C(=O)NC[C@H](N)C(=O)N[C@@H](CC(C)C)B2O[C@@H]3C[C@@H]4C[C@@H](C4(C)C)[C@]3(C)O2)cc1]

(2S)-2-[(1,1-Dimethylethoxycarbonyl)amino]-3-[(4-methylbenzoyl)-amino]-propanamide, N-[(1R)-1-[(3aS,4S,6S,7aR)-hexahydro-3a,5,5-trimethyl-4,6-methano-1,3,2-benzodioxaborol-2-yl]-3-methylbutyl]-, Example B.4, (740 mg, 1.65 mmol, 1 eq.), was dissolved in 1,4-dioxane (20 ml). To this solution, HCl 4N in 1,4-dioxane (5 ml, 19.8 mmol, 12 eq.) was added and the solution stirred overnight at r.t. The solvent was removed under reduced pressure to give 800 mg of a glassy solid (quantitative yield).

$^1$H NMR (DMSO-d$_6$) 8.63 (1H, d, J=5.5 Hz); 8.38 (1H, t, J=8.4 Hz); 8.34 (3H, br); 7.80 (2H, t, J=8.2); 7.28 (2H, d, J=8.2 Hz); 4.15 (1H, dd, J=8.8, 1.8); 4.02 (1H, br); 3.66 (1H, m); 3.55 (1H, m); 2.99 (1H, m); 2.35 (3H, s); 2.19 (1H, m); 2.06 (1H, m); 1.86 (1H, t, J=5.7); 1.80 (1H, m); 1.64 (2H, m); 1.41 (1H, m); 1.33-1.19 (2H, m); 1.27 (3H, s), 1.21 (3H, s); 1.16 (1H, d, J=10.6); 0.82 (3H, d); 0.80 (3H, d); 0.78 (3H, s).

Example C.5

2-S-amino-3-(hexanoylamino)-propionamide, N-[(1S)-1-[[(1R)-1-[(3aS,4S,6S,7aR)-hexahydro-3a, 5,5-trimethyl-4,6-methano-1,3,2-benzodioxaborol-2-yl]-3-methylbutyl]amino]carbonyl], hydrochloride salt

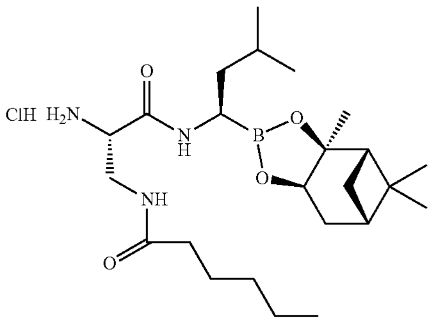 [SMILES: Cl ; CCCCCC(=O)NC[C@H](N)C(=O)N[C@@H](CC(C)C)B1O[C@@H]2C[C@@H]3C[C@@H](C3(C)C)[C@]2(C)O1]

2-S-[(1,1-dimethylethoxycarbonyl)amino]-3-(hexanoylamino)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], of Example B.5, (450 mg, 0.8 mmol, 1 eq.), was dissolved in 1,4-dioxane (15 ml). To this solution, HCl 4N in 1,4-dioxane (2.45 ml, 0.98 mmol, 12 eq.) was added and the solution stirred overnight at r.t. The solvent was removed under reduced pressure to give 400 mg of a glassy solid. Yield quantitative.

Analytical data: $^1$H NMR (DMSO-d$_6$).

$\delta_H$: 8.54 (1H, d, J=5.3 Hz); 8.18 (3H, br); 7.74 (1H, t, J=5.7); 4.29 (1H, dd, J=1.8, 8.8); 3.83 (1H, m); 3.40 (2H, m); 3.00 (1H, m); 2.29 (1H, m); 2.11 (1H, m); 2.08 (2H, t, J=7.5); 1.93 (1H, t, J=5.5); 1.84 (1H, m); 1.75-1.15 (11H, m); 1.32 (3H, s); 1.24 (3H, s); 0.86 (3H, d, J=6.6); 0.84 (3H, d, J=6.6); 0.81 (3H, s).

Example C.6

2-S-amino-3-(4-fluorosulfonylamino)propionamide, N-[(1S)-1-[[(1R)-1-[(3aS,4S,6S,7aR)-hexahydro-3a, 5,5-trimethyl-4,6-methano-1,3,2-benzodioxaborol-2-yl]-3-methylbutyl]amino]carbonyl], hydrochloride salt

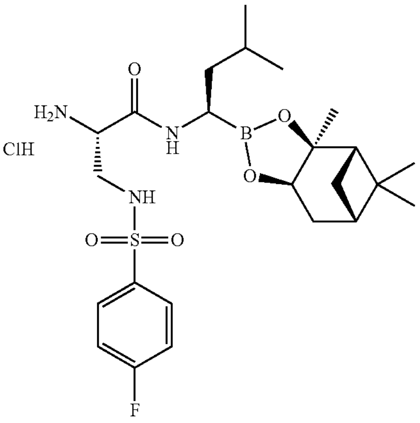 [SMILES: Cl ; CC(C)C[C@H](NC(=O)[C@@H](N)CNS(=O)(=O)c1ccc(F)cc1)B1O[C@@H]2C[C@@H]3C[C@@H](C3(C)C)[C@]2(C)O1]

2-S-[(1,1-dimethylethoxycarbonyl)amino]-3-(4-fluorosulfonylamino)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], of Example B.6, (0.7 g, 1.14 mmol, 1 eq.), was dissolved in 1,4-dioxane (20 ml). To this solution, HCl 4N in 1,4-dioxane (3.4 ml, 13.68 mmol, 12 eq.) was added and the solution stirred overnight at r.t. The solvent was removed under reduced pressure to give 440 mg of a white solid. Yield 71%. Analytical data:

$^1$H NMR (DMSO-d$_6$).

$\delta_H$, 8.54 (1H, d, J=5.5 Hz); 8.26 (3H, br); 7.89 (3H, m); 7.48 (3H, t, J=8.8); 4.26 (1H, dd, J=1.3, 8.6); 3.84 (1H, m); 3.06 (2H, m); 2.97 (1H, m); 2.25 (1H, m); 2.03 (1H, m); 1.83 (2H, m); 1.64 (2H, m); 1.42 (1H, m); 1.35-1.15 (3H, m); 1.28 (3H, s); 1.22 (3H, s); 1.11 (1H, d, J=10.8); 0.85 (6H, m); 0.80 (3H, s).

Example C.7

2-S-amino-3-(3,4-dimethoxyphenylacetamido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt

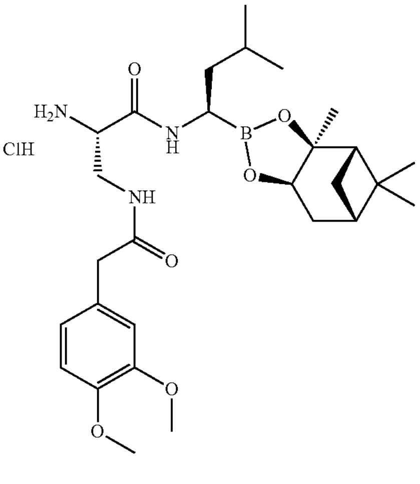 [SMILES: Cl ; COc1ccc(CC(=O)NC[C@H](N)C(=O)N[C@@H](CC(C)C)B2O[C@@H]3C[C@@H]4C[C@@H](C4(C)C)[C@]3(C)O2)cc1OC]

2-S-[(1,1-dimethylethoxycarbonyl)amino]-3-(3,4-dimethoxyphenylacetamido)-propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], of Example B.7, (0.3 g, 0.47 mmol, 1 eq.), was dissolved in 1,4-dioxane (20 ml). To this solution, HCl 4N in 1,4-dioxane (1.43 ml, 5.71 mmol, 12 eq.) was added and the solution stirred overnight at r.t. The solvent was removed under reduced pressure, diethyl ether was added and evaporated to give 230 mg of a white solid. Yield 85%.

Analytical data:

$^1$H NMR (DMSO-$d_6$).

$\delta_H$, 8.57 (1H, br); 8.12 (3H, br); 7.91 (1H, t, J=5.7 Hz); 6.86 (2H, m); 6.76 (1H, dd, J=1.8, 8.2); 4.26 (1H, br d, J=7.3); 3.82 (1H, m); 3.72 (3H, s); 3.71 (3H, s); 3.36 (2H, s); 3.34 (2H, m); 2.99 (1H, m); 2.26 (1H, m); 2.10 (1H, m); 1.92 (1H, t, J=5.3); 1.83 (1H, m); 1.67 (2H, m); 1.45-1.15 (3H, m); 1.31 (3H, s); 1.23 (3H, s); 0.86 (3H, d, J=6.6); 0.84 (3H, d, J=6.6); 0.80 (3H, s).

Example C.8

2-S-amino-3-(3-phenyl-ureido)-propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt

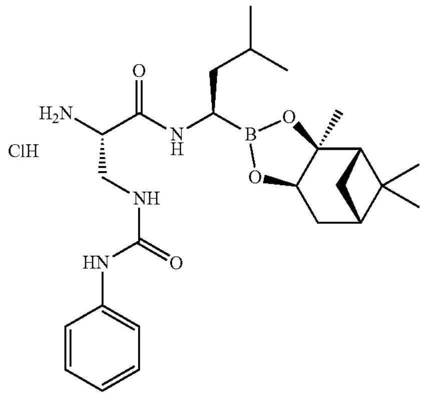 [SMILES: Cl ; CC(C)C[C@H](NC(=O)[C@@H](N)CNC(=O)Nc1ccccc1)B1O[C@@H]2C[C@@H]3C[C@@H](C3(C)C)[C@]2(C)O1]

2-S-[(1,1-dimethylethoxycarbonyl)amino]-3-(3-phenylureido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], of Example B.8, (0.58 g, 0.1 mmol, 1 eq.), was dissolved in 1,4-dioxane (25 ml). To this solution, HCl 4N in 1,4-dioxane (3 ml, 12.1 mmol, 12 eq.) was added and the solution stirred overnight at r.t. The solvent was removed under reduced pressure, diethyl ether was added and evaporated to give 0.52 g of desired product. Yield 100%.

Analytical data:

$^1$H NMR (DMSO-$d_6$).

$\delta_H$: 8.82 (1H, s); 8.59 (1H, d, J=5.7 Hz); 8.18 (3H, br); 7.40 (2H, d, J=7.9); 7.22 (2H, t, J=8.1); 6.90 (1H, t, J=7.3); 6.31 (1H, t, J=5.7); 4.26 (1H, dd, J=1.5, 8.6); 3.89 (1H, m); 3.48 (1H, m); 3.36 (1H, m); 3.01 (1H, m); 2.24 (1H, m); 2.10 (1H, m); 1.92 (1H, t, J=5.3); 1.82 (1H, m); 1.67 (2H, m); 1.50-1.15 (3H, m); 1.31 (3H, s); 1.21 (3H, s); 0.85 (3H, d, J=6.6); 0.84 (3H, d, J=6.6); 0.79 (3H, s).

Example C.9

Synthesis of Further Compounds

Following the procedures of Examples C.4-C.8, the following compounds can be prepared starting from intermediates of Example B.9.

| | | |
|---|---|---|
| C.9.1 | 2-S-amino-3-(acetamido)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt. | 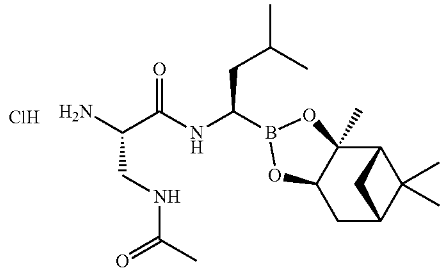 [SMILES: Cl ; CC(=O)NC[C@H](N)C(=O)N[C@@H](CC(C)C)B1O[C@@H]2C[C@@H]3C[C@@H](C3(C)C)[C@]2(C)O1] |

-continued

C.9.2 2-S-amino-3-(9-fluorenylmethyloxycarbamoyl)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt.

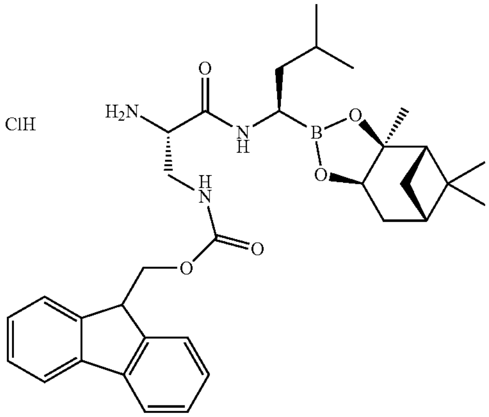

C.9.3 2-S-amino-3-(pentylureido)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt.

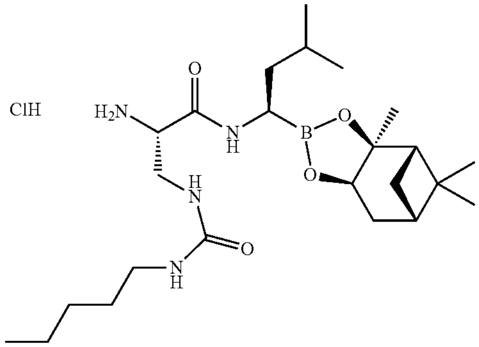 [SMILES: CCCCCNC(=O)NC[C@H](N)C(=O)N[C@@H](CC(C)C)B1O[C@@H]2C[C@@H]3C[C@@H](C3(C)C)[C@]2(C)O1 ; Cl]

C.9.4 2-S-amino-3-(methanesolfonamido)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt.

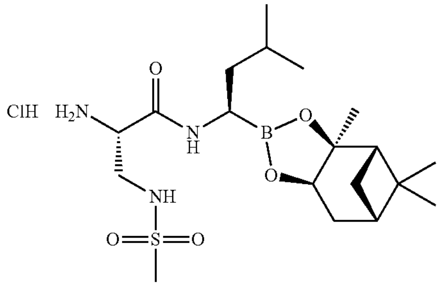 [SMILES: Cl ; CC(C)C[C@H](NC(=O)[C@@H](N)CNS(C)(=O)=O)B1O[C@@H]2C[C@@H]3C[C@@H](C3(C)C)[C@]2(C)O1]

C.9.5 2-S-amino-3-[(ethoxycarbonylsuccinyl]-amide)ethyl]-)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt.

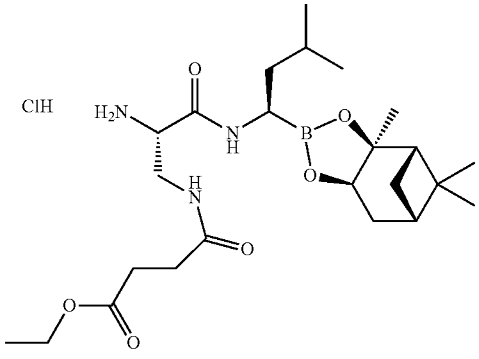 [SMILES: CCOC(=O)CCC(=O)NC[C@H](N)C(=O)N[C@@H](CC(C)C)B1O[C@@H]2C[C@@H]3C[C@@H](C3(C)C)[C@]2(C)O1 ; Cl]

-continued

| | | |
|---|---|---|
| C.9.6 | 2-S-amino-3-(benzyloxycarbamoyl)-propionamide,N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], HCl salt. | 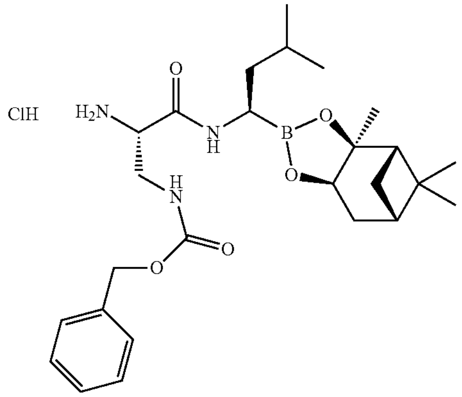 [SMILES: Cl ; CC(C)C[C@H](NC(=O)[C@@H](N)CNC(=O)OCc1ccccc1)B1O[C@@H]2C[C@@H]3C[C@@H](C3(C)C)[C@]2(C)O1] |
| C.9.7 | 3-[2-(1H-pyrazol)ethyl]-N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl] HCl salt. | 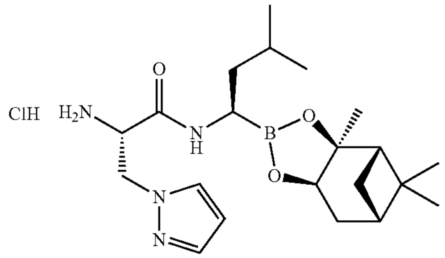 [SMILES: Cl ; CC(C)C[C@H](NC(=O)[C@@H](N)Cn1cccn1)B1O[C@@H]2C[C@@H]3C[C@@H](C3(C)C)[C@]2(C)O1] |

Example D.1

Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-

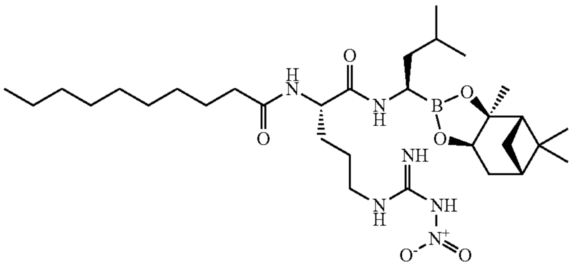 [SMILES: CCCCCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1]

To a solution of decanoic acid (0.84 g, 4.83 mmol) in anhydrous DMF (30 ml) HATU (1.84 g, 4.83 mmol) and HOAt (0.66 g, 4.83 mmol) were added. After stirring at room temperature for 15 minutes the mixture was cooled at 0° C. and N-methylmorpholine (1.33 ml, 12.1 mmol) was added. After further 20 minutes (2S)-2-amino-5-[[imino(nitroamino)methyl]amino]pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-hydrochloride salt of Example C.1 (2.2 g, 4.03 mmol) was added. The mixture was allowed to warm to room temperature and stirred for 5 hours, then diluted with ethyl acetate (150 ml), washed with a 2% solution of citric acid (2×100 ml), 2% solution of $NaHCO_3$ (2×100 ml), and 2% solution of NaCl (2×100 ml). The organic phases were dried over sodium sulfate and concentrated. The residue was purified by column chromatography eluting with AcOEt/n-Hexane mixtures from 80/20 to 100/0. The resulting solid was triturated with diethyl ether, collected by filtration and dried under vacuum giving 1.8 g of product (72% yield).

M.P. 89-94° C.

| El. Anal. | | | | |
|---|---|---|---|---|
| | Calculated: | C 59.99% | H 9.26% | N 13.54% |
| | Found | C 59.47% | H 9.51% | N 13.42% |

$^1$H NMR (DMSO-$d_6$): 8.82 (1H, d, J=2.7 Hz); 8.53 (1H, br); 7.99 (1H, d, J=8.05); 7.88 (2H, br); 4.33 (1H, m); 4.08 (1H, dd, J=1.6, 8.6); 3.14 (2H, m); 2.56 (1H, m); 2.20 (1H, m); 2.11 (2H, m); 2.01 (1H, m); 1.84 (1H, t, J=5.7); 1.79 (1H, m); 1.74-1.58 (3H, m); 1.57-1.39 (5H, m); 1.32 (1H, d, J=9.9); 1.24 (19H, m); 0.85 (9H, m); 0.80 (3H, s).

Starting with the (2S)-2-amino-5-[[imino(nitroamino)methyl]amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl] hydrochloride salt of Example C.1 and the appropriate carboxylic acids, further compounds prepared fundamentally in accordance with the above experimental procedures are reported in Table D-1.

TABLE D-1

| Ex # | Structure | Chemical Name and Analytical Data |
|---|---|---|
| D.1.1 | 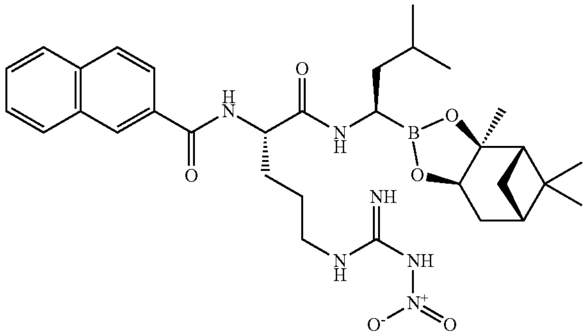 [SMILES: CC(C)C[C@H](NC(=O)[C@H](CCCNC(=N)N[N+](=O)[O-])NC(=O)c1ccc2ccccc2c1)B1O[C@@H]2C[C@@H]3C[C@@H](C3(C)C)[C@]2(C)O1] | Chemical Name:<br>Naphthalen-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.97 (1H, d, J = 2.8 Hz); 8.71 (1H, d, J = 8.0 Hz); 8.54 (1H, br); 8.50 (1H, s); 8.1-7.9 (4H, m); 7.85 (2H, br); 7.6 (2H, m); 4.63 (1H, m); 4.09 (1H, m); 3.20 (2H, m); 2.61 (1H, m); 2.20 (1H, m); 2.01 (1H, m); 1.9-1.2 (11H, m); 1.23 (3H, s); 1.21 (3H, s); 0.85 (6H, d, J = 6.6); 0.79 (3H, s). |
| D.1.2 | 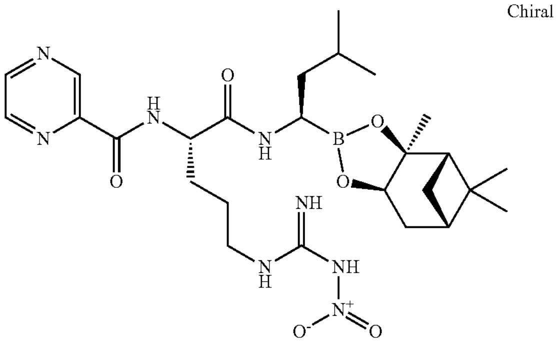 [SMILES: CC(C)C[C@H](NC(=O)[C@H](CCCNC(=N)N[N+](=O)[O-])NC(=O)c1cnccn1)B1O[C@@H]2C[C@@H]3C[C@@H](C3(C)C)[C@]2(C)O1] Chiral | Chemical Name:<br>2-Pyrazinecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-<br>Analytical Data:<br>1H-NMR (DMSO-d6): 9.18 (1H, d, J = 1.3 Hz); 8.89 (1H, d, J = 2.4); 8.8-8.65 (3H, m): 8.5 (2H, br); 4.59 (1H, m); 4.15 (1H, dd, J = 1.8, 8.6); 3.14 (2H, m); 2.72 (1H, m); 2.20 (1H, m); 2.02 (1H, m); 1.9-1.2 (11H, m); 1.23 (3H, s); 1.21 (3H, s); 0.83 (6H, 2 d, J = 6.6); 0.79 (3H, s). |
| D.1.3 | 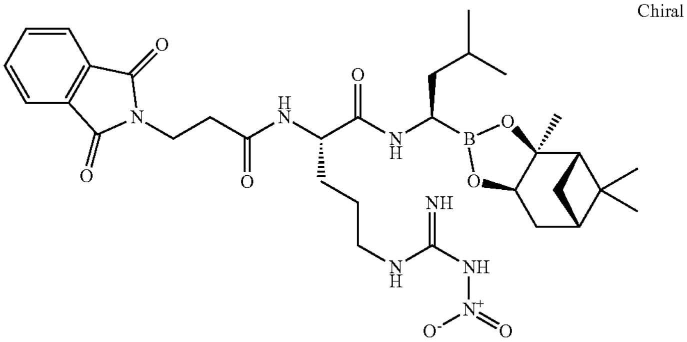 [SMILES: CC(C)C[C@H](NC(=O)[C@H](CCCNC(=N)N[N+](=O)[O-])NC(=O)CCN1C(=O)c2ccccc2C1=O)B1O[C@@H]2C[C@@H]3C[C@@H](C3(C)C)[C@]2(C)O1] Chiral | Chemical Name:<br>3-(1,3-Dioxo-1,3-dihydro-isoindol-2-yl)-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.79 (1H, br); 8.51 (1H, br); 8.44 (1H, d, J = 7.8 Hz); 8.2-7.6 (2H, br); 7.85 (4H, m); 4.30 (1H, m); 4.08 1H, dd, J = 1.8, 8.6); 3.78 (2H, t, J = 6.3); 3.11 (2H, m); 2.59 (3H, m); 2.20 (1H, m); 2.01 (1H, m); 1.9-1.2 (11H, m); 1.23 (3H, s); 1.22 (3H, s); 0.84 (6H, d, J = 6.6); 0.80 (3H, s). |
| D.1.4 | 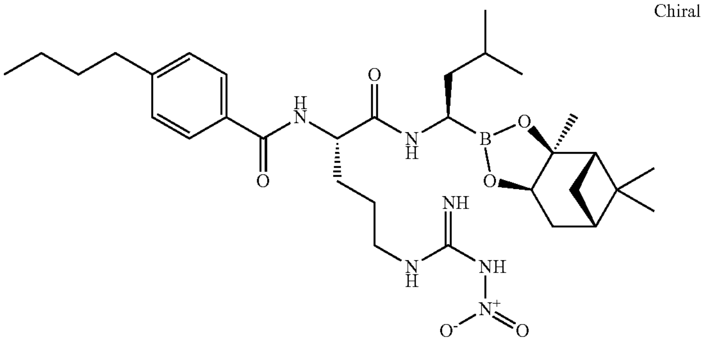 [SMILES: CCCCc1ccc(C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chiral<br>Chemical Name:<br>4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.93 (1H, d, J = 2.9 Hz); 8.51 (1H, br); 8.24 (1H, d, J = 7.8); 8.2-7.6 (2H, br); 7.86 (2H, d, J = 8.2); 7.29 (2H, d, J = 8.2); 4.56 (1H, m); 4.07 1H, dd, J = 1.8, 8.6); 3.16 (2H, m); 2.63 (2H, t, J = 7.7); 2.57 (1H, dt, J = 2.5, 7.1); 2.20 (1H, m); 2.01 (1H, m); 1.9-1.2 (15H, m); 1.23 (3H, s); 1.22 (3H, s); 0.90 (3H, d, J = 7.3); 0.84 (6H, d, J = 6.6); 0.80 (3H, s). |

TABLE D-1-continued

| Ex # | Structure | Chemical Name and Analytical Data |
|---|---|---|
| D.1.5 | 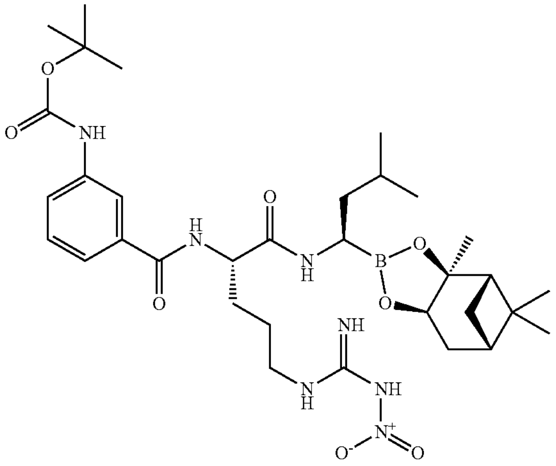 [SMILES: CC(C)C[C@H](NC(=O)[C@H](CCCNC(=N)N[N+](=O)[O-])NC(=O)c1cccc(NC(=O)OC(C)(C)C)c1)B1O[C@@H]2C[C@@H]3C[C@@H](C3(C)C)[C@]2(C)O1] | Chemical Name:<br>3-[(1,1-dimethylethoxy)carbonylamino]benzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-<br>Analytical Data:<br>1H-NMR (DMSO-d6): 9.48 (1H, s); 8.88 (1H, d, J = 2.8 Hz); 8.51 (1H, br); 8.42 (1H, d, J = 8.0); 7.6-8.4 (2H, br): 7.97 (1H, s); 7.55 (1H, dd, J = 7.8, 1.1); 7.47(1H, d, J = 7.8); 7.34 (1H, t, J = 7.8); 4.55 (1H, m); 4.09 (1H, dd, J = 1.8, 8.6); 3.17 (2H, m); 2.60 (1H, dt, J = 2.9, 8.4); 2.20 (1H, m); 2.02 (1H, m); 1.9-1.2 (11H, m); 1.48 (9H, s); 1.23 (3H, s); 1.21 (3H, s); 0.85 (6H, d, J = 6.6); 0.80 (3H, s). |
| D.1.6 | 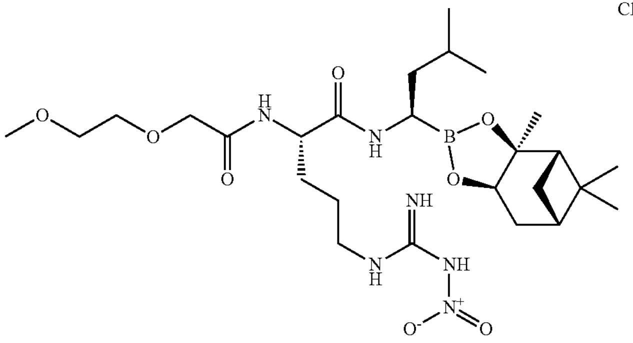 Chiral | Chemical Name:<br>2-(2-methoxyethoxy) acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl<br>Analytical Data:<br>1H-NMR (DMSO-d6): 8.74 (1H, d, J = 2.8 Hz); 8.51 (1H, br); 8.2-7.4 (2H, br); 7.69 (1H, d, J = 8.6); 4.39 (1H, m); 4.12 (1H, dd, J = 1.8, 8.6); 3.91 (2H, s); 3.57 (2H, m); 3.46 (2H, t, J = 4.6); 3.26 (3H, s); 3.13 (2H, m); 2.63 (1H, m); 2.21 (1H, m); 2.03 (1H, m); 1.9-1.2 (11H, m); 1.24 (3H, s); 1.21 (3H, s); 0.85 (3H, d, J = 6.6); 0.83 (3H, d, J = 6.6); 0.80 (3H, s). |
| D.1.7 | 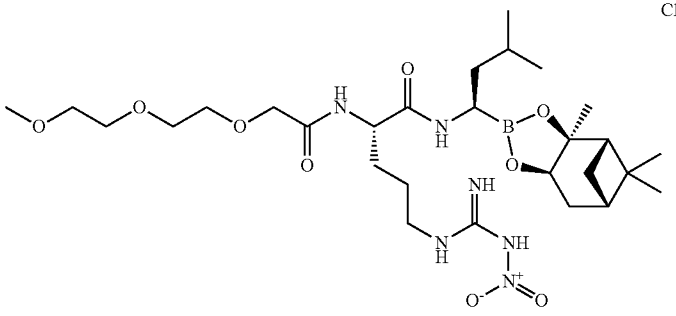 Chiral | Chemical Name:<br>2-[2-(2-methoxyethoxy)ethoxy]acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl<br>Analytical Data:<br>1H-NMR (DMSO-d6): 8.74 (1H, d, J = 2.8 Hz); 8.52 (1H, br); 8.2-7.6 (2H, br); 7.69 (1H, d, J = 8.6); 4.40 (1H, m); 4.11 (1H, dd, J = 1.8, 8.6); 3.91 (2H, s); 3.6-3.4 (8H, m); 3.23 (3H, s); 3.13 (2H, m); 2.63 (1H, m); 2.20 (1H, m); 2.02 (1H, m); 1.9-1.2 (11H, m); 1.24 (3H, s); 1.21 (3H, s); 0.84 (3H, d, J = 6.6); 0.83 (3H, d, J = 6.6); 0.79 |
| D.1.8 | 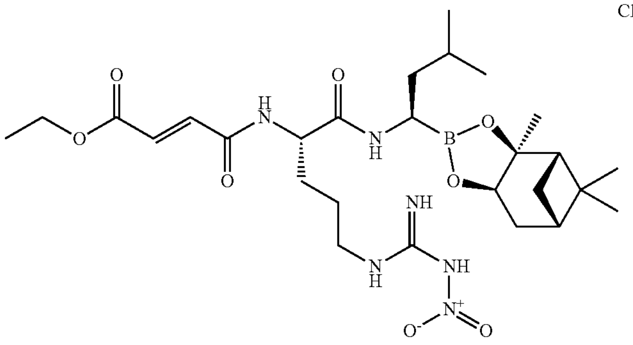 Chiral | Chemical Name:<br>(E)-3-(Ethoxycarbonyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.78 (1H, d, J = 8.6 Hz); 8.77 (1H, s); 8.55 (1H, br); 8.3-7.6 (2H, br); 7.12 (1H, d, J = 15.5); 6.58 (1H, d, J = 15.5); 4.45 (1H, m); 4.19 (2H, q, J = 7.1); 4.12 (1H, dd, J = 1.8, 8.6); 3.15 (2H, m); 2.63 (1H, dt, J = 3.3, 8.6); 2.21 (1H, m); 2.04 (1H, m); 1.9-1.2 (11H, m); 1.25 (3H, s); 1.24 (3H, t, J = 6.9); 1.23 (3H, s); 0.85 (3H, d, J = 6.6); 0.83 (3H, d, J = 6.6); 0.80 (3H, s). |

TABLE D-1-continued

| Ex # | Structure | Chemical Name and Analytical Data |
|---|---|---|
| D.1.9 | 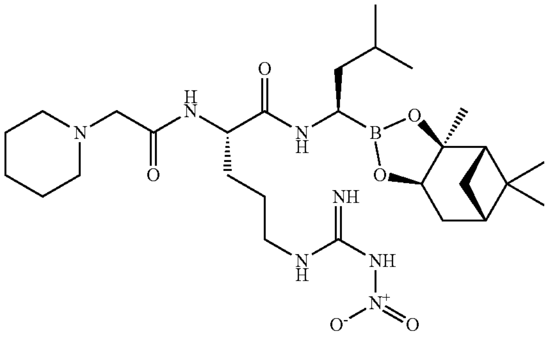 [SMILES: CC(C)C[C@H](NC(=O)[C@H](CCCNC(=N)N[N+](=O)[O-])NC(=O)CN1CCCCC1)B1O[C@@H]2C[C@@H]3C[C@@H](C3(C)C)[C@]2(C)O1] | Chemical Name:<br>2-Piperidin-1-yl-acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.79 (1H, d, J = 1.8 Hz); 8.53 (1H, br); 8.3-7.5 (2H, br); 7.79 (1H, br); 4.37 (1H, m); 4.12 (1H, dd, J = 1.8, 8.6); 3.13 (2H, m); 2.87 (2H, br); 2.62 (1H, m); 2.36 (4H, m); 2.20 (1H, m); 2.03 (1H, m); 1.9-1.2 (17H, m); 1.24 (3H, s); 1.21 (3H, s); 0.83 (6H, d, J = 6.6); 0.79 (3H, s). |
| D.1.10 | 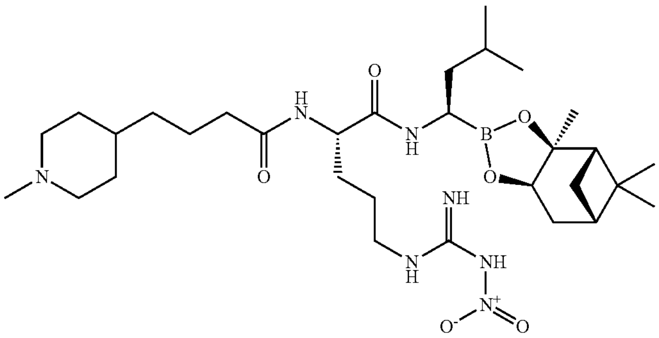 | Chemical Name:<br>4-(1-Methyl-piperidin-4-yl)-butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.82 (1H, d, J = 2.7 Hz); 8.51 (1H, br); 8.01 (1H, d, J = 8.0 Hz); 8.3-7.5 (2H, br); 6.94 (1H, t, J = 5.8): 4.33 (1H, m); 4.07 (1H, dd, J = 1.8, 8.6); 3.13 (2H, m); 2.78 (2H, br); 2.68 (3H, br s); 2.55 (1H, m); 2.19 (1H, m); 2.10 (2H, t, J = 7.5); 2.00 (1H, m); 1.85-1.1 (22H, m); 1.23 (3H, s); 1.21 (3H, s); 0.83 (6H, 2 d, J = 6.6); 0.79 (3H, s). |
| D.1.11 | 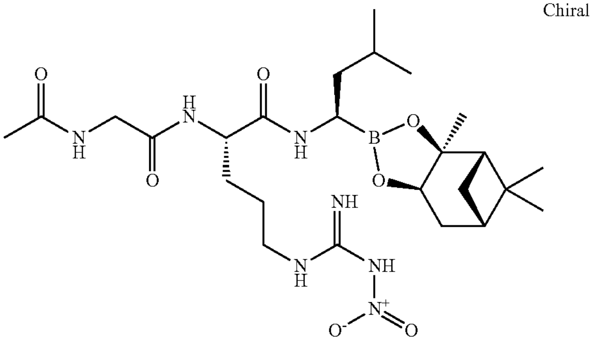 [SMILES: CC(=O)NCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1]<br>Chiral | Chemical Name:<br>2-Acetylamino-acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.67 (1H, d, J = 2.7 Hz); 8.51 (1H, br); 8.14 (1H, t, J = 5.7); 8.08 (1H, d, J = 8.0 Hz); 8.3-7.5 (2H, br); 4.34 (1H, m); 4.09 (1H, dd, J = 1.8, 8.6); 3.68 (2H, m); 3.13 (2H, m); 2.56 (1H, m); 2.20 (1H, m); 2.01 (1H, m); 1.84 (3H, s); 1.85-1.2 (11H, m); 1.24 (3H, s); 1.21 (3H, s); 0.83 (6H, d, J = 6.6); 0.79 (3H, s). |

Following the above described procedure for Example D.1 and using as starting material the (2S)-2-amino-5-[[imino (nitroamino)methyl]amino]pentanamide, N-[(1R)-1-[(3aS, 4S,6S,7aR)-hexahydro-3a,5,5-trimethyl-4,6-methano-1,3,2-benzodioxaborol-2-yl]-3-methylbutyl]-hydrochloride salt of Example C.1 and the appropriate carboxylic acids, the compounds reported in Table D-1A are prepared.

TABLE D-1A

| Ex # | Structure | Chemical Name and Analytical Data |
|---|---|---|
| D.1.12 | 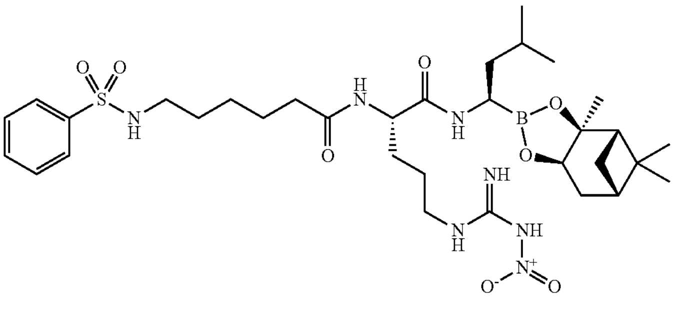 [SMILES: CC(C)C[C@H](NC(=O)[C@H](CCCNC(=N)N[N+](=O)[O-])NC(=O)CCCCCNS(=O)(=O)c1ccccc1)B1O[C@@H]2C[C@@H]3C[C@@H](C3(C)C)[C@]2(C)O1] | Chemical Name:<br>6-Benzenesulfonylaminohexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.83 (1H, d, J = 2.8 Hz); 8.51 (1H, br); 7.97 (1H, d, J = 7.8 Hz); 8.2-7.6 (2H, br); 7.77 (2H, m); 7.65-7.5 (4H, m); 4.31 (1H, m); 4.05 (1H, dd, J = 1.8, 8.6); 3.12 (2H, m); 2.69 (2H, q, J = 7.0); 2.54 (1H, m); 2.20 (1H, m); 2.05 (2H, t, J = 7.5); 2.01 (1H, m); 1.85-1.1 (21H, m); 1.22 (3H, s); 1.21 (3H, s); 0.82 (6H, d, J = 6.6); 0.79 (3H, s). |

TABLE D-1A-continued

| Ex # | Structure | Chemical Name and Analytical Data |
| --- | --- | --- |
| D.1.13 | 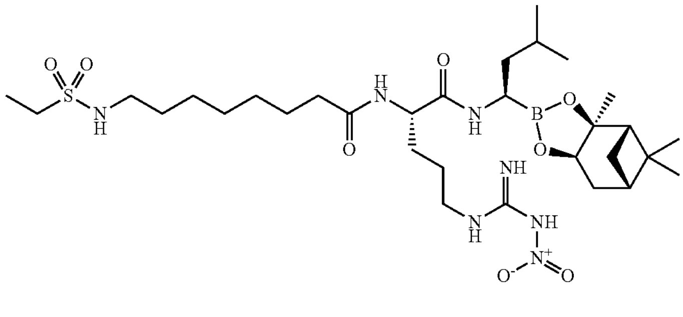 [SMILES: CCS(=O)(=O)NCCCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] | Chemical Name: 8-(Ethanesulfonylamino)octanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl Analytical Data: 1H-NMR (DMSO-d6): 8.81 (1H, br s); 8.51 (1H, br); 7.98 (1H, d, J = 7.8 Hz); 8.3-7.5 (2H, br); 6.93 (1H, t, J = 5.7): 4.32 (1H, m); 4.06 (1H, dd, J = 1.8, 8.6); 3.13 (2H, m); 2.95 (2H, q, J = 7.3); 2.87 (2H, q, J = 6.7); 2.55 (1H, m); 2.19 (1H, m); 2.10 (2H, t, J = 7.0); 2.00 (1H, m); 1.85-1.1 (17H, m); 1.23 (3H, s); 1.21 (3H, s); 1.16 (3H, t, J = 7.3); 0.83 (6H, d, J = 6.6); 0.79 (3H, s). |
| D.1.14 | 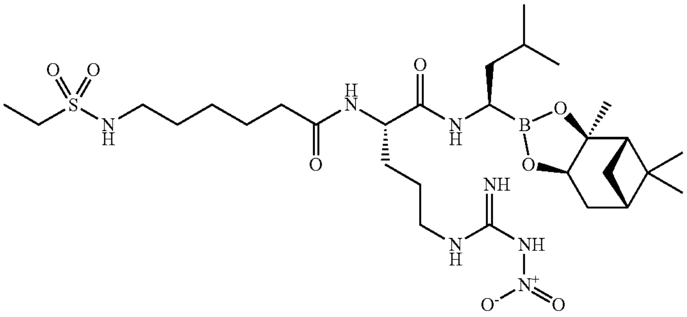 [SMILES: CCS(=O)(=O)NCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] | Chemical Name: 6-(Ethanesulfonylamino)hexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: 1H-NMR (DMSO-d6): 8.83 (1H, d, J = 2.7 Hz); 8.51 (1H, br); 8.00 (1H, d, J = 8.0 Hz); 8.3-7.5 (2H, br); 6.94 (1H, t, J = 5.8): 4.32 (1H, m); 4.06 (1H, dd, J = 1.8, 8.6); 3.13 (2H, m); 2.95 (2H, q, J = 7.3); 2.87 (2H, q, J = 6.7); 2.55 (1H, m); 2.19 (1H, m); 2.10 (2H, t, J = 7.5); 2.00 (1H, m); 1.85-1.1 (17H, m); 1.24 (3H, s); 1.21 (3H, s); 1.16 (3H, t, J = 7.5); 0.83 (6H, d, J = 6.6); 0.79 (3H, s). |

Example D.2

10-(1,3-Dioxo-1,3-dihydro-isoindol-2-yl)-decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-

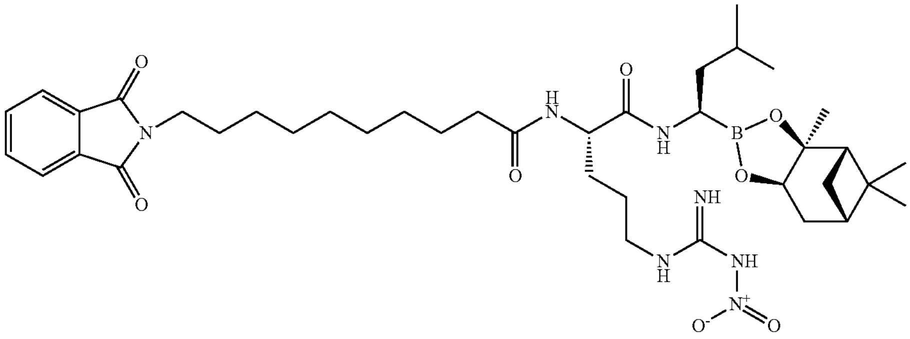 [SMILES: CC(C)C[C@H](NC(=O)[C@H](CCCNC(=N)N[N+](=O)[O-])NC(=O)CCCCCCCCCN1C(=O)c2ccccc2C1=O)B1O[C@@H]2C[C@@H]3C[C@@H](C3(C)C)[C@]2(C)O1]

To a solution of 10-(1,3-Dioxo-1,3-dihydro-isoindol-2-yl)-decanoic acid (353 mg, 1.11 mmol), prepared according to Example G.1, in anhydrous dichloromethane (10 ml), N-methylmorpholine was added (122 μl, 1.11 mmol). The mixture was cooled to −15° C., then isobutyl chloroformate (144 μl, 1.11 mmol) was slowly added. After 15 minutes (2S)-2-amino-5-[[imino(nitro amino)methyl]amino]pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-hydrochloride salt of Example C.1 (508 mg, 1.01 mmol) and further N-methylmorpholine (122 μl, 1.11 mmol) were added. The reaction mixture was stirred at −15 to 10° C. for 4 h, then concentrated to small volume and partitioned between ethyl acetate (20 ml) and water (10 ml). The aqueous phase was further extracted with ethyl acetate (10 ml). The combined organic phases were dried over sodium sulfate and concentrated. The residue was taken up with ethyl acetate (3 ml) and the solution was dropwise added to hexane (120 ml) while stirring at room temperature. The solid was collected by decantation and dried under vacuum (730 mg, 94%).

$^1$H NMR (DMSO-$d_6$): 8.81 (1H, d, J=2.7 Hz); 8.52 (1H, br); 7.98 (1H, d, J=8.05); 7.88 (2H, br); 7.85 (4H, m); 4.34 (1H, m); 4.06 (1H, dd, J=7.1); 3.56 (2H, t, J=7.14); 3.14 (2H, m); 2.55 (1H, m); 2.19 (1H, m); 2.10 (2H, t, J=7.14); 2.0 (1H, m); 1.82 (1H, t, J=5.7); 1.78 (1H, m); 1.73-1.35 (10H, m); 1.31 (1H, d, J=9.9); 1.24 (19H, m); 0.84 (9H, m); 0.79 (3H, s).

Further compounds prepared fundamentally in accordance with the above experimental procedures are reported in Table D-2.

Table D-2

| Ex # | Structure | Chemical Name and Analytical Data |
|---|---|---|
| D.2.1 | 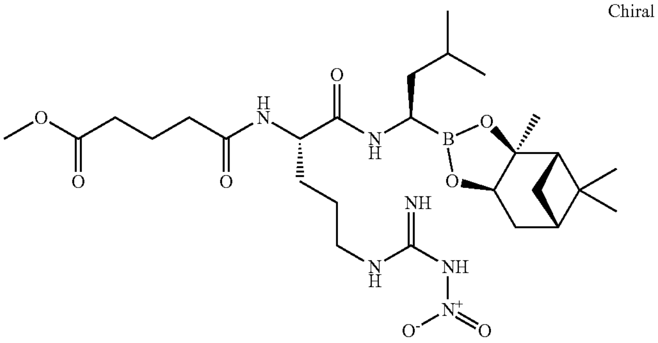 Chiral | Chemical Name: 4-(methoxycarbonyl)butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: 1H-NMR (DMSO-d6): 8.79 (1H, d, J = 2.7 Hz); 8.51 (1H, br); 8.04 (1H, d, J = 7.9 Hz); 8.3-7.5 (2H, br); 4.31 (1H, m); 4.07 (1H, dd, J = 1.8, 8.6); 3.57 (3H, s); 3.13 (2H, m); 2.55 (1H, m); 2.28 (2H, t, J = 7.7); 2.20 (1H, m); 2.28 (2H, t, J = 7.5); 2.01 (1H, m); 1.85-1.2 (13H, m); 1.23 (3H, s); 1.21 (3H, s); 0.83 (6H, d, J = 6.6); 0.79 (3H, s). |
| D.2.2 | 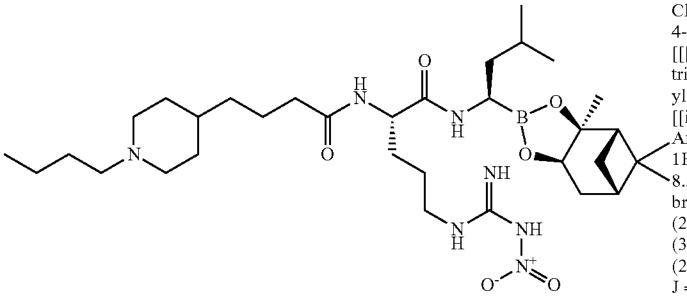 | Chemical Name: 4-(1-Butyl-piperidin-4-yl)-butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: 1H-NMR (DMSO-d6): 8.78 (1H, d, J = 2.7 Hz); 8.51 (1H, br); 7.97 (1H, d, J = 8.0 Hz); 8.3-7.5 (2H, br); 4.32 (1H, m); 4.07 (1H, dd, J = 1.8, 8.6); 3.13 (2H, m); 2.78 (2H, br d, J = 11.2); 2.55 (1H, m); 2.19 (3H, m); 2.09 (2H, t, J = 7.5); 2.00 (1H, m); 1.85-1.0 (26H, m); 1.23 (3H, s); 1.21 (3H, s); 0.85 (3H, t, J = 7.9); 0.83 (6H, 2 d, J = 6.6); 0.79 (3H, s). |
| D.2.3 | 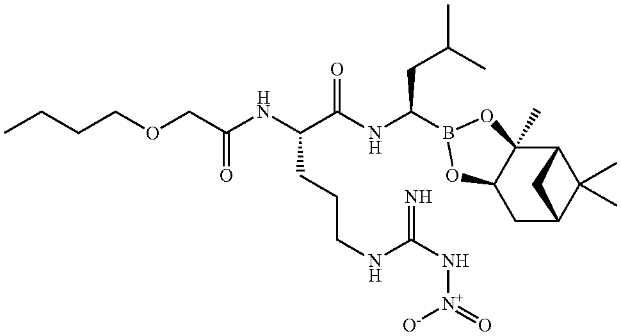 [SMILES: CCCCOCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] | Chemical Name: 2-Butoxyacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: 1H-NMR (DMSO-d6): 8.74 (1H, d, J = 2.8 Hz); 8.51 (1H, br); 8.3-7.5 (2H, br); 7.61 (1H, d, J = 8.0); 4.39 (1H, m); 4.12 (1H, br d, J = 8.2); 3.85 (2H, s); 3.42 (2H, t, J = 6.4); 3.13 (2H, m); 2.64 (1H, m); 2.20 (1H, m); 2.03 (1H, m); 1.95-1.2 (15H, m); 1.24 (3H, s); 1.21 (3H, s); 0.87 (3H, t, J = 7.3); 0.83 (6H, d, J = 6.6); 0.79 (3H, s). |

Further compounds prepared according to the above reported procedure in Example D.2 are reported in Table D-2A The compound of Example D.2.6, was prepared starting from 2-aminoacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]-amino]carbonyl]-4-[[imino(nitroamino)methyl]-amino]-butyl], hydrochloride salt of Example D.14. The compounds of example D.2.7 and D.2.8 were prepared from 2-aminoacetamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-1-methylbutyl]; hydrochloride salt of Example C.3. The compounds of Examples 2.9 and 2.10 were prepared from (2S)-2-amino-5-ureidopentanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt of Example C.3

TABLE D-2A

| Ex # | Structure | Chemical Name and Analytical Data |
|---|---|---|
| D.2.4 | 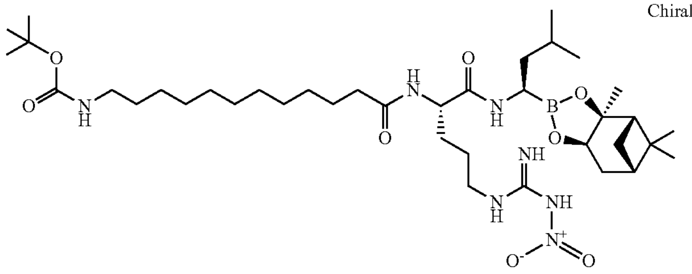 Chiral | Chemical Name:<br>12-[(1,1-dimethylethoxy) carbonylamino]dodecanamide,N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-<br>Analytical Data:<br>$^{1}$H NMR (DMSO-d6) 8.81 (1H, d, J = 2.4); 8.52 (1H, br); 7.98 (1H, d, J = 8.05); 7.85 (2H, v. br); 6.73 (1H, t, J = 5.3); 4.33 (1H, m); 4.07 (1H, d, J = 8.4); 3.14 (2H, m); 2.88 (2H, q, J = 6.6); 2.56 (1H, m); 2.19 (1H, m); 2.10 (2H, t, J = 7.1); 2.01 (1H, m); 1.83 (1H, t, J = 5.7); 1.78 (1H, m); 1.73-1.41 (8H, m); 1.36 (9H, s); 1.33-1.15 (25H, m); 0.84 (6H, d, J = 6.5); 0.80 (3H, s). |
| D.2.5 | 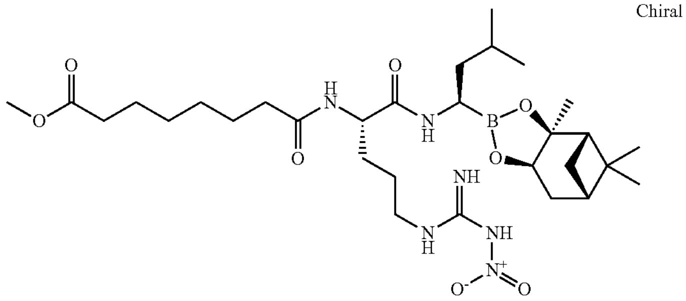 Chiral | Chemical Name:<br>4-(methoxycarbonyl)heptanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>1H-NMR (DMSO-d6): 8.80 (1H, br s); 8.51 (1H, br); 7.98 (1H, d, J = 8.0 Hz); 8.3-7.5 (2H, br); 4.32 (1H, m); 4.06 (1H, br d, J = 8.4); 3.12 (2H, m); 2.55 (1H, m); 2.26 (2H, t, J = 7.3); 2.18 (1H, m); 2.09 (2H, t, J = 7.1); 2.01 (1H, m); 1.85-1.2 (19H, m); 1.23 (3H, s); 1.21 (3H, s); 0.83 (6H, d, J = 6.6); 0.79 (3H, s). |
| D.2.6 | 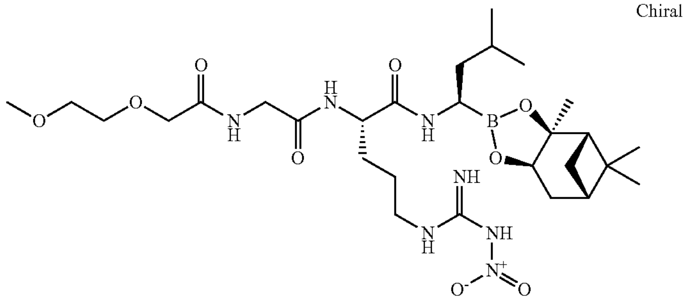 Chiral | Chemical Name:<br>2-[2-(2-methoxyethoxy)acetylamino]acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl<br>Analytical Data:<br>1H-NMR (DMSO-d6): 8.71-8.68 (1H, m); 8.53 (1H, m); 8.15 (1H, d, J = 8.1); 8.10-7.60 (3H, m); 4.40-4.33 (1H, m); 4.13-4.08 (1H, m); 3.92 (2H, s); 3.82-3.78 (2H, m); 3.64-3.58 (2H, m); 3.52-3.46 (2H, m); 3.27 (3H, s); 2.62-2.56 (1H, m); 2.26-2.16 (1H, m); 2.08-2.00 (1H, m); 1.85 (1H, t, J = 5.5); 1.82-1.76 (1H, m); 1.72-1.60 (3H, m); 1.59-1.40 (4H, m); 1.32-1.26 (4H, m); 1.25 (3H, s); 1.22 (3H, s); 0.86-0.83 (6H, m); 0.81 (3H, s). |
| D.2.7 | 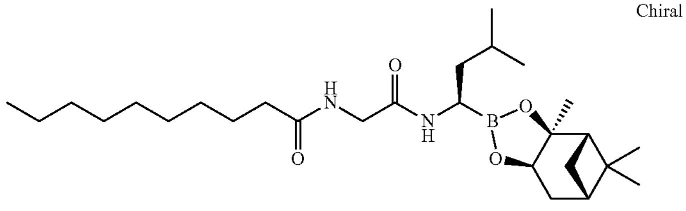 [SMILES: CCCCCCCCCC(=O)NCC(=O)N[C@@H](CC(C)C)B1O[C@@H]2C[C@@H]3C[C@@H](C3(C)C)[C@]2(C)O1] Chiral | Chemical Name:<br>Decanamide, N-[1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]methyl]<br>Analytical Data:<br>1H-NMR (DMSO-d6): 8.85 (1H, s); 8.11 (1H, t, J = 5.9); 4.07-4.03 (1H, m); 3.83-3.78 (2H, d, J = 6.4); 2.24-2.16 (1H, m); 2.11 (2H, t, J = 7.40); 2.05-1.95 (1H, m); 1.84 (1h, t, J = 5.6); 1.81-1.75 (1H, m); 1.74-1.60 (2H, m); 1.54-1.45 (2H, m); 1.35-1.30 (1H, d, J = 10.1); 1.28-1.20 (21H, m); 0.90-0.84 (9H, m); 0.81 (3H, s). |

TABLE D-2A-continued

| Ex # | Structure | Chemical Name and Analytical Data |
| --- | --- | --- |
| D.2.8 | 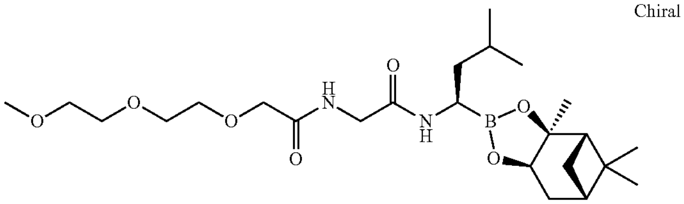 Chiral | Chemical Name: 2-[2-(2-methoxyethoxy)ethoxy]acetamide, N-[1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]methyl] Analytical Data: 1H-NMR (DMSO-d6): 8.81 (1H, m); 7.97 (1H, t, J = 6.0); 4.09-4.04 (1H, m); 3.93 (2H, s); 3.85 (2H, d, J = 6.0); 3.64-3.57 (2H, m); 3.57-3.50 (4H, m); 3.45-3.40 (2H, m); 3.23 (3H, s); 2.58-2.52 (1H, m); 2.24-2.15 (1H, m); 2.05-1.97 (1H, m); 1.83 (1H, t, J = 5.6); 1.80-1.76 (1H, m); 1.72-1.58 (2H, m); 1.31 (1H, d, J = 10.1); 1.28-1.25 (2H, m); 1.23 (3H, s); 1.21 (3H, s); 0.86-0.82 (6H, m); 0.80 (3H, s). |
| D.2.9 | 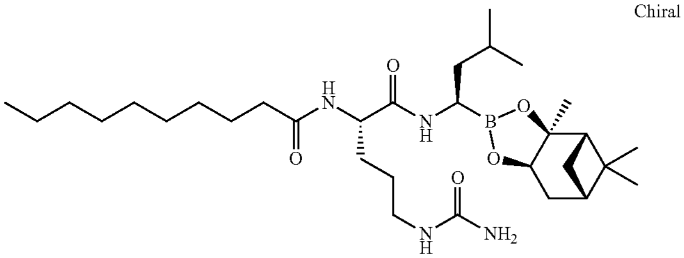 [SMILES: CCCCCCCCCC(=O)N[C@@H](CCCNC(N)=O)C(=O)N[C@@H](CC(C)C)B1O[C@@H]2C[C@@H]3C[C@@H](C3(C)C)[C@]2(C)O1] Chiral | Chemical Name: Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-5-ureidopentyl]- |
| D.2.10 | 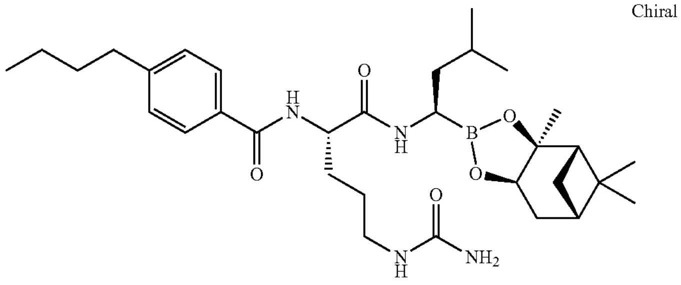 [SMILES: CCCCc1ccc(C(=O)N[C@@H](CCCNC(N)=O)C(=O)N[C@@H](CC(C)C)B2O[C@@H]3C[C@@H]4C[C@@H](C4(C)C)[C@]3(C)O2)cc1] Chiral | Chemical Name: 4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-5-ureidopentyl]- |

Example D.3

11-Cyanoundecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]

0.85 mmol) were added to a solution of 11-cyanoundecanoic acid (115 mg, 0.54 mmol) in dichloromethane (DCM) (9 mL). After stirring for 10 minutes (2S)-2-amino-5-[[imino(nitroamino)methyl]amino]pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-, hydrochloride salt of Example C.1 (251 mg, 0.50 mmol) and DIPEA (0.128 ml,

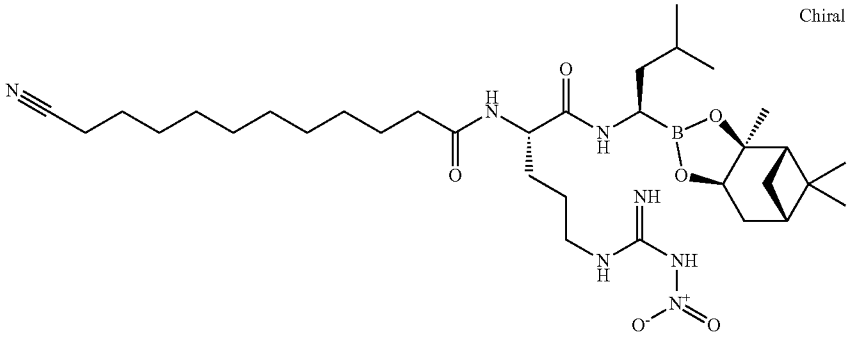 [SMILES: CC(C)C[C@H](NC(=O)[C@H](CCCNC(=N)N[N+](=O)[O-])NC(=O)CCCCCCCCCCC#N)B1O[C@@H]2C[C@@H]3C[C@@H](C3(C)C)[C@]2(C)O1]

Chiral

PS-Carbodiimide (N-cyclohexylcarbodiimide-N'-propyloxymethyl polystyrene, 769 mg, 1 mmol, loading 1.31 mmol/g) and HOAt (1-Hydroxy-7-azabenzotriazole, 115 mg, 0.75 mmol) were added. The suspension was shaken overnight at room temperature and then the PS-Carbodiimide was filtered off and washed several times with DCM (4×6 mL).

The organic phase was passed through a VARIAN CHEM ELUT cartridge for liquid-liquid extraction pre-conditioned with saturated aqueous $NaHCO_3$ and finally washed with DCM (15 mL). The solvent was evaporated and the crude reaction was purified with normal-phase ISOLUTE SPE-SI column (DCM 9, MeOH 1) to afford 200 mg of the desired compound (yield 61%).

NMR ($CDCl_3$): 7.53 (s, br, 2H); 7.36 (d, br, J=4.7 Hz, 1H); 6.88 (d, J=8.2 Hz, 1H); 4.46 (m, 1H); 4.15 (dd, J=8.5, 1.9 Hz, 1H); 3.19 (m, 2H); 2.93 (m, 1H); 2.23 (t, J=7.2 Hz, 2H); 2.21 (m, 1H); 2.09 (t, J=7.5, 2H); 2.04 (m, 1H); 1.88 (t, J=5.4 Hz, 1H); 1.77 (m, 1H); 1.69 (m, 1H); 1.64-1.43 (m, 9H); 1.40-1.26 (m, 4H); 1.26 (s, 3H); 1.24-1.12 (m, 16H); 0.80 (d, J=6.6, 3H); 0.79 (d, J=6.6, 3H); 0.73 (s, 3H).

LC-MS 659.7, MH+. ESI POS; AQA; spray 4 kV/skimmer: 20V/probe 250 C.

Further compounds prepared fundamentally in accordance with the above experimental procedures are reported in Table D-3.

TABLE D-3

| Ex # | Structure | Chemical Name and Analytical Data |
|---|---|---|
| D.3.1 | 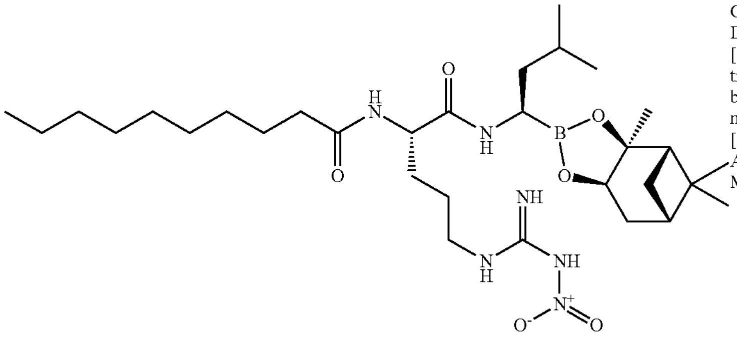 | Chemical Name: Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 621.5 |
| D.3.2 | 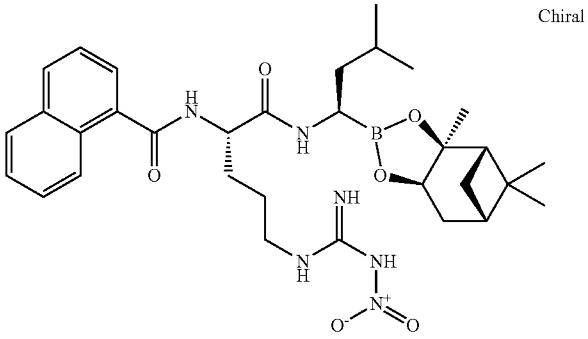 [SMILES: CC(C)C[C@H](NC(=O)[C@H](CCCNC(=N)N[N+](=O)[O-])NC(=O)c1cccc2ccccc12)B1O[C@@H]2C[C@@H]3C[C@@H](C3(C)C)[C@]2(C)O1] Chiral | Chemical Name: Naphthalen-1-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 621.4 |
| D.3.3 | 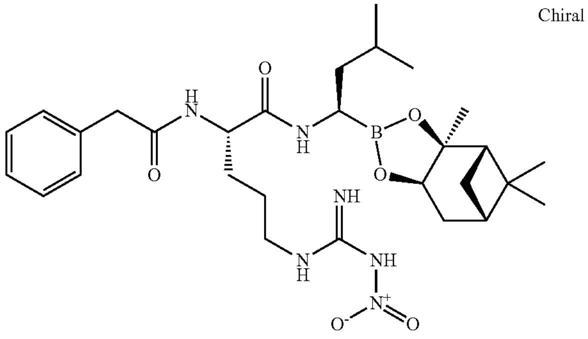 [SMILES: CC(C)C[C@H](NC(=O)[C@H](CCCNC(=N)N[N+](=O)[O-])NC(=O)Cc1ccccc1)B1O[C@@H]2C[C@@H]3C[C@@H](C3(C)C)[C@]2(C)O1] Chiral | Chemical Name: 2-Phenylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 585.3 |

TABLE D-3-continued

| Ex # | Structure | Chemical Name and Analytical Data |
| --- | --- | --- |
| D.3.4 | 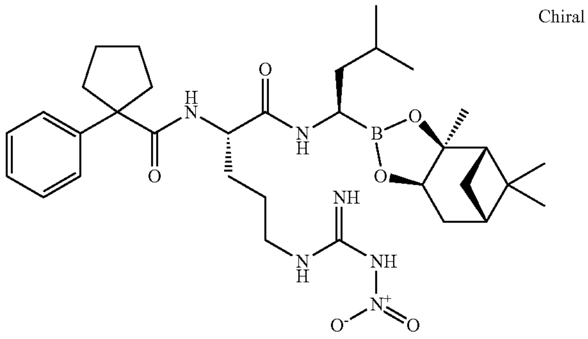 [SMILES: CC(C)C[C@H](NC(=O)[C@H](CCCNC(=N)N[N+](=O)[O-])NC(=O)C1(c2ccccc2)CCCC1)B1O[C@@H]2C[C@@H]3C[C@@H](C3(C)C)[C@]2(C)O1] Chiral | Chemical Name: 1-Phenylcyclopentanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 639.4 |
| D.3.5 | 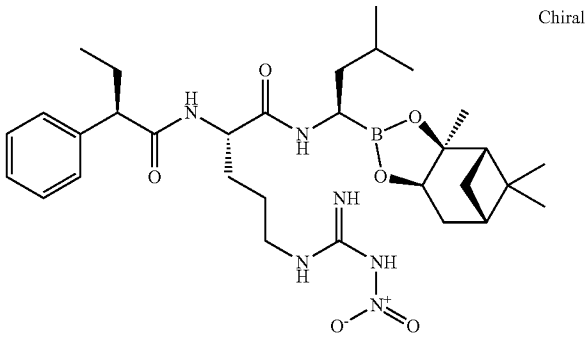 [SMILES: CC[C@@H](C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1)c1ccccc1] Chiral | Chemical Name: (2R)-2-Phenylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 613.4 |
| D.3.6 | 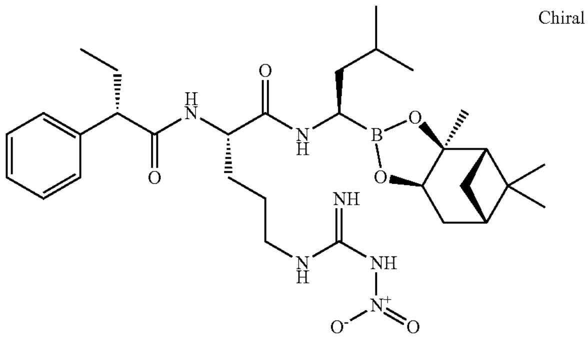 [SMILES: CC[C@H](C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1)c1ccccc1] Chiral | Chemical Name: (2S)-2-Phenylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 613.4 |
| D.3.7 | 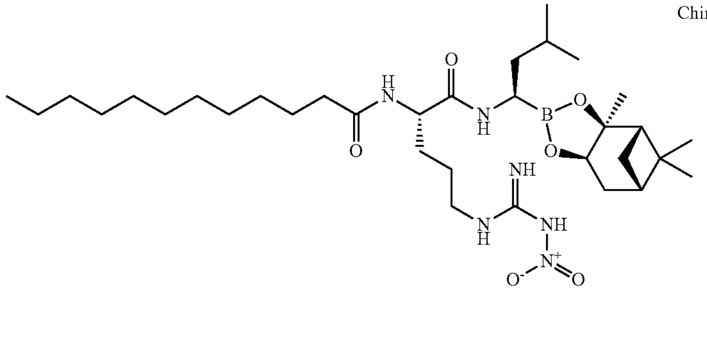 Chiral | Chemical Name: Dodecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 649.5 |

TABLE D-3-continued

| Ex # | Structure | Chemical Name and Analytical Data |
|---|---|---|
| D.3.8 | 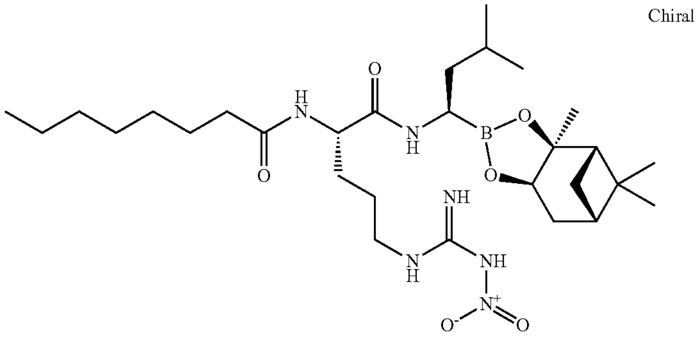 [SMILES: CCCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Octanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 593.4 |
| D.3.9 | 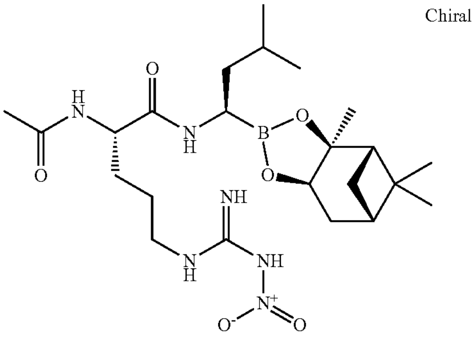 [SMILES: CC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 509.3 |
| D.3.10 | 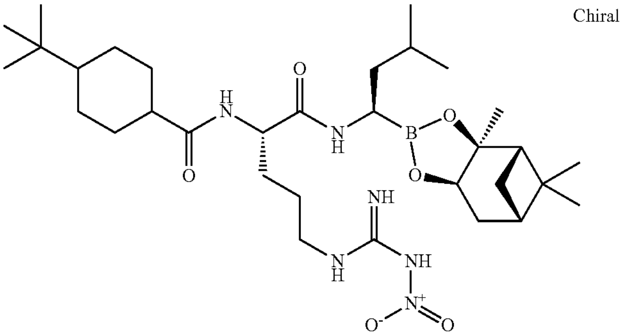 [SMILES: CC(C)C[C@H](NC(=O)[C@H](CCCNC(=N)N[N+](=O)[O-])NC(=O)C1CCC(C(C)(C)C)CC1)B1O[C@@H]2C[C@@H]3C[C@@H](C3(C)C)[C@]2(C)O1] Chiral | Chemical Name: 4-(1,1-Dimethylethyl)cyclohexanecarboxamide, N-[(1S)-1-[[[(1R)-1-[(3aS,4S,6S,7aR-) hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 633.5 |
| D.3.11 | 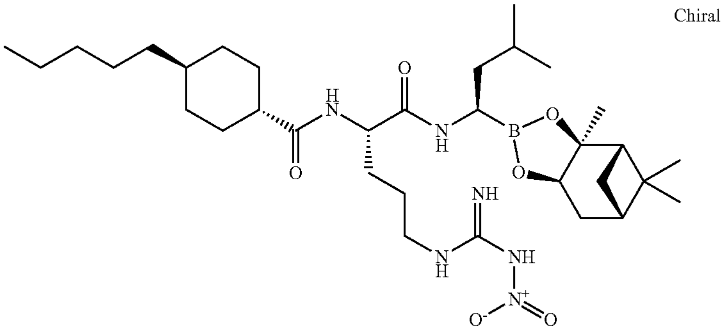 [SMILES: CCCCC[C@H]1CC[C@H](C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)CC1] Chiral | Chemical Name: trans-4-Pentylcyclohexanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 647.5 |

TABLE D-3-continued

| Ex # | Structure | Chemical Name and Analytical Data |
|---|---|---|
| D.3.12 | 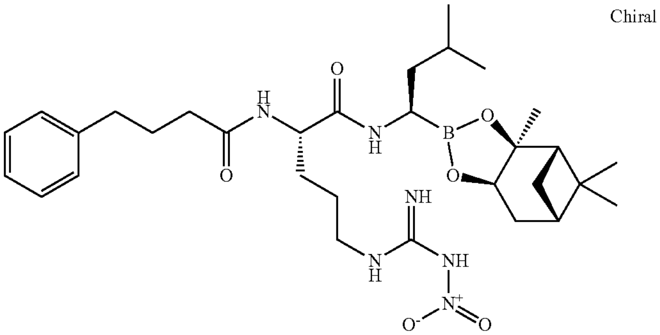 [SMILES: CC(C)C[C@H](NC(=O)[C@H](CCCNC(=N)N[N+](=O)[O-])NC(=O)CCCc1ccccc1)B1O[C@@H]2C[C@@H]3C[C@@H](C3(C)C)[C@]2(C)O1] Chiral | Chemical Name: 4-Phenylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 613.4 |
| D.3.13 | 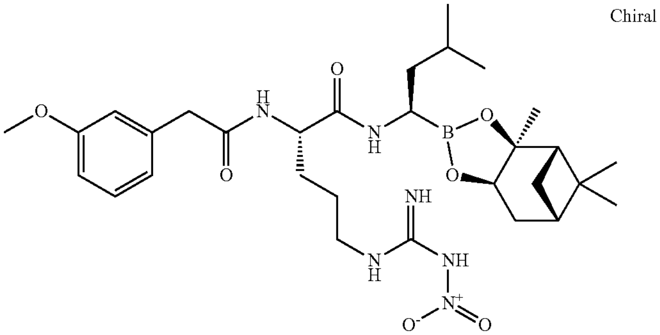 Chiral | Chemical Name: 2-(3-Methoxyphenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 615.3 |
| D.3.14 | 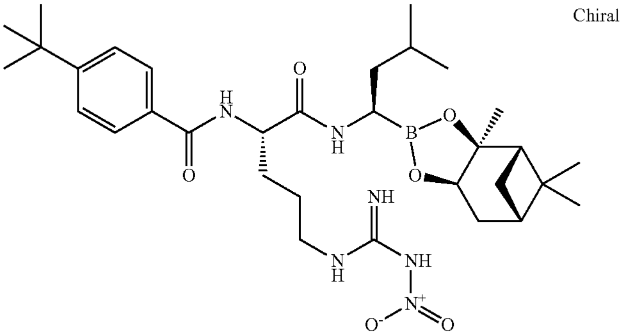 [SMILES: CC(C)C[C@H](NC(=O)[C@H](CCCNC(=N)N[N+](=O)[O-])NC(=O)c1ccc(C(C)(C)C)cc1)B1O[C@@H]2C[C@@H]3C[C@@H](C3(C)C)[C@]2(C)O1] Chiral | Chemical Name: 4-(1,1-Dimethylethyl)benzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 627.5 |
| D.3.15 | 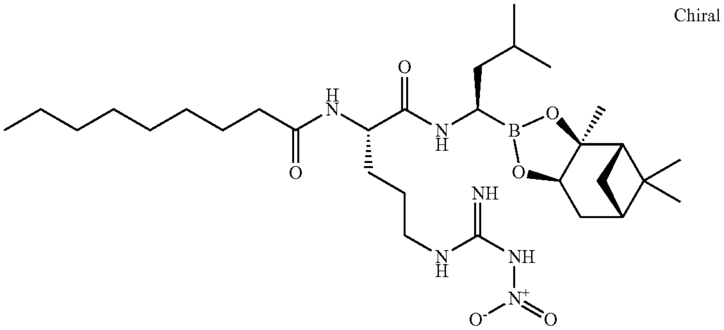 [SMILES: CCCCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Nonanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 607.4 |

TABLE D-3-continued

| Ex # | Structure | Chemical Name and Analytical Data |
| --- | --- | --- |
| D.3.16 | 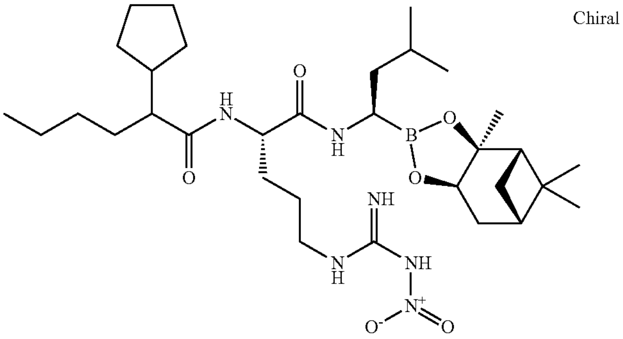 [SMILES: CCCCC(C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1)C1CCCC1] Chiral | Chemical Name: (RS)-2-Cyclopentylhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 633.5 |
| D.3.17 | 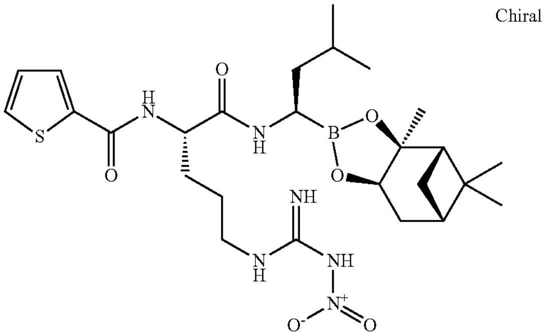 [SMILES: CC(C)C[C@H](NC(=O)[C@H](CCCNC(=N)N[N+](=O)[O-])NC(=O)c1cccs1)B1O[C@@H]2C[C@@H]3C[C@@H](C3(C)C)[C@]2(C)O1] Chiral | Chemical Name: Thiophene-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 577.2 |
| D.3.18 | 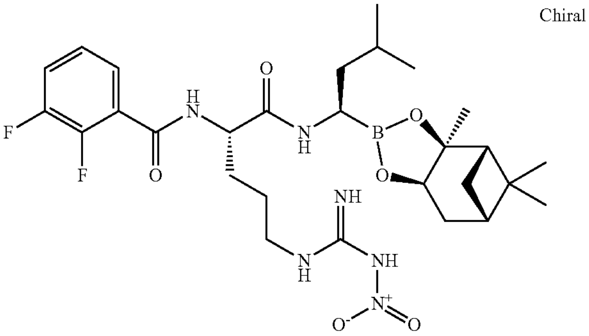 [SMILES: CC(C)C[C@H](NC(=O)[C@H](CCCNC(=N)N[N+](=O)[O-])NC(=O)c1cccc(F)c1F)B1O[C@@H]2C[C@@H]3C[C@@H](C3(C)C)[C@]2(C)O1] Chiral | Chemical Name: 2,3-Difluorobenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 607.3 |
| D.3.19 | 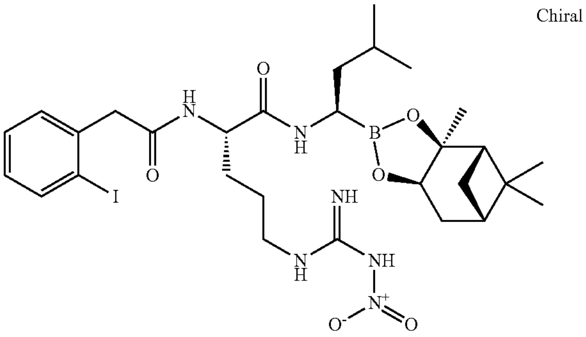 [SMILES: CC(C)C[C@H](NC(=O)[C@H](CCCNC(=N)N[N+](=O)[O-])NC(=O)Cc1ccccc1I)B1O[C@@H]2C[C@@H]3C[C@@H](C3(C)C)[C@]2(C)O1] Chiral | Chemical Name: 2-(2-Iodophenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 711.3 |

TABLE D-3-continued

| Ex # | Structure | Chemical Name and Analytical Data |
|---|---|---|
| D.3.20 | 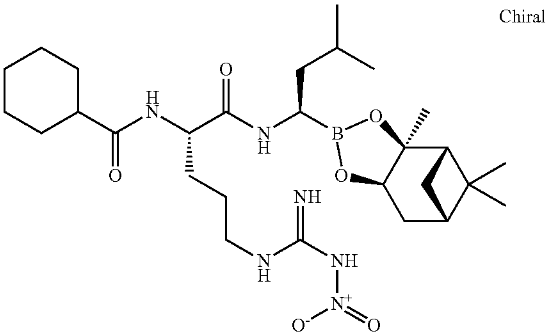 [SMILES: CC(C)C[C@H](NC(=O)[C@H](CCCNC(=N)N[N+](=O)[O-])NC(=O)C1CCCCC1)B1O[C@@H]2C[C@@H]3C[C@@H](C3(C)C)[C@]2(C)O1] Chiral | Chemical Name: Cyclohexanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 577.3 |
| D.3.21 | 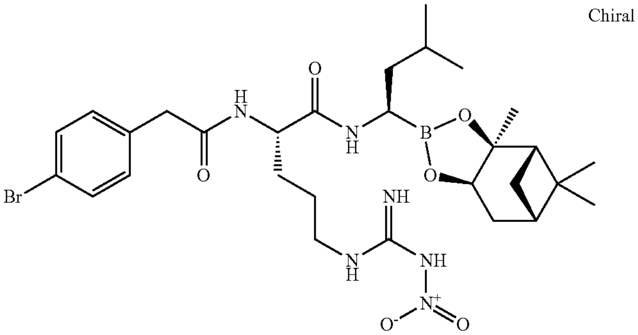 Chiral | Chemical Name: 2-(4-Bromophenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 663.2 |
| D.3.22 | 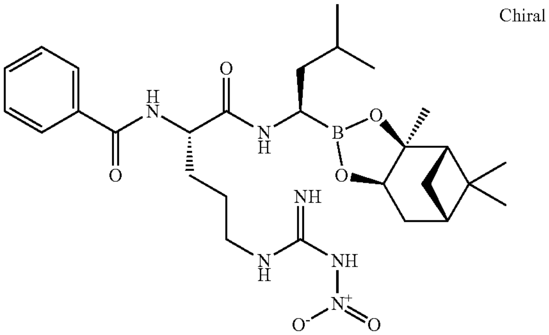 [SMILES: CC(C)C[C@H](NC(=O)[C@H](CCCNC(=N)N[N+](=O)[O-])NC(=O)c1ccccc1)B1O[C@@H]2C[C@@H]3C[C@@H](C3(C)C)[C@]2(C)O1] Chiral | Chemical Name: Benzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 571.3 |
| D.3.23 | 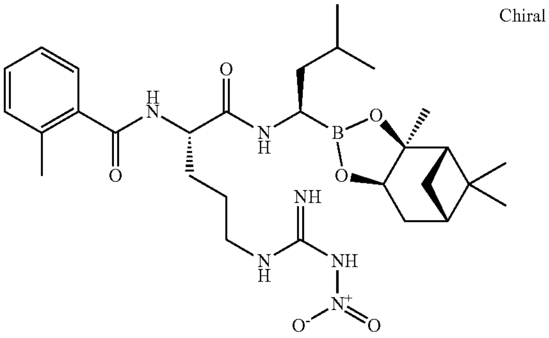 [SMILES: Cc1ccccc1C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 2-Methylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 585.3 |

TABLE D-3-continued

| Ex # | Structure | Chemical Name and Analytical Data |
|---|---|---|
| D.3.24 | 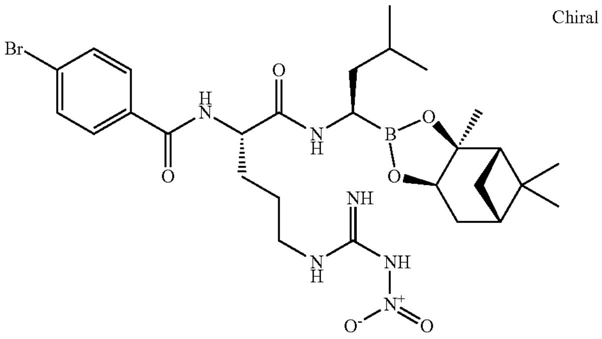 [SMILES: CC(C)C[C@H](NC(=O)[C@H](CCCNC(=N)N[N+](=O)[O-])NC(=O)c1ccc(Br)cc1)B1O[C@@H]2C[C@@H]3C[C@@H](C3(C)C)[C@]2(C)O1] Chiral | Chemical Name:<br>4-Bromobenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 649.3 |
| D.3.25 | 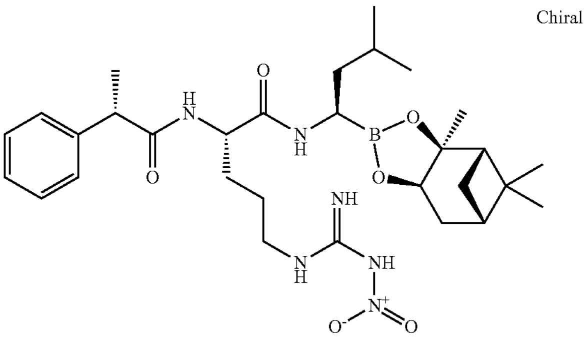 [SMILES: CC(C)C[C@H](NC(=O)[C@H](CCCNC(=N)N[N+](=O)[O-])NC(=O)[C@@H](C)c1ccccc1)B1O[C@@H]2C[C@@H]3C[C@@H](C3(C)C)[C@]2(C)O1] Chiral | Chemical Name:<br>(2S)-2-Phenylpropanamide, N-[(1S)-1-3a,5,5-trimethyl-4,6-methano-1,3,2-[[[(1R)-1-[(3aS,4S,6S,7aR)-hexahydro-benzodioxaborol-2-yl]-3-methylbutyl]amino]carbonyl]-4-[[imino(nitroamino)methyl]amino]butyl]<br>Analytical Data:<br>MS: MH+ 599.3 |
| D.3.26 | 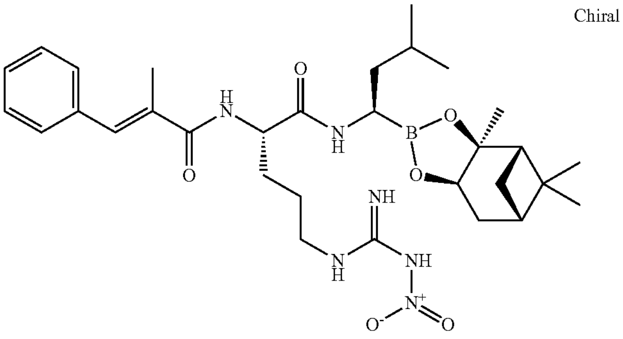 [SMILES: C/C(=C\c1ccccc1)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name:<br>(E)-2-Methyl-3-phenyl-acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 611.4 |
| D.3.27 | 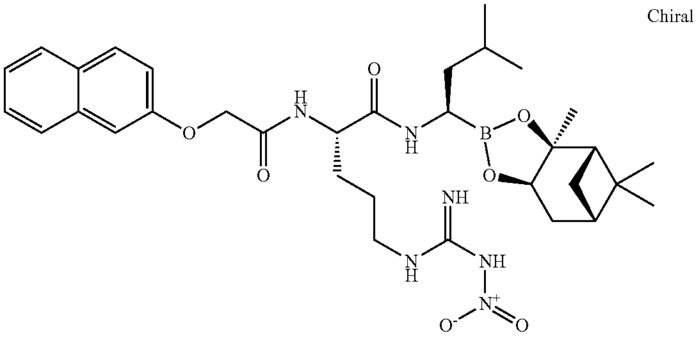 Chiral | Chemical Name:<br>2-[(Naphthalen-2-yl)oxy]acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 651.4 |

TABLE D-3-continued

| Ex # | Structure | Chemical Name and Analytical Data |
|---|---|---|
| D.3.28 | Chiral 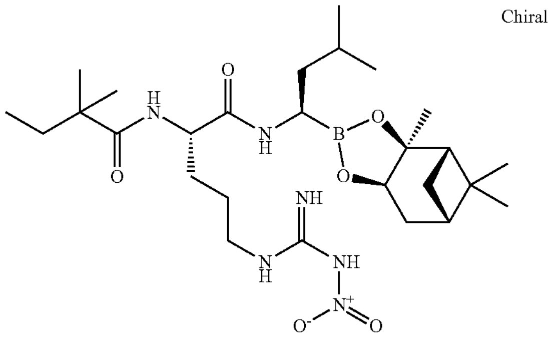 [SMILES: CCC(C)(C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] | Chemical Name: 2,2-Dimethylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 565.4 |
| D.3.29 | Chiral 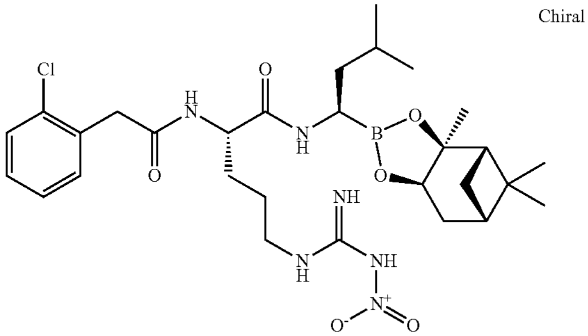 [SMILES: CC(C)C[C@H](NC(=O)[C@H](CCCNC(=N)N[N+](=O)[O-])NC(=O)Cc1ccccc1Cl)B1O[C@@H]2C[C@@H]3C[C@@H](C3(C)C)[C@]2(C)O1] | Chemical Name: 2-(2-Chlorophenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.3 |
| D.3.30 | Chiral 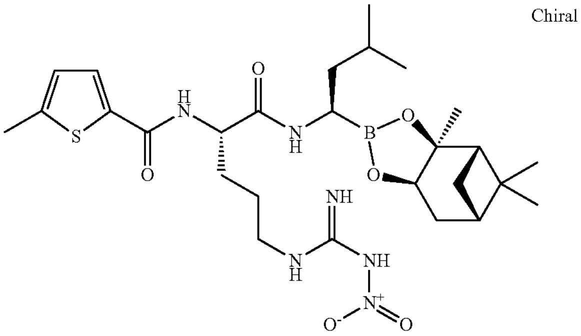 | Chemical Name: 5-Methylthiophene-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 591.3 |
| D.3.31 | Chiral 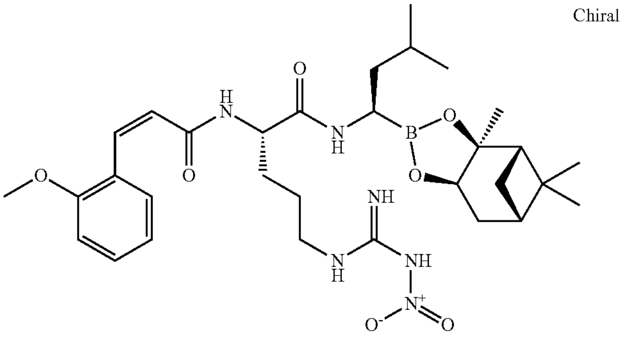 | Chemical Name: cis-3-(2-Methoxyphenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 627.4 |

TABLE D-3-continued

| Ex # | Structure | Chemical Name and Analytical Data |
| --- | --- | --- |
| D.3.32 | 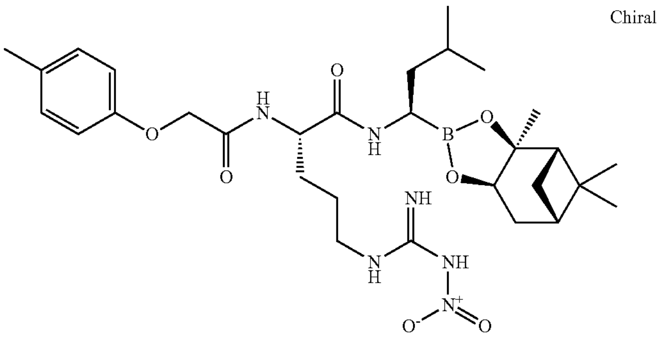 Chiral | Chemical Name: (2-Methylphenoxy)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 615.4 |
| D.3.33 | 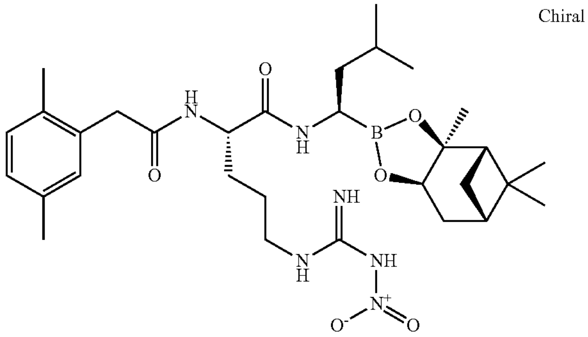 [SMILES: Cc1ccc(C)c(CC(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)c1] Chiral | Chemical Name: 2-(2,5-Dimethylphenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 613.4 |
| D.3.34 | 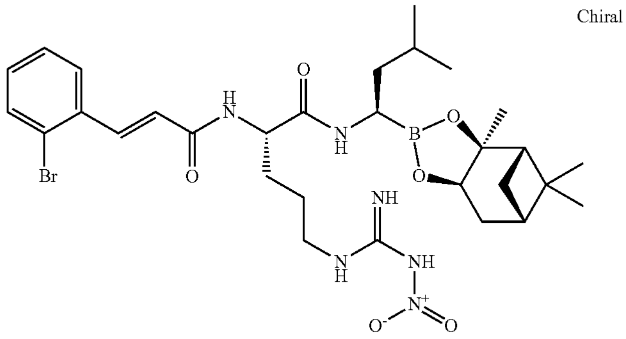 [SMILES: CC(C)C[C@H](NC(=O)[C@H](CCCNC(=N)N[N+](=O)[O-])NC(=O)/C=C/c1ccccc1Br)B1O[C@@H]2C[C@@H]3C[C@@H](C3(C)C)[C@]2(C)O1] Chiral | Chemical Name: trans-3-(2-Bromophenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 675.3 |
| D.3.35 | 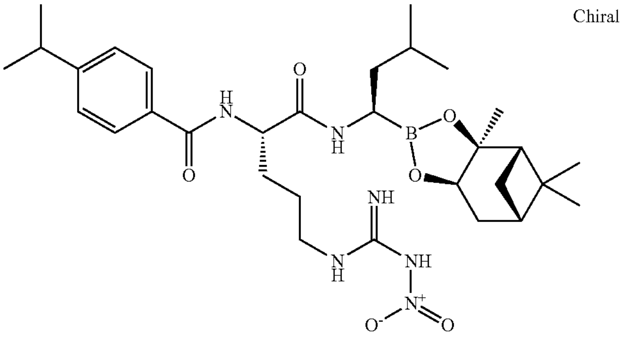 [SMILES: CC(C)C[C@H](NC(=O)[C@H](CCCNC(=N)N[N+](=O)[O-])NC(=O)c1ccc(C(C)C)cc1)B1O[C@@H]2C[C@@H]3C[C@@H](C3(C)C)[C@]2(C)O1] Chiral | Chemical Name: 4-Isopropylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 613.4 |

TABLE D-3-continued

| Ex # | Structure | Chemical Name and Analytical Data |
|---|---|---|
| D.3.36 | 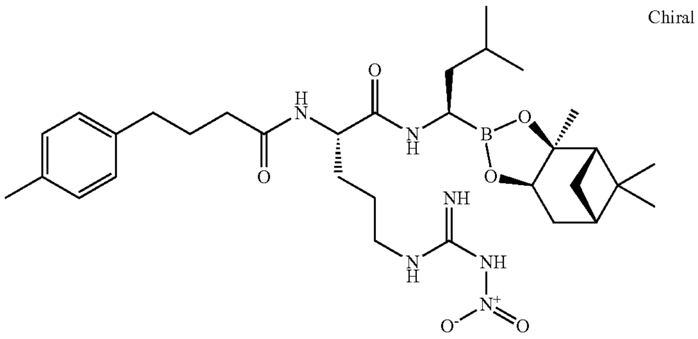 Chiral | Chemical Name: 4-(4-methylphenyl)butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-qimino(nitroamino)methyl]amino]butyl] Analytical Data: MS: MH+ 627.4 |
| D.3.37 | 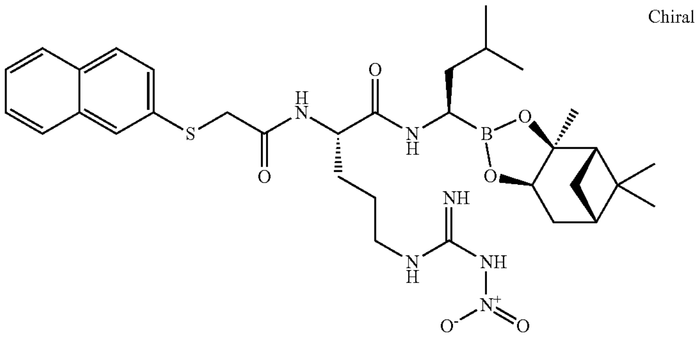 Chiral | Chemical Name: 2-(2-Naphthylsulfanyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 667.3 |
| D.3.38 | 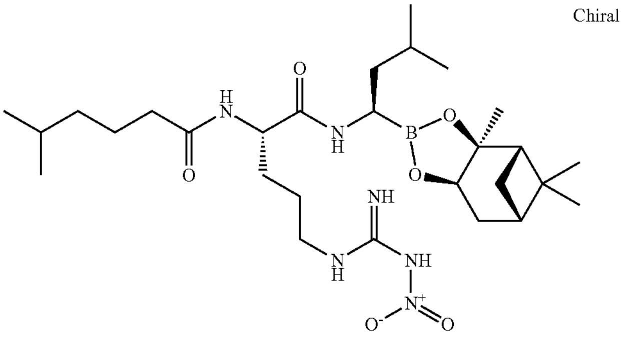 [SMILES: CC(C)CCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 5-Methylhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 579.4 |
| D.3.39 | 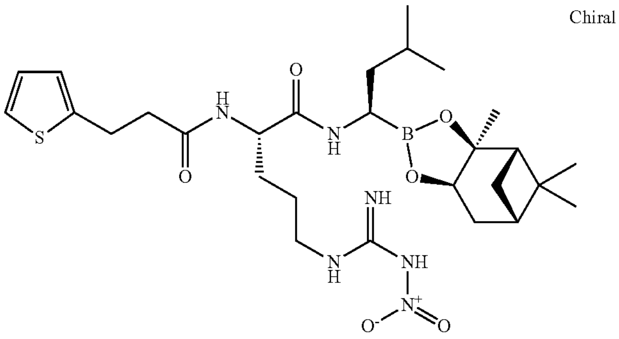 [SMILES: CC(C)C[C@H](NC(=O)[C@H](CCCNC(=N)N[N+](=O)[O-])NC(=O)CCc1cccs1)B1O[C@@H]2C[C@@H]3C[C@@H](C3(C)C)[C@]2(C)O1] Chiral | Chemical Name: 3-Thiophen-2-yl-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 605.4 |

TABLE D-3-continued

| Ex # | Structure | Chemical Name and Analytical Data |
| --- | --- | --- |
| D.3.40 | 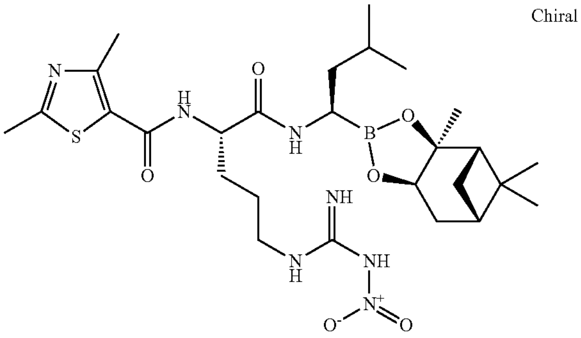 Chiral | Chemical Name: 2,4-Dimethylthiazole-5-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 606.4 |
| D.3.41 | 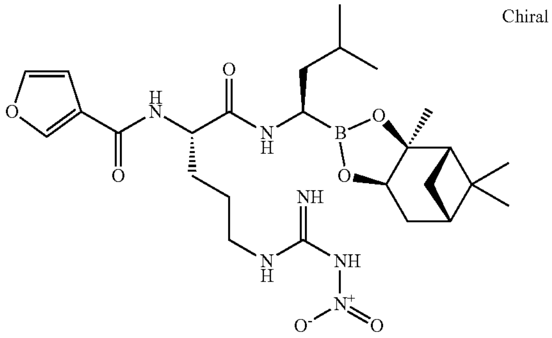 [SMILES: CC(C)C[C@H](NC(=O)[C@H](CCCNC(=N)N[N+](=O)[O-])NC(=O)c1ccoc1)B1O[C@@H]2C[C@@H]3C[C@@H](C3(C)C)[C@]2(C)O1] Chiral | Chemical Name: Furan-3-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 561.3 |
| D.3.42 | 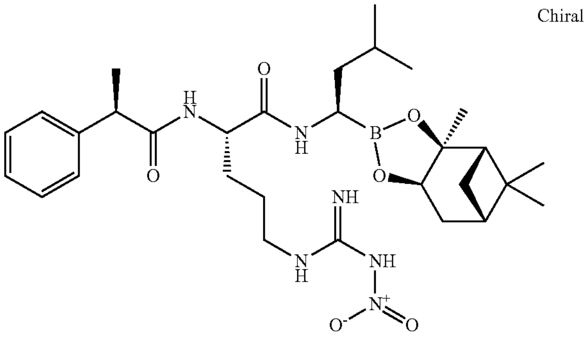 [SMILES: CC(C)C[C@H](NC(=O)[C@H](CCCNC(=N)N[N+](=O)[O-])NC(=O)[C@H](C)c1ccccc1)B1O[C@@H]2C[C@@H]3C[C@@H](C3(C)C)[C@]2(C)O1] Chiral | Chemical Name: (2R)-2-Phenylpropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 599.4 |
| D.3.43 | 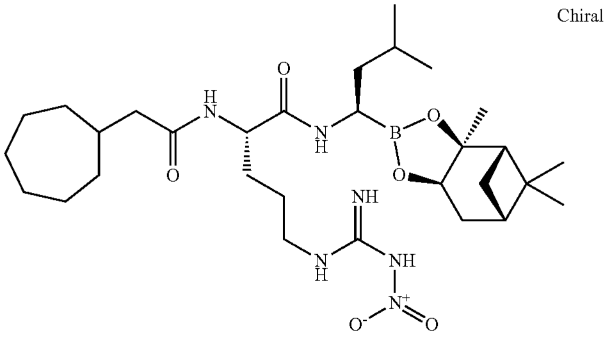 [SMILES: CC(C)C[C@H](NC(=O)[C@H](CCCNC(=N)N[N+](=O)[O-])NC(=O)CC1CCCCCC1)B1O[C@@H]2C[C@@H]3C[C@@H](C3(C)C)[C@]2(C)O1] Chiral | Chemical Name: 2-Cycloheptylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 605.4 |

TABLE D-3-continued

| Ex # | Structure | Chemical Name and Analytical Data |
|---|---|---|
| D.3.44 | 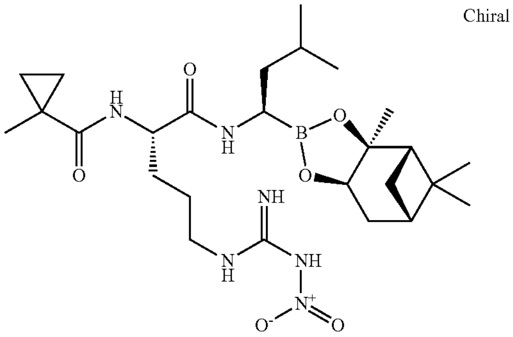 Chiral | Chemical Name: 1-Methylcyclopropanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 549.3 |
| D.3.45 | 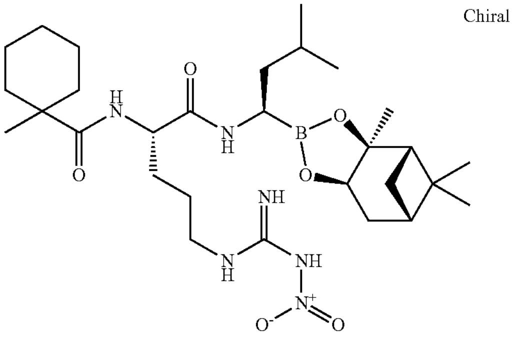 Chiral | Chemical Name: 1-Methyl-cyclohexanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 591.3 |
| D.3.46 | 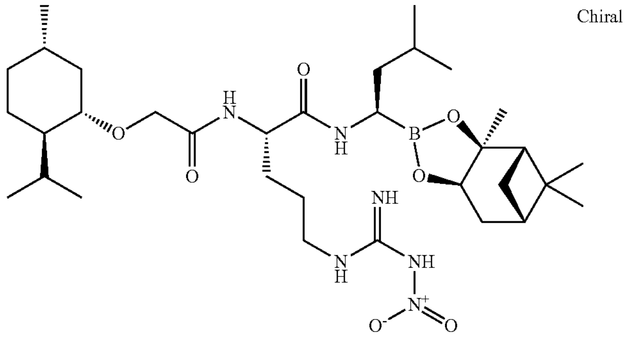 [SMILES: CC(C)C[C@H](NC(=O)[C@H](CCCNC(=N)N[N+](=O)[O-])NC(=O)CO[C@H]1C[C@@H](C)CC[C@@H]1C(C)C)B1O[C@@H]2C[C@@H]3C[C@@H](C3(C)C)[C@]2(C)O1] Chiral | Chemical Name: 2-[(1S,2R,5S)-2-isopropyl-5-methylcyclohexyl]oxyacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 663.3 |
| D.3.47 | 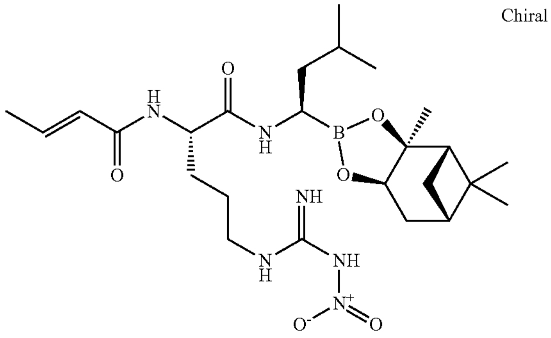 [SMILES: C/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (E)-2-Butenamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 535.6 |

TABLE D-3-continued

| Ex # | Structure | Chemical Name and Analytical Data |
|---|---|---|
| D.3.48 | 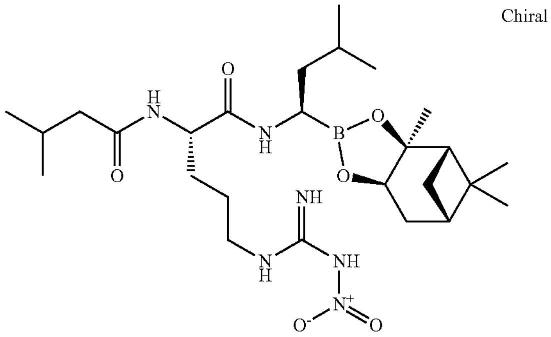 [SMILES: CC(C)CC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 3-Methylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 551.3 |
| D.3.49 | 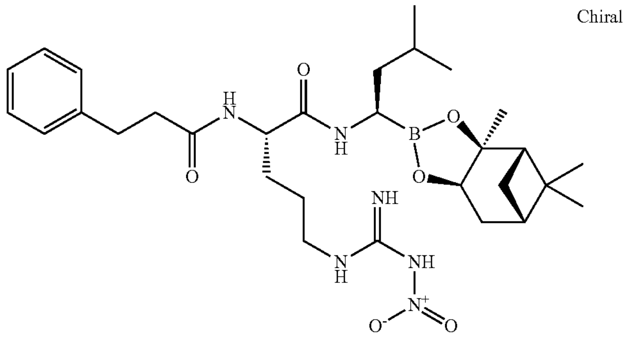 [SMILES: CC(C)C[C@H](NC(=O)[C@H](CCCNC(=N)N[N+](=O)[O-])NC(=O)CCc1ccccc1)B1O[C@@H]2C[C@@H]3C[C@@H](C3(C)C)[C@]2(C)O1] Chiral | Chemical Name: 3-Phenylpropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 599.3 |
| D.3.50 | 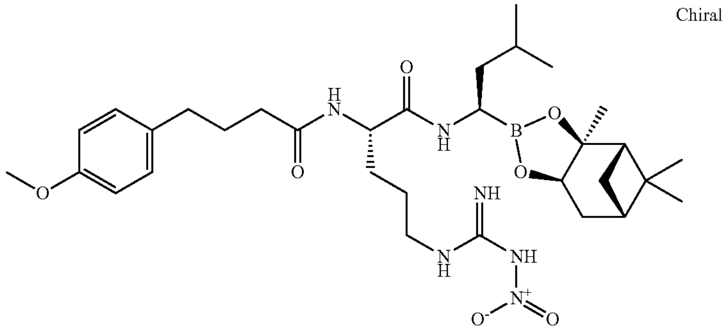 Chiral | Chemical Name: 4-(4-Methoxyphenyl)-butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 643.4 |
| D.3.51 | 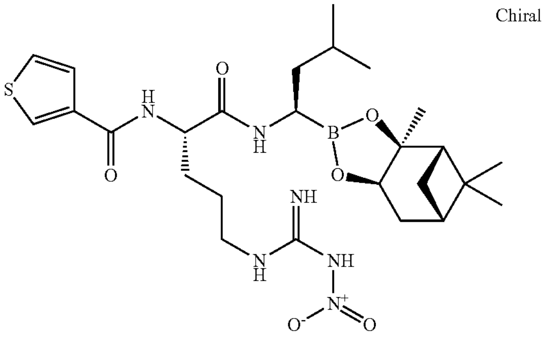 [SMILES: CC(C)C[C@H](NC(=O)[C@H](CCCNC(=N)N[N+](=O)[O-])NC(=O)c1ccsc1)B1O[C@@H]2C[C@@H]3C[C@@H](C3(C)C)[C@]2(C)O1] Chiral | Chemical Name: Thiophene-3-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 577.2 |

TABLE D-3-continued

| Ex # | Structure | Chemical Name and Analytical Data |
|---|---|---|
| D.3.52 | 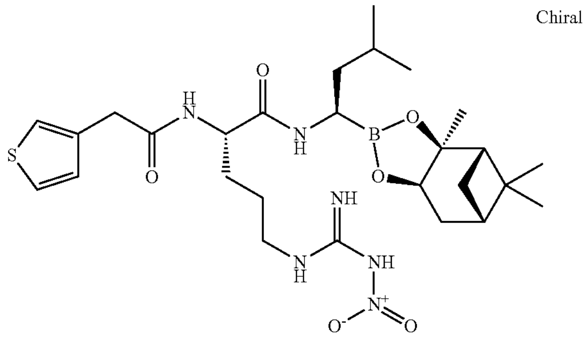 [SMILES: CC(C)C[C@H](NC(=O)[C@H](CCCNC(=N)N[N+](=O)[O-])NC(=O)Cc1ccsc1)B1O[C@@H]2C[C@@H]3C[C@@H](C3(C)C)[C@]2(C)O1] Chiral | Chemical Name: 2-Thiophen-3-yl-acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4- Analytical Data: MS: MH+ 591.4 |
| D.3.53 | 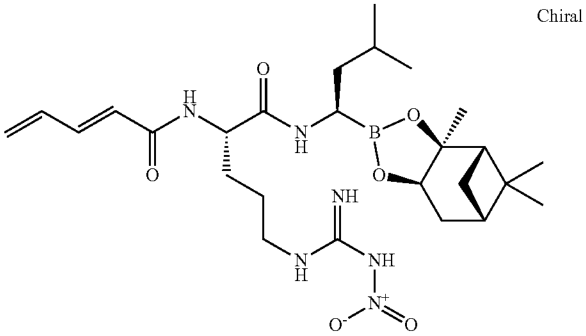 [SMILES: C=C/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (E)-Penta-2,4-dienoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 547.3 |
| D.3.54 | 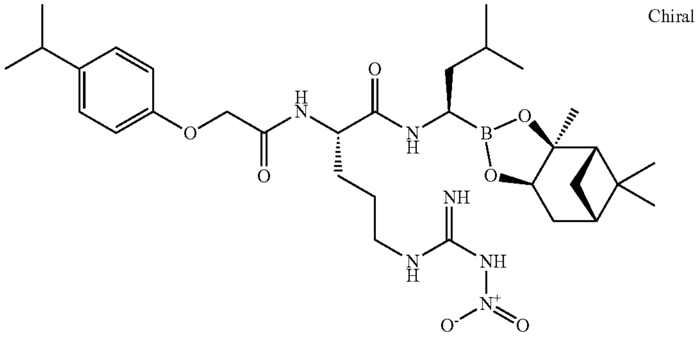 [SMILES: CC(C)C[C@H](NC(=O)[C@H](CCCNC(=N)N[N+](=O)[O-])NC(=O)COc1ccc(C(C)C)cc1)B1O[C@@H]2C[C@@H]3C[C@@H](C3(C)C)[C@]2(C)O1] Chiral | Chemical Name: 2-(4-Isopropylphenoxy)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 643.4 |
| D.3.55 | 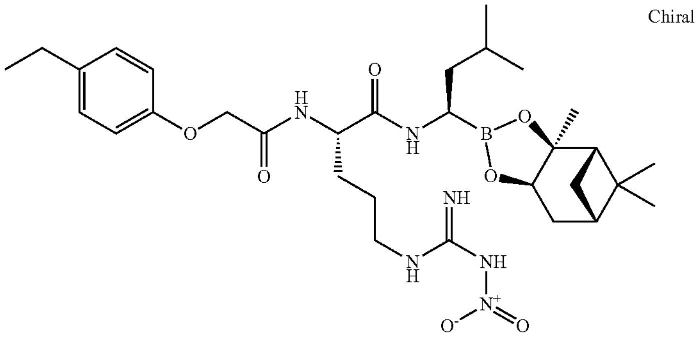 [SMILES: CCc1ccc(OCC(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: 2-(4-Ethylphenoxy)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 629.4 |

TABLE D-3-continued

| Ex # | Structure | Chemical Name and Analytical Data |
|---|---|---|
| D.3.56 | 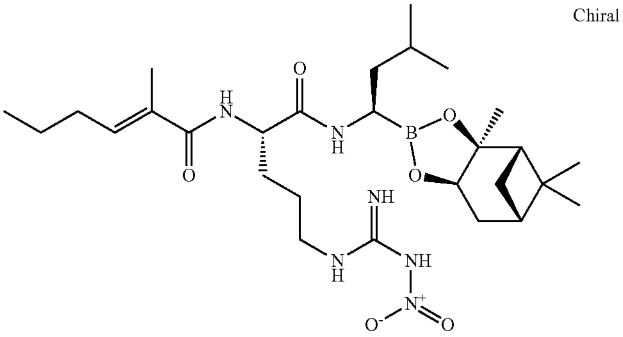 [SMILES: CCC/C=C(\C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (E)-2-Methylhex-2-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 577.2 |
| D.3.57 | 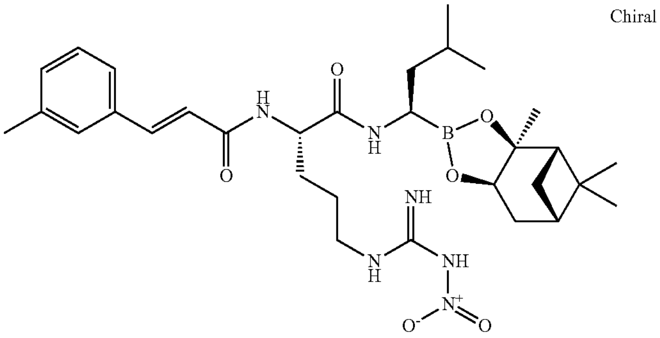 Chiral | Chemical Name: 3-(3-Methylphenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4- Analytical Data: MS: MH+ 611.4 |
| D.3.58 | 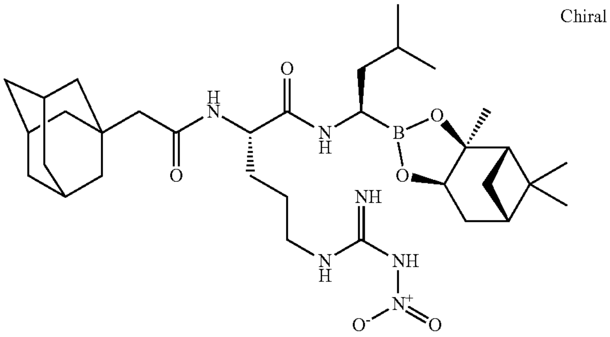 [SMILES: CC(C)C[C@H](NC(=O)[C@H](CCCNC(=N)N[N+](=O)[O-])NC(=O)CC12CC3CC(CC(C3)C1)C2)B1O[C@@H]2C[C@@H]3C[C@@H](C3(C)C)[C@]2(C)O1] Chiral | Chemical Name: 2-Adamantan-1-ylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 643.3 |
| D.3.59 | 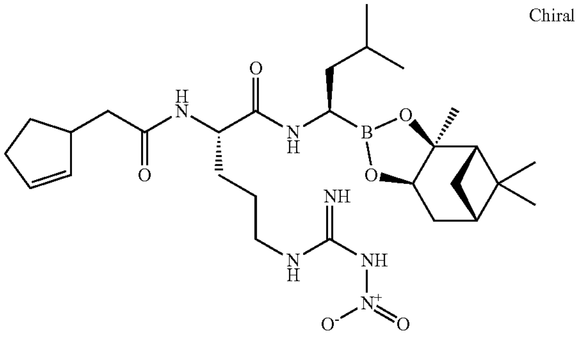 [SMILES: CC(C)C[C@H](NC(=O)[C@H](CCCNC(=N)N[N+](=O)[O-])NC(=O)CC1C=CCC1)B1O[C@@H]2C[C@@H]3C[C@@H](C3(C)C)[C@]2(C)O1] Chiral | Chemical Name: (RS)-2-Cyclopent-2-enylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 575.3 |

TABLE D-3-continued

| Ex # | Structure | Chemical Name and Analytical Data |
|---|---|---|
| D.3.60 | 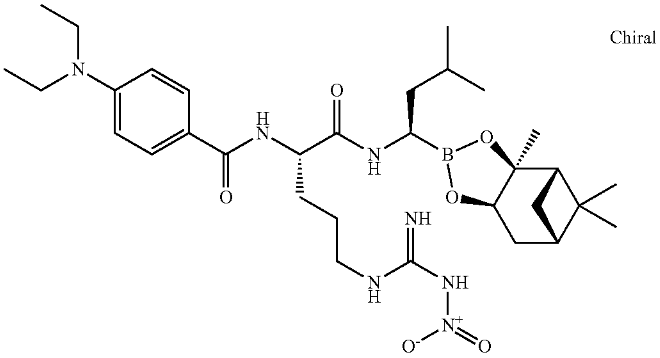 [SMILES: CCN(CC)c1ccc(C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: 4-Diethylaminobenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 642.4 |
| D.3.61 | 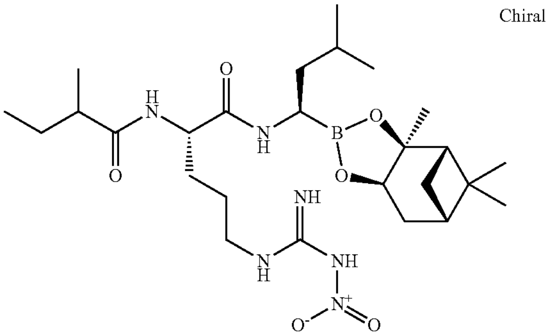 [SMILES: CCC(C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (RS)-2-Methylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 551.3 |
| D.3.62 | 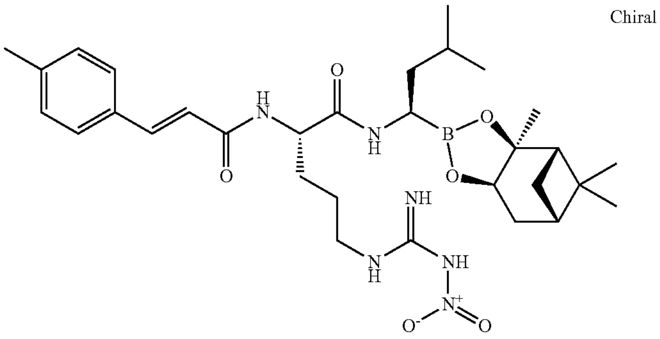 Chiral | Chemical Name: 3-(4-Methylphenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 611.4 |
| D.3.63 | 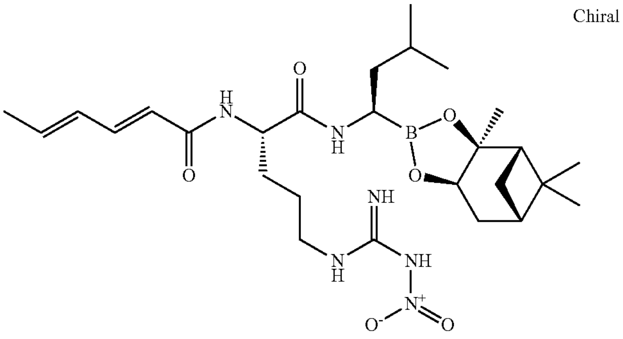 [SMILES: C/C=C/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Hexa-2,4-dienoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 561.5 |

TABLE D-3-continued

| Ex # | Structure | Chemical Name and Analytical Data |
| --- | --- | --- |
| D.3.64 | 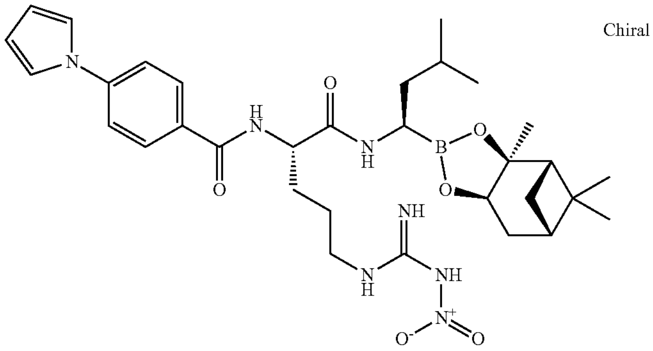 [SMILES: CC(C)C[C@H](NC(=O)[C@H](CCCNC(=N)N[N+](=O)[O-])NC(=O)c1ccc(-n2cccc2)cc1)B1O[C@@H]2C[C@@H]3C[C@@H](C3(C)C)[C@]2(C)O1] Chiral | Chemical Name: 4-Pyrrol-1-yl-benzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 636.3 |
| D.3.65 | 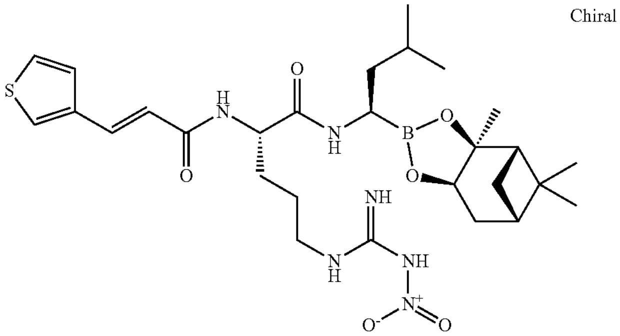 [SMILES: CC(C)C[C@H](NC(=O)[C@H](CCCNC(=N)N[N+](=O)[O-])NC(=O)/C=C/c1ccsc1)B1O[C@@H]2C[C@@H]3C[C@@H](C3(C)C)[C@]2(C)O1] Chiral | Chemical Name: (E)-3-Thiophen-3-yl-acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 603.3 |
| D.3.66 | 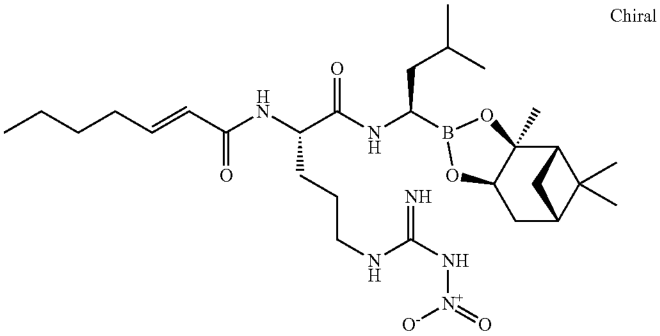 [SMILES: CCCC/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Hept-2-enamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 577.3 |
| D.3.67 | 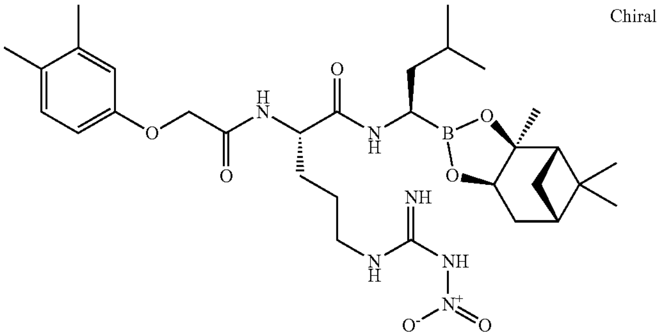 Chiral | Chemical Name: 2-(3,4-Dimethylphenoxy)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 629.3 |

TABLE D-3-continued

| Ex # | Structure | Chemical Name and Analytical Data |
|---|---|---|
| D.3.68 | 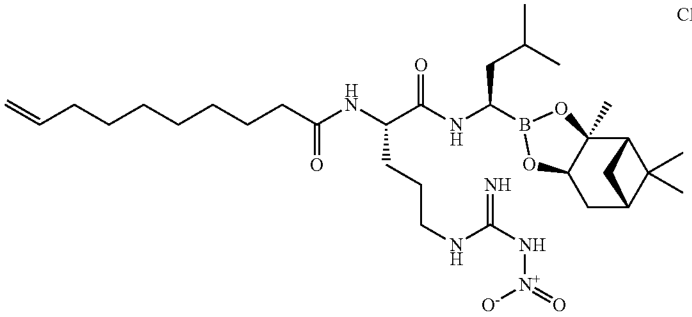 Chiral | Chemical Name:<br>Dec-9-enamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 619.3 |
| D.3.69 | 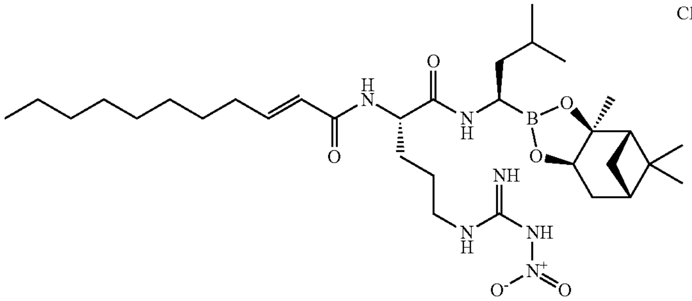 Chiral | Chemical Name:<br>(E)-Undec-2-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 633.4 |
| D.3.70 | 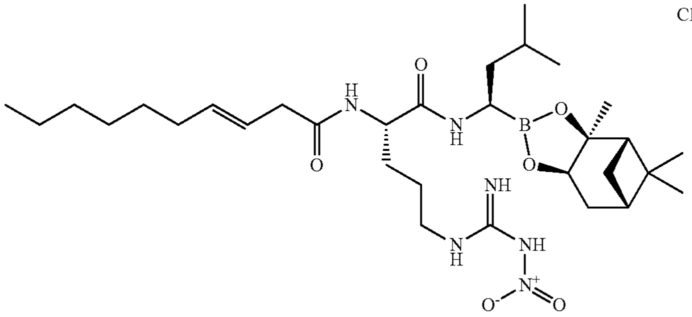 Chiral | Chemical Name:<br>(E)-Dec-3-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 619.4 |
| D.3.71 | 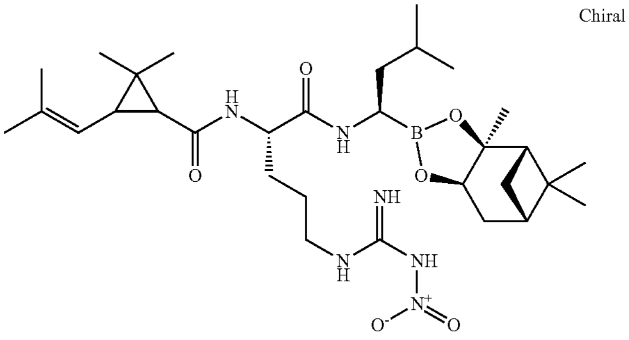 [SMILES: CC(C)=CC1C(C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)C1(C)C] Chiral | Chemical Name:<br>2,2-Dimethyl-3-(2-methylpropenyl)-cyclopropanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 616.9 |

TABLE D-3-continued

| Ex # | Structure | Chemical Name and Analytical Data |
| --- | --- | --- |
| D.3.72 | 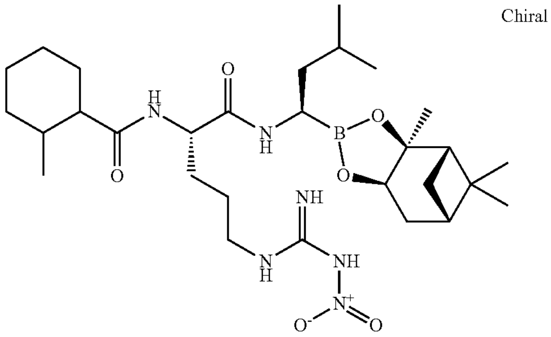 [SMILES: CC(C)C[C@H](NC(=O)[C@H](CCCNC(=N)N[N+](=O)[O-])NC(=O)C1CCCCC1C)B1O[C@@H]2C[C@@H]3C[C@@H](C3(C)C)[C@]2(C)O1] Chiral | Chemical Name: 2-Methylcyclohexanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 591.4 |
| D.3.73 | 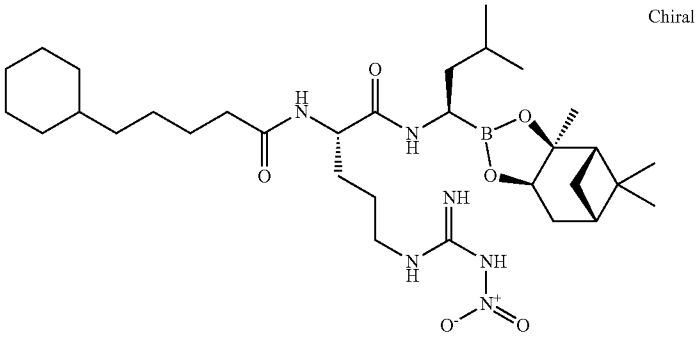 [SMILES: CC(C)C[C@H](NC(=O)[C@H](CCCNC(=N)N[N+](=O)[O-])NC(=O)CCCCC1CCCCC1)B1O[C@@H]2C[C@@H]3C[C@@H](C3(C)C)[C@]2(C)O1] Chiral | Chemical Name: 5-Cyclohexylpentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 633.5 |
| D.3.74 | 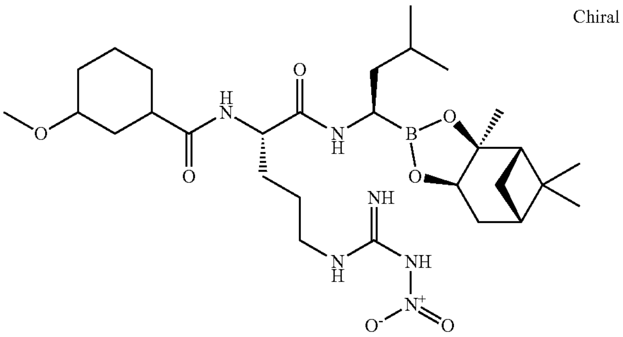 Chiral | Chemical Name: 3-Methoxycyclohexanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 607.3 |
| D.3.75 | 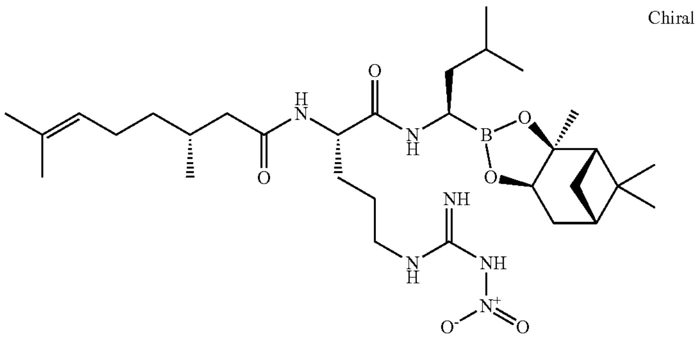 [SMILES: CC(C)=CCC[C@@H](C)CC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (3R)-3,7-Dimethyl-oct-6-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.4 |

TABLE D-3-continued

| Ex # | Structure | Chemical Name and Analytical Data |
|---|---|---|
| D.3.76 | 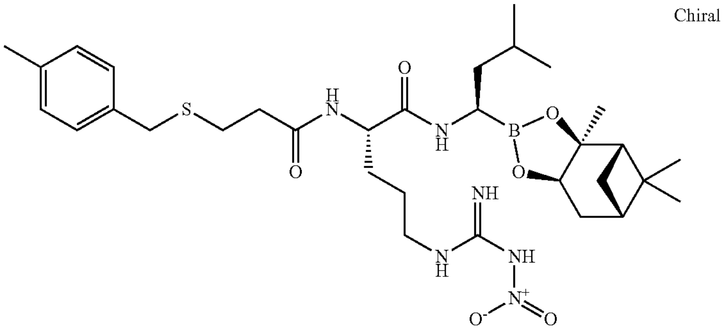 Chiral | Chemical Name: 3-[(4-methylbenzyl)sulfanyl]propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 659.3 |
| D.3.77 | 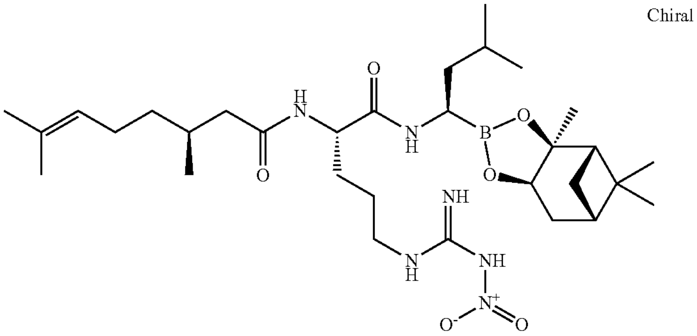 [SMILES: CC(C)=CCC[C@H](C)CC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (3S)-3,7-Dimethyl-oct-6-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.4 |
| D.3.78 | 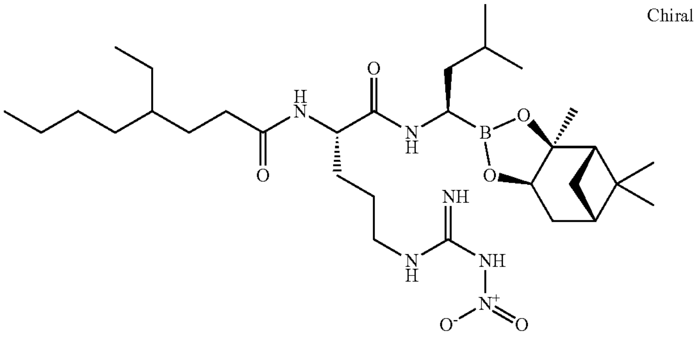 [SMILES: CCCCC(CC)CCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (RS)-4-Ethyloctanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 621.4 |
| D.3.79 | 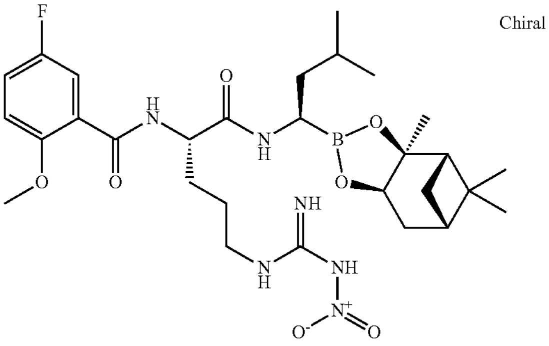 [SMILES: COc1ccc(F)cc1C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 5-Fluoro-2-methoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.2 |

TABLE D-3-continued

| Ex # | Structure | Chemical Name and Analytical Data |
|---|---|---|
| D.3.80 | 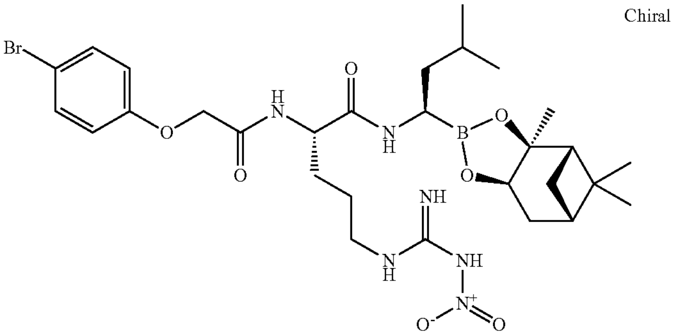 [SMILES: CC(C)C[C@H](NC(=O)[C@H](CCCNC(=N)N[N+](=O)[O-])NC(=O)COc1ccc(Br)cc1)B1O[C@@H]2C[C@@H]3C[C@@H](C3(C)C)[C@]2(C)O1] Chiral | Chemical Name: 2-(4-Bromophenoxy)-acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 679.6 |
| D.3.81 | 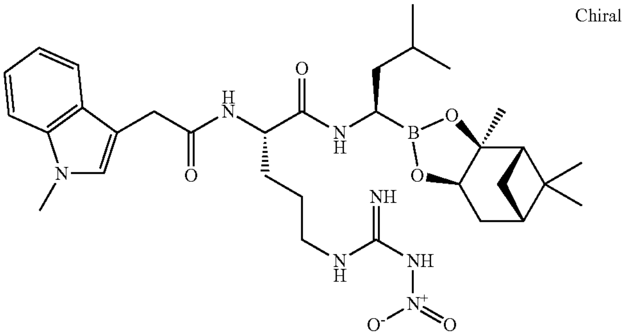 [SMILES: CC(C)C[C@H](NC(=O)[C@H](CCCNC(=N)N[N+](=O)[O-])NC(=O)Cc1cn(C)c2ccccc12)B1O[C@@H]2C[C@@H]3C[C@@H](C3(C)C)[C@]2(C)O1] Chiral | Chemical Name: 2-(1-Methyl-1H-indol-3-yl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 638.3 |
| D.3.82 | 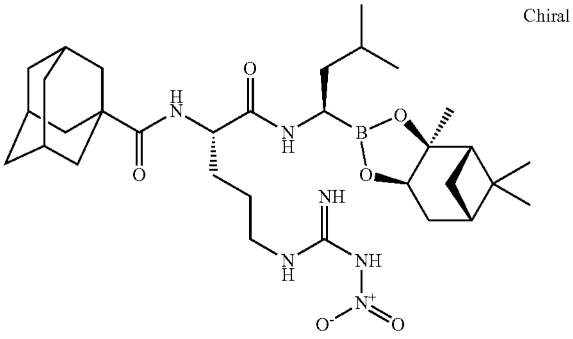 Chiral | Chemical Name: Hexahydro-2,5-methanopentalene-3a(1H)-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 615.2 |
| D.3.83 | 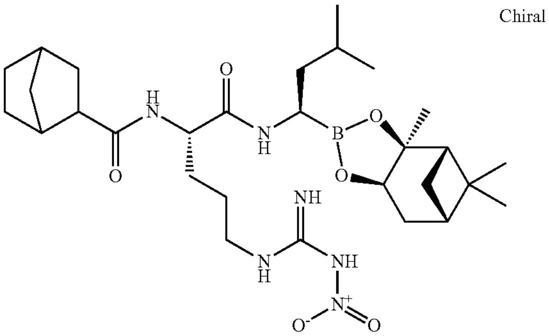 [SMILES: CC(C)C[C@H](NC(=O)[C@H](CCCNC(=N)N[N+](=O)[O-])NC(=O)C1CC2CCC1C2)B1O[C@@H]2C[C@@H]3C[C@@H](C3(C)C)[C@]2(C)O1] Chiral | Chemical Name: Bicyclo[2.2.1]heptane-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 589.2 |

TABLE D-3-continued

| Ex # | Structure | Chemical Name and Analytical Data |
|---|---|---|
| D.3.84 | 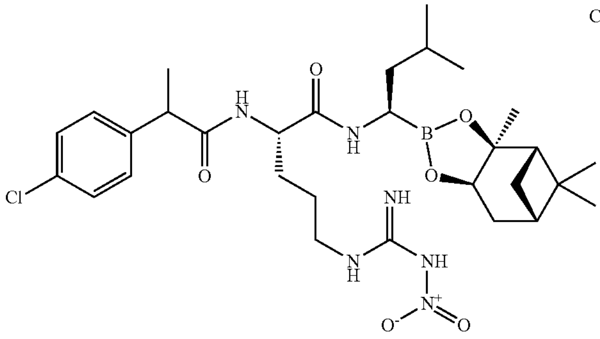 Chiral | Chemical Name: (RS)-2-(4-Chlorophenyl)propionamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 633.6 |
| D.3.85 | 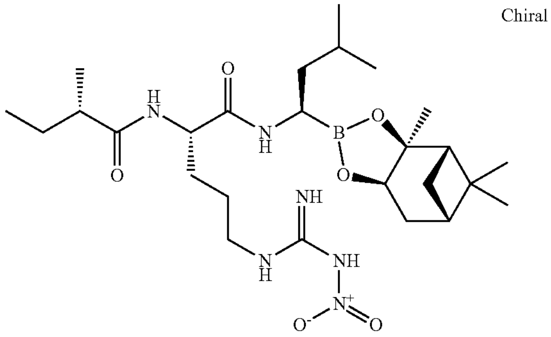 [SMILES: CC[C@H](C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (2S)-2-methylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 551.8 |
| D.3.86 | 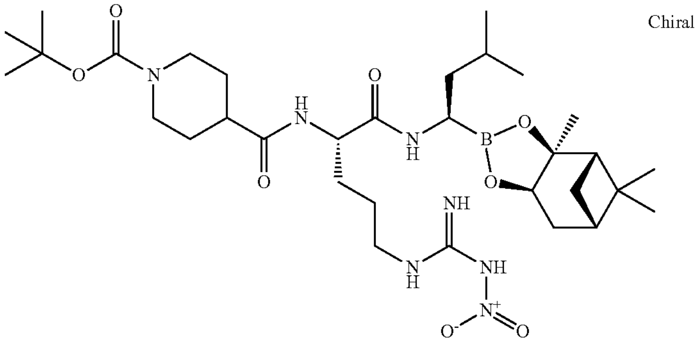 [SMILES: CC(C)C[C@H](NC(=O)[C@H](CCCNC(=N)N[N+](=O)[O-])NC(=O)C1CCN(C(=O)OC(C)(C)C)CC1)B1O[C@@H]2C[C@@H]3C[C@@H](C3(C)C)[C@]2(C)O1] Chiral | Chemical Name: (4RS)-1-[(1,1-dimethylethoxy)carbonyl]-piperidine-4-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 678.4 |
| D.3.87 | 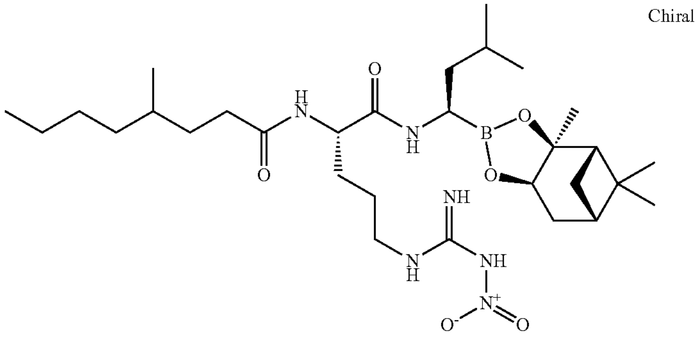 [SMILES: CCCCC(C)CCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (RS)-4-Methyloctanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-qimino(nitroamino)methyl]amino]butyl] Analytical Data: MS: MH+ 607.3 |

TABLE D-3-continued

| Ex # | Structure | Chemical Name and Analytical Data |
| --- | --- | --- |
| D.3.88 | 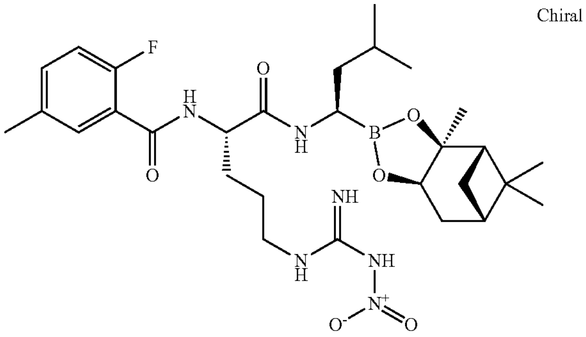 Chiral | Chemical Name: 2-Fluoro-5-methylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-qimino(nitroamino)methyl]amino]butyl] Analytical Data: MS: MH+ 603.2 |
| D.3.89 | 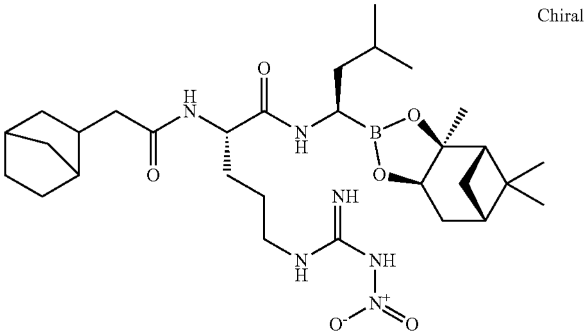 [SMILES: CC(C)C[C@H](NC(=O)[C@H](CCCNC(=N)N[N+](=O)[O-])NC(=O)CC1CC2CCC1C2)B1O[C@@H]2C[C@@H]3C[C@@H](C3(C)C)[C@]2(C)O1] Chiral | Chemical Name: 2-(Bicyclo[2.2.1]hept-2-yl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 603.8 |
| D.3.90 | 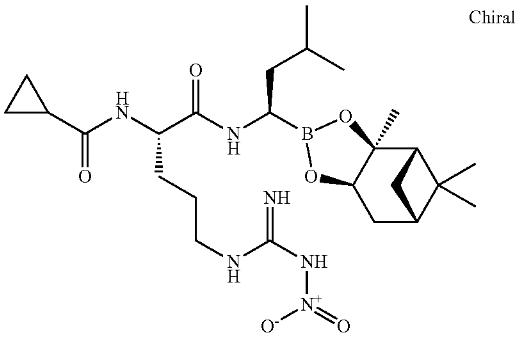 [SMILES: CC(C)C[C@H](NC(=O)[C@H](CCCNC(=N)N[N+](=O)[O-])NC(=O)C1CC1)B1O[C@@H]2C[C@@H]3C[C@@H](C3(C)C)[C@]2(C)O1] Chiral | Chemical Name: Cyclopropanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-qimino(nitroamino)methyl]amino]butyl] Analytical Data: MS: MH+ 535.3 |
| D.3.91 | 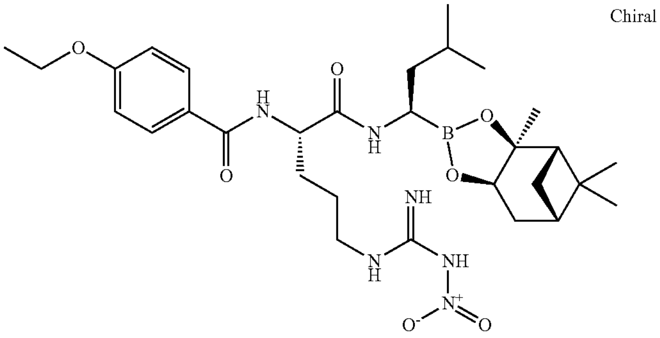 [SMILES: CCOc1ccc(C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: 4-Ethoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 615.2 |

TABLE D-3-continued

| Ex # | Structure | Chemical Name and Analytical Data |
| --- | --- | --- |
| D.3.92 | 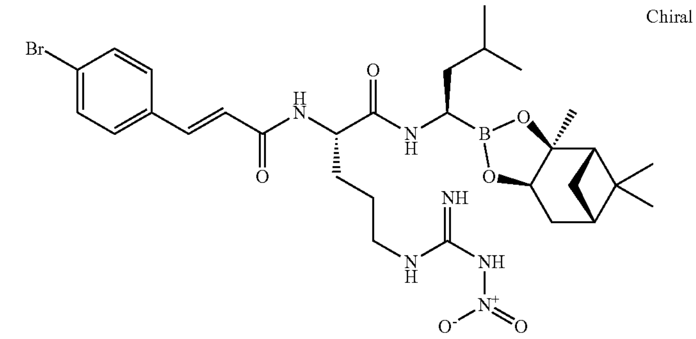 [SMILES: CC(C)C[C@H](NC(=O)[C@H](CCCNC(=N)N[N+](=O)[O-])NC(=O)/C=C/c1ccc(Br)cc1)B1O[C@@H]2C[C@@H]3C[C@@H](C3(C)C)[C@]2(C)O1] Chiral | Chemical Name: (E)-3-(4-Bromophenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 675.1 |
| D.3.93 | 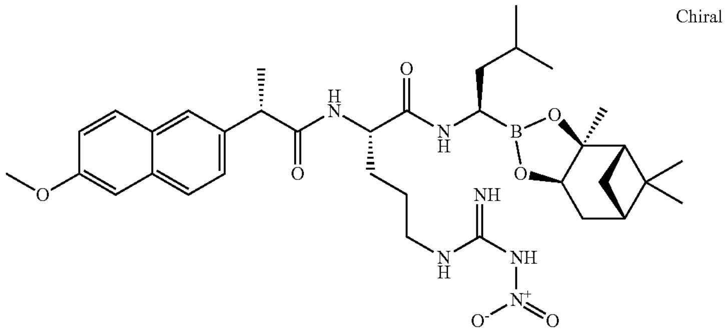 Chiral | Chemical Name: (2S)-2-(6-Methoxynaphthalen-2-yl)-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 679.3 |
| D.3.94 | 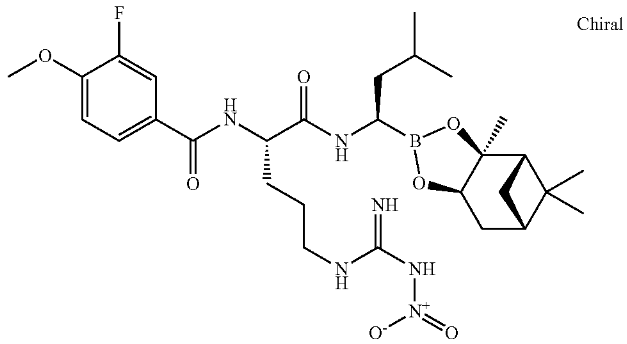 Chiral | Chemical Name: 3-Fluoro-4-methoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.5 |
| D.3.95 | 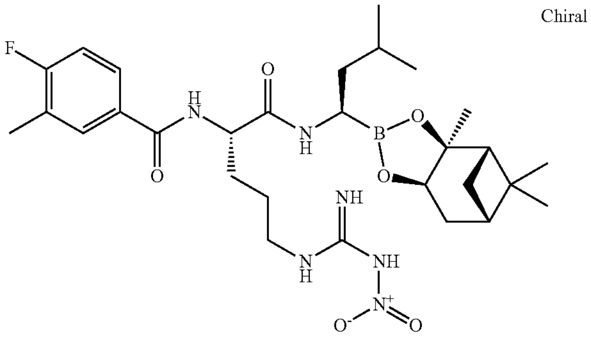 [SMILES: Cc1cc(C(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)ccc1F] Chiral | Chemical Name: 4-Fluoro-3-methylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 603.2 |

TABLE D-3-continued

| Ex # | Structure | Chemical Name and Analytical Data |
|---|---|---|
| D.3.96 | 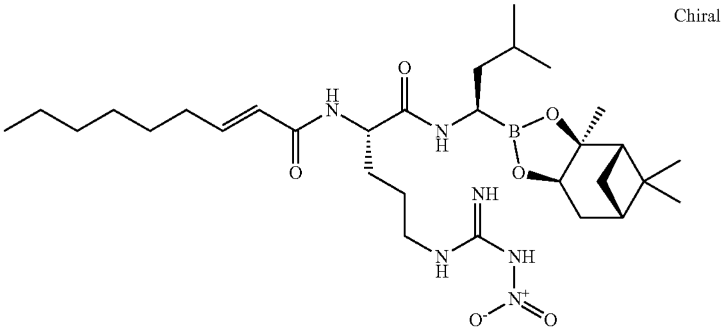 [SMILES: CCCCCC/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Non-2-enoic acid amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 605.3 |
| D.3.97 | 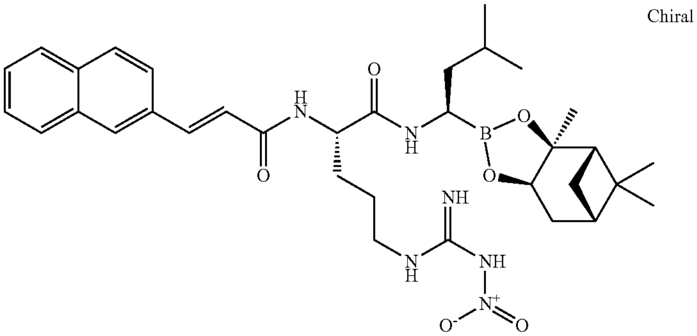 [SMILES: CC(C)C[C@H](NC(=O)[C@H](CCCNC(=N)N[N+](=O)[O-])NC(=O)/C=C/c1ccc2ccccc2c1)B1O[C@@H]2C[C@@H]3C[C@@H](C3(C)C)[C@]2(C)O1] Chiral | Chemical Name: (E)-3-(Naphthalen-2-yl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 647.3 |
| D.3.98 | 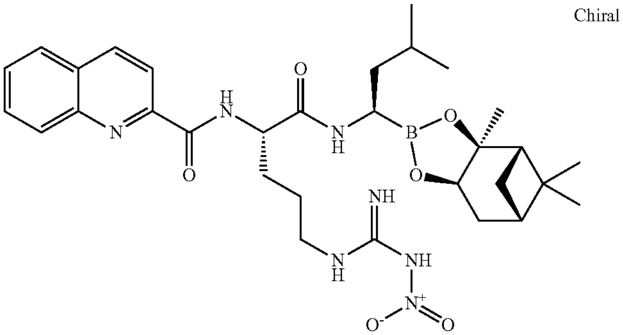 [SMILES: CC(C)C[C@H](NC(=O)[C@H](CCCNC(=N)N[N+](=O)[O-])NC(=O)c1ccc2ccccc2n1)B1O[C@@H]2C[C@@H]3C[C@@H](C3(C)C)[C@]2(C)O1] Chiral | Chemical Name: Quinoline-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 622.3 |
| D.3.99 | 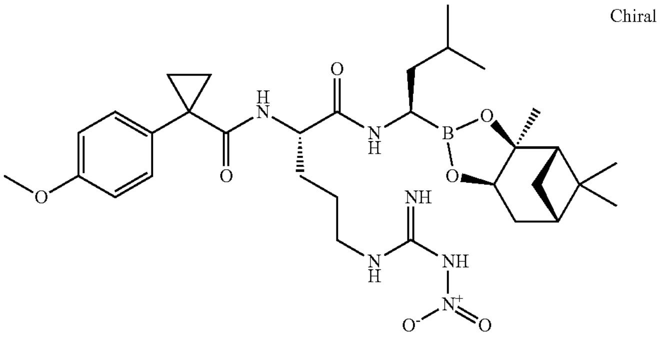 Chiral | Chemical Name: 1-(4-Methoxyphenyl)-cyclopropanecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 641.4 |

TABLE D-3-continued

| Ex # | Structure | Chemical Name and Analytical Data |
| --- | --- | --- |
| D.3.101 | 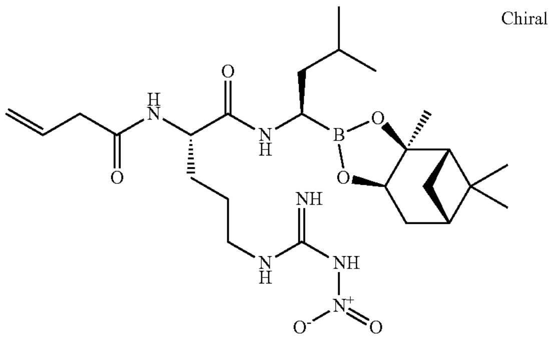 [SMILES: C=CCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 3-Butenamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 535.0 |
| D.3.102 | 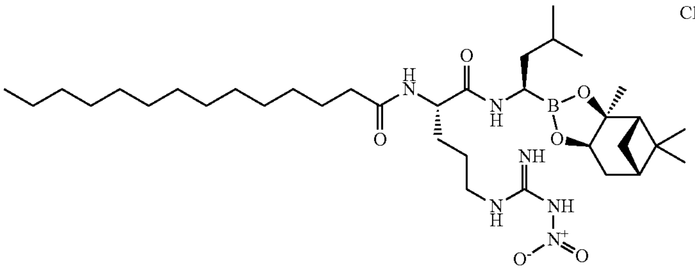 Chiral | Chemical Name: Tetradecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 677.3 |
| D.3.103 | 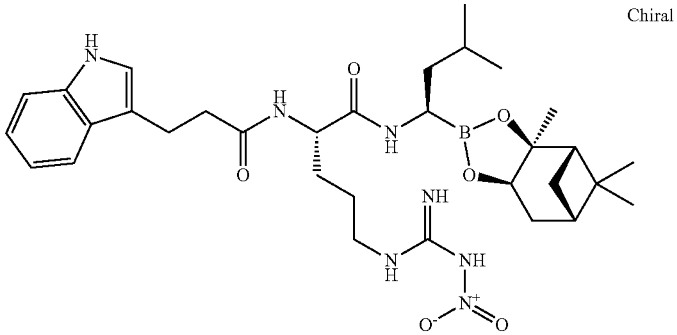 [SMILES: CC(C)C[C@H](NC(=O)[C@H](CCCNC(=N)N[N+](=O)[O-])NC(=O)CCc1c[nH]c2ccccc12)B1O[C@@H]2C[C@@H]3C[C@@H](C3(C)C)[C@]2(C)O1] Chiral | Chemical Name: 3-(1H-Indol-3-yl)-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 638.2 |
| D.3.104 | 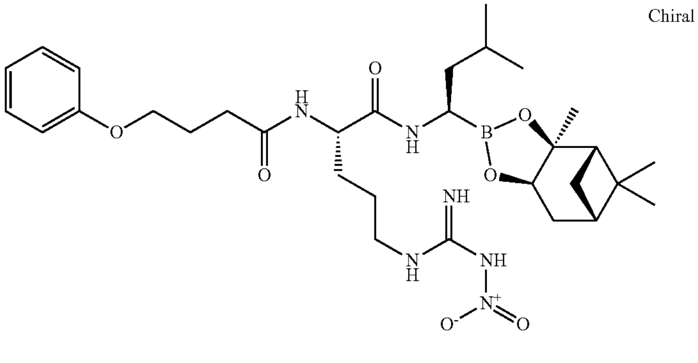 [SMILES: CC(C)C[C@H](NC(=O)[C@H](CCCNC(=N)N[N+](=O)[O-])NC(=O)CCCOc1ccccc1)B1O[C@@H]2C[C@@H]3C[C@@H](C3(C)C)[C@]2(C)O1] Chiral | Chemical Name: 4-Phenoxybutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 628.9 |

TABLE D-3-continued

| Ex # | Structure | Chemical Name and Analytical Data |
|---|---|---|
| D.3.105 | 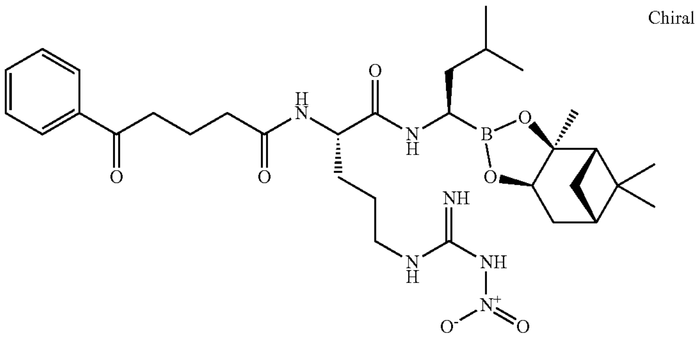 [SMILES: CC(C)C[C@H](NC(=O)[C@H](CCCNC(=N)N[N+](=O)[O-])NC(=O)CCCC(=O)c1ccccc1)B1O[C@@H]2C[C@@H]3C[C@@H](C3(C)C)[C@]2(C)O1] Chiral | Chemical Name: 5-Oxo-5-phenyl-pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 641.1 |
| D.3.106 | 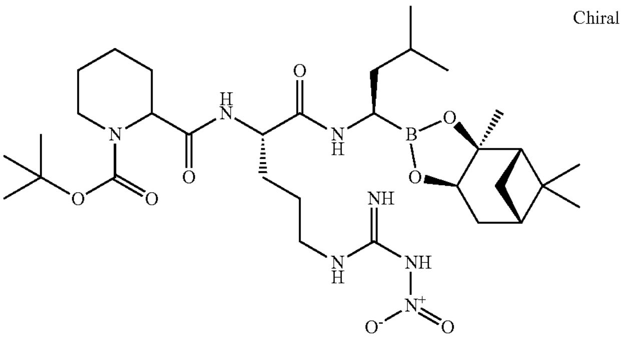 Chiral | Chemical Name: (2RS)-1-((1,1-dimethylethoxy)carbonyl)-piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 678.2 |
| D.3.107 | 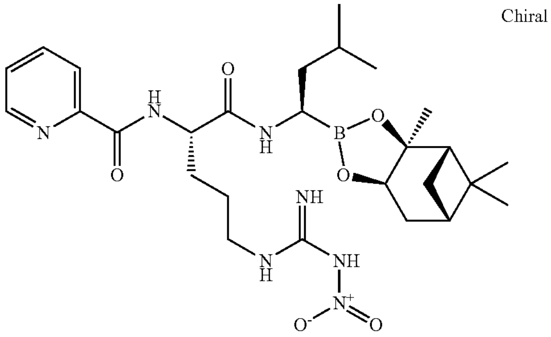 Chiral | Chemical Name: Pyridine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 572.1 |
| D.3.108 | 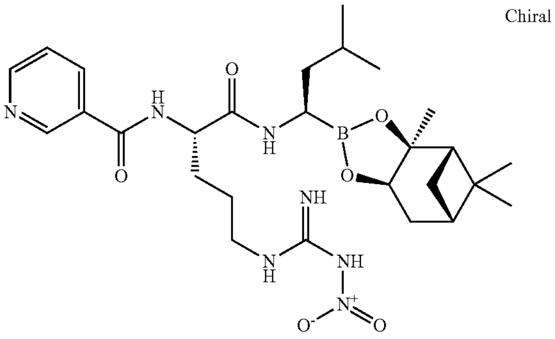 [SMILES: CC(C)C[C@H](NC(=O)[C@H](CCCNC(=N)N[N+](=O)[O-])NC(=O)c1cccnc1)B1O[C@@H]2C[C@@H]3C[C@@H](C3(C)C)[C@]2(C)O1] Chiral | Chemical Name: Pyridine-3-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 572.1 |

TABLE D-3-continued

| Ex # | Structure | Chemical Name and Analytical Data |
| --- | --- | --- |
| D.3.109 | 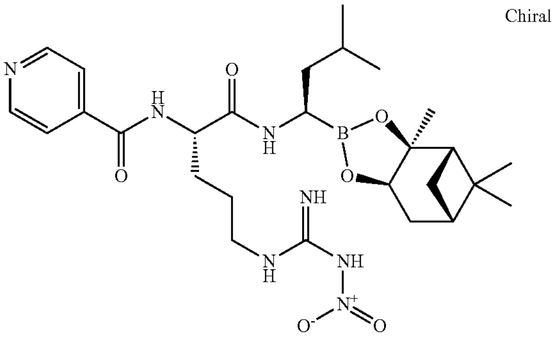 [SMILES: CC(C)C[C@H](NC(=O)[C@H](CCCNC(=N)N[N+](=O)[O-])NC(=O)c1ccncc1)B1O[C@@H]2C[C@@H]3C[C@@H](C3(C)C)[C@]2(C)O1] Chiral | Chemical Name:<br>Pyridine-4-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 572.5 |
| D.3.110 | 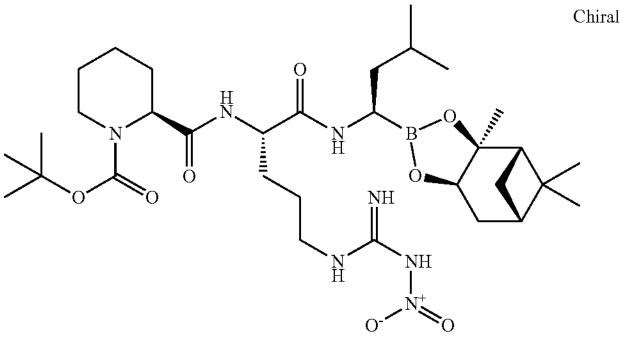 [SMILES: CC(C)C[C@H](NC(=O)[C@H](CCCNC(=N)N[N+](=O)[O-])NC(=O)[C@@H]1CCCCN1C(=O)OC(C)(C)C)B1O[C@@H]2C[C@@H]3C[C@@H](C3(C)C)[C@]2(C)O1] Chiral | Chemical Name:<br>(2S)-1-((1,1-dimethylethoxy)carbonyl)-piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 678.1 |
| D.3.111 | 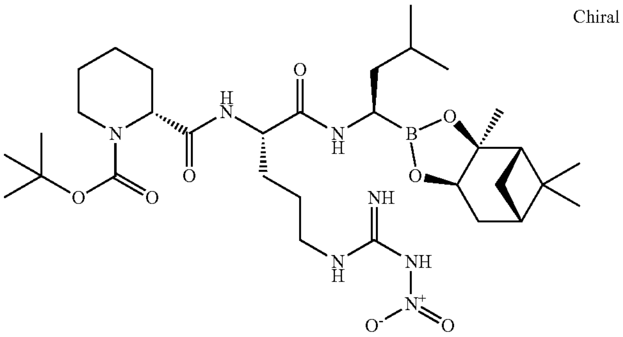 [SMILES: CC(C)C[C@H](NC(=O)[C@H](CCCNC(=N)N[N+](=O)[O-])NC(=O)[C@H]1CCCCN1C(=O)OC(C)(C)C)B1O[C@@H]2C[C@@H]3C[C@@H](C3(C)C)[C@]2(C)O1] Chiral | Chemical Name:<br>(2R)-1-((1,1-dimethylethoxy)carbonyl)-piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 678.2 |
| D.3.112 | 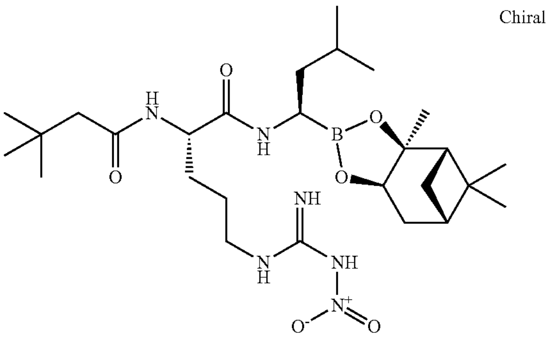 [SMILES: CC(C)C[C@H](NC(=O)[C@H](CCCNC(=N)N[N+](=O)[O-])NC(=O)CC(C)(C)C)B1O[C@@H]2C[C@@H]3C[C@@H](C3(C)C)[C@]2(C)O1] Chiral | Chemical Name:<br>3,3-Dimethyl-butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: MH+ 565.0 |

TABLE D-3-continued

| Ex # | Structure | Chemical Name and Analytical Data |
| --- | --- | --- |
| D.3.113 | 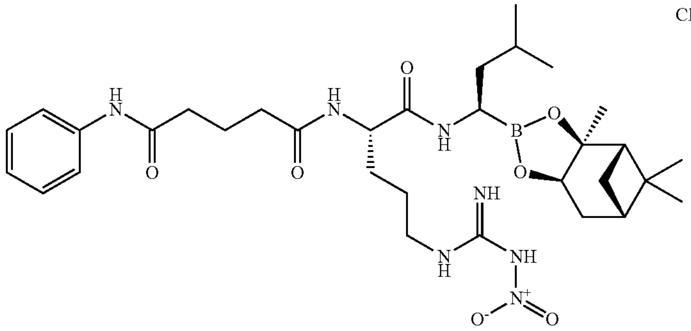 Chiral | Chemical Name: 4-[(Phenylamino)carbonyl]butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 656.2 |
| D.3.114 | 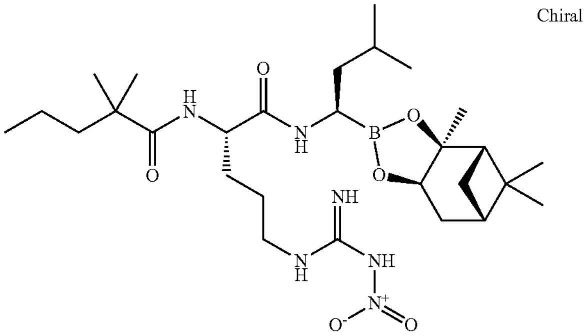 [SMILES: CCCC(C)(C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 2,2-Dimethylpentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 579.2 |
| D.3.115 | 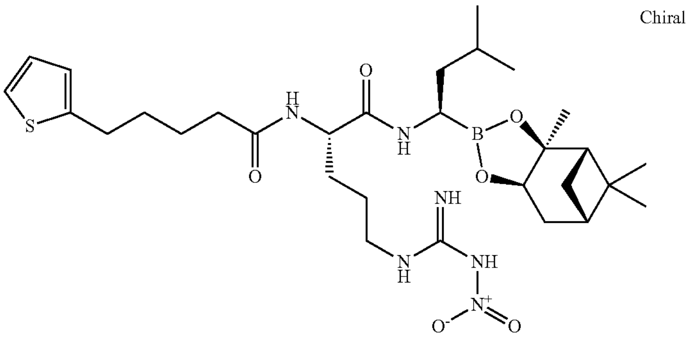 [SMILES: CC(C)C[C@H](NC(=O)[C@H](CCCNC(=N)N[N+](=O)[O-])NC(=O)CCCCc1cccs1)B1O[C@@H]2C[C@@H]3C[C@@H](C3(C)C)[C@]2(C)O1] Chiral | Chemical Name: 5-Thiophen-2-yl-pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 633.2 |
| D.3.116 | 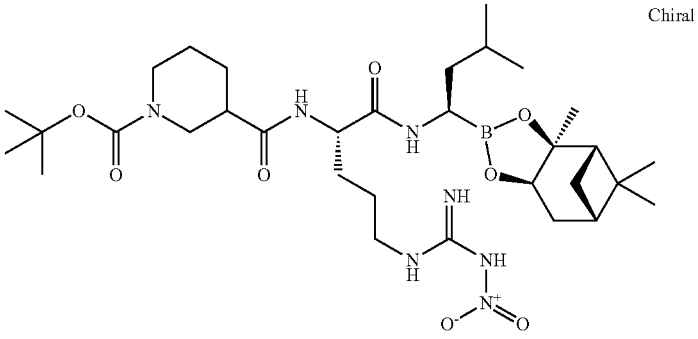 [SMILES: CC(C)C[C@H](NC(=O)[C@H](CCCNC(=N)N[N+](=O)[O-])NC(=O)C1CCCN(C(=O)OC(C)(C)C)C1)B1O[C@@H]2C[C@@H]3C[C@@H](C3(C)C)[C@]2(C)O1] Chiral | Chemical Name: (3RS)-1-((1,1-dimethylethoxy)carbonyl)-piperidine-3-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 678.0 |

TABLE D-3-continued

| Ex # | Structure | Chemical Name and Analytical Data |
|---|---|---|
| D.3.117 | 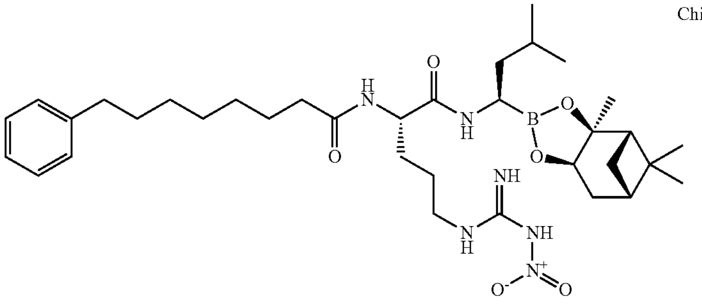 Chiral | Chemical Name: 8-Phenyl-octanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 669.1 |
| D.3.118 | 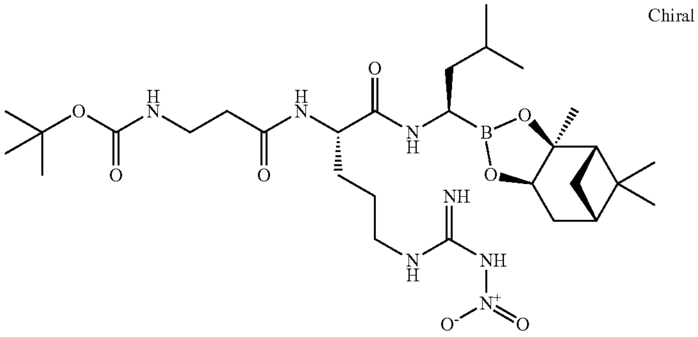 [SMILES: CC(C)C[C@H](NC(=O)[C@H](CCCNC(=N)N[N+](=O)[O-])NC(=O)CCNC(=O)OC(C)(C)C)B1O[C@@H]2C[C@@H]3C[C@@H](C3(C)C)[C@]2(C)O1] Chiral | Chemical Name: 3-[[(1,1-dimethylethoxy) carbonyl]amino]propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 638.2 |
| D.3.119 | 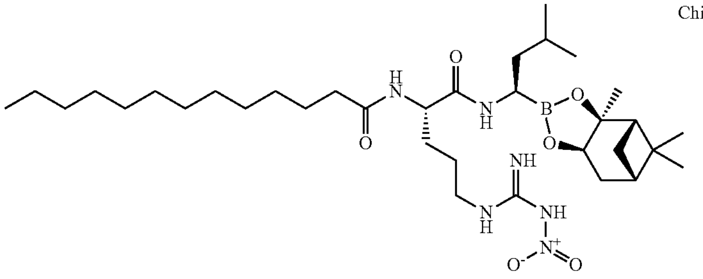 Chiral | Chemical Name: Tridecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 663.3 |
| D.3.120 | 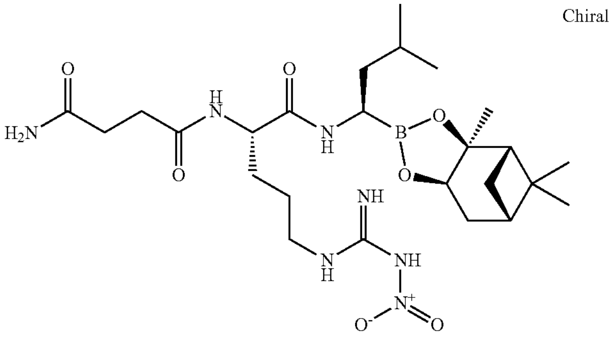 [SMILES: CC(C)C[C@H](NC(=O)[C@H](CCCNC(=N)N[N+](=O)[O-])NC(=O)CCC(N)=O)B1O[C@@H]2C[C@@H]3C[C@@H](C3(C)C)[C@]2(C)O1] Chiral | Chemical Name: Succinamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 566.1 |

TABLE D-3-continued

| Ex # | Structure | Chemical Name and Analytical Data |
|---|---|---|
| D.3.121 | 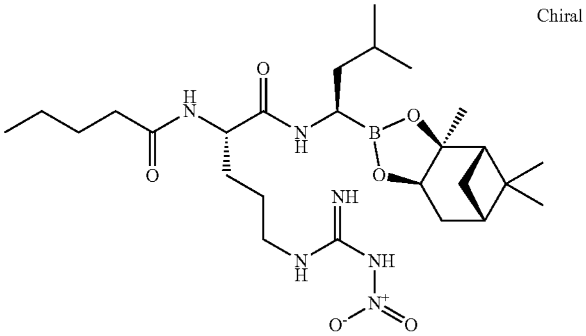 [SMILES: CCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 551.2 |
| D.3.122 | 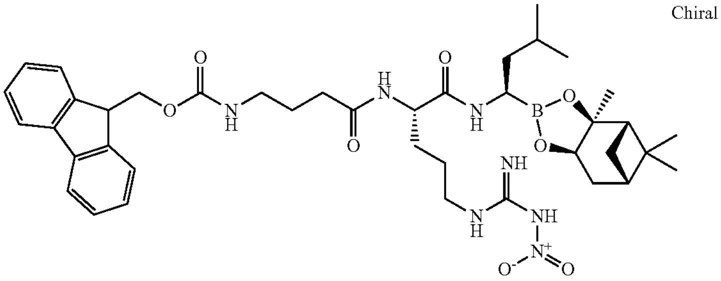 [SMILES: CC(C)C[C@H](NC(=O)[C@H](CCCNC(=N)N[N+](=O)[O-])NC(=O)CCCNC(=O)OCC1c2ccccc2-c2ccccc21)B1O[C@@H]2C[C@@H]3C[C@@H](C3(C)C)[C@]2(C)O1] Chiral | Chemical Name: [[[(9H-fluoren-9-yl)methoxy]carbonyl]amino]butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 775.3 |
| D.3.123 | 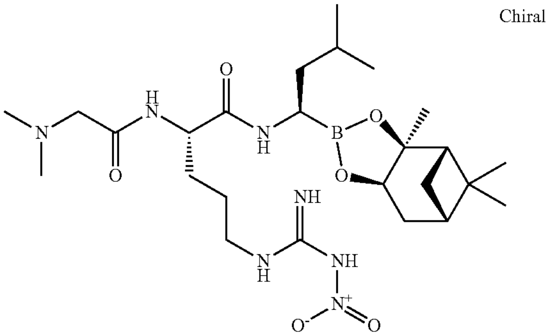 Chiral | Chemical Name: 2-(Dimethylamino)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 552.5 |
| D.3.124 | 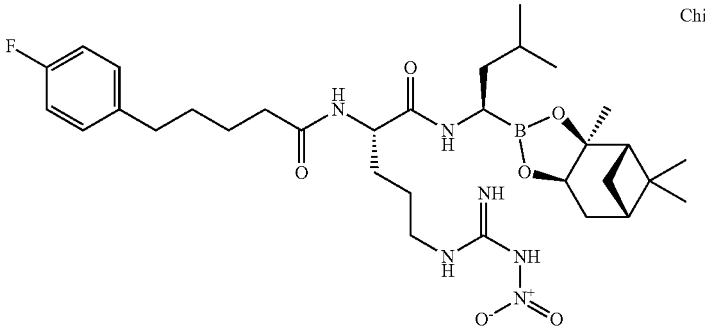 Chiral | Chemical Name: 5-(4-Fluorophenyl)-pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 645.2 |
| D.3.125 | 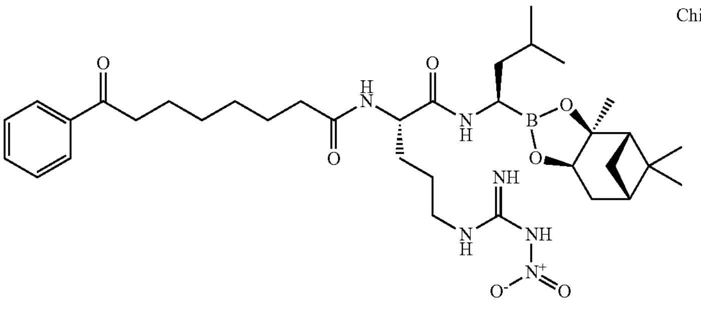 Chiral | Chemical Name: 8-Oxo-8-phenyloctanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 683.1 |

TABLE D-3-continued

| Ex # | Structure | Chemical Name and Analytical Data |
|---|---|---|
| D.3.126 | 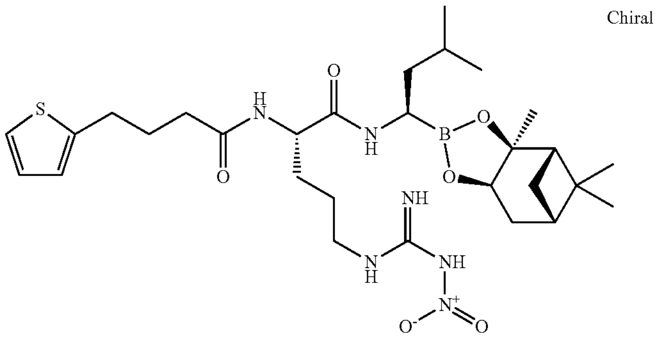 [SMILES: CC(C)C[C@H](NC(=O)[C@H](CCCNC(=N)N[N+](=O)[O-])NC(=O)CCCc1cccs1)B1O[C@@H]2C[C@@H]3C[C@@H](C3(C)C)[C@]2(C)O1] Chiral | Chemical Name: 4-(Thiophen-2-yl)butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 619.0 |
| D.3.127 | 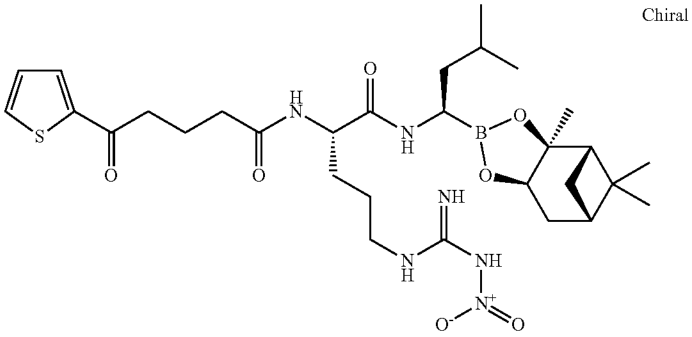 [SMILES: CC(C)C[C@H](NC(=O)[C@H](CCCNC(=N)N[N+](=O)[O-])NC(=O)CCCC(=O)c1cccs1)B1O[C@@H]2C[C@@H]3C[C@@H](C3(C)C)[C@]2(C)O1] Chiral | Chemical Name: 5-Oxo-5-(thiophen-2-yl)pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 647.1 |
| D.3.128 | 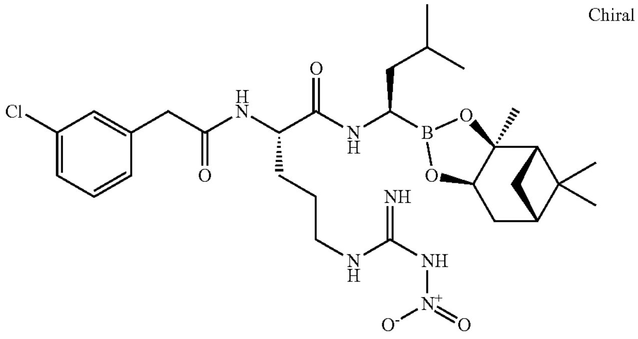 [SMILES: CC(C)C[C@H](NC(=O)[C@H](CCCNC(=N)N[N+](=O)[O-])NC(=O)Cc1cccc(Cl)c1)B1O[C@@H]2C[C@@H]3C[C@@H](C3(C)C)[C@]2(C)O1] Chiral | Chemical Name: 2-(3-Chlorophenyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 619.1 |
| D.3.129 | 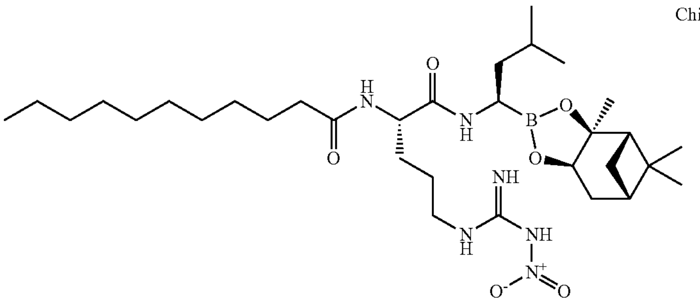 Chiral | Chemical Name: Undecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 635.2 |

TABLE D-3-continued

| Ex # | Structure | Chemical Name and Analytical Data |
|---|---|---|
| D.3.130 | 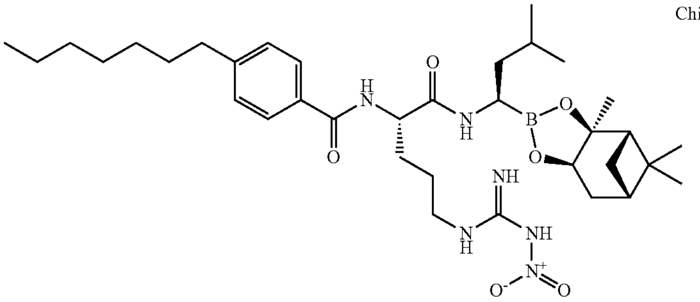 Chiral | Chemical Name: 4-Heptylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 669.6 |
| D.3.131 | 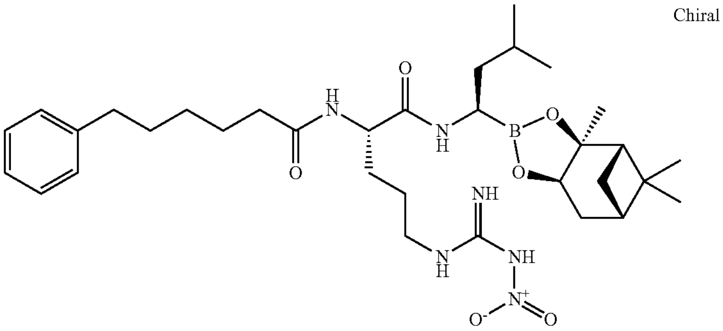 [SMILES: CC(C)C[C@H](NC(=O)[C@H](CCCNC(=N)N[N+](=O)[O-])NC(=O)CCCCCc1ccccc1)B1O[C@@H]2C[C@@H]3C[C@@H](C3(C)C)[C@]2(C)O1] Chiral | Chemical Name: 6-Phenylhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 641.5 |
| D.3.132 | 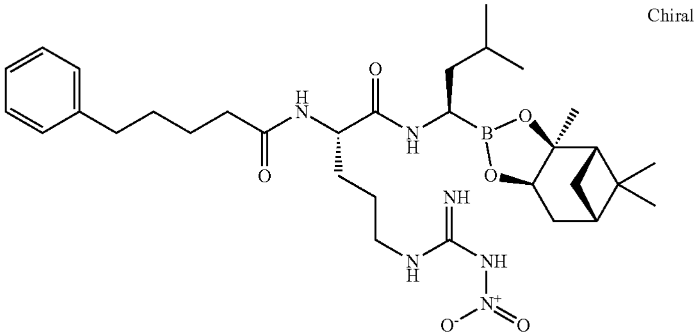 [SMILES: CC(C)C[C@H](NC(=O)[C@H](CCCNC(=N)N[N+](=O)[O-])NC(=O)CCCCc1ccccc1)B1O[C@@H]2C[C@@H]3C[C@@H](C3(C)C)[C@]2(C)O1] Chiral | Chemical Name: 5-Phenylpentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 627.5 |
| D.3.133 | 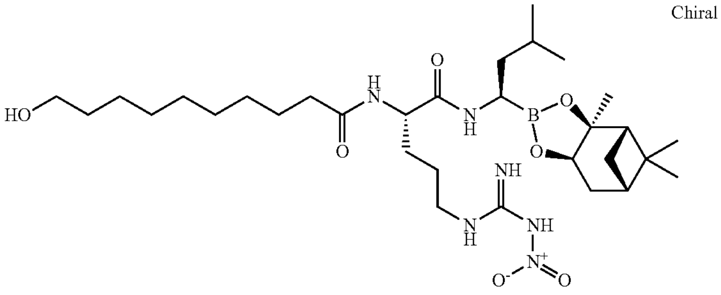 [SMILES: CC(C)C[C@H](NC(=O)[C@H](CCCNC(=N)N[N+](=O)[O-])NC(=O)CCCCCCCCCO)B1O[C@@H]2C[C@@H]3C[C@@H](C3(C)C)[C@]2(C)O1] Chiral | Chemical Name: 10-Hydroxydecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 637.7 |
| D.3.134 | 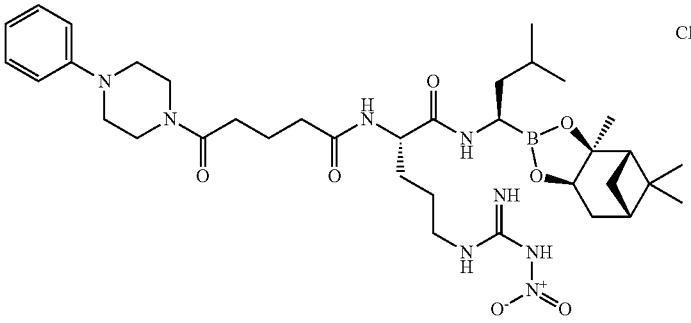 Chiral | Chemical Name: 5-Oxo-5-(4-phenylpiperazin-1-yl)pentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 725.4 |

TABLE D-3-continued

| Ex # | Structure | Chemical Name and Analytical Data |
|---|---|---|
| D.3.135 | 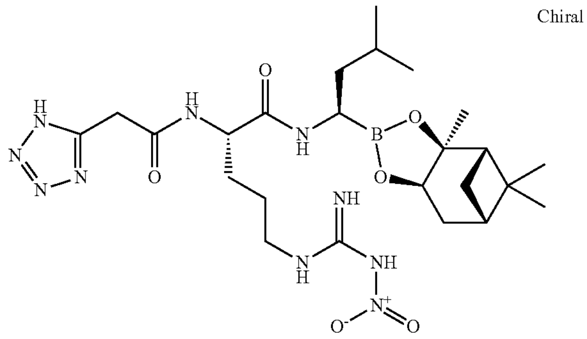 [SMILES: CC(C)C[C@H](NC(=O)[C@H](CCCNC(=N)N[N+](=O)[O-])NC(=O)Cc1nnn[nH]1)B1O[C@@H]2C[C@@H]3C[C@@H](C3(C)C)[C@]2(C)O1] Chiral | Chemical Name: 2-(1H-Tetrazol-5-yl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 577.0 |
| D.3.136 | 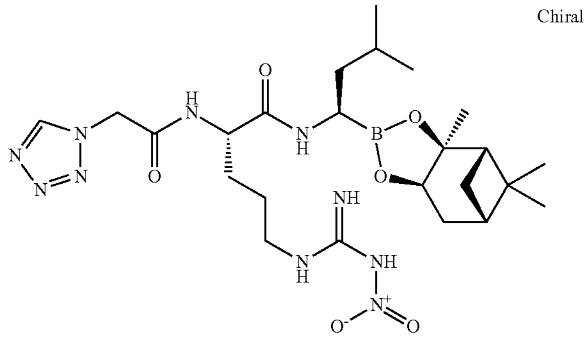 [SMILES: CC(C)C[C@H](NC(=O)[C@H](CCCNC(=N)N[N+](=O)[O-])NC(=O)Cn1cnnn1)B1O[C@@H]2C[C@@H]3C[C@@H](C3(C)C)[C@]2(C)O1] Chiral | Chemical Name: 2-(Tetrazol-1-yl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 576.9 |
| D.3.137 | 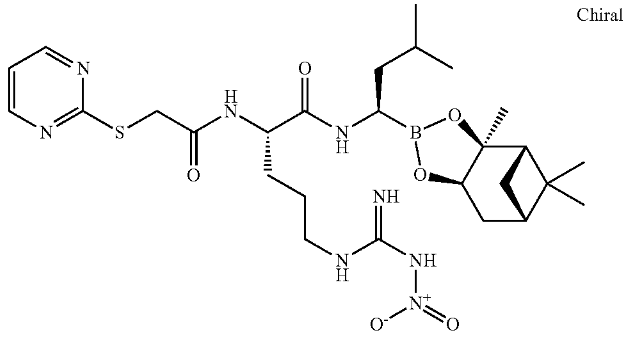 [SMILES: CC(C)C[C@H](NC(=O)[C@H](CCCNC(=N)N[N+](=O)[O-])NC(=O)CSc1ncccn1)B1O[C@@H]2C[C@@H]3C[C@@H](C3(C)C)[C@]2(C)O1] Chiral | Chemical Name: 2-(Pyrimidin-2-ylsulfanyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 618.9 |
| D.3.138 | 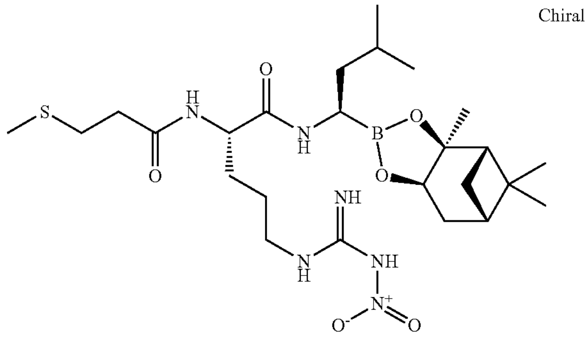 Chiral | Chemical Name: 3-Methylsulfanylpropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 569.4 |

TABLE D-3-continued

| Ex # | Structure | Chemical Name and Analytical Data |
| --- | --- | --- |
| D.3.139 | 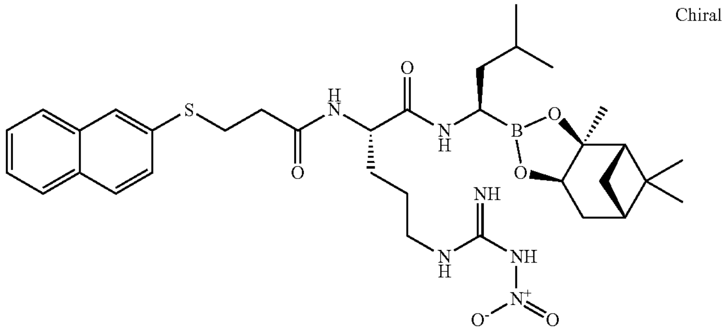 [SMILES: CC(C)C[C@H](NC(=O)[C@H](CCCNC(=N)N[N+](=O)[O-])NC(=O)CCSc1ccc2ccccc2c1)B1O[C@@H]2C[C@@H]3C[C@@H](C3(C)C)[C@]2(C)O1] Chiral | Chemical Name: 3-(Naphthalen-2-ylsulfanyl)-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 681.5 |
| D.3.140 | 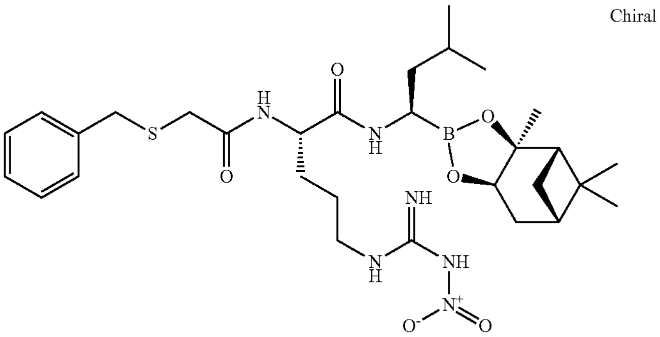 [SMILES: CC(C)C[C@H](NC(=O)[C@H](CCCNC(=N)N[N+](=O)[O-])NC(=O)CSCc1ccccc1)B1O[C@@H]2C[C@@H]3C[C@@H](C3(C)C)[C@]2(C)O1] Chiral | Chemical Name: 2-[(Phenylmethyl)sulfanyl]acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 631.5 |
| D.3.141 | 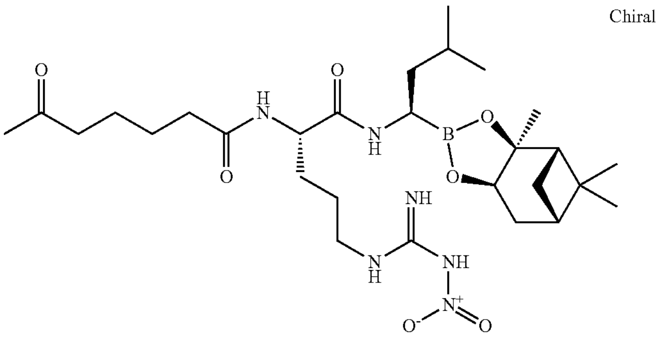 [SMILES: CC(=O)CCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 6-Oxoheptanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 593.5 |
| D.3.142 | 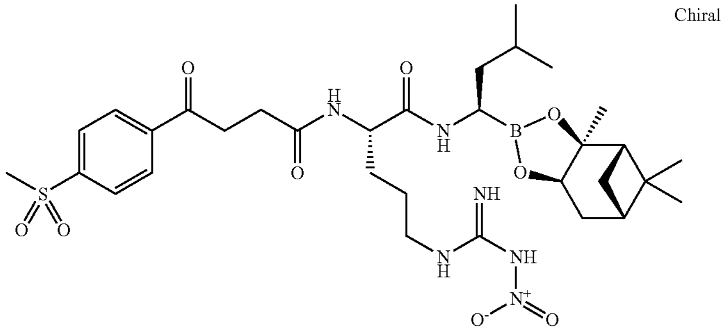 Chiral | Chemical Name: 4-(4-Methanesulfonylphenyl)-4-oxobutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 705.0 |

TABLE D-3-continued

| Ex # | Structure | Chemical Name and Analytical Data |
|---|---|---|
| D.3.143 | 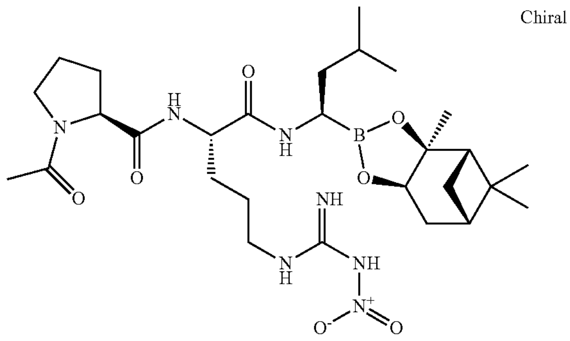 [SMILES: CC(=O)N1CCC[C@H]1C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (2S)-1-Acetylpyrrolidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 605.9 |
| D.3.144 | 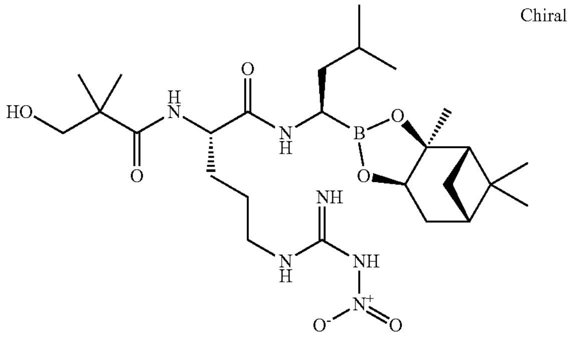 [SMILES: CC(C)C[C@H](NC(=O)[C@H](CCCNC(=N)N[N+](=O)[O-])NC(=O)C(C)(C)CO)B1O[C@@H]2C[C@@H]3C[C@@H](C3(C)C)[C@]2(C)O1] Chiral | Chemical Name: 3-Hydroxy-2,2-dimethylpropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 566.9 |
| D.3.145 | 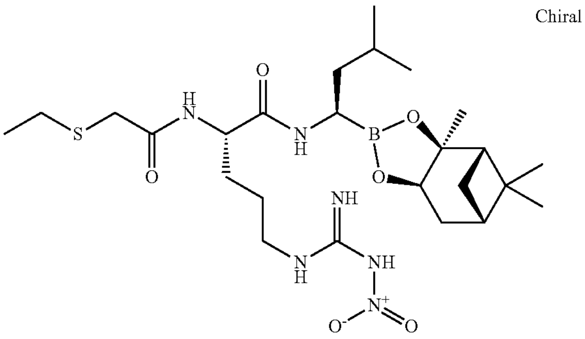 [SMILES: CCSCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 2-Ethylsulfanylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 569.8 |
| D.3.146 | 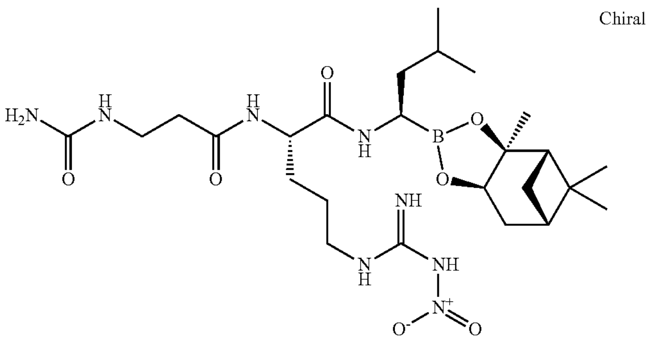 [SMILES: CC(C)C[C@H](NC(=O)[C@H](CCCNC(=N)N[N+](=O)[O-])NC(=O)CCNC(N)=O)B1O[C@@H]2C[C@@H]3C[C@@H](C3(C)C)[C@]2(C)O1] Chiral | Chemical Name: 3-Ureidopropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 581.5 |

TABLE D-3-continued

| Ex # | Structure | Chemical Name and Analytical Data |
|---|---|---|
| D.3.147 | 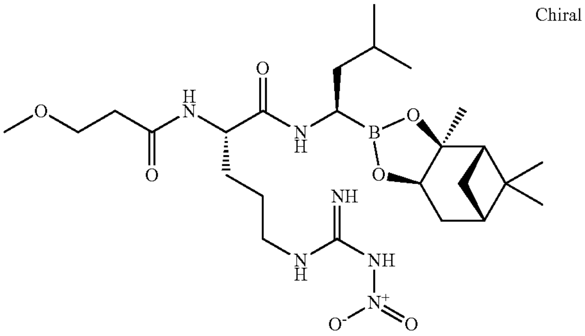 Chiral | Chemical Name: 3-Methoxypropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 552.9 |
| D.3.148 | 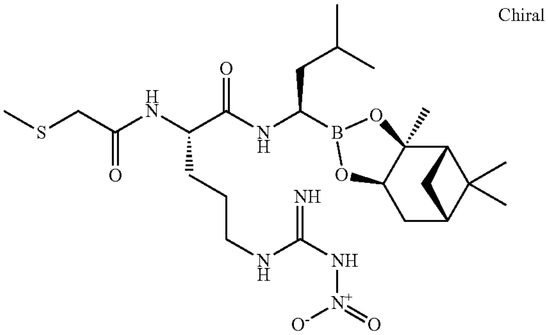 Chiral | Chemical Name: 2-Methylsulfanylacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 555.6 |
| D.3.149 | 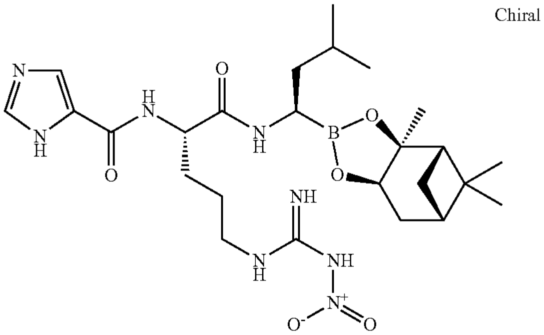 [SMILES: CC(C)C[C@H](NC(=O)[C@H](CCCNC(=N)N[N+](=O)[O-])NC(=O)c1cnc[nH]1)B1O[C@@H]2C[C@@H]3C[C@@H](C3(C)C)[C@]2(C)O1] Chiral | Chemical Name: 3H-Imidazole-4-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 561.0 |
| D.3.150 | 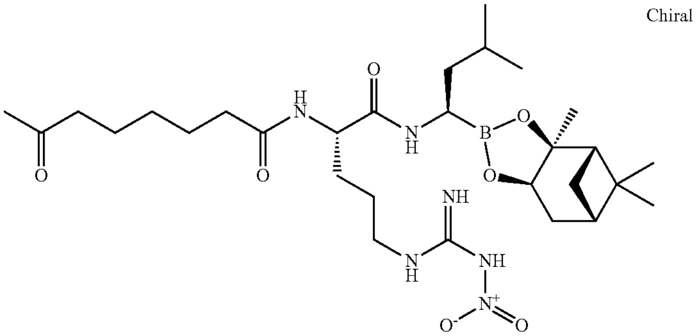 [SMILES: CC(=O)CCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 7-Oxo-octanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 607.1 |

TABLE D-3-continued

| Ex # | Structure | Chemical Name and Analytical Data |
| --- | --- | --- |
| D.3.151 | 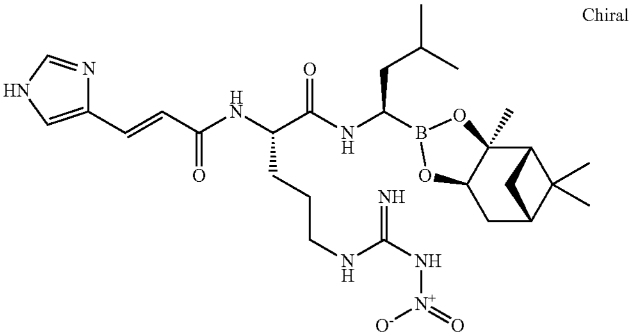 [SMILES: CC(C)C[C@H](NC(=O)[C@H](CCCNC(=N)N[N+](=O)[O-])NC(=O)/C=C/c1c[nH]cn1)B1O[C@@H]2C[C@@H]3C[C@@H](C3(C)C)[C@]2(C)O1] Chiral | Chemical Name: (E)-3-(Imidazol-4-yl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 587.4 |
| D.3.152 | 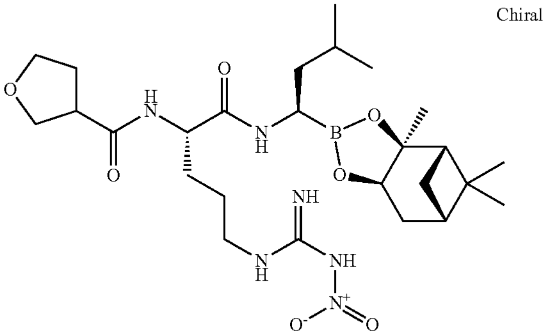 [SMILES: CC(C)C[C@H](NC(=O)[C@H](CCCNC(=N)N[N+](=O)[O-])NC(=O)C1CCOC1)B1O[C@@H]2C[C@@H]3C[C@@H](C3(C)C)[C@]2(C)O1] Chiral | Chemical Name: (RS)-Tetrahydrofuran-3-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 565.3 |
| D.3.153 | 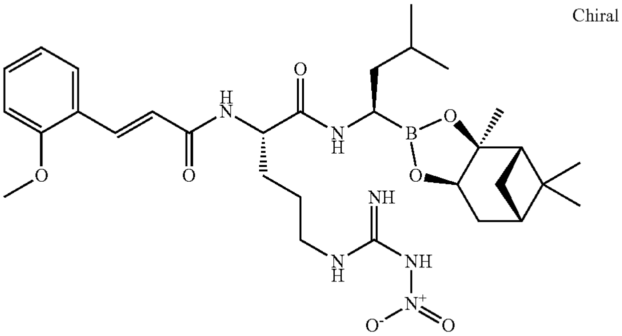 [SMILES: COc1ccccc1/C=C/C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (E)-3-(2-Methoxyphenyl)acrylamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 627.7 |
| D.3.154 | 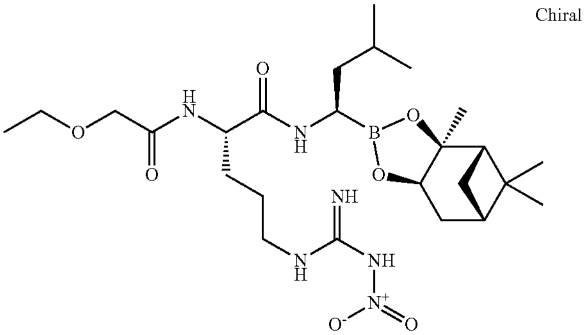 Chiral | Chemical Name: 2-Ethoxyacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 553.0 |

TABLE D-3-continued

| Ex # | Structure | Chemical Name and Analytical Data |
|---|---|---|
| D.3.155 | 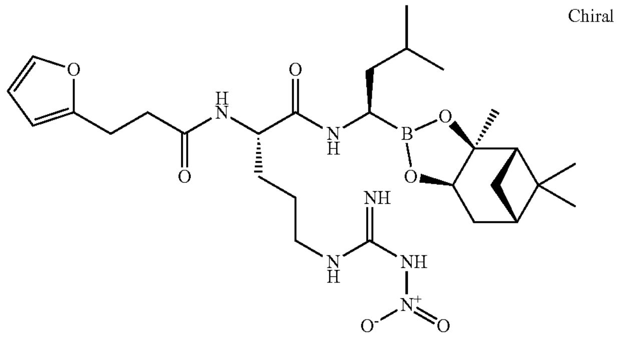 [SMILES: CC(C)C[C@H](NC(=O)[C@H](CCCNC(=N)N[N+](=O)[O-])NC(=O)CCc1ccco1)B1O[C@@H]2C[C@@H]3C[C@@H](C3(C)C)[C@]2(C)O1] Chiral | Chemical Name: 3-Furan-2-yl-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 589.5 |
| D.3.156 | 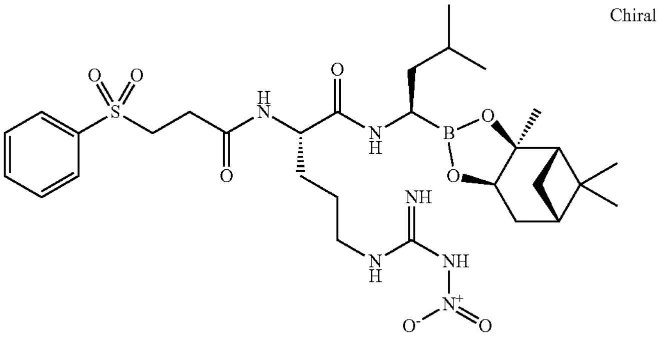 [SMILES: CC(C)C[C@H](NC(=O)[C@H](CCCNC(=N)N[N+](=O)[O-])NC(=O)CCS(=O)(=O)c1ccccc1)B1O[C@@H]2C[C@@H]3C[C@@H](C3(C)C)[C@]2(C)O1] Chiral | Chemical Name: 3-(Benzenesulfonyl)propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 663.0 |
| D.3.157 | 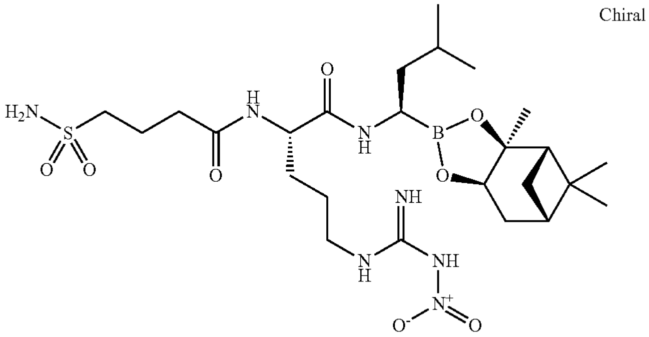 [SMILES: CC(C)C[C@H](NC(=O)[C@H](CCCNC(=N)N[N+](=O)[O-])NC(=O)CCCS(N)(=O)=O)B1O[C@@H]2C[C@@H]3C[C@@H](C3(C)C)[C@]2(C)O1] Chiral | Chemical Name: 4-Sulfamoylbutanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 615.8 |
| D.3.158 | 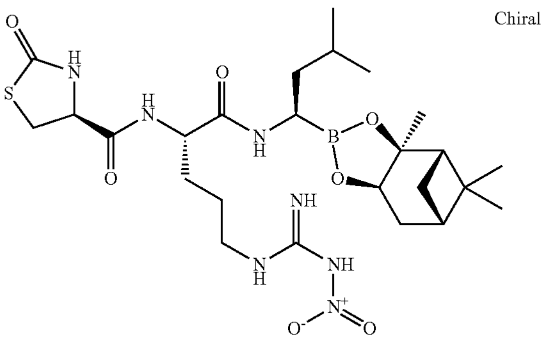 [SMILES: CC(C)C[C@H](NC(=O)[C@H](CCCNC(=N)N[N+](=O)[O-])NC(=O)[C@H]1CSC(=O)N1)B1O[C@@H]2C[C@@H]3C[C@@H](C3(C)C)[C@]2(C)O1] Chiral | Chemical Name: (4S)-2-Oxo-1,3-thiazolidine-4-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 595.8 |

TABLE D-3-continued

| Ex # | Structure | Chemical Name and Analytical Data |
|---|---|---|
| D.3.159 | 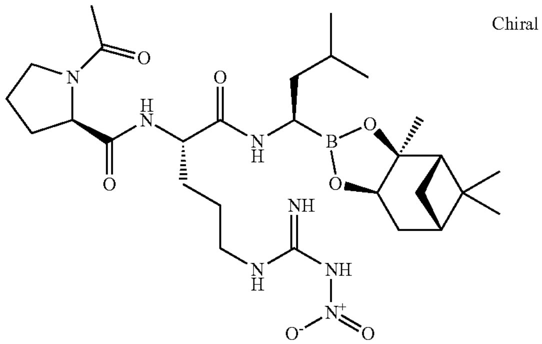 [SMILES: CC(=O)N1CCC[C@@H]1C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (2R)-1-Acetylpyrrolidine-2-carboxamide, S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 605.9 |
| D.3.160 | 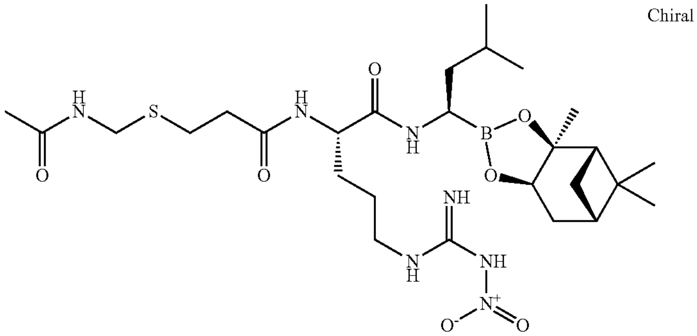 [SMILES: CC(=O)NCSCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 3-[(Acetylamino)methylsulfanyl]-propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 626.0 |
| D.3.161 | 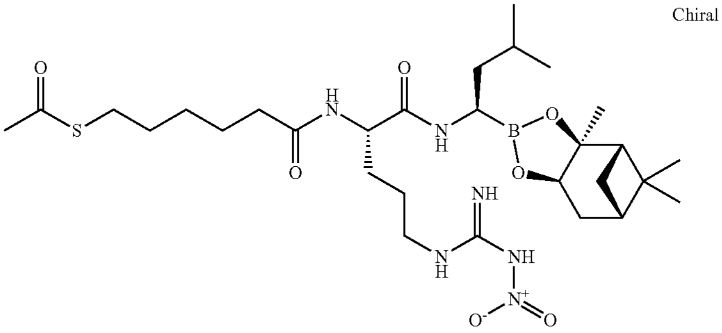 [SMILES: CC(=O)SCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 6-(Acetylsulfanyl)hexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 638.9 |
| D.3.162 | 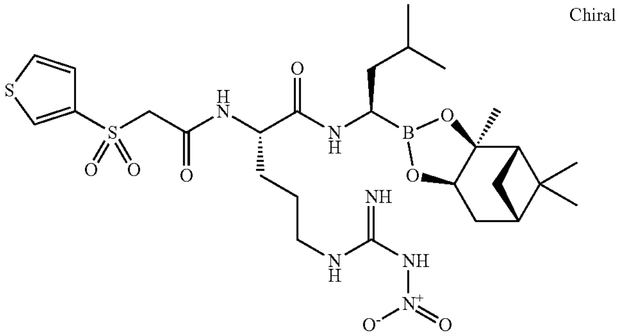 [SMILES: CC(C)C[C@H](NC(=O)[C@H](CCCNC(=N)N[N+](=O)[O-])NC(=O)CS(=O)(=O)c1ccsc1)B1O[C@@H]2C[C@@H]3C[C@@H](C3(C)C)[C@]2(C)O1] Chiral | Chemical Name: (Thiophene-2-sulfonyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 655.0 |

TABLE D-3-continued

| Ex # | Structure | Chemical Name and Analytical Data |
|---|---|---|
| D.3.163 | 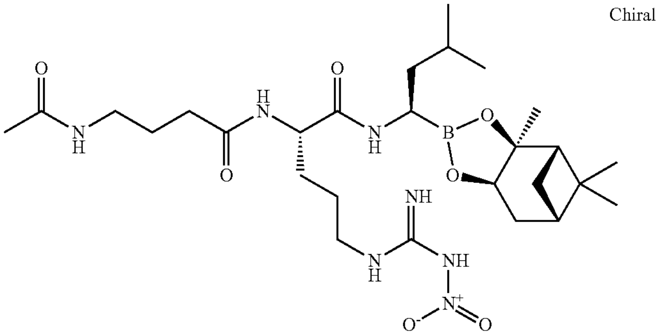 [SMILES: CC(=O)NCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 4-(Acetylamino)butanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 593.7 |
| D.3.164 | 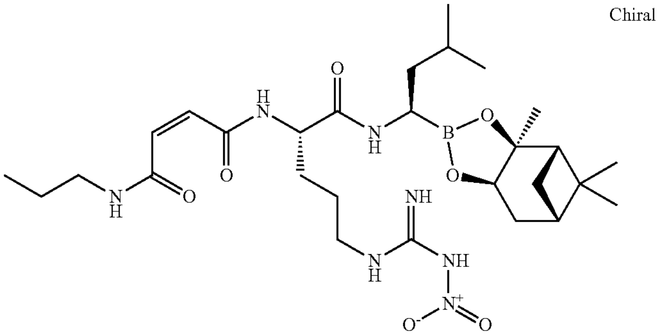 [SMILES: CCCNC(=O)/C=C\C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (2Z)-3-(Propylaminocarbonyl)-2-propenamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 606.1 |
| D.3.165 | 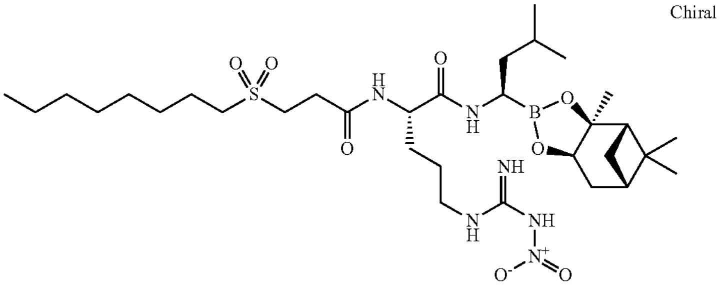 [SMILES: CCCCCCCCS(=O)(=O)CCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 3-(Octylsulfonyl)propanamide, N-R1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 699.29 |
| D.3.166 | 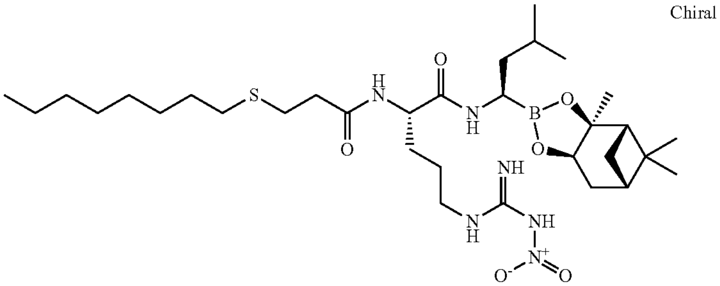 [SMILES: CCCCCCCCSCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 3-(Octylsulfanyl)propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 667.35 |
| D.3.167 | 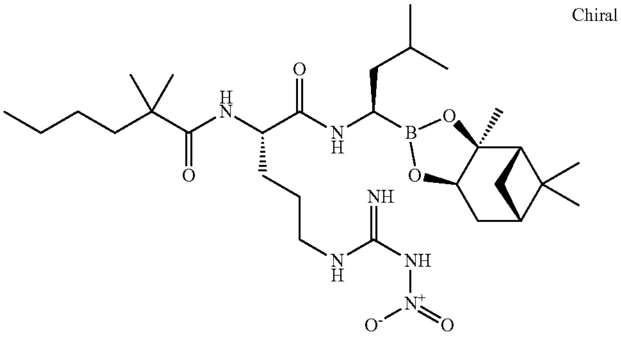 [SMILES: CCCCC(C)(C)C(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 2,2-Dimethylhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 593.65 |

TABLE D-3-continued

| Ex # | Structure | Chemical Name and Analytical Data |
|---|---|---|
| D.3.168 | 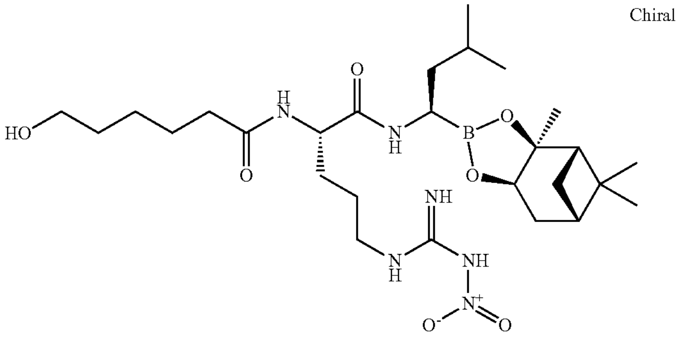 [SMILES: CC(C)C[C@H](NC(=O)[C@H](CCCNC(=N)N[N+](=O)[O-])NC(=O)CCCCCO)B1O[C@@H]2C[C@@H]3C[C@@H](C3(C)C)[C@]2(C)O1] Chiral | Chemical Name: 6-Hydroxyhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 581.16 |
| D.3.169 | 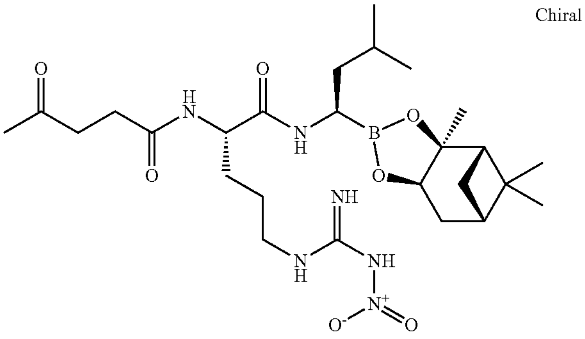 [SMILES: CC(=O)CCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 4-Oxopentanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 565.60 |
| D.3.170 | 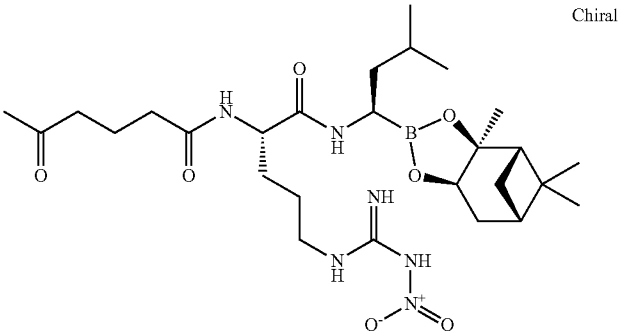 [SMILES: CC(=O)CCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 5-Oxohexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 579.17 |
| D.3.171 | 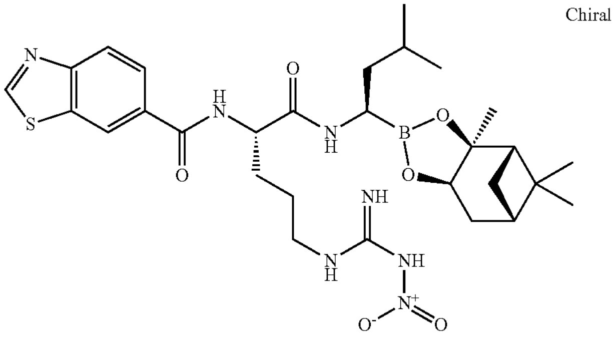 [SMILES: CC(C)C[C@H](NC(=O)[C@H](CCCNC(=N)N[N+](=O)[O-])NC(=O)c1ccc2ncsc2c1)B1O[C@@H]2C[C@@H]3C[C@@H](C3(C)C)[C@]2(C)O1] Chiral | Chemical Name: Benzothiazole-6-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 628.70 |

TABLE D-3-continued

| Ex # | Structure | Chemical Name and Analytical Data |
|---|---|---|
| D.3.172 | 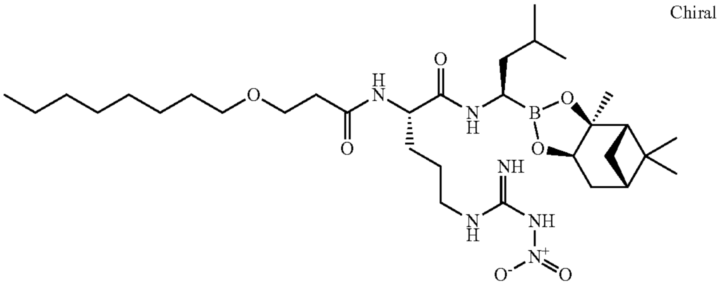 Chiral | Chemical Name:<br>3-(Octyloxy)propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: [MH]+ 651.33 |
| D.3.173 | 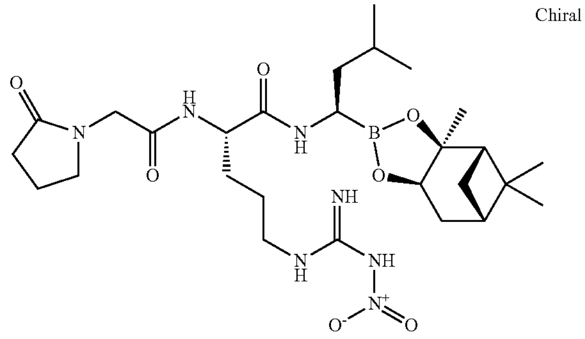 [SMILES: CC(C)C[C@H](NC(=O)[C@H](CCCNC(=N)N[N+](=O)[O-])NC(=O)CN1CCCC1=O)B1O[C@@H]2C[C@@H]3C[C@@H](C3(C)C)[C@]2(C)O1] Chiral | Chemical Name:<br>2-(2-Oxo-pyrrolidin-1-yl)-acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: [MH]+ 592.75 |
| D.3.174 | 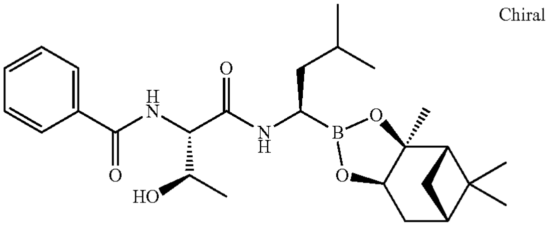 [SMILES: CC(C)C[C@H](NC(=O)[C@@H](NC(=O)c1ccccc1)[C@@H](C)O)B1O[C@@H]2C[C@@H]3C[C@@H](C3(C)C)[C@]2(C)O1] Chiral | Chemical Name:<br>Benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]<br>Analytical Data:<br>MS: [MH]+ 471.47 |
| D.3.175 | 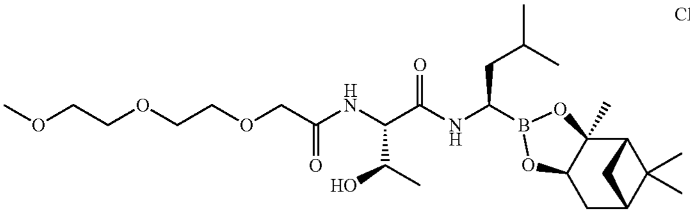 Chiral | Chemical Name:<br>2-[2-(2-Methoxyethoxy)ethoxy]acetamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]<br>Analytical Data:<br>MS: [MH]+ 527.12 |
| D.3.176 | 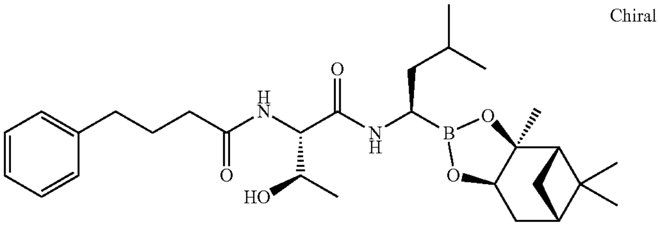 [SMILES: CC(C)C[C@H](NC(=O)[C@@H](NC(=O)CCCc1ccccc1)[C@@H](C)O)B1O[C@@H]2C[C@@H]3C[C@@H](C3(C)C)[C@]2(C)O1] Chiral | Chemical Name:<br>4-Phenylbutanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]<br>Analytical Data:<br>MS: [MH]+ 513.10 |
| D.3.177 | 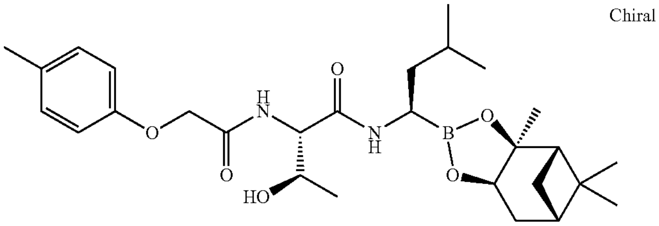 Chiral | Chemical Name:<br>(4-Methylphenoxy)acetamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]<br>Analytical Data:<br>MS: [MH]+ 515.57 |

TABLE D-3-continued

| Ex # | Structure | Chemical Name and Analytical Data |
|---|---|---|
| D.3.178 | 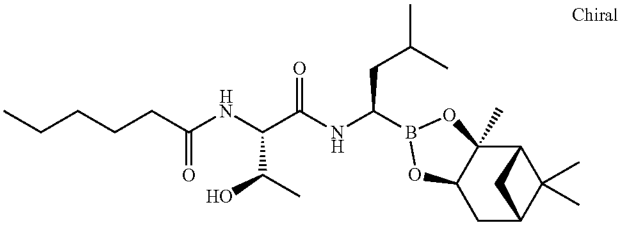 [SMILES: CCCCCC(=O)N[C@H](C(=O)N[C@@H](CC(C)C)B1O[C@@H]2C[C@@H]3C[C@@H](C3(C)C)[C@]2(C)O1)[C@@H](C)O] Chiral | Chemical Name: Hexanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl] Analytical Data: MS: [MH]+ 465.40 |
| D.3.179 | 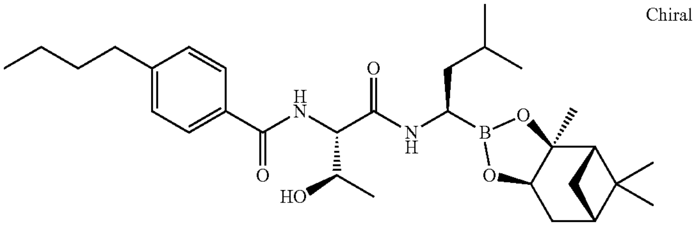 [SMILES: CCCCc1ccc(C(=O)N[C@H](C(=O)N[C@@H](CC(C)C)B2O[C@@H]3C[C@@H]4C[C@@H](C4(C)C)[C@]3(C)O2)[C@@H](C)O)cc1] Chiral | Chemical Name: 4-Butylbenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl] Analytical Data: MS: [MH]+ 527.16 |
| D.3.180 | 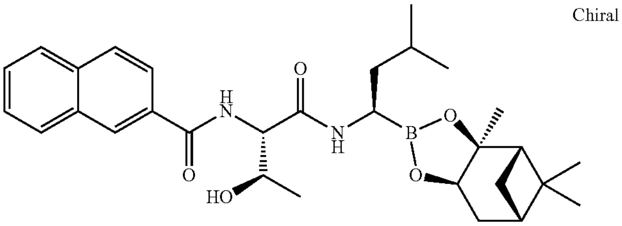 [SMILES: CC(C)C[C@H](NC(=O)[C@@H](NC(=O)c1ccc2ccccc2c1)[C@@H](C)O)B1O[C@@H]2C[C@@H]3C[C@@H](C3(C)C)[C@]2(C)O1] Chiral | Chemical Name: Naphthalene-2-carboxamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl] Analytical Data: MS: [MH]+ 521.14 |
| D.3.181 | 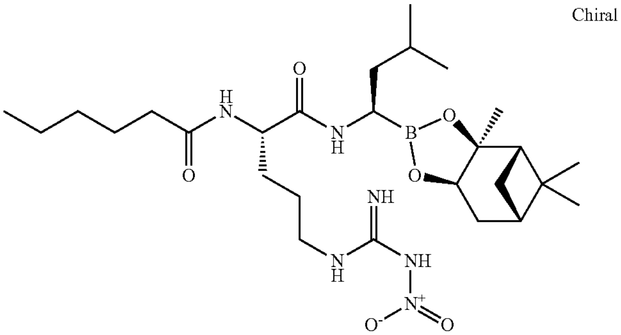 [SMILES: CCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Hexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 565.33 |
| D.3.182 | 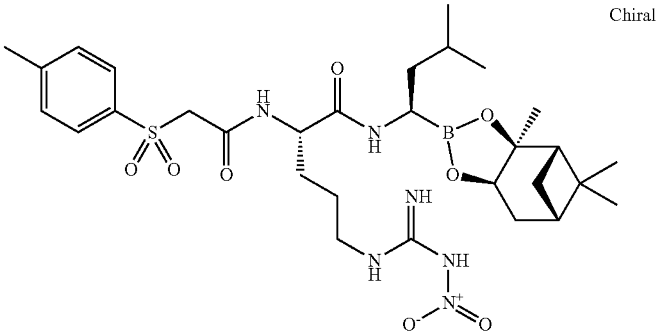 Chiral | Chemical Name: 2-(4-Methylbenzenesulfonyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 663.30 |

TABLE D-3-continued

| Ex # | Structure | Chemical Name and Analytical Data |
|---|---|---|
| D.3.183 | 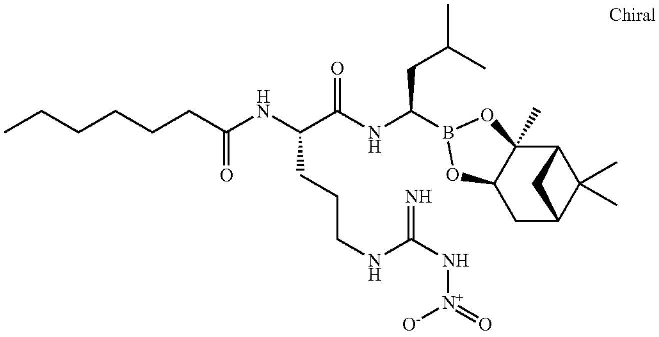 [SMILES: CCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Heptanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 579.34 |
| D.3.184 | 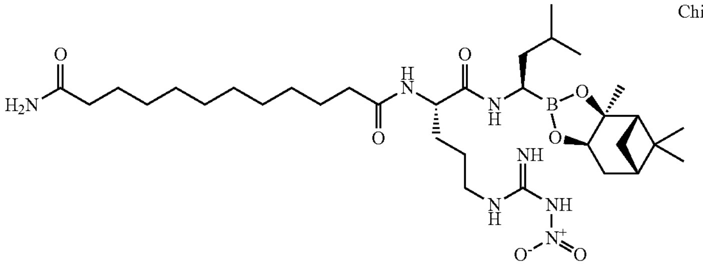 Chiral | Chemical Name: 11-(Carbamoyl)undecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 678.44 |
| D.3.185 | 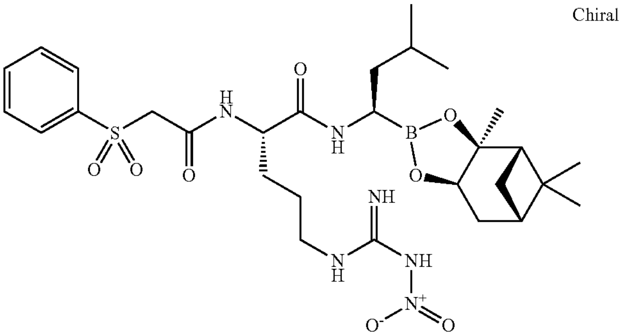 [SMILES: CC(C)C[C@H](NC(=O)[C@H](CCCNC(=N)N[N+](=O)[O-])NC(=O)CS(=O)(=O)c1ccccc1)B1O[C@@H]2C[C@@H]3C[C@@H](C3(C)C)[C@]2(C)O1] Chiral | Chemical Name: 2-(Benzenesulfonyl)acetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 649.28 |

Further compounds prepared according to the above Example D.3 are reported in Table D-3A.

TABLE D-3A

| Ex # | Structure | Chemical Name and Analytical Data |
|---|---|---|
| D.3.186 | 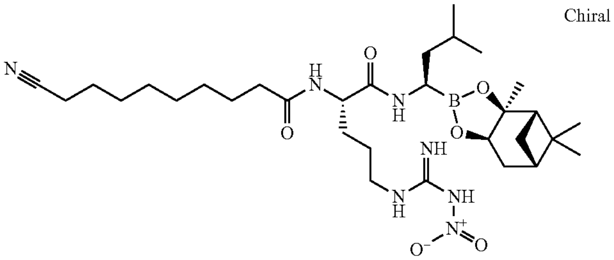 [SMILES: CC(C)C[C@H](NC(=O)[C@H](CCCNC(=N)N[N+](=O)[O-])NC(=O)CCCCCCCCC#N)B1O[C@@H]2C[C@@H]3C[C@@H](C3(C)C)[C@]2(C)O1] Chiral | Chemical Name: 9-Cyanononamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 632.5 |

TABLE D-3A-continued

| Ex # | Structure | Chemical Name and Analytical Data |
|---|---|---|
| D.3.187 | 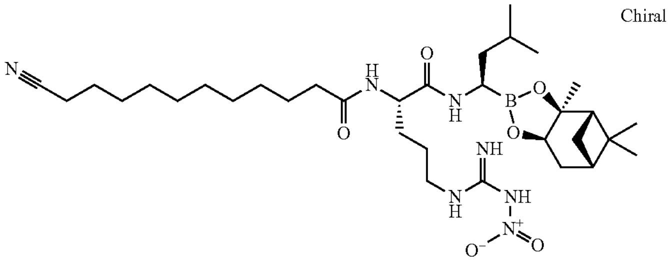 [SMILES: CC(C)C[C@H](NC(=O)[C@H](CCCNC(=N)N[N+](=O)[O-])NC(=O)CCCCCCCCCCC#N)B1O[C@@H]2C[C@@H]3C[C@@H](C3(C)C)[C@]2(C)O1] Chiral | Chemical Name: 11-Cyanoundecanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 659.7; 1H-NMR(CDCl3): 7.53 (s, br, 2H); 7.36 (d, br, J = 4.7 Hz, 1H); 6.88 (d, J = 8.2 Hz, 1H); 4.46 (m, 1H); 4.15 (dd, J = 8.5, 1.9 Hz, 1H); 3.19 (m, 2H); 2.93 (m, 1H); 2.23 (t, J = 7.2 Hz, 2H); 2.21 (m, 1H); 2.09 (t, J = 7.5, 2H); 2.04 (m, 1H); 1.88 (t, J = 5.4 Hz, 1H); 1.77 (m, 1H); 1.69 (m, 1H); 1.64-1.43 (m, 9H); 1.40-1.26 (m, 4H); 1.26 (s, 3H); 1.24-1.12 (m, 16H); 0.80 (d, J = 6.6, 3H); 0.79 (d, J = 6.6, 3H); 0.73 (s, 3H). |
| D.3.188 | 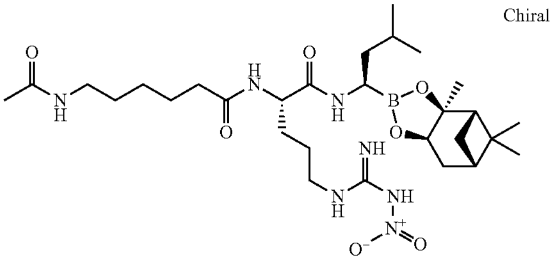 [SMILES: CC(=O)NCCCCCC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: 6-(Acetylamino)hexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 622.3 |
| D.3.189 | 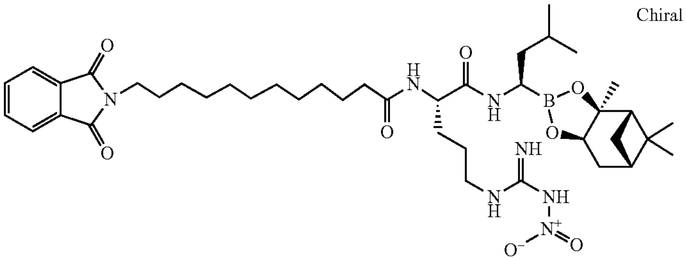 [SMILES: CC(C)C[C@H](NC(=O)[C@H](CCCNC(=N)N[N+](=O)[O-])NC(=O)CCCCCCCCCCCN1C(=O)c2ccccc2C1=O)B1O[C@@H]2C[C@@H]3C[C@@H](C3(C)C)[C@]2(C)O1] Chiral | Chemical Name: 12-(1,3-Dioxo-1,3-dihydro-isoindol-2-yl)-dodecanamide,N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [MH]+ 794.42 |
| D.3.190 | 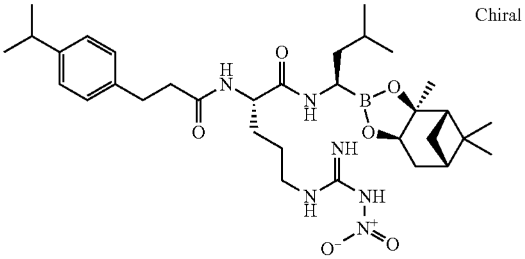 [SMILES: CC(C)C[C@H](NC(=O)[C@H](CCCNC(=N)N[N+](=O)[O-])NC(=O)CCc1ccc(C(C)C)cc1)B1O[C@@H]2C[C@@H]3C[C@@H](C3(C)C)[C@]2(C)O1] Chiral | Chemical Name: 3-[4-(2-Propyl)phenyl]propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [M]H+ 641.5 |
| D.3.191 | 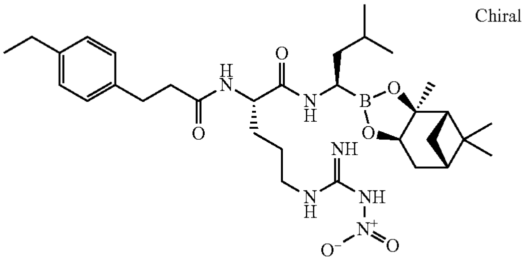 [SMILES: CCc1ccc(CCC(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: 3-[4-(Ethyl)phenyl]propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [M]H+ 627.7 |

TABLE D-3A-continued

| Ex # | Structure | Chemical Name and Analytical Data |
|---|---|---|
| D.3.192 | 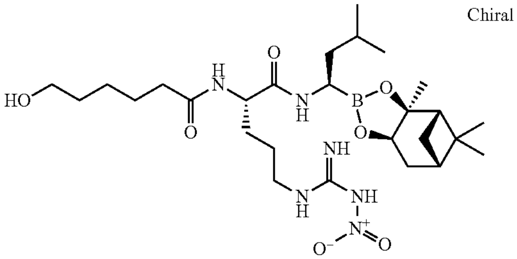 [SMILES: CC(C)C[C@H](NC(=O)[C@H](CCCNC(=N)N[N+](=O)[O-])NC(=O)CCCCCO)B1O[C@@H]2C[C@@H]3C[C@@H](C3(C)C)[C@]2(C)O1] Chiral | Chemical Name: 6-hydroxyhexanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [M]H+ 581.5 |

Example D.4

Naphthalene-2-sulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-

Chiral

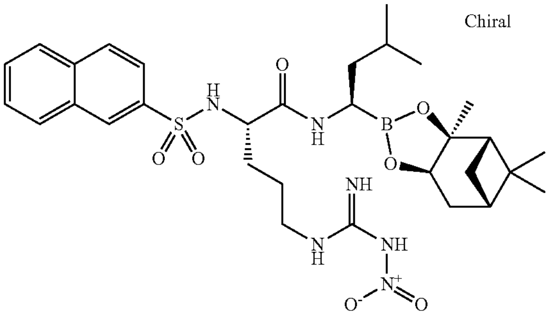 [SMILES: CC(C)C[C@H](NC(=O)[C@H](CCCNC(=N)N[N+](=O)[O-])NS(=O)(=O)c1ccc2ccccc2c1)B1O[C@@H]2C[C@@H]3C[C@@H](C3(C)C)[C@]2(C)O1]

To a solution of (2S)-2-amino-5-[[imino(nitroamino)methyl]-amino]-pentanamide, N-[(1R)-1-[(3aS,4S,6S,7aR)-hexahydro-3a,5,5-trimethyl-4,6- methano-1,3,2-benzodioxaborol-2-yl]-3-methylbutyl]-, hydrochloride salt of Example C.1 (70 mg, 0.14 mmol) in DCM (4 mL), TEA (0.04 mL, 0.31 mmol) and naphthalene-2-sulfonyl chloride (35.1 mg, 0.16 mmol) were added at room temperature. After stirring overnight a second portion of TEA (0.04 mL, 0.31 mmol) and naphthalene-2-sulfonyl chloride (35.1 mg, 0.16 mmol) was added and the reaction was allowed to stir for a further night. The reaction mixture was then washed with saturated aqueous $K_2CO_3$ and the separated organic phase was concentrated to dryness. The reaction crude was purified on SPE-SI normal phase cartridge to afford the title compound (64 mg, yield 70%).

NMR ($CDCl_3$): 8.42 (s, br, 1H); 7.96 (dd, J=7.5, 2.2 Hz, 1H); 7.95 (d, J=8.5 Hz, 1H); 7.89 (d, br, J=7.9 Hz, 1H); 7.81 (dd, J=8.8, 1.9 Hz, 1H); 7.68-7.57 (m, 2H); 7.23 (s br, 2H); 6.23 (s br, 1H); 6.03 (d, J=8.5 Hz, 1H); 4.19 (dd, J=9.1, 2.2 Hz, 1H); 3.92 (s, br, 1H); 3.31 (m, 2H); 2.97 (m, 1H); 2.26 (m, 1H); 2.12 (m, 1H); 1.93 (t, J=5.7 Hz, 1H); 1.90-1.68 (m, 6H); 1.30 (s, 3H); 1.28 (m, 1H); 1.25 (s, 3H); 1.06 (m, 4H); 0.79 (s, 3H); 0.58 (d, J=9.4 Hz, 3H); 0.56 (d, J=9.4 Hz, 3H).

LC-MS 657.3, MH+, ESI POS; AQA; spray 4 kV/skimmer: 20 V/probe 250 C.

Further compounds prepared fundamentally in accordance with the above experimental procedures are reported in Table D-4.

TABLE D-4

| Ex # | Structure | Chemical Name and Analytical Data |
|---|---|---|
| D.4.1 | 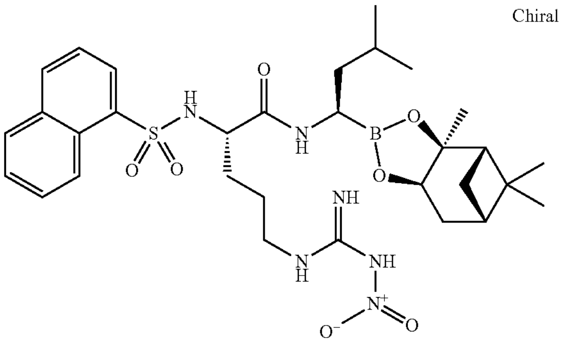 [SMILES: CC(C)C[C@H](NC(=O)[C@H](CCCNC(=N)N[N+](=O)[O-])NS(=O)(=O)c1cccc2ccccc12)B1O[C@@H]2C[C@@H]3C[C@@H](C3(C)C)[C@]2(C)O1] Chiral | Chemical Name: Naphthalene-1-sulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl] amino]carbonyl]-4-[[imino(nitroamino)methyl]amino]butyl] Analytical Data: MS: MH+ 657.3 |

TABLE D-4-continued

| Ex # | Structure | Chemical Name and Analytical Data |
| --- | --- | --- |
| D.4.2 | 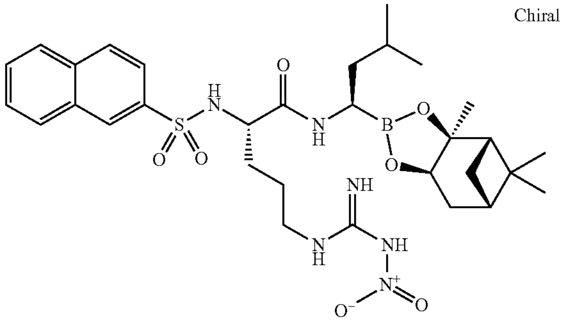 [SMILES: CC(C)C[C@H](NC(=O)[C@H](CCCNC(=N)N[N+](=O)[O-])NS(=O)(=O)c1ccc2ccccc2c1)B1O[C@@H]2C[C@@H]3C[C@@H](C3(C)C)[C@]2(C)O1] Chiral | Chemical Name: Naphthalene-2-sulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 657.3; 1H-NMR(CDCl3): 8.42 (s, br, 1H); 7.96 (dd, J = 7.5, 2.2 Hz, 1H); 7.95 (d, J = 8.5 Hz, 1H); 7.89 (d, br, J = 7.9 Hz, 1H); 7.81 (dd, J = 8.8, 1.9 Hz, 1H); 7.68-7.57 (m, 2H); 7.23 (s br, 2H); 6.23 (s br, 1H); 6.03 (d, J = 8.5 Hz, 1H); 4.19 (dd, J = 9.1, 2.2 Hz, 1H); 3.92 (s, br, 1H); 3.31 (m, 2H); 2.97 (m, 1H); 2.26 (m, 1H); 2.12 (m, 1H); 1.93 (t, J = 5.7 Hz, 1H); 1.90-1.68 (m, 6H); 1.30 (s, 3H); 1.28 (m, 1H); 1.25 (s, 3H); 1.06 (m, 4H); 0.79 (s, 3H); 0.58 (d, J = 9.4 Hz, 3H); 0.56 (d, J = 9.4 Hz, 3H). |
| D.4.3 | 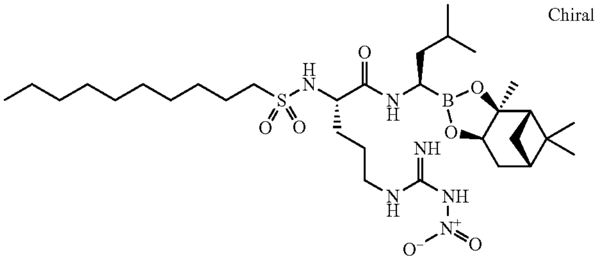 [SMILES: CCCCCCCCCCS(=O)(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Decane-1-sulfonamide, N-[( 1S)-1-[[[(1R)-1 -[(3aS,4S,6SJaR)-hexahydro-3a,5,5-trimethyl-4,6-methano-l,3,2-benzodioxaborol-2-yl]-3-methylbutyl] amino] carbonyl]-4-[[imino(nitroamino)methyl]amino]butyl] Analytical Data: MS: MH+ 671.4 |
| D.4.4 | 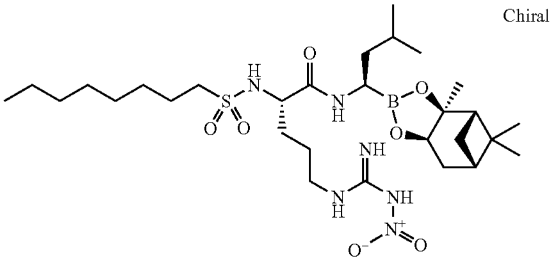 [SMILES: CCCCCCCCS(=O)(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: Octanesulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 643.4 |
| D.4.5 | 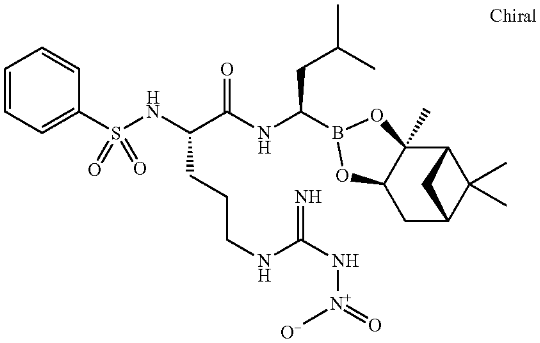 [SMILES: CC(C)C[C@H](NC(=O)[C@H](CCCNC(=N)N[N+](=O)[O-])NS(=O)(=O)c1ccccc1)B1O[C@@H]2C[C@@H]3C[C@@H](C3(C)C)[C@]2(C)O1] Chiral | Chemical Name: Benzenesulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: MH+ 607.3 |
| D.4.6 | 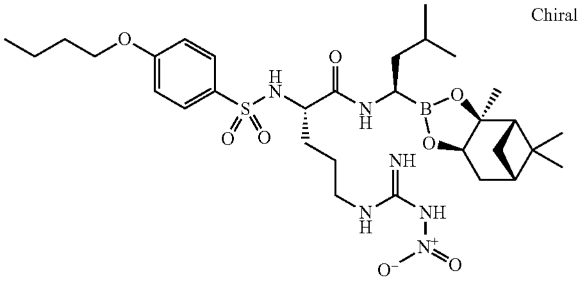 [SMILES: CCCCOc1ccc(S(=O)(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: 4-Butoxyenzenesulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl] Analytical Data: MS: [M + H]+ 679.5 |

TABLE D-4-continued

| Ex # | Structure | Chemical Name and Analytical Data |
|---|---|---|
| D.4.7 | 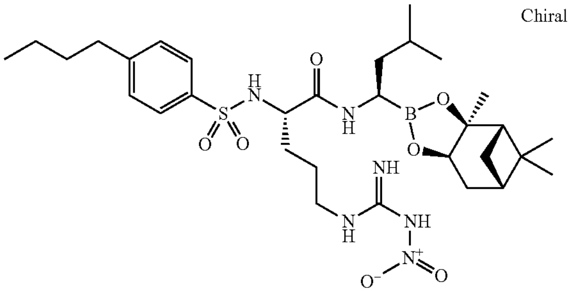 [SMILES: CCCCc1ccc(S(=O)(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name:<br>4-Butyl-benzenesulfonamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]<br>Analytical Data:<br>MS: [M + H]+ 663.5 |
| D.4.8 | 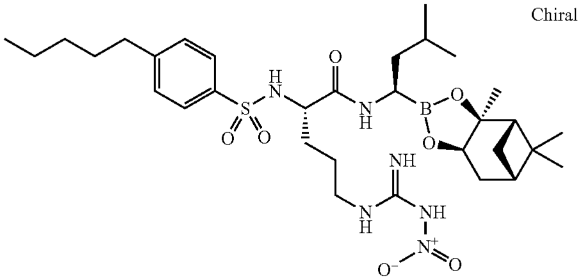 [SMILES: CCCCCc1ccc(S(=O)(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name:<br>4-Pentyl-benzenesulfonamide, N-[(1S)-1-[[[(1R)-1-[(3aS,4S,6S,7aR)-hexahydro-3a,5,5-trimethyl-4,6-methano-1,392-benzodioxaborol-2-yl]-3-methylbutyl]amino]carbonyl] -4-[[imino(nitroamino)methyl]amino]butyl]<br>Analytical Data:<br>MS: [M]H+ 677.3 |

Example D.4.9

Naphthalene-2-sulfonamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]

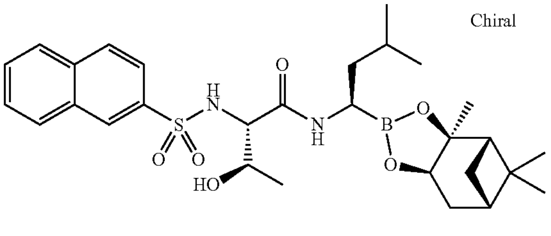 [SMILES: CC(C)C[C@H](NC(=O)[C@@H](NS(=O)(=O)c1ccc2ccccc2c1)[C@@H](C)O)B1O[C@@H]2C[C@@H]3C[C@@H](C3(C)C)[C@]2(C)O1]

Chiral

Naphthalene-2-sulfonyl chloride (144 mg, 0.637 mmol) was added to a solution of (2S)-amino-(3R)-hydroxy-butyric amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]-carbonyl] hydrochloride salt, of Example C.3, and NMM (0.175 ml, 1.59 mmol) in anhydrous dichloromethane, while stirring at 0° C. under nitrogen. After 6 hours the mixture was allowed to warm to room temperature and stirred overnight. A 10% solution of $NaHCO_3$ (10 ml) was added and the layers were separated. The aqueous phase was further extracted with dichloromethane (5 ml). The organic phases were washed with a 20% solution of $NaH_2PO_4$, dried over sodium sulfate and concentrated. The residue was purified by column chromatography (Silica gel, 25 g) eluting with a 1:1 (v/v) mixture of hexane and ethyl acetate. The product was obtained as a white glassy solid (219 mg, 74% yield) but still containing some pinanediol. A sample of that product (160 mg) was triturated with a mixture of diethyl ether (3 ml) and hexane (3 ml) affording the pure product as a white solid (80 mg, 27% yield). M.p. 147-149° C.

$^1$H NMR (DMSO-d6): 8.40 (1H, s); 8.28-8.22 (1H, m); 8.11 (1H, d, J=7.7); 8.05 (1H, d, J=8.7); 8.01 (1H, d, J=7.8); 7.81 (1H, dd, J=8.7, 1.7); 7.75 (1H, s br.); 7.72-7.61 (2H, m); 4.84 (1H, s br.); 4.03 (1H, dd, J=8.5, 1.7); 3.82-3.72 (2H, m); 2.41-2.33 (1H, m); 2.20-2.10 (1H, m); 2.02-1.93 (1H, m); 1.82-1.72 (2H, m); 1.58-1.50 (1H, m); 1.36-1.24 (1H, m); 1.20 (3H, s); 1.18 (3H, s); 0.99 (3H, d, J=6.1); 0.94-0.82 (2H, m); 0.77 (3H, s); 0.63 (3H, d, J=7.1); 0.61 (3H, d, J=7.1).

Example D.5

(2S)-4-[[imino(nitroamino)methyl]amino]-2-[(2-naphthylmethyl)-amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl]

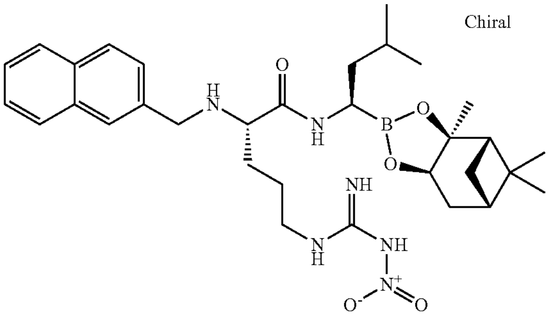 [SMILES: CC(C)C[C@H](NC(=O)[C@H](CCCNC(=N)N[N+](=O)[O-])NCc1ccc2ccccc2c1)B1O[C@@H]2C[C@@H]3C[C@@H](C3(C)C)[C@]2(C)O1]

Chiral

A solution of (2S)-2-amino-5-[[imino(nitroamino)methyl]amino]pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-, hydrochloride salt of Example C.1 (88 mg, 0.175 mmol) in MeOH (4 mL) was passed through a ISOLUTE PSA cartridge in order to obtain the starting material as a free base. To a solution of the free base in MeOH (4 mL), 2-naphtaldehyde (45 mg, 0.28 mmol) and $NaCNBH_3$ (18 mg, 0.28 mmol) were added at room temperature; AcOH was added until the pH of the solution was 4-5. The reaction mixture was stirred overnight, then $H_2O$ (1 mL) was added and the resulting solution was concentrated; the residue, dissolved in AcOEt, was washed with brine and the organic phase was concentrated to dryness. Purification by silica gel flash chromatography (DCM/MeOH/$NH_4OH$, 97.5/2.5/0.25) of the reaction crude, afforded the desired compound (30 mg, yield 28%).

NMR ($CDCl_3$+$D_2O$): 7.81 (m, 3H); 7.71 (s, br, 1H); 7.52-7.38 (m, 3H); 4.66 (s, br, 1H); 4.27 (dd, J=8.8, 1.9 Hz, 1H);

3.91 and 3.83 (ABq, 2H); 3.39-3.11 (m, 3H); 2.30 (m, 1H); 2.13 (m, 1H); 1.98-1.45 (m, 8H); 1.45 (m, 2H); 1.38 (s, 3H); 1.23 (s, 3H); 1.22 (m, 1H); 0.91 (d, J=6.3 Hz, 6H); 0.81 (s, 3H).

LC-MS 607.1, MH+. ESI POS; AQA; spray 4 kV/skimmer: 20 V/probe 250 C.

Further compounds prepared fundamentally in accordance with the above experimental procedures are reported in Table D-5.

TABLE D-5

| Ex # | Structure | Chemical Name and Analytical Data |
|---|---|---|
| D.5.1 | 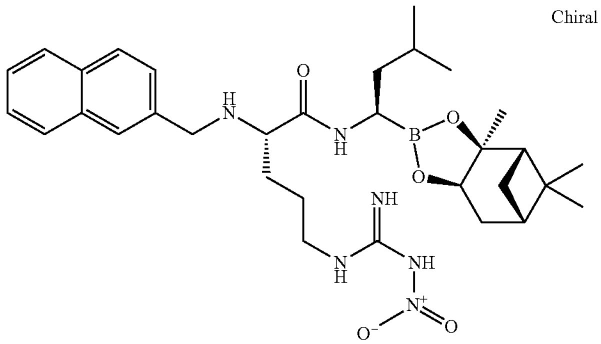 [SMILES: CC(C)C[C@H](NC(=O)[C@H](CCCNC(=N)N[N+](=O)[O-])NCc1ccc2ccccc2c1)B1O[C@@H]2C[C@@H]3C[C@@H](C3(C)C)[C@]2(C)O1] Chiral | Chemical Name: (2S)-4-[[imino(nitroamino)methyl]amino]-2-[(2-naphthylmethyl)-amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl] Analytical Data: MS: MH+ 607.1; 1H-NMR (CDCl3 + D2O): 7.81 (m, 3H); 7.71 (s, br, 1H); 7.52-7.38 (m, 3H); 4.66 (s, br, 1H); 4.27 (dd, J = 8.8, 1.9 Hz, 1H); 3.91 and 3.83 (ABq, 2H); 3.39-3.11 (m, 3H); 2.30 (m, 1H); 2.13 (m, 1H); 1.98-1.45 (m, 8H); 1.45 (m, 2H); 1.38 (s, 3H); 1.23 (s, 3H); 1.22 (m, 1H); 0.91 (d, J = 6.3 Hz, 6H); 0.81 (s,3H). |
| D.5.2 | 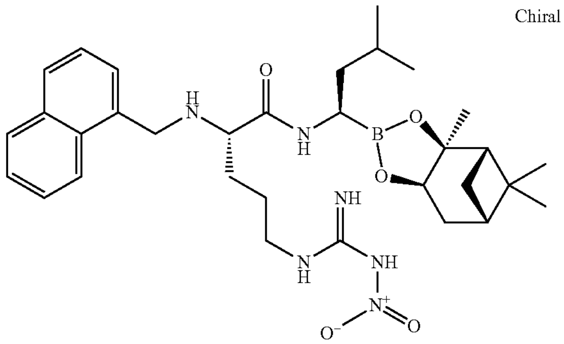 [SMILES: CC(C)C[C@H](NC(=O)[C@H](CCCNC(=N)N[N+](=O)[O-])NCc1cccc2ccccc12)B1O[C@@H]2C[C@@H]3C[C@@H](C3(C)C)[C@]2(C)O1] Chiral | Chemical Name: (2S)-4-[[imino(nitroamino)methyl]amino]-2-[(1-naphthylmethyl)-amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl] Analytical Data: MS: MH+ 607.2 |
| D.5.3 | 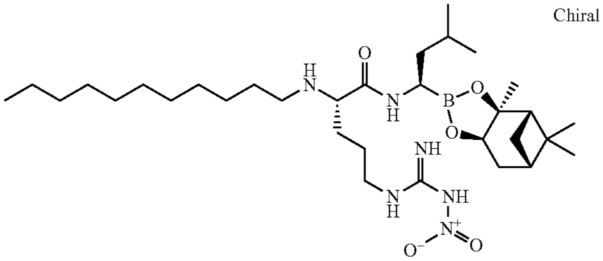 [SMILES: CCCCCCCCCCCN[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: (2S)-4-[[imino(nitroamino)methyl]amino]-2-[undecylamino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl] Analytical Data: MS: MH+ 621.2 |
| D.5.4 | 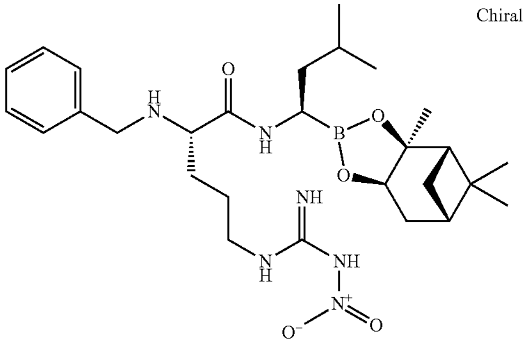 [SMILES: CC(C)C[C@H](NC(=O)[C@H](CCCNC(=N)N[N+](=O)[O-])NCc1ccccc1)B1O[C@@H]2C[C@@H]3C[C@@H](C3(C)C)[C@]2(C)O1] Chiral | Chemical Name: (2S)-4-[[imino(nitroamino)methyl]amino]-2-[(phenylmethyl)amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl] Analytical Data: MS: MH+ 557.2 |

Example D.6

N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-V-(1-naphthyl) urea Chiral

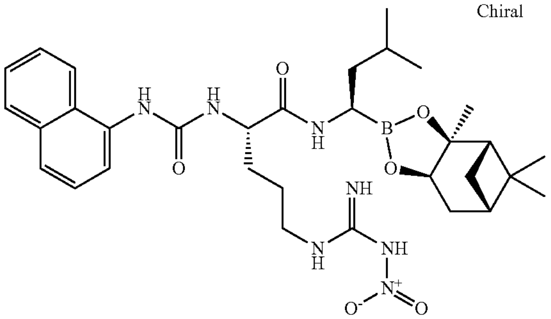 [SMILES: CC(C)C[C@H](NC(=O)[C@H](CCCNC(=N)N[N+](=O)[O-])NC(=O)Nc1cccc2ccccc12)B1O[C@@H]2C[C@@H]3C[C@@H](C3(C)C)[C@]2(C)O1]

To a solution of (2S)-2-amino-5-[[imino(nitroamino)methyl]amino]-pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-, hydrochloride salt of Example C.1 (50 mg, 0.10 mmol) in $CH_3CN$ (4 mL), TEA (0.014 mL, 0.10 mmol) and naphthalene-1-isocyanate (0.014 mL, 0.10 mmol) were added at room temperature. The reaction mixture was stirred for 4 hours and then concentrated to dryness. The residue, dissolved in DCM, was washed with $H_2O$: the organic layer was separated and the solvent removed under vacuum. Purification by silica gel flash chromatography (DCM 95, MeOH 5) gave the title compound as a white powder (60 mg, yield 94%).

NMR ($CDCl_3$): 8.08 (s, br, 1H); 7.98 (m, 1H); 7.79 (m, 2H); 7.57 (d, J=8.2 Hz, 1H); 7.51-7.35 (m, 4H); 7.36 (d, J=7.5 Hz, 1H); 7.17 (s, br, 1H); 6.67 (d, br, J=6.6 Hz, 1H); 4.49 (m, 1H); 4.20 (dd, J=8.5, 1.9 Hz, 1H); 3.39 (m, 1H); 3.20 (m, 1H); 3.04 (m, 1H); 2.26 (m, 1H); 2.08 (m, 2H); 1.93 (t, J=5.6 Hz, 1H); 1.89-1.55 (m, 7H); 1.39 (m, 1H); 1.32 (s, 3H); 1.31 (m, 1H); 1.21 (s, 3H); 1.20 (m, 1H); 0.85 (d, J=6.0 Hz, 6H); 0.79 (s, 3H).

LC-MS 636.3, MH+. ESI POS; AQA; spray 4 kV/skimmer: 20 V/probe 250° C.

Further compounds prepared fundamentally in accordance with the above experimental procedures are reported in Table D-6.

TABLE D-6

| Ex # | Structure | Chemical Name and Analytical Data |
| --- | --- | --- |
| D.6.1 | 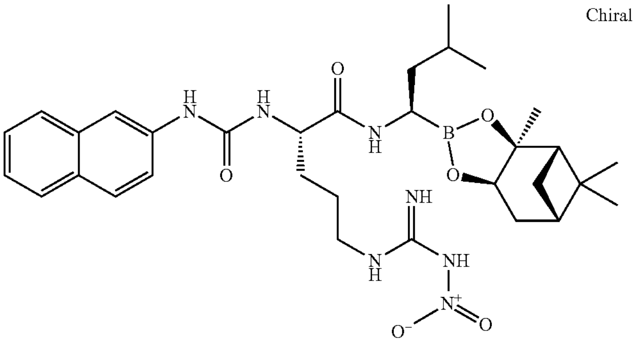 [SMILES: CC(C)C[C@H](NC(=O)[C@H](CCCNC(=N)N[N+](=O)[O-])NC(=O)Nc1ccc2ccccc2c1)B1O[C@@H]2C[C@@H]3C[C@@H](C3(C)C)[C@]2(C)O1] Chiral | Chemical Name: N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-(2-naphthyl) urea<br>Analytical Data:<br>MS: MH+ 636.4 |
| D.6.2 | 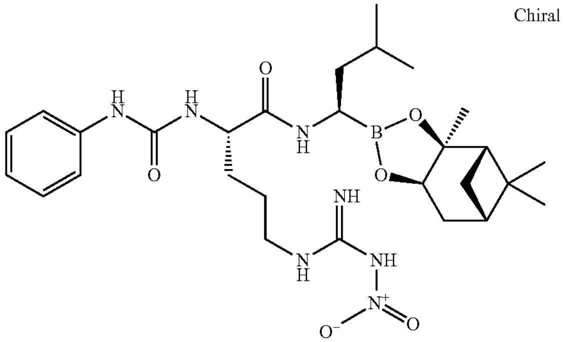 [SMILES: CC(C)C[C@H](NC(=O)[C@H](CCCNC(=N)N[N+](=O)[O-])NC(=O)Nc1ccccc1)B1O[C@@H]2C[C@@H]3C[C@@H](C3(C)C)[C@]2(C)O1] Chiral | Chemical Name: N-[(1S)-1-[[[(1R)1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-phenyl urea<br>Analytical Data:<br>MS: MH+ 586.3 |

TABLE D-6-continued

| Ex # | Structure | Chemical Name and Analytical Data |
|---|---|---|
| D.6.3 | 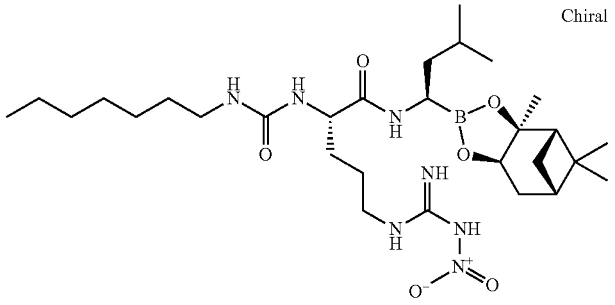 [SMILES: CCCCCCCNC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-heptyl urea Analytical Data: MS: MH+ 608.4 |
| D.6.4 | 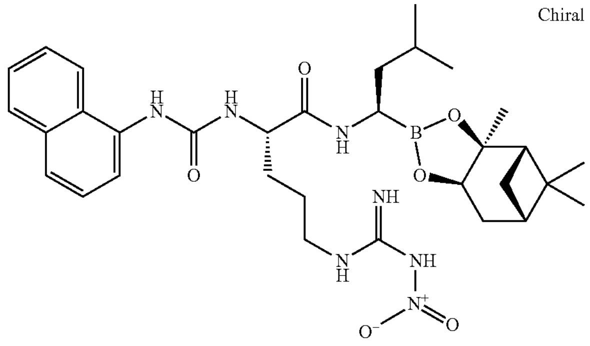 [SMILES: CC(C)C[C@H](NC(=O)[C@H](CCCNC(=N)N[N+](=O)[O-])NC(=O)Nc1cccc2ccccc12)B1O[C@@H]2C[C@@H]3C[C@@H](C3(C)C)[C@]2(C)O1] Chiral | Chemical Name: N-[(1S)-1-[[[(1R)-1-[(3aS,4S,6S,7aR)-hexahydro-3a,5,5 -trimethyl-4,6-methano-1,3,2-benzodioxaborol-2-yl]-3-methylbutyl]amino]carbonyl]-4-[[imino(nitroamino)methyl]amino]butyl]-N'-(1-naphthyl) urea Analytical Data: MS: MH+ 636.3; 1H-NMR (CDCl3): 8.08 (s, br, 1H); 7.98 (m, 1H); 7.79 (m, 2H); 7.57 (d, J = 8.2 Hz, 1H); 7.51-7.35 (m, 4H); 7.36 (d, J = 7.5 Hz, 1H); 7.17 (s, br, 1H); 6.67 (d, br, J = 6.6 Hz, 1H); 4.49 (m, 1H); 4.20 (dd, J = 8.5, 1.9 Hz, 1H); 3.39 (m, 1H); 3.20 (m, 1H); 3.04 (m, 1H); 2.26 (m, 1H); 2.08 (m, 2H); 1.93 (t, J = 5.6 Hz, 1H); 1.89-1.55 (m, 7H); 1.39 (m, 1H); 1.32 (s, 3H); 1.31 (m, 1H); 1.21 (s, 3H); 1.20 (m, 1H); 0.85 (d, J = 6.0 Hz, 6H); 0.79 (s, 3H). |
| D.6.5 | 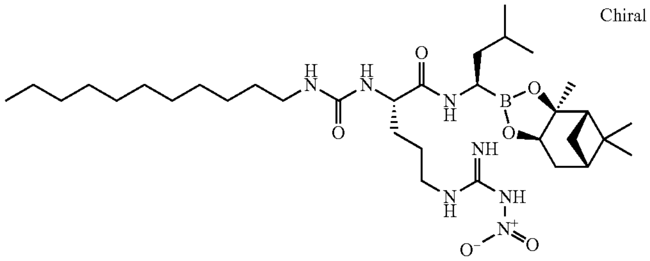 [SMILES: CCCCCCCCCCCNC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: N-[(1S)-1-[[[(1R)-1-[(3aS,4S,6S,7aR)-hexahydro-3a,5,5-trimethyl-4,6-methano-1,3,2 -benzodioxaborol-2-yl]-3-methylbutyl]amino]carbonyl]-4-[[imino(nitroamino)methyl]amino]butyl]-N'-undecylurea Analytical Data: MS: MH+ 664.4 |
| D.6.6 | 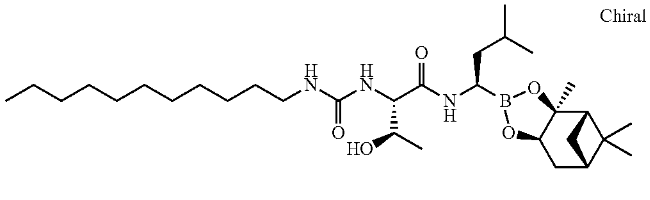 [SMILES: CCCCCCCCCCCNC(=O)N[C@H](C(=O)N[C@@H](CC(C)C)B1O[C@@H]2C[C@@H]3C[C@@H](C3(C)C)[C@]2(C)O1)[C@@H](C)O] Chiral | Chemical Name: N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]-N'-undecylurea Analytical Data: MS: [MH]+ 564.40 |

TABLE D-6-continued

| Ex # | Structure | Chemical Name and Analytical Data |
|---|---|---|
| D.6.7 | 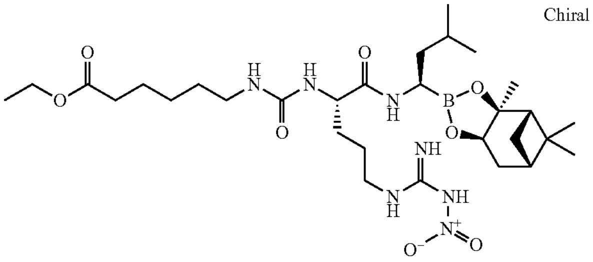 [SMILES: CCOC(=O)CCCCCNC(=O)N[C@@H](CCCNC(=N)N[N+](=O)[O-])C(=O)N[C@@H](CC(C)C)B1O[C@@H]2C[C@@H]3C[C@@H](C3(C)C)[C@]2(C)O1] Chiral | Chemical Name: N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-[5-(ethoxycarbonyl)pentyl] urea<br>Analytical Data:<br>MS: [MH]+ 652.40 |
| D.6.8 | 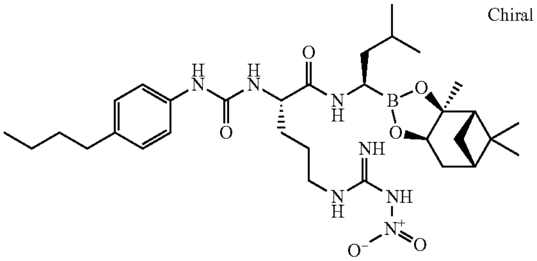 [SMILES: CCCCc1ccc(NC(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-(4-butylphenyl) urea<br>Analytical Data:<br>MS: [M]H+ 642.5 |
| D.6.9 | 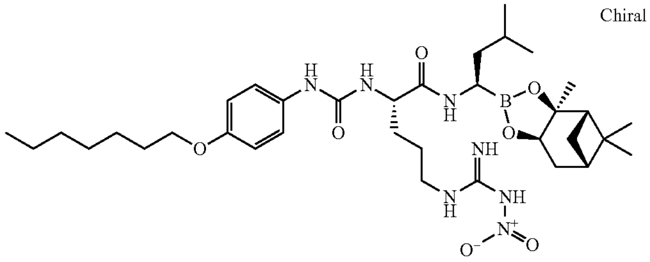 [SMILES: CCCCCCCOc1ccc(NC(=O)N[C@@H](CCCNC(=N)N[N+](=O)[O-])C(=O)N[C@@H](CC(C)C)B2O[C@@H]3C[C@@H]4C[C@@H](C4(C)C)[C@]3(C)O2)cc1] Chiral | Chemical Name: N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]-N'-(4-heptyloxylphenyl) urea<br>Analytical Data:<br>MS: [M]H+ 700.7 |

Example D.7

Boronic acid, [(1R)-1-[[(2S)-5-[[imino(nitroamino)methyl]amino]-2-IRE)-3-(naphthalen-2-yl)prop-2-enoyl]amino]-1-oxopentyl]amino]-3-methylbutyl]-

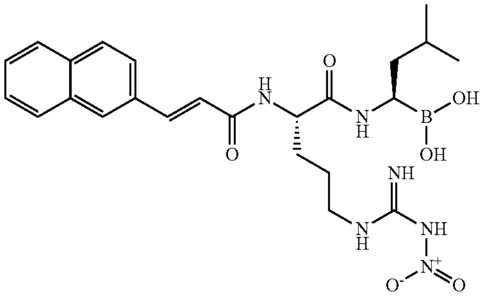

Chiral

To a suspension of PS-HOBT (1-hydroxybenzotriazole-6-sulfonamidomethyl polystyrene, 277 mg, 0.31 mmol, loading 1.12 mmol/g) in DCM (6 mL) and DMF (0.6 mL), 3-naphthalen-2-yl-acrylic acid (91.2 mg, 0.46 mmol), DIC (Diisopropylcarbodiimide, 0.22 mL, 1.40 mmol) and DIPEA (0.05 mL, 0.19 mmol) were added. The suspension was shaken for 3 hours at room temperature and then the resin was filtered under nitrogen and washed several times with DMF (3×5 mL), DCM (3×5 mL), DMF (3×5 mL) and THF (3×5 mL). The well dried resin was suspended in DCM (6 mL) and DMF (0.6 mL) and [(1R)-1-[[(2S)-2-amino-5-[[imino(nitro amino) methyl]amino]-1-oxopentyl]amino]-3-methylbutyl]-boronic acid hydrochloride salt of Example C.2 (50 mg, 0.14 mmol) and DIPEA (0.06 mL, 0.20 mmol) were added. The reaction mixture was shaken overnight at room temperature. The resin was filtered off and washed with DMF (10 mL) and DCM (2 mL) and the solvent was concentrated to dryness. Purification of the crude compound by ISOLUTE SPE-SI normal phase cartridge (DCM 1, MeOH 1), afforded the title compound (25 mg, yield 35%).

NMR (DMSO+$D_2O$, 343 K): 8.06 (s, 1H); 7.95 (d, J=9.0 Hz, 1H); 7.94 (m, 2H); 7.72 (d, 1H); 7.61 (d, J=14.9 Hz, 1H); 7.55 (d, J=9.0 Hz, 1H); 7.55 (m, 2H); 6.89 (d, J=14.9 Hz, 1H); 4.40 (m, 1H); 3.30-3.10 (m, 3H); 1.82 (m, 1H); 1.73-1.53 (m, 4H); 1.50-1.32 (m, 2H); 0.87 (d, J=6.1 Hz, 3H); 0.86 (d, J=6.1 Hz, 3H).

LC-MS 495.0, [M-18]H+. ESI POS; AQA; spray 5 kV/skimmer: 15 V/probe 250 C.

Further compounds prepared fundamentally in accordance with the above experimental procedures are reported in Table D-7.

TABLE D-7

| Ex # | Structure | Chemical Name and Analytical Data |
|---|---|---|
| D.7.1 | 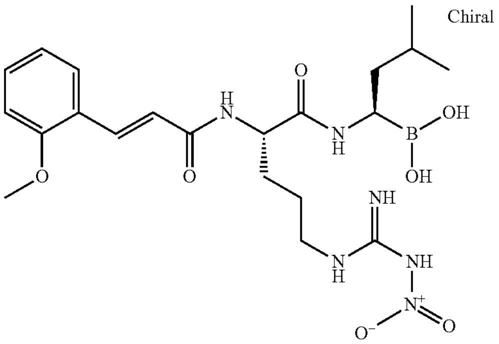 [SMILES: COc1ccccc1/C=C/C(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[[(2E)-3-(2-methoxyphenyl)-1-oxoprop-2-enyl]amino]-1-oxopentyl]amino]-3-methylbutyl]<br>Analytical Data:<br>MS: MH+ 475.0 |
| D.7.2 | 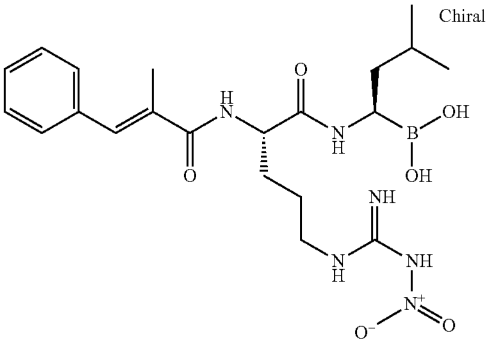 | Chemical Name:<br>Boronic acid, [(1R)-1-[[(2S)-5-[[imino(nitroamino)methyl]amino]-2-[((E)-2-methyl-3-phenylacryl)amino]-1-oxopentyl]amino]-3-methylbutyl]<br>Analytical Data:<br>MS: [M − 18]H+ 458.0 |
| D.7.3 | 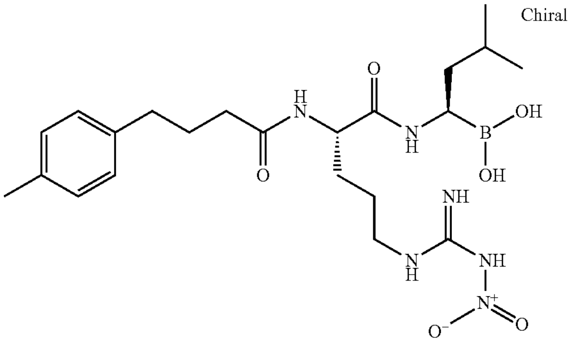 | Chemical Name:<br>Boronic acid, [(1R)-1-[[(2S)-5-[[imino(nitroamino)methyl]amino]-2-[(4-(4-methylphenyl)butanoyl)amino]-1-oxopentyl]amino]-3-methylbutyl]<br>Analytical Data:<br>MS: [M − 18]H+ 474.0 |
| D.7.4 | 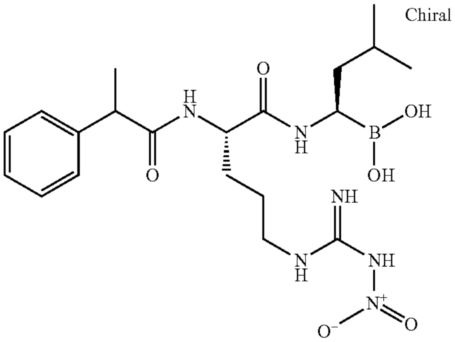 [SMILES: CC(C)C[C@H](NC(=O)[C@H](CCCNC(=N)N[N+](=O)[O-])NC(=O)C(C)c1ccccc1)B(O)O] | Chemical Name:<br>Boronic acid, [(1R)-1-[[(2S)-5-[[imino(nitroamino)methyl]amino]-2-[((2RS)-2-phenylpropanoyl)amino]-1-oxopentyl]amino]-3-methylbutyl]<br>Analytical Data:<br>MS: [M −18]H+ 447.2 |

TABLE D-7-continued

| Ex # | Structure | Chemical Name and Analytical Data |
|---|---|---|
| D.7.5 | 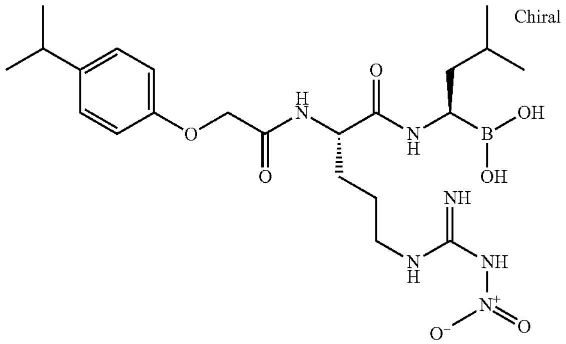 [SMILES: CC(C)C[C@H](NC(=O)[C@H](CCCNC(=N)N[N+](=O)[O-])NC(=O)COc1ccc(C(C)C)cc1)B(O)O] | Chemical Name: Boronic acid, [(1R)-1-[[(2S)-5-[[imino(nitroamino)methyl]amino]-2-[(2-(4 - isopropylphenoxy)acetyl)amino]-1-oxopentyl]amino]-3-methylbutyl] Analytical Data: MS: [M − 18]H+ 491.5 |
| D.7.6 | 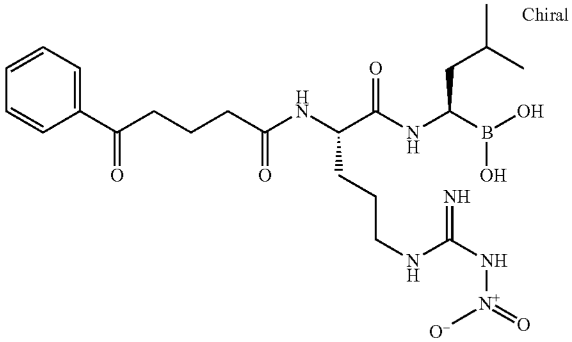 [SMILES: CC(C)C[C@H](NC(=O)[C@H](CCCNC(=N)N[N+](=O)[O-])NC(=O)CCCC(=O)c1ccccc1)B(O)O] | Chemical Name: Boronic acid, [(1R)-1-[[(2S)-5-[[imino(nitroamino)methyl]amino]-2-[(5-oxo-5-phenylpentanoyl)amino]-1-oxopentyl]amino]-3-methylbutyl] Analytical Data: MS: [M − 18]H+ 489.5 |
| D.7.7 | 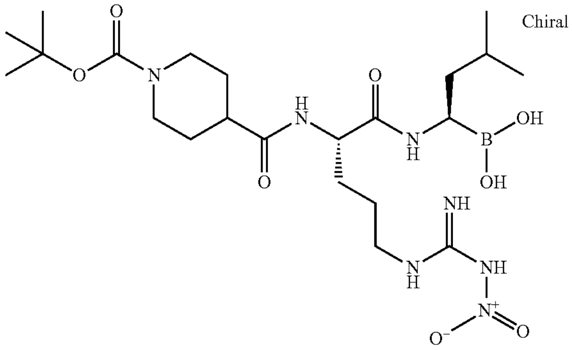 [SMILES: CC(C)C[C@H](NC(=O)[C@H](CCCNC(=N)N[N+](=O)[O-])NC(=O)C1CCN(C(=O)OC(C)(C)C)CC1)B(O)O] | Chemical Name: Boronic acid, [(1R)-1-[[(2S)-5-[[immo(nitroamino)methyl]amino]-2-[[(4RS)-1-[(1,1-dimethylethoxy)carbonyl]piperidine-4-carbonyl]amino]-1-oxopentyl]amino]-3-methylbutyl] Analytical Data: MS: [M − 18]H+ 526.1 |
| D.7.8 | 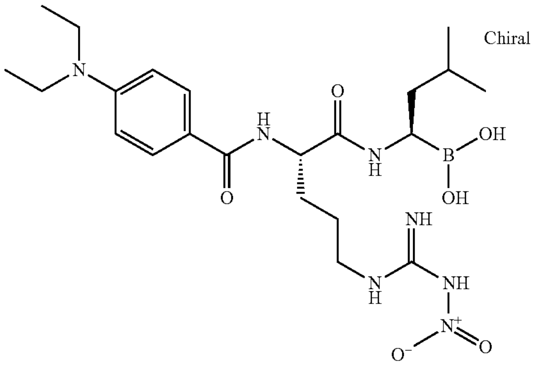 [SMILES: CCN(CC)c1ccc(C(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl] amino]-2-[(4-diethylaminobenzoyl)amino]-1-oxopentyl] amino]-3-methylbutyl] Analytical Data: MS: [M − 18]H+ 508.1 |

TABLE D-7-continued

| Ex # | Structure | Chemical Name and Analytical Data |
|---|---|---|
| D.7.9 | 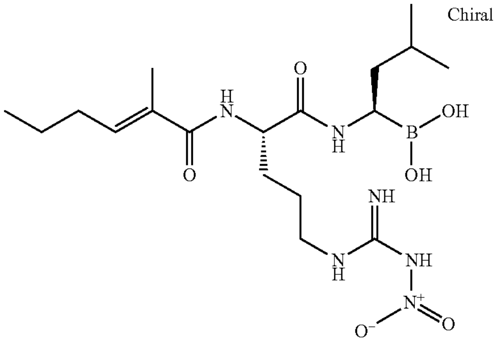 [SMILES: CCC/C=C(\C)C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl] amino]-2-[((E)-2-methylhex-2-enoyl)amino]-1-oxopentyl]amino]-3-methylbutyl] Analytical Data: MS: [M − 18]H+ 443.0 |
| D.7.10 | 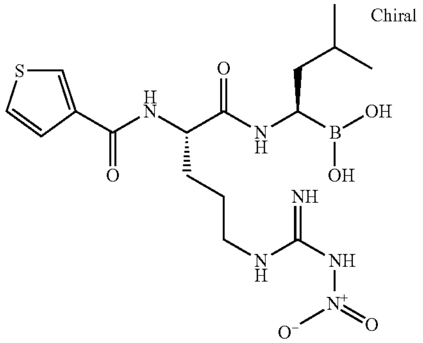 [SMILES: CC(C)C[C@H](NC(=O)[C@H](CCCNC(=N)N[N+](=O)[O-])NC(=O)c1ccsc1)B(O)O] | Chemical Name: Boronic acid, [(1R)-1-[[(2S)-5-[[imino(nitroamino)methyl]amino]-2-[(tiophen-3-carbonyl)amino]-1-oxopentyl]amino]-3-methylbutyl] Analytical Data: MS: [M − 18]H+ 425.6 |
| D.7.11 | 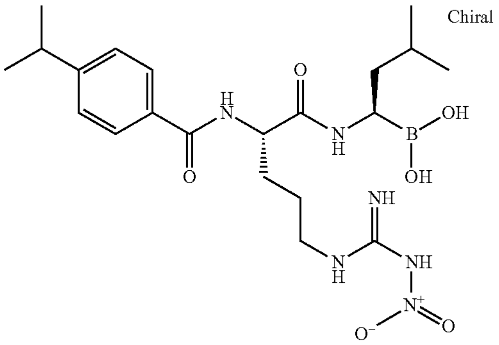 [SMILES: CC(C)C[C@H](NC(=O)[C@H](CCCNC(=N)N[N+](=O)[O-])NC(=O)c1ccc(C(C)C)cc1)B(O)O] | Chemical Name: Boronic acid, [(1R)-1-[[(2S)-5-[[imino(nitroamino)methyl]amino]-2-[(4-isopropylbenzoyl)amino]-1-oxopentyl]amino]-3-methylbutyl] Analytical Data: MS: [M − 18]H+ 461.3 |
| D.7.12 | 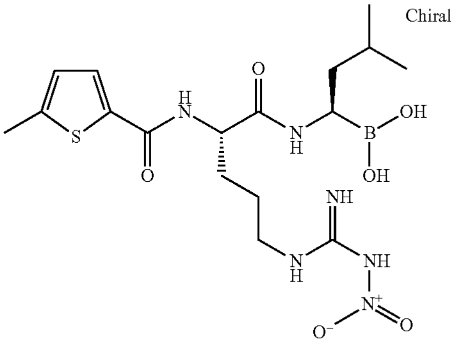 [SMILES: Cc1ccc(C(=O)N[C@@H](CCCNC(=N)N[N+](=O)[O-])C(=O)N[C@@H](CC(C)C)B(O)O)s1] | Chemical Name: Boronic acid, [(1R)-1-[[(2S)-5-[[imino(nitroamino)methyl]ammo]-2-[(5-methylthiophene-2-carbonyl)amino]-1-oxopentyl]amino]-3-methylbutyl] Analytical Data: MS: [M − 18]H+ 439.3 |

TABLE D-7-continued

| Ex # | Structure | Chemical Name and Analytical Data |
|---|---|---|
| D.7.13 | 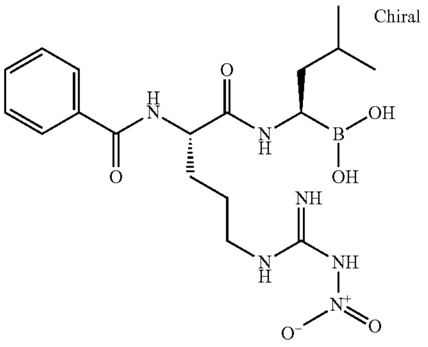 [SMILES: CC(C)C[C@H](NC(=O)[C@H](CCCNC(=N)N[N+](=O)[O-])NC(=O)c1ccccc1)B(O)O] | Chemical Name: Boronic acid, [(1R)-1-[[(2S)-5-[[imino(nitroamino)methyl]amino]-2-[(benzoyl)amino]-1-oxopentyl]amino]-3-methylbutyl] Analytical Data: MS: [M − 18]H+ 419.4 |
| D.7.14 | 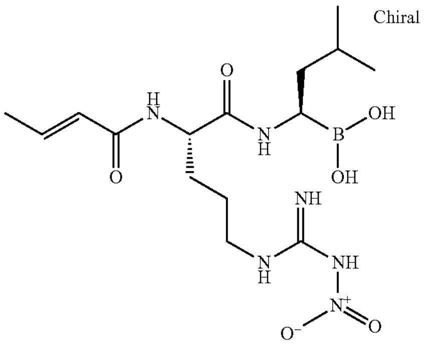 [SMILES: C/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitro amino)methyl] amino]-2-[((E)-2-butenoyl)amino]-1-oxopentyl]amino]-3-methylbutyl] Analytical Data: MS: [M − 18]H+ 383.2 |
| D.7.15 | 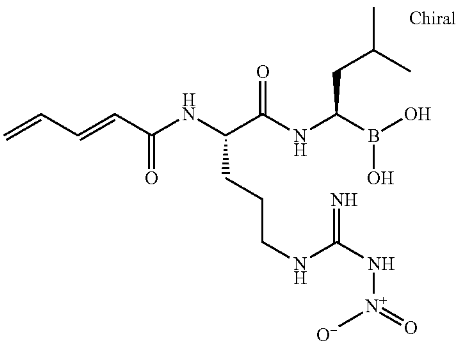 [SMILES: C=C/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[((E)-penta-2,4-dienoyl)amino]-1-oxopentyl]amino]-3-methylbutyl] Analytical Data: MS: [M − 18]H+ 395.4 |
| D.7.16 | 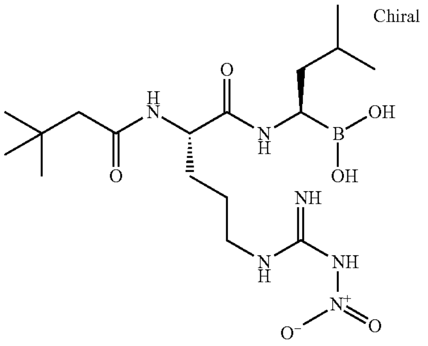 [SMILES: CC(C)C[C@H](NC(=O)[C@H](CCCNC(=N)N[N+](=O)[O-])NC(=O)CC(C)(C)C)B(O)O] | Chemical Name: Boronic acid, [(1R)-1-[[(2S)-5-[[imino(nitroamino)methyl]amino]-2-[(3,3-dimethyl-butanoyl)amino]-1-oxopentyl]amino]-3-methylbutyl] Analytical Data: MS: [M − 18]H+ 413.0 |

TABLE D-7-continued

| Ex # | Structure | Chemical Name and Analytical Data |
|---|---|---|
| D.7.17 | 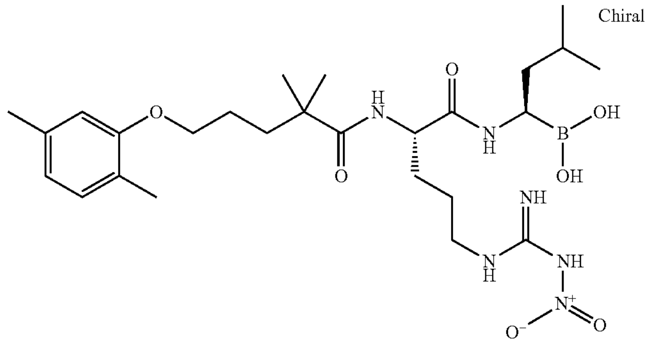 [SMILES: Cc1ccc(C)c(OCCCC(C)(C)C(=O)N[C@@H](CCCNC(=N)N[N+](=O)[O-])C(=O)N[C@@H](CC(C)C)B(O)O)c1] | Chemical Name: Boronic acid, [(1R)-1-[[(2S)-5-[[imino(nitroamino)methyl]amino]-2-[[5-(2,5-dimethylphenoxy)-2,2-dimethylpentanoyl]amino]-1-oxopentyl]amino]-3-methylbutyl] Analytical Data: MS: [M − 18]H+ 547.2 |
| D.7.18 | 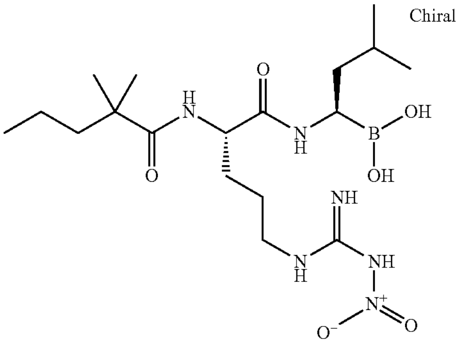 [SMILES: CCCC(C)(C)C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(2,2-dimethylpentanoyl)amino]-1-oxopentyl]amino]-3-methylbutyl] Analytical Data: MS: [M − 18]H+ 427.5 |
| D.7.19 | 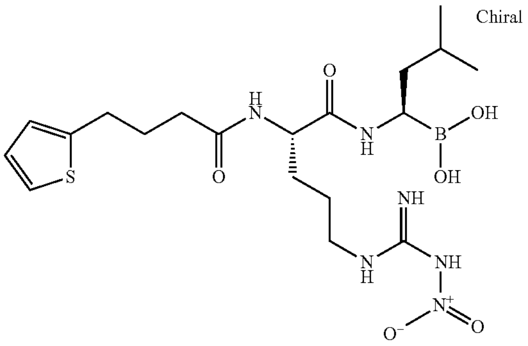 [SMILES: CC(C)C[C@H](NC(=O)[C@H](CCCNC(=N)N[N+](=O)[O-])NC(=O)CCCc1cccs1)B(O)O] | Chemical Name: Boronic acid, [(1R)-1-[[(2S)-5-[[imino(nitroamino)methyl]amino]-2-[[4-(thiophen-2-yl)butanoyl]amino]-1-oxopentyl]amino]-3-methylbutyl] Analytical Data: MS: [M − 18]H+ 467.5 |
| D.7.20 | 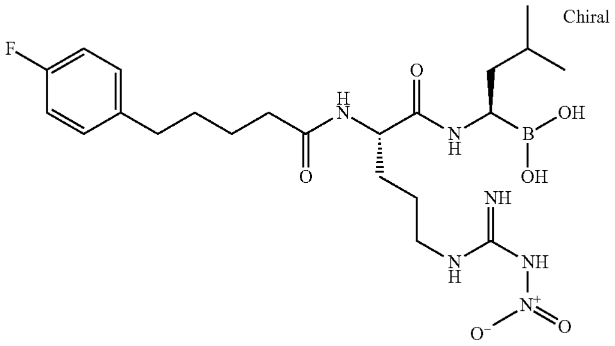 [SMILES: CC(C)C[C@H](NC(=O)[C@H](CCCNC(=N)N[N+](=O)[O-])NC(=O)CCCCc1ccc(F)cc1)B(O)O] | Chemical Name: Boronic acid, [(1R)-1-[[(2S)-5-[[imino(nitroamino)methyl]amino]-2-[[5-(4-fluorophenyl)pentanoyl]amino]-1-oxopentyl]amino]-3-methylbutyl] Analytical Data: MS: [M − 18]H+ 493.4 |

TABLE D-7-continued

| Ex # | Structure | Chemical Name and Analytical Data |
| --- | --- | --- |
| D.7.21 | 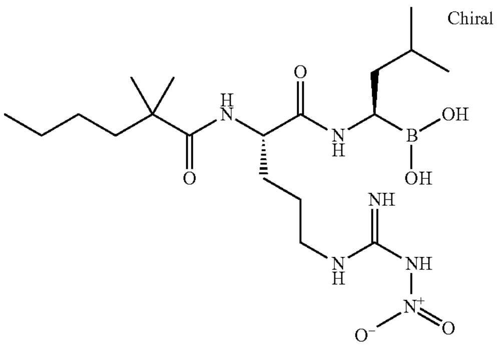 [SMILES: CCCCC(C)(C)C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(2,2-dimethylhexanoyl)amino]-1-oxopentyl]amino]-3-methylbutyl] Analytical Data: MS: [M − 18]H+ 441.0 |
| D.7.22 | 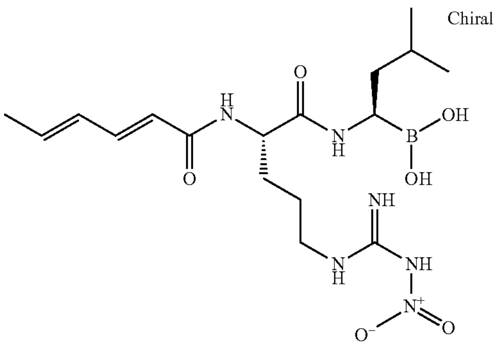 [SMILES: C/C=C/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(hex-2,4-enoyl)amino]-1-oxopentyl] amino]-3-methylbutyl] Analytical Data: MS: [M − 18]H+ 409.3 |
| D.7.23 | 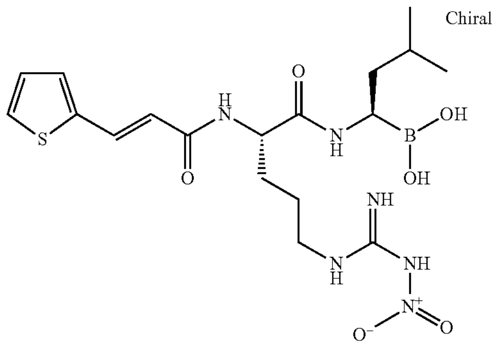 [SMILES: CC(C)C[C@H](NC(=O)[C@H](CCCNC(=N)N[N+](=O)[O-])NC(=O)/C=C/c1cccs1)B(O)O] | Chemical Name: Boronic acid, [(1R)-1-[[(2S)-5-[[imino(nitroamino)methyl]amino]-2-[[3-(thiophen-2-yl)propenoyl]amino]-1-oxopentyl]amino]-3-methylbutyl] Analytical Data: MS: [M − 18]H+ 451.4 |
| D.7.24 | 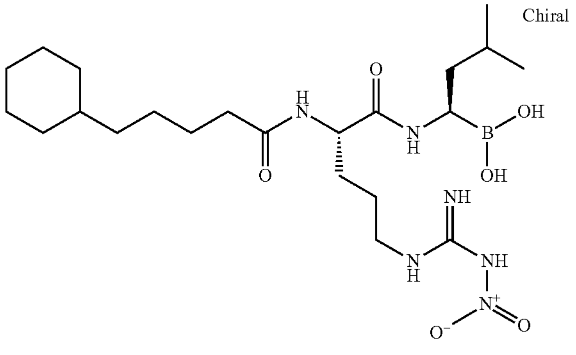 [SMILES: CC(C)C[C@H](NC(=O)[C@H](CCCNC(=N)N[N+](=O)[O-])NC(=O)CCCCC1CCCCC1)B(O)O] | Chemical Name: Boronic acid, [(1R)-1-[[(2S)-5-[[imino(nitroamino)methyl]amino]-2-[(5-cyclohexylpentanoyl)amino]-1-oxopentyl]amino]-3-methylbutyl] Analytical Data: MS: [M − 18]H+ 481.1 |

TABLE D-7-continued

| Ex # | Structure | Chemical Name and Analytical Data |
|---|---|---|
| D.7.25 | 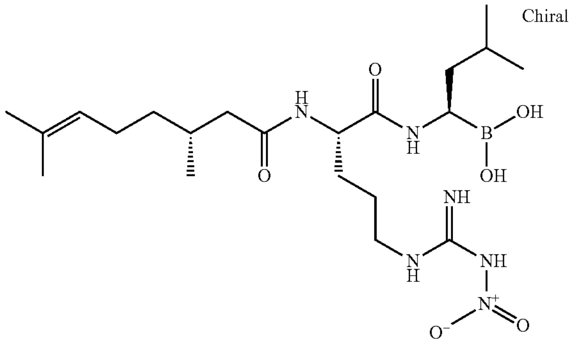 [SMILES: CC(C)=CCC[C@@H](C)CC(=O)N[C@@H](CCCNC(=N)N[N+](=O)[O-])C(=O)N[C@@H](CC(C)C)B(O)O] Chiral | Chemical Name: Boronic acid, [(1R)-1-[[(2S)-5-[[imino(nitroamino)methyl]amino]-2-[((3R)-3,7-dimethyloct-6-enoyl)amino]-1-oxopentyl]amino]-3-methylbutyl] Analytical Data: MS: [M − 18]H+ 467.3 |
| D.7.26 | 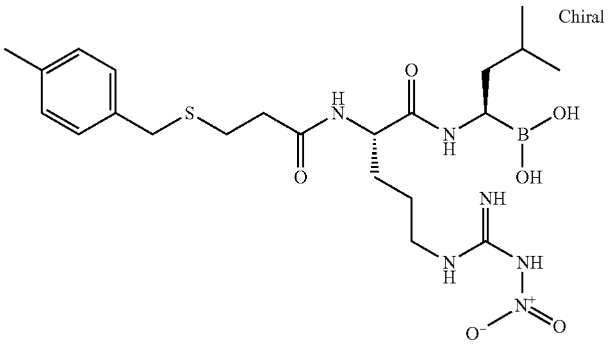 [SMILES: Cc1ccc(CSCCC(=O)N[C@@H](CCCNC(=N)N[N+](=O)[O-])C(=O)N[C@@H](CC(C)C)B(O)O)cc1] Chiral | Chemical Name: Boronic acid, [(1R)-1-[[(2S)-5-[[imino(nitroamino)methyl]amino]-2-[[3-[(4-methylbenzyl)sulfanyl]propanoyl]amino]-1-oxopentyl]amino]-3-methylbutyl] Analytical Data: MS: [M − 18]H+ 507.0 |
| D.7.27 | 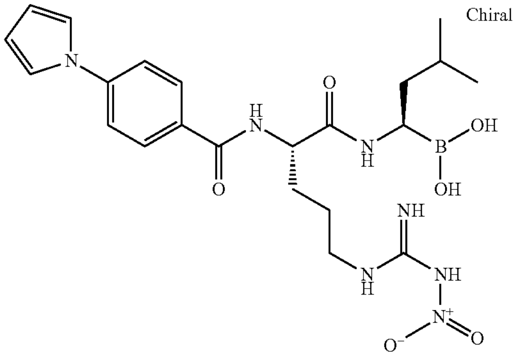 [SMILES: CC(C)C[C@H](NC(=O)[C@H](CCCNC(=N)N[N+](=O)[O-])NC(=O)c1ccc(-n2cccc2)cc1)B(O)O] Chiral | Chemical Name: Boronic acid, [(1R)-1-[[(2S)-5-[[imino(nitroamino)methyl]amino]-2-[(4-pyrrol-1-ylbenzoyl)amino]-1-oxopentyl]amino]-3-methylbutyl] Analytical Data: MS: [M − 18]H+ 484.4 |
| D.7.28 | 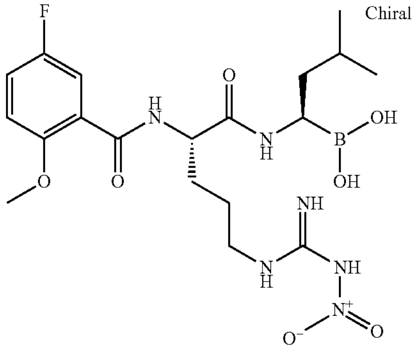 [SMILES: COc1ccc(F)cc1C(=O)N[C@@H](CCCNC(=N)N[N+](=O)[O-])C(=O)N[C@@H](CC(C)C)B(O)O] Chiral | Chemical Name: Boronic acid, [(1R)-1-[[(2S)-5-[[imino(nitroamino)methyl]amino]-2-[(5-fluoro-2-methoxybenzoyl)amino]-1-oxopentyl]amino]-3-methylbutyl] Analytical Data: MS: [M − 18]H+ 466.9 |

TABLE D-7-continued

| Ex # | Structure | Chemical Name and Analytical Data |
| --- | --- | --- |
| D.7.29 | 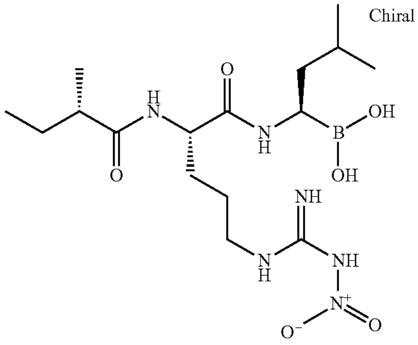 [SMILES: CC[C@H](C)C(=O)N[C@@H](CCCNC(=N)N[N+](=O)[O-])C(=O)N[C@@H](CC(C)C)B(O)O] Chiral | Chemical Name:<br>Boronic acid, [(1R)-1-[[(2S)-5-[[immo(nitroamino)methyl]amino]-2-[((2S)-2-methylbutanoyl)amino]-1-oxopentyl]amino]-3-methylbutyl]<br>Analytical Data:<br>MS: [M − 18]H+ 399.0 |
| D.7.30 | 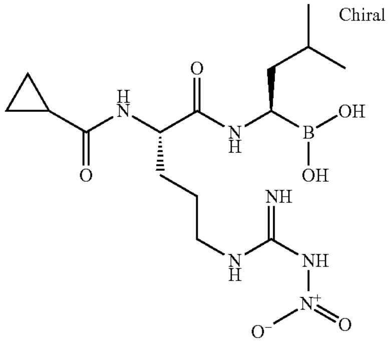 [SMILES: CC(C)C[C@H](NC(=O)[C@H](CCCNC(=N)N[N+](=O)[O-])NC(=O)C1CC1)B(O)O] Chiral | Chemical Name:<br>Boronic acid, [(1R)-1-[[(2S)-5-[[imino(nitroamino)methyl]amino]-2-[(cyclopropanecarbonyl)amino]-1-oxopentyl]amino]-3-methylbutyl]<br>Analytical Data:<br>MS: [M − 18]H+ 383.0 |
| D.7.31 | 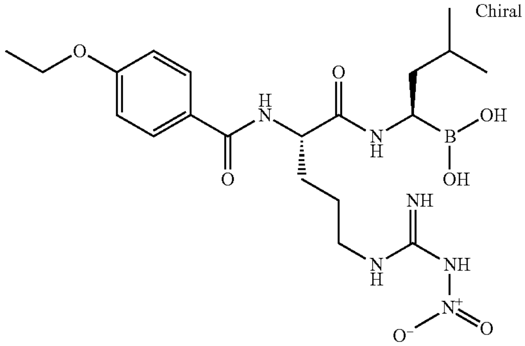 [SMILES: CCOc1ccc(C(=O)N[C@@H](CCCNC(=N)N[N+](=O)[O-])C(=O)N[C@@H](CC(C)C)B(O)O)cc1] Chiral | Chemical Name:<br>Boronic acid, [(1R)-1-[[(2S)-5-[[imino(nitroamino)methyl]amino]-2-[(4-ethoxybenzoyl)amino]-1-oxopentyl]amino]-3-methylbutyl]<br>Analytical Data:<br>MS: [M − 18]H+ 463.5 |
| D.7.32 | 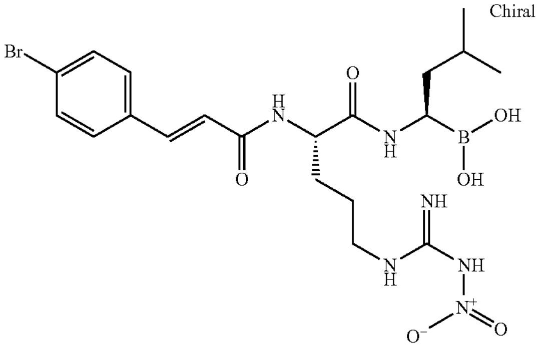 [SMILES: CC(C)C[C@H](NC(=O)[C@H](CCCNC(=N)N[N+](=O)[O-])NC(=O)/C=C/c1ccc(Br)cc1)B(O)O] Chiral | Chemical Name:<br>Boronic acid, [(1R)-1-[[(2S)-5-[[imino(nitroamino)methyl]ammo]-2-[((E)-3-(4-bromophenyl)prop-2-enoyl)amino]-1-oxopentyl]amino]-3-methylbutyl]<br>Analytical Data:<br>MS: [M − 18]H+ 523.6 |

TABLE D-7-continued

| Ex # | Structure | Chemical Name and Analytical Data |
|---|---|---|
| D.7.33 | 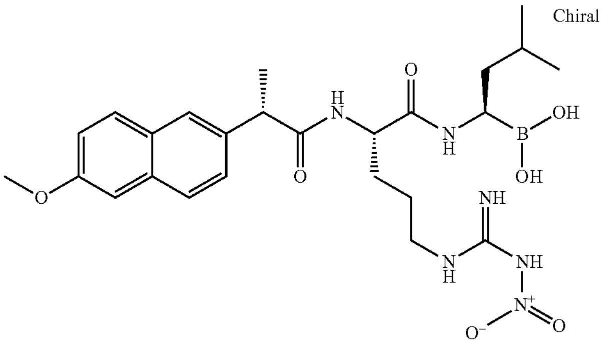 [SMILES: COc1ccc2cc([C@H](C)C(=O)N[C@@H](CCCNC(=N)N[N+](=O)[O-])C(=O)N[C@@H](CC(C)C)B(O)O)ccc2c1] | Chemical Name:<br>Boronic acid, [(1R)-1-[[(2S)-5-[[immo(nitroamino)methyl]amino]-2-[[(2S)-2-(6-methoxynaphthalen-2-yl)-propanoyl]amino]-1-oxopentyl]amino]-3-methylbutyl]<br>Analytical Data:<br>MS: [M − 18]H+ 527.5 |
| D.7.34 | 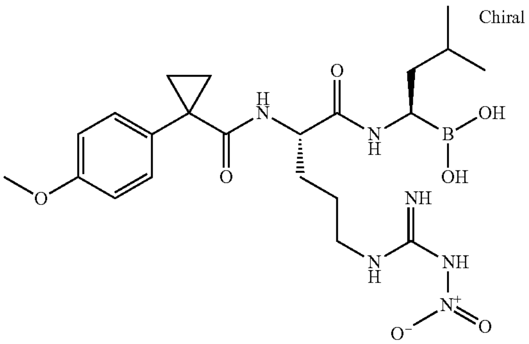 [SMILES: COc1ccc(C2(C(=O)N[C@@H](CCCNC(=N)N[N+](=O)[O-])C(=O)N[C@@H](CC(C)C)B(O)O)CC2)cc1] | Chemical Name:<br>Boronic acid, [(1R)-1-[[(2S)-5-[[imino(nitroamino)methyl]amino]-2-[[1-(4-methoxyphenyl)-cyclopropanecarbonyl]amino]-1-oxopentyl]amino]-3-methylbutyl]<br>Analytical Data:<br>MS: [M − 18]H+ 489.4 |
| D.7.35 | 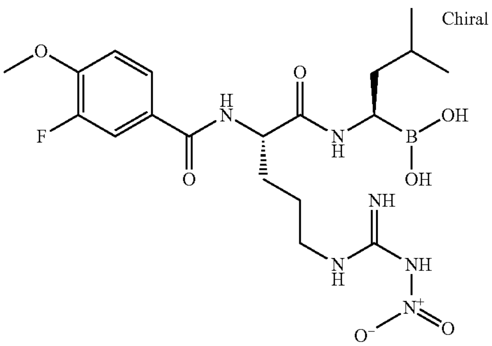 [SMILES: COc1ccc(C(=O)N[C@@H](CCCNC(=N)N[N+](=O)[O-])C(=O)N[C@@H](CC(C)C)B(O)O)cc1F] | Chemical Name:<br>Boronic acid, [(1R)-1-[[(2S)-5-[[imino(nitroamino)methyl]amino]-2-[(3-fluoro-4-methoxybenzoyl)amino]-1-oxopentyl]amino]-3-methylbutyl]<br>Analytical Data:<br>MS: [M − 18]H+ 466.9 |
| D.7.36 | 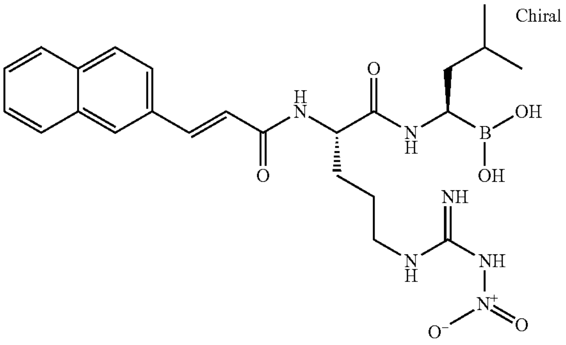 [SMILES: CC(C)C[C@H](NC(=O)[C@H](CCCNC(=N)N[N+](=O)[O-])NC(=O)/C=C/c1ccc2ccccc2c1)B(O)O] | Chemical Name:<br>Boronic acid, [(1R)-1-[[(2S)-5-[[imino(nitroamino)methyl]ammo]-2-[[(E)-3-(naphthalen-2-yl)prop-2-enoyl]amino]-1-oxopentyl]amino]-3-methylbutyl]<br>Analytical Data:<br>MS: [M − 18]H+ 495.0; 1H-NMR: (DMSO + D2O, 343 K): 8.06 (s, 1H); 7.95 (d, J = 9.0 Hz, 1H); 7.94 (m, 2H); 7.72 (d, 1H); 7.61 (d, J = 14.9 Hz, 1H); 7.55 (d, J = 9.0 Hz, 1H); 7.55 (m, 2H); 6.89 (d, J = 14.9 Hz, 1H); 4.40 (m, 1H); 3.30-3.10 (m, 3H); 1.82 (m, 1H); 1.73-1.53 (m, 4H); 1.50-1.32 (m, 2H); 0.87 (d, J = 6.1 Hz, 3H); 0.86 (d, J = 6.1 Hz, 3H). |

TABLE D-7-continued

| Ex # | Structure | Chemical Name and Analytical Data |
|---|---|---|
| D.7.37 | 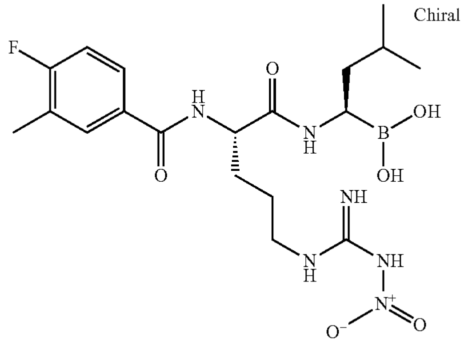 [SMILES: Cc1cc(C(=O)N[C@@H](CCCNC(=N)N[N+](=O)[O-])C(=O)N[C@@H](CC(C)C)B(O)O)ccc1F] | Chemical Name: Boronic acid, [(1R)-1-[[(2S)-5-[[imino(nitroamino)methyl]amino]-2-[(4-fluoro-3-methylbenzyl)amino]-1-oxopentyl]amino]-3-methylbutyl] Analytical Data: MS: [M − 18]H+ 451.3 |
| D.7.38 | 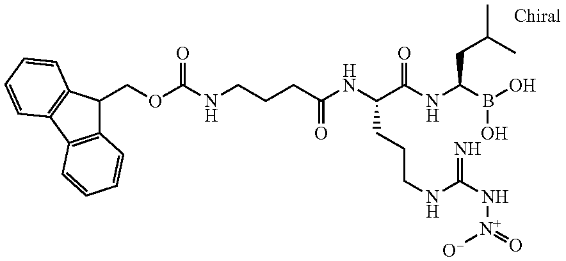 [SMILES: CC(C)C[C@H](NC(=O)[C@H](CCCNC(=N)N[N+](=O)[O-])NC(=O)CCCNC(=O)OCC1c2ccccc2-c2ccccc21)B(O)O] | Chemical Name: Boronic acid, [(1R)-1-[[(2S)-5-[[imino(nitroamino)methyl]amino]-2-[[[[[(9H-fluoren-9-yl)methoxy]carbonyl]amino]butanoyl]amino]-1-oxopentyl]amino]-3-methylbutyl] Analytical Data: MS: [M − 18]H+ 622.2 |
| D.7.39 | 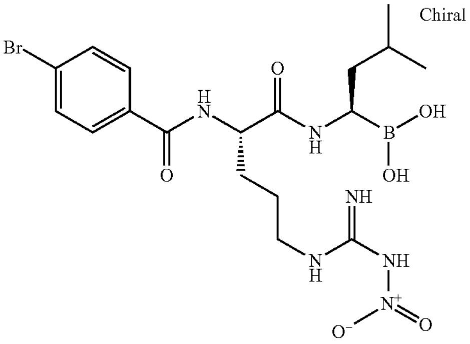 [SMILES: CC(C)C[C@H](NC(=O)[C@H](CCCNC(=N)N[N+](=O)[O-])NC(=O)c1ccc(Br)cc1)B(O)O] | Chemical Name: Boronic acid, [(1R)-1-[[(2S)-5-[[imino(nitroamino)methyl]amino]-2-[(4-bromobenzoyl)amino]-1-oxopentyl]amino]-3-methylbutyl] Analytical Data: MS: [M − 18]H+ 497.1 |
| D.7.40 | 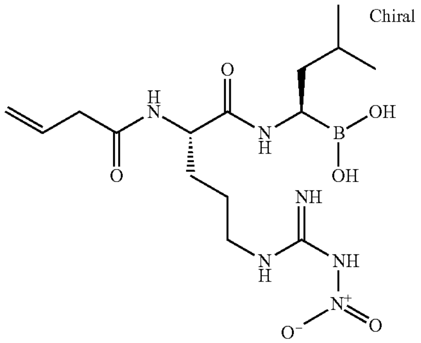 [SMILES: C=CCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(3-butenoyl)amino]-1-oxopentyl]amino]-3-methylbutyl] Analytical Data: MS: [M − 18]H+ 383.2 |

TABLE D-7-continued

| Ex # | Structure | Chemical Name and Analytical Data |
|---|---|---|
| D.7.41 | 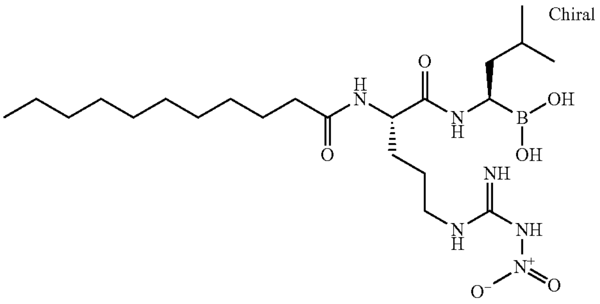 [SMILES: CCCCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(undecanoyl)amino]-1-oxopentyl]amino]-3-methylbutyl] Analytical Data: MS: [M − 18]H+ 483.4 |
| D.7.42 | 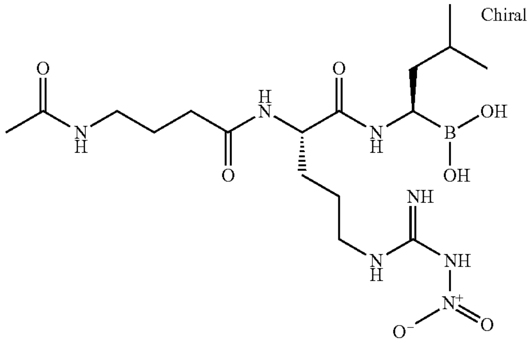 [SMILES: CC(=O)NCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[[4-(acetylamino)butanoyl]amino]-1-oxopentyl]amino]-3-methylbutyl] Analytical Data: MS: [M − 18]H+ 442.2 |
| D.7.43 | 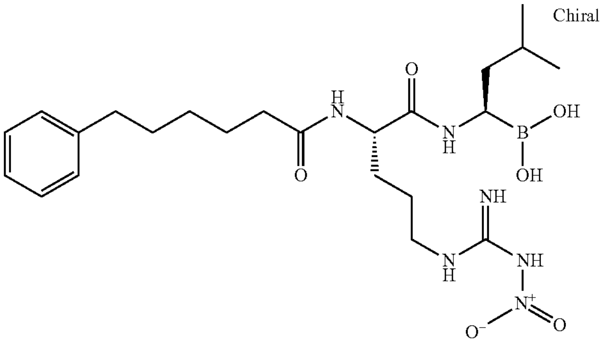 [SMILES: CC(C)C[C@H](NC(=O)[C@H](CCCNC(=N)N[N+](=O)[O-])NC(=O)CCCCCc1ccccc1)B(O)O] | Chemical Name: Boronic acid, [(1R)-1-[[(2S)-5-[[imino(nitroamino)methyl]amino]-2-[(6-phenylhexanoyl)amino]-1-oxopentyl]amino]-3-methylbutyl]- Analytical Data: MS: [M − 18]H+ 489.27 |
| D.7.44 | 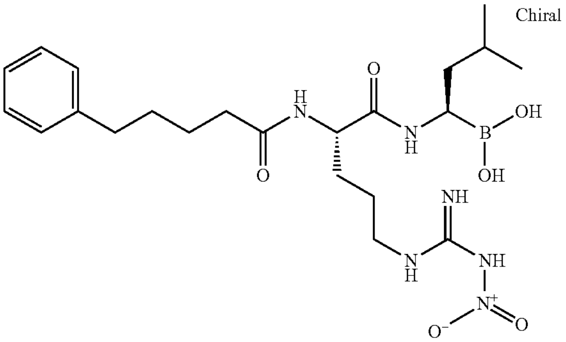 [SMILES: CC(C)C[C@H](NC(=O)[C@H](CCCNC(=N)N[N+](=O)[O-])NC(=O)CCCCc1ccccc1)B(O)O] | Chemical Name: Boronic acid, [(1R)-1-[[(2S)-5-[[imino(nitroamino)methyl]amino]-2-[(5-phenylpentanoyl)amino]-1-oxopentyl]amino]-3-methylbutyl]- Analytical Data: MS: [M − 18]H+ 475.23 |

TABLE D-7-continued

| Ex # | Structure | Chemical Name and Analytical Data |
|---|---|---|
| D.7.45 | 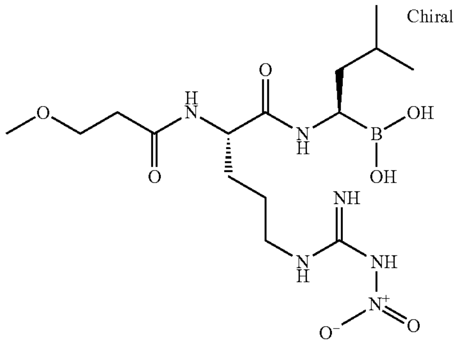 [SMILES: COCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[(3-methoxypropanoyl)amino]-1-oxopentyl]amino]-3-methylbutyl]-<br>Analytical Data:<br>MS: [M − 18]H+ 401.16 |
| D.7.46 | 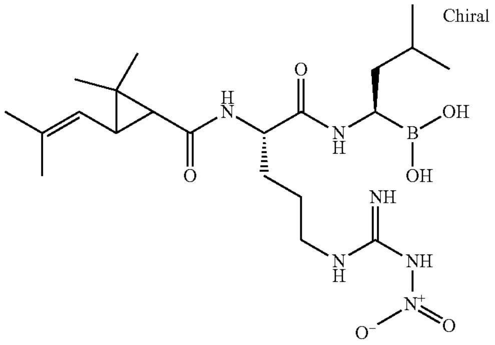 [SMILES: CC(C)=CC1C(C(=O)N[C@@H](CCCNC(=N)N[N+](=O)[O-])C(=O)N[C@@H](CC(C)C)B(O)O)C1(C)C] | Chemical Name: Boronic acid, [(1R)-1-[[(2S)-5-[[immo(nitroamino)methyl]amino]-2-[[2,2-dimethyl-3-(2-methylpropenyl)-cyclopropanecarbonyl]amino]-1-oxopentyl]amino]-3-methylbutyl]-<br>Analytical Data:<br>MS: [M − 18]H+ 465.29 |
| D.7.47 | 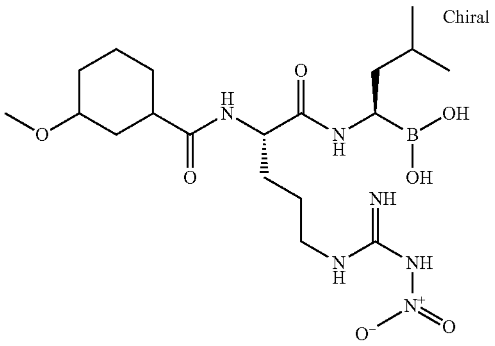 [SMILES: COC1CCCC(C(=O)N[C@@H](CCCNC(=N)N[N+](=O)[O-])C(=O)N[C@@H](CC(C)C)B(O)O)C1] | Chemical Name:<br>Boronic acid, [(1R)-1-[[(2S)-5-[[imino(nitroamino)methyl]amino]-2-[(3-methoxycyclohexanecarbonyl)amino]-1-oxopentyl]amino]-3-methylbutyl]-<br>Analytical Data:<br>MS: [M − 18]H+ 455.57 |
| D.7.48 | 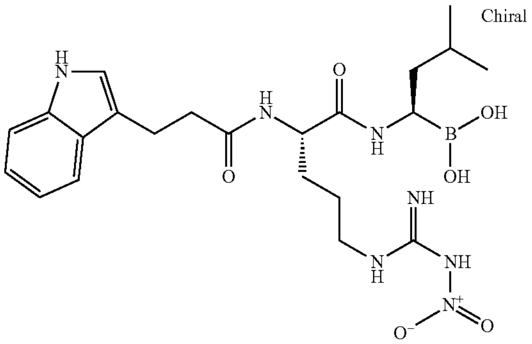 [SMILES: CC(C)C[C@H](NC(=O)[C@H](CCCNC(=N)N[N+](=O)[O-])NC(=O)CCc1c[nH]c2ccccc12)B(O)O] | Chemical Name:<br>Boronic acid, [(1R)-1-[[(2S)-5-[[imino(nitroamino)methyl]ammo]-2-[[3-(1H-indol-3-yl)-propanoyl]amino]-1-oxopentyl]amino]-3-methylbutyl]-<br>Analytical Data:<br>MS: [M − 18]H+ 486.24 |

TABLE D-7-continued

| Ex # | Structure | Chemical Name and Analytical Data |
| --- | --- | --- |
| D.7.49 | 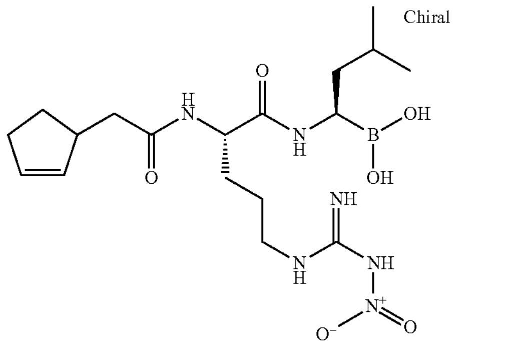 [SMILES: CC(C)C[C@H](NC(=O)[C@H](CCCNC(=N)N[N+](=O)[O-])NC(=O)CC1C=CCC1)B(O)O] | Chemical Name: Boronic acid, [(1R)-1-[[(2S)-5-[[imino(nitroamino)methyl]amino]-2-[((RS)-2-cyclopent-2-enyl-acetyl)amino]-1-oxopentyl]amino]-3-methylbutyl] Analytical Data: MS: [M − 18]H+ 422.99 |
| D.7.50 | 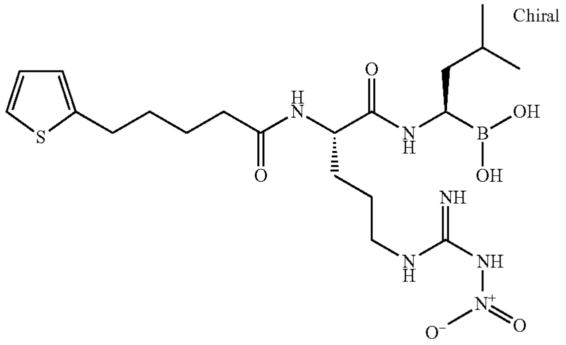 [SMILES: CC(C)C[C@H](NC(=O)[C@H](CCCNC(=N)N[N+](=O)[O-])NC(=O)CCCCc1cccs1)B(O)O] | Chemical Name: Boronic acid, [(1R)-1-[[(2S)-5-[[imino(nitroamino)methyl]amino]-2-[(5-thiophen-2-yl-pentanoyl)amino]-1-oxopentyl]amino]-3-methylbutyl] Analytical Data: MS: [M − 18]H+ 481.19 |
| D.7.51 | 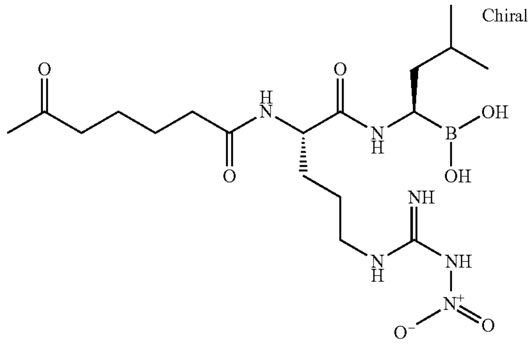 [SMILES: CC(=O)CCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(6-oxo-heptanoyl) amino]-1-oxopentyl]amino]-3-methylbutyl] Analytical Data: MS: [M − 18]H+ 441.24 |
| D.7.52 | 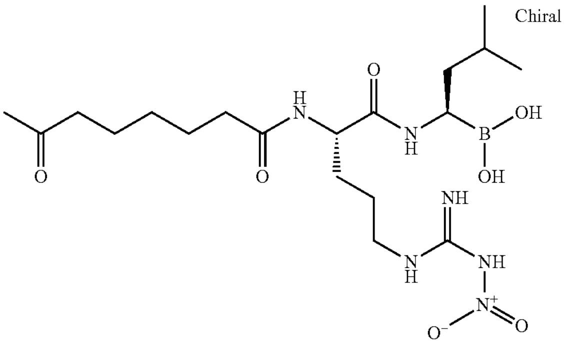 [SMILES: CC(=O)CCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]ammo]-2-[(7-oxo-octanoyl)amino]-1-oxopentyl]amino]-3-methylbutyl] Analytical Data: MS: [M − 18]H+ 455.47 |

TABLE D-7-continued

| Ex # | Structure | Chemical Name and Analytical Data |
|---|---|---|
| D.7.53 | 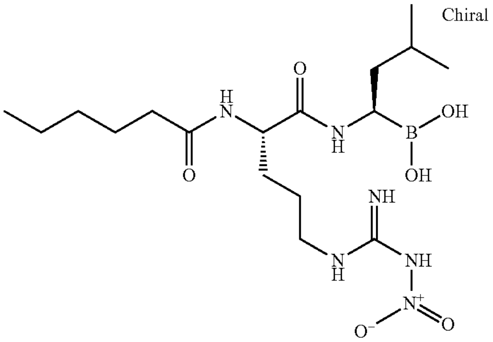 [SMILES: CCCCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[(hexanoyl)amino]-1-oxopentyl]amino]-3-methylbutyl]<br>Analytical Data:<br>MS: [M − 18]H+ 413.06 |
| D.7.54 | 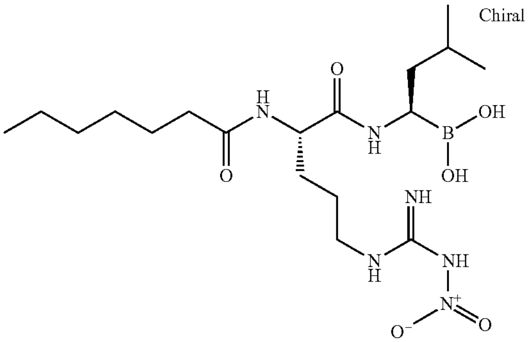 [SMILES: CCCCCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[(heptanoyl)amino]-1-oxopentyl]amino]-3-methylbutyl]<br>Analytical Data:<br>MS: [M − 18]H+ 427.14 |
| D.7.55 | 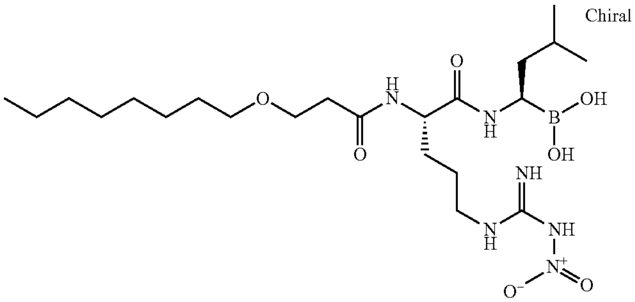 [SMILES: CCCCCCCCOCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]ammo]-2-[(3-octyloxy-propanoyl)amino]-1-oxopentyl]amino]-3-methylbutyl]<br>Analytical Data:<br>MS: [M − 18]H+ 499.17 |
| D.7.56 | 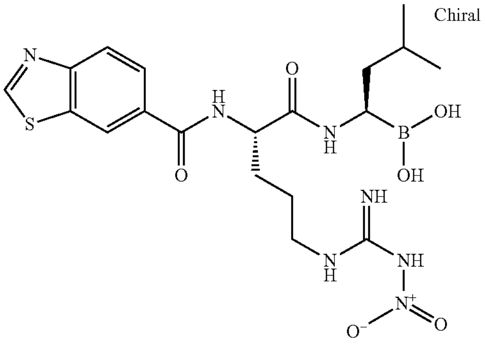 [SMILES: CC(C)C[C@H](NC(=O)[C@H](CCCNC(=N)N[N+](=O)[O-])NC(=O)c1ccc2ncsc2c1)B(O)O] | Chemical Name:<br>Boronic acid, [(1R)-1-[[(2S)-5-[[imino(nitroamino)methyl]amino]-2-[(benzothiazol-6-carbonyl)amino]-1-oxopentyl]amino]-3-methylbutyl]<br>Analytical Data:<br>MS: [M − 18]H+ 476.31 |

TABLE D-7-continued

| Ex # | Structure | Chemical Name and Analytical Data |
| --- | --- | --- |
| D.7.57 | 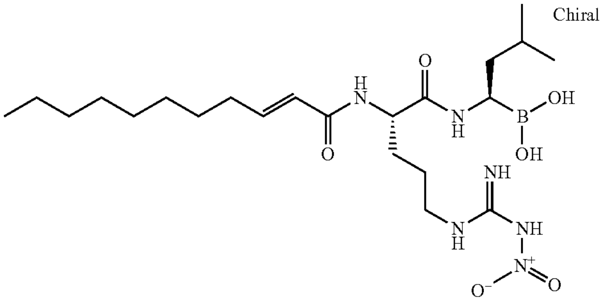 [SMILES: CCCCCCCC/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(undec-2-enoyl)amino]-1-oxopentyl]amino]-3-methylbutyl] Analytical Data: MS: [M − 18]H+ 481.41 |
| D.7.58 | 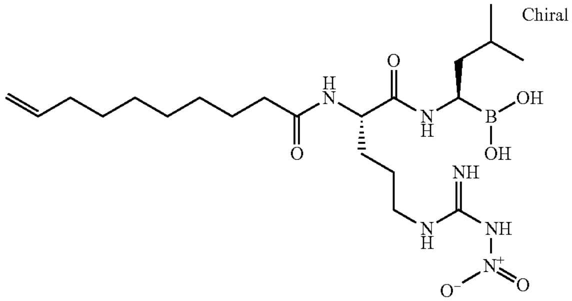 [SMILES: C=CCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(9-decenoyl)amino]-1-oxopentyl]amino]-3-methylbutyl] Analytical Data: MS: [M − 18]H+ 467.31 |
| D.7.59 | 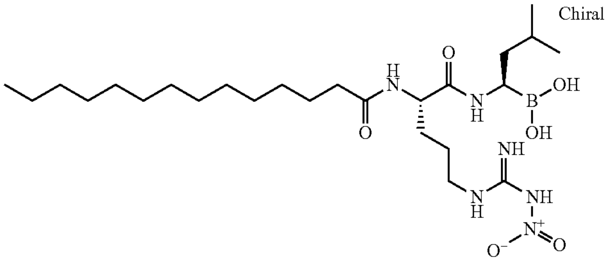 [SMILES: CCCCCCCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(tetradecanoyl)amino]-1-oxopentyl]amino]-3-methylbutyl] Analytical Data: MS: [M − 18]H+ 525.10 |

Further compounds prepared according to the above procedure for Example D.7 are reported in Table D-7A.

TABLE D-7A

| Ex # | Structure | Chemical Name and Analytical Data |
| --- | --- | --- |
| D.7.60 | 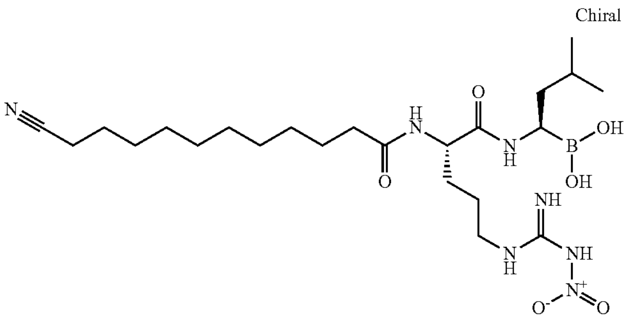 [SMILES: CC(C)C[C@H](NC(=O)[C@H](CCCNC(=N)N[N+](=O)[O-])NC(=O)CCCCCCCCCCC#N)B(O)O] | Chemical Name: Boronic acid, [(1R)-1-[[(2S)-5-[[imino (nitroamino)methyl]amino]-2-[(11-cianoundecanoyl)amino]-1-oxopentyl]amino]-3-methylbutyl] Analytical Data: MS: [M − 18]H+ 508.5 |

TABLE D-7A-continued

| Ex # | Structure | Chemical Name and Analytical Data |
| --- | --- | --- |
| D.7.61 | Chiral 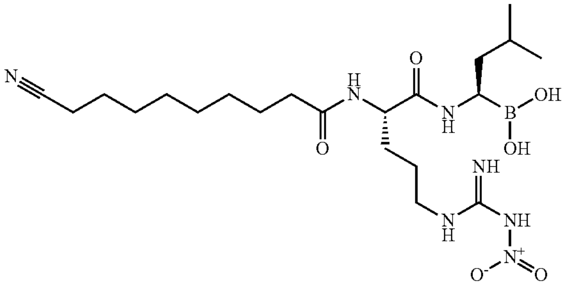 | Chemical Name: Boronic acid, [(1R)-1-[[(2S)-5-[[imino(nitroamino) methyl]amino]-2-[(9-cyanononanoyl)amino]-1-oxopentyl]amino]-3-methylbutyl] Analytical Data: MS: [M − 18]H+ 480.1 |

Example D.8

Decanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]-

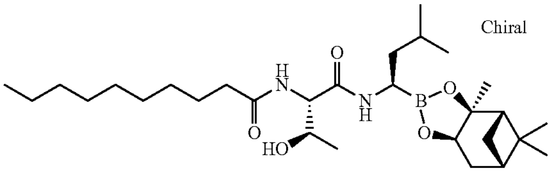 [SMILES: CCCCCCCCCC(=O)N[C@H](C(=O)N[C@@H](CC(C)C)B1O[C@@H]2C[C@@H]3C[C@@H](C3(C)C)[C@]2(C)O1)[C@@H](C)O]
Chiral

Decanoic acid (220 mg, 1.28 mmol, 1.2 eq.) was dissolved in DMF dry (15 ml) at r.t., TBTU (410 mg, 1.28 mmol, 1.2 eq.) was added and the resulting solution was stirred for 10'. The mixture was cooled at 0°-5° C., NMM (0.35 ml, 3.2 mmol, 3 eq.) was added and then (2S)-amino-(3R)-hydroxy-butyric amide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl] hydrochloride salt, of Example C.3, (430 mg, 1.067 mmol, 1 eq.) was added. The solution was stirred for 2 h, then was poured in water (200 ml) and extracted with ethyl acetate (100 ml). The organic layer was washed with the following solutions: citric acid 2% (20 ml), sodium bicarbonate 2% (20 ml), NaCl 2% (25 ml). The organic solution was dried over sodium sulphate anhydrous, filtered and evaporated under reduced pressure to give 600 mg of oil that was purified by silica gel chromatography (ethyl acetate/n-hexane 1/1) to give 540 mg of white solid that was suspended overnight in diethyl ether (5 ml) and n-hexane (20 ml). The suspension was filtered to give 110 mg of white solid. Yield 20%.

Analytical data: m.p. 108°-110° C., TLC silica gel (n-hexane/ethyl acetate 1/1 r.f. 0.33). E.A. calculated C (66.91%), H (10.26%), N (5.38%), B (2.08%). found C (66.82%), H (10.61%), N (5.35%), B (1.93%).

$^1$H-NMR (DMSO-$d_6$) $\delta_H$: 8.81 (1H, br); 7.68 (1H, d, J=8.80 Hz); 4.93 (1H, d, J=5.2); 4.28 (1H, dd, J=8.8, 4.3); 4.05 (1H, dd, J=8.6, 1.8); 3.92 (1H, m); 2.52 (1H, m); 2.20 (1H, m), 2.17 (2H, t, J=7.1); 2.00 (1H, m); 1.83 (1H, t, J=5.8); 1.78 (1H, m); 1.64 (1H, m); 1.62 (1H, m); 1.49 (2H, m); 1.34 (1H, d, J=10.0); 1.31-1.17 (21H, m); 1.04 (3H, d, J=6.4); 0.91-0.83 (9H, m); 0.81 (3H, s).

Further compounds prepared according to the above procedure include the following:

Example D.8.1

(2S)-2-[(Benzyloxycarbonyl)amino]-4-methylpentanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]

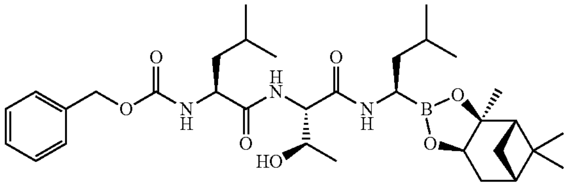 [SMILES: CC(C)C[C@H](NC(=O)[C@@H](NC(=O)[C@H](CC(C)C)NC(=O)OCc1ccccc1)[C@@H](C)O)B1O[C@@H]2C[C@@H]3C[C@@H](C3(C)C)[C@]2(C)O1]

Analytical data: TLC($CHCl_3$ 9/MeOH 1, R.f. 0.63), m.p. 38°-40° C., E.A. calculated C (64.60%), H (8.54%), N (6.85%). found C (62.44%), H (8.24%), N (7.47%).

$^1$H NMR (DMSO-$d_6$) $\delta_H$: 8.78 (1H, br); 7.82 (1H, d, J=8.60 Hz); 7.52 (1H, d, J=8.1); 7.40-7.27 (6H, m); 5.02 (2H, br s); 5.00 (1H, d, J=5.1); 4.28 (1H, dd, J=8.6, J=4.2); 4.12 (1H, q, J 7.8); 4.05 (1H, dd, J=8.6, J=1.8); 3.94 (1H, m); 2.52 (1H, m); 2.19 (1H, m); 2.01 (1H, m); 1.83 (1H, t, J=5.8); 1.78 (1H, m); 1.74-1.55 (5H, m); 1.46 (2H, m); 1.32 (1H, d, J=10.1); 1.24 (3H, s); 1.22 (3H, s); 1.04 (3H, d, J=6.2); 0.91-0.82 (12H, m); 0.80 (3H, s).

Example D.8.2

10-(1,3-dioxo-1,3-dihydro-isoindol-2-yl)-decanoic-amide-N-[(1S),(2R)-2-hydroxy, 1-[[(1R)-1-[(3aS,4S,6S,7aR)-hexahydro-3a,5,5-trimethyl-4,6-methano-1,3,2-benzodioxaborol-2-yl]-3-methylbutyl]aminocarbonyl]-propyl]-

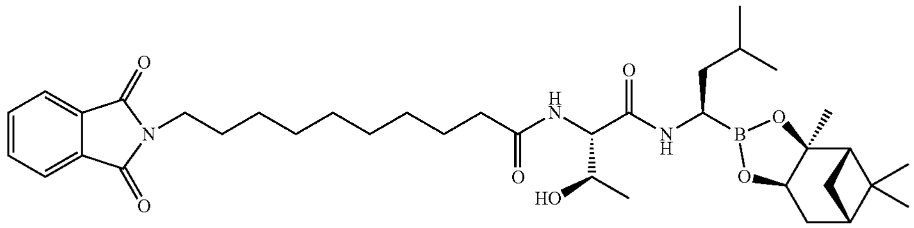 [SMILES: CC(C)C[C@H](NC(=O)[C@@H](NC(=O)CCCCCCCCCN1C(=O)c2ccccc2C1=O)[C@@H](C)O)B1O[C@@H]2C[C@@H]3C[C@@H](C3(C)C)[C@]2(C)O1]

Analytical data: TLC($CHCl_3$ 9/MeOH 1 RS. 0.83), E.A. calculated C (66.52%), H (8.43%), N (6.37%). found C (66.76%), H (8.48%), N (6.31

$^1$H NMR (DMSO-$d_6$) $\delta_H$: 8.80 (1H, br); 7.85 (4H, m), 7.67 (1H, d, J=8.80 Hz); 4.93 (1H, d, J=5.5), 4.28 (1H, dd, J=8.6, 4.0); 4.04 (1H, dd); 3.92 (1H, m); 3.56 (2H, t, J=8.1); 2.49 (1H, m); 2.23-2.12 (3H, m); 2.00 (1H, m); 1.82 (1H, t, J=6.6); 1.78 (1H, m); 1.73-1.53 (5H, m); 1.48 (2H, m); 1.33 (1H, d, J=10.1); 1.31-1.17 (20H, m); 1.03 (3H, d, J=6.2); 0.84 (6H, d, J=6.6); 0.80 (3H, s).

Further compounds prepared according to the above procedures for Example D.8, D.8.1 and D.8.2 are reported in Table D-8.

TABLE D-8

| Ex # | Structure | Chemical Name |
| --- | --- | --- |
| D.8.3 | 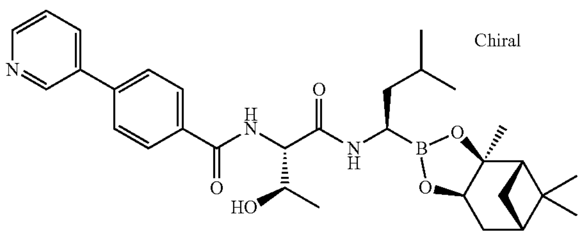 [SMILES: CC(C)C[C@H](NC(=O)[C@@H](NC(=O)c1ccc(-c2cccnc2)cc1)[C@@H](C)O)B1O[C@@H]2C[C@@H]3C[C@@H](C3(C)C)[C@]2(C)O1] Chiral | Chemical Name: 4-(Pyridin-3-yl)benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H NMR (DMSO-$d_6$): 9.02 (1H, s); 8.99 (1H, s); 8.63 (1H, d, J = 4.7); 8.22 (1H, d, J = 8.4); 8.17 (1H, d, J = 8.1); 8.04 (2H, d, J = 8.3); 7.89 (2H, d, J = 8.3); 7.53 (1H, dd, J = 7.8, 4.8); 5.18 (1H, d, J = 5.1); 4.53 (1H, dd, J = 8.3, 5.1); 4.11-4.01 (2H, m); 2.60-2.53 (1H, m); 2.25-2.15 (1H, m); 2.05-1.97 (1H, m); 1.86-1.75 (2H, m); 1.73-1.58 (2H, m); 1.37-1.24 (3H, m); 1.25 (3H, s); 1.22 (3H, s); 1.13 (3H, d, J = 6.2); 0.85 (6H, d, J = 6.4); 0.81 (3H, s). |
| D.8.4 | 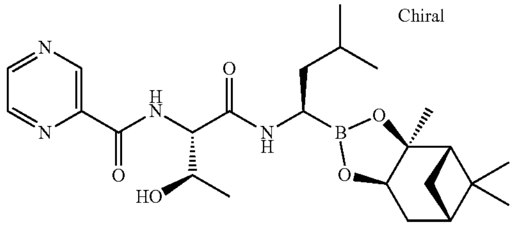 [SMILES: CC(C)C[C@H](NC(=O)[C@@H](NC(=O)c1cnccn1)[C@@H](C)O)B1O[C@@H]2C[C@@H]3C[C@@H](C3(C)C)[C@]2(C)O1] Chiral | Chemical Name: 2-Pyrazinecarbossamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |
| D.8.5 | 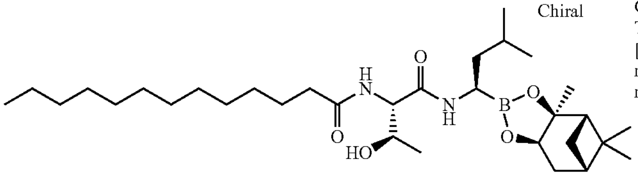 Chiral | Chemical Name: Tridecanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |

TABLE D-8-continued

| Ex # | Structure | Chemical Name |
|---|---|---|
| D.8.6 | 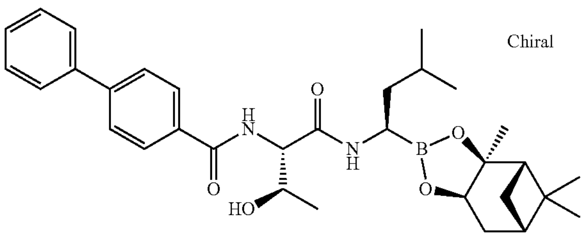 [SMILES: CC(C)C[C@H](NC(=O)[C@@H](NC(=O)c1ccc(-c2ccccc2)cc1)[C@@H](C)O)B1O[C@@H]2C[C@@H]3C[C@@H](C3(C)C)[C@]2(C)O1] | Chemical Name: 4-Phenylbenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.04 (1H, bs); 8.18 (1H, d, J = 8.5); 8.00 (2H, d, J = 8.5); 7.81 (2H, d, J = 8.4; 7.77-7.73 (2H, m); 7.51 (2H, t, J = 7.5); 7.43 (1H, t, J = 7.3); 5.07 (1H, d, J = 6.2); 4.55-4.50 (1H, m); 4.10-4.01 (2H, m); 2.60-2.54 (1H, m); 2.25-2.16 (1H, m); 2.06-1.98 (1H, m); 1.84 (1H, t, J = 5.6); 1.82-1.76 (1H, m); 1.74-1.60 (2H, m); 1.35 (1H, d, J = 10); 1.30-1.26 (2H, m); 1.25 (3H, s); 1.22 (3H, s); 1.13 (3H, d, J = 6.2); 0.87-0.83 (6H, m); 0.81 (3H, s). |
| D.8.7 | 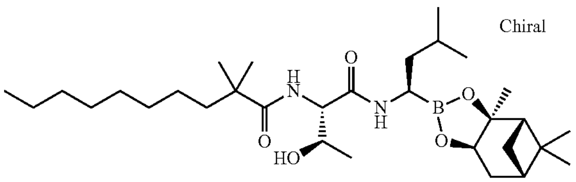 [SMILES: CCCCCCCCC(C)(C)C(=O)N[C@H](C(=O)N[C@@H](CC(C)C)B1O[C@@H]2C[C@@H]3C[C@@H](C3(C)C)[C@]2(C)O1)[C@@H](C)O] | Chemical Name: 2,2-Dimethyldecanamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 8.93 (1H, bs); 7.03 (1H, d, J = 8.6); 5.06 (1H, d, J = 5.9); 4.36-4.31 (1H, m); 4.06-4.01 (2H, m); 3.99-3.92 (1H, m); 2.24-2.14 (1H, m); 1.90-1.76 (2H, m); 1.70-1.58 (2H, m); 1.50-1.42 (2H, m); 1.38-1.32 (1H, m); 1.28-1.20 (15H, m); 1.19-1.12 (6H, m); 1.12-1.08 (6H, m); 1.03 (3H, d, J = 6.3); 0.87-0.83 (9H, m); 0.81 (3H, s). |
| D.8.8 | 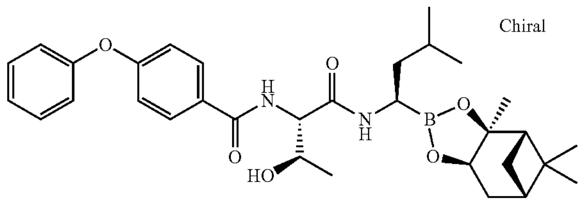 [SMILES: CC(C)C[C@H](NC(=O)[C@@H](NC(=O)c1ccc(Oc2ccccc2)cc1)[C@@H](C)O)B1O[C@@H]2C[C@@H]3C[C@@H](C3(C)C)[C@]2(C)O1] | Chemical Name: (4-phenoxy)benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.01 (1H, bs); 8.07 (1H, d, J = 8.5); 7.96-7.92 (2H, m); 7.47-7.42 (2H, m); 7.22 (1H, t, J = 7.4); 7.11-7.06 (4H, m); 5.04 (1H, d, J = 6.2); 4.52-4.47 (1H, m); 4.10-3.98 (2H, m); 2.60-2.52 (1H, m); 2.24-2.16 (1H, m); 2.08-1.98 (1H, m); 1.86-1.74 (2H, m); 1.62-1.58 (2H, m); 1.35 (1H, t, J = 10.0); 1.30-1.24 (2H, m); 1.23 (3H, s); 1.22 (3H, s); 1.10 (3H, d, J = 6.3); 0.86-0.84 (6H, m); 0.80 (3H, s). |
| D.8.9 | 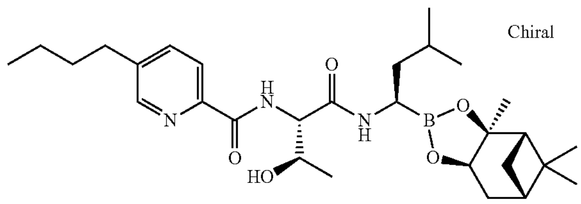 [SMILES: CCCCc1ccc(C(=O)N[C@H](C(=O)N[C@@H](CC(C)C)B2O[C@@H]3C[C@@H]4C[C@@H](C4(C)C)[C@]3(C)O2)[C@@H](C)O)nc1] | Chemical Name: 5-Butyl-2-pyridinecarboxamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |
| D.8.10 | 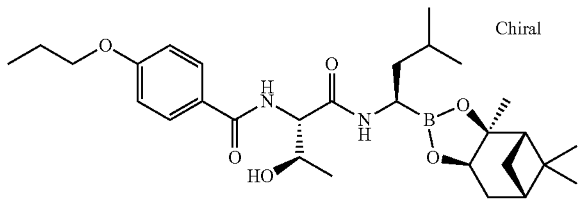 [SMILES: CCCOc1ccc(C(=O)N[C@H](C(=O)N[C@@H](CC(C)C)B2O[C@@H]3C[C@@H]4C[C@@H](C4(C)C)[C@]3(C)O2)[C@@H](C)O)cc1] | Chemical Name: 4-propoxybenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H NMR (DMSO-d6): 9.02 (1H, s); 7.95 (1H, d, J = 8.6); 7.87 (2H, d, J = 8.8); 7.02 (2H, d, J = 8.8); 5.03 (1H, d, J = 6.2); 4.49 (1H, dd, J = 8.4, 4.9); 4.03-3.98 (4H, m); 2.58-2.50 (1H, m); 2.24-2.15 (1H, m); 2.04-1.97 (1H, m); 1.85-1.59 (7H, m); 1.23 (3H, s); 1.22 (3H, s); 1.18 (2H, t, J = 7.1); 1.10 (3H, d, J = 6.3); 0.99 (3H, t, J = 7.4); 0.85 (3H, d, J = 6.4); 0.84 (3H, d, J = 6.4); 0.81 (3H, s). |

TABLE D-8-continued

| Ex # | Structure | Chemical Name |
|---|---|---|
| D.8.11 | 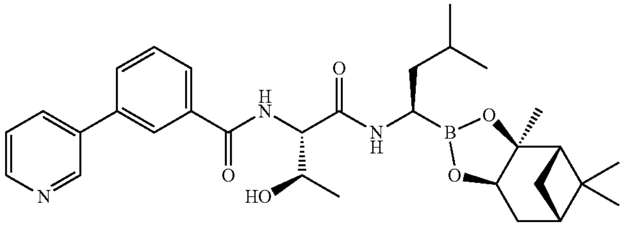 [SMILES: CC(C)C[C@H](NC(=O)[C@@H](NC(=O)c1cccc(-c2cccnc2)c1)[C@@H](C)O)B1O[C@@H]2C[C@@H]3C[C@@H](C3(C)C)[C@]2(C)O1] | Chemical Name: 3-(3-Pyridyl)benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.05-8.95 (2H, m); 8.63 (1H, dd, J = 1.53 Hz, J = 4.76 Hz); 8.39 (1H, d, J = 8.51 Hz); 8.25 (1H, m); 8.19-8.14 (1H, m); 7.96-7.90 (2H, m); 7.64 (1H, t, J = 7.74 Hz); 7.57-7.51 (1H, m); 5.053 (1H, d, J = 6.06 Hz); 4.54 (1H, dd, J = 5.36 Hz, J = 8.43 Hz); 4.12-4.00 (2H, m); 2.61-2.54 (1H, m); 2.25-2.14 (1H, m); 2.05-1.95 (2H, m); 1.82 (1H, t, J = 5.55 Hz); 1.80-1.74 1H, m); 1.73-1.56 (1H, m); 1.34 (1H, d, J = 10.04 Hz); 1.31-1.25 (2H, m); 1.22 (6H, d, J = 9.04 Hz); 1.14 (3H, d, J = 6.33 Hz); 0.87-0.83 (6H, m); 0.79 (3H, bs). |
| D.8.12 | 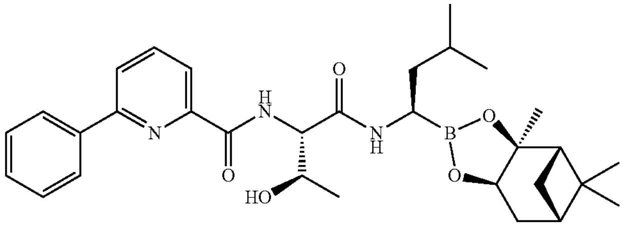 [SMILES: CC(C)C[C@H](NC(=O)[C@@H](NC(=O)c1cccc(-c2ccccc2)n1)[C@@H](C)O)B1O[C@@H]2C[C@@H]3C[C@@H](C3(C)C)[C@]2(C)O1] | Chemical Name: 6-Phenyl-2-pyridinecarboxamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.02-8.95 (1H, m); 8.76 (1H, d, J = 8.55 Hz); 8.26-8.16 (4H, m); 8.12 (1H, t, J = 7.77 Hz); 8.02 (1H, d, J = 7.56 Hz); 7.60-7.47 (4H, m); 5.27 (1H, d, J = 4.97 Hz); 4.50 (1H, dd, J = 4.22 Hz, J = 8.50 Hz); 4.16-4.07 (2H, m); 2.65-2.56 (1H, m); 2.25-2.15 (1H, m); 2.09-1.98 (1H, m); 1.84 (1H, t, J = 5.62 Hz); 1.79-1.73 (1H, m); 1.73-1.66 (1H, m); 1.66-1.59 (1H, m); 1.40-1.26 (4H, m); 1.23 (7H, d, J = 10.89 Hz); 1.15-1.10 (4H, m); 0.85 (7H, d, J = 6.56 Hz); 0.79 (1H, bs). |
| D.8.13 | 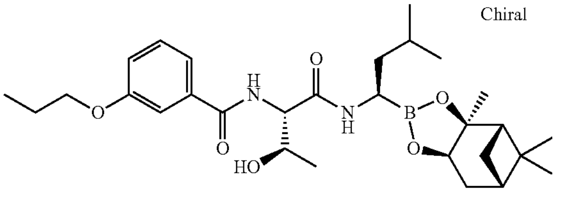 [SMILES: CCCOc1cccc(C(=O)N[C@H](C(=O)N[C@@H](CC(C)C)B2O[C@@H]3C[C@@H]4C[C@@H](C4(C)C)[C@]3(C)O2)[C@@H](C)O)c1] Chiral | Chemical Name: 3-propoxybenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.05-9.0 (1H, m); 8.11 (1H, d, J = 8.49 Hz); 7.48-7.43 (2H, m); 7.40 (1H, t, J = 7.80 Hz); 7.15-7.10 (1H, m); 5.04 (1H, d, J = 6.26 Hz); 4.49 (1H, dd, J = 5.15, J = 8.43 Hz); 4.10-4.05 (1H, m); 4.05-4.01 (1H, m); 3.99 (2H, t, J = 6.50 Hz); 2.25-2.15 (1H, m); 2.05-1.96 (1H, m); 1.83 (1H, t, J = 5.56 Hz); 1.81-1.72 (3H, m); 1.72-1.57 (2H, m); 1.34 (1H, d, J = 10.06 Hz); 1.31-1.25 (2H, m); 1.24 (4H, bs); 1.22 (3H, bs); 1.10 (3H, d, J = 6.31 Hz); 1.02 (3H, t, J = 7.40 Hz); 0.84 (6H, dd, J = 1.84 Hz, J = 6.56 Hz), 0.81 (3H, bs). |
| D.8.14 | 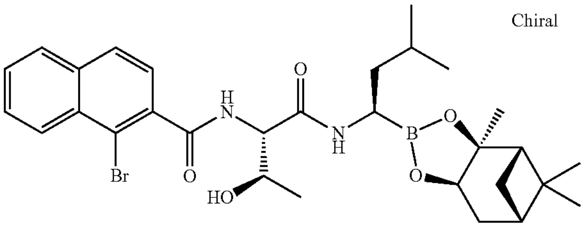 [SMILES: CC(C)C[C@H](NC(=O)[C@@H](NC(=O)c1ccc2ccccc2c1Br)[C@@H](C)O)B1O[C@@H]2C[C@@H]3C[C@@H](C3(C)C)[C@]2(C)O1] Chiral | Chemical Name: 1-Bromonaphthalene-2-carboxamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |
| D.8.15 | 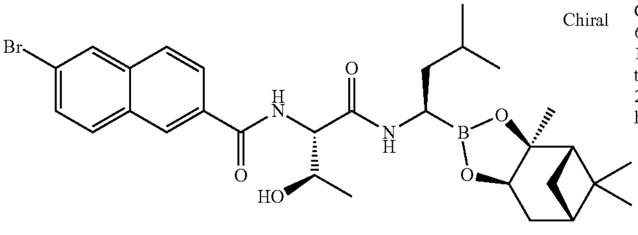 Chiral | Chemical Name: 6-Bromonaphthalene-2-carboxamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |

TABLE D-8-continued

| Ex # | Structure | Chemical Name |
|---|---|---|
| D.8.16 | 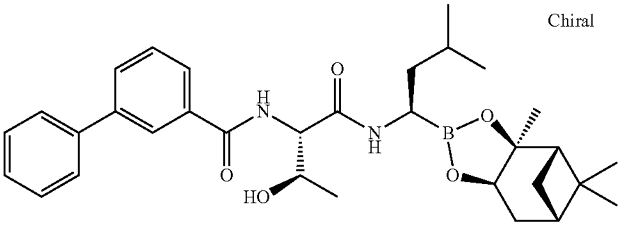 [SMILES: CC(C)C[C@H](NC(=O)[C@@H](NC(=O)c1cccc(-c2ccccc2)c1)[C@@H](C)O)B1O[C@@H]2C[C@@H]3C[C@@H](C3(C)C)[C@]2(C)O1] Chiral | Chemical Name: 3-Phenylbenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. Analytical Data: $^1$H-NMR (DMSO-d6): 9.03 (1H, s); 8.34 (1H, d, J = 8.5); 8.18 (1H, s); 7.87 (2H, t, J = 7.1); 7.75 (2H, d, J = 7.8); 7.60 (1H, t, J = 7.7); 7.52 (2H, t, J = 7.6); 7.42 (1H, t, J = 7.4); 5.05 (1H, d, J = 6.2); 4.54 (1H, dd, J = 8.4, 5.3); 4.10-4.00 (2H, m); 2.60-2.53 (1H, m); 2.24-2.14 (1H, m); 2.05-1.97 (1H, m); 1.82 (1H, t, J = 5.5); 1.80-1.74 (1H, m); 1.73-1.57 (2H, m); 1.37-1.22 (3H, m); 1.24 (3H, s); 1.21 (3H, s); 1.13 (3H, d, J = 6.2); 0.85 (3H, d, J = 6.5); 0.84 (3H, d, J = 6.5); 0.80 (3H, s). |
| D.8.17 | 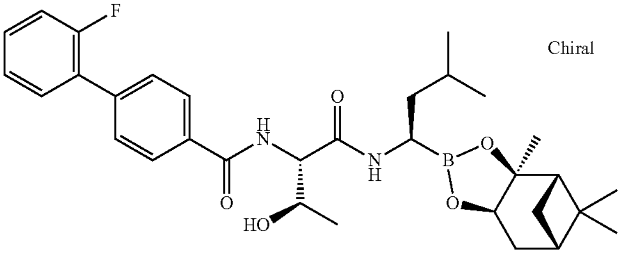 [SMILES: CC(C)C[C@H](NC(=O)[C@@H](NC(=O)c1ccc(-c2ccccc2F)cc1)[C@@H](C)O)B1O[C@@H]2C[C@@H]3C[C@@H](C3(C)C)[C@]2(C)O1] Chiral | Chemical Name: 4-(2-Fluorophenyl)benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]. |

The intermediate carboxylic acids for the synthesis of examples D.8.3, D.8.7, D.8.11, D.8.12 and D.8.13 were prepared according to literature procedures. Compound 2,2-dimethyldecanoic acid was prepared as described by Roth et al. in *J. Med. Chem.* 1992, 35, 1609-1617. Compounds 4-(3-pyridyl)benzoic acid, 3-(3-Pyridyl)benzoic acid and 6-phenyl-2-pyridinecarboxilic acid were prepared according the procedure described by Gong et al. in *Synlett*, 2000, (6), 829-831. Compound 3-propoxybenzoic acid was prepared according the procedure described by Jones in *J. Chem. Soc.* 1943, 430-432.

Example D.8.18

2-Pyrazinecarboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-carbamoylethyl]

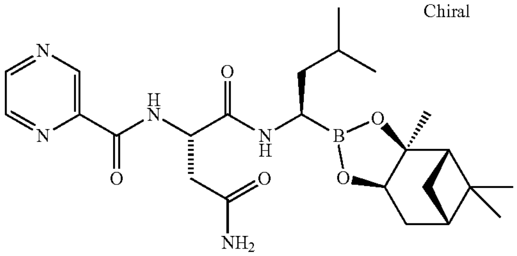 [SMILES: CC(C)C[C@H](NC(=O)[C@H](CC(N)=O)NC(=O)c1cnccn1)B1O[C@@H]2C[C@@H]3C[C@@H](C3(C)C)[C@]2(C)O1]

Chiral

This compound has been prepared essentially according to the above procedures for Example D.8, D.8.1 and D.8.2 starting from (2S)-2-amino-3-carbamoylpropanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt of Example C.3.

$^1$H-NMR (DMSO-d6): 9.20 (1H, d, J=1.29 Hz); 9.02 (1H, d, J=8.52 Hz); 8.91 (1H, d, J=2.45 Hz); 8.81-8.76 (2H, m); 7.42 (1H, s); 6.95 (1H, s); 5.00-4.80 (1H, m); 4.30-4.08 (1H, m); 2.85-2.72 (1H, m); 2.62-2.56 (2H, m); 2.25-2.15 (1H, m); 2.06-1.98 (1H, m); 1.84 (1H, t, J=5.54 Hz); 1.81-1.76 (1H, m); 1.72-1.58 (2H, m); 1.32-1.26 (1H, m); 1.23 (8H, d, J=5.36 Hz); 0.85-0.79 (9H, m).

Example D.8.19

Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-carbamoylethyl]

Chiral

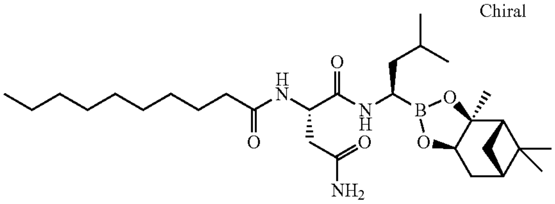 [SMILES: CCCCCCCCCC(=O)N[C@@H](CC(N)=O)C(=O)N[C@@H](CC(C)C)B1O[C@@H]2C[C@@H]3C[C@@H](C3(C)C)[C@]2(C)O1]

This compound has been prepared essentially according to the above procedures for Example D.8, D.8.1 and D.8.2 starting from (2S)-2-amino-3-carbamoylpropanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt of Example C.3.

Example D.8.20

4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-carbamoylethyl]

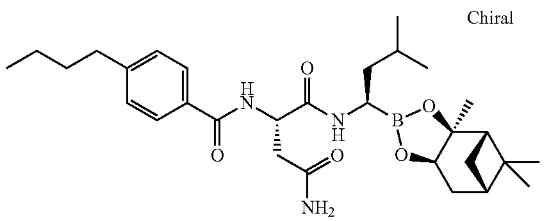 [SMILES: CCCCc1ccc(C(=O)N[C@@H](CC(N)=O)C(=O)N[C@@H](CC(C)C)B2O[C@@H]3C[C@@H]4C[C@@H](C4(C)C)[C@]3(C)O2)cc1]

This compound has been prepared essentially according to the above procedures for Example D.8, D.8.1 and D.8.2 starting from (2S)-2-amino-3-carbamoylpropanamide, N-[(1R)-1-[(3aS,4S,6S,7aR)-hexahydro-3a,5,5-trimethyl-4,6-methano-1,3,2-benzodioxaborol-2-yl]-3-methylbutyl]; hydrochloride salt of Example C.3.

Example D.9

Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(4-methylbenzoyl)amino]ethyl]-

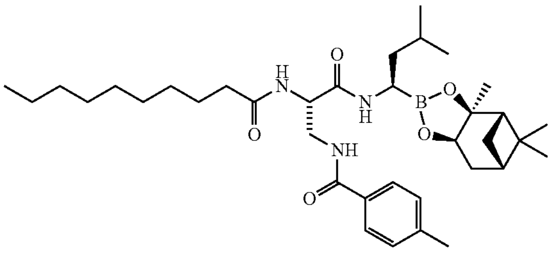 [SMILES: CCCCCCCCCC(=O)N[C@@H](CNC(=O)c1ccc(C)cc1)C(=O)N[C@@H](CC(C)C)B1O[C@@H]2C[C@@H]3C[C@@H](C3(C)C)[C@]2(C)O1]

Decanoic acid (330 mg, 1.95 mmol, 1.2 eq.) was dissolved in DMF dry, (20 ml) and TBTU (620 mg, 1.95 mmol, 1.2 eq.) was added at r.t. under nitrogen. The solution was stirred for 10', cooled at 0°-5° C. and NMM (0.53 ml, 4.9 mmol, 3 eq.) and (2S)-2-amino-3-[(4-methylbenzoyl)amino]propanamide, N-[(1R)-1-[(3aS,4S,6S,7aR)-hexahydro-3a,5,5-trimethyl-4,6-methano-1,3,2-benzodioxaborol-2-yl]-3-methylbutyl]-, hydrochloride salt (800 mg, 1.58 mmol, 1 eq.) of Example C.4, were added and the resulting mixture was stirred at r.t. for 3 h. The solution was poured in water (200 ml) extracted with ethyl acetate (100 ml), washed with solutions of citric acid 2% (50 ml), sodium bicarbonate 2% (50 ml), NaCl 2% (50 ml). The organic solution was dried over sodium sulphate anhydrous, filtered, evaporated and suspended in diethyl ether (20 ml) for 30'. The suspension was filtered and dried to give 330 mg of white solid. Yield 33%. M.P.: 134° C.-136° C., TLC, silica gel, (eluent n-hexane/ethyl acetate, r.f. 0.5). E.A. calculated C (69.33%), H (9.37%), N (6.74%), B (1.73%). found C (%), H (%), N (23%), B (%).

$^1$H NMR (DMSO-$d_6$) 8.74 (1H, d, J=3.5 Hz); 8.25 (1H, t, J=5.6); 7.95 (1H, d, J=7.9); 7.71 (2H, d, J=8.1); 7.25 (2H, t, J=8.1); 4.59 (1H, m); 4.1 (1H, dd, J=1.8, 8.8); 3.49 (2H, m); 2.59 (1H, m); 2.35 (3H, s); 2.20 (1H, m); 2.09 (1H, t, J=7.3); 2.02 (1H, m); 1.83 (1H, t, J=5.5); 1.78 (1H, m); 1.62 (2H, m); 1.44 (2H, m); 1.36-1.21 (17H, m); 1.25 (3H, s), 1.22 (3H, s); 0.85 (3H, t, J=6.8); 0.80 (9H, m).

Example D.10

2-S-decanoylamino-3-(hexanoylamino)-propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

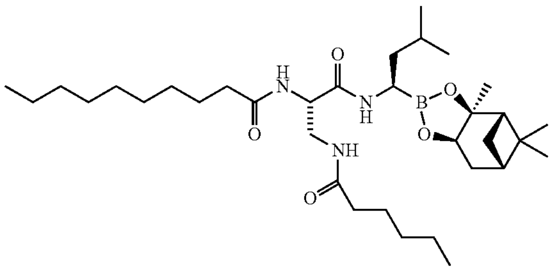 [SMILES: CCCCCCCCCC(=O)N[C@@H](CNC(=O)CCCCC)C(=O)N[C@@H](CC(C)C)B1O[C@@H]2C[C@@H]3C[C@@H](C3(C)C)[C@]2(C)O1]

Decanoic acid (170 mg, 0.98 mmol, 1.2 eq.) was dissolved in DMF dry, (15 ml) and TBTU (310 mg, 0.98 mmol, 1.2 eq.) was added at r.t. under nitrogen. The solution was stirred for 20', cooled at 0°-5° C. and NMM (0.271 ml, 2.46 mmol, 2.5 eq.) and 2-S-amino-3-(hexanoylamino)-propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt, (400 mg, 0.82 mmol, 1 eq.) of Example C.5, were added and the resulting mixture was stirred at r.t. for 3 h. The solution was poured in water (150 ml) extracted with ethyl acetate (100 ml), washed with solutions of citric acid 2% (50 ml), sodium bicarbonate 2% (50 ml), NaCl 2% (50 ml). The organic solution was dried over sodium sulphate anhydrous, filtered, evaporated and suspended in ethyl acetate (20 ml) for 30'. The suspension was filtered and dried to give 230 mg of white solid. Yield 47%.

Analytical data: m.p. 135°-137° C., TLC silica gel (eluent hexane/ethyl acetate 2/1, R.f.=0.27). E.A. calculated C (67.64%), H (10.35%), N (6.96%). found C (66.93%), H (10.29%), N (7.14%).

$^1$H NMR (DMSO-$d_6$) $\delta_H$: 8.67 (1H, d, J=2.9 Hz); 7.83 (1H, d, J=8.2); 7.67 (1H, t, J=5.5); 4.41 (1H, m); 4.10 (1H, dd, J=1.5, 8.6); 3.25 (2H, m); 2.56 (1H, m); 2.20 (1H, m); 2.13-1.95 (5H, m); 1.84 (1H, t, J=5.5); 1.78 (1H, m); 1.64 (2H, m); 1.46 (4H, m); 1.35-1.15 (27H, m); 0.84 (9H, m); 0.79 (3H, s).

Example D.11

2-S-decanoylamino-3-(4-fluorosulfonylamino)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

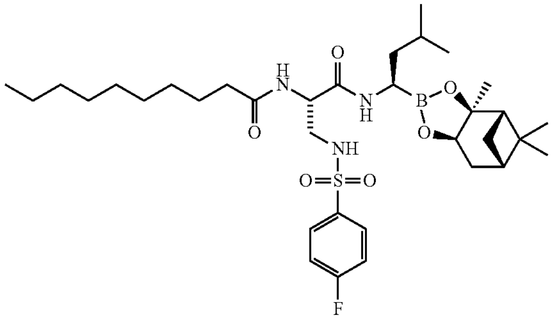 [SMILES: CCCCCCCCCC(=O)N[C@@H](CNS(=O)(=O)c1ccc(F)cc1)C(=O)N[C@@H](CC(C)C)B1O[C@@H]2C[C@@H]3C[C@@H](C3(C)C)[C@]2(C)O1]

Decanoic acid (160 mg, 0.94 mmol, 1.2 eq.) was dissolved in DMF dry, (20 ml) and TBTU (300 mg, 0.94 mmol, 1.2 eq.) was added at r.t. under nitrogen. The solution was stirred for 20', cooled at 0°-5° C. and NMM (0.259 ml, 2.36 mmol, 2.5 eq.) and 2-S-amino-3-(4-fluorosulfonylamino)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt, (430 mg, 0.78 mmol, 1 eq.) of Example C.6, were added and the resulting mixture was stirred at r.t. for 2 h. The solution was poured in water (200 ml) extracted with ethyl acetate (100 ml), washed with the following solutions: citric acid 2% (50 ml), sodium bicarbonate 2% (50 ml), NaCl 2% (50 ml). The organic solution was dried over sodium sulphate anhydrous, filtered, evaporated and purified by silica gel chromatography (eluent n-hexane/ethyl acetate 2/1). The solvent was evaporated and n-hexane was added to give 100 mg of solid. Yield 19%.

Analytical data: m.p. 83°-85° C., TLC silica gel (eluent hexane/ethyl acetate 2/1, R.f.=0.53).

$^1$H NMR (DMSO-$d_6$) $\delta_H$: 8.45 (1H, d, J=3.8 Hz); 7.83 (3H, m); 7.63 (1H, t, J=6.2); 7.42 (2H, t, J=8.8); 4.40 (1H, m); 4.12 (1H, dd, J=1.5, 8.6); 2.95 (2H, m); 2.64 (1H, m); 2.21 (1H, m); 2.17 (2H, t, J=7.3); 2.01 (1H, m); 1.83 (1H, t, J=5.5); 1.78 (1H, m); 1.62 (2H, m); 1.45 (2H, m); 1.4-1.1 (23H, m); 0.87-0.8 (9H, m); 0.79 (3H, s).

Example D.12

2-S-decanoylamino-3-(3,4-dimethoxyphenylacetamido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

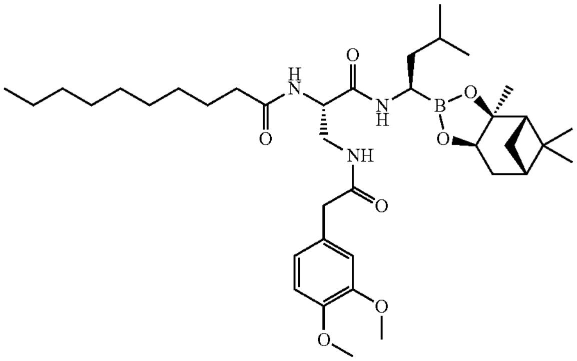 [SMILES: CCCCCCCCCC(=O)N[C@@H](CNC(=O)Cc1ccc(OC)c(OC)c1)C(=O)N[C@@H](CC(C)C)B1O[C@@H]2C[C@@H]3C[C@@H](C3(C)C)[C@]2(C)O1]

Decanoic acid (80 mg, 0.48 mmol, 1.2 eq.) was dissolved in DMF dry, (20 ml) and TBTU (150 mg, 0.48 mmol, 1.2 eq.) was added at r.t. under nitrogen. The solution was stirred for 20', cooled at 0°-5° C. and NMM (0.13 ml, 1.2 mmol, 2.5 eq.) and 2-S-amino-3-(3,4-dimethoxyphenylacetamido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt, (230 mg, 0.4 mmol, 1 eq.) of Example C.7, were added and the resulting mixture was stirred at r.t. for 2 h. The solution was poured in water (200 ml) extracted with ethyl acetate (100 ml), washed with the following solutions: citric acid 2% (50 ml), sodium bicarbonate 2% (50 ml), NaCl 2% (50 ml). The organic solution was dried over sodium sulphate anhydrous, filtered, evaporated and purified by silica gel chromatography (eluent n-hexane/ethyl acetate 1/1). The solvent was evaporated to give 100 mg of glassy solid. Yield 35.7%.

Analytical data: TLC silica gel (eluent hexane/ethyl acetate 1/1, R.f.=0.53). E.A. calculated C (67.13%), H (9.25%), N (6.02%). found C (65.38%), H (9.20%), N (5.49).

$^1$H NMR (DMSO-$d_6$) $\delta_H$: 8.65 (1H, d, J=3.5 Hz); 7.84 (2H, m); 6.83 (2H, m); 6.72 (1H, dd, J=1.7, 8.1); 4.43 (1H, m); 4.10 (1H, dd, J=1.8, 8.6); 3.72 (3H, s); 3.70 (3H, s); 3.30 (2H, s); 3.27 (2H, m); 2.58 (1H, m); 2.19 (1H, m); 2.02 (3H, m); 1.84 (1H, t, J=5.5); 1.78 (1H, m); 1.63 (2H, m); 1.43 (2H, m); 1.35-1.15 (23H, m); 0.87-0.8 (9H, m); 0.79 (3H, s).

Example D.13

2-S-decanoylamino-3-(phenylureido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

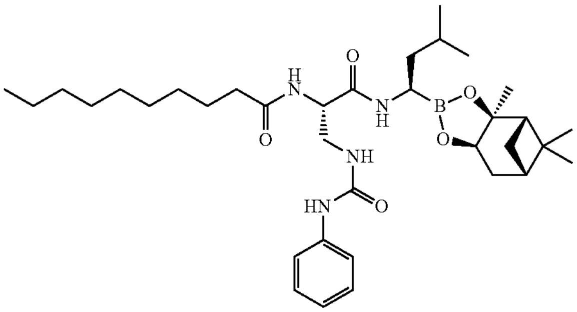 [SMILES: CCCCCCCCCC(=O)N[C@@H](CNC(=O)Nc1ccccc1)C(=O)N[C@@H](CC(C)C)B1O[C@@H]2C[C@@H]3C[C@@H](C3(C)C)[C@]2(C)O1]

Decanoic acid (170 mg, 0.99 mmol, 1.2 eq.) was dissolved in DMF dry, (20 ml) and TBTU (310 mg, 0.99 mmol, 1.2 eq.) was added at r.t. under nitrogen. The solution was stirred for 20', cooled at 0°-5° C. and NMM (0.27 ml, 2.4 mmol, 2.5 eq.) and 2-S-amino-3-(phenylureido)propionamide, N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], hydrochloride salt, (420 mg, 0.82 mmol, 1 eq.) of Example C.8, were added and the resulting mixture was stirred at 0° C. for 2 h. The solution was poured in water (200 ml) extracted with ethyl acetate (100 ml), washed with the following solutions: citric acid 2% (50 ml), sodium bicarbonate 2% (50 ml), NaCl 2% (50 ml). The organic solution was dried over sodium sulphate anhydrous, filtered, evaporated and suspended in diethyl ether (20 ml) for 1 h, filtered and dried under vacuum to give 140 mg of white solid that was purified by silica gel chromatography (n-hexane/ethyl acetate 1/1). Yield 25%.

Analytical data: TLC silica gel (eluent hexane/ethyl acetate 1/1, R.f.=0.4).

$^1$H NMR (DMSO-$d_6$) $\delta_H$: 8.73 (1H, d, J=3.1 Hz); 8.64 (1H, br s); 7.97 (1H, d, J=8.2); 7.36 (2H, d, J=8.1); 7.19 (2H, t, J=8.1); 6.87 (1H, t, J=8.1); 6.1 (1H, t, J=6.0); 4.44 (1H, m); 4.10 (1H, dd, J=1.8, 8.6); 3.41 (1H, m); 3.22 (1H, m); 2.59 (1H, m); 2.19 (1H, m); 2.10 (2H, t, J=7.3); 2.02 (1H, m); 1.84 (1H, t, J=5.5); 1.78 (1H, m); 1.64 (2H, m); 1.46 (2H, m); 1.35-1.15 (23H, m); 0.87-0.8 (9H, m); 0.79 (3H, s).

Example D.14

2-Aminoacetamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl], Hydrochloride salt

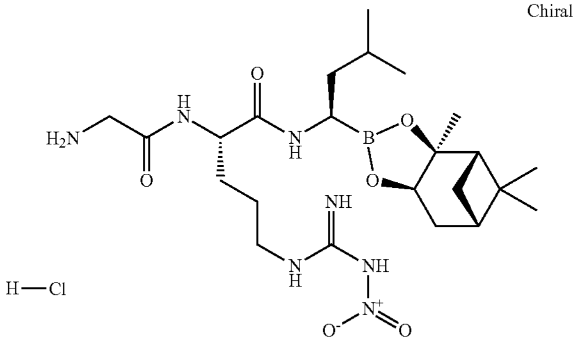 [SMILES: Cl ; CC(C)C[C@H](NC(=O)[C@H](CCCNC(=N)N[N+](=O)[O-])NC(=O)CN)B1O[C@@H]2C[C@@H]3C[C@@H](C3(C)C)[C@]2(C)O1]

To a solution of N-Boc-Glycine (383 mg, 2.18 mmol), in anhydrous dichloromethane (20 ml), N-methylmorpholine was added (275 μl, 2.5 mmol). The mixture was cooled to −15° C., then isobutyl chloroformate (286 μl, 1.2 mmol) was slowly added. After 15 minutes (2S)-2-amino-5-[[imino(nitroamino)methyl]amino]pentanamide, N-[(1R)-1-[(3aS,4S,6S,7aR)-hexahydro-3a,5,5-trimethyl-4,6-methano-1,3,2-benzodioxaborol-2-yl]-3-methylbutyl]-hydrochloride salt of Example C.1 (1.00 g, 2.0 mmol) and further N-methylmorpholine (275 μl, 2.5 mmol) were added. The reaction mixture was stirred at −15° C.-10° C. for 4 h, then concentrated to small volume and partitioned between ethyl acetate (100 ml) and water (50 ml). The aqueous phase was further extracted with ethyl acetate (20 ml). The combined organic phases were dried over sodium sulfate and concentrated. The residue was taken up with ethyl acetate (5 ml) and the solution was drop-wise added to hexane (120 ml) while stirring at room temperature. The solid was collected by decantation and dried under vacuum (1.18 g, 95%). Part of this Boc-protected intermediate (1.08 g, 1.73 mmol) was dissolved in THF (15 ml), then a 4N solution of HCl in dioxane was added. After stirring for 5 hours at room temperature the mixture was concentrated and the residue was triturated with diethyl ether (50 ml). The resulting white solid was collected by filtration, washed with diethyl ether and dried under vacuum, yielding 856 mg of the title compound (88% yield).

$^1$H NMR (DMSO-d6): 8.76 (1H, d, J=3.1 Hz); 8.68 (1H, d, J=8.1); 8.56 (1H, br); 8.06 (3H, m); 7.91 (2H, br); 4.43 (1H, m); 4.14 (1H, dd, J=8.6, J=1.6); 3.60 (2H, m); 3.15 (2H, br); 2.67 (1H, m); 2.23 (1H, m); 2.04 (1H, m); 1.87 (1H, t, J=5.8); 1.81 (1H, m); 1.75-1.60 (3H, m); 1.52 (3H, m); 1.41-1.28 (3H, m); 1.27 (3H, s); 1.23 (3H, s); 0.86 (3H, d, J=6.4); 0.84 (3H, d, J=6.4); 0.81 (3H, s).

Example D.15

3-Aminopropanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]; hydrochloride salt

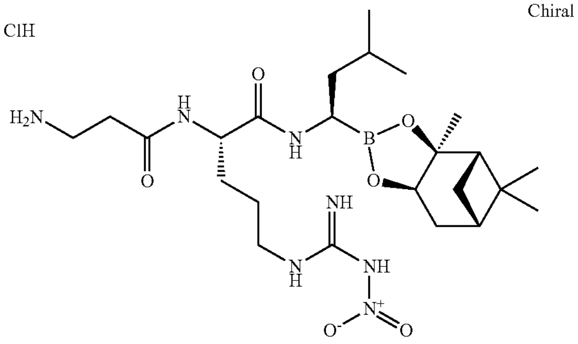 [SMILES: Cl ; CC(C)C[C@H](NC(=O)[C@H](CCCNC(=N)N[N+](=O)[O-])NC(=O)CCN)B1O[C@@H]2C[C@@H]3C[C@@H](C3(C)C)[C@]2(C)O1]

To a solution of 3-[[(1,1-dimethylethoxy)carbonyl]amino]propanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitro amino)methyl-]amino]butyl]-, of Example D.3.118 (42 mg, 0.075 mmol) in diethyl ether (1.0 ml), cooled at 0° C., a 10% v/v solution of hydrogen chloride in diethyl ether (2 ml) was added. The mixture was stirred for 5 hours while allowing to warm to room temperature. The resulting solid was collected by filtration, washed with diethyl ether (3×3 ml) and dried under vacuum, giving 33 mg of the title compound (76% yield).

LC-MS 538.7, MH+. ESI POS; AQA; spray 4 kV/skimmer: 20V/probe 250 C.

Further compounds prepared according to the above Example, starting from the corresponding Boc protected compound of Table D.3, are reported in the following Table D-15.

TABLE D-15

| Ex # | Structure | Chemical Name and Analytical Data |
|---|---|---|
| D.15.1 | 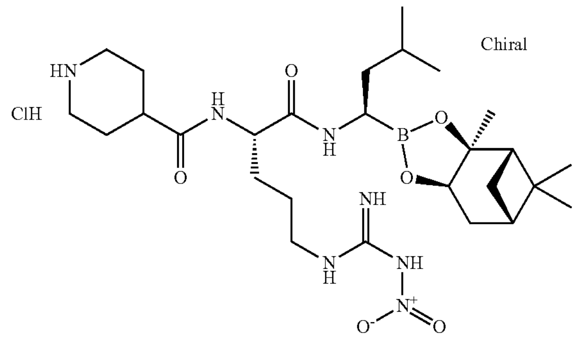 [SMILES: Cl ; CC(C)C[C@H](NC(=O)[C@H](CCCNC(=N)N[N+](=O)[O-])NC(=O)C1CCNCC1)B1O[C@@H]2C[C@@H]3C[C@@H](C3(C)C)[C@]2(C)O1] | Chemical Name: (4RS)-piperidine-4-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl], HCl salt<br>Analytical Data: MS: MH+ 578.1 |

TABLE D-15-continued

| Ex # | Structure | Chemical Name and Analytical Data |
|---|---|---|
| D.15.2 | 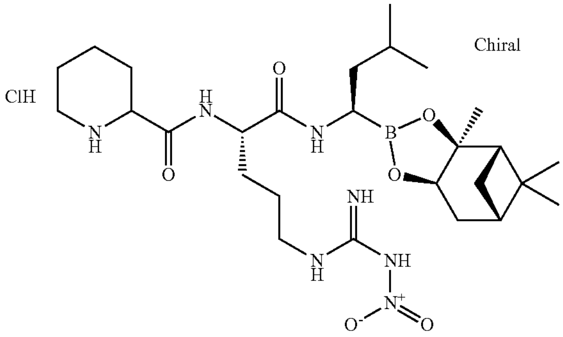 [SMILES: Cl ; CC(C)C[C@H](NC(=O)[C@H](CCCNC(=N)N[N+](=O)[O-])NC(=O)C1CCCCN1)B1O[C@@H]2C[C@@H]3C[C@@H](C3(C)C)[C@]2(C)O1] | Chemical Name: (RS)-Piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]; HCl salt<br>Analytical Data: MS: [MH]+ 578.2 |
| D.15.3 | 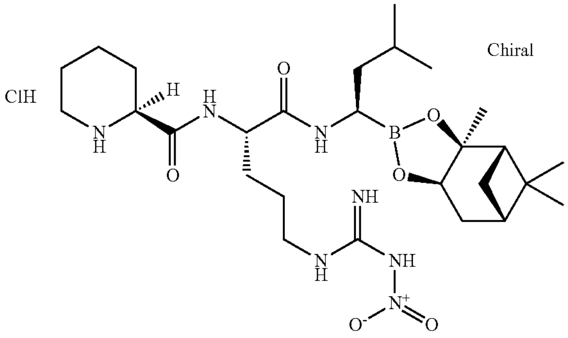 [SMILES: Cl ; CC(C)C[C@H](NC(=O)[C@H](CCCNC(=N)N[N+](=O)[O-])NC(=O)[C@@H]1CCCCN1)B1O[C@@H]2C[C@@H]3C[C@@H](C3(C)C)[C@]2(C)O1] | Chemical Name: (2S)-Piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]; HCl salt<br>Analytical Data: MS: [MH]+ 578.2 |
| D.15.4 | 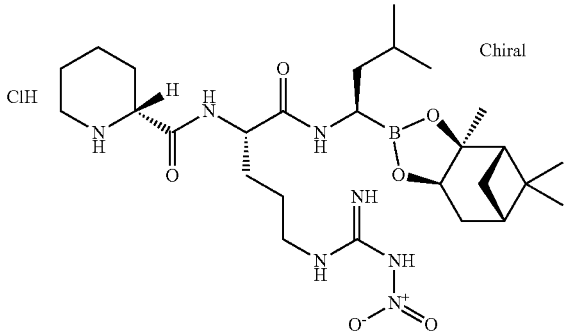 [SMILES: Cl ; CC(C)C[C@H](NC(=O)[C@H](CCCNC(=N)N[N+](=O)[O-])NC(=O)[C@H]1CCCCN1)B1O[C@@H]2C[C@@H]3C[C@@H](C3(C)C)[C@]2(C)O1] | Chemical Name: (2R)-Piperidine-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]; HCl salt<br>Analytical Data: MS: [MH]+ 578.8 |

Example D.16

Synthesis of Further Compounds

Following the procedures of Examples D.9-D.13, the following compounds can be prepared by reaction of decanoic acid with the intermediates of Example C.9.

| | | |
|---|---|---|
| D.16.1 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(acetamido)ethyl]- | 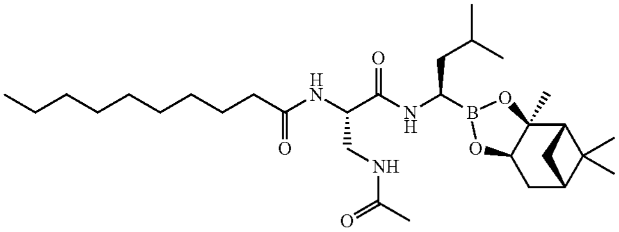 [SMILES: CCCCCCCCCC(=O)N[C@@H](CNC(C)=O)C(=O)N[C@@H](CC(C)C)B1O[C@@H]2C[C@@H]3C[C@@H](C3(C)C)[C@]2(C)O1] |

-continued

| | | |
|---|---|---|
| D.16.2 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(9-fluorenylmethyloxycarbamoyl)ethyl]- | 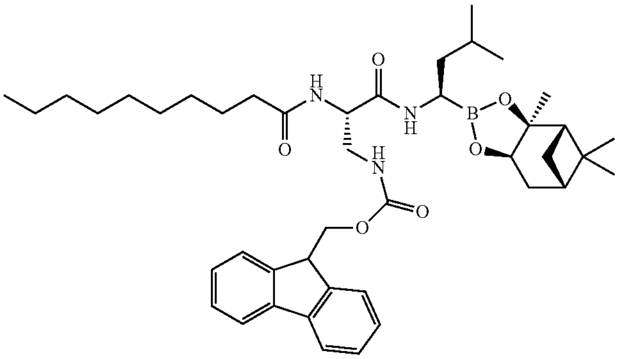 [SMILES: CCCCCCCCCC(=O)N[C@@H](CNC(=O)OCC1c2ccccc2-c2ccccc21)C(=O)N[C@@H](CC(C)C)B1O[C@@H]2C[C@@H]3C[C@@H](C3(C)C)[C@]2(C)O1] |
| D.16.3 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(pentyl-ureido)ethyl]- | 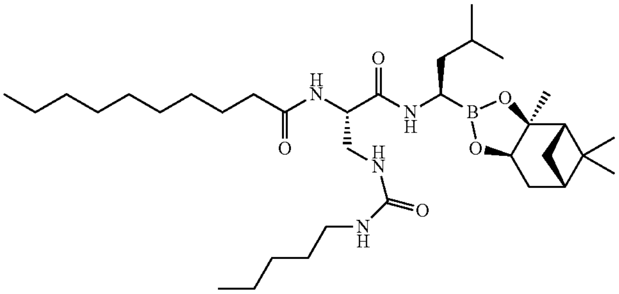 [SMILES: CCCCCCCCCC(=O)N[C@@H](CNC(=O)NCCCCC)C(=O)N[C@@H](CC(C)C)B1O[C@@H]2C[C@@H]3C[C@@H](C3(C)C)[C@]2(C)O1] |
| D.16.4 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(methanesulfonamido)ethyl]- | 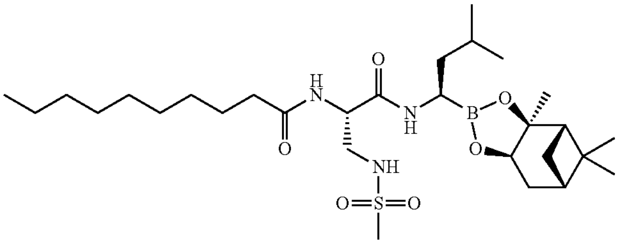 [SMILES: CCCCCCCCCC(=O)N[C@@H](CNS(C)(=O)=O)C(=O)N[C@@H](CC(C)C)B1O[C@@H]2C[C@@H]3C[C@@H](C3(C)C)[C@]2(C)O1] |
| D.16.5 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(ethoxycarbonyl-succinyl]-amide)ethyl]- | 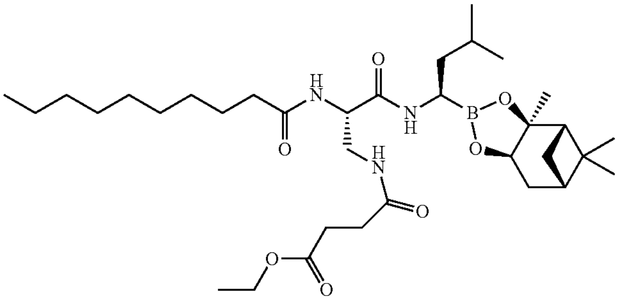 [SMILES: CCCCCCCCCC(=O)N[C@@H](CNC(=O)CCC(=O)OCC)C(=O)N[C@@H](CC(C)C)B1O[C@@H]2C[C@@H]3C[C@@H](C3(C)C)[C@]2(C)O1] |
| D.16.6 | 4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]- $^1$H NMR (DMSO-d6): 9.79 (1H, d); 8.32 (1H, d); 7.8 (2H, d); 7.3 (8H, m); 5.05 (2H, q) 4.7 (1H, q); 4.1 (1H, d); 3.45 (2H, m); 2.6 (3H, m); 2.2 (1H, m); 2.0 (1H, m); 1.85 (2H, m); 1.65 (4H, m); 1.3 (5H, m); 1.25 (6H, d) 0.9 (3H, t); 0.80 (9H, m). M.p. 95°-100° C. | 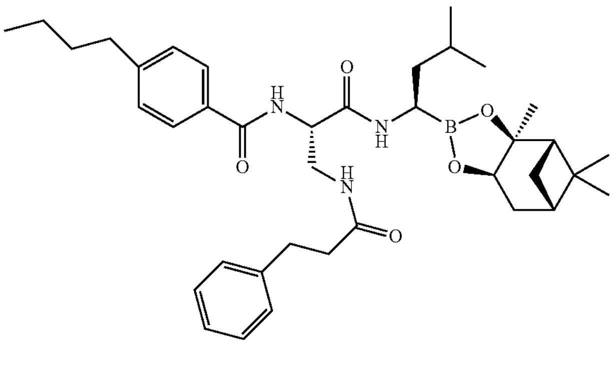 [SMILES: CCCCc1ccc(C(=O)N[C@@H](CNC(=O)CCc2ccccc2)C(=O)N[C@@H](CC(C)C)B2O[C@@H]3C[C@@H]4C[C@@H](C4(C)C)[C@]3(C)O2)cc1] |

-continued

| | | |
|---|---|---|
| D.16.7 | 4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl-]-3-methylbutyl]amino]carbonyl]-2-(1H-pyrazol)ethyl]- | 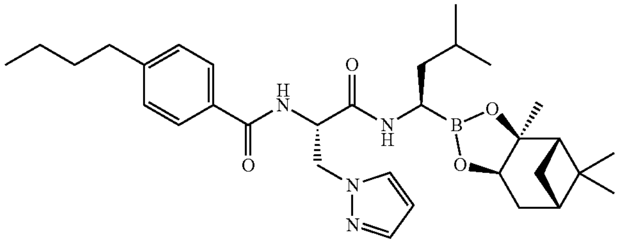 [SMILES: CCCCc1ccc(C(=O)N[C@@H](Cn2cccn2)C(=O)N[C@@H](CC(C)C)B2O[C@@H]3C[C@@H]4C[C@@H](C4(C)C)[C@]3(C)O2)cc1] |
| D.16.8 | Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]- $^1$H NMR (DMSO-d6): 8.69 (1H, d); 7.85 (1H, d); 7.35 (5H, m); 7.05 (1H, t); 5.05 (2H, m) 4.45 (1H, q); 4.1 (1H, d); 3.3 (2H, m); 2.65 (1H, m); 2.2 (1H, m); 2.1 (3H, m); 1.85 (2H, m); 1.65 (2H, m); 1.45 (2H, m); 1.25 (22H, m); 0.8 (12H, m) | 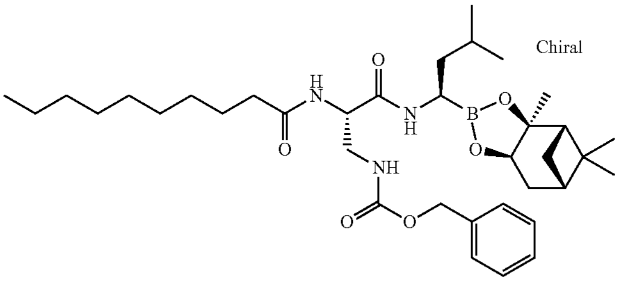 [SMILES: CCCCCCCCCC(=O)N[C@@H](CNC(=O)OCc1ccccc1)C(=O)N[C@@H](CC(C)C)B1O[C@@H]2C[C@@H]3C[C@@H](C3(C)C)[C@]2(C)O1] Chiral |
| D.16.9 | 4-Phenoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]- $^1$H NMR (DMSO-d6): 9.8 (1H, d); 8.4 (1H, d); 7.9 (2H, d); 7.4 (2H, t); 7.3 (6H, m); 7.25 (2H, m); 7.05 (4H, m); 5.05 (2H, q) 4.7 (1H, q); 4.05 (1H, d); 3.45 (2H, m); 2.65 (1H, m); 2.2 (1H, m); 2.0 (1H, m); 1.80 (2H, m); 1.65 (2H, m); 1.3 (4H, m); 1.25 (6H, d) 0.8 (9H, m). M.p. 100°-103° C. | 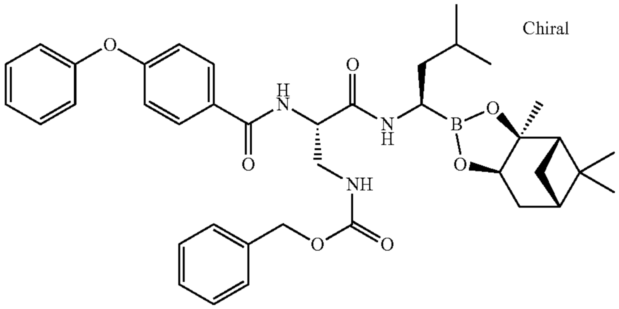 [SMILES: CC(C)C[C@H](NC(=O)[C@H](CNC(=O)OCc1ccccc1)NC(=O)c1ccc(Oc2ccccc2)cc1)B1O[C@@H]2C[C@@H]3C[C@@H](C3(C)C)[C@]2(C)O1] Chiral |

Example D.17

4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(aminoethyl)-hydrochloride salt

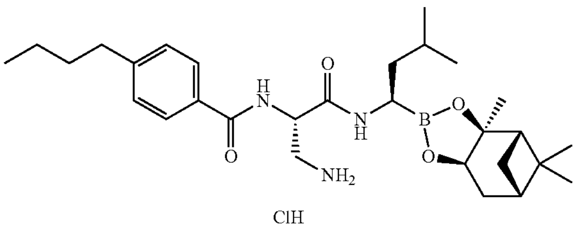 [SMILES: CCCCc1ccc(C(=O)N[C@@H](CN)C(=O)N[C@@H](CC(C)C)B2O[C@@H]3C[C@@H]4C[C@@H](C4(C)C)[C@]3(C)O2)cc1 ; Cl]

4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]-, of Example D.16.6, (400 mg, 0.62 mmol, 1 eq.), was dissolved in 1,4-dioxane (10 ml) and methanol (5 ml). To this solution, Pd/C 10% (40 mg) and HCl 4N 1,4-dioxane (1.1 eq.) were added. The mixture was hydrogenated at 1 bar. At the end of the reaction, Pd/C was filtered over celite, the solvent removed under reduced pressure to give a white foam. Yield 95%, 320 mg. Analytical data:

$^1$H NMR (DMSO-d6): 8.76 (1H, d); 8.55 (1H, d); 8.15 (3H, br s); 7.95 (2H, d); 7.25 (2H, d); 4.8 (1H, m); 4.2 (1H, d); 2.80 (1H, m); 2.62 (2H, t); 2.23 (1H, m); 2.04 (1H, m); 1.87 (1H, t); 1.80 (1H, m); 1.75-1.50 (2H, m), (2H, m); 1.41-1.20 (6H, d), (6H, m); 1.0-0.80 (3H, d); (3H, d); (3H, s), (3H t).

Example D.18

2-S-(4-Butylbenzoylamino)-3-(2-pyrazinocarbonylamino)-N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]

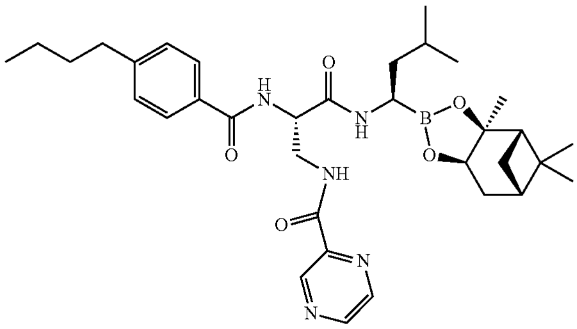 [SMILES: CCCCc1ccc(C(=O)N[C@@H](CNC(=O)c2cnccn2)C(=O)N[C@@H](CC(C)C)B2O[C@@H]3C[C@@H]4C[C@@H](C4(C)C)[C@]3(C)O2)cc1]

2-Pyrazine carboxylic acid, (76 mg, 0.61 mmol, 1.1 eq.) was dissolved in DMF dry, (5 ml) and TBTU (200 mg, 0.61 mmol, 1.1 eq.) was added at r.t. under nitrogen. The solution was stirred for 15', cooled at 0°-5° C. and NMM (0.20 ml, 1.85 mmol, 3.3 eq.) and 4-butylbenzamide,N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(aminoethyl)-hydrochloride salt, from Example D.17, (310 mg, 0.56 mmol, 1 eq.) were added and the resulting mixture was stirred at 25° C. for 4 h. The solution was poured in water (100 ml) extracted with ethyl acetate (50 ml), washed with the following solutions: citric acid 2% (50 ml), NaCl 2% (50 ml), sodium bicarbonate 2% (50 ml), NaCl 2% (50 ml). The organic solution was dried over sodium sulphate anhydrous, filtered, evaporated and suspended in diethyl ether-n-hexane for 1 h, to give a white solid that was filtered and dried under vacuum to give a white powder. Yield 52%. 180 mg.

Analytical data: M.p. 70°-72° C.

$^1$H NMR (DMSO-d6): 9.20 (1H, s); 9.0 (1H, t); 8.85 (1H, d); 8.8 (1H, d); 8.78 (1H, d); 8.60 (1H, d); 7.82 (2H, d); 7.35 (2H, d); 4.8 (1H, m); 4.1 (1H, d); 3.80 (1H, m); 3.62 (1H, m); 2.82 (1H, b); 2.65 (2H, m); 2.2-2.0 (2H, m); 1.80 (1H, m); 1.75-1.50 (2H, m), (2H, m); 1.41-1.20 (6H, d), (6H, m); 1.0-0.80 (3H, d); (3H, d); (3H, s), (3H t).

Example D.19

4-Butylbenzamide, N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-[4-fluoro-benzenesulfonammide]ethyl]-

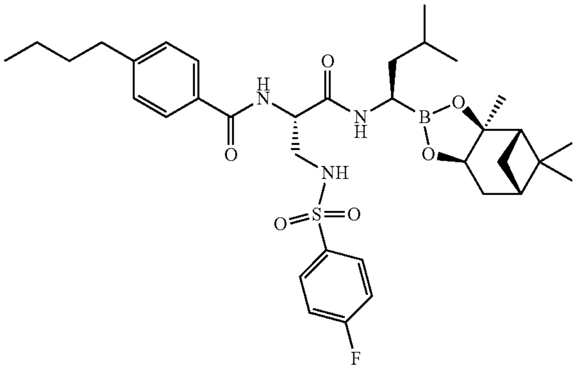 [SMILES: CCCCc1ccc(C(=O)N[C@@H](CNS(=O)(=O)c2ccc(F)cc2)C(=O)N[C@@H](CC(C)C)B2O[C@@H]3C[C@@H]4C[C@@H](C4(C)C)[C@]3(C)O2)cc1]

4-Butylbenzamide,N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]-, of Example D.17, (2.75 g, 5.02 mmol, 1 eq.), was dissolved in dry methylene chloride at 0°-5° C. To this solution 4-fluorobenzenesulfonyl chloride (1.07 g, 5.52 mmol, 1.1 eq.) was added and N-methylmorpholine (NMM) (1.11 g, 11.04 mmol, 2.2 eq.) was added dropwise, after few minutes. The mixture was stirred at 0-5° C. for 30', then at 10° C. for 1 h. The solvent was removed under reduced pressure, the crude was dissolved in Ethyl acetate and washed with a solution of citric acid 2% (50 ml) then with a solution of sodium bicarbonate 2% (50 ml) and a solution of sodium chloride 2% (50 ml). The solution was dried over anhydrous sodium sulfate and the solvent evaporated under reduced pressure. The crude was purified by silica gel chromatography (eluent ethyl acetate/n-hexane 1/2), the collected fractions have been evaporated under reduced pressure and the white solid was suspended in diethyl ether, filtered and dried under vacuum to give a white wax. Yield 60%, 2 g. Analytical data:

$^1$H NMR (DMSO-d6): 8.60 (1H, d); 8.30 (1H, d); 7.85 (3H, m); 7.8 (2H, d); 7.38 (2H, d); 7.30 (2H, d); 4.62 (1H, m); 4.15 (1H, d); 3.25 (2H, br); 2.61 (3H, m); 2.3-2.0 (1H, m); (1H, m); 1.80 (1H, m); 1.75-1.50 (2H, m), (2H, m); 1.41-1.20 (6H, d), (6H, m); 1.0-0.80 (3H, d); (3H, d); (3H, s), (3H t).

Example D.20

4-Butylbenzamide, N-[(1S)-1-[[[(1R)-1-[(3aS,aS,6S, 7aR)-hexahydro-3a,5,5-trimethyl-4,6-methano-1,3,2-benzodioxaborol-2-yl-]-3-methylbutyl]amino]carbonyl]-2-[(2,5-dimethyl-2H-pyrazole) carbonylamino] ethyl]-

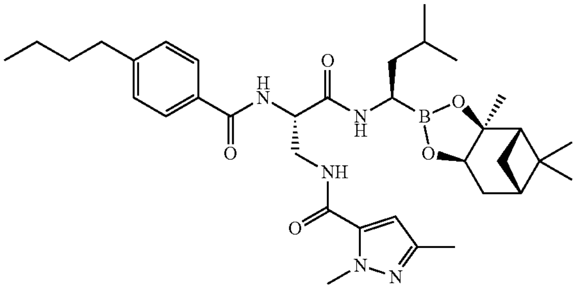 [SMILES: CCCCc1ccc(C(=O)N[C@@H](CNC(=O)c2cc(C)nn2C)C(=O)N[C@@H](CC(C)C)B2O[C@@H]3C[C@@H]4C[C@@H](C4(C)C)[C@]3(C)O2)cc1]

4-Butylbenzamide,N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]-, of Example D.17, (0.9 g, 1.64 mmol, 1 eq.), was dissolved in dry dichloromethane (10 ml). The resulting solution was cooled to 0°<T<5° C. and N-methyl-morpholine (0.381 g, 3.78 mmol, 2.3 eq.) was added. To the mixture, 1,3-dimethyl-1H-pyrazole-5-carbonyl chloride (Rn [55458-67-8]) (0.286 mg, 1.8 mmol, 1.1 eq.) was added. The mixture was stirred for 1 h, then the temperature was raised to 20° C. The mixture was evaporated under reduced pressure, suspended in ethyl acetate (50 ml), washed with 2% citric acid solution (30 ml), 2% sodium bicarbonate (30 ml), 2% sodium chloride (30 ml). The organic layer was dried over anhydrous sodium sulfate and evaporated under reduced pressure. The crude was purified by silica gel chromatography (eluent Ethyl acetate/n-hexane 8/2). The collected fractions were evaporated to give a white powder, that was suspended in diethyl ether and filtered to give the desired compound. Yield 65%, 650 mg. Rf. 0.62.

Analytical data: M.p. 62°-64° C.

$^1$H NMR (DMSO-d6): 8.82 (1H, d); 8.40 (2H, m); 7.85 (2H, d); 7.3 (2H, d); 6.5 (1H, s); 4.8 (1H, m); 4.15 (1H, d); 3.9 (3H, s); 3.61 (2H, m); 2.65 (3H, m); 2.25 (1H, m); 2.15 (3H, s); 2.0 (1H, m); 1.80 (1H, m); 1.75-1.50 (4H, m), 1.41-1.20 (5H, m), (6H, m); 0.90 (3H, t); 0.8 (9H, m);

Example D.21

4-Butylbenzamide, N-[(1S)-1-[[[(1R)-1-[(3aS,aS,6S, 7aR)-hexahydro-3a,5,5-trimethyl-4,6-methano-1,3,2-benzodioxaborol-2-yl-]-3-methylbutyl]amino]carbonyl]-2-(4-methylphenyluriedosulfonylamino)ethyl]-

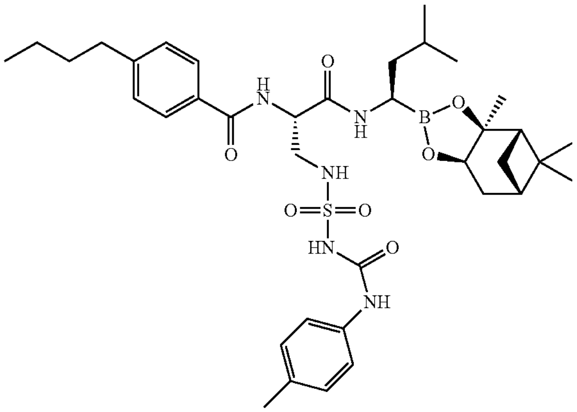 [SMILES: CCCCc1ccc(C(=O)N[C@@H](CNS(=O)(=O)NC(=O)Nc2ccc(C)cc2)C(=O)N[C@@H](CC(C)C)B2O[C@@H]3C[C@@H]4C[C@@H](C4(C)C)[C@]3(C)O2)cc1]

4-Butylbenzamide,N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]-, of Example D.17, (0.7 g, 1.27 mmol, 1 eq.), was dissolved in dry THF (10 ml), the solution was cooled at 0°-5° C. Triethylamine (0.4 ml, 1.8 mmol, 2.2 eq.) and (4-methylphenyl)-ureido-sulfonylchloride (0.34 g, 1.38 mmol, 1.09 eq.) of example G.1x have been added. The suspension was stirred at 25° C. for 1 h, then was poured in a citric acid 1% solution (30 ml) and extracted with Ethyl acetate (50 ml). The organic solution was washed with sodium chloride 2% solution, dried over anhydrous sodium sulfate, filtered and evaporated under reduced pressure to give acrude thata was purified by silica gel chromatography (eluent Ethyl acetate/n-hexane 1/1) Rf 0.64. The collected fractions have been evaporated and the oil was coevaporated with diethyl ether to give a white foam. Yield 31%, 280 mg.

Analytical data: M.p. 115°-120° C.

$^{1}$H NMR (DMSO-d6): 8.80 (1H, s); 8.40 (1H, d); 7.82 (2H, d); 7.3 (2H, d); 7.25 (2H, d); 7.00 (2H, d); 4.62 (1H, m); 4.15 (1H, d); 2.61 (3H, m); 2.3-2.0 (3H, s); 1.80 (1H, m); 1.75 (2H, m), 1.6 (4H, m), 1.2 (13H, m); 0.9 (3H, s), 0.8 (9H m).

Example D.22

4-Phenoxybenzamide,N-[(1S)-1-[[[(1R)-1-[(3aS,4S, 6S,7aR)-hexahydro-3a,5,5-trimethyl-4,6-methano-1, 3,2-benzodioxaborol-2-yl]-3-methylbutyl]amino] carbonyl]-2-(3-phenyl-ureido)ethyl]-

Chiral

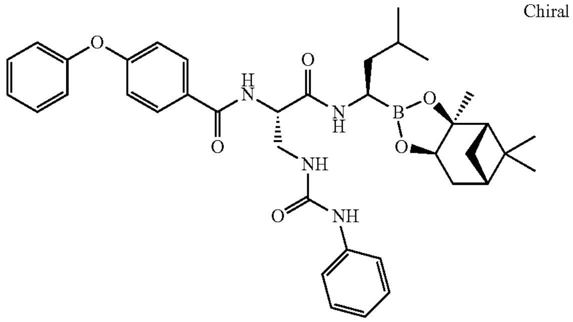 [SMILES: CC(C)C[C@H](NC(=O)[C@H](CNC(=O)Nc1ccccc1)NC(=O)c1ccc(Oc2ccccc2)cc1)B1O[C@@H]2C[C@@H]3C[C@@H](C3(C)C)[C@]2(C)O1]

4-Phenoxybenzamide, N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-(amino)ethyl]-hydrochloride salt, from example D.25.2, (1 g, 17 mmol, 1 eq.), was dissolved in dry dichloromethane (30 ml) and N-methyl-morpholine (0.2 g, 18.8 mmol, 1.1 eq.) was added. The solution was cooled at 0°-5° C. and phenylisocyanate (0.22 g, 17.7 mmol, 1.1 eq.) in dichloromethane (ml) was added. The mixture was stirred for 1 h at 0°-5° C. The solution was washed with sodium chloride 2% solution (50 ml), dried over anhydrous sodium sulfate and evaporated under vacuum. The crude was suspended in diethyl ether (20 ml), stirred for 2 h, filtered and dried under vacuum at 50° C. to give a white powder. Yield 74.3%, 0.84 g.

Analytical data: M.p. 143°-145° C.

$^{1}$H NMR (DMSO-d6): 8.9 (1H, d); 8.75 (1H, s); 8.59 (1H, d); 7.95 (2H, d); 7.45 (2H, t); 7.35 (2H, d); 7.2 (3H, m); 7.1 (4H, m); 6.9 (1H, m); 6.25 (1H, t); 4.65 (1H, m); 4.10 (1H, d); 3.65 (1H, m); 3.4 (1H, m); 2.6 (1H, m); 2.2 (1H, m); 2.1 (1H, m); 1.85 (2H, m); 1.65 (2H, m), 1.3 (3H, m); (6H, d); 0.80 (9H, t).

Example D.23

4-Butylbenzamide, N-[(1S)-1-[[[(1R)-1-[(3aS,aS,6S, 7aR)-hexahydro-3a,5,5-trimethyl-4,6-methano-1,3,2-benzodioxaborol-2-yl-]-3-methylbutyl]amino]carbonyl]-2-(4-methylphenylsulfonylureido)ethyl]-

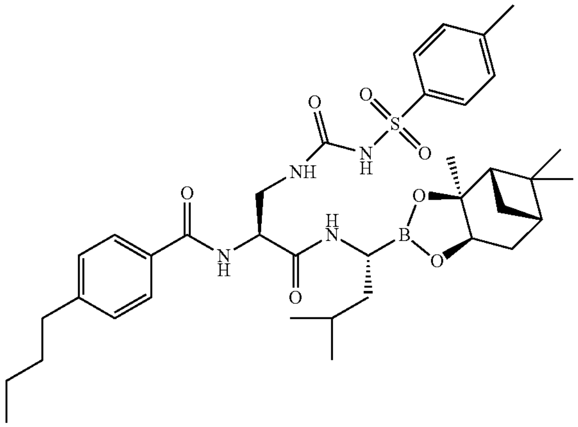 [SMILES: CCCCc1ccc(C(=O)N[C@@H](CNC(=O)NS(=O)(=O)c2ccc(C)cc2)C(=O)N[C@@H](CC(C)C)B2O[C@@H]3C[C@@H]4C[C@@H](C4(C)C)[C@]3(C)O2)cc1]

4-Butylbenzamide, N-[(1S)-1-[[[(1R)-1-[(3aS,4S,6S, 7aR)-hexahydro-3a,5,5-trimethyl-4,6-methano-1,3,2-benzodioxaborol-2-yl]-3-methylbutyl]amino]carbonyl]-2-(aminoethyl)-hydrochloride salt, from Example D.17, (560 mg, 1.07 mmol, 1 eq.) was dissolved in dichloromethane dry (20 ml), and the solution was cooled at 0°-5° C. N-methyl-morpholine (0.125 ml, 1.129 mmol, 1.1 eq,); and 4-toluenesulfonylisocyanate (0.22 g, 1.12 mmol, 1.1 eq,) were added and the mixture was stirred at room temperature for 2 h. The mixture was washed with a solution of citric acid 2% (20 ml) and a sodium chloride 2% solution (25 ml). The organic layer was dried over anhydrous sodium sulfate, filtered and evaporated under reduced pressure. The crude was dissolved in diethyl ether (40 ml) and the solvent was evaporated. The crude was suspended in n-hexane (20 ml), stirred for 1 h at room temperature, filtered and dried under vacuum at 50° C. to give a white powder. Yield 75.6%, 0.55 g.

Analytical data: M.p. 168°-170° C.

$^{1}$H NMR (DMSO-d6): 10.8 (1H, s); 8.75 (1H, d); 8.35 (1H, d); 7.75 (4H, m); 7.35 (5H, m); 6.65 (1H, t); 4.5 (1H, t); 4.1 (1H, d); 3.5 (1H, m); 3.25 (1H, m); 2.65 (3H, m); 2.3 (3H, d); 2.2 (1H, m); 2.1 (1H, m); 1.80 (2H, m); 1.65 (4H, m), 1.3 (12H, m); 0.80 (12H, m).

Example D.24

Synthesis of Further Compounds

Following the procedures of Examples D.18-D.23, the following compounds can be prepared by reaction of the intermediates of Example D.17 or D.25 with the appropriate commercially available carboxylic acids, acyl halides, sulphonyl halides, isocyanates, sulphonylisocyanates, or with the compounds of Examples G.14, G.15 and G.16. All the obtained compounds have been characterized by $^1$H-NMR.

TABLE D-24

| | | |
|---|---|---|
| D.24.1 | 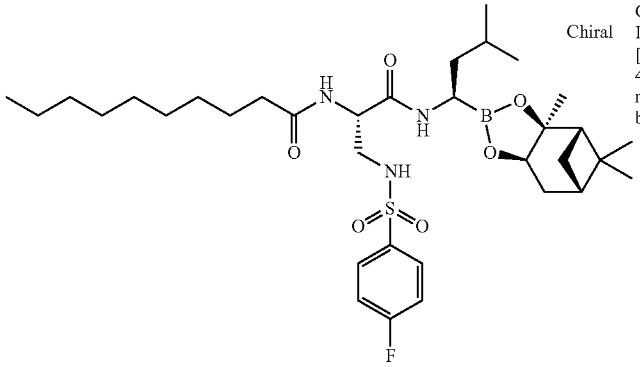 Chiral | Chemical Name: Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[4-fluoro-benzenesulfonamide]ethyl]- |
| D.24.2 | 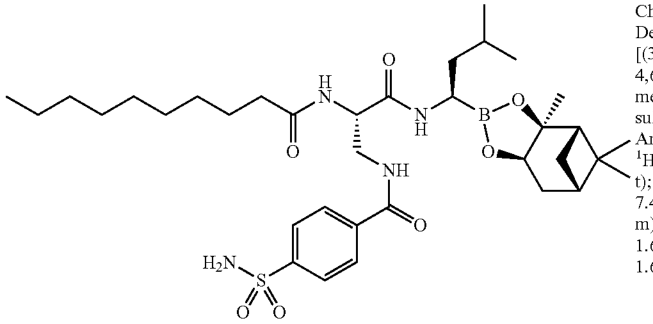 | Chemical Name: Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(4-sulfonamidophenyl)carbonylamido]ethyl]- Analytical Data: $^1$H NMR (DMSO-d6): 8.8 (1H, d); 8.55 (1H, t); 8.35 (1H, d); 7.92 (2H, d); 7.88 (2H, d); 7.45 (2H, s); 4.6 (1H, t); 3.5 (2H, m); 2.2 (1H, m); 2.1 (2H, m); 2.05 (1H, m); 1.8 (2H, m); 1.6 (2H, m); 1.45 (3H, m); 1.25 (24H, m); 1.65 (4H, m), 0.80 (12H, m). M.p. 178°-181° C. |
| D.24.3 | 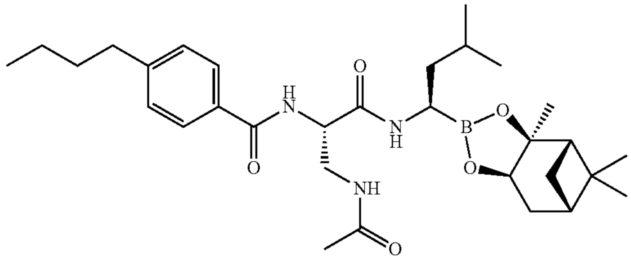 [SMILES: CCCCc1ccc(C(=O)N[C@@H](CNC(C)=O)C(=O)N[C@@H](CC(C)C)B2O[C@@H]3C[C@@H]4C[C@@H](C4(C)C)[C@]3(C)O2)cc1] | Chemical Name: 4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(acetamido)ethyl]- Analytical Data: $^1$H NMR (DMSO-d6): 8.8 (1H, d); 8.5 (1H, m), 8.0 (1H, t), 7.8 (2H, d); 7.25 (2H, d); 7.2 (2H, t); 4.7 (1H, q); 4.1 (1H, d), 3.7-3.4 (2H, m); 2.7 (2H, t); 2.2 (1H, m); 2.0 (1H, m), 1.9 (1H, t); 1.8 (3H, s), 1.7-1.5 (4H, m); 1.4-1.1 (10H, m) 1.1 (1H, t), 0.95 (3H, t), 0.8 (9H, m). M.p. 133°-135° C. |
| D.24.4 | 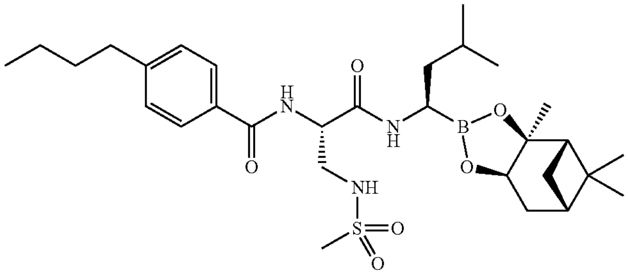 [SMILES: CCCCc1ccc(C(=O)N[C@@H](CNS(C)(=O)=O)C(=O)N[C@@H](CC(C)C)B2O[C@@H]3C[C@@H]4C[C@@H](C4(C)C)[C@]3(C)O2)cc1] | Chemical Name: 4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(methanesulfonamido)ethyl]- Analytical Data: $^1$H NMR (DMSO-d6): 8.8 (1H, d); 8.5 (1H, m), 8.0 (1H, t), 7.8 (2H, d); 7.25 (2H, d); 7.2 (2H, t); 4.7 (1H, q); 4.1 (1H, d), 3.7-3.4 (2H, m); 2.9 (3H, s), 2.7 (2H, t); 2.2 (1H, m), 2.0 (1H, m), 1.9 (1H, t); 1.7-1.5 (4H, m); 1.4-1.1 (10H, m), 1.1 (1H, t), 0.95 (3H, t), 0.8 (9H, m). M.p. 53°-55° C. |

TABLE D-24-continued

D.24.5

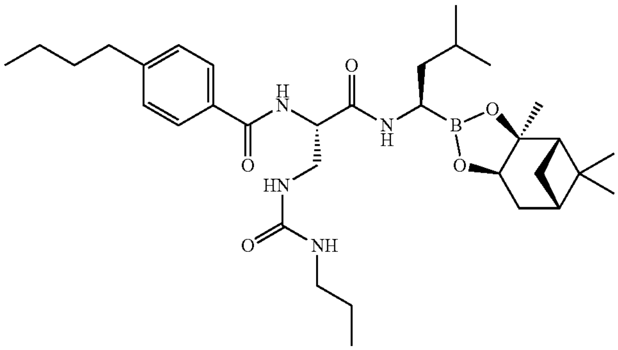 [SMILES: CCCCc1ccc(C(=O)N[C@@H](CNC(=O)NCCC)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(propylureido)ethyl]-
Analytical Data:
$^1$H NMR (DMSO-d6): 8.9 (1H, s); 8.6 (1H, d); 7.8 (2H, d); 7.25 (2H, d); 6.2 (1H, t); 6.05 (1H, t); 4.5 (1H, t); 4.05 (1H, t); 3.4 (1H, m); 2.9 (1H, m); 2.65 (2H, t); 2.2 (1H, m); 2.0 (1H, m); 1.8 (2H, m); 1.65 (4H, m); 1.2 (15H, m), 0.80 (16H, m).

D.24.6

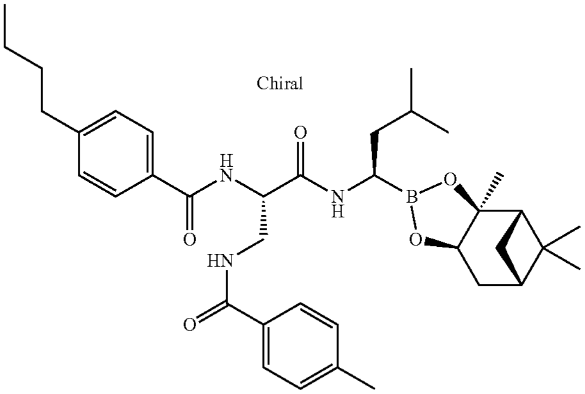 [SMILES: CCCCc1ccc(C(=O)N[C@@H](CNC(=O)c2ccc(C)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(4-methylphenyl)carbonylamino]ethyl]-
Analytical Data:
$^1$H NMR (DMSO-d6): 8.8 (1H, d); 8.5 (2H, m), 7.9 (2H, d), 7.8 (2H, d); 7.3 (2H, d) 7.25 (2H, d); 4.7 (1H, q); 4.1 (1H, d), 3.7-3.4 (2H, m); 2.6 (3H, m), 2.2 (1H, m), 2.0 (1H, m), 1.7-1.5 (4H, m); 1.4-1.1 (12H, m) 1.1 (1H, t), 0.95 (3H, t), 0.8 (12H, m). M.p. 150°-152° C.

D.24.7

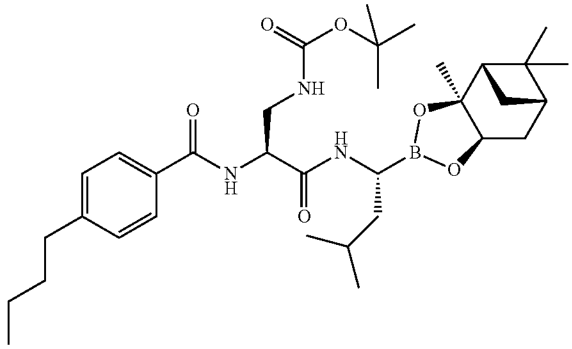 [SMILES: CCCCc1ccc(C(=O)N[C@@H](CNC(=O)OC(C)(C)C)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3a,aS,6S,7aR)-hexahydro-3a,5,5-trimethyl-4,6-methano-1,3,2-benzodioxaborol-2-yl-]-3-methylbutyl]amino]carbonyl]-2-[(1,1-dimethylethoxycarbonyl)amino]ethyl]-
Analytical Data:
$^1$H NMR (DMSO-d6): 8.8 (1H, s); 8.25 (1H, d); 7.8 (2H, d); 7.3 (2H, d); 6.9 (1H, t); 4.65 (1H, t); 4.1 (1H, d); 2.65 (2H, m); 2.2 (1H, m); 2.1 (1H, m); 1.8 (2H, m); 1.6 (4H, m); 1.3 (20H, m); 0.9-0.80 (12H, m).

D.24.8

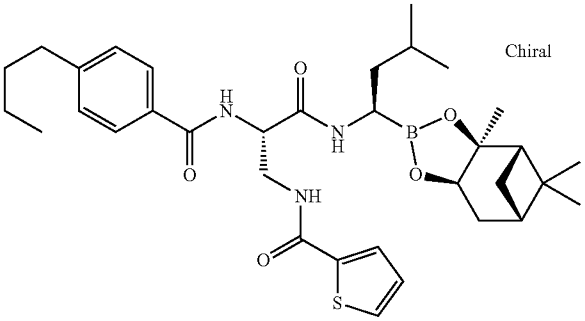 [SMILES: CCCCc1ccc(C(=O)N[C@@H](CNC(=O)c2cccs2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(thien-2-ylcarbonyl)amino]ethyl]-
Analytical Data:
$^1$H NMR (DMSO-d6): 8.8 (1H, d); 8.5 (1H, m), 8.0 (1H, t), 7.80 (2H, d), 7.7 (2H, m); 7.3 (2H, d); 7.2 (1H, t); 4.7 (1H, q); 4.1 (1H, d), 2.2 (1H, m); 2.0 (1H, m), 1.9 (1H, t); 1.7-1.5 (4H, m); 1.4-1.1 (10H, m) 1.1 (1H, t), 0.95 (3H, t), 0.8 (9H, m).

TABLE D-24-continued

D.24.9

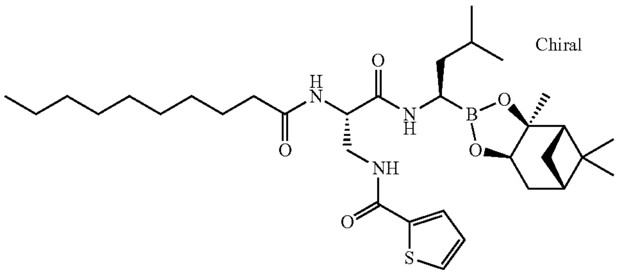 [SMILES: CCCCCCCCCC(=O)N[C@@H](CNC(=O)c1cccs1)C(=O)N[C@@H](CC(C)C)B1O[C@@H]2C[C@@H]3C[C@@H](C3(C)C)[C@]2(C)O1]

Chemical Name:
Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(thien-2-ylcarbonyl)amino]ethyl]-
Analytical Data:
$^1$H NMR (DMSO-d6): 8.8 (1H, d); 8.5 (1H, m), 8.0 (1H, t), 7.80 (2H, d); 7.7 (2H, m); 7.3 (2H, d); 7.2 (1H, t); 4.7 (1H, q); 4.1 (1H, d), 3.5 (2H, t), 2.9 (1H, m); 2.8 (1H, m); 2.4 (4H, m); 2.2 (1H, m); 2.0 (1H, m), 1.9 (1H, t); 1.7-1.5 (4H, m); 1.4-1.1 (10H, m) 1.1 (1H, t), 0.95 (3H, t), 0.8 (9H, m). 2.9 (1H, m); 2.8 (1H, m); 2.4 (4H, m); 1.9 (1H, m); 1.85 (1H, m); 1.65 (2H, m); 1.50 (2H, m); 1.35 (1H, m); 0.85 (12H, m). M.p. 110° C.

D.24.10

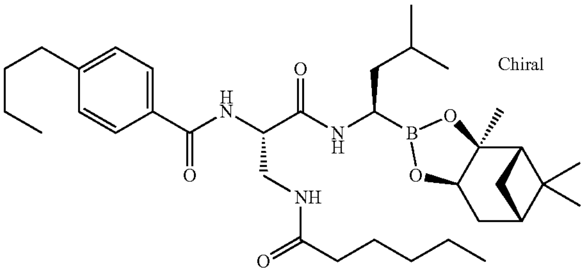 [SMILES: CCCCCC(=O)NC[C@H](NC(=O)c1ccc(CCCC)cc1)C(=O)N[C@@H](CC(C)C)B1O[C@@H]2C[C@@H]3C[C@@H](C3(C)C)[C@]2(C)O1]

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(hexanoylamino)ethyl]-
Analytical Data:
$^1$H NMR (DMSO-d6): 8.8 (1H, d); 8.5 (1H, d), 8.0 (1H, t), 7.80 (2H, d); 7.3 (2H, d); 4.7 (1H, q); 4.1 (1H, d), 3.5 (2H, t), 2.6 (3H, m), 2.2 (1H, m), 2.0 (3H, t), 1.9-1.75 (2H, m); 1.7-1.5 (4H, m); 1.5 (2H, m), 1.4-1.1 (16H, m), 0.95-0.8 (16H, m)

D.24.11

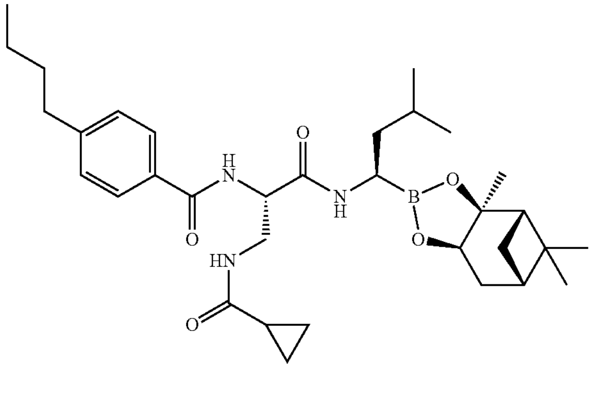 [SMILES: CCCCc1ccc(C(=O)N[C@@H](CNC(=O)C2CC2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[3aS,aS,6S,7aR)-hexahydro-3a,5,5-trimethyl-4,6-methano-1,3,2-benzodioxaborol-2-yl-]-3-methylbutyl]amino]carbonyl]-2-(cyclopropanecarbonylamino)ethyl]-
Analytical Data:
$^1$H NMR (DMSO-d6): 8.8 (1H, d); 8.5 (1H, d), 8.0 (1H, t), 7.80 (2H, d); 7.3 (2H, d); 4.7 (1H, q); 4.1 (1H, d), 3.5 (2H, t), 2.6 (3H, m), ), 2.2 (1H, m), 2.0 (1H, m), 1.9 (1H, t); 1.7-1.5 (4H, m); 1.4-1.1 (10H, m) 1.1 (1H, t), 0.95 (3H, t), 0.8 (9H, m), 0.7 (4H, m).

D.24.12

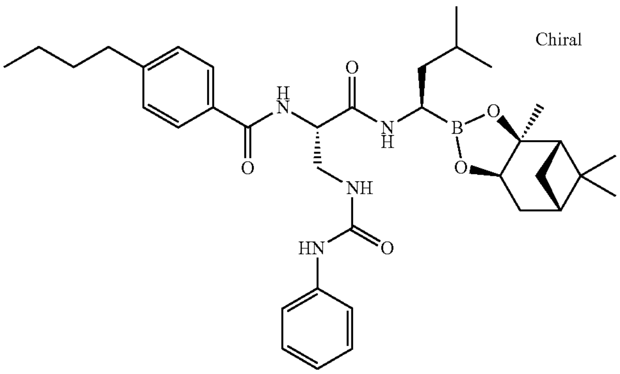 [SMILES: CCCCc1ccc(C(=O)N[C@@H](CNC(=O)Nc2ccccc2)C(=O)N[C@@H](CC(C)C)B2O[C@@H]3C[C@@H]4C[C@@H](C4(C)C)[C@]3(C)O2)cc1]

Chemical Name:
4-Butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(3-phenyl-ureido)ethyl]-
Analytical Data:
$^1$H NMR (DMSO-d6): 8.9 (1H, m); 8.8 (1H, s), 8.5 (1H, s), 7.9 (2H, d), 7.5 (2H, d); 7.4 (2H, d); 7.3 (2H, d), 6.9 (1H, t); 4.7 (1H, q); 4.1 (1H, d), 3.7-3.4 (2H, m); 2.6 (3H, m), 2.2 (1H, m), 2.0 (1H, m), 1.7-1.5 (4H, m); 1.4-1.1 (12H, m) 1.1 (1H, t), 0.95 (3H, t), 0.8 (9H, m)

TABLE D-24-continued

D.24.13

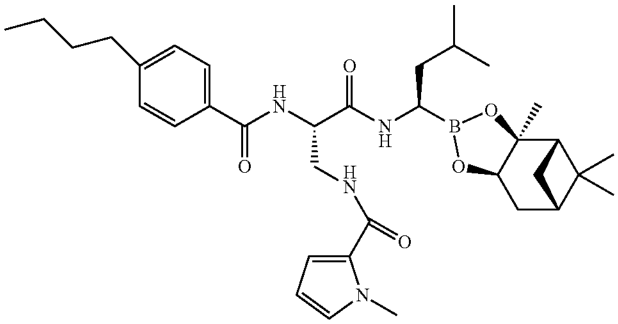 [SMILES: CCCCc1ccc(C(=O)N[C@@H](CNC(=O)c2cccn2C)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(N-methyl-2-pyrrolylcarbonylamide)ethyl]-
Analytical Data:
$^1$H NMR (DMSO-d6): 8.9 (1H, d); 8.45 (1H, d), 8.05 (1H, t), 7.8 (2H, d), 7.3 (2H, d); 6.9 (1H, s); 6.7 (1H, t), 5.95 (1H, t); 4.7 (1H, q); 4.1 (1H, d), 3.8 (3H, s); 3.6 (2H, m); 2.6 (3H, m), 2.2 (1H, m), 2.05 (1H, m), 1.8 (4H, m); 1.3 (12H, m) 0.91 (3H, t), 0.8 (9H, m).
M.p. 88°-92° C.

D.24.14

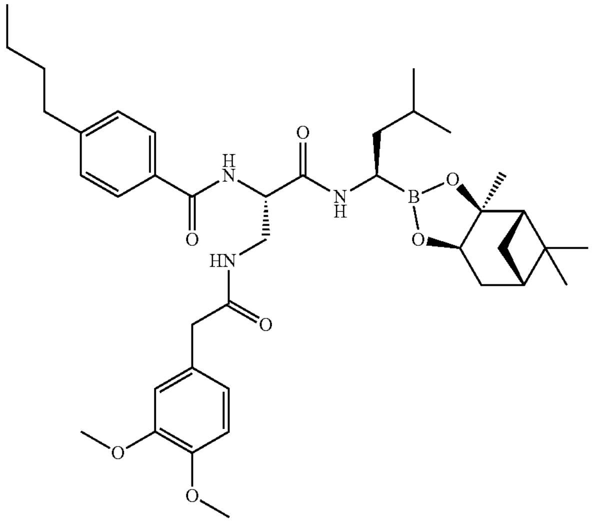 [SMILES: CCCCc1ccc(C(=O)N[C@@H](CNC(=O)Cc2ccc(OC)c(OC)c2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[3aS,aS,6S,7aR)-hexahydro-3a,5,5-trimethyl-4,6-methano,1,3,2-benzodioxaborol-2-yl-]-3-methylbutyl]amino]carbonyl]-2-[(3,4-dimethoxyphenyl)acetylamino]ethyl]-
Analytical Data:
$^1$H NMR (DMSO-d6): 8.8 (1H, m); 8.4 (1H, d), 8.1 (1H, t), 7.9 (2H, d), 7.3 (2H, d), 6.8 (1H, s); 6.6 (2H, t), 4.7 (1H, q); 4.1 (1H, d), 3.7-3.4 (2H, m); 2.6 (3H, m), 2.2 (1H, m), 2.0 (1H, m), 1.7-1.5 (4H, m); 1.4-1.1 (12H, m), 1.1 (1H, t), 0.95 (3H, t), 0.8 (9H, m).

D.24.15

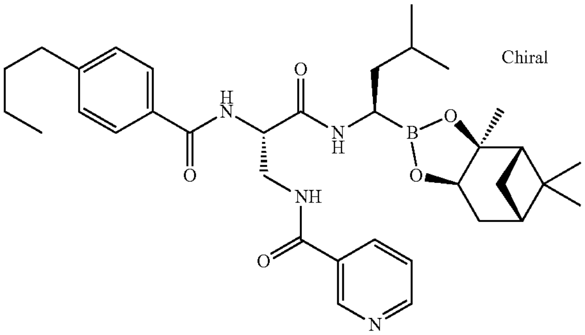 [SMILES: CCCCc1ccc(C(=O)N[C@@H](CNC(=O)c2cccnc2)C(=O)N[C@@H](CC(C)C)B2O[C@@H]3C[C@@H]4C[C@@H](C4(C)C)[C@]3(C)O2)cc1]

Chiral

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(nicotinonylamino)ethyl]-
Analytical Data:
$^1$H NMR (DMSO-d6): 9.1 (1H, s) 8.9 (1H, m); 8.7 (1H, t), 8.6 (1H, d), 8.5 (1H, d), 8.1 (1H, d), 7.9 (2H, d), 7.5 (1H, m), 7.3 (2H, d), 4.7 (1H, q); 4.1 (1H, d), 3.7-3.4 (2H, m); 2.6 (3H, m), 2.2 (1H, m), 2.0 (1H, m), 1.7-1.5 (4H, m); 1.4-1.1 (12H, m) 1.1 (1H, t), 0.95 (3H, t), 0.8 (9H, m).

D.24.16

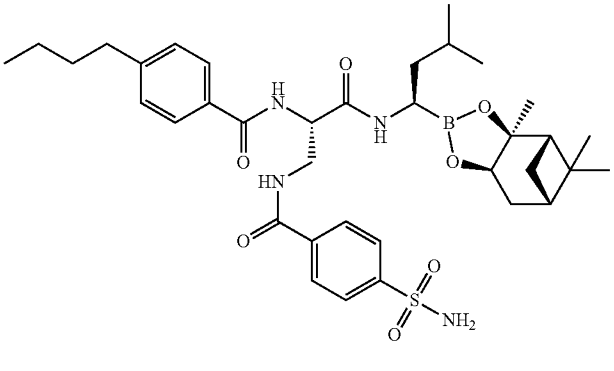 [SMILES: CCCCc1ccc(C(=O)N[C@@H](CNC(=O)c2ccc(S(N)(=O)=O)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[3aS,aS,6S,7aR)-hexahydro-3a,5,5-trimethyl-4,6-methano,1,3,2-benzodioxaborol-2-yl-]-3-methylbutyl]amino]carbonyl]-2-[(4-sulfonylamino)benzoylamino]ethyl]-
Analytical Data:
$^1$H NMR (DMSO-d6): 8.9 (1H, m); 8.7 (1H, t), 8.6 (1H, d), 8.0 (2H, d), 7.9 (2H, d), 7.8 (2H, d), 7.5 (2H, s), 7.3 (2H, d), 4.7 (1H, q); 4.1 (1H, d), 3.7-3.4 (2H, m); 2.6 (3H, m), 2.2 (1H, m), 2.0 (1H, m), 1.7-1.5 (4H, m); 1.4-1.1 (12H, m) 1.1 (1H, t), 0.95 (3H, t), 0.8 (9H, m).
M.p. 145°-147° C.

TABLE D-24-continued

D.24.17

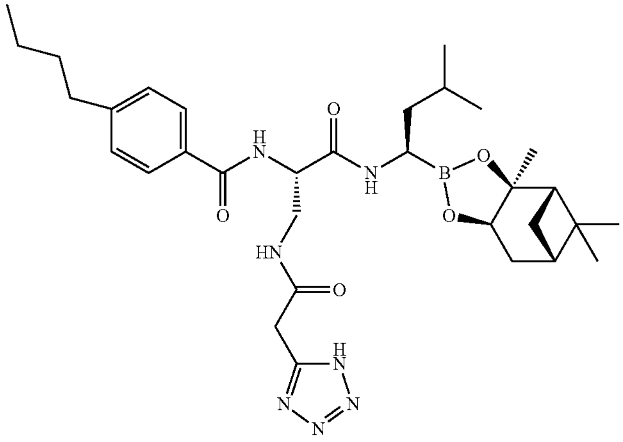 [SMILES: CCCCc1ccc(C(=O)N[C@@H](CNC(=O)Cc2nnn[nH]2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[3aS,aS,6S,7aR)-hexahydro-3a,5,5-trimethyl-4,6-methano,1,3,2-benzodioxoaborol-2-yl-]-3-methylbutyl]amino]carbonyl]-2-[(1H-tetrazol-5-yl-acetylamino]ethyl]-
Analytical Data:
$^1$H NMR (DMSO-d6): 9 (1H, s); 8.55 (1H, d); 8.5 (1H, br); 7.75 (2H, d); 7.3 (2H, t); 4.6 (1H, t); 3.4 (2H, m); 2.65 (2H, m); 2.2 (1H, m); 2.1 (1H, m); 1.8 (2H, m); 1.6 (4H, m); 1.3 (14H, m); 0.9-0.80 (12H, m).

D.24.18

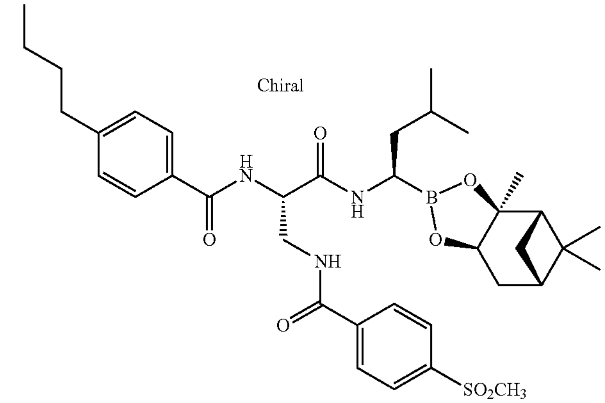 [SMILES: CCCCc1ccc(C(=O)N[C@@H](CNC(=O)c2ccc(S(C)(=O)=O)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(4-methylsulfonylphenyl)carbonylamino]ethyl]-

D.24.19

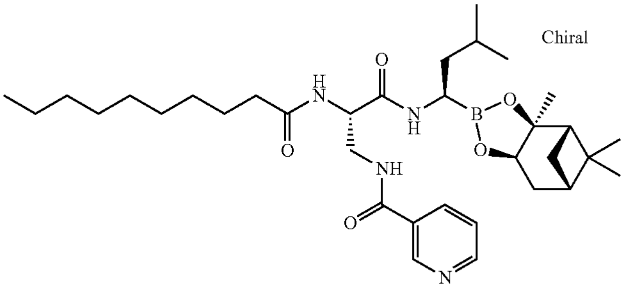 [SMILES: CCCCCCCCCC(=O)N[C@@H](CNC(=O)c1cccnc1)C(=O)N[C@@H](CC(C)C)B1O[C@@H]2C[C@@H]3C[C@@H](C3(C)C)[C@]2(C)O1]

Chemical Name:
Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(nicotinonylaminoamino)ethyl]-
Analtyical Data:
$^1$H NMR (DMSO-d6): 8.95 (1H, s); 8.75 (1H, m); 8.7 (1H, d); 8.55 (1H, t), 8.15 (1H, d); 8.0 (1H, d); 7.50 (1H, m); 4.6 (1H, q); 4.1 (1H, d); 3.5 (2H, t); 2.62 (1H, m); 2.2 (1H, m); 2.10 (2H, m); 2.08 (1H, m); 1.80 (2H, m); 1.60 (2H, m); 1.45 (2H, m); 1.48 (3H, m); 1.04 (22H, m); 0.8 (12H, m).

D.24.20

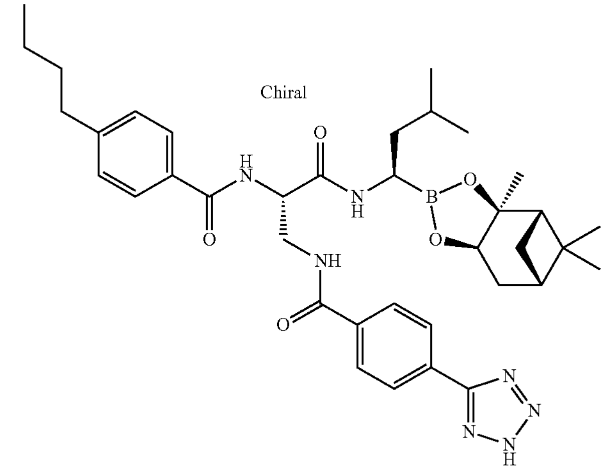 [SMILES: CCCCc1ccc(C(=O)N[C@@H](CNC(=O)c2ccc(-c3nn[nH]n3)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[[4-(2H-tetrazol-5-yl)phenyl)carbonylamino]ethyl]-

TABLE D-24-continued

D.24.21

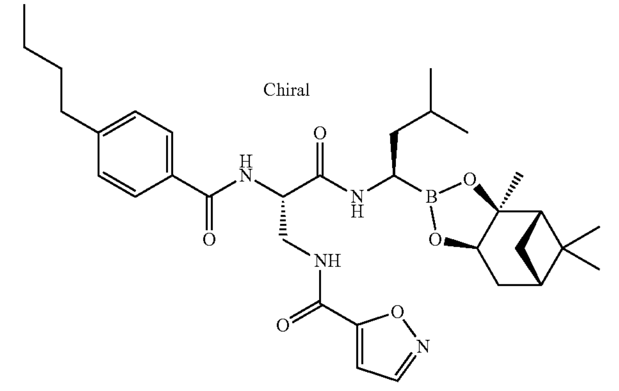 [SMILES: CCCCc1ccc(C(=O)N[C@@H](CNC(=O)c2ccno2)C(=O)N[C@@H](CC(C)C)B2O[C@@H]3C[C@@H]4C[C@@H](C4(C)C)[C@]3(C)O2)cc1]

Chemical Name:
4-butylbenzamide, N-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(1-isoxazol-5-yl)-carbonylamino]ethyl]-
Analytical Data:
$^1$H NMR (DMSO-d6): 8.95 (1H, t); 8.75 (1H, m); 8.65 (2H, m); 8.5 (2H, d), 7.65 (2H, d); 7.3 (2H, d); 7.05 (1H, s); 4.7 (1H, q); 4.1 (1H, d); 3.65 (2H, m); 2.82 (1H, s); 2.65 (3H, m); 2.2 (1H, m); 2.10 (2H, m); 2.08 (1H, m); 1.80 (2H, m); 1.60 (4H, m); 1.25 (12H, m); 0.85 (12H, m). M.p. 128°-130°C.

D.24.22

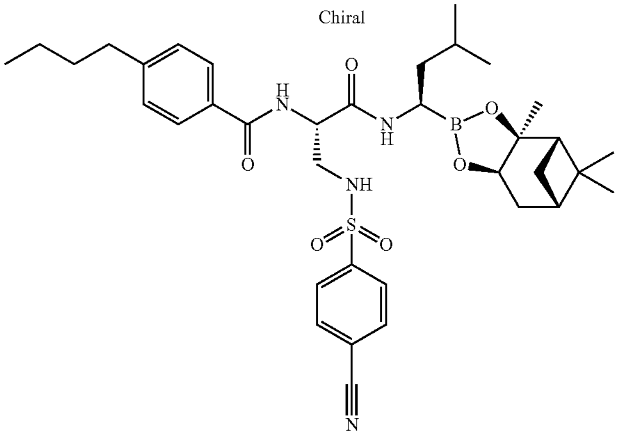 [SMILES: CCCCc1ccc(C(=O)N[C@@H](CNS(=O)(=O)c2ccc(C#N)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(4-cyanophenyl)sulfonylamino]ethyl]-
Analytical Data:
$^1$H NMR (DMSO-d6): 8.6 (1H, d); 8.3 (1H, d); 8.1 (1H, t); 8.02 (2H, d); 7.98 (2H, d); 7.8 (2H, d); 7.25 (2H, d); 4.6 (1H, t); 4.15 (1H, d); 3.2 (2H, m); 2.2 (1H, m); 2.1 (1H, m); 1.8 (2H, m); 1.6 (4H, m); 1.3 (12H, m); 0.9-0.80 (12H, m).

D.24.23

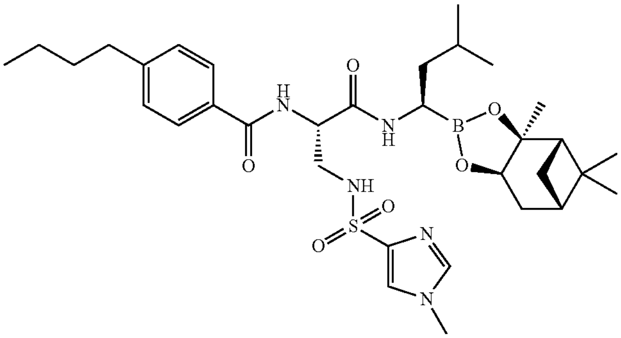 [SMILES: CCCCc1ccc(C(=O)N[C@@H](CNS(=O)(=O)c2cn(C)cn2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(1-methyl-1H-imidazole-4-)sulfonylamino]ethyl]-
Analytical Data:
$^1$H NMR (DMSO-d6): 8.61 (1H, d); 8.25 (1H, d); 8.1 (1H, t); 7.8 (2H, d); 7.74 (2H, d); 7.55 (1H, br); 7.3 (2H, d); 4.6 (1H, t); 4.15 (1H, d); 3.25 (2H, m); 2.65 (3H, m); 2.2 (1H, m); 2.04 (1H, m); 1.8 (2H, m); 1.6 (4H, m); 1.3 (12H, m); 0.9-0.80 (12H, m). M.p. 69°-71°C.

D.24.24

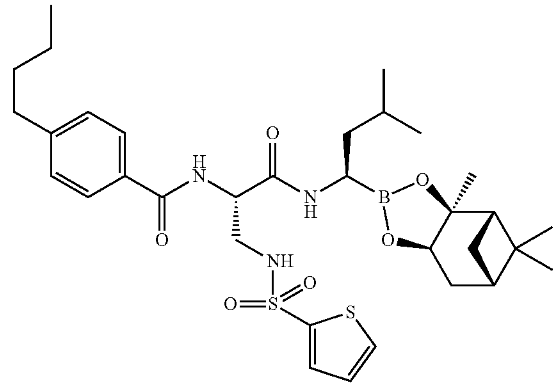 [SMILES: CCCCc1ccc(C(=O)N[C@@H](CNS(=O)(=O)c2cccs2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(2-thiophene)sulfonylamino)ethyl]-

TABLE D-24-continued

D.24.25

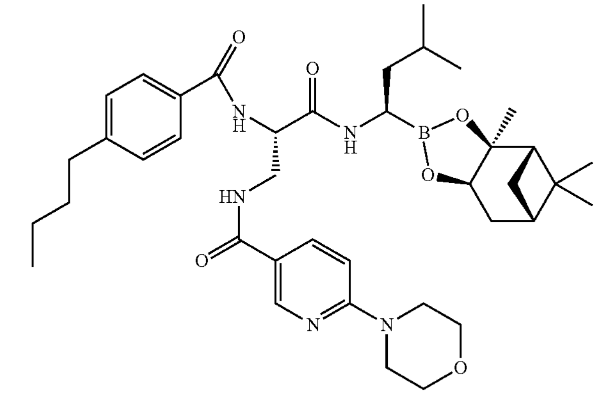 [SMILES: CCCCc1ccc(C(=O)N[C@@H](CNC(=O)c2ccc(N3CCOCC3)nc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(6-morpholin-4-nicotinoylamino)ethyl]-

D.24.26

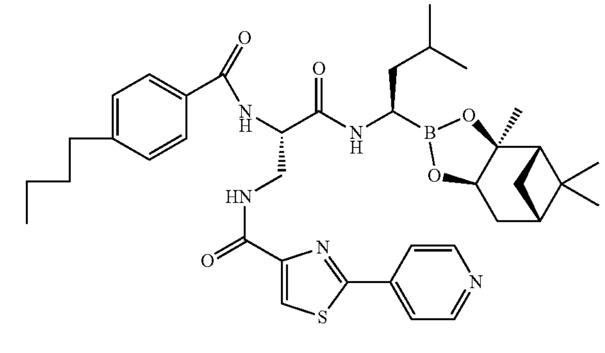 [SMILES: CCCCc1ccc(C(=O)N[C@@H](CNC(=O)c2csc(-c3ccncc3)n2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(2-pyridin-4-thiazolecarbonylamino)ethyl]-

D.24.27

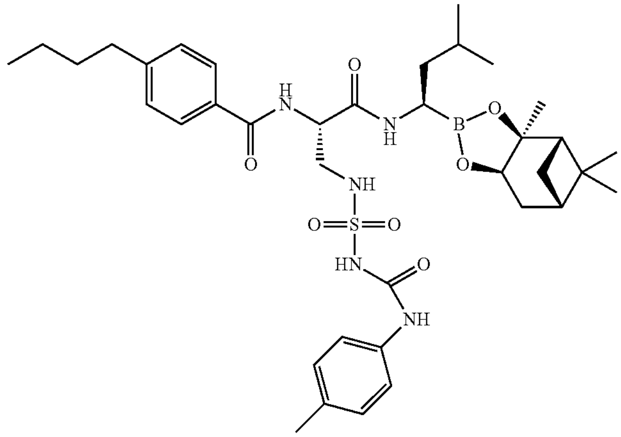 [SMILES: CCCCc1ccc(C(=O)N[C@@H](CNS(=O)(=O)NC(=O)Nc2ccc(C)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(4-methylphenylureidosulfonylamino)ethyl]-
Analytical Data:
$^{1}$H NMR (DMSO-d6): 10 (1H, br); 8.8 (1H, s); 8.4 (2H, d); 7.8 (2H, d); 7.3 (2H, d); 7.25 (2H, d); 4.6 (1H, t); 4.2 (1H, d); 2.65 (3H, m); 2.2 (4H, m); 2.0 (1H, m); 1.8 (2H, m); 1.6 (4H, m); 1.3 (12H, m); 0.9-0.80 (12H, m).

D.24.28

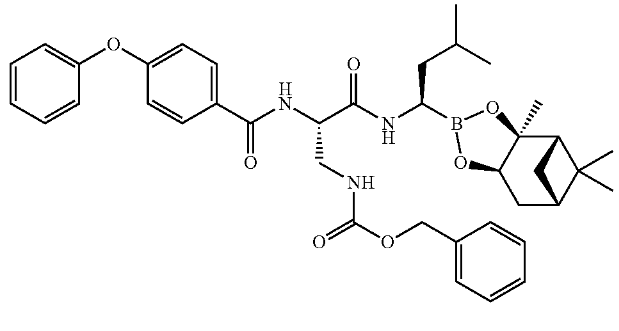 [SMILES: CC(C)C[C@H](NC(=O)[C@H](CNC(=O)OCc1ccccc1)NC(=O)c1ccc(Oc2ccccc2)cc1)B1O[C@@H]2C[C@@H]3C[C@@H](C3(C)C)[C@]2(C)O1]

Chemical Name:
4-phenoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(benzyloxycarbonylamide)ethyl]-
Analytical Data:
1H NMR (DMSO-d6): 8.78 (1H, br); 8.4 (1H, d); 7.9 (2H, d); 7.45 (2H, t); 7.3 (6H, m); 7.21 (2H, m); 7.05 (4H, m); 5.0 (2H, q); 4.7 (1H, t); 4.1 (1H, d); 3.4 (2H, m); 2.6 (1H, m); 2.2 (4H, m); 2.0 (1H, m); 1.8 (2H, m); 1.65 (2H, m); 1.3 (9H, m); 0.9-0.80 (9H, m). M.p. 100°-103° C.

TABLE D-24-continued

D.24.29

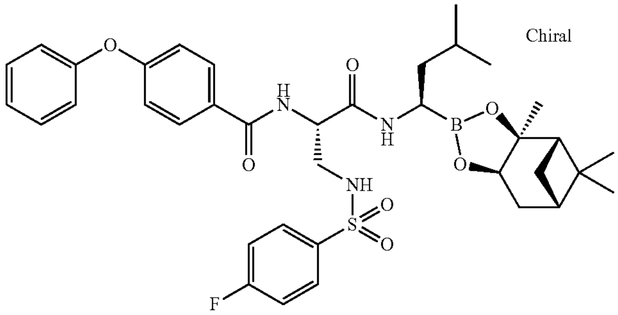 [SMILES: CC(C)C[C@H](NC(=O)[C@H](CNS(=O)(=O)c1ccc(F)cc1)NC(=O)c1ccc(Oc2ccccc2)cc1)B1O[C@@H]2C[C@@H]3C[C@@H](C3(C)C)[C@]2(C)O1]

Chiral

Chemical Name:
4-phenoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[4-fluoro-benzenesulfonamide]ethyl]-
Analytical Data:
1H NMR (DMSO-d6): 8.6 (1H, br); 8.35 (1H, d); 7.9 (5H, m); 7.45 (4H, m); 7.2 (1H, m); 7.05 (4H, m); 4.6 (1H, q); 4.1 (1H, d); 3.1 (2H, m); 2.6 (1H, m); 2.2 (4H, m); 2.0 (1H, m); 1.8 (2H, m); 1.65 (2H, m); 1.3 (9H, m); 0.9-0.80 (9H, m). M.p. 90°-93° C.

D.24.30

Chiral

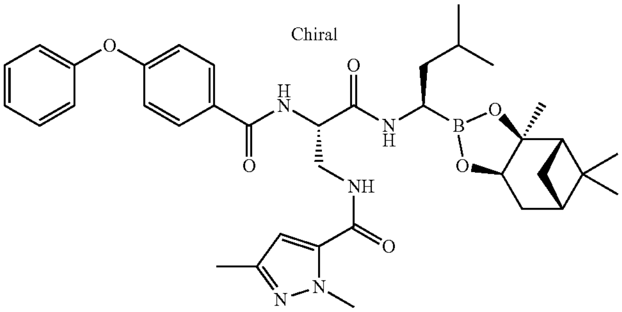 [SMILES: Cc1cc(C(=O)NC[C@H](NC(=O)c2ccc(Oc3ccccc3)cc2)C(=O)N[C@@H](CC(C)C)B2O[C@@H]3C[C@@H]4C[C@@H](C4(C)C)[C@]3(C)O2)n(C)n1]

Chemical Name:
4-phenoxybenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-[(2,5-dimethyl-2H-pyrazole)carbonylamino]ethyl]-
Analytical Data:
1H NMR (DMSO-d6): 8.9 (1H, br); 8.55 (1H, d); 8.48 (1H, m); 7.9 (2H, m); 7.48 (2H, m); 7.2 (1H, m); 7.05 (4H, m); 6.55 (1H, s); 4.75 (1H, q); 4.1 (1H, d); 3.6 (2H, m); 2.2 (4H, m); 2.1 (3H, s); 2.0 (1H, m); 1.8 (2H, m); 1.65 (2H, m); 1.25 (9H, m); 0.8 (9H, m). M.p. 100°-103° C.

D.24.31

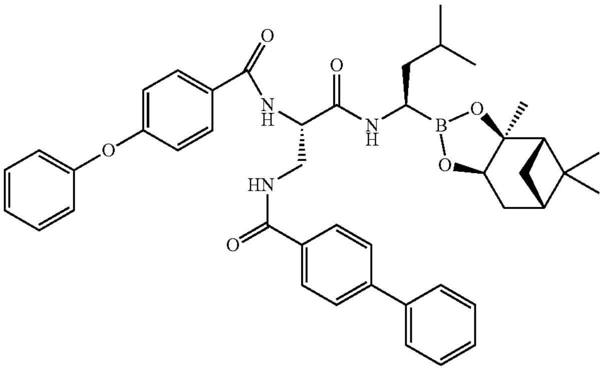 [SMILES: CC(C)C[C@H](NC(=O)[C@H](CNC(=O)c1ccc(-c2ccccc2)cc1)NC(=O)c1ccc(Oc2ccccc2)cc1)B1O[C@@H]2C[C@@H]3C[C@@H](C3(C)C)[C@]2(C)O1]

Chemical Name:
4-phenoxybenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(4-phenylbenzoylamino)ethyl]-
Analytical Data:
1H NMR (DMSO-d6): 8.85 (1H, br); 8.55 (2H, m); 7.9 (4H, d); 7.75 (4H, m); 7.48 (5H, m); 7.2 (1H, t); 7.05 (4H, m); 4.8 (1H, q); 4.1 (1H, d); 3.7 (2H, m); 2.65 (1H, m); 2.2 (1H, m); 2.0 (1H, m); 1.8 (2H, m); 1.6 (2H, m); 1.25 (9H, m); 0.8 (9H, m). M.p. 150°-152° C.

D.24.32

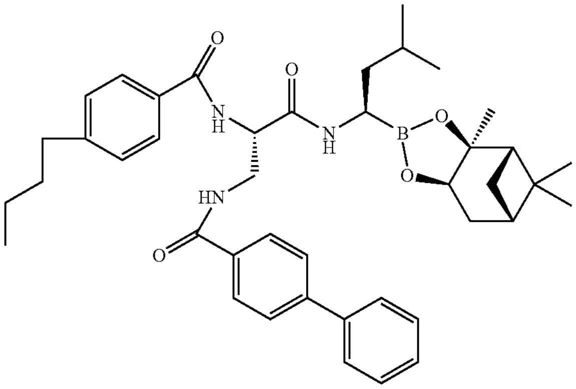 [SMILES: CCCCc1ccc(C(=O)N[C@@H](CNC(=O)c2ccc(-c3ccccc3)cc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(4-phenylbenzoylamino)ethyl]-
Analytical Data:
1H NMR (DMSO-d6): 8.85 (1H, br); 8.6 (1H, m); 8.5 (1H, d); 7.9 (2H, m); 7.75 (5H, m); 7.5 (2H, t); 7.4 (1H, m); 7.3 (2H, m); 4.8 (1H, q); 4.1 (1H, d); 3.7 (2H, m); 2.6 (3H, m); 2.2 (1H, m); 2.0 (1H, m); 1.8 (2H, m); 1.6 (4H, m); 1.25 (9H, m); 0.8 (12H, m). M.p. 195°-198° C.

TABLE D-24-continued

D.24.33

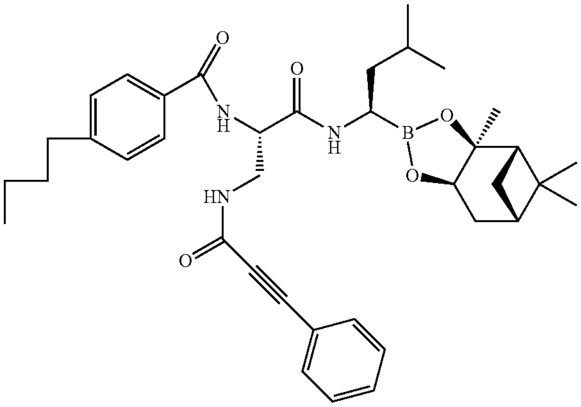 [SMILES: CCCCc1ccc(C(=O)N[C@@H](CNC(=O)C#Cc2ccccc2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(3-phenylpropynoylamino)ethyl]-
Analytical Data:
1H NMR (DMSO-d6): 8.85 (1H, m); 8.7 (1H, m); 8.42 (1H, d); 7.8 (2H, m); 7.5 (5H, m); 7.3 (3H, m); 4.7 (1H, q); 4.1 (1H, d); 3.55 (2H, m); 2.85 (2H, m); 2.65 (4H, m); 2.2 (1H, m); 2.0 (1H, m); 1.8 (2H, m); 1.6 (6H, m); 1.25 (12H, m); 0.8 (12H, m). M.p. 118°-120° C.

D.24.34

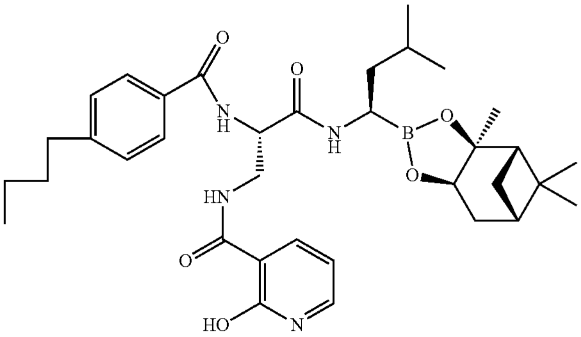 [SMILES: CCCCc1ccc(C(=O)N[C@@H](CNC(=O)c2cccnc2O)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(2-hydroxy-3-nicotinoylamino)ethyl]-

D.24.35

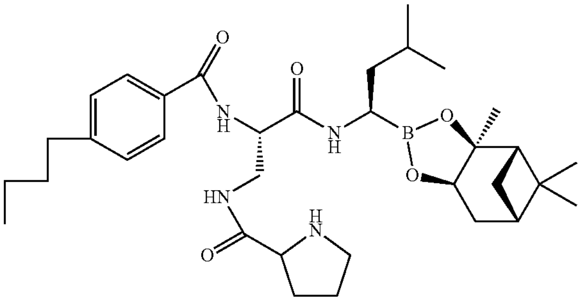 [SMILES: CCCCc1ccc(C(=O)N[C@@H](CNC(=O)C2CCCN2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(D-piroglutamoylamino)ethyl]-
Analytical Data:
$^1$H NMR (DMSO-d6): 9.85 (1H, d); 8.3 (1H, d); 8.1 (1H, t); 7.8 (3H, m); 7.3 (2H, d); 4.7 (1H, t); 4.15 (1H, d); 3.9 (1H, m); 3.5 (2H, m); 2.65 (3H, m); 2.2 (2H, m); 2.0 (3H, m); 1.8 (3H, m); 1.6 (4H, m); 1.3 (11H, m); 0.9-0.80 (12H, m).

D.24.36

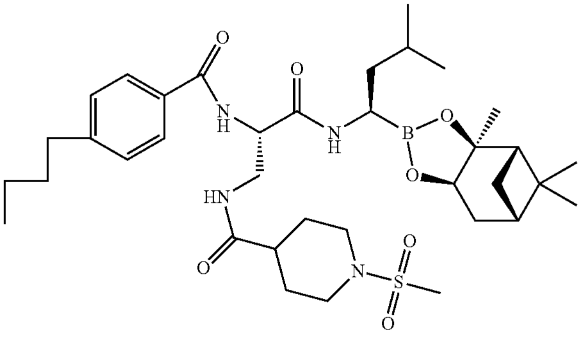 [SMILES: CCCCc1ccc(C(=O)N[C@@H](CNC(=O)C2CCN(S(C)(=O)=O)CC2)C(=O)N[C@@H](CC(C)C)B2O[C@@H]3C[C@@H]4C[C@@H](C4(C)C)[C@]3(C)O2)cc1]

Chemical Name:
4-butylbenzamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(1-methanesulfonyl-piperidine-4-carbonylamino)ethyl]-
Analytical Data:
1H NMR (DMSO-d6): 9.9 (1H, d); 8.4 (1H, d); 8.0 (1H, t); 7.75 (2H, d); 7.3 (2H, d); 4.68 (1H, q); 4.15 (1H, d); 3.5 (4H, m); 2.8 (3H, s); 2.65 (3H, m); 2.2 (2H, m); 2.0 (1H, m); 1.9-1.5 (10H, m); 1.3 (12H, m); 0.9-0.80 (12H, m). M.p. 170°-172° C.

TABLE D-24-continued

| | | |
|---|---|---|
| D.24.37 | Chiral 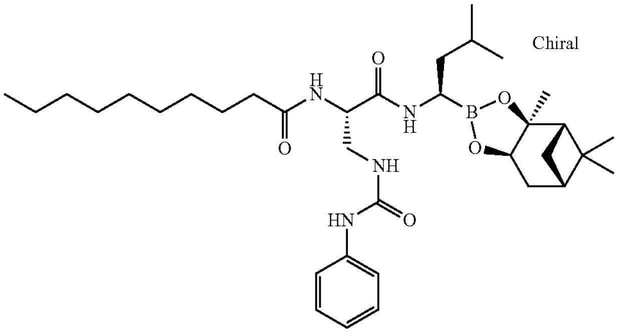 [SMILES: CCCCCCCCCC(=O)N[C@@H](CNC(=O)Nc1ccccc1)C(=O)N[C@@H](CC(C)C)B1O[C@@H]2C[C@@H]3C[C@@H](C3(C)C)[C@]2(C)O1] | Chemical Name: Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(3-phenyl-ureido)ethyl]- |
| D.24.38 | 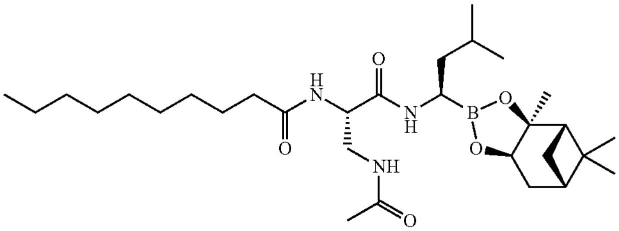 [SMILES: CCCCCCCCCC(=O)N[C@@H](CNC(C)=O)C(=O)N[C@@H](CC(C)C)B1O[C@@H]2C[C@@H]3C[C@@H](C3(C)C)[C@]2(C)O1] | Chemical Name: Decanamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-(acetamido)ethyl]- |

Example D.25

Synthesis of Further Compounds

Following the procedures of Example D17, the following compounds can be prepared starting from the compounds of Example D.16.8 and D.16.9.

TABLE D-25

| Ex # | Structure | Chemical Name and Analytical Data |
|---|---|---|
| D.25.1 | Chiral 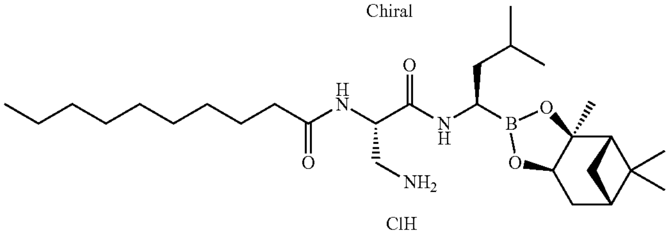 [SMILES: CCCCCCCCCC(=O)N[C@@H](CN)C(=O)N[C@@H](CC(C)C)B1O[C@@H]2C[C@@H]3C[C@@H](C3(C)C)[C@]2(C)O1 ; Cl] | Chemical Name: Decanamide, N-[(1S)-1-[[[(1R)-1-[(3aS,aS,6S,7aR)-hexahydro-3a,5,5-trimethyl-4,6-methano-1,3,2-benzodioxaborol-2-yl-]-3-methylbutyl]amino]carbonyl]-2-amino]ethyl]-hydrochloride salt<br>Analytical Data:<br>$^1$H NMR (DMSO-d6): 8.4 (1H, d); 8.25 (1H, d); 8.15 (3H, br s); 4.58 (1H, m); 4.2 (1H, m); 3.1 (1H, m); 2.9 (1H, m); 2.8 (1H, m); 2.4 (4H, m); 1.9 (1H, m); 1.85 (1H, m); 1.65 (2H, m); 1.50 (2H, m); 1.35 (1H, m); 0.85 (12H, m). |

TABLE D-25-continued

| Ex # | Structure | Chemical Name and Analytical Data |
|---|---|---|
| D.25.2 | 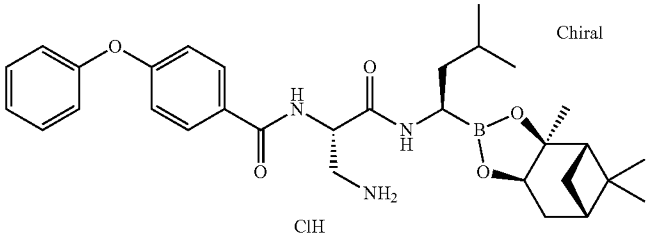 [SMILES: CC(C)C[C@H](NC(=O)[C@H](CN)NC(=O)c1ccc(Oc2ccccc2)cc1)B1O[C@@H]2C[C@@H]3C[C@@H](C3(C)C)[C@]2(C)O1 ; Cl] | Chemical Name: 4-phenoxybenzamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(amino)ethyl]-hydrochloride salt<br>Analytical Data:<br>$^1$H NMR (DMSO-d6): 8.72 (1H, d); 8.54 (1H, d); 7.45 (2H, t); 7.22 (1H, t); 7.05 (4H, m); 4.8 (1H, m); 4.21 (1H, d); 3.25 (1H, m); 3.15 (1H, m); 2.8 (1H, m); 2.25 (1H, m); 2.05 (1H, m); 1.9 (1H, t); 1.82 (1H, m); 1.65 (2H, m); 1.28 (3H, s); 1.22 (3H, s); 0.85 (9H, m). |

Example D.26

4-Butylbenzamide, N-[(1R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-[(4-methylbenzoyl)amino]ethyl]-

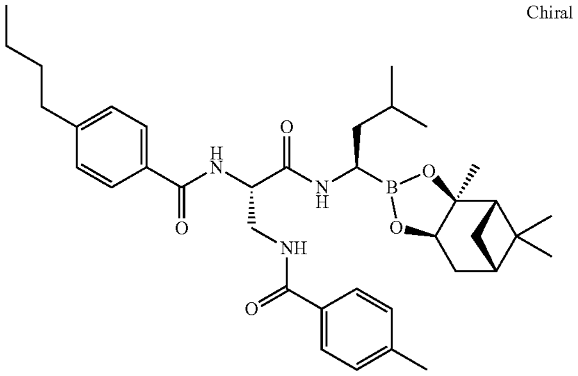 [SMILES: CCCCc1ccc(C(=O)N[C@@H](CNC(=O)c2ccc(C)cc2)C(=O)N[C@@H](CC(C)C)B2O[C@@H]3C[C@@H]4C[C@@H](C4(C)C)[C@]3(C)O2)cc1]

Following the same procedures used for the preparation of the compound of Example D.17, the intermediate 4-butylbenzamide, N-[(1R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-(aminoethyl)-hydrochloride salt is prepared using D-asparagine as starting material. This latter intermediate is then reacted with 4-methylbenzoic acid following the procedure described in Example D.18 to give the title compound.

$^1$H NMR (MeOD-d4): 8.88 (2H, d); 8.45 (2H, m); 7.8 (2H, d); 7.7 (2H, d); 7.35 (2H, m); 7.25 (2H, d); 4.75 (1H, m); 4.1 (1H, d); 3.8 (1H, m); 3.65 (2H, m); 2.65 (3H, m); 2.2 (1H, m); 2.1 (1H, m); 1.8 (2H, m); 1.6 (4H, m); 1.3-1.1 (2H, m); 0.9-0.80 (14H, m).

Example E.1

Boronic acid, [(1R)-1-[[(2S)-5-[[imino(nitroamino)methyl]amino]-2-[(2-naphthoyl)amino]-1-oxopentyl]amino]-3-methylbutyl]-

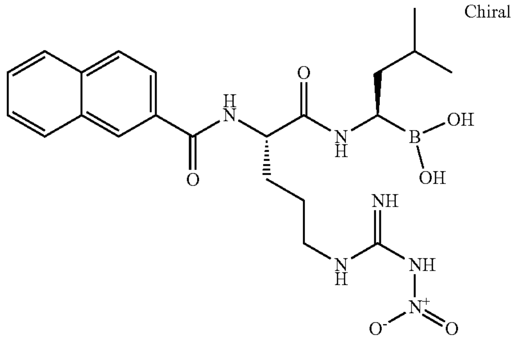 [SMILES: CC(C)C[C@H](NC(=O)[C@H](CCCNC(=N)N[N+](=O)[O-])NC(=O)c1ccc2ccccc2c1)B(O)O]

A mixture of naphthalene-2-carboxamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]-amino]carbonyl]-4-[[imino(nitroamino)methyl]amino]butyl]- of Example D.1.1 (564 mg, 0.90 mmol), 2-methylpropylboronic acid (222 mg, 2.19 mmol) and 4N hydrogen chloride dioxane solution (225 μl) in a 40:60 heterogeneous mixture of methanol:hexane (10 ml) was stirred at room temperature for 4 hours. Hexane (4 ml) was added, the mixture was stirred for a while, then the hexane layer was removed. Fresh hexane (5 ml) and 2-methylpropylboronic acid (100 mg, 0.99 mmol) were added and the mixture was stirred at room temperature for 3 hours. The hexane layer was removed and the methanol phase was washed with hexane (2×5 ml). The residue obtained upon concentration of the methanol phase was purified by silica gel column chromatography eluting with ethyl acetate first, then with 40:40:20 acetone:methanol:hexane mixture. The product was redissolved in a mixture of ethyl acetate (250 ml) and methanol (6 ml) and the organic phase was washed with water (2×25 ml), dried over sodium sulfate and concentrated. The residue was dried under vacuum at 80° C. for 3 hours affording the product as a white solid (280 mg, 64% yield). M.p. 170-190° C.

$^1$H NMR (DMSO-$d_6$): 8.76 (1H, m); 8.51 (2H, br); 8.09-7.09 (5H, m); 7.88 (2H, br); 7.60 (2H, br); 4.67 (1H, m); 3.17 (2H, m); 2.58 (1H, m); 1.81 (2H, m); 1.56 (3H, m); 1.38-1.11 (4H, m); 0.83 (1H, m); 0.81 (1H, m); 0.74 (3H, d, J=6.4); 0.74 (3H, d, J=6.4).

| | | | | | |
|---|---|---|---|---|---|
| El. Anal. | Calculated: | C 54.33% | H 6.43% | N 17.28% | B 2.22% |
| | Found | C 54.87% | H 6.64% | N 17.00% | B 2.12% |

Further compounds prepared fundamentally in accordance with the above experimental procedures are reported in Table E-1.

TABLE E-1

| Ex # | Structure | Chemical Name and Analytical Data |
|---|---|---|
| E.1.1 | 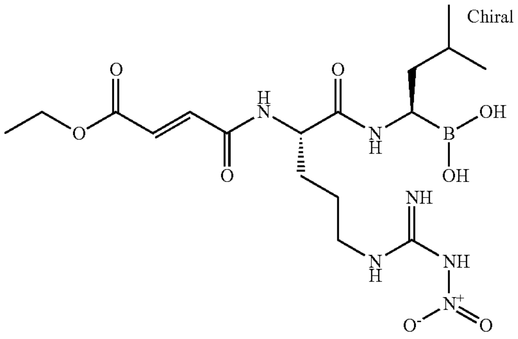 [SMILES: CCOC(=O)/C=C/C(=O)N[C@@H](CCCNC(=N)N[N+](=O)[O-])C(=O)N[C@@H](CC(C)C)B(O)O] | Chemical Name: Boronic acid, N-[(1R)-1-[[(2S)-5-[[imino(nitroamino)methyl]amino]-2-[((2E)-3-ethoxycarbonyl-1-oxoprop-2-enyl)amino]-1-oxopentyl]amino]-3-methylbutyl] Analytical Data: 1H-NMR (MeOH-d4): 7.07 (1H, d, J = 15.6 Hz); 6.74 (1H, d, J = 15.6 Hz); 4.64 (1H, dd, J = 6.3, 8.1); 4.25 (2H, q, J = 7.1); 2.75 (1H, t, J = 7.4); 2.0-1.6 (5H, m); 1.34 (2H, m); 1.31 (3H, t, J = 7.1); 0.92 (6H, d, J = 6.6). |
| E.1.2 | 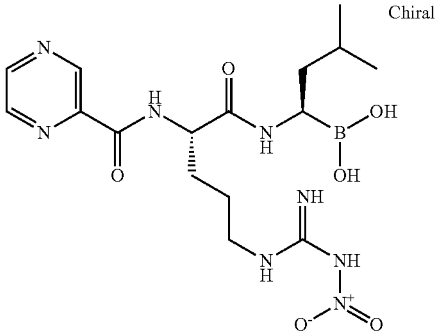 [SMILES: CC(C)C[C@H](NC(=O)[C@H](CCCNC(=N)N[N+](=O)[O-])NC(=O)c1cnccn1)B(O)O] | Chemical Name: Boronic acid, [(1R)-1-[[(2S)-5-[[imino(nitroamino)methyl]amino]-2-[(2-pyrazinecarbonyl)amino]-1-oxopentyl]amino]-3-methylbutyl] Analytical Data: 1H-NMR (DMSO-d6): 9.18 (1H, br); 8.96 (1H, d, J = 8.2); 8.87 (1H, d, J = 2.4 Hz); 8.76 (2H, m); 8.51 (1H, br); 8.3-7.5 (2H, br); 4.63 (1H, m); 3.13 (2H, m); 2.53 (1H, m); 1.9-1.1 (7H, m); 0.73 (6H, d, J = 6.6). |
| E.1.3 | 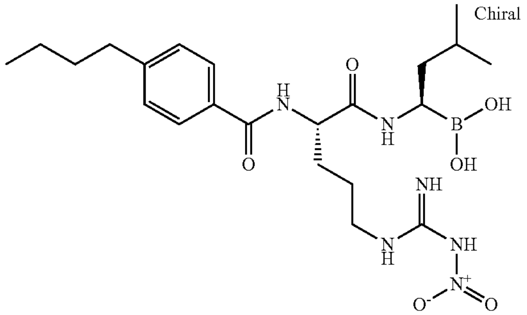 [SMILES: CCCCc1ccc(C(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[(4-butylbenzoyl)amino]-1-oxopentyl]amino]-3-methylbutyl] Analytical Data: 1H-NMR (DMSO-d6): 8.68 (1H, d, J = 2.5 Hz); 8.51 (1H, br); 8.48 (1H, d, J = 7.8 Hz); 8.3-7.5 (2H, br); 7.80 (2H, d, J = 8.1); 7.27 (2H, d, J = 8.1 Hz); 4.59 (1H, m); 3.15 (2H, m); 2.61 (2H, t, J = 7.7); 2.54 (1H, m); 1.9-1.1 (11H, m); 0.89 (3H, t, J = 7.3); 0.77 (3H, t, J = 6.8);. 0.74 (6H, d, J = 6.6). |
| E.1.4 | 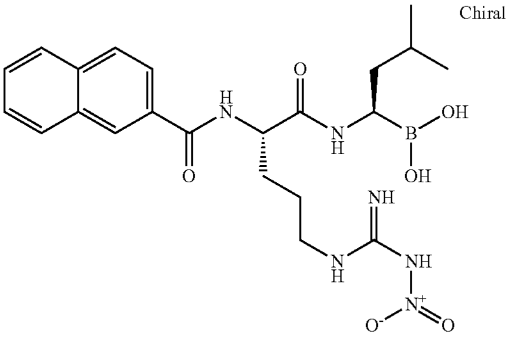 [SMILES: CC(C)C[C@H](NC(=O)[C@H](CCCNC(=N)N[N+](=O)[O-])NC(=O)c1ccc2ccccc2c1)B(O)O] | Chemical Name: Boronic acid, [(1R)-1-[[(2S)-5-[[imino(nitroamino)methyl]amino]-2-[(2-naphthoyl)amino]-1-oxopentyl]amino]-3-methylbutyl] Analytical Data: 1H-NMR (DMSO-d6): 8.77 (1H, br); 8.76 (1H, d, J = 8.0); 8.51 (1H, br); 8.50 (1H, s); 8.0 (4H, m); 8.3-7.5 (2H, br); 7.6 (2H, m); 4.67 (1H, m); 3.17 (2H, m); 2.57 (1H, m); 1.9-1.1 (7H, m); 0.73 (6H, d, J = 6.6). |

TABLE E-1-continued

| Ex # | Structure | Chemical Name and Analytical Data |
|---|---|---|
| E.1.5 | 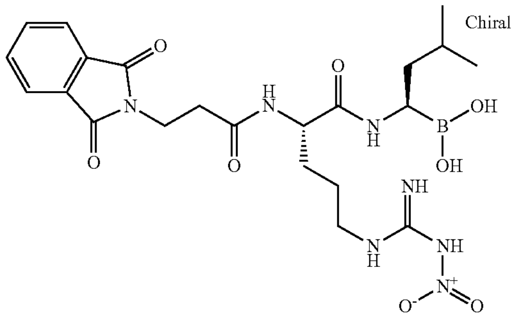 [SMILES: CC(C)C[C@H](NC(=O)[C@H](CCCNC(=N)N[N+](=O)[O-])NC(=O)CCN1C(=O)c2ccccc2C1=O)B(O)O] | Chemical Name: Boronic acid, [(1R)-1-[[(2S)-5-[[imino(nitroamino)methyl]amino]-2-[(3-(1,3-dihydro-1,3-dioxo-2H-isoindol-2-yl)-1-oxopropylamino]-1-oxopentyl]amino]-3-methylbutyl] Analytical Data: 1H-NMR (DMSO-d6): 8.59 (1H, br); 8.43 (1H, br); 8.27 (1H, d, J = 7.9 Hz); 7.82 (4H, m); 8.2-7.5 (2H, br); 4.31 (1H, m); 3.77 (2H, m); 3.08 (2H, m); 2.51 (3H, m); 1.7-1.1 (7H, m); 0.78 (6H, m). |
| E.1.6 | 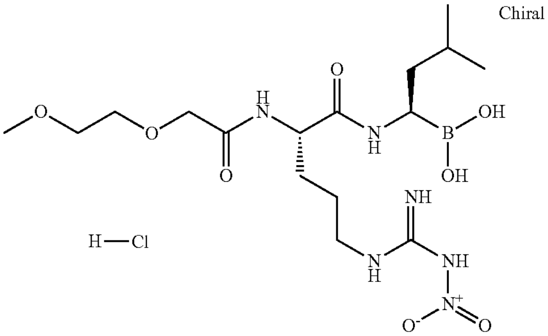 [SMILES: COCCOCC(=O)N[C@@H](CCCNC(=N)N[N+](=O)[O-])C(=O)N[C@@H](CC(C)C)B(O)O ; Cl] | Chemical Name: Boronic acid, [(1R)-1-[[(2S)-5-[[imino(nitroamino)methyl]amino]-2-[[2-(2-methoxyethoxy)acetyl]amino]-1-oxopentyl]amino]-3-methylbutyl], HCl salt Analytical Data: 1H-NMR (DMSO-d4): 4.65 (1H, dd, J = 6.1, 8.6 Hz); 4.04 (2H, s); 3.70 (2H, m); 3.60 (2H, t, J = 4.04) 3.42 (3H, s); 3.30 (2H, t, J = 6.9); 2.75 (1H, t, J = 7.5); 2.0-1.6 (5H, m); 1.34 (2H, m); 0.92 (6H, d, J = 6.6). |
| E.1.7 | 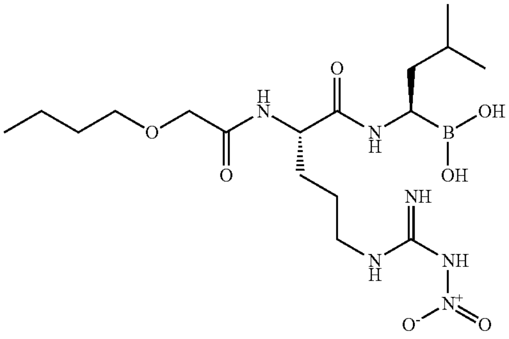 [SMILES: CCCCOCC(=O)N[C@@H](CCCNC(=N)N[N+](=O)[O-])C(=O)N[C@@H](CC(C)C)B(O)O] | Chemical Name: Boronic acid, [(1)-1-[[(2S)-5-[[imino(nitroamino)methyl]amino]-2-[(2-butoxyacetyl]amino]-1-oxopentyl]amino]-3-methylbutyl] Analytical Data: 1H-NMR (MeOH-d4): 4.65 (1H, dd, J = 6.1, 8.6 Hz); 3.98 (2H, s); 3.54 (2H, t, J = 6.6); 3.28 (2H, t, J = 6.9); 2.77 (1H, t, J = 7.6); 2.0-1.3 (11H, m); 0.95 (3H, t, J = 7.58); 0.92 (6H, d, J = 6.6). |
| E.1.8 | 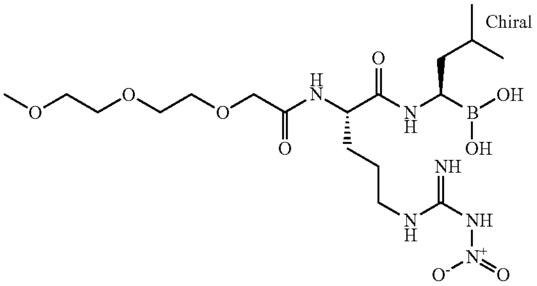 [SMILES: COCCOCCOCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[[2-[2-(2-methoxyethoxy)ethoxy]acetyl]amino]-1-oxopentyl]amino]-3-methylbutyl] Analytical Data: 1H-NMR (MeOH-d4): 4.66 (1H, dd, J = 6.0, 8.8 Hz); 4.06 (2H, AB q, J = 15.7); 3.7 (6H, m); 3.58 (2H, m); 3.37 (3H, s); 3.29 (2H, t, J = 6.9); 2.75 (1H, t, J = 7.7); 2.0-1.6 (5H, m); 1.34 (2H, m); 0.92 (6H, d, J = 6.6). |

TABLE E-1-continued

| Ex # | Structure | Chemical Name and Analytical Data |
|---|---|---|
| E.1.9 | 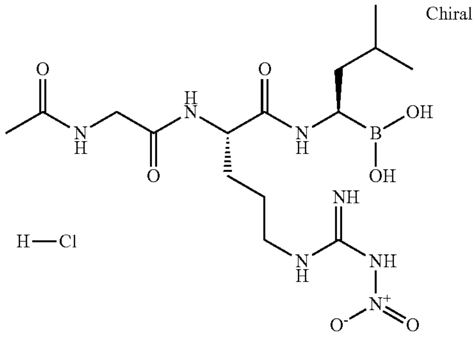 [SMILES: CC(=O)NCC(=O)N[C@@H](CCCNC(=N)N[N+](=O)[O-])C(=O)N[C@@H](CC(C)C)B(O)O ; Cl] | Chemical Name:<br>Boronic acid, [(1R)-1-[[(2S)-5-[[imino(nitroamino)methyl]amino]-2-[[2-(acetylamino)acetyl]amino]-1-oxopentyl]amino]-3-methylbutyl], HCl salt<br>Analytical Data:<br>1H-NMR (MeOD-d4): 4.61 (1H, dd, J = 5.7, 8.9 Hz); 3.86 (2H, s); 3.37 (3H, s); 3.30 (2H, t, J = 7.0); 2.75 (1H, t, J = 7.7); 2.01 (3H, s); 2.0-1.6 (5H, m); 1.33 (2H, m); 0.92 (6H, d, J = 6.6). |
| E.1.10 | 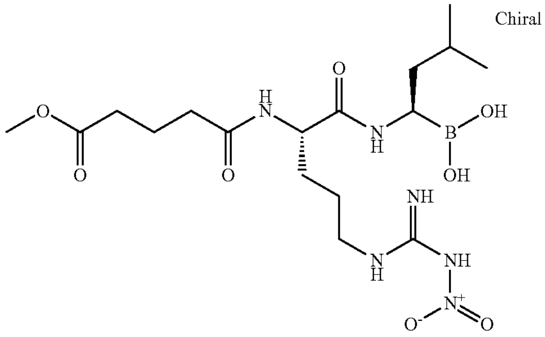 [SMILES: COC(=O)CCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[[4-(methoxycarbonyl)butanoyl]amino]-1-oxopentyl]amino]-3-methylbutyl]<br>Analytical Data:<br>$^1$H NMR (DMSO-d6): 8.50 (1H, br); 8.44 (1H, d, J = 5.6 Hz); 8.17 (1H, d, J = 7.5); 7.92 (2H, br); 4.37 (1H, m); 3.58 (3H, s); 3.14 (2H, m); 2.57 (1H, m); 2.30 (2H, t, J = 7.3); 2.19 (2H, t, J = 7.5); 1.75 (2H, quint, J = 7.3); 1.71 (1H, br); 1.64-1.39 (4H, br); 1.23 (2H, m); 0.86 (2H, m); 0.82 (3H, d, J = 6.4); 0.81 (3H, d, J = 6.4). |
| E.1.11 | 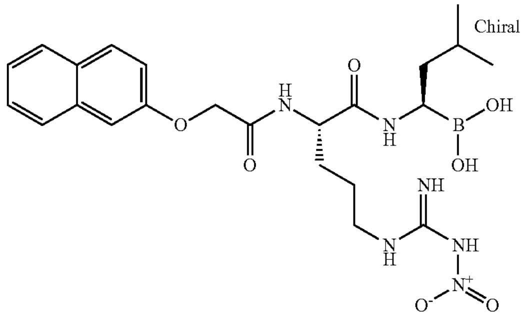 [SMILES: CC(C)C[C@H](NC(=O)[C@H](CCCNC(=N)N[N+](=O)[O-])NC(=O)COc1ccc2ccccc2c1)B(O)O] | Chemical Name:<br>Boronic acid, [(1R)-1-[[(2S)-5-[[imino(nitroamino)methyl]amino]-2-[(2-(napthalen-2-yloxy)acetyl]amino]-1-oxopentyl]amino]-3-methylbutyl]<br>Analytical Data:<br>$^1$H NMR (DMSO-d6): 8.81 (1H, br); 8.51 (1H, br); 8.40 (1H, d, J = 7.5 Hz); 7.88 (2H, br); 7.83 (2H, m); 7.75 (1H, m); 7.44 (1H, m); 7.35 (1H, m); 7.26 (2H, m); 4.69 (2H, m); 4.51 (1H, m); 3.12 (2H, m); 2.60 (1H, m); 1.78 (1H, m); 1.73-1.39 (3H, m); 1.39-1.11 (3H, m); 0.80 (6H, m). |
| E.1.12 | 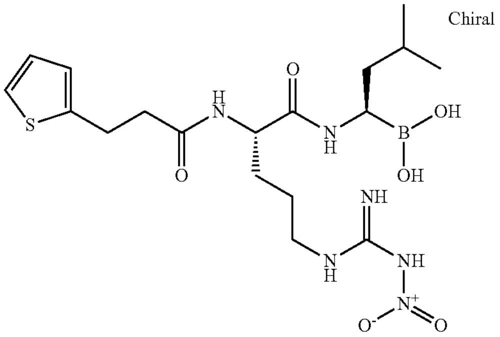 [SMILES: CC(C)C[C@H](NC(=O)[C@H](CCCNC(=N)N[N+](=O)[O-])NC(=O)CCc1cccs1)B(O)O] | Chemical Name:<br>Boronic acid, [(1R)-1-[[(2S)-5-[[imino(nitroamino)methyl]amino]-2-[(3-thiophen-2-yl-propanoyl)amino]-1-oxopentyl]amino]-3-methylbutyl]<br>Analytical Data:<br>$^1$H NMR (DMSO-d6): 8.65 (1H, br); 8.49 (1H, br); 8.20 (1H, d, J = 8.2 Hz); 7.86 (2H, br); 7.27 (1H, dd, J = 4.9, J = 0.9); 6.91 (1H, dd, J = 5.1, J = 3.4); 6.84 (1H, m); 4.38 (1H, m); 3.11 (2H, m); 3.02 (2H, m); 2.56 (1H, m); 2.50 (2H, m); 1.69 (1H, m); 1.64-1.35 (4H, m); 1.27 (1H, m); 1.20 (1H, m); 0.82 (3H, d, J = 6.4); 0.81 (3H, d, J = 6.4). |

TABLE E-1-continued

| Ex # | Structure | Chemical Name and Analytical Data |
|---|---|---|
| E.1.13 | 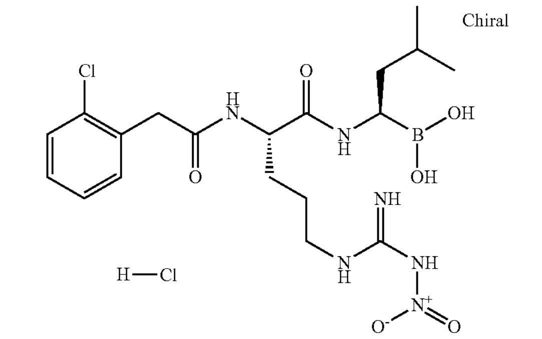 [SMILES: CC(C)C[C@H](NC(=O)[C@H](CCCNC(=N)N[N+](=O)[O-])NC(=O)Cc1ccccc1Cl)B(O)O ; Cl] | Chemical Name: Boronic acid, [(1R)-1-[[(2S)-5-[[imino(nitroamino)methyl]amino]-2-[2-(2-chlorophenyl)acetyl]amino]-3-methylbutyl] HCl salt Analytical Data: $^{1}$H NMR (DMSO-d6): 8.69 (1H, br); 8.51 (1H, br); 8.41 (1H, d, J = 7.9 Hz); 7.87 (2H, br); 7.40 (1H, m); 7.32 (1H, m); 7.26 (2H, m); 4.42 (1H, m); 3.66 (2H, m); 3.14 (2H, m); 2.60 (1H, m); 1.73 (1H, m); 1.68-1.40 (4H, m); 1.26 (2H, m); 0.83 (3H, d, J = 6.4); 0.82 (3H, d, J = 6.4). |
| E.1.14 | 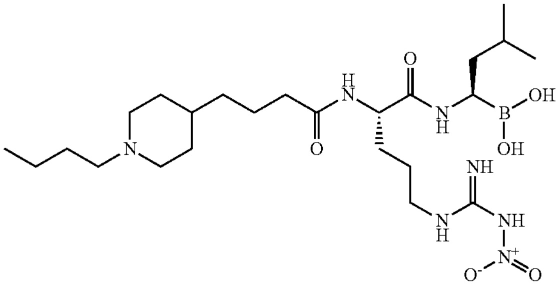 [SMILES: CCCCN1CCC(CCCC(=O)N[C@@H](CCCNC(=N)N[N+](=O)[O-])C(=O)N[C@@H](CC(C)C)B(O)O)CC1] | Chemical Name: Boronic acid, [(1R)-1-[[(2S)-5-[[imino(nitroamino)methyl]amino]-2-[(1-oxo-4-(1-butylpiperidin-4-yl)butyl)amino]-1-oxopentyl]amino]-3-methylbutyl] Analytical Data: $^{1}$H NMR (DMSO-d6): 8.60 (1H, br); 8.50 (1H, br); 8.10 (1H, br); 8.00 (2H, br); 4.36 (1H, m); 3.13 (2H, br); 2.86 (2H, br); 2.50 (1H, m); 2.27 (1H, br); 2.11 (2H, m); 1.76-1.34 (11H, m); 1.34-0.98 (11H, m); 0.87 (3H, t, J = 7.1 Hz), 0.82 (3H, d, J = 6.4); 0.81 (3H, d, J = 6.4). |
| E.1.15 | 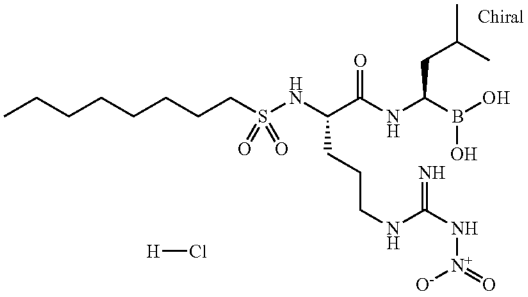 [SMILES: CCCCCCCCS(=O)(=O)N[C@@H](CCCNC(=N)N[N+](=O)[O-])C(=O)N[C@@H](CC(C)C)B(O)O ; Cl] | Chemical Name: Boronic acid, [(1R)-1-[[(2S)-5-[[imino(nitroamino)methyl]amino]-2-[(1-octanesulfonyl)amino]-1-oxopentyl]amino]-3-methylbutyl], HCl salt Analytical Data: $^{1}$H NMR (DMSO-d6): 8.80 (1H, br); 8.50 (1H, br); 7.87 (2H, br); 7.52 (1H, d, J = 8.6 Hz); 3.92 (1H, m); 3.15 (2H, m); 2.94 (2H, t, J = 7.7); 2.62 (1H, m); 1.75-1.43 (7H, m); 1.38-1.31 (4H, m); 1.24 (8H, s); 0.92-0.75 (9H, m). |
| E.1.16 | 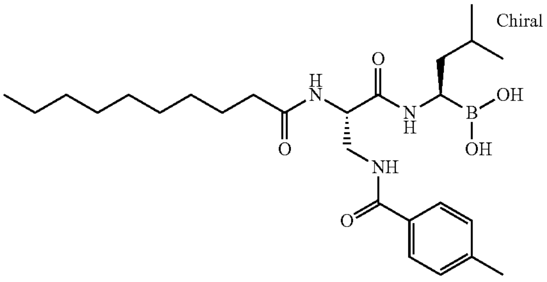 [SMILES: CCCCCCCCCC(=O)N[C@@H](CNC(=O)c1ccc(C)cc1)C(=O)N[C@@H](CC(C)C)B(O)O] | Chemical Name: Boronic acid, [(1R)-1-[[(2S)-3-[(4-methylbenzoyl)amino]-2-[(decanoylamino)]-1-oxopropyl]amino]-3-methylbutyl] Analytical Data: $^{1}$H NMR (CD3OD): 7.73 (2H, d, J = 8.0 Hz); 7.28 (2H, d, J = 8.0); 4.78 (1H, t, J = 6.5); 3.82 (1H, dd, J = 6.9, 13.5); 3.61 (1H, dd, J = 6.9, 13.5); 2.74 (1H, m); 2.39 (3H, s); 2.24 (2H, t, J = 7.4); 1.6-1.15 (17H, m); 0.89 (6H, m); 0.80 (3H, d, J = 6.5). |
| E.1.17 | 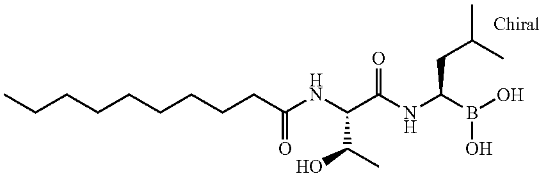 [SMILES: CCCCCCCCCC(=O)N[C@H](C(=O)N[C@@H](CC(C)C)B(O)O)[C@@H](C)O] | Chemical Name: Boronic acid, [(1R)-1-[[(2S,3R)-3-hydroxy-2-[(decanoyl)amino]-1-oxobutyl]amino]-3-methylbutyl] Analytical Data: $^{1}$H NMR (DMSO-d6): 8.58 (1H, br); 7.70 (1H, d, J = 8.6 Hz), 4.93 (1H, br); 4.31 (1H, dd, J = 4.0, 8.6); 3.96 (1H, m); 2.56 (1H, m); 2.18 (2H, m); 1.60 (1H, m); 1.49 (2H, m); 1.35-1.15 (14H, m); 1.03 (3H, d, J = 6.4); 0.83 (9H, m). |

TABLE E-1-continued

| Ex # | Structure | Chemical Name and Analytical Data |
|---|---|---|
| E.1.18 | 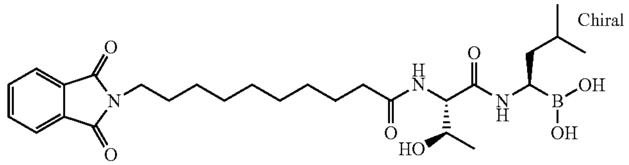 [SMILES: CC(C)C[C@H](NC(=O)[C@@H](NC(=O)CCCCCCCCCN1C(=O)c2ccccc2C1=O)[C@@H](C)O)B(O)O] | Chemical Name:<br>Boronic acid, [(1R)-1-[[(2S,3R)-3-hydroxy-2-[[10-(1,3-dioxo-1,3-dihydro-isoindol-2-yl)-decanoyl]amino]-1-oxobutyl]amino]-3-methylbutyl]<br>Analytical Data:<br>$^1$H NMR (DMSO-d6): 8.55 (1H, br); 7.84 (4H, m); 7.69 (1H, d, J = 8.4 Hz), 4.94 (1H, d, J = 5.4); 4.30 (1H, dd, J = 4.0, 8.6); 3.95 (1H, m); 3.55 (2H, m); 2.55 (1H, m); 2.17 (2H, m); 1.65-1.35 (5H, m); 1.3-1.1 (12H, m); 1.02 (3H, d, J = 6.4); 0.83 (9H, m). |

Further compounds prepared according to the above procedure for Example E.1 are reported in Table E-1A.

TABLE E-1A

| Ex # | Structure | Chemical Name and Analytical Data |
|---|---|---|
| E.1.19 | 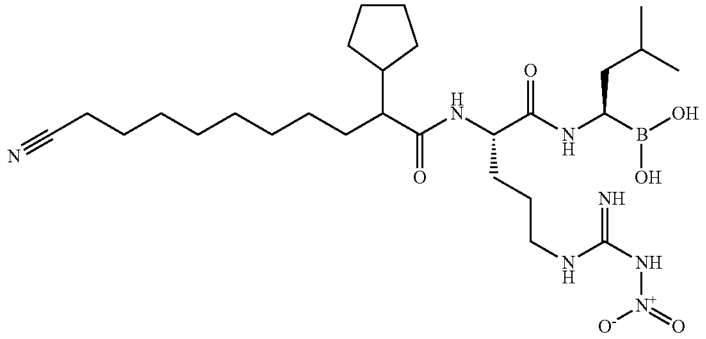 [SMILES: CC(C)C[C@H](NC(=O)[C@H](CCCNC(=N)N[N+](=O)[O-])NC(=O)C(CCCCCCCCC#N)C1CCCC1)B(O)O] | Chemical Name:<br>Boronic acid, [(1R)-1-[[(2S)-5-[[imino(nitroamino)methyl]amino]-2-[((RS)-10-cyano-2-cyclopentydecanoyl)amino]-1-oxopentyl]amino]-3-methylbutyl]<br>Analytical Data:<br>1H-NMR (MeOH-d4): 4.57 (1H, m); 3.29 (2H, m); 3.20 (2H, m); 2.76 (1H, t, J = 7.5 Hz); 2.43 (2H, t, J = 7.1); 2.05 (1H, m); 2.0-1.1 (11H, m); 0.93 (6H, d, J = 6.6). |
| E.1.20 | 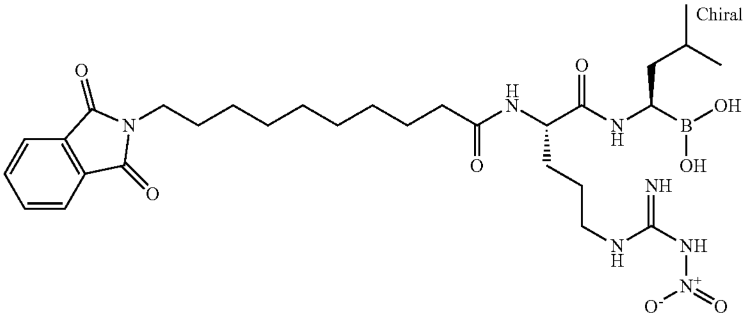 [SMILES: CC(C)C[C@H](NC(=O)[C@H](CCCNC(=N)N[N+](=O)[O-])NC(=O)CCCCCCCCCN1C(=O)c2ccccc2C1=O)B(O)O] | Chemical Name:<br>Boronic acid, [(1R)-1-[[(2S)-5-[[imino(nitroamino)methyl]amino]-2-[(10-(1,3-dihydro-1,3-dioxo-2H-isoindol-2-yl)-1-oxodecyl]-)amino]-1-oxopentyl]amino]-3-methylbutyl]<br>Analytical Data:<br>1H-NMR (MeOH-d4): 7.82 (4H, m); 4.52 (1H, m); 3.66 (2H, t, J = 7.3); 3.27 (2H, m); 2.75 (1H, m); 2.24 (2H, t, J = 7.3 Hz); 1.9-1.2 (20H, m); 0.91 (6H, d, J = 6.6). |
| E.1.21 | 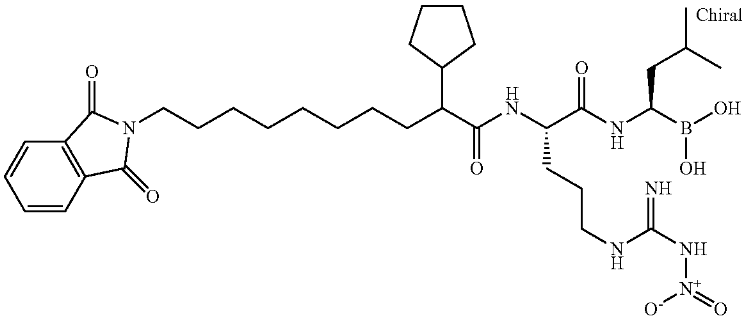 [SMILES: CC(C)C[C@H](NC(=O)[C@H](CCCNC(=N)N[N+](=O)[O-])NC(=O)C(CCCCCCCCN1C(=O)c2ccccc2C1=O)C1CCCC1)B(O)O] | Chemical Name:<br>Boronic acid, [(1R)-1-[[(2S)-5-[[imino(nitroamino)methyl]amino]-2-[(2-cyclopentyl-10-(1,3-dihydro-1,3-dioxo-2H-isoindol-2-yl)-1-oxodecyl]-)amino]-1-oxopentyl]amino]-3-methylbutyl]<br>Analytical Data:<br>1H-NMR (MeOH-d4): 7.82 (4H, m); 4.57 (1H, m); 3.66 (2H, t, J = 7.3); 3.28 (2H, m); 2.75 (1H, m); 2.05 (1H, m); 2.0-1.1 (30H, m); 0.91 (6H, two d, J = 6.6). |

TABLE E-1A-continued

| Ex # | Structure | Chemical Name and Analytical Data |
|---|---|---|
| E.1.22 | 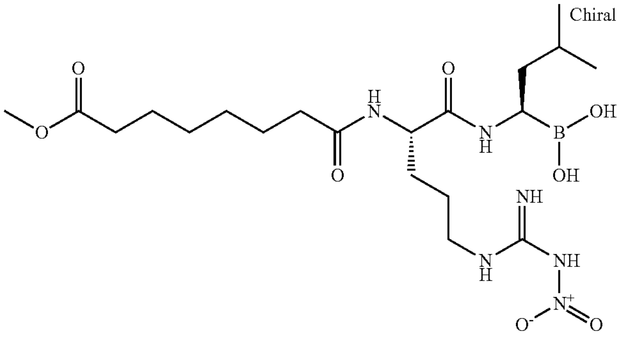 [SMILES: COC(=O)CCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[[7-(methoxycarbonyl)heptanoyl]amino]-1-oxophenyl]amino]-3-methylbutyl] Analytical Data: $^{1}$H NMR (DMSO-d6): 8.60 (1H, d, J = 8.4 Hz); 8.50 (1H, br); 8.06 (1H, d, J = 7.9); 7.92 (2H, br); 4.36 (1H, m); 3.58 (3H, s); 3.13 (2H, m); 2.55 (1H, m); 2.28 (2H, t, J = 7.5); 2.12 (2H, m); 1.69 (1H, m); 1.49 (7H, m); 1.24 (7H, m); 0.81 (6H, m). |

Further compounds prepared according to the above procedure for Example E.1 are reported in Table E-1B.

TABLE E-1B

| Ex # | Structure | Chemical Name and Analytical Data |
|---|---|---|
| E.1.23 | 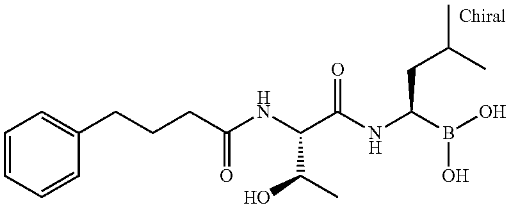 [SMILES: CC(C)C[C@H](NC(=O)[C@@H](NC(=O)CCCc1ccccc1)[C@@H](C)O)B(O)O] | Chemical Name: Boronic acid, [(1R)-1-[[(2S,3R)-3-hydroxy-2-[(4-phenylbutanoyl)amino]-1-oxobutyl]amino]-3-methylbutyl]. Analytical Data: $^{1}$H NMR (MeOH-d4): 7.29-7.13 (5H, m); 4.53 (1H, d, J = 3.9); 4.21-4.14 (1H, m); 2.72 (1H, d, J = 7.6); 2.65 (2H, t, J = 7.6); 2.34 (2H, t, J = 7.5); 2.10-2.89 (2H, m); 1.70-1.59 (1H, m); 1.37-1.27 (2H, m); 1.21 (3H, d, J = 6.4); 0.94-0.89 (6H, m). |
| E.1.24 | 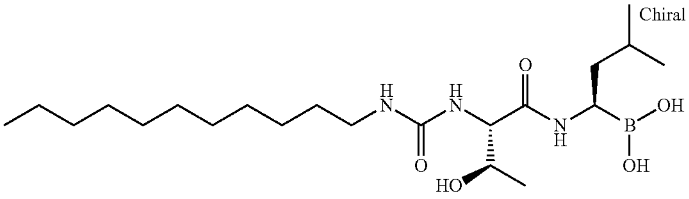 [SMILES: CCCCCCCCCCCNC(=O)N[C@H](C(=O)N[C@@H](CC(C)C)B(O)O)[C@@H](C)O] | Chemical Name: Boronic acid, [(1R)-1-[[(2S,3R)-3-hydroxy-2-[(undecylaminocarbonyl)amino]-1-oxobutyl]amino]-3-methylbutyl]. Analytical Data: $^{1}$H NMR (MeOH-d4): 4.43 (1H, d, J = 2.9); 4.27-4.20 (1H, m); 3.16 (2H, t, J = 6.9); 2.74 (1H, t, J = 7.6); 1.76-1.66 (1H, m); 1.58-1.46 (3H, m); 1.42-1.30 (26H, m); 1.25 (3H, d, J = 6.4). |
| E.1.25 | 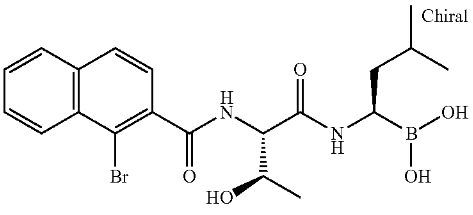 [SMILES: CC(C)C[C@H](NC(=O)[C@@H](NC(=O)c1ccc2ccccc2c1Br)[C@@H](C)O)B(O)O] | Chemical Name: Boronic acid, [(1R)-1-[[(2S,3R)-3-hydroxy-2-[(1-Bromo-2-naphthoyl)amino]-1-oxobutyl]amino]-3-methylbutyl]. Analytical Data: $^{1}$H NMR (MeOH-d4): 8.37 (1H, d, J = 8.52); 7.99 (2H, dd, J = 8.2, J = 13.0); 7.75-7.60 (2H, m); 4.82 (1H, d, J = 4.19); 4.31-4.23 (1H, m); 2.81 (1H, dd, J = 6.10, J = 9.14); 1.77-1.64 (1H, m); 1.48-1.38 (2H, m); 1.36 (3H, d, J = 6.38); 1.0-0.9 (6H, m). |
| E.1.26 | 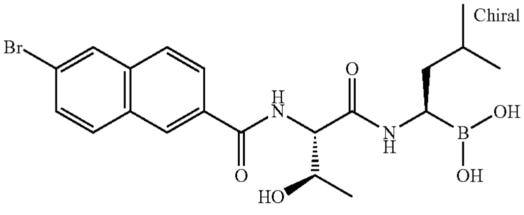 [SMILES: CC(C)C[C@H](NC(=O)[C@@H](NC(=O)c1ccc2cc(Br)ccc2c1)[C@@H](C)O)B(O)O] | Chemical Name: Boronic acid, [(1R)-1-[[(2S,3R)-3-hydroxy-2-[(6-Bromo-2-naphthoyl)amino]-1-oxobutyl]amino]-3-methylbutyl]. Analytical Data: $^{1}$H NMR (MeOH-d4): 8.49 (1H, s); 8.17 (1H, d, J = 1.4); 7.99 (1H, dd, J = 1.65, J = 8.66); 7.95 (2H, dd, J = 2.70, J = 8.62); 7.69 (1H, dd, J = 1.90, J = 8.77); 4.81 (1H, d, J = 4.26); 4.38-4.30 (1H, m); 2.77 (1H, t, J = 7.63); 1.71-1.59 (1H, m); 1.40-1.33 (2H, m); 1.31 (3H, d, J = 6.39); 0.94-0.90 (6H, m). |

Further compounds prepared according to the above procedure for Example E.1 are reported in Table E-1C. starting from the compounds of Example D.8.19 and D.8.20.

TABLE E-1C

| Ex # | Structure | Chemical Name and Analytical Data |
|---|---|---|
| E.1.27 | 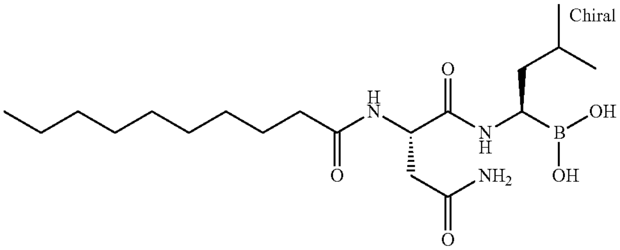 [SMILES: CCCCCCCCCC(=O)N[C@@H](CC(N)=O)C(=O)N[C@@H](CC(C)C)B(O)O] | Chemical Name: Boronic acid, [(1R)-1-[[(2S)-3-carbamoyl-2-[(decanoyl)amino]-1-oxopropyl]amino]-3-methylbutyl] Analytical Data: 1H-NMR (MeOH-d4): 4.76 (1H, t, J = 6.0); 2.58-2.52 (3H, m); 2.14-2.09 (2H, m); 1.64-1.52 (1H, m); 1.51-1.40 (2H, m); 1.30-1.12 (14H, m); 0.84-0.80 (9H, m). |
| E.1.28 | 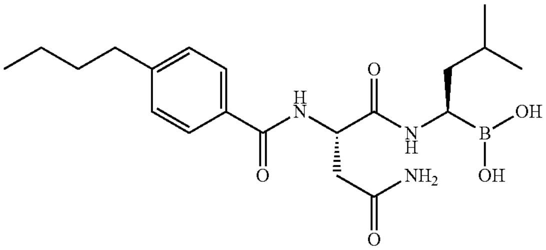 [SMILES: CCCCc1ccc(C(=O)N[C@@H](CC(N)=O)C(=O)N[C@@H](CC(C)C)B(O)O)cc1] | Chemical Name: Boronic acid, [(1R)-1-[[(2S)-3-carbamoyl-2-[4-butyl(benzoyl)amino]-1-oxopropyl]amino]-3-methylbutyl] Analytical Data: 1H-NMR (MeOH-d4): 7.78 (2H, d, J = 8.24 Hz); 7.32 (2H, d, J = 8.22 Hz); 5.16 (1H, T, J = 6.52); 2.91 (2H, dd, J = 2.09 Hz, J = 6.53 Hz); 2.78 (1H, t, J = 7.59 Hz); 2.74-2.66 (2H, m); 1.72-1.60 (3H, m); 1.44-1.30 (5H, m); 1.00-0.9 (9H, m). |

Further compounds prepared according to the above procedure for Example E.1 are reported in Table E-1D. starting from the compounds of Example D.2.9 and D.2.10.

TABLE E-1D

| Ex # | Structure | Chemical Name and Analytical Data |
|---|---|---|
| E.1.29 | 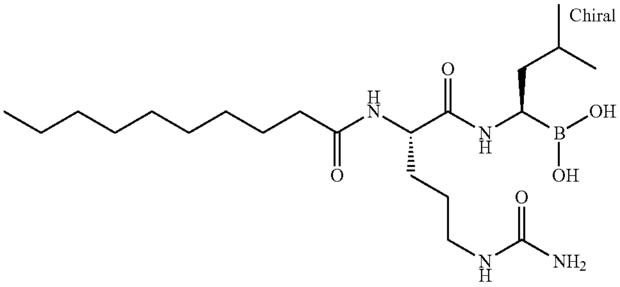 [SMILES: CCCCCCCCCC(=O)N[C@@H](CCCNC(N)=O)C(=O)N[C@@H](CC(C)C)B(O)O] | Chemical Name: Boronic acid, [(1R)-1-[[(2S)-2-[(decanoyl)amino]-1-oxo-5-ureido-pentyl]amino]-3-methylbutyl] Analytical Data: 1H-NMR (DMSO-d6): 8.56 (1H, s); 8.07 (1H, d, J = 8.03 Hz); 5.96 (1H, t, J = 5.18 Hz); 5.38 (2H, s); 4.42-4.20 (1H, m); 3.01-2.85 (2H, m); 2.65-2.40 (1H, m); 2.25-2.00 (2H, m); 1.70-1.52 (2H, m); 1.52-1.40 (3H, m); 1.40-1.10 (16H, m); 0.90-0.75 (9H, m). |
| E.1.30 | 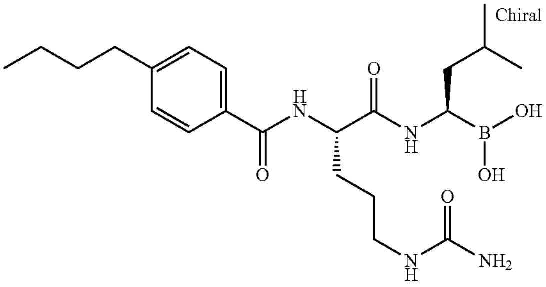 [SMILES: CCCCc1ccc(C(=O)N[C@@H](CCCNC(N)=O)C(=O)N[C@@H](CC(C)C)B(O)O)cc1] | Chemical Name: Boronic acid, [(1R)-1-[[(2S)-2-[(4-butylbenzoyl)amino]-1-oxo-5-ureido-pentyl]amino]-3-methylbutyl] Analytical Data: 1H-NMR (MeOH-d4 + DMSO-d6): 7.80 (2H, d, J = 8.08 Hz); 7.28 (2H, d, J = 8.16 Hz); 4.58 (1H, t, J = 7.41 Hz); 3.00 (2H, t, J = 6.72 Hz); 2.63 (2H, t, J = 7.64 Hz); 1.82-1.74 (2H, m); 1.68-1.52 (4H, m); 1.52-1.36 (2H, m); 1.34-1.26 (2H, m); 1.21 (2H, t, J = 7.23 Hz); 0.89 (3H, t, J = 7.35 Hz); 0.84 (6H, d, J = 6.55 Hz). |

Example E.2

Boronic acid, [(1R)-1-[[(2S)-5-[[imino(nitroamino) methyl]amino]-2-[(decanoyl)amino]-1-oxopentyl] amino]-3-methylbutyl]-

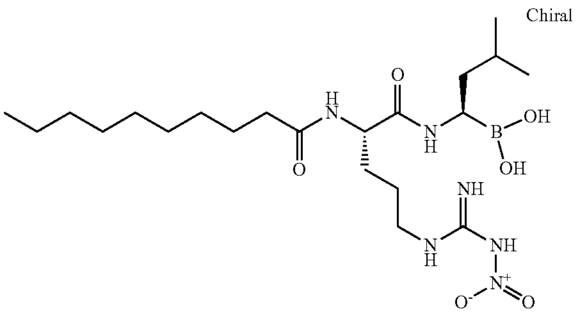 [SMILES: CCCCCCCCCC(=O)N[C@@H](CCCNC(=N)N[N+](=O)[O-])C(=O)N[C@@H](CC(C)C)B(O)O]

Decanamide, N-[(1S)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-4-[[imino(nitroamino)methyl]amino]butyl]- of Example D.1 (77 mg, 0.12 mmol), was dissolved in $Et_2O$ (1 mL) and HCl 37% (2 mL) was added carefully at 0° C. The reaction mixture was allowed to warm to room temperature and to shake overnight. The mixture was concentrated to dryness and the residue, dissolved in MeOH (1 mL), was passed through ISOLUTE PSA cartridge, and washed with MeOH. The solvent was evaporated and the reaction crude product was purified with ISOLUTE SPE-DIOL cartridges (DCM:MeOH 1:1) to afford the title compound (19 mg, yield 33%).

NMR (DMSO+$D_2O$, 343 K): 4.20 (m, 1H); 3.13 (m, 2H); 3.05 (m, 1H); 2.10 (t, J=6.2 Hz, 2H); 1.69 (m, 1H); 1.53-1.40 (m, 4H); 1.39-1.20 (m, 14H); 0.84 (m, 9H).

LC-MS 468.9, MH+. ESI POS; AQA; spray 4 kV/skimmer: 20V/probe 250° C.

Further compounds prepared fundamentally in accordance with the above experimental procedures are reported in Table E-2.

TABLE E-2

| Ex # | Structure | Chemical Name and Analytical Data |
| --- | --- | --- |
| E.2.1 | 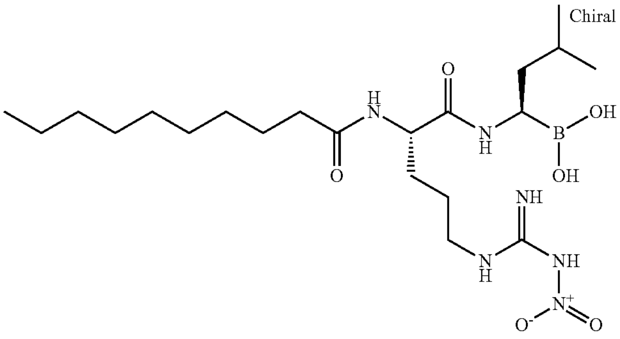 [SMILES: CCCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(1-oxodecyl)amino]-1-oxopentyl]amino]-3-methylbutyl] Analytical Data: MS: MH+ 468.9; 1H-NMR: (DMSO + D2O, 343K): 4.20 (m, 1H); 3.13 (m, 2H); 3.05 (m, 1H); 2.10 (t, J = 6.2 Hz, 2H); 1.69 (m, 1H); 1.58-1.40 (m, 4H); 1.39-1.20 (m, 14H); 0.84 (m, 9H). |
| E.2.2 | 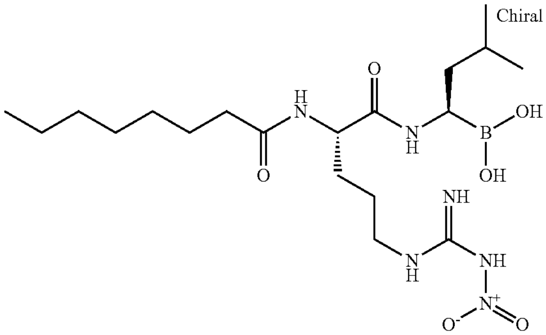 [SMILES: CCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(octanoyl)amino]-1-oxopentyl]amino]-3-methylbutyl] Analytical Data: MS: [M − 18]H+ 441.4 |
| E.2.3 | 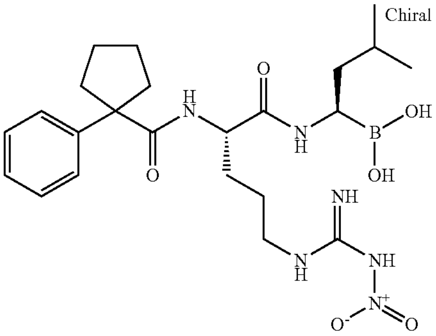 [SMILES: CC(C)C[C@H](NC(=O)[C@H](CCCNC(=N)N[N+](=O)[O-])NC(=O)C1(c2ccccc2)CCCC1)B(O)O] | Chemical Name: Boronic acid, [(1R)-1-[[(2S)-5-[[imino(nitroamino)methyl]amino]-2-[(1-phenylcyclopentanecarbnyl)amino]-1-oxopentyl]amino]-3-methylbutyl] Analytical Data: MS: [M − 18]H+ 487.0 |

TABLE E-2-continued

| Ex # | Structure | Chemical Name and Analytical Data |
|---|---|---|
| E.2.4 | 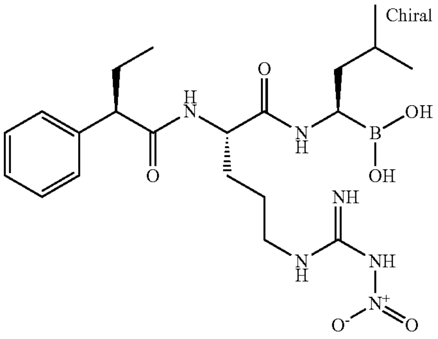 [SMILES: CC[C@@H](C(=O)N[C@@H](CCCNC(=N)N[N+](=O)[O-])C(=O)N[C@@H](CC(C)C)B(O)O)c1ccccc1] | Chemical Name:<br>Boronic acid, [(1R)-1-[[(2S)-5-[[imino(nitroamino)methyl]amino]-2-[((2R)-2-phenylbutanoyl)amino]-1-oxopentyl]amino]-3-methylbutyl]<br>Analytical Data:<br>MS: [M − 18]H+ 461.2 |
| E.2.5 | 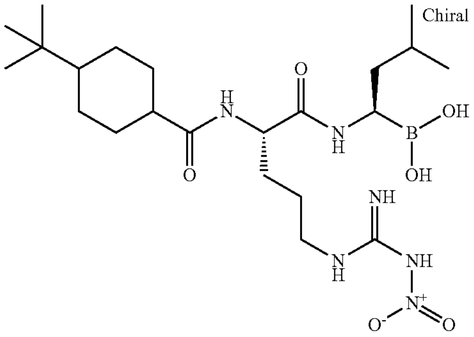 [SMILES: CC(C)C[C@H](NC(=O)[C@H](CCCNC(=N)N[N+](=O)[O-])NC(=O)C1CCC(C(C)(C)C)CC1)B(O)O] | Chemical Name:<br>Boronic acid, [(1R)-1-[[(2S)-5-[[imino(nitroamino)methyl]amino]-2-[[4-(1,1-Dimethylethyl)cyclohexanecarbonyl]amino]-1-oxopentyl]amino]-3-methylbutyl]<br>Analytical Data:<br>MS: [M − 18]H+ 481.1 |
| E.2.6 | 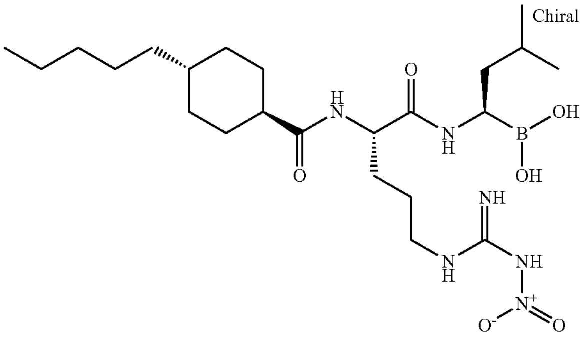 [SMILES: CCCCC[C@H]1CC[C@H](C(=O)N[C@@H](CCCNC(=N)N[N+](=O)[O-])C(=O)N[C@@H](CC(C)C)B(O)O)CC1] | Chemical Name:<br>Boronic acid, [(1R)-1-[[(2S)-5-[[imino(nitroamino)methyl]amino]-2-[(trans-4-pentylcyclohexanecarbonyl)amino]-1-oxopentyl]amino]-3-methylbutyl]<br>Analytical Data:<br>MS: [M − 18]H+ 495.4 |
| E.2.7 | 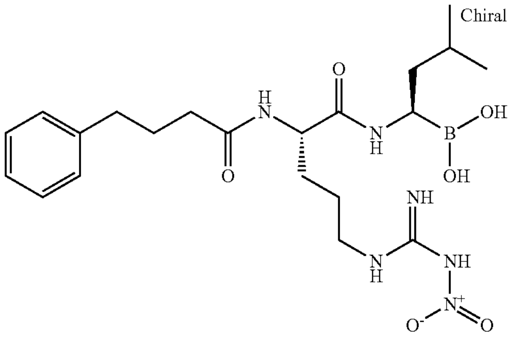 [SMILES: CC(C)C[C@H](NC(=O)[C@H](CCCNC(=N)N[N+](=O)[O-])NC(=O)CCCc1ccccc1)B(O)O] | Chemical Name:<br>Boronic acid, [(1R)-1-[[(2S)-5-[[imino(nitroamino)methyl]amino]-2-[(4-phenylbutanoyl)amino]-1-oxopentyl]amino]-3-methylbutyl]<br>Analytical Data:<br>MS: [M − 18]H+ 461.4 |

TABLE E-2-continued

| Ex # | Structure | Chemical Name and Analytical Data |
| --- | --- | --- |
| E.2.8 | 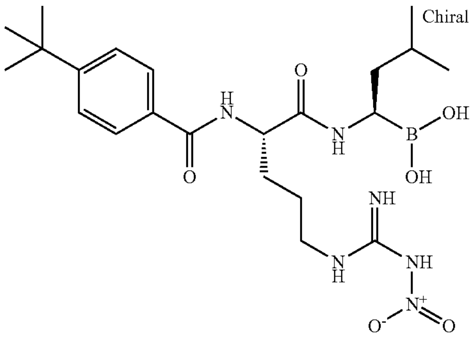 [SMILES: CC(C)C[C@H](NC(=O)[C@H](CCCNC(=N)N[N+](=O)[O-])NC(=O)c1ccc(C(C)(C)C)cc1)B(O)O] | Chemical Name: Boronic acid, [(1R)-1-[[(2S)-5-[[imino(nitroamino)methyl]amino]-2-[(4-(1,1-dimethylethyl)benzoyl)amino]-1-oxopentyl]amino]-3-methylbutyl] Analytical Data: MS: [M − 18]H+ 475.1 |
| E.2.9 | 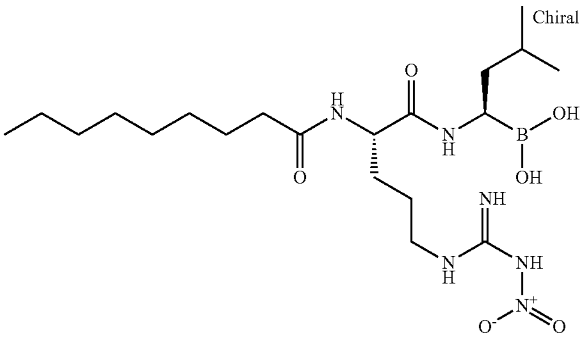 [SMILES: CCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(nonanoyl)amino]-1-oxopentyl]amino]-3-methylbutyl] Analytical Data: MS: [M − 18]H+ 455.1 |
| E.2.10 | 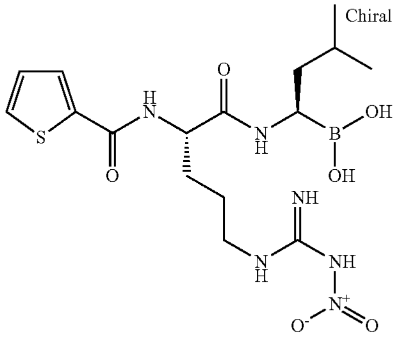 [SMILES: CC(C)C[C@H](NC(=O)[C@H](CCCNC(=N)N[N+](=O)[O-])NC(=O)c1cccs1)B(O)O] | Chemical Name: Boronic acid, [(1R)-1-[[(2S)-5-[[imino(nitroamino)methyl]amino]-2-[(2-thiophenecarbonyl)amino]-1-oxopentyl]amino]-3-methylbutyl] Analytical Data: MS: [M − 18]H+ 425.3 |
| E.2.11 | 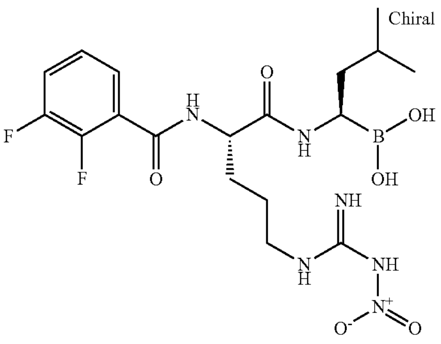 [SMILES: CC(C)C[C@H](NC(=O)[C@H](CCCNC(=N)N[N+](=O)[O-])NC(=O)c1cccc(F)c1F)B(O)O] | Chemical Name: Boronic acid, [(1R)-1-[[(2S)-5-[[imino(nitroamino)methyl]amino]-2-[(2,3-difluorobenzoyl)amino]-1-oxopentyl]amino]-3-methylbutyl] Analytical Data: MS: [M − 18]H+ 455.0 |

TABLE E-2-continued

| Ex # | Structure | Chemical Name and Analytical Data |
|---|---|---|
| E.2.12 | 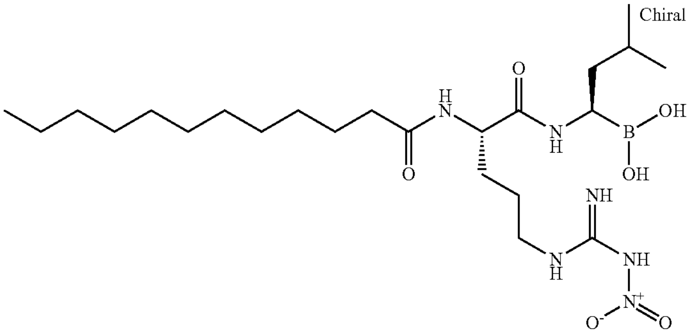 [SMILES: CCCCCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(dodecanoyl)amino]-1-oxopentyl]amino]-3-methylbutyl] Analytical Data: MS: [M − 18]H+ 497.2 |
| E.2.13 | 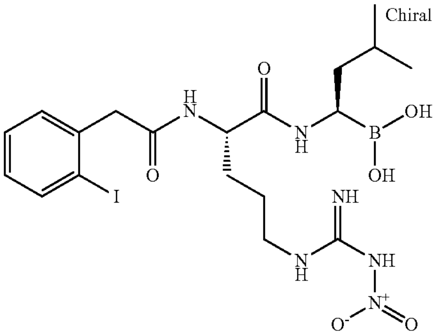 [SMILES: CC(C)C[C@H](NC(=O)[C@H](CCCNC(=N)N[N+](=O)[O-])NC(=O)Cc1ccccc1I)B(O)O] | Chemical Name: Boronic acid, [(1R)-1-[[(2S)-5-[[imino(nitroamino)methyl]amino]-2-[[2-(2-iodophenyl)acetyl]amino]-1-oxopentyl]amino]-3-methylbutyl] Analytical Data: MS: [M − 18]H+ 558.9 |
| E.2.14 | 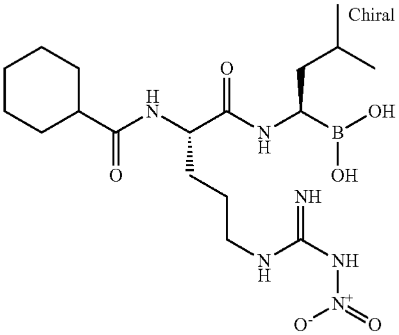 [SMILES: CC(C)C[C@H](NC(=O)[C@H](CCCNC(=N)N[N+](=O)[O-])NC(=O)C1CCCCC1)B(O)O] | Chemical Name: Boronic acid, [(1R)-1-[[(2S)-5-[[imino(nitroamino)methyl]amino]-2-[(cyclohexanecarbonyl)amino]-1-oxopentyl]amino]-3-methylbutyl] Analytical Data: MS: [M − 18]H+ 425.0 |
| E.2.15 | 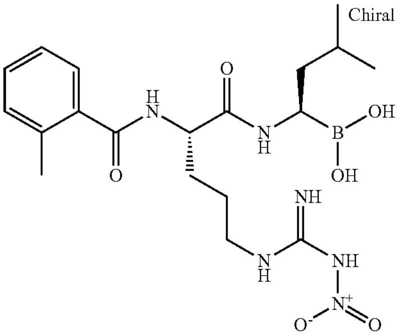 [SMILES: Cc1ccccc1C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(2-methylbenzoyl)amino]-1-oxopentyl]amino]-3-methylbutyl] Analytical Data: MS: [M − 18]H+ 433.0 |

TABLE E-2-continued

| Ex # | Structure | Chemical Name and Analytical Data |
|---|---|---|
| E.2.16 | 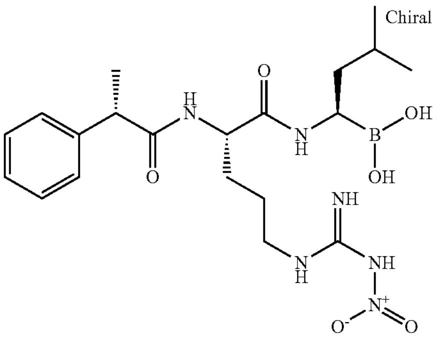 [SMILES: CC(C)C[C@H](NC(=O)[C@H](CCCNC(=N)N[N+](=O)[O-])NC(=O)[C@@H](C)c1ccccc1)B(O)O] | Chemical Name: Boronic acid, [(1R)-1-[[(2S)-5-[[imino(nitroamino)methyl]amino]-2-[((2S)-2-phenylpropanoyl)amino]-1-oxopentyl]amino]-3-methylbutyl] Analytical Data: MS: [M − 18]H+ 447.3 |
| E.2.17 | 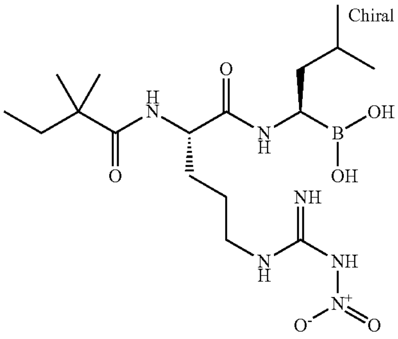 [SMILES: CCC(C)(C)C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(2,2-dimethylbutanoyl)amino]-1-oxopentyl]amino]-3-methylbutyl] Analytical Data: MS: [M − 18]H+ 413.3 |
| E.2.18 | 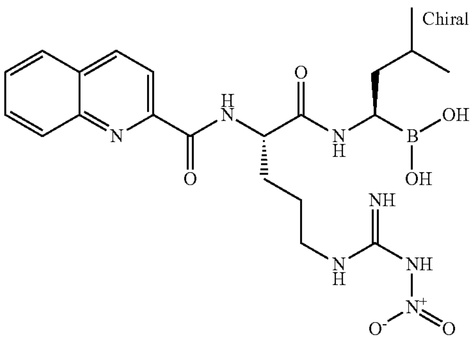 [SMILES: CC(C)C[C@H](NC(=O)[C@H](CCCNC(=N)N[N+](=O)[O-])NC(=O)c1ccc2ccccc2n1)B(O)O] | Chemical Name: Boronic acid, [(1R)-1-[[(2S)-5-[[imino(nitroamino)methyl]amino]-2-[(quinoline-2-carbonyl)amino]-1-oxopentyl]amino]-3-methylbutyl] Analytical Data: MS: [M − 18]H+ 470.0 |
| E.2.19 | 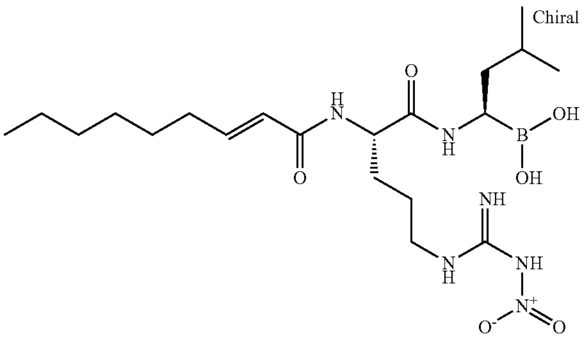 [SMILES: CCCCCC/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(non-2-enoyl)amino]-1-oxopentyl]amino]-3-methylbutyl] Analytical Data: MS: [M − 18]H+ 453.1 |

TABLE E-2-continued

| Ex # | Structure | Chemical Name and Analytical Data |
|---|---|---|
| E.2.20 | 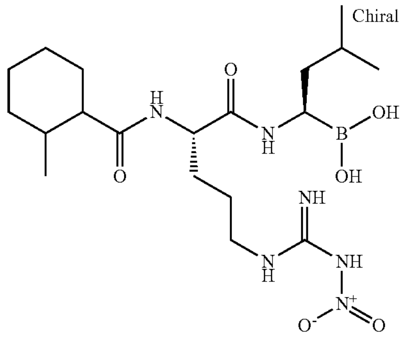 [SMILES: CC(C)C[C@H](NC(=O)[C@H](CCCNC(=N)N[N+](=O)[O-])NC(=O)C1CCCCC1C)B(O)O] | Chemical Name: Boronic acid, [(1R)-1-[[(2S)-5-[[imino(nitroamino)methyl]amino]-2-[(2-methylcyclohexanecarbonyl)amino]-1-oxopentyl]amino]-3-methylbutyl] Analytical Data: MS: [M − 18]H+ 439.4 |
| E.2.21 | 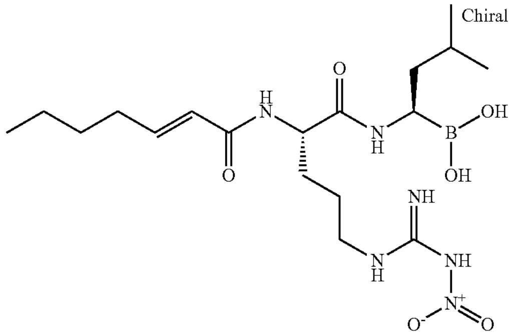 [SMILES: CCCC/C=C/C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(hept-2-enoyl)amino]-1-oxopentyl]amino]-3-methylbutyl] Analytical Data: MS: [M − 18]H+ 425.4 |
| E.2.22 | 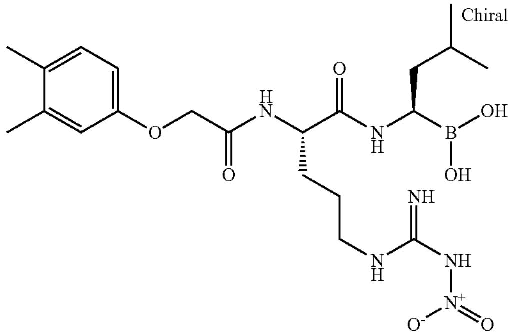 [SMILES: Cc1ccc(OCC(=O)N[C@@H](CCCNC(=N)N[N+](=O)[O-])C(=O)N[C@@H](CC(C)C)B(O)O)cc1C] | Chemical Name: Boronic acid, [(1R)-1-[[(2S)-5-[[imino(nitroamino)methyl]amino]-2-[[2-(3,4-dimethylphenoxy)acetyl]amino]-1-oxopentyl]amino]-3-methylbutyl] Analytical Data: MS: [M − 18]H+ 477.3 |
| E.2.23 | 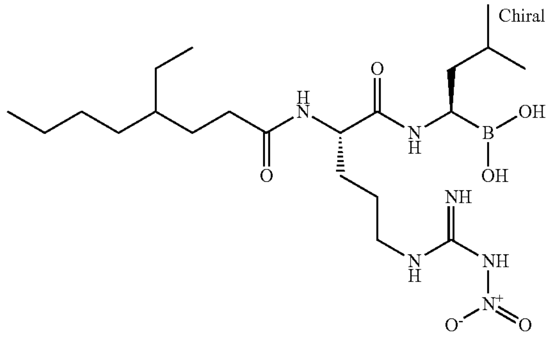 [SMILES: CCCCC(CC)CCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[((RS)-4-ethyloctanoyl)amino]-1-oxopentyl]amino]-3-methylbutyl] Analytical Data: MS: [M − 18]H+ 469.5 |

TABLE E-2-continued

| Ex # | Structure | Chemical Name and Analytical Data |
| --- | --- | --- |
| E.2.24 | 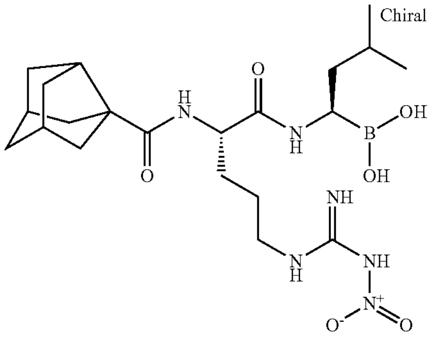 [SMILES: CC(C)C[C@H](NC(=O)[C@H](CCCNC(=N)N[N+](=O)[O-])NC(=O)C12CC3CC(CC1C3)C2)B(O)O] | Chemical Name:<br>Boronic acid, [(1R)-1-[[(2S)-5-[[imino(nitroamino)methyl]amino]-2-[(hexahydro-2,5-methanopentalene-3a(1H)-carbonyl)amino]-1-oxopentyl]amino]-3-methylbutyl]<br>Analytical Data:<br>MS: [M − 18]H+ 463.5 |
| E.2.25 | 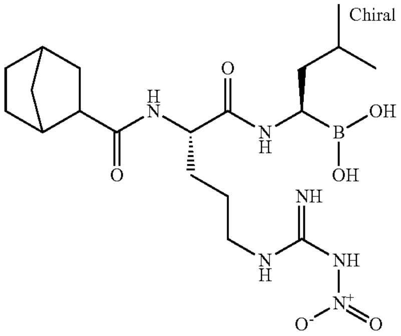 [SMILES: CC(C)C[C@H](NC(=O)[C@H](CCCNC(=N)N[N+](=O)[O-])NC(=O)C1CC2CCC1C2)B(O)O] | Chemical Name:<br>Boronic acid, [(1R)-1-[[(2S)-5-[[imino(nitroamino)methyl]amino]-2-[(bicyclo[2.2.1]heptane-2-carbonyl)amino]-1-oxopentyl]amino]-3-methylbutyl]<br>Analytical Data:<br>MS: [M − 18]H+ 437.4 |
| E.2.26 | 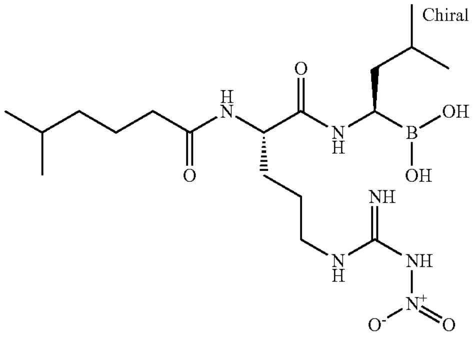 [SMILES: CC(C)CCCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[(5-methylhexanoyl)amino]-1-oxopentyl]amino]-3-methylbutyl]<br>Analytical Data:<br>MS: [M − 18]H+ 427.0 |
| E.2.27 | 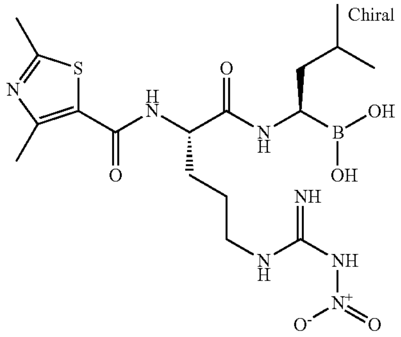 [SMILES: Cc1nc(C)c(C(=O)N[C@@H](CCCNC(=N)N[N+](=O)[O-])C(=O)N[C@@H](CC(C)C)B(O)O)s1] | Chemical Name:<br>Boronic acid, [(1R)-1-[[(2S)-5-[[imino(nitroamino)methyl]amino]-2-[(2,4-dimethylthiazole-5-carbonyl)amino]-1-oxopentyl]amino]-3-methylbutyl]<br>Analytical Data:<br>MS: [M − 18]H+ 454.3 |

TABLE E-2-continued

| Ex # | Structure | Chemical Name and Analytical Data |
|---|---|---|
| E.2.28 | 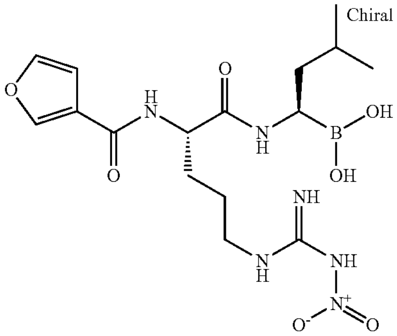 [SMILES: CC(C)C[C@H](NC(=O)[C@H](CCCNC(=N)N[N+](=O)[O-])NC(=O)c1ccoc1)B(O)O] | Chemical Name: Boronic acid, [(1R)-1-[[(2S)-5-[[imino(nitroamino)methyl]amino]-2-[(furan-3-carbonyl)amino]-1-oxopentyl]amino]-3-methylbutyl] Analytical Data: MS: [M − 18]H+ 408.8 |
| E.2.29 | 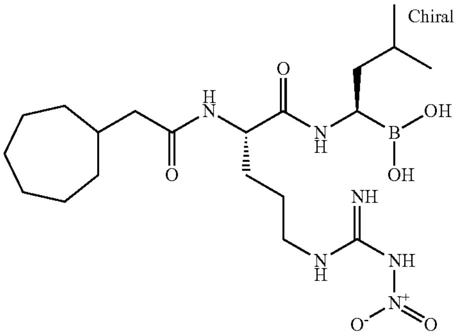 [SMILES: CC(C)C[C@H](NC(=O)[C@H](CCCNC(=N)N[N+](=O)[O-])NC(=O)CC1CCCCCC1)B(O)O] | Chemical Name: Boronic acid, [(1R)-1-[[(2S)-5-[[imino(nitroamino)methyl]amino]-2-[(2-cycloheptylacetyl)amino]-1-oxopentyl]amino]-3-methylbutyl] Analytical Data: MS: [M − 18]H+ 453.2 |
| E.2.30 | 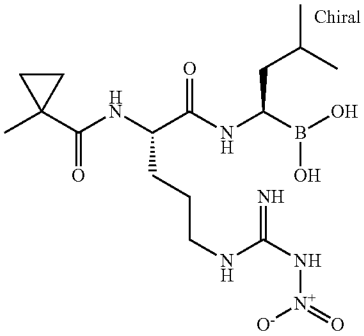 [SMILES: CC(C)C[C@H](NC(=O)[C@H](CCCNC(=N)N[N+](=O)[O-])NC(=O)C1(C)CC1)B(O)O] | Chemical Name: Boronic acid, [(1R)-1-[[(2S)-5-[[imino(nitroamino)methyl]amino]-2-[(1-methylcyclopropanecarbonyl)amino]-1-oxopentyl]amino]-3-methylbutyl] Analytical Data: MS: [M − 18]H+ 397.2 |
| E.2.31 | 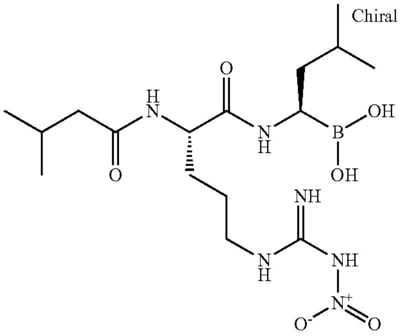 [SMILES: CC(C)CC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(3-methylbutanoyl)amino]-1-oxopentyl]amino]-3-methylbutyl] Analytical Data: MS: [M − 18]H+ 399.4 |

TABLE E-2-continued

| Ex # | Structure | Chemical Name and Analytical Data |
| --- | --- | --- |
| E.2.32 | 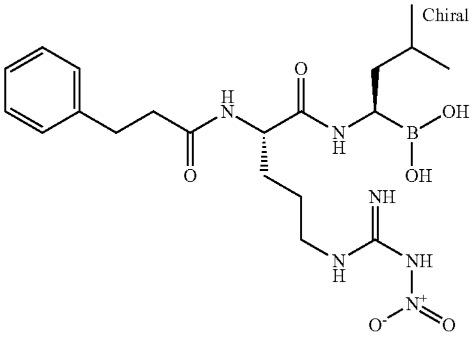 [SMILES: CC(C)C[C@H](NC(=O)[C@H](CCCNC(=N)N[N+](=O)[O-])NC(=O)CCc1ccccc1)B(O)O] | Chemical Name: Boronic acid, [(1R)-1-[[(2S)-5-[[imino(nitroamino)methyl]amino]-2-[(3-phenylpropanoyl)amino]-1-oxopentyl]amino]-3-methylbutyl] Analytical Data: MS: [M − 18]H+ 447.3 |
| E.2.33 | 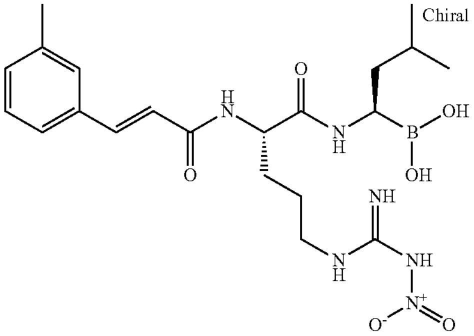 [SMILES: Cc1cccc(/C=C/C(=O)N[C@@H](CCCNC(=N)N[N+](=O)[O-])C(=O)N[C@@H](CC(C)C)B(O)O)c1] | Chemical Name: Boronic acid, [(1R)-1-[[(2S)-5-[[imino(nitroamino)methyl]amino]-2-[[(E)-3-(3-methylphenyl)acryl]amino]-1-oxopentyl]amino]-3-methylbutyl] Analytical Data: MS: [M − 18]H+ 459.5 |
| E.2.34 | 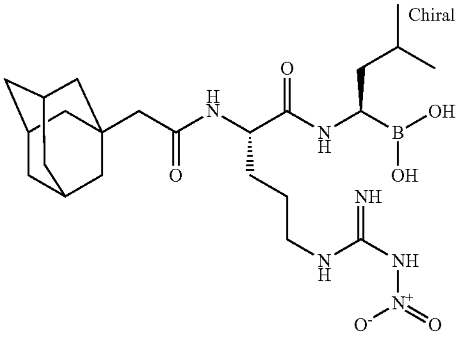 [SMILES: CC(C)C[C@H](NC(=O)[C@H](CCCNC(=N)N[N+](=O)[O-])NC(=O)CC12CC3CC(CC(C3)C1)C2)B(O)O] | Chemical Name: Boronic acid, [(1R)-1-[[(2S)-5-[[imino(nitroamino)methyl]amino]-2-[(2-adamantan-1-ylacetyl)amino]-1-oxopentyl]amino]-3-methylbutyl] Analytical Data: MS: [M − 18]H+ 491.2 |
| E.2.35 | 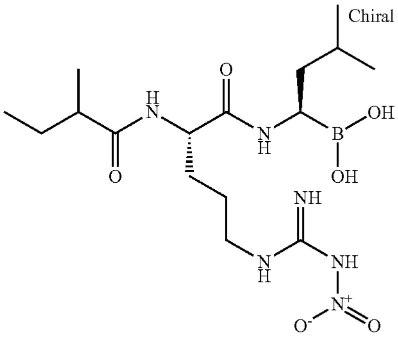 [SMILES: CCC(C)C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[((RS)-2-methylbutanoyl)amino]-1-oxopentyl]amino]-3-methylbutyl] Analytical Data: MS: [M − 18]H+ 398.9 |

TABLE E-2-continued

| Ex # | Structure | Chemical Name and Analytical Data |
| --- | --- | --- |
| E.2.36 | 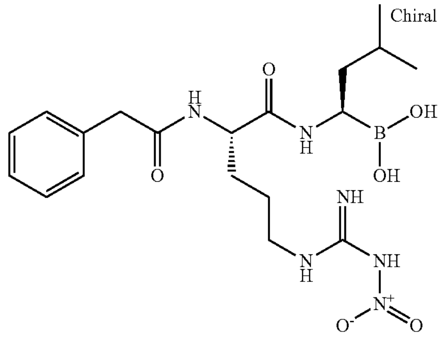 [SMILES: CC(C)C[C@H](NC(=O)[C@H](CCCNC(=N)N[N+](=O)[O-])NC(=O)Cc1ccccc1)B(O)O] | Chemical Name: Boronic acid, [(1R)-1-[[(2S)-5-[[imino(nitroamino)methyl]amino]-2-[(2-phenylacetyl)amino]-1-oxopentyl]amino]-3-methylbutyl] Analytical Data: MS: [M − 18]H+ 433.4 |
| E.2.37 | 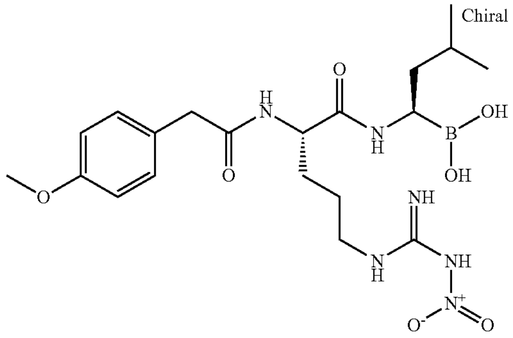 [SMILES: COc1ccc(CC(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[[2-(4-methoxyphenyl)acetyl]amino]-1-oxopentyl]amino]-3-methylbutyl] Analytical Data: MS: [M − 18]H+ 463.5 |
| E.2.38 | 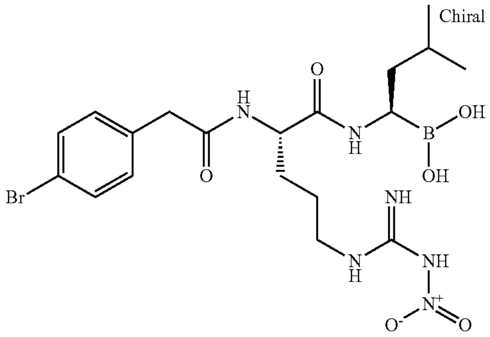 [SMILES: CC(C)C[C@H](NC(=O)[C@H](CCCNC(=N)N[N+](=O)[O-])NC(=O)Cc1ccc(Br)cc1)B(O)O] | Chemical Name: Boronic acid, [(1R)-1-[[(2S)-5-[[imino(nitroamino)methyl]amino]-2-[[2-(4-bromophenyl)acetyl]amino]-1-oxopentyl]amino]-3-methylbutyl] Analytical Data: MS: [M − 18]H+ 511.3 |
| E.2.39 | 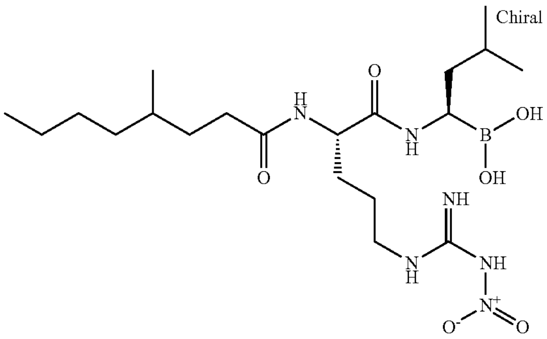 [SMILES: CCCCC(C)CCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[((RS)-4-methyloctanoyl)amino]-1-oxopentyl]amino]-3-methylbutyl] Analytical Data: MS: [M − 18]H+ 455.0 |

TABLE E-2-continued

| Ex # | Structure | Chemical Name and Analytical Data |
|---|---|---|
| E.2.40 | 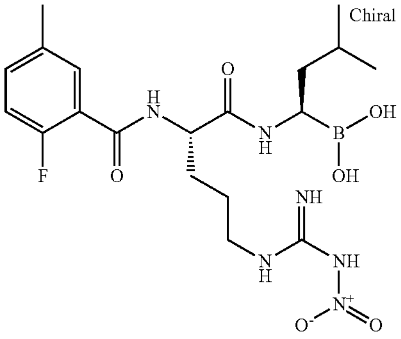 [SMILES: Cc1ccc(F)c(C(=O)N[C@@H](CCCNC(=N)N[N+](=O)[O-])C(=O)N[C@@H](CC(C)C)B(O)O)c1] | Chemical Name: Boronic acid, [(1R)-1-[[(2S)-5-[[imino(nitroamino)methyl]amino]-2-[(2-fluoro-5-methylbenzoyl)amino]-1-oxopentyl]amino]-3-methylbutyl] Analytical Data: MS: [M − 18]H+ 451.4 |
| E.2.41 | 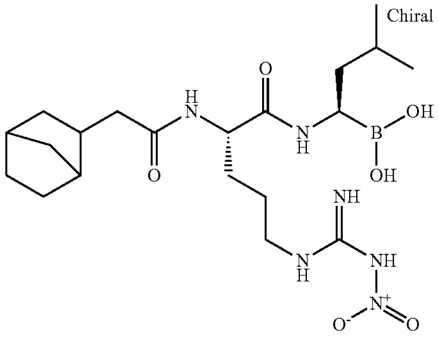 [SMILES: CC(C)C[C@H](NC(=O)[C@H](CCCNC(=N)N[N+](=O)[O-])NC(=O)CC1CC2CCC1C2)B(O)O] | Chemical Name: Boronic acid, [(1R)-1-[[(2S)-5-[[imino(nitroamino)methyl]amino]-2-[[2-(bicyclo[2.2.1]hept-2-yl)acetyl]amino]-1-oxopentyl]amino]-3-methylbutyl] Analytical Data: MS: [M − 18]H+ 451.0 |
| E.2.42 | 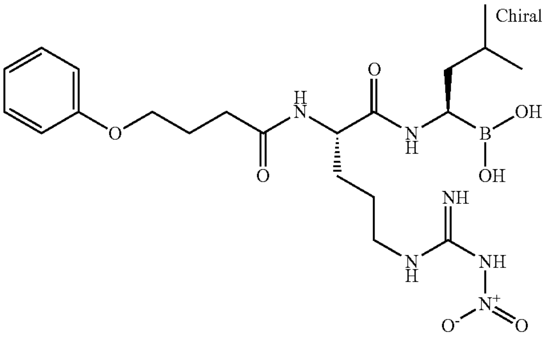 [SMILES: CC(C)C[C@H](NC(=O)[C@H](CCCNC(=N)N[N+](=O)[O-])NC(=O)CCCOc1ccccc1)B(O)O] | Chemical Name: Boronic acid, [(1R)-1-[[(2S)-5-[[imino(nitroamino)methyl]amino]-2-[(4-phenoxybutanoyl)amino]-1-oxopentyl]amino]-3-methylbutyl] Analytical Data: MS: [M − 18]H+ 477.4 |
| E.2.43 | 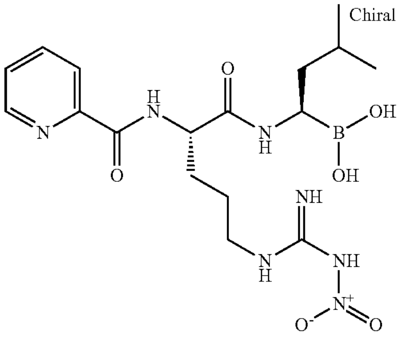 [SMILES: CC(C)C[C@H](NC(=O)[C@H](CCCNC(=N)N[N+](=O)[O-])NC(=O)c1ccccn1)B(O)O] | Chemical Name: Boronic acid, [(1R)-1-[[(2S)-5-[[imino(nitroamino)methyl]amino]-2-[(2-pyridinecarbonyl)amino]-1-oxopentyl]amino]-3-methylbutyl] Analytical Data: MS: [M − 18]H+ 419.9 |

TABLE E-2-continued

| Ex # | Structure | Chemical Name and Analytical Data |
|---|---|---|
| E.2.44 | 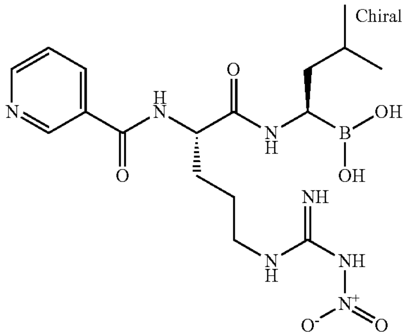 [SMILES: CC(C)C[C@H](NC(=O)[C@H](CCCNC(=N)N[N+](=O)[O-])NC(=O)c1cccnc1)B(O)O] | Chemical Name: Boronic acid, [(1R)-1-[[(2S)-5-[[imino(nitroamino)methyl]amino]-2-[(3-pyridinecarbonyl)amino]-1-oxopentyl]amino]-3-methylbutyl] Analytical Data: MS: [M − 18]H+ 420.3 |
| E.2.45 | 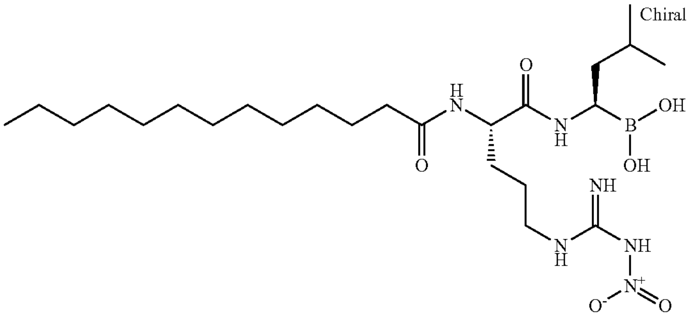 [SMILES: CCCCCCCCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(tridecanoyl)amino]-1-oxopentyl]amino]-3-methylbutyl] Analytical Data: MS: [M − 18]H+ 511.6 |
| E.2.46 | 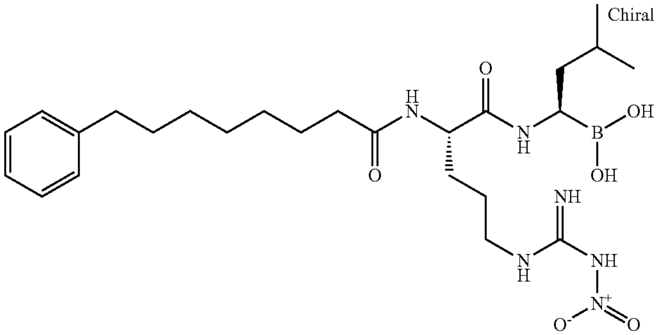 [SMILES: CC(C)C[C@H](NC(=O)[C@H](CCCNC(=N)N[N+](=O)[O-])NC(=O)CCCCCCCc1ccccc1)B(O)O] | Chemical Name: Boronic acid, [(1R)-1-[[(2S)-5-[[imino(nitroamino)methyl]amino]-2-[(8-phenyloctanoyl)amino]-1-oxopentyl]amino]-3-methylbutyl] Analytical Data: MS: [M − 18]H+ 517.3 |
| E.2.47 | 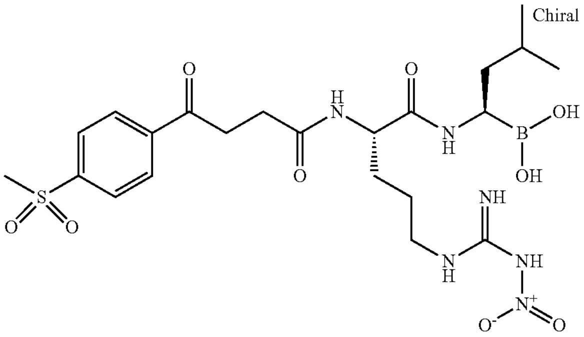 [SMILES: CC(C)C[C@H](NC(=O)[C@H](CCCNC(=N)N[N+](=O)[O-])NC(=O)CCC(=O)c1ccc(S(C)(=O)=O)cc1)B(O)O] | Chemical Name: Boronic acid, [(1R)-1-[[(2S)-5-[[imino(nitroamino)methyl]amino]-2-[[4-(4-methanesulfonylphenyl)-4-oxobutanoyl]amino]-1-oxopentyl]amino]-3-methylbutyl] Analytical Data: MS: [M − 18]H+ 553.3 |

TABLE E-2-continued

| Ex # | Structure | Chemical Name and Analytical Data |
| --- | --- | --- |
| E.2.48 | 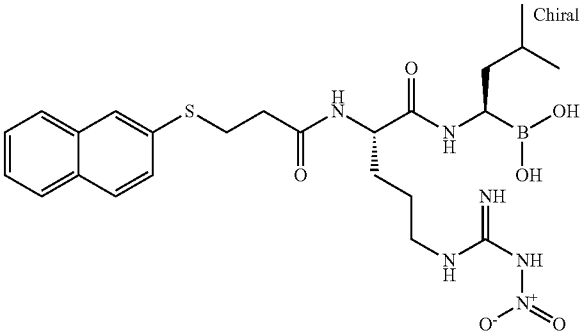 [SMILES: CC(C)C[C@H](NC(=O)[C@H](CCCNC(=N)N[N+](=O)[O-])NC(=O)CCSc1ccc2ccccc2c1)B(O)O] | Chemical Name: Boronic acid, [(1R)-1-[[(2S)-5-[[imino(nitroamino)methyl]amino]-2-[[3-(naphthalen-2-ylsulfanyl)-propanoyl]amino]-1-oxopentyl]amino]-3-methylbutyl] Analytical Data: MS: [M − 18]H+ 529.3 |
| E.2.49 | 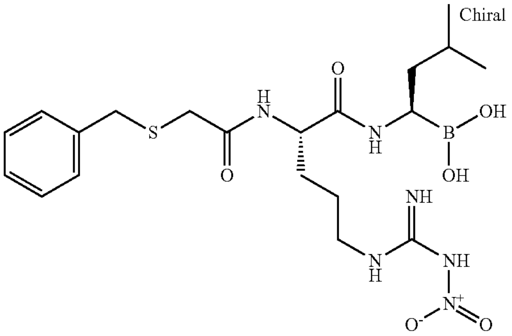 [SMILES: CC(C)C[C@H](NC(=O)[C@H](CCCNC(=N)N[N+](=O)[O-])NC(=O)CSCc1ccccc1)B(O)O] | Chemical Name: Boronic acid, [(1R)-1-[[(2S)-5-[[imino(nitroamino)methyl]amino]-2-[[2-[(phenylmethyl)sulfanyl]acetyl]amino]-1-oxopentyl]amino]-3-methylbutyl] Analytical Data: MS: [M − 18]H+ 479.5 |
| E.2.50 | 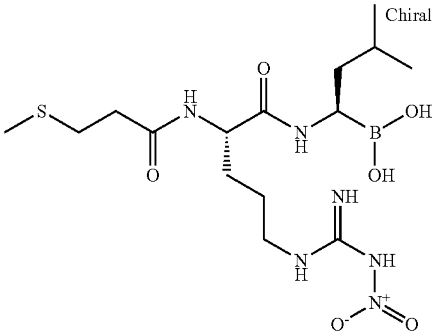 [SMILES: CSCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(3-Methylsulfanylpropanoyl)amino]-1-oxopentyl]amino]-3-methylbutyl] Analytical Data: MS: [M − 18]H+ 416.9 |
| E.2.51 | 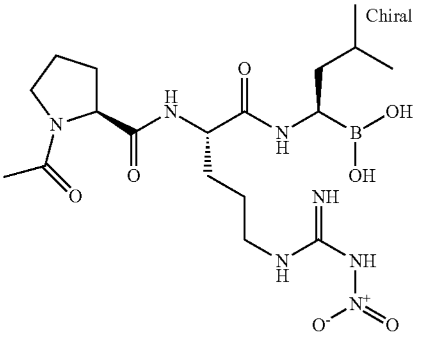 [SMILES: CC(=O)N1CCC[C@H]1C(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[((2S)-1-acetylpyrrolidine-2-carbonyl)amino]-1-oxopentyl]amino]-3-methylbutyl] Analytical Data: MS: [M − 18]H+ 454.1 |

TABLE E-2-continued

| Ex # | Structure | Chemical Name and Analytical Data |
| --- | --- | --- |
| E.2.52 | 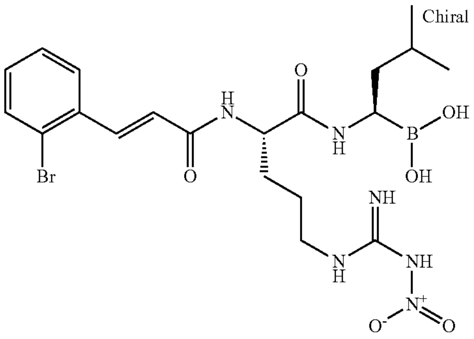 [SMILES: CC(C)C[C@H](NC(=O)[C@H](CCCNC(=N)N[N+](=O)[O-])NC(=O)/C=C/c1ccccc1Br)B(O)O] | Chemical Name: Boronic acid, [(1R)-1-[[(2S)-5-[[imino(nitroamino)methyl]amino]-2-[[trans-3-(2-bromophenyl)acryl]amino]-1-oxopentyl]amino]-3-methylbutyl] Analytical Data: MS: [M − 18]H+ 523.0 |
| E.2.53 | 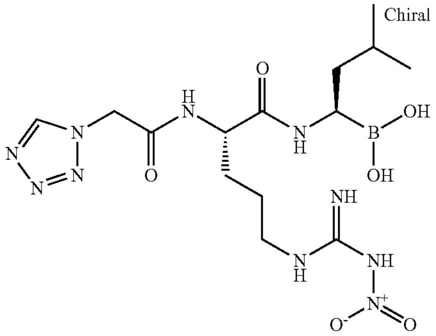 [SMILES: CC(C)C[C@H](NC(=O)[C@H](CCCNC(=N)N[N+](=O)[O-])NC(=O)Cn1cnnn1)B(O)O] | Chemical Name: Boronic acid, [(1R)-1-[[(2S)-5-[[imino(nitroamino)methyl]amino]-2-[[2-(tetrazol-1-yl)acetyl]amino]-1-oxopentyl]amino]-3-methylbutyl] Analytical Data: MS: [M − 18]H+ 425.0 |
| E.2.54 | 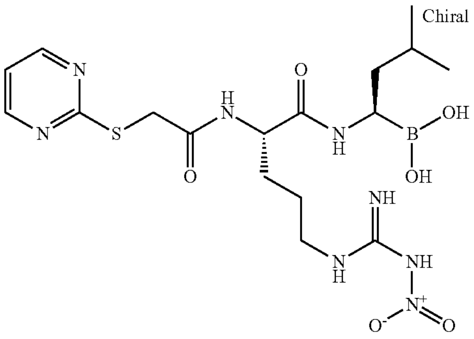 [SMILES: CC(C)C[C@H](NC(=O)[C@H](CCCNC(=N)N[N+](=O)[O-])NC(=O)CSc1ncccn1)B(O)O] | Chemical Name: Boronic acid, [(1R)-1-[[(2S)-5-[[imino(nitroamino)methyl]amino]-2-[[2-(pyrimidin-2-ylsulfanyl)acetyl]amino]-1-oxopentyl]amino]-3-methylbutyl] Analytical Data: MS: [M − 18]H+ 467.0 |
| E.2.55 | 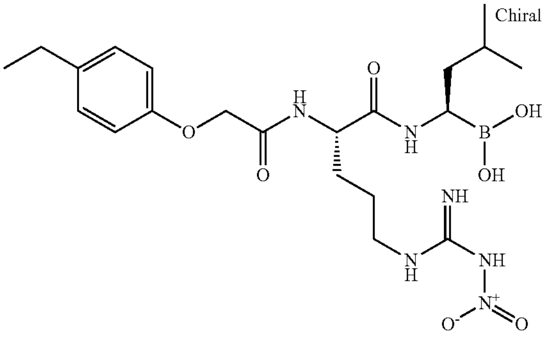 [SMILES: CCc1ccc(OCC(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[[2-(4-ethylphenoxy)acetyl]amino]-1-oxopentyl]amino]-3-methylbutyl] Analytical Data: MS: [M − 18]H+ 476.9 |

TABLE E-2-continued

| Ex # | Structure | Chemical Name and Analytical Data |
| --- | --- | --- |
| E.2.56 | 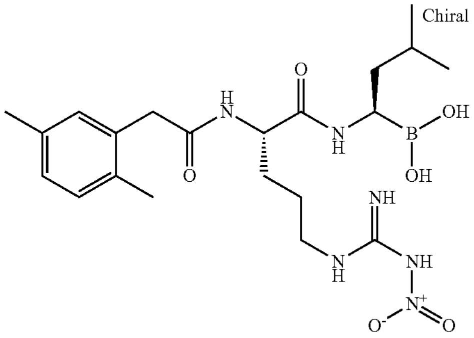 [SMILES: Cc1ccc(C)c(CC(=O)N[C@@H](CCCNC(=N)N[N+](=O)[O-])C(=O)N[C@@H](CC(C)C)B(O)O)c1] | Chemical Name: Boronic acid, [(1R)-1-[[(2S)-5-[[imino(nitroamino)methyl]amino]-2-[[2-(2,5-dimethylphenyl)acetyl]amino]-1-oxopentyl]amino]-3-methylbutyl] Analytical Data: MS: [M − 18]H+ 461.4 |
| E.2.57 | 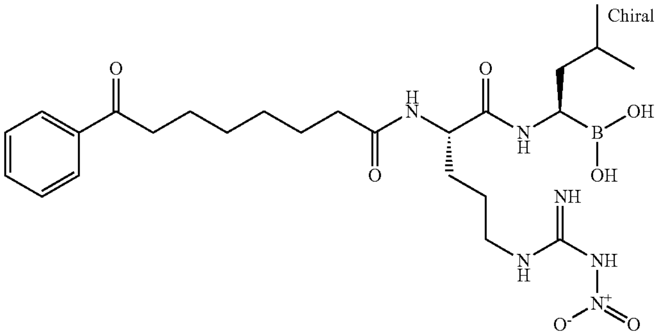 [SMILES: CC(C)C[C@H](NC(=O)[C@H](CCCNC(=N)N[N+](=O)[O-])NC(=O)CCCCCCC(=O)c1ccccc1)B(O)O] | Chemical Name: Boronic acid, [(1R)-1-[[(2S)-5-[[imino(nitroamino)methyl]amino]-2-[(8-oxo-8-phenyloctanoyl)amino]-1-oxopentyl]amino]-3-methylbutyl] Analytical Data: MS: [M − 18]H+ 531.0 |
| E.2.58 | 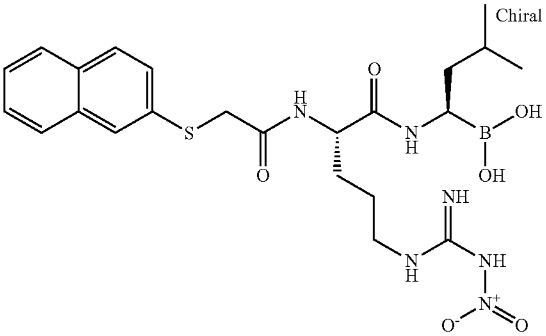 [SMILES: CC(C)C[C@H](NC(=O)[C@H](CCCNC(=N)N[N+](=O)[O-])NC(=O)CSc1ccc2ccccc2c1)B(O)O] | Chemical Name: Boronic acid, [(1R)-1-[[(2S)-5-[[imino(nitroamino)methyl]amino]-2-[[2-(2-naphthylsulfanyl)acetyl]amino]-1-oxopentyl]amino]-3-methylbutyl] Analytical Data: MS: [M − 18]H+ 515.6 |
| E.2.59 | 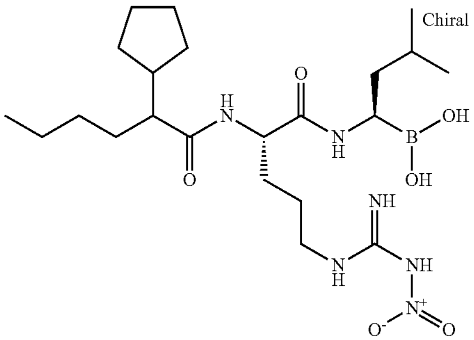 [SMILES: CCCCC(C(=O)N[C@@H](CCCNC(=N)N[N+](=O)[O-])C(=O)N[C@@H](CC(C)C)B(O)O)C1CCCC1] | Chemical Name: Boronic acid, [(1R)-1-[[(2S)-5-[[imino(nitroamino)methyl]amino]-2-[[(RS)-2-cyclopentylhexanoyl]amino]-1-oxopentyl]amino]-3-methylbutyl] Analytical Data: MS: [M − 18]H+ 481.1 |

TABLE E-2-continued

| Ex # | Structure | Chemical Name and Analytical Data |
|---|---|---|
| E.2.60 | 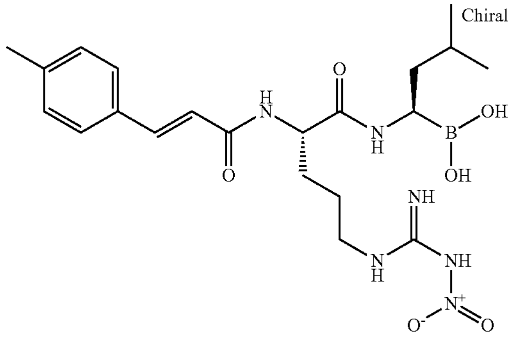 [SMILES: Cc1ccc(/C=C/C(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[[3-(4-methylphenyl)acryl]amino]-1-oxopentyl]amino]-3-methylbutyl] Analytical Data: MS: [M − 18]H+ 459.0 |
| E.2.61 | 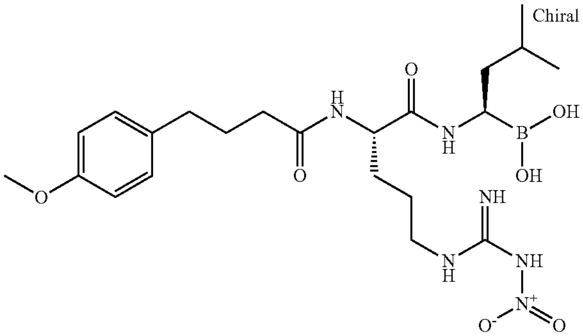 [SMILES: COc1ccc(CCCC(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[[4-(4-methoxyphenyl)-butanoyl]amino]-1-oxopentyl]amino]-3-methylbutyl] Analytical Data: MS: [M − 18]H+ 491.6 |
| E.2.62 | 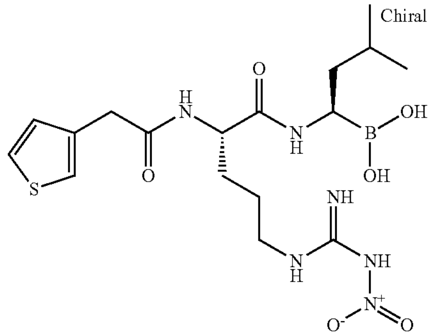 [SMILES: CC(C)C[C@H](NC(=O)[C@H](CCCNC(=N)N[N+](=O)[O-])NC(=O)Cc1ccsc1)B(O)O] | Chemical Name: Boronic acid, [(1R)-1-[[(2S)-5-[[imino(nitroamino)methyl]amino]-2-[(2-thiophen-3-yl-acetyl)amino]-1-oxopentyl]amino]-3-methylbutyl] Analytical Data: MS: [M − 18]H+ 438.9 |
| E.2.63 | 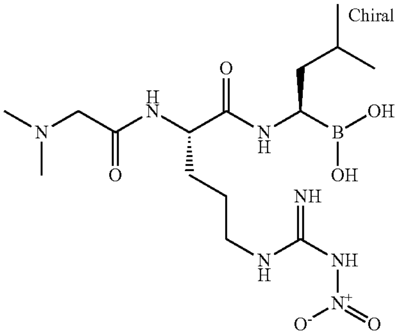 [SMILES: CC(C)C[C@H](NC(=O)[C@H](CCCNC(=N)N[N+](=O)[O-])NC(=O)CN(C)C)B(O)O] | Chemical Name: Boronic acid, [(1R)-1-[[(2S)-5-[[imino(nitroamino)methyl]amino]-2-[[2-(dimethylamino)acetyl]amino]-1-oxopentyl]amino]-3-methylbutyl] Analytical Data: MS: [M − 18]H+ 400.2 |

TABLE E-2-continued

| Ex # | Structure | Chemical Name and Analytical Data |
| --- | --- | --- |
| E.2.64 | 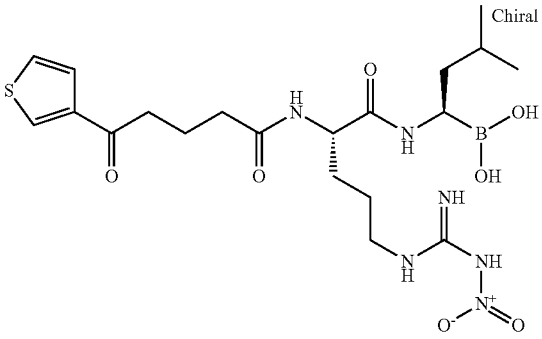 [SMILES: CC(C)C[C@H](NC(=O)[C@H](CCCNC(=N)N[N+](=O)[O-])NC(=O)CCCC(=O)c1ccsc1)B(O)O] | Chemical Name: Boronic acid, [(1R)-1-[[(2S)-5-[[imino(nitroamino)methyl]amino]-2-[[5-oxo-5-(thiophen-3-yl)pentanoyl]amino]-1-oxopentyl]amino]-3-methylbutyl] Analytical Data: MS: [M − 18]H+ 494.9 |
| E.2.65 | 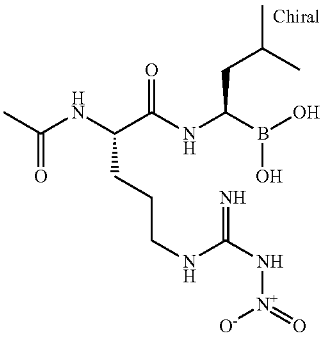 [SMILES: CC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(acetyl)amino]-1-oxopentyl]amino]-3-methylbutyl] Analytical Data: MS: [M − 18]H+ 357.2 |
| E.2.66 | 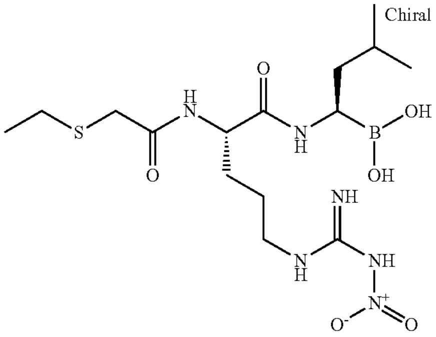 [SMILES: CCSCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(2-ethylsulfanylacetyl)amino]-1-oxopentyl]amino]-3-methylbutyl] Analytical Data: MS: [M − 18]H+ 417.4 |
| E.2.67 | 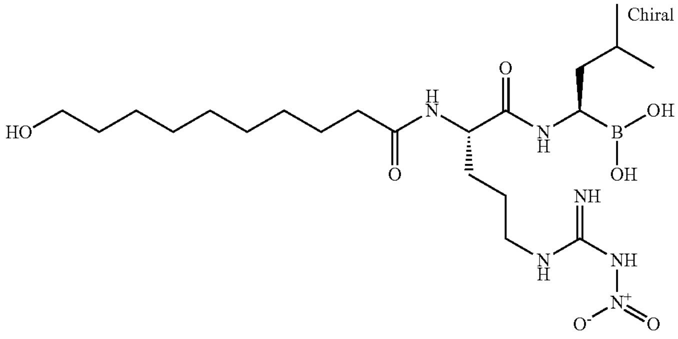 | Chemical Name: Boronic acid, [(1R)-1-[[(2S)-5-[[imino(nitroamino)methyl]amino]-2-[(10-hydroxydecanoyl)amino]-1-oxopentyl]amino]-3-methylbutyl] Analytical Data: MS: [M − 2H2O]H+ 467.0 |

TABLE E-2-continued

| Ex # | Structure | Chemical Name and Analytical Data |
| --- | --- | --- |
| E.2.68 | 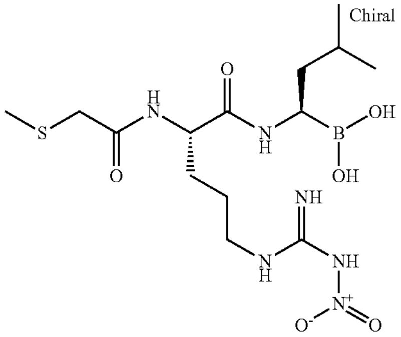 [SMILES: CSCC(=O)N[C@@H](CCCNC(=N)N[N+](=O)[O-])C(=O)N[C@@H](CC(C)C)B(O)O] | Chemical Name:<br>Boronic acid, [(1R)-1-[[(2S)-5-[[imino(nitroamino)methyl]amino]-2-[(2-methylfulanylacetyl)amino]-1-oxopentyl]amino]-3-methylbutyl]<br>Analytical Data:<br>MS: [M − 18]H+ 402.9 |
| E.2.69 | 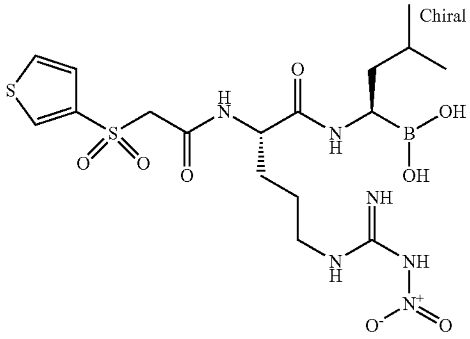 [SMILES: CC(C)C[C@H](NC(=O)[C@H](CCCNC(=N)N[N+](=O)[O-])NC(=O)CS(=O)(=O)c1ccsc1)B(O)O] | Chemical Name:<br>Boronic acid, [(1R)-1-[[(2S)-5-[[imino(nitroamino)methyl]amino]-2-[[(thiophene-2-sulfonyl)acetyl]amino]-1-oxopentyl]amino]-3-methylbutyl]<br>Analytical Data:<br>MS: [M − 18]H+ 503.1 |
| E.2.70 | 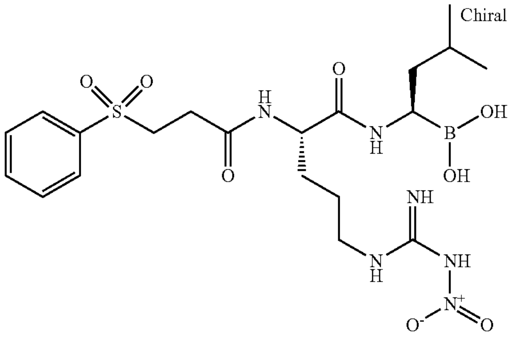 [SMILES: CC(C)C[C@H](NC(=O)[C@H](CCCNC(=N)N[N+](=O)[O-])NC(=O)CCS(=O)(=O)c1ccccc1)B(O)O] | Chemical Name:<br>Boronic acid, [(1R)-1-[[(2S)-5-[[imino(nitroamino)methyl]amino]-2-[[3-(benzenesulfonyl)propanoyl]amino]-1-oxopentyl]amino]-3-methylbutyl]<br>Analytical Data:<br>MS: [M − 18]H+ 510.9 |
| E.2.71 | 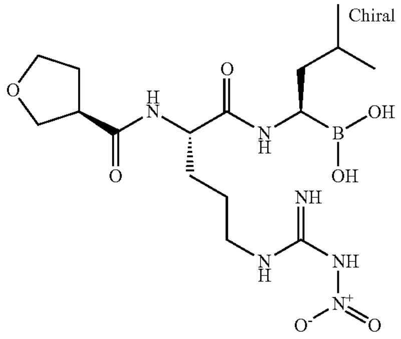 [SMILES: CC(C)C[C@H](NC(=O)[C@H](CCCNC(=N)N[N+](=O)[O-])NC(=O)[C@@H]1CCOC1)B(O)O] | Chemical Name:<br>Boronic acid, [(1R)-1-[[(2S)-5-[[imino(nitroamino)methyl]amino]-2-[[(RS)-tetrahydrofuran-3-carbonyl]amino]-1-oxopentyl]amino]-3-methylbutyl]<br>Analytical Data:<br>MS: [M − 18]H+ 413.2 |

TABLE E-2-continued

| Ex # | Structure | Chemical Name and Analytical Data |
| --- | --- | --- |
| E.2.72 | 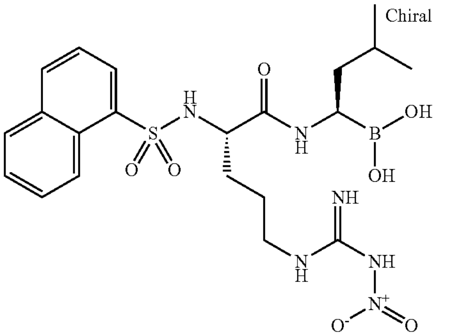 [SMILES: CC(C)C[C@H](NC(=O)[C@H](CCCNC(=N)N[N+](=O)[O-])NS(=O)(=O)c1cccc2ccccc12)B(O)O] | Chemical Name: Boronic acid, [(1R)-1-[[(2S)-5-[[imino(nitroamino)methyl]amino]-2-[(naphthalene-1-sulfonyl)amino]-1-oxopentyl]amino]-3-methylbutyl]- Analytical Data: MS: [M − 18]H+ 505.23 |
| E.2.73 | 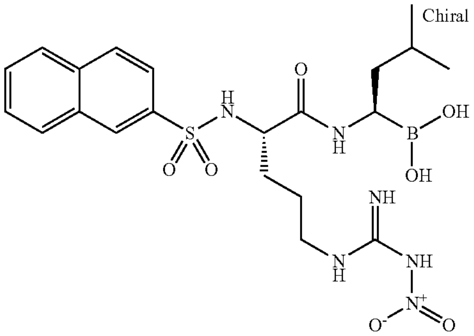 [SMILES: CC(C)C[C@H](NC(=O)[C@H](CCCNC(=N)N[N+](=O)[O-])NS(=O)(=O)c1ccc2ccccc2c1)B(O)O] | Chemical Name: Boronic acid, [(1R)-1-[[(2S)-5-[[imino(nitroamino)methyl]amino]-2-[(naphthalene-2-sulfonyl)amino]-1-oxopentyl]amino]-3-methylbutyl]- Analytical Data: MS: [M − 18]H+ 505.49 |
| E.2.74 | 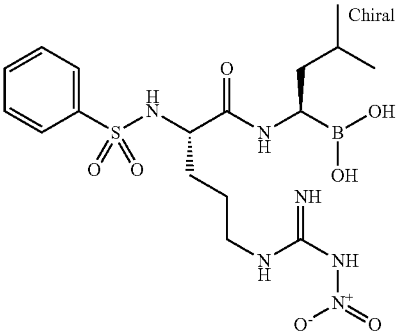 [SMILES: CC(C)C[C@H](NC(=O)[C@H](CCCNC(=N)N[N+](=O)[O-])NS(=O)(=O)c1ccccc1)B(O)O] | Chemical Name: Boronic acid, [(1R)-1-[[(2S)-5-[[imino(nitroamino)methyl]amino]-2-[(benzenesulfonyl)amino]-1-oxopentyl]amino]-3-methylbutyl]- Analytical Data: MS: [M − 18]H+ 455.37 |

Further compounds prepared according to the above procedure for Example E.2 are reported in Table E-2A.

TABLE E-2A

| Ex # | Structure | Chemical Name and Analytical Data |
| --- | --- | --- |
| E.2.75 | 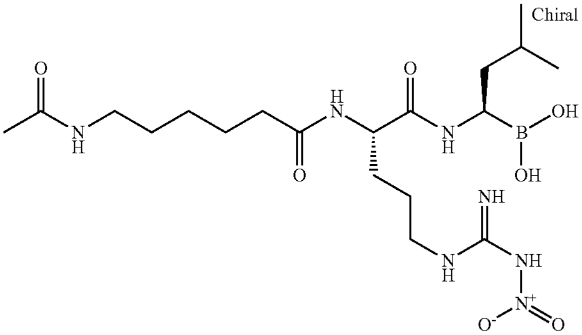 [SMILES: CC(=O)NCCCCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[[6-(acetylamino)hexanoyl]amino]-1-oxopentyl]amino]-3-methylbutyl] Analytical Data: MS: [M − 18]H+ 470.2 |

TABLE E-2A-continued

| Ex # | Structure | Chemical Name and Analytical Data |
| --- | --- | --- |
| E.2.76 | 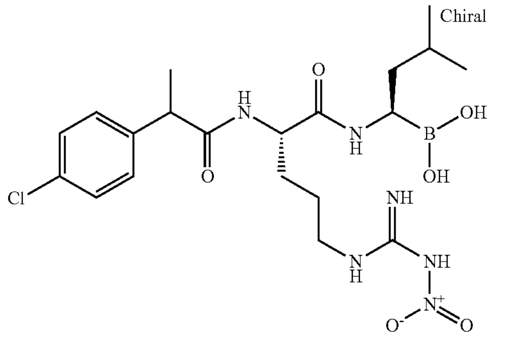 [SMILES: CC(C)C[C@H](NC(=O)[C@H](CCCNC(=N)N[N+](=O)[O-])NC(=O)C(C)c1ccc(Cl)cc1)B(O)O] | Chemical Name: Boronic acid, [(1R)-1-[[(2S)-5-[[imino(nitroamino)methyl]amino]-2-[[(RS)-2-(4-chlorophenyl)propanoyl]amino]-1-oxopentyl]amino]-3-methylbutyl] Analytical Data: MS: [M − 18]H+ 481.1 |
| E.2.77 | 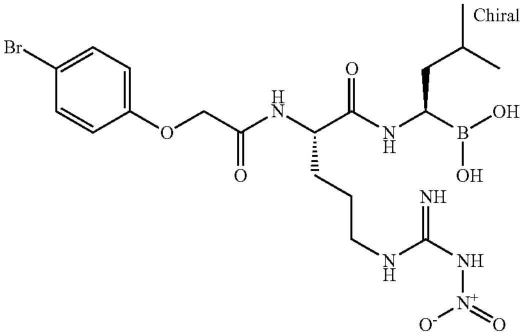 | Chemical Name: Boronic acid, [(1R)-1-[[(2S)-5-[[imino(nitroamino)methyl]amino]-2-[[2-(4-bromophenoxy)acetyl]amino]-1-oxopentyl]amino]-3-methylbutyl] Analytical Data: MS: [M − 18]H+ 524.1 |
| E.2.78 | 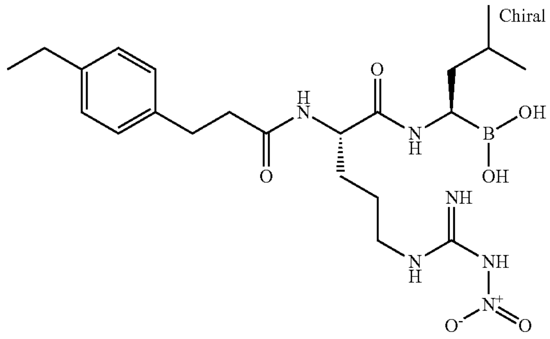 [SMILES: CCc1ccc(CCC(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[[3-(4-ethylphenyl)propanoyl]amino]-1-oxopentyl]amino]-3-methylbutyl] Analytical Data: MS: [M − 18]H+ 475.2 |
| E.2.79 | 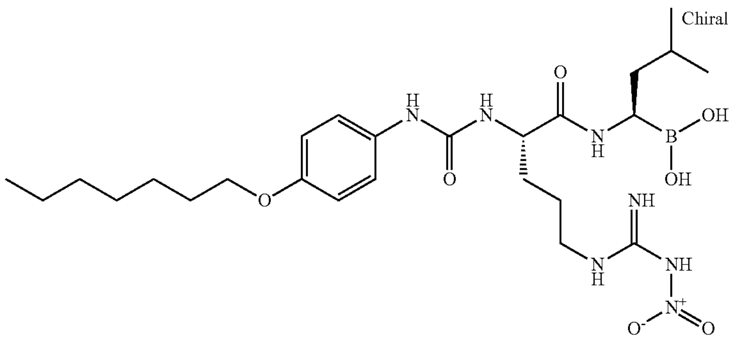 [SMILES: CCCCCCCOc1ccc(NC(=O)N[C@@H](CCCNC(=N)N[N+](=O)[O-])C(=O)N[C@@H](CC(C)C)B(O)O)cc1] | Chemical Name: Boronic acid, [(1R)-1-[[(2S)-5-[[imino(nitroamino)methyl]amino]-2-[3-[4-(heptyloxy)phenyl]-ureido]-1-oxopentyl]amino]-3-methylbutyl] Analytical Data: MS: [M − 18]H+ 548.3 |

TABLE E-2A-continued

| Ex # | Structure | Chemical Name and Analytical Data |
|---|---|---|
| E.2.80 | 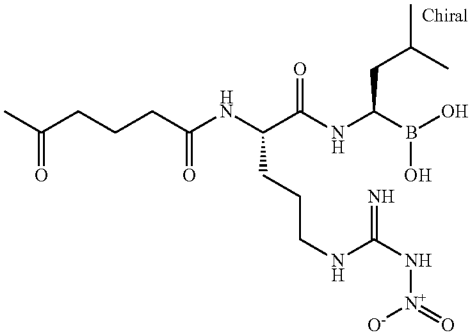 [SMILES: CC(=O)CCCC(=O)N[C@@H](CCCNC(=N)N[N+](=O)[O-])C(=O)N[C@@H](CC(C)C)B(O)O] | Chemical Name: Boronic acid, [(1R)-1-[[(2S)-5-[[imino(nitroamino)methyl]amino]-2-[(5-oxohexanoyl)amino]-1-oxopentyl]amino]-3-methylbutyl] Analytical Data: MS: [M − 18]H+ 427.2 |
| E.2.81 | 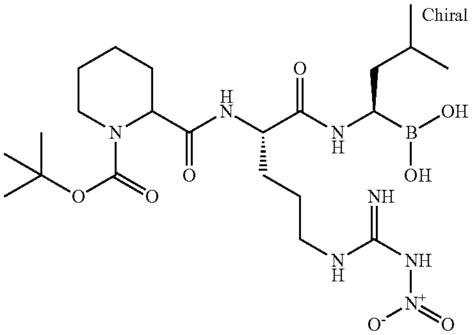 [SMILES: CC(C)C[C@H](NC(=O)[C@H](CCCNC(=N)N[N+](=O)[O-])NC(=O)C1CCCCN1C(=O)OC(C)(C)C)B(O)O] | Chemical Name: Boronic acid, [(1R)-1-[[(2S)-5-[[imino(nitroamino)methyl]amino]-2-[[(2RS)-1-[(1,1-dimethylethoxy)carbonyl]piperidine-2-carbonyl]amino]-1-oxopentyl]amino]-3-methylbutyl] Analytical Data: MS: [M − 18]H+ 526.2 |

Example E.3

Boronic acid, [(1R)-1-[[(2S,3R)-3-hydroxy-2-[(4-butylbenzoyl)amino]-1-oxobutyl]amino]-3-methylbutyl]

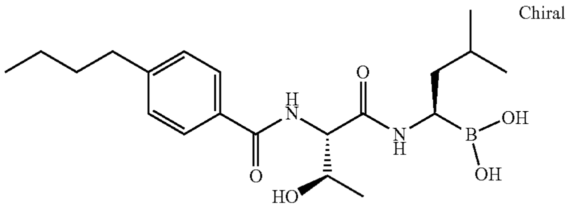 [SMILES: CCCCc1ccc(C(=O)N[C@H](C(=O)N[C@@H](CC(C)C)B(O)O)[C@@H](C)O)cc1]

A mixture of 4-butylbenzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]-carbonyl]-2-hydroxypropyl]- of Example D.3.179 (1.38 g, 2.63 mmol), 2-methylpropylboronic acid (0.75 g, 7.37 mmol) and 2N aqueous hydrochloric acid (2 ml) in a heterogeneous mixture of methanol (20 ml) and hexane (20 ml) was stirred at room temperature for 16 hours. The mixture was diluted with methanol (20 ml) and hexane (20 ml) then the hexane layer was removed. Ethyl acetate (50 ml) was added to the methanol layer which was then concentrated. The residue was taken up with ethyl acetate and the mixture was concentrated. This step was repeated (2-3 times) until an amorphous white solid was obtained. The solid was then triturated with diethyl ether (10-15 ml) and the surnatant was removed by decantation. This step was repeated 4 times. After a further trituration with diethyl ether (15 ml) the white solid was collected by filtration and dried under vacuum at room temperature (0.724 g, 70% yield).

$^1$H NMR (MeOH-$d_4$): 7.83 (2H, d, J=8.2); 7.34 (2H, d, J=8.2); 4.77 (1H, d, J=6.4); 4.36-4.28 (1H, m); 2.77 (1H, t, J=7.6); 2.71 (2H, t, J=7.6); 1.72-1.58 (3H, m); 1.46-1.32 (4H, m); 1.29 (3H, d, J=6.4); 0.97 (3H, t, J=7.34); 0.94 (6H, dd, J=1.1, 6.6)

Further compounds prepared according to the above procedure for Example E.3 are reported in Table E-3.

TABLE E-3

| Ex # | Structure | Chemical Name and Analytical Data |
|---|---|---|
| E.3.1 | 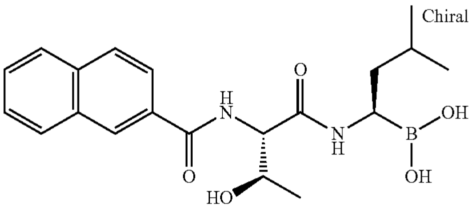 [SMILES: CC(C)C[C@H](NC(=O)[C@@H](NC(=O)c1ccc2ccccc2c1)[C@@H](C)O)B(O)O] | Chemical Name: Boronic acid, [(1R)-1-[[(2S,3R)-3-hydroxy-2-[(2-naphthoyl)amino]-1-oxobutyl]amino]-3-methylbutyl]. Analytical Data: $^1$H NMR (MeOH-d4): 8.51 (1H, s); 8.10-7.95 (4H, m); 7.66-7.58 (1H, m); 4.84 (1H, d, J = 4.1); 4.42-4.33 (1H, m); 2.77 (1H, t, J = 7.6); 1.75-1.62 (1H, m); 1.41-1.36 (2H, m); 1.34 (3H, d, J = 6.4); 0.94 (6H, d, J = 6.5). |

TABLE E-3-continued

| Ex # | Structure | Chemical Name and Analytical Data |
|---|---|---|
| E.3.2 | 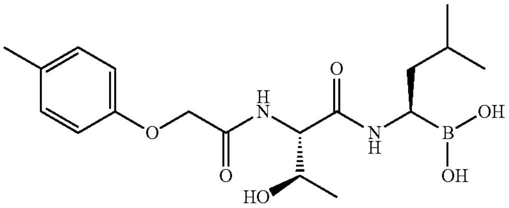 [SMILES: Cc1ccc(OCC(=O)N[C@H](C(=O)N[C@@H](CC(C)C)B(O)O)[C@@H](C)O)cc1] | Chemical Name: Boronic acid, [(1R)-1-[[(2S,3R)-3-hydroxy-2-[(p-tolyloxyacetamide]-1-oxobutyl]amino]-3-methylbutyl]. Analytical Data: $^1$H NMR (MeOH-d4): 7.14 (2H, d, J = 8.5); 6.92 (2H, d, J = 8.6); 4.63-4.59 (3H, m); 4.31-4.24 (1H, m); 2.75 (1H, t, J = 7.5); 1.72-1.60 (1H, m); 1.38-1.33 (2H, m); 1.31 (3H, s); 1.17 (3H, d, J = 6.4); 0.95-0.92 (6H, m). |
| E.3.3 | 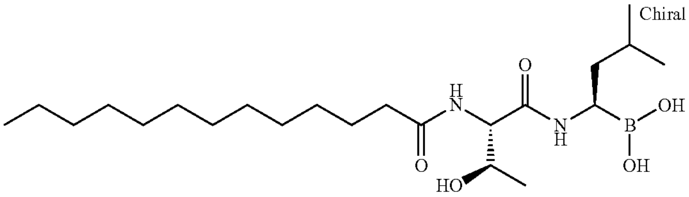 [SMILES: CCCCCCCCCCCCC(=O)N[C@H](C(=O)N[C@@H](CC(C)C)B(O)O)[C@@H](C)O] | Chemical Name: Boronic acid, [(1R)-1-[[(2S,3R)-3-hydroxy-2-[(tridecanoyl)amino]-1-oxobutyl]amino]-3-methylbutyl]. Analytical Data: M.p 97-116° C. $^1$H NMR (MeOH-d4): 4.55 (1H, d, J = 3.9); 4.23-4.16 (1H, m); 2.73 (1H, t, J = 7.6); 2.36-2.30 (2H, m); 1.73-1.60 (3H, m); 1.40-1.26 (20H, m); 1.22 (3H, d, J = 6.4); 0.97-0.90 (9H, m). |
| E.3.4 | 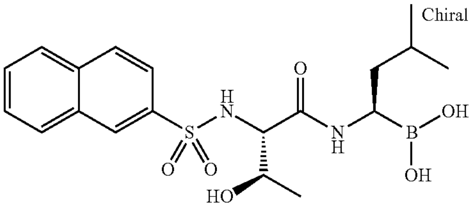 [SMILES: CC(C)C[C@H](NC(=O)[C@@H](NS(=O)(=O)c1ccc2ccccc2c1)[C@@H](C)O)B(O)O] | Chemical Name: Boronic acid, [(1R)-1-[[(2S,3R)-3-hydroxy-2-[(naphthalene-2-sulfonyl)amino]-1-oxobutyl]amino]-3-methylbutyl]. Analytical Data: $^1$H NMR (MeOH-d4): 8.44 (1H, s); 8.04 (2H, d, J = 8.6); 7.98 (1H, d, J = 7.9); 7.87 (1H, d, J = 8.7); 7.71-7.61 (2H, m); 4.10-4.02 (2H, m); 2.36 (1H, dd, J = 6.5, 8.7); 1.40-1.26 (1H, m); 1.12 (3H, d, J = 5.9); 1.07-0.87 (2H, m); 0.74 (3H, d, J = 6.6); 0.72 (3H, d, J = 6.6). |
| E.3.5 | 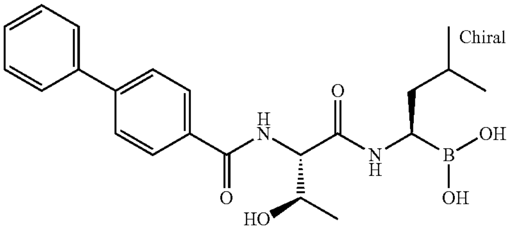 [SMILES: CC(C)C[C@H](NC(=O)[C@@H](NC(=O)c1ccc(-c2ccccc2)cc1)[C@@H](C)O)B(O)O] | Chemical Name: Boronic acid, [(1R)-1-[[(2S,3R)-3-hydroxy-2-[(4-phenylbenzoyl)amino]-1-oxobutyl]amino]-3-methylbutyl]. Analytical Data: Mp 200-208° C. $^1$H NMR (MeOH-d4): 8.00 (2H, d, J = 8.4); 7.79 (2H, d, J = 8.4); 7.70 (2H, d, J = 7.3); 7.49 (2H, t, J = 7.5); 7.41 (1H, t, J = 7.3); 4.80 (1H, d, J = 4.1); 4.38-4.31 (1H, m); 2.78 (1H, t, J = 7.6); 1.73-1.62 (1H, m); 1.41-1.35 (2H, m); 1.31 (3H, d, J = 6.4); 0.94 (6H, d, J = 6.5). |
| E.3.6 | 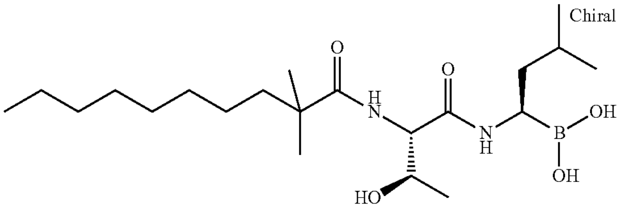 [SMILES: CCCCCCCCC(C)(C)C(=O)N[C@H](C(=O)N[C@@H](CC(C)C)B(O)O)[C@@H](C)O] | Chemical Name: Boronic acid, [(1R)-1-[[(2S,3R)-3-hydroxy-2-[(2,2dimethyl-decanoyl)amino]-1-oxobutyl]amino]-3-methylbutyl]. Analytical Data: $^1$H NMR (MeOH-d4): 4.40 (1H, m); 4.05-3.95 (1H, m); 1.65-1.55 (1H, m); 1.50-1.40 (2H, m); 1.25-1.15 (14H, m); 1.10 (6H, d, J = 8.8); 1.06 (3H, d, J = 6.3); 0.82-0.88 (9H, m). |
| E.3.7 | 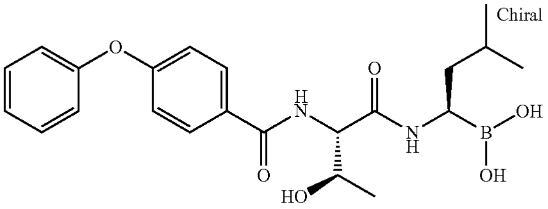 [SMILES: CC(C)C[C@H](NC(=O)[C@@H](NC(=O)c1ccc(Oc2ccccc2)cc1)[C@@H](C)O)B(O)O] | Chemical Name: Boronic acid, [(1R)-1-[[(2S,3R)-3-hydroxy-2-[(4-Phenoxybenzoyl)amino]-1-oxobutyl]amino]-3-methylbutyl]. Analytical Data: $^1$H NMR (DMSO-d6 + MeOH-d4): 7.90 (2H, d, J = 8.7); 7.38 (2H, t, J = 7.9); 7.16 (1H, t, J = 7.4); 7.02 (4H, t, J = 8.6); 4.53 (1H, d, J = 4.83); 4.10-3.95 (2H, m); 2.53-2.44 (1H, m); 1.62-1.48 (1H, m); 1.22-1.49 (2H, m); 1.09 (3H, d, J = 6.35); 0.83-0.76 (6H, m). |

TABLE E-3-continued

| Ex # | Structure | Chemical Name and Analytical Data |
|---|---|---|
| E.3.8 | 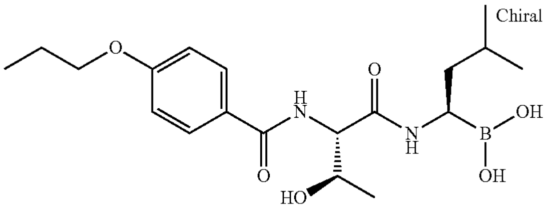 [SMILES: CCCOc1ccc(C(=O)N[C@H](C(=O)N[C@@H](CC(C)C)B(O)O)[C@@H](C)O)cc1] | Chemical Name:<br>Boronic acid, [(1R)-1-[[(2S,3R)-3-hydroxy-2-[[4-(1-propoxy)butylbenzoyl]amino]-1-oxobutyl]amino]-3-methylbutyl].<br>Analytical Data:<br>$^{1}$H NMR (MeOH-d4): 7.88 (2H, d, J = 8.9); 7.02 (2H, d, J = 8.9); 4.76 (1H, d, J = 4.0); 4.32 (1H, dq, J = 4.2, 6.4); 4.03 (2H, t, J = 6.5); 2.76 (1H, t, J = 7.6); 1.89-1.79 (2H, m); 1.72-1.60 (1H, m); 1.36 (2H, t, J = 6.9); 1.28 (3H, d, J = 6.4); 1.08 (3H, t, J = 7.4); 0.93 (1H, dd, J = 1.8, 6.6) |
| E.3.9 | 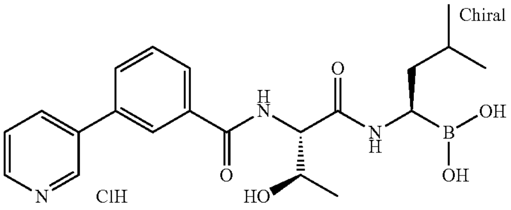 [SMILES: CC(C)C[C@H](NC(=O)[C@@H](NC(=O)c1cccc(-c2cccnc2)c1)[C@@H](C)O)B(O)O ; Cl] | Chemical Name:<br>Boronic acid, [(1R)-1-[[(2S,3R)-3-hydroxy-2-[(3-pyridin-3-yl-benzoyl)amino]-1-oxobutyl]amino]-3-methylbutyl], hydrochloride salt.<br>Analytical Data:<br>$^{1}$H NMR (MeOH-d4): 8.90 (1H, s); 8.58 (1H, d, J = 4.26); 8.22 (1H, t, J = 1.59); 8.21-8.16 (1H, m); 7.97 (1H, m); 7.93-7.89 (1H, m); 7.66 (1H, t, J = 7.78); 7.60-7.54 (1H, m); 4.80 (1H, d, J = 4.41); 4.38-4.28 (1H, m); 2.77 (1H, t, J = 7.63); 1.71-1.60 (1H, m); 1.39-1.33 (2H, m); 1.29 (3H, d, J = 6.38); 0.95-0.90 (6H, m). |
| E.3.10 | 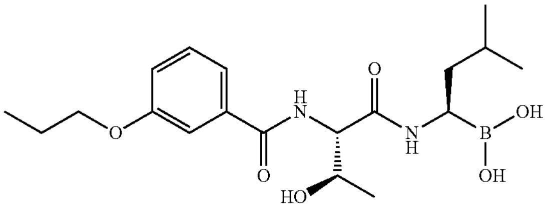 [SMILES: CCCOc1cccc(C(=O)N[C@H](C(=O)N[C@@H](CC(C)C)B(O)O)[C@@H](C)O)c1] | Chemical Name:<br>Boronic acid, [(1R)-1-[[(2S,3R)-3-hydroxy-2-[(3-propoxy-benzoyl)amino]-1-oxobutyl]amino]-3-methylbutyl].<br>Analytical Data:<br>$^{1}$H NMR (MeOH-d4): 7.49-7.44 (2H, m); 7.41 (1H, t, J = 7.82); 7.18-7.12 (1H, m); 4.76 (1H, d, J = 4.21); 4.36-4.27 (1H, m); 4.02 (2H, t, J = 6.45); 2.77 (1H, t, J = 7.61); 1.90-1.79 (2H, m); 1.72-1.60 (1H, m); 1.40-1.34 (2H, m); 1.29 (3H, t, J = 6.39); 1.08 (3H, t, J = 7.42); 0.94 (6H, d, J = 6.48). |
| E.3.11 | 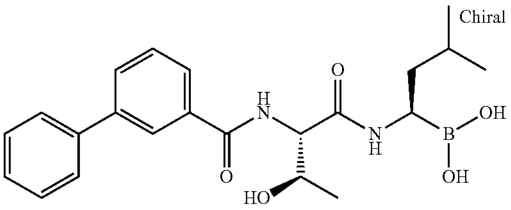 [SMILES: CC(C)C[C@H](NC(=O)[C@@H](NC(=O)c1cccc(-c2ccccc2)c1)[C@@H](C)O)B(O)O] | Chemical Name:<br>Boronic acid, [(1R)-1-[[(2S,3R)-3-hydroxy-2-[(3-phenylbenzoyl)amino]-1-oxobutyl]amino]-3-methylbutyl].<br>Analytical Data:<br>$^{1}$H NMR (MeOH-d4): 8.18 (1H, t, 1.7); 7.92-7.85 (2H, m); 7.73-7.69 (2H, m); 7.61 (1H, 7, J = 7.8); 7.52-7.46 (2H, m); 7.43-7.37 (1H, m); 4.81 (1H, d, J = 4.3); 4.38-4.31 (1H, m); 2.78 (1H, t, J = 7.6); 1.72-1.62 (1H, m); 1.38 (2H, t, J = 8.7); 1.31 (3H, d, J = 6.4); 0.94 (6H, d, J = 6.5). |
| E.3.12 | 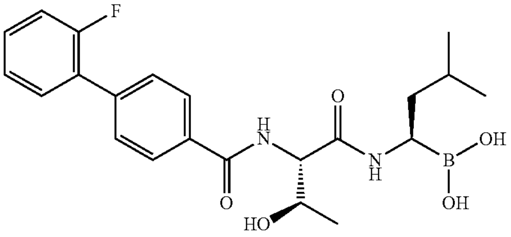 [SMILES: CC(C)C[C@H](NC(=O)[C@@H](NC(=O)c1ccc(-c2ccccc2F)cc1)[C@@H](C)O)B(O)O] | Chemical Name:<br>Boronic acid, [(1R)-1-[[(2S,3R)-3-hydroxy-2-[(4-(2-fluorophenyl)benzoyl)amino]-1-oxobutyl]amino]-3-methylbutyl].<br>Analytical Data:<br>$^{1}$H NMR (MeOH-d4): 8.04-7.99 (2H, m); 7.75-7.69 (2H, m); 7.59-7.53 (1H, m); 7.47-7.40 (1H, m); 7.34-7.28 (1H, m); 7.28-7.20 (1H, m); 4.81 (1H, d, J = 4.2); 4.39-4.30 (1H, m); 2.79 (1H, 7.63); 1.74-1.62 (1H, m); 1.42-1.34 (2H, m); 1.32 (3H, d, J = 6.39); 0.98-0.92 (6H, m). |

Example E.4

Boronic acid, [(1R)-1-[[(2S,3R)-3-hydroxy-2-[[4-(3-pyridyl)benzoyl]amino]-1-oxobutyl]amino]-3-methylbutyl]

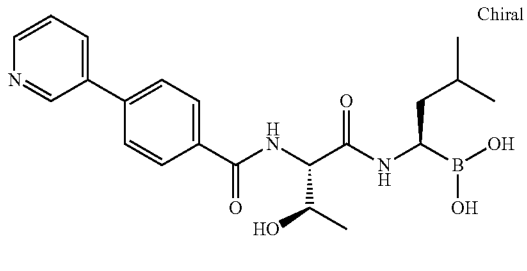 [SMILES: CC(C)C[C@H](NC(=O)[C@@H](NC(=O)c1ccc(-c2cccnc2)cc1)[C@@H](C)O)B(O)O]

A mixture of 4-(pyridin-3-yl)benzamide, N-[(1S,2R)-1-[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-hydroxypropyl]- of Example D.8.3 (155 mg, 0.283 mmol), 2-methylpropylboronic acid (81 mg, 0.793 mmol) and 2N aqueous hydrochloric acid (0.3 ml) in a heterogeneous mixture of methanol (3 ml) and hexane (3 ml) was stirred at room temperature for 24 hours. The hexane layer was removed and the methanolic layer was washed with fresh hexane (about 5 ml). Ethyl acetate (10 ml) was added to the methanol layer which was then concentrated. The residue was taken up with ethyl acetate and the mixture was concentrated. This step was repeated (2-3 times) until an amorphous white solid was obtained. The solid was then triturated with diethyl ether (5 ml) and the surnatant was removed by decantation. This step was repeated. The residue (126 mg) was combined with the product of a similar preparation (140 mg) and dissolved in ethyl acetate (about 40 ml) and a small amount of methanol (2-3 ml). The solution was washed with a mixture of NaCl saturated solution (7 ml) and 10% $NaHCO_3$ (2 ml). The layers were separated and the aqueous phase was further washed with ethyl acetate (2×20 ml). The combined organic phases were dried over sodium sulfate and concentrated. The residue was taken up with ethyl acetate (about 20 ml) and the minimum amount of methanol, and then concentrated to small volume (about 5 ml). The resulting white was collected by filtration and dried under vacuum at 50° C. (160 mg, 65% overall yield).

$^1$H NMR (MeOH-$d_4$): 8.90 (1H, s); 8.49 (1H, d, J=4.0); 8.20 (1H, d, J=8.1); 8.06 (2H, d, J=8.1); 7.85 (2H, d, J=8.1); 7.58 (1H, t br., J=6.0); 4.80 (1H, d, J=3.9); 4.40-4.29 (1H, m); 2.78 (1H, t, J=7.5); 1.73-1.61 (1H, m); 1.38 (2H, t, J=6.9); 1.31 (3H, d, J=6.3); 0.94 (6H, d, J=6.31).

Further compounds prepared according to the above procedure for Example E.4 are reported in Table E-4.

TABLE E-4

| Ex # | Structure | Chemical Name and Analytical Data |
|---|---|---|
| E.4.1 | 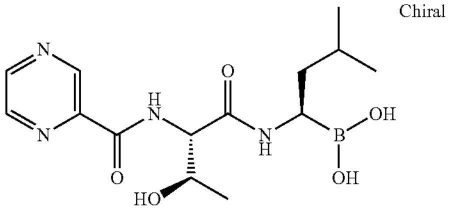 [SMILES: CC(C)C[C@H](NC(=O)[C@@H](NC(=O)c1cnccn1)[C@@H](C)O)B(O)O] | Chemical Name:<br>Boronic acid, [(1R)-1-[[(2S,3R)-3-hydroxy-2-[(2-pyrazinecarbonyl)amino]-1-oxobutyl]amino]-3-methylbutyl].<br>Analytical Data:<br>$^1$H NMR (MeOH-d4): 9.29 (1H, d, J = 1.3); 8.86 (1H, d, J = 1.3); 8.76-8.74 (1H, m); 4.75 (1H, d, J = 3.2); 4.43-4.36 (1H, m); 2.77 (1H, t, J = 7.6); 1.72-1.60 (1H, m); 1.40-1.36 (2H, m); 1.27 (3H, d, J = 7.6); 0.92 (6H, d, J = 7.6). |
| E.4.2 | 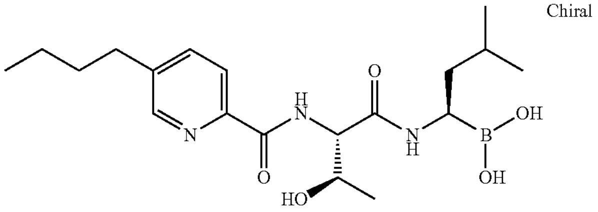 [SMILES: CCCCc1ccc(C(=O)N[C@H](C(=O)N[C@@H](CC(C)C)B(O)O)[C@@H](C)O)nc1] | Chemical Name:<br>Boronic acid, [(1R)-1-[[(2S,3R)-3-hydroxy-2-[(5-butyl-pyridine-2-carbonyl)amino]-1-oxobutyl]amino]-3-methylbutyl].<br>Analytical Data:<br>$^1$H NMR (MeOH-d4): 8.55 (1H, s); 8.04 (1H, d, J = 7.97); 7.84 (1H, d, J = 7.96); 4.73 (1H, d, J = 2.15); 4.42-4.33 (1H, m); 2.81-2.71 (3H, m); 1.75-1.6 (3H, m); 1.5-1.3 (5H, m); 1.27 (3H, d, J = 5.64); 1.02-0.95 (3H, m); 0.94-0.89 (6H, m). |
| E.4.3 | 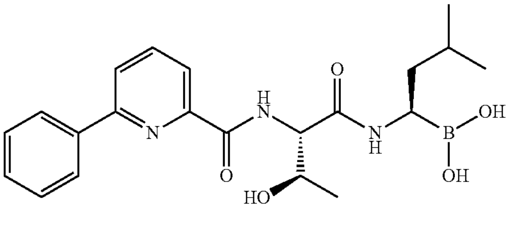 [SMILES: CC(C)C[C@H](NC(=O)[C@@H](NC(=O)c1cccc(-c2ccccc2)n1)[C@@H](C)O)B(O)O] | Chemical Name:<br>Boronic acid, [(1R)-1-[[(2S,3R)-3-hydroxy-2-[(6-phenyl-pyridine-2-carbonyl)amino]-1-oxobutyl]amino]-3-methylbutyl].<br>Analytical Data:<br>$^1$H NMR (MeOH-d4): 8.20 (2H, d, J = 7.52); 8.18-8.12 (1H, m); 8.11-8.06 (2H, m); 7.60-7.43 (3H, m); 4.77 (1H, d, J = 2.66); 4.48-4.40 (1H, m); 2.77 (1H, t, J = 7.54); 1.73-1.60 (1H, m); 1.37 (2H, d, J = 7.3); 1.31 (3H, d, J = 6.36); 0.92 (6H, d, J = 6.55). |

Example E.5

Boronic acid, [(1R)-1-[[(2S)-3-(2-pyrazincarbonylamino)-2-[(4-butylbenzoylamino)]-1-oxopropyl]amino]-3-methylbutyl]

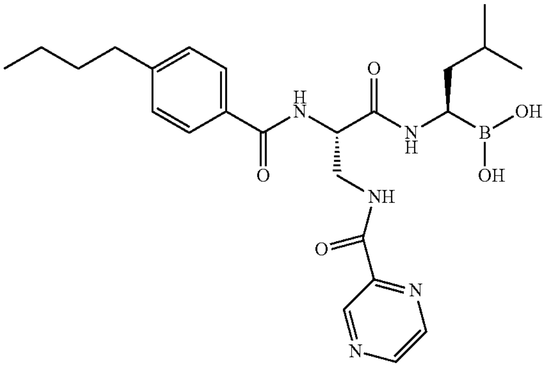 [SMILES: CCCCc1ccc(C(=O)N[C@@H](CNC(=O)c2cnccn2)C(=O)N[C@@H](CC(C)C)B(O)O)cc1]

2-S-(4-Butylbenzoylamino)-3-(2-pyrazinocarbonylamino)-N-[(1S)-1-[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl], from example D.18, (120 mg, 0.19 mmol, 1 eq.), was dissolved in methanol (2 ml), and n-hexane (2 ml). The this solution, Isobutylboronic acid (60 mg, 0.57 mmol, 3 eq,) and HCl 4N 1,4-dioxane (0.07 ml, 0.28 mmol, 1.5 eq.) have been added. The resulting bifasic mixture was stirred at room temperature for 20 h, the n-hexane was removed, the methanolic solution was washed with n-hexane (2 ml) and evaporated under reduced pressure. The crude was suspended in diethyl ether/n-hexane/4 ml), stirred at room temperature and filtered, to give a white powder. Yield 65%, 69 mg.

Analytical data: M.p. 145°-150° C.

$^1$H NMR (MeOD-d4): 9.3 (1H, s); 8.85 (1H, s); 8.75 (1H, s); 7.8 (2H, d); 7.3 (2H, d); 5.1 (2H, t); 4 (2H, dd); 2.8 (1H, t); 2.75 (2H, t); 1.65 (3H, m); 1.4 (4H, m); 1.0 (3H, t) 0.9 (6H, dd).

Further compounds prepared according to the above procedure for Example E.5 are reported in Table E-5.

TABLE E-5

| Ex # | Structure | Chemical Name and Analytical Data |
|---|---|---|
| E.5.1 | 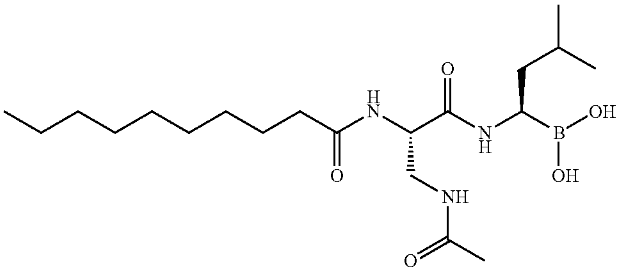 [SMILES: CCCCCCCCCC(=O)N[C@@H](CNC(C)=O)C(=O)N[C@@H](CC(C)C)B(O)O] | Chemical Name:<br>Boronic acid, [(1R)-1-[[(2S)-3-(acetylamino)-2-[(decanoylamino)]-1-oxopropyl]amino]-3-methylbutyl]<br>Analytical Data:<br>$^1$H NMR (MeOD-d4): 4.70 (1H, d); 3.50 (2H, m); 2.75 (1H, t); 2.25 (2H, t); 2.8 (1H, t); 1.95 (3H, s); 1.65 (3H, m); 1.35 (14H, m); 0.9 (9H, m) |
| E.5.2 | 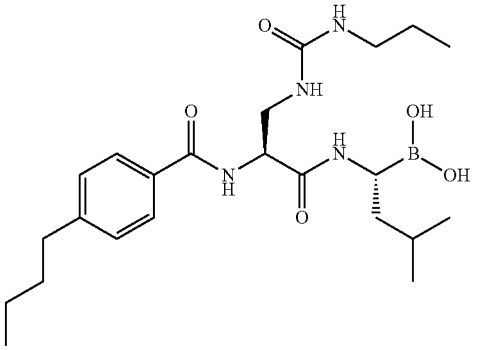 [SMILES: CCCCc1ccc(C(=O)N[C@@H](CNC(=O)NCCC)C(=O)N[C@@H](CC(C)C)B(O)O)cc1] | Chemical Name:<br>Boronic acid, [(1R)-1-[[(2S)-3-(propylureido)-2-[(4-butyl)-benzoylamino]-1-oxopropyl]amino]-3-methylbutyl]<br>Analytical Data:<br>$^1$H NMR (MeOD-d4): 7.80 (2H, d); 7.28 (7H, m); 4.45 (1H, br); 3.7 (1H, br); 3.1 (2H, t); 2.65 (2H, t); 1.7-1.2 (10H, m); 0.9 (12H, m) |
| E.5.3 | 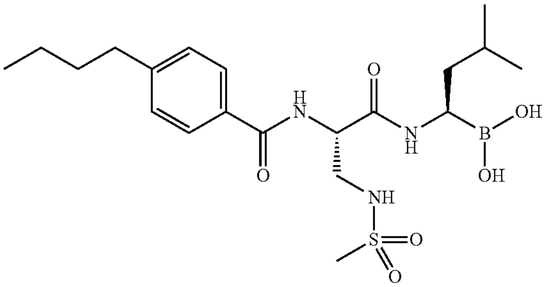 [SMILES: CCCCc1ccc(C(=O)N[C@@H](CNS(C)(=O)=O)C(=O)N[C@@H](CC(C)C)B(O)O)cc1] | Chemical Name:<br>Boronic acid, [(1R)-1-[[(2S)-3-(methanesulfamido)-2-[(4-butyl)-benzoylamino]-1-oxopropyl]amino]-3-methylbutyl]<br>Analitical Data:<br>$^1$H NMR (MeOD-d4): 7.80 (2H, d); 7.28 (7H, m); 3.65 (2H, m); 3.0 (3H, s); 2.8 (1H, br); 1.65 (3H, m); 1.35 (4H, m); 0.9 (12H, m). M.p. 120°-123° C. |

TABLE E-5-continued

| Ex # | Structure | Chemical Name and Analytical Data |
|---|---|---|
| E.5.4 | 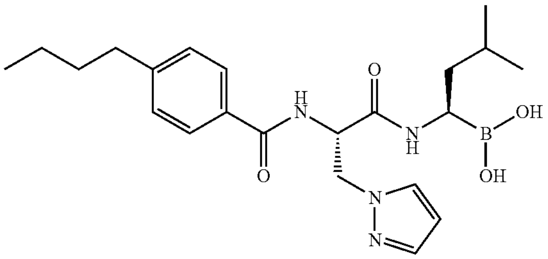 [SMILES: CCCCc1ccc(C(=O)N[C@@H](Cn2cccn2)C(=O)N[C@@H](CC(C)C)B(O)O)cc1] | Chemical Name:<br>Boronic acid, [(1R)-1-[[(2S)-3-[2-(1H-pyrazol)ethyl]-2-[(4-butyl)-benzoylamino]-1-oxopropyl]amino]-3-methylbutyl]<br>Analytical Data:<br>$^1$H NMR (MeOD-d4): 7.68 (2H, d); 7.65 (1H, d); 7.43 (1H, d); 7.27 (1H, m); 7.24 (2H, d); 5.06 (1H, t); 4.54 (2H, m); 2.60 (2H, m); 1.5 (3H, m), 1.60-1.3 (4H, m); 0.86 (3H, t); 0.80 (6H, d). |
| E.5.5 | Chiral<br>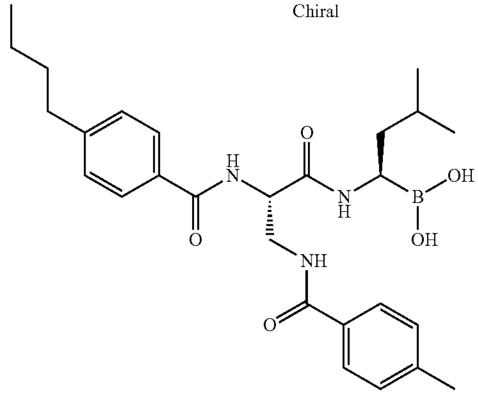 [SMILES: CCCCc1ccc(C(=O)N[C@@H](CNC(=O)c2ccc(C)cc2)C(=O)N[C@@H](CC(C)C)B(O)O)cc1] | Chemical Name:<br>Boronic acid, [(1R)-1-[[(2S)-3-(methanesulfamido)-2-[(4-butyl)-benzoylamino]-1-oxopropyl]amino]-3-methylbutyl]<br>Analytical Data:<br>$^1$H NMR (MeOD-d4): 7.85 (2H, d); 7.75 (2H, d); 7.35-7.25 (4H, dd); 4.85 (1H, t); 3.9 (2H, dd); 2.8 (1H, t); 2.75 (2H, t); 2.4 (3H, s), 1.65 (3H, m); 1.35 (5H, m); 1.05-0.80 (9H, m). |
| E.5.6 | 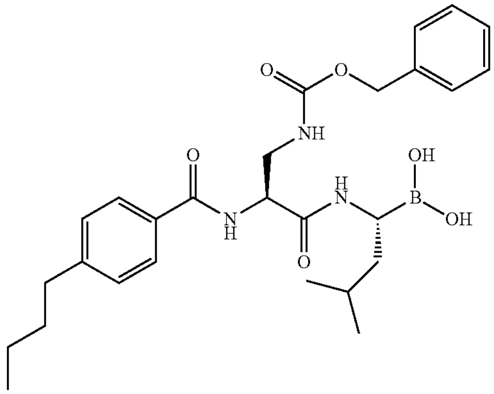 [SMILES: CCCCc1ccc(C(=O)N[C@@H](CNC(=O)OCc2ccccc2)C(=O)N[C@@H](CC(C)C)B(O)O)cc1] | Chemical Name:<br>Boronic acid, [(1R)-1-[[(2S)-3-[(carbobenzyloxyamino]-2-[(4-butylbenzoylamino)]-1-oxopropyl]amino]-3-methylbutyl]<br>Analytical Data:<br>$^1$H NMR (MeOD-d4): 7.80 (2H, d); 7.28 (7H, m); 5.2 (2H, dd); 3.6 (2H, d); 2.8 (1H, t); 2.75 (2H, t); 1.65 (3H, m); 1.3 (4H, m); 1.0 (9H, m). M.p. 92°-96° C. |
| E.5.7 | 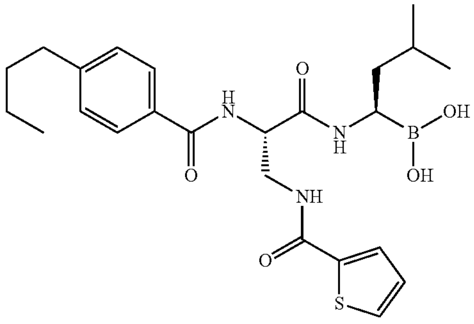 [SMILES: CCCCc1ccc(C(=O)N[C@@H](CNC(=O)c2cccs2)C(=O)N[C@@H](CC(C)C)B(O)O)cc1] | Chemical Name:<br>Boronic acid, [(1R)-1-[[(2S)-3-[(thien-2-ylcarbonyl)amino]-2-[(4-butylbenzoylamino)]-1-oxopropyl]amino]-3-methylbutyl]<br>Analytical Data:<br>$^1$H NMR (MeOD-d4): 7.80 (2H, d); 7.7 (2H, m); 7.3 (2H, d); 7.2 (1H, t); 4.9 (2H, dd); 3.9 (2H, dd); 2.8 (1H, t); 2.75 (2H, t); 1.65 (3H, m); 1.3 (4H, m); 1.0 (3H, t) 0.9 (6H, dd). |

TABLE E-5-continued

| Ex # | Structure | Chemical Name and Analytical Data |
|---|---|---|
| E.5.8 | 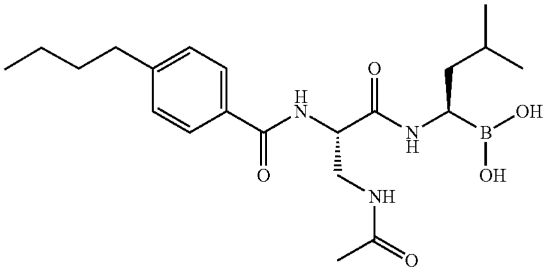 [SMILES: CCCCc1ccc(C(=O)N[C@@H](CNC(C)=O)C(=O)N[C@@H](CC(C)C)B(O)O)cc1] | Chemical Name:<br>Boronic acid, [(1R)-1-[[(2S)-3-(acetylamino)-2-[4-butyl-benzoylamino)]-1-oxopropyl]amino]-3-methylbutyl]<br>Analytical Data:<br>$^{1}$H NMR (MeOD-d4): 7.8 (2H, d); 7.3 (2H, d); 4.8 (1H, m); 3.7 (2H, dd); 2.8 (1H, t); 2.75 (2H, t); 2 (3H, s); 1.65 (3H, m); 1.4 (4H, m); 1.0-0.9 (3H, t), (6H, dd). M.p. 107°-109° C. |
| E.5.9 | 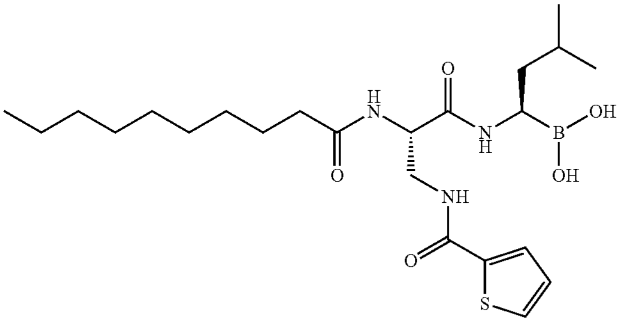 Chiral | Chemical Name:<br>Boronic acid, [(1R)-1-[[(2S)-3-[(thien-2-ylcarbonyl)amino)]-2-[(decanoylamino)]-1-oxopropyl]amino]-3-methylbutyl]<br>Analytical Data:<br>$^{1}$H NMR (MeOD-d4): t 7.7 (2H, d); 7.15 (1H, t); 4.8 (1H, m); 3.7 (2H, dd); 2.8 (1H, t); 2.75 (2H, t); 2.25 (2H, t); 1.65 (3H, m); 1.4 (14H, m); 1.0-0.9 (3H, t). |
| E.5.10 | 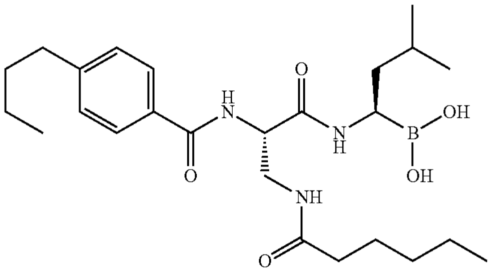 Chiral | Chemical Name:<br>Boronic acid, [(1R)-1-[[(2S)-3-(hexanoylamino)-2-[(4-butylbenzoylamino)]-1-oxopropyl]amino]-3-methylbutyl]<br>Analytical Data:<br>$^{1}$H NMR (MeOD-d4): 7.8 (2H, d); 7.3 (2H, d); 3.7 (2H, dd); 2.8 (1H, t); 2.75 (2H, t); 2.2 (2H, t); 1.65 (5H, m); 1.4 (9H, m); 1.0-0.9 (12H, t). |
| E.5.11 | 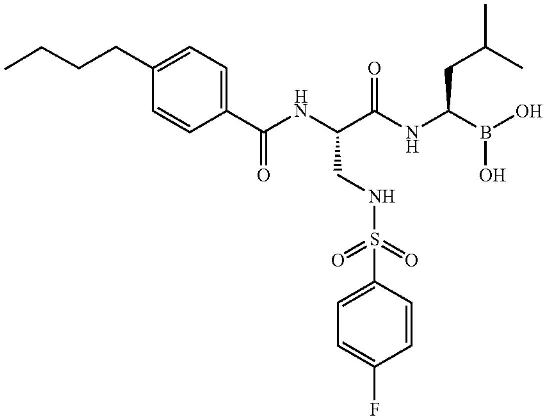 [SMILES: CCCCc1ccc(C(=O)N[C@@H](CNS(=O)(=O)c2ccc(F)cc2)C(=O)N[C@@H](CC(C)C)B(O)O)cc1] | Chemical Name:<br>Boronic acid, [(1R)-1-[[(2S)-3-[4-fluoro-benzenesulfonamide]-2-[4-butylbenzoyl)amino]-1-oxopropyl]amino]-3-methylbutyl]<br>Analytical Data:<br>$^{1}$H NMR (MeOD-d4): 7.95 (2H, dd); 7.8 (2H, d); 7.3 (4H, m); 4.8 (1H, m); 3.4 (2H, m); 2.85 (1H, t); 2.7 (2H, t); 1.7 (3H, m); 1.4 (4H, m); 1.0-0.9 (9H, t). M.p. 130°-132° C. |

TABLE E-5-continued

| Ex # | Structure | Chemical Name and Analytical Data |
| --- | --- | --- |
| E.5.12 | 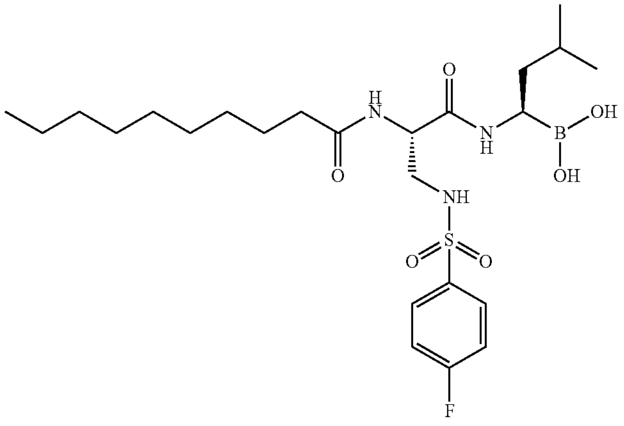 [SMILES: CCCCCCCCCC(=O)N[C@@H](CNS(=O)(=O)c1ccc(F)cc1)C(=O)N[C@@H](CC(C)C)B(O)O] | Chemical Name: Boronic acid, [(1R)-1-[[(2S)-3-[4-fluoro-benzenesulfonamide]-2-[(decanoyl)amino]-1-oxopropyl]amino]-3-methylbutyl] Analytical Data: $^{1}$H NMR (MeOD-d4): 7.95 (2H, dd); 7.35 (2H, t); 4.45 (1H, t); 3.0 (2H, m); 3.4 (2H, m); 2.1 (2H, t); 1.65-1.35 (3H, m); 1.25 (14H, m); 0.85 (9H, m). |
| E.5.13 | 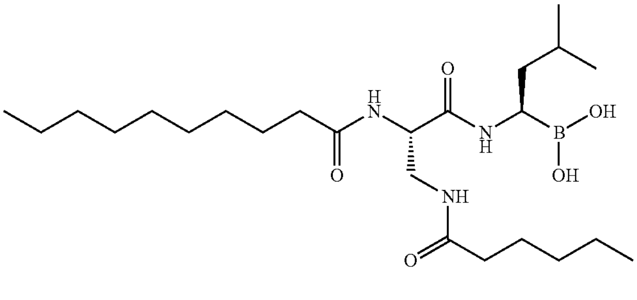 [SMILES: CCCCCCCCCC(=O)N[C@@H](CNC(=O)CCCCC)C(=O)N[C@@H](CC(C)C)B(O)O] | Chemical Name: Boronic acid, [(1R)-1-[[(2S)-3-(hexanonylamino)-2-[(decanoylamino)]-1-oxopropyl]amino]-3-methylbutyl] Analytical Data: $^{1}$H NMR (MeOD-d4): 4.45 (1H, t); 3.3 (2H, m); 2.1 (4H, tt); 1.65-1.35 (3H, m); 1.25 (18H, m); 0.85 (12H, m). |
| E.5.14 | 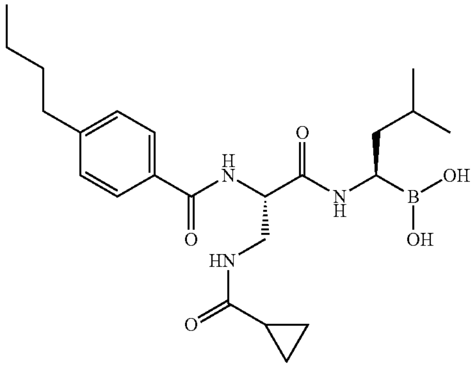 [SMILES: CCCCc1ccc(C(=O)N[C@@H](CNC(=O)C2CC2)C(=O)N[C@@H](CC(C)C)B(O)O)cc1] | Chemical Name: Boronic acid, [(1R)-1-[[(2S)-3-(hexanonylamino)-2-[(cyclopropancarbonylamino)]-1-oxopropyl]amino]-3-methylbutyl] 3-methylbutyl]amino]carbonyl]-2-(cyclopropancarbonylamino)ethyl]- Analytical Data: $^{1}$H NMR (MeOD-d4): 7.8 (2H, d); 7.2 (2H, d); 4.6 (1H, br); 3.4 (2H, m); 3.0 (2H, s); 2.7 (2H, m); 1.5 (4H, m); 1.3 (3H, m); 1.2 (4H, m); 0.9-0.6 (15H, m). |
| E.5.15 | 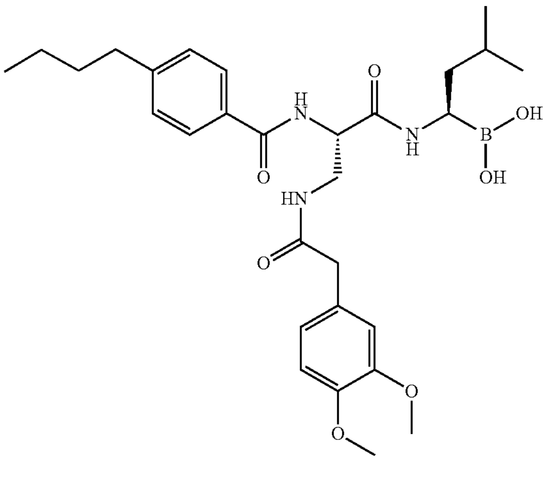 [SMILES: CCCCc1ccc(C(=O)N[C@@H](CNC(=O)Cc2ccc(OC)c(OC)c2)C(=O)N[C@@H](CC(C)C)B(O)O)cc1] | Chemical Name: Boronic acid, [(1R)-1-[[(2S)-3-[(3,4-dimethoxyphenyl)acetylamino]-2-[(4-butylbenzoylamino)]-1-oxopropyl]amino]-3-methylbutyl] Analytical Data: M.p. 150°-152° C. $^{1}$H NMR (MeOD-d4): 7.7 (2H, d); 7.2 (2H, d); 6.8 (1H, s); 6.75 (2H, m); 4.7 (1H, m); 3.7 (6H, m); 3.54 (2H, s); 3.35 (2H, s); 2.66 (3H, t); 1.6 (2H, t); 1.4-1.2 (2H, m); (2H, m); (2H, m); 0.9 (3H, t), 0.8 (6H, d). |

TABLE E-5-continued

| Ex # | Structure | Chemical Name and Analytical Data |
|---|---|---|
| E.5.16 | 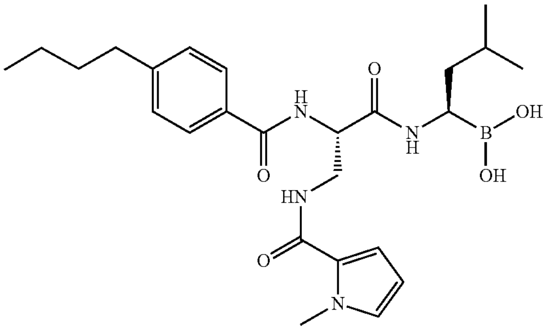 [SMILES: CCCCc1ccc(C(=O)N[C@@H](CNC(=O)c2cccn2C)C(=O)N[C@@H](CC(C)C)B(O)O)cc1] | Chemical Name: Boronic acid, [(1R)-1-[[(2S)-3-[1-N-methyl-2-pyrrolylcarbonylamino]-2-[(4-butylbenzoyl)amino]-1-oxopropyl]amino]-3-methylbutyl] Analytical Data: $^{1}$H NMR (MeOD-d4): 7.8 (2H, d); 7.3 (2H, d); 6.9 (1H, d); 6.7 (1H, d); 6 (1H, t); 4.8 (1H, t); 3.9 (3H, s); 3.7 (2H, m); 2.7 (3H, m); 1.65 (3H, m); 1.35 (4H, m); 0.9-0.6 (9H, m). M.p. 130°-135° C. |
| E.5.17 | 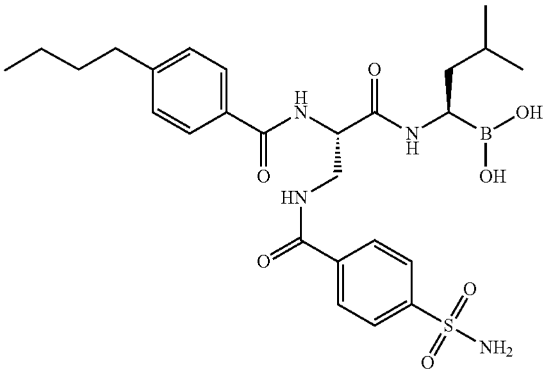 [SMILES: CCCCc1ccc(C(=O)N[C@@H](CNC(=O)c2ccc(S(N)(=O)=O)cc2)C(=O)N[C@@H](CC(C)C)B(O)O)cc1] | Chemical Name: Boronic acid, [(R)-1-[[(2S)-3-[4-sulfamylbenzoylamino]-2-[(4-butylbenzoyl)amino]-1-oxopropyl]amino]-3-methylbutyl] Analytical Data: $^{1}$H NMR (MeOD-d4): 7.95 (4H, dd); 7.8 (2H, d); 7.3 (2H, d); 4.9 (1H, t); 3.7 (2H, d); 2.7 (2H, t); 2.6 (1H, t); 1.6 (3H, m); 1.2 (4H, m); 0.95-0.8 (9H, m). M.p. 156°-159° C. |
| E.5.18 | 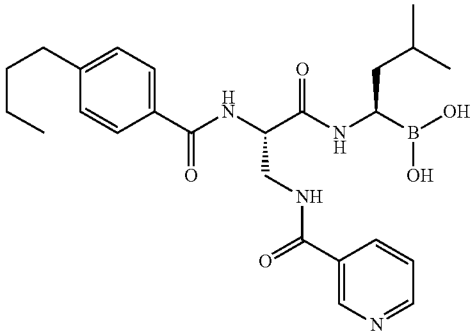 [SMILES: CCCCc1ccc(C(=O)N[C@@H](CNC(=O)c2cccnc2)C(=O)N[C@@H](CC(C)C)B(O)O)cc1] | Chemical Name: Boronic acid, [(1R)-1-[[(2S)-3-(nicotinoylamino)-2-[(4-butylbenzoylamino)]-1-oxopropyl]amino]-3-methylbutyl] Analytical Data: $^{1}$H NMR (MeOD-d4): 9.1 (1H, s); 8.8 (1H, d); 8.4 (1H, d); 7.8 (2H, d); 7.7 (1H, t); 7.3 (2H, d); 4.9 (1H, t); 3.7 (2H, m); 2.7 (2H, t); 2.6 (1H, t); 1.6 (3H, m); 1.4-1.2 (7H, m); 0.95-0.8 (9H, m). |
| E.5.19 | 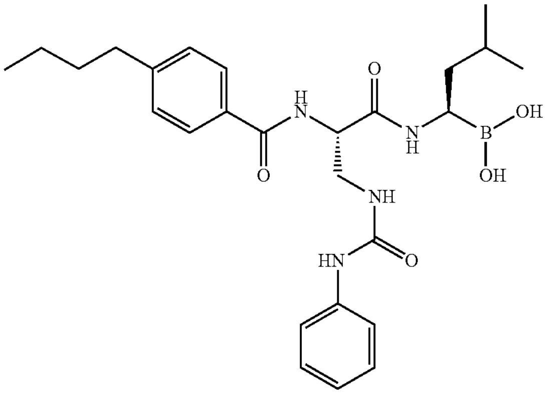 [SMILES: CCCCc1ccc(C(=O)N[C@@H](CNC(=O)Nc2ccccc2)C(=O)N[C@@H](CC(C)C)B(O)O)cc1] | Chemical Name: Boronic acid, [(1R)-1-[[(2S)-3-(3-phenylureido)-2-(4-butylbenzoylamino)-1-oxopropyl]amino]-3-methylbutyl] Analytical Data: $^{1}$H NMR (MeOD-d4): 8.8 (1H, d); 7.35 (2H, d); 7.25 (2H, d); 7.2 (2H, t); 6.9 (1H, t); 4.7 (1H, t); 3.7-3.4 (2H, m); 2.7 (2H, t); 2.6 (1H, t); 1.6 (3H, m); 1.4-1.2 (4H, m); 0.95-0.8 (9H, m). |

TABLE E-5-continued

| Ex # | Structure | Chemical Name and Analytical Data |
|---|---|---|
| E.5.20 | 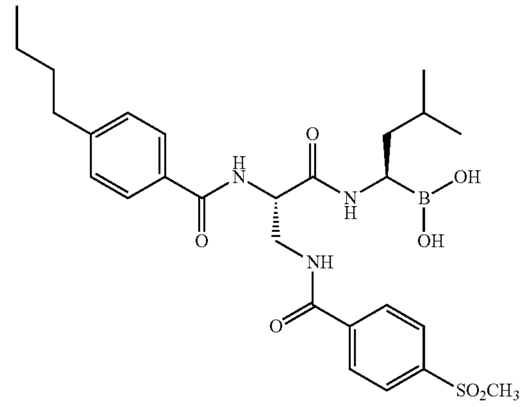 [SMILES: CCCCc1ccc(C(=O)N[C@@H](CNC(=O)c2ccc(S(C)(=O)=O)cc2)C(=O)N[C@@H](CC(C)C)B(O)O)cc1] | Chemical Name: Boronic acid, [(1R)-1-[[(2S)-3-[(4-methylsulfonyl)benzoylamino]-2-[(4-butylbenzoylamino)]-1-oxopropyl]amino]-3-methylbutyl] Analytical Data: $^1$H NMR (MeOD-d4): 8.0 (4H, m); 7.8 (2H, d); 7.25 (2H, d); 4.9 (1H, br); 3.75 (2H, m); 3.2 (3H, s); 2.7 (2H, t); 2.6 (1H, t); 1.6 (3H, m); 1.4-1.2 (4H, m); 0.95-0.8 (9H, m). M.p. 168°-170° C. |
| E.5.21 | 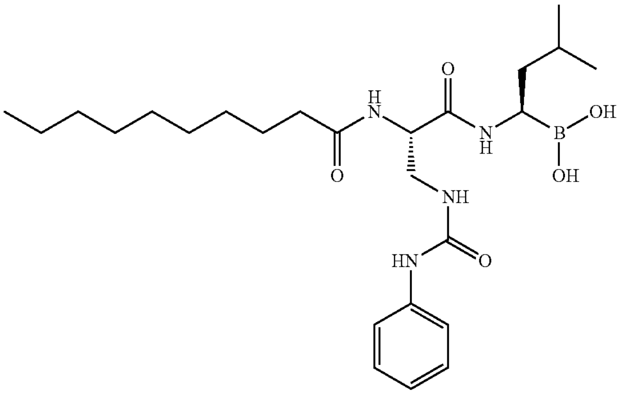 Chiral | Chemical Name: Boronic acid, [(1R)-1-[[(2S)-3-(3-phenylureido)-2-(decanoylamino)-1-oxopropyl]amino]-3-methylbutyl] Analytical Data: $^1$H NMR (MeOD-d4): 7.35 (2H, d); 7.28 (2H, dd); 7.0 (2H, t); 3.6 (2H, d); 2.75 (1H, t); 2.2 (2H, t); 1.65 (3H, m); 1.3 (14H, m); 0.9 (9H, m) |
| E.5.22 | 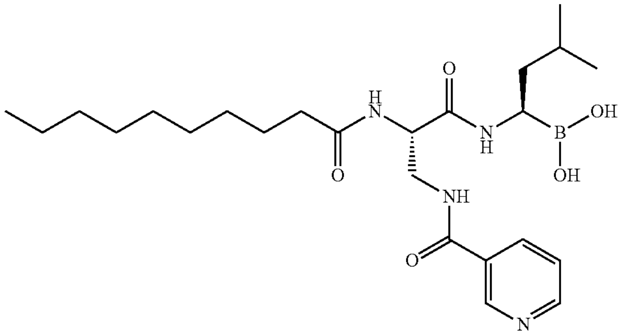 [SMILES: CCCCCCCCCC(=O)N[C@@H](CNC(=O)c1cccnc1)C(=O)N[C@@H](CC(C)C)B(O)O] | Chemical Name: Boronic acid, [(1R)-1-[[(2S)-3-(nicotinoylamino)-2-(decanoylamino)-1-oxopropyl]amino]-3-methylbutyl] Analytical Data: $^1$H NMR (MeOD-d4): 9.0 (1H, s); 8.8 (1H, d); 8.3 (1H, d); 7.5 (1H, t); 4.9 (1H, m); 3.9- 3.6 (2H, m); 2.75 (1H, t); 2.2 (2H, t); 1.65 (3H, m); 1.3 (14H, m); 1.0-0.9 (9H, m). M.p. 136°-141° C. |
| E.5.23 | 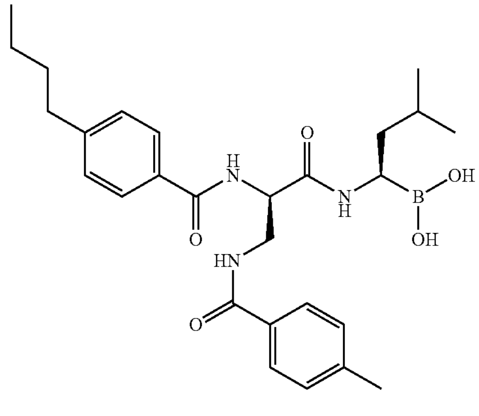 [SMILES: CCCCc1ccc(C(=O)N[C@H](CNC(=O)c2ccc(C)cc2)C(=O)N[C@@H](CC(C)C)B(O)O)cc1] | Chemical Name: Boronic acid, [(1R)-1-[[(2R)-3-(4-methylphenylcarbonyl)-2-(decanoylamino)-1-oxopropyl]amino]-3-methylbutyl] Analytical Data: $^1$H NMR (MeOD-d4): 8.85 (2H, d); 8.0 (2H, d); 7.3 (4H, m); 5.0 (1H, m); 3.9 (2H, m); 2.75 (3H, m); 1.65 (3H, m); 1.3 (9H, m); 0.9 (9H, m) |

TABLE E-5-continued

| Ex # | Structure | Chemical Name and Analytical Data |
|---|---|---|
| E.5.24 | Chiral 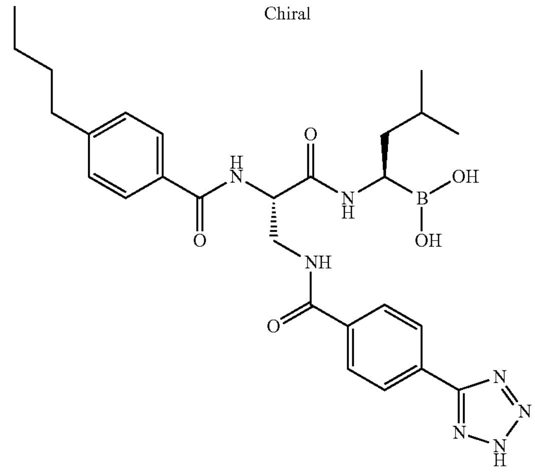 [SMILES: CCCCc1ccc(C(=O)N[C@@H](CNC(=O)c2ccc(-c3nn[nH]n3)cc2)C(=O)N[C@@H](CC(C)C)B(O)O)cc1] | Chemical Name: Boronic acid, [(1R)-1-[[(2S)-3-[4-(1H-tetrazolyl)-phenylcarbonylamino]-2-[(4-butylbenzoylamino)]-1-oxopropyl]amino]-3-methylbutyl] Analytical Data: $^1$H NMR (MeOD-d4): 8.15 (2H, d); 7.9 (2H, d); 7.8 (2H, d); 7.3 (2H, d); 5.0 (1H, t); 3.9 (2H, m); 2.8 (1H, t); 2.7 (2H, t); 1.65 (3H, m); 1.3 (4H, m); 0.9 (9H, m). M.p. >250° C. |
| E.5.25 | Chiral 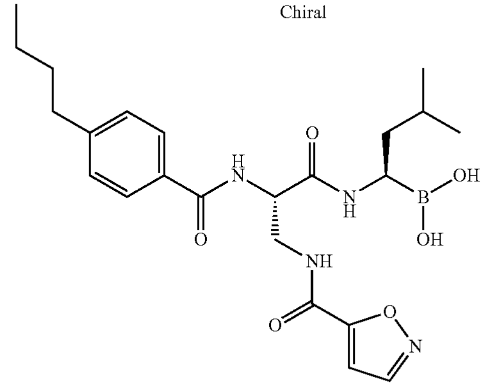 [SMILES: CCCCc1ccc(C(=O)N[C@@H](CNC(=O)c2ccno2)C(=O)N[C@@H](CC(C)C)B(O)O)cc1] | Chemical Name: Boronic acid, [(1R)-1-[[(2S)-3-(2-isoxazolylcarbonylamino)-2-[(4-butylbenzoylamino)]-1-oxopropyl]amino]-3-methylbutyl] Analytical Data: $^1$H NMR (MeOD-d4): 8.4 (1H, s); 7.7 (2H, d); 7.2 (2H, d); 6.9 (1H, s); 4.9 (1H, t); 3.8 (2H, m); 2.7 (1H, t); 2.6 (2H, t); 1.5 (3H, m); 1.25 (4H, m); 0.8 (9H, m) M.p. 175°-180° C. |
| E.5.26 | 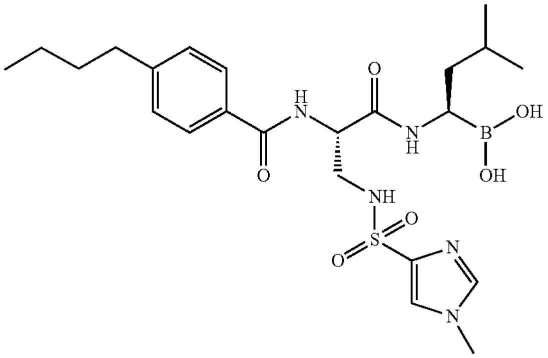 [SMILES: CCCCc1ccc(C(=O)N[C@@H](CNS(=O)(=O)c2cn(C)cn2)C(=O)N[C@@H](CC(C)C)B(O)O)cc1] | Chemical Name: Boronic acid, [(1R)-1-[[(2S)-3-[1-methyl-1H-imidazole-4-sulfamoyl]-2-[(4-butylbenzoyl)amino]-1-oxopropyl]amino]-3-methylbutyl] Analytical Data: $^1$H NMR (MeOD-d4): 8.8 (2H, d); 8.7 (2H, s); 7.3 (2H, d); 4.9 (1H, br); 3.8 (3H, s); 3.5 (2H, m); 2.8 (1H, t); 2.7 (2H, t); 1.65 (3H, m); 1.35 (4H, m); 0.9 (9H, m), M.p. 120°-123° C. |

TABLE E-5-continued

| Ex # | Structure | Chemical Name and Analytical Data |
|---|---|---|
| E.5.27 | 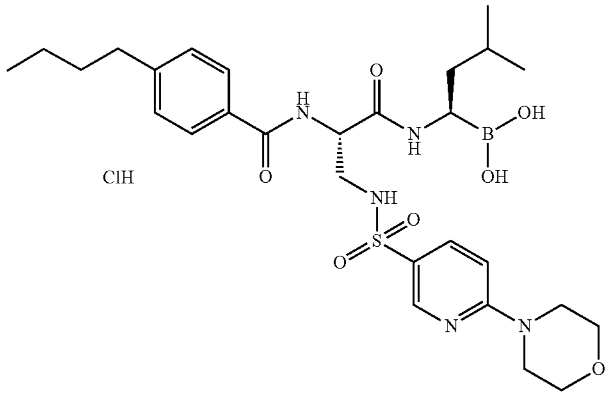 [SMILES: CCCCc1ccc(C(=O)N[C@@H](CNS(=O)(=O)c2ccc(N3CCOCC3)nc2)C(=O)N[C@@H](CC(C)C)B(O)O)cc1 ; Cl] | Chemical Name:<br>Boronic acid, [(1R)-1-[[(2S)-3-[6-morpholin-4-yl-pyridine-3-sulfamoyl]-2-[(4-butylbenzoyl)amino]-1-oxopropyl]amino]-3-methylbutyl]hydrochloride<br>Analytical Data:<br>$^{1}$H NMR (MeOD-d4): 8.35 (1H, s); 8.1 (1H, d); 7.8 (2H, d); 7.3 (3H, m); 4.9 (1H, br); 3.9 (4H, t); 3.8 (4H, t); 3.5 (2H, m); 2.8 (1H, t); 2.7 (2H, t); 1.65 (3H, m); 1.35 (4H, m); 0.9 (9H, m). M.p. 182°-184° C. |
| E.5.28 | 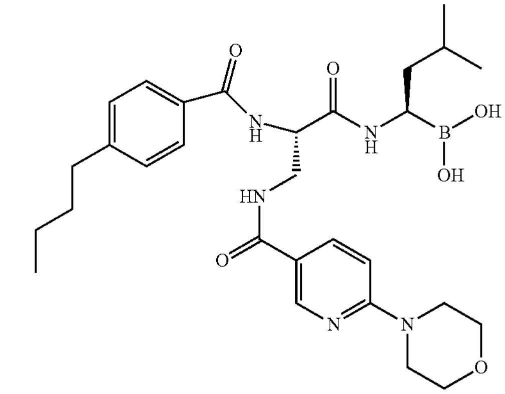 [SMILES: CCCCc1ccc(C(=O)N[C@@H](CNC(=O)c2ccc(N3CCOCC3)nc2)C(=O)N[C@@H](CC(C)C)B(O)O)cc1] | Chemical Name:<br>Boronic acid, [(1R)-1-[[(2S)-3-(6-morpholinonicotinamide]-2-[(4-butylbenzoyl)amino]-1-oxopropyl]amino]-3-methylbutyl]<br>Analytical Data:<br>$^{1}$H NMR (MeOD-d4): 8.5 (1H, s); 7.9 (1H, d); 7.7 (2H, d); 7.2 (2H, d); 6.7 (1H, d); 4.9 (1H, t); 3.8 (2H, ts); 3.7 (4H, d); 3.4 (4H, d); 2.65 (1H, t); 2.6 (2H, t); 1.60 (3H, m); 1.25 (4H, m); 0.9 (9H, m). M.p. 178°-180° C. |
| E.5.29 | 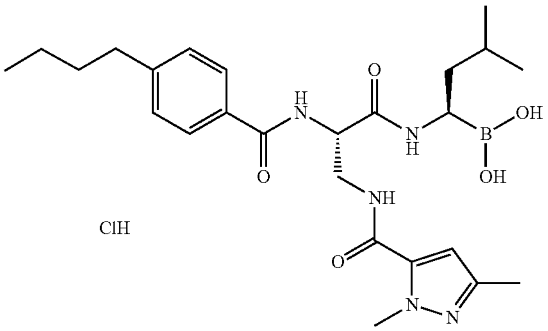 [SMILES: CCCCc1ccc(C(=O)N[C@@H](CNC(=O)c2cc(C)nn2C)C(=O)N[C@@H](CC(C)C)B(O)O)cc1 ; Cl] | Chemical Name:<br>Boronic acid, [(1R)-1-[[(2S)-3-(4-(1,3-dimethyl-1H-pyrazole-5-carbonylamino]-2-[(4-butylbenzoyl)amino]-1-oxopropyl]amino]-3-methylbutyl]hydrochloride<br>Analytical Data:<br>$^{1}$H NMR (MeOD-d4): 7.8 (1H, d); 7.3 (2H, d); 6.65 (1H, s); 5.0 (1H, t); 3.9 (2H, m); 2.8 (1H, t); 2.7 (2H, t); 2.3 (3H, s); 1.60 (3H, m); 1.35 (4H, m); 0.9 (9H, m). |
| E.5.30 | 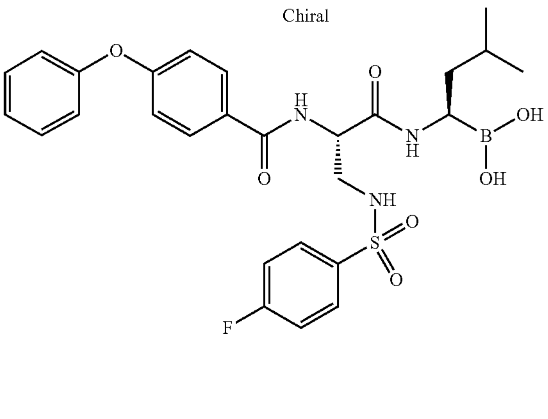 [SMILES: CC(C)C[C@H](NC(=O)[C@H](CNS(=O)(=O)c1ccc(F)cc1)NC(=O)c1ccc(Oc2ccccc2)cc1)B(O)O] | Chemical Name:<br>Boronic acid, [(1R)-1-[[(2S)-3-[4-fluoro-benzenesulfonamide]-2-[(4-phenoxybenzoyl)amino]-1-oxopropyl]amino]-3-methylbutyl]<br>Analytical Data:<br>$^{1}$H NMR (MeOD-d4): 7.95 (2H, m); 7.9 (2H, d); 7.4 (2H, m); 7.3 (2H, t); 7.25 (1H, t); 7.1 (2H, d); 7.0 (2H, d); 3.4 (2H, m); 2.8 (1H, br); 1.7 (1H, m); 1.40 (2H, m); 0.9 (6H, d). M.p. 150°-155° C. |

TABLE E-5-continued

| Ex # | Structure | Chemical Name and Analytical Data |
| --- | --- | --- |
| E.5.31 | 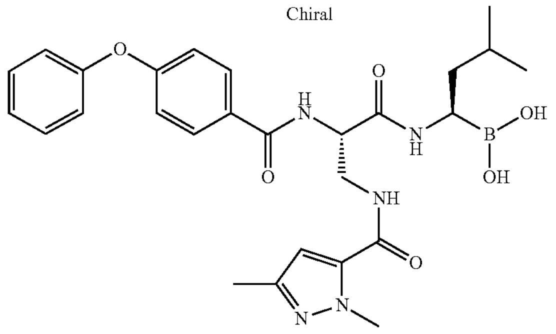 [SMILES: Cc1cc(C(=O)NC[C@H](NC(=O)c2ccc(Oc3ccccc3)cc2)C(=O)N[C@@H](CC(C)C)B(O)O)n(C)n1] | Chemical Name: Boronic acid, [(1R)-1-[[(2S)-3-(4-(1,3-dimethyl-1H-pyrazole-5-carbonylamino]-2-[(4-phenoxybenzoyl)amino]-1-oxopropyl]amino]-3-methylbutyl]carbonylamino]ethyl]- Analytical Data: $^{1}$H NMR (MeOD-d4): 7.9 (2H, d); 7.45 (2H, t); 7.25 (1H, t); 7.11 (2H, d); 7.05 (2H, d); 6.55 (1H, s); 5.0 (1H, t); 4.1 (3H, s); 3.9 (2H, m); 2.8 (1H, t); 2.25 (3H, s); 1.6 (1H, m); 1.35 (2H, m); 0.9 (6H, d). M.p. 145°-148° C. |
| E.5.32 | 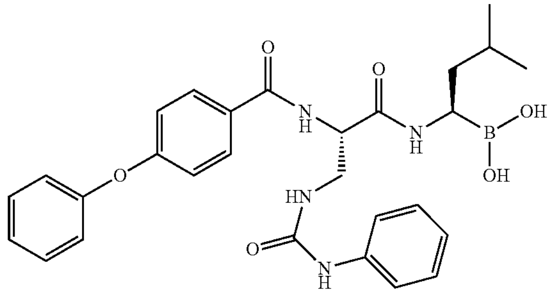 [SMILES: CC(C)C[C@H](NC(=O)[C@H](CNC(=O)Nc1ccccc1)NC(=O)c1ccc(Oc2ccccc2)cc1)B(O)O] | Chemical Name: Boronic acid, [(1R)-1-[[(2S)-3-(4-phenylureido]-2-[(4-phenoxybenzoyl)amino]-1-oxopropyl]amino]-3-methylbutyl] Analytical Data: $^{1}$H NMR (MeOD-d4): 7.9 (2H, d); 7.40 (2H, t); 7.35 (2H, d); 7.25 (3H, m); 7.10 (2H, d); 7.05 (3H, d); 3.75 (2H, m); 2.8 (1H, t); 1.75 (1H, m); 1.4 (2H, m); 0.9 (6H, d). M.p. 155°-158° C. |
| E.5.33 | 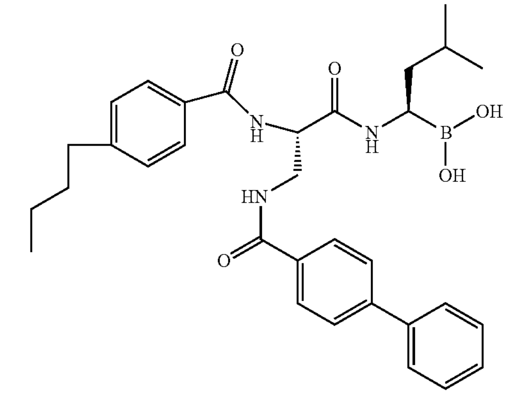 [SMILES: CCCCc1ccc(C(=O)N[C@@H](CNC(=O)c2ccc(-c3ccccc3)cc2)C(=O)N[C@@H](CC(C)C)B(O)O)cc1] | Chemical Name: Boronic acid, [(1R)-1-[[(2S)-3-(4-phenybenzamide]-2-[4-butylbenzoyl)amino]-1-oxopropyl]amino]-3-methylbutyl] Analytical Data: $^{1}$H NMR (MeOD-d4): 7.9 (2H, d); 7.8 (2H, d); 7.75 (2H, d); 7.70 (2H, d); 7.45 (2H, t); 7.35 (1H, d); 7.30 (1H, d); 5.0 (1H, t); 3.95 (2H, m); 2.8 (1H, t); 2.7 (2H, t); 1.65 (3H, m); 1.4 (2H, m); 1.0 (3H, t) 0.9 (6H, d). M.p. 178°-180° C. |
| E.5.34 | 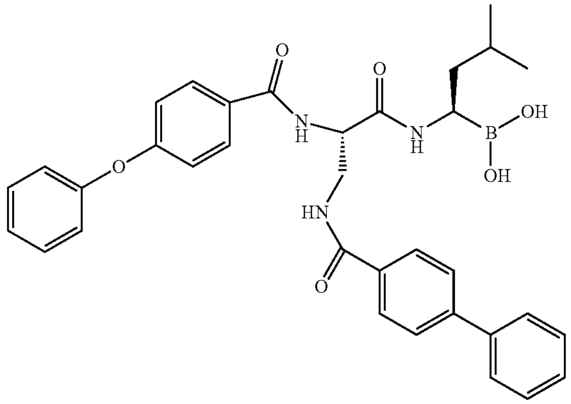 [SMILES: CC(C)C[C@H](NC(=O)[C@H](CNC(=O)c1ccc(-c2ccccc2)cc1)NC(=O)c1ccc(Oc2ccccc2)cc1)B(O)O] | Chemical Name: Boronic acid, [(1R)-1-[[(2S)-3-(4-phenylbenzamide]-2-[(4-phenoxybenzoyl)amino]-1-oxopropyl]amino]-3-methylbutyl] Analytical Data: $^{1}$H NMR (MeOD-d4): 7.9 (4H, m); 7.80 (2H, d); 7.70 (2H, d); 7.4 (4H, m); 7.20 (1H, t); 7.05 (4H, d); 5.0 (1H, t); 3.9 (2H, m); 2.8 (1H, t); 1.6 (1H, m); 1.4 (2H, m); 0.9 (6H, d). M.p. 158°-160° C. |

TABLE E-5-continued

| Ex # | Structure | Chemical Name and Analytical Data |
|---|---|---|
| E.5.35 | 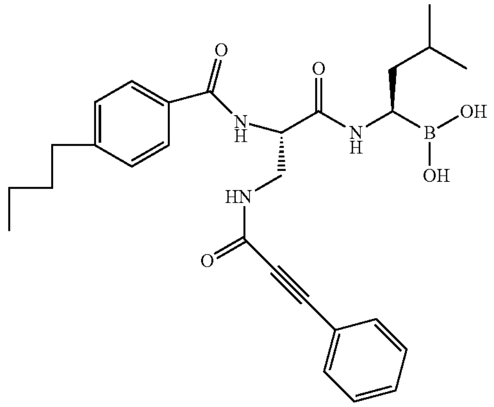 [SMILES: CCCCc1ccc(C(=O)N[C@@H](CNC(=O)C#Cc2ccccc2)C(=O)N[C@@H](CC(C)C)B(O)O)cc1] | Chemical Name:<br>Boronic acid, [(1R)-1-[[(2S)-3-(phenylpropionamide]-2-[(4-butylbenzoyl)amino]-1-oxopropyl]amino]-3-methylbutyl]<br>Analytical Data:<br>$^1$H NMR (MeOD-d4): 7.85 (2H, m); 7.4 (2H, d); 7.5 (1H, d); 7.45 (2H, m); 7.35 (2H, d); 5.0 (1H, t); 3.95 (2H, m); 2.8 (1H, t); 2.7 (2H, t); 1.7 (3H, m); 1.4 (4H, m); 1.0 (3H, t) 0.9 (9H, m). M.p. 138°-140° C. |
| E.5.36 | 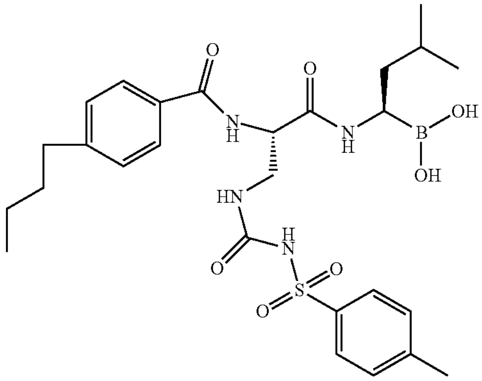 Chiral | Chemical Name:<br>Boronic acid, [(1R)-1-[[(2S)-3-(4-methylphenylsulfonyl)-ureido]-2-[(4-butylbenzoyl)amino]-1-oxopropyl]amino]-3-methylbutyl]<br>Analytical Data:<br>$^1$H NMR (MeOD-d4): 7.85 (2H, d); 7.75 (2H, d); 7.3 (2H, d); 7.25 (2H, d); 4.7 (1H, t); 3.65 (2H, m); 2.75 (1H, t); 2.7 (2H, t); 1.7 (3H, m); 1.4 (4H, m); 1.0-0.9 (9H, m). M.p. 175°-177° C. |
| E.5.37 | 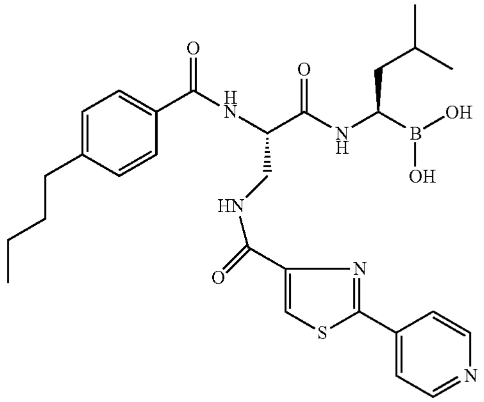 [SMILES: CCCCc1ccc(C(=O)N[C@@H](CNC(=O)c2csc(-c3ccncc3)n2)C(=O)N[C@@H](CC(C)C)B(O)O)cc1] | Chemical Name:<br>Boronic acid, [(1R)-1-[[(2S)-3-(4-(2-(4-pyridyl)-1,3-thiazole-4-carbonylamino)]-2-[(4-butylbenzoyl)amino]-1-oxopropyl]amino]-3-methylbutyl]<br>Analytical Data:<br>$^1$H NMR (MeOD-d4): 8.7 (2H, d); 8.45 (1H, s); 8.05 (2H, d) 7.8 (2H, d); 7.3 (2H, d); 5.05 (1H, t); 4.0 (2H, m); 2.8 (1H, t); 2.7 (2H, t); 1.7 (3H, m); 1.4 (4H, m); 0.9 (3H, t); 0.8 (6H, dd). M.p. 155°-158° C. |
| E.5.38 | 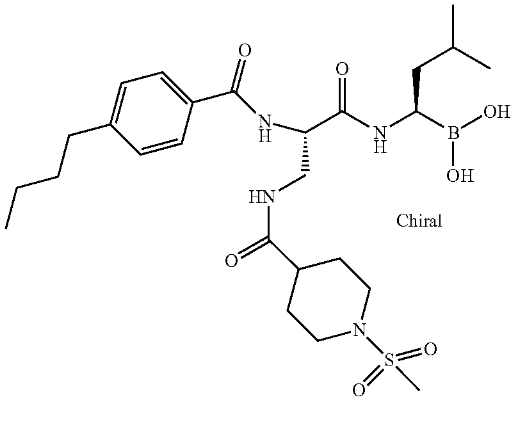 [SMILES: CCCCc1ccc(C(=O)N[C@@H](CNC(=O)C2CCN(S(C)(=O)=O)CC2)C(=O)N[C@@H](CC(C)C)B(O)O)cc1] Chiral | Chemical Name:<br>Boronic acid, [(1R)-1-[[(2S)-3-(1-methanesulfonylpiperidine-4-carbonylamino)-2-[(4-butylbenzoylamino)]-1-oxopropyl]amino]-3-methylbutyl]<br>Analytical Data:<br>$^1$H NMR (MeOD-d4): 9.9 (1H, br); 8.35 (1H, t); 7.8 (2H, d); 7.3 (2H, d); 4.9 (1H, t); 3.7 (4H, m); 2.8 (3H, s); 2.75 (4H, m); 2.3 (1H, m); 1.85-1.6 (7H, m); 1.3 (4H, m) 0.9 (9H, m); M.p. 170°-173° C. |

TABLE E-5-continued

| Ex # | Structure | Chemical Name and Analytical Data |
| --- | --- | --- |
| E.5.39 | 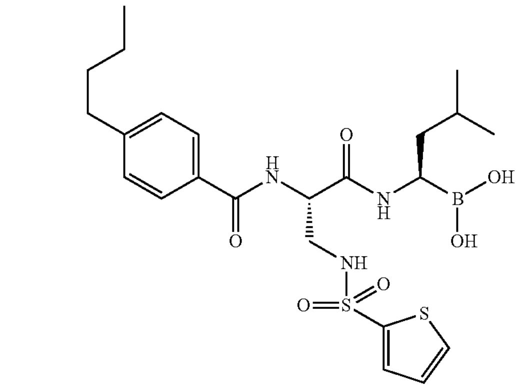 [SMILES: CCCCc1ccc(C(=O)N[C@@H](CNS(=O)(=O)c2cccs2)C(=O)N[C@@H](CC(C)C)B(O)O)cc1] | Chemical Name: Boronic acid, [(1R)-1-[[(2S)-3-[(2-thiophene)sulfonylamino]-2-[(4-butylbenzoylamino)]-1-oxopropyl]amino]-3-methylbutyl] Analytical Data: $^1$H NMR (MeOD-d4): 7.95 (1H, dd); 7.8 (2H, d); 7.58 (1H, dd); 7.32 (2H, d); 7.18 (1H, dd); 4.8 (1H, m); 3.23 (2H, m); 2.66 (1H, t); 1.3-1.23 (8H, m); 0.9 (3H, t), 0.8 (6H, d). |
| E.5.40 | 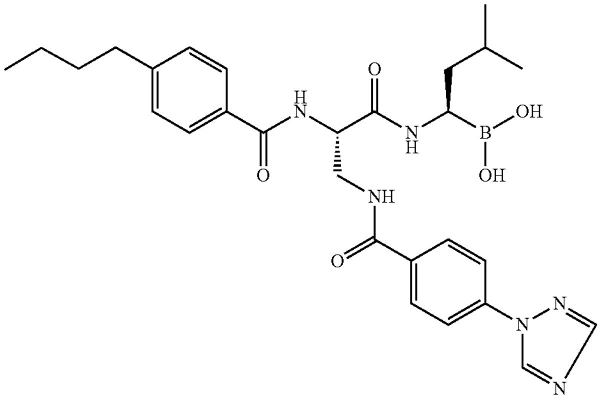 [SMILES: CCCCc1ccc(C(=O)N[C@@H](CNC(=O)c2ccc(-n3cncn3)cc2)C(=O)N[C@@H](CC(C)C)B(O)O)cc1] | Chemical Name: Boronic acid, [(1R)-1-[[(2S)-3-(4-(1H-1,2,4-triazol-1-yl)benzoylamide)]-2-[(4-butylbenzoyl)amino]-1-oxopropyl]amino]-3-methylbutyl] hydrochloride Analytical Data: $^1$H NMR (MeOD-d4): 9.8 (1H, s); 8.6 (1H, s); 8.08 (2H, d); 8.01 (2H, d); 7.8 (2H, d); 7.3 (2H, d); 5.05 (1H, t); 3.9 (2H, m); 2.8 (1H, t); 2.7 (2H, t); 1.6 (3H, m); 1.3 (4H, m); 1.0 (3H, t); 0.9 (6H, dd). M.p. 192°-195° C. |
| E.5.41 | 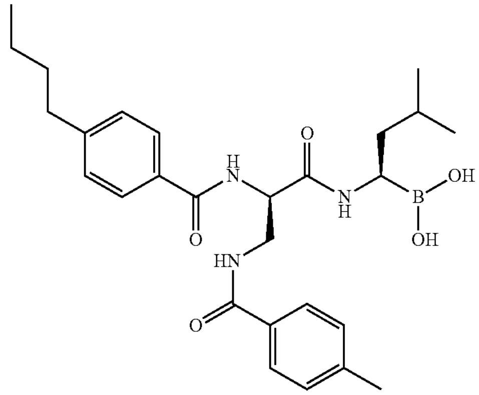 [SMILES: CCCCc1ccc(C(=O)N[C@H](CNC(=O)c2ccc(C)cc2)C(=O)N[C@@H](CC(C)C)B(O)O)cc1] | Chemical Name: Boronic acid, [(1R)-1-[[(2R)-3-(4-methylphenylcarbonyl)-2-(decanoylamino)-1-oxopropyl]amino]-3-methylbutyl] Analytical Data: $^1$H NMR (MeOD-d4): 7.85 (2H, d); 7.8 (2H, d); 7.35 (4H, m); 5 (1H, m); 4.05 (1H, m); 3.95 (1H, m); 2.75 (2H, t); 1.65 (2H, m); 1.35 (10H, m): 1.0 (3H, t), 0.85 (6H, d). |
| E.5.42 | 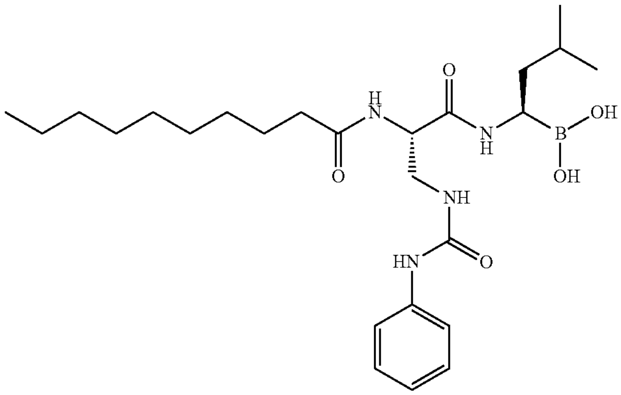 Chiral | Chemical Name: Boronic acid, [(1R)-1-[[(2S)-3-(4-phenylureido]-2-(decanoylamino)-1-oxopropyl]amino]-3-methylbutyl] |

TABLE E-5-continued

| Ex # | Structure | Chemical Name and Analytical Data |
|---|---|---|
| E.5.43 | 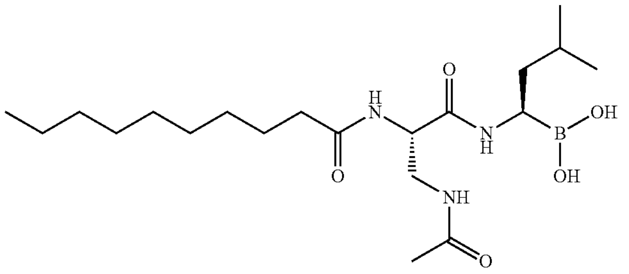 [SMILES: CCCCCCCCCC(=O)N[C@@H](CNC(C)=O)C(=O)N[C@@H](CC(C)C)B(O)O] | Chemical Name: Boronic acid, [(1R)-1-[[(2S)-3-acetylamino-2-decanoylamino-1-oxopropyl]amino]-3-methylbutyl] |

Example F.1

Decanamide, N-[(1S)-1-[[[(1R)-1-[(4R,5R)-4,5-dicyclohexyl-[1,3,2]dioxaborolan-2-yl]-3-methylbutyl] amino]carbonyl]-4-[[imino(nitroamino)methyl] amino]butyl]-

Chiral

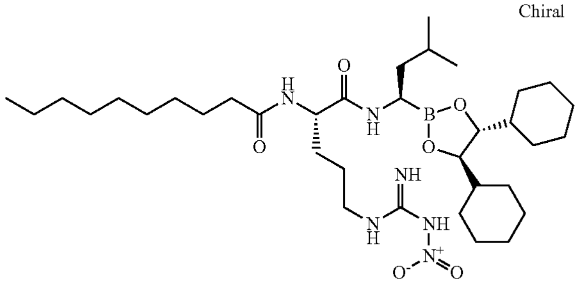 [SMILES: CCCCCCCCCC(=O)N[C@@H](CCCNC(=N)N[N+](=O)[O-])C(=O)N[C@@H](CC(C)C)B1O[C@H](C2CCCCC2)[C@@H](C2CCCCC2)O1]

To a suspension of boronic acid, [(1R)-1-[[(2S)-5-[[imino(nitroamino)methyl]amino]-2-[(decanoyl)amino]-1-oxopentyl]amino]-3-methylbutyl]-, (125 mg, 0.26 mmol) obtained as in Example E.2, in a mixture of diethyl ether (0.5 ml) and dichloromethane (1 ml), a few drops of methanol were added until complete dissolution of the solid. (1R,2R)-1,2-dicyclohexyl-1,2-ethanediol (61 mg, 0.26 mmol) was added and the mixture was stirred at room temperature for 5 hours. The reaction mixture was concentrated to dryness and the residue was purified by column chromatography (silica gel) eluting with a 50:50 ethyl acetater:hexane mixture. The product was then triturated with hexane and the solvent was removed by decantation. The trituration was repeated two further times. The product was obtained as a waxy solid (65 mg, 37% yield).

M.p. 75-100° C.

$^1$H NMR (DMSO-$d_6$): 8.99 (1H, d, J=2.5 Hz); 8.52 (1H, br); 7.98 (1H, d, J=8.05); 7.88 (2H, br); 3.48 (2H, d, J=5.7); 3.14 (2H, m); 2.55 (1H, m); 2.19 (1H, m); 2.10 (2H, m); 1.79 (2H, m); 1.74-1.35 (16H, m); 1.24 (22H, m); 1.12 (5H, m); 0.89 (4H, m); 0.84 (9H, m).

Example F.2

4-Phenylbutanamide, N-[(1S)-1-[[[(1R)-1-[13,15-dioxa-14-bora-dispiro[5.0.5.3]-pentadec-14-yl]-3-methylbutyl]amino]carbonyl]-4-[[imino(nitroamino) methyl]-amino]butyl]-

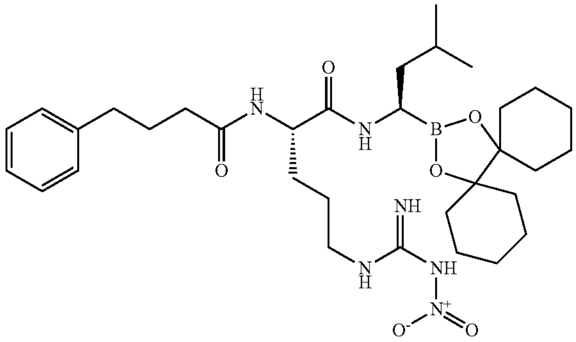 [SMILES: CC(C)C[C@H](NC(=O)[C@H](CCCNC(=N)N[N+](=O)[O-])NC(=O)CCCc1ccccc1)B1OC2(CCCCC2)C2(CCCCC2)O1]

The title compound was prepared according to the above procedure for Example F.1 using the appropriate boronic acid starting material and bicyclohexyl-1,1'-diol.

Analytical results: $^1$H NMR (DMSO-$d_6$): 8.79 (1H, d, J=2.5 Hz); 8.52 (1H, br); 8.00 (1H, d, J=7.94); 7.85 (2H, br); 7.31-7.23 (2H, m); 7.20-7.14 (3H, m); 4.40-4.30 (1H, m); 3.15 (2H, m); 2.55 (3H, m); 2.14 (2H, t, J=7.3 Hz); 1.78 (2H, q, J=7.3 Hz); 1.70-0.97 (27H, m); 0.84 (3H, t, J=6.7 Hz); 0.83 (3H, t, J=6.7 Hz).

Example F.2.1

4-Butylbenzamide, N-[(1S,2R)-1-[[[(1R)-1-[13,15-dioxa-14-bora-dispiro[5.0.5.3]pentadec-14-yl]-3-methylbutyl]amino]carbonyl]-2-hydroxypropyl]-

Chiral

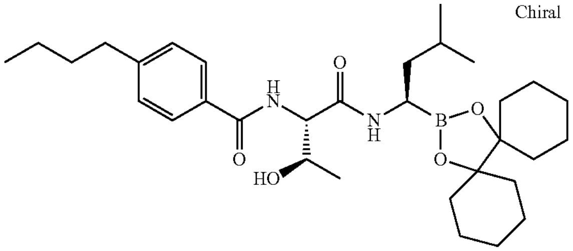 [SMILES: CCCCc1ccc(C(=O)N[C@H](C(=O)N[C@@H](CC(C)C)B2OC3(CCCCC3)C3(CCCCC3)O2)[C@@H](C)O)cc1]

The title compound was prepared according to the above procedure for Example F.1 using the appropriate boronic acid starting material and bicyclohexyl-1,1'-diol.

Analytical results: $^1$H NMR (DMSO-$d_6$): 8.98 (1H, s br.); 8.00 (1H, d, J=8.5); 7.81 (2H, d, J=8.2); 7.31 (2H, d, J=8.2); 5.03 (1H, d, J=6.2); 4.49 (1H, dd, J=8.5, 5.0); 4.07-3.98 (1H, m); 2.64 (1H, t, J=7.6); 2.57-2.50 (1H, m); 1.65-1.21 (21H, m); 1.14-1.00 (9H, m); 0.90 (3H, t, J=7.4); 0.85 (6H, d, 6.5).

Example G.1

10-(1,3-Dioxo-1,3-dihydro-isoindol-2-yl)-decanoic acid

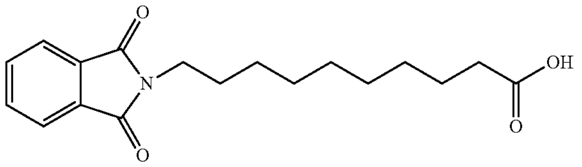 [SMILES: O=C(O)CCCCCCCCCN1C(=O)c2ccccc2C1=O]

Step 1: 2-undec-10-enyl-1,3-dioxo-1,3-dihydroisoindole

To a mixture of 10-undecen-1-ol (4.23 g, 24.8 mmol), phthalimide (3.65 g, 24.8 mmol) and triphenylphosphine (6.51 g, 24.8 mmol) in anhydrous tetrahydrofuran (30 ml), a solution of DEAD (3.9 ml, 24.8 mmol) in anhydrous tetrahydrofuran (10 ml) was slowly added while keeping the temperature below 8-10° C. After 2 hours further DEAD (1.0 ml, 6.37 mmol) and triphenylphosphine (1.3 g, 4.96 mmol) were added and the mixture was stirred at room temperature overnight. The reaction mixture was concentrated and the residue was triturated with diethyl ether (50 ml). The solid was removed by filtration and washed with diethyl ether (2×50 ml). The combined filtrates were concentrated and the residue was triturated with hexane (50 ml) at 40° C. The resulting solid was removed by filtration and washed with hexane (2×50 ml). The combined filtrates were concentrated and the residue was purified by column chromatography eluting with 10:2 hexane:ethyl acetate mixture. The product was obtained as a low-melting white solid (4.9 g, 66% yield).

M.p. 25-30° C.

$^1$H NMR (DMSO-$d_6$) 7.83 (4H, m); 5.76 (1H, m); 4.96 (1H, dq, J=17.2, 1.6 Hz); 4.90 (1H, ddt, J=10.2, 2.2, 1.1); 3.54 (2H, t, J=7.1), 1.97 (2H, q, J=6.7); 1.56 (2H, m); 1.35-1.15 (14H, m).

Step 2: 10-(1,3-Dioxo-1,3-dihydroisoindol-2-yl)decanoic acid

A solution of 2-undec-10-enyl-1,3-dioxo-1,3-dihydroisoindole (2 g, 6.68 mmol) of Step 1 and Aliquat® 336 (0.2 g) in a mixture of hexane (20 ml) and acetic acid (6 ml) was added dropwise to a solution of potassium permanganate (2.76 g, 20 mmol) in water (28 ml) while cooling at 0° C. The reaction mixture was stirred at room temperature for 7 hours, then an aqueous solution of sodium bisulfite was added until disappearance of the purple colour. The mixture was then extracted with ethyl acetate and the organic phase was dried over sodium sulfate and concentrated. The residue was purified by silica gel column chromatography eluting with 2:1 hexane:ethyl acetate mixture. The product was obtained as a white solid (1.29 g, 61% yield). M.p. 58-60° C.

$^1$H NMR (DMSO-$d_6$) 11.95 (1H, br); 7.85 (4H, m); 3.55 (2H, t, J=7.2 Hz); 2.17 (2H, t, J=7.2 Hz); 1.7-1.4 (4H, m); 1.22 (10H, m).

Example G.2

6-(Benzenesulfonylamino)hexanoic acid

Benzenesulfonyl chloride (2.5 ml, 19 mmol) was added to a solution of 6-aminohexanoic acid (1 g, 7.62 mmol) in 2N NaOH (22 ml) and dioxane (3 ml), while stirring at 0° C.-5° C. The mixture was allowed to warm to room temperature and stirred for 1 hour. The reaction mixture was washed with ethyl acetate (50 ml), then acidified to pH 2 with 37% hydrochloric acid and extracted with ethyl acetate (2×50 ml). The combined organic layers were dried over sodium sulfate and concentrated. The residue was triturated with hexane. The solid was collected by filtration and dried under vacuum at 50° C. affording 1.1 g of the title compound (55% yield). M.p. 113-115° C.

$^1$H NMR (DMSO-$d_6$): 11.96 (1H, s); 7.79 (2H, m); 7.60 (4H, m); 2.71 (2H, m); 2.13 (2H, t, J=7.14 Hz); 1.38 (4H, m); 1.21 (2H, m).

Example G.3

6-(Ethylsulfonylamino)hexanoic acid

A solution of ethanesulfonyl chloride (3.9 ml, 41.1 mmol) in dioxane (10 ml) was added to a solution of 6-aminohexanoic acid (2 g, 15.2 mmol) in 1N NaOH (56 ml) and dioxane (10 ml), while stirring at 0° C.-5° C. The pH of the reaction mixture was adjusted to 8-9 by addition of 25% sodium hydroxide solution. The mixture was allowed to warm to room temperature and stirred for 30 minutes. Further 25% NaOH solution was added to adjust the pH to about 11. After 3.5 h 1N hydrochloric acid (15 ml) and ethyl acetate (60 ml) were added. The organic layer was dried over sodium sulfate and concentrated. The residue was triturated with a mixture of diethyl ether (5 ml) and hexane (15 ml). The solid was collected by filtration and dried affording 1.3 g of the title compound (40% yield).

$^1$H NMR (DMSO-$d_6$): 11.9 (1H, s); 6.97 (1H, t, J=5.7 Hz); 2.97 (2H, q, J=7.1); 2.88 (2H, q, J=6.6); 2.2 (2H, t, J=7.3); 1.47 (4H, m); 1.29 (2H, m); 1.18 (3H, t, J=7.3).

Example G.4

8-(Ethylsulfonylamino)octanoic acid

A solution of ethanesulfonyl chloride (1.5 ml, 15.7 mmol) in dioxane (5 ml) was added to a solution of 8-aminooctanoic acid (1 g, 6.28 mmol) in 1N NaOH (22 ml) and dioxane (5 ml), while stirring at 0° C.-5° C. The mixture was allowed to warm to room temperature and stirred for 3.5 minutes. During this period, at 1 hour intervals, the pH was adjusted to 7-8 by addition of 25% NaOH solution. The reaction mixture was washed with diethyl ether (30 ml). The pH was adjusted to 1-2 by addition of 1N HCl and the mixture was extracted with ethyl acetate (70 ml). The organic layer was dried over sodium sulfate and concentrated. The residue was triturated with a mixture of diethyl ether. The solid was collected by filtration and dried under vacuum affording 600 mg of the title compound (38% yield).

$^1H$ NMR (DMSO-$d_6$): 11.9 (1H, s); 6.96 (1H, t, J=6 Hz); 2.96 (2H, q, J=7.1); 2.88 (2H, q, J=6.6); 2.2 (2H, t, J=7.3); 1.45 (4H, m); 1.26 (6H, m); 1.18 (3H, t, J=7.3).

Example G.5

3-Amino-2-S-[(1,1-dimethylethoxycarbonyl)amino]-propionic acid, benzyl ester

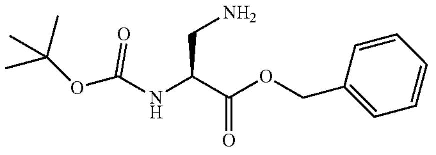 [SMILES: CC(C)(C)OC(=O)N[C@@H](CN)C(=O)OCc1ccccc1]

Step 1: N-tert-butoxycarbonyl-L-asparagine [Commercially available]

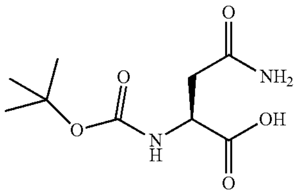 [SMILES: CC(C)(C)OC(=O)N[C@@H](CC(N)=O)C(=O)O]

L-asparagine (15 g, 0.113 mol, 1 eq.) and sodium carbonate (12 g, 0.113 mol) were dissolved in water (225 ml) and 1,4-dioxane (225 ml) at r.t. To this solution, di-tert-butyl-dicarbonate (30 g, 0.137 mol, 1.2 eq.) was added and the mixture was stirred overnight. The solvent was evaporated under reduced pressure till 1,4-dioxane was distilled and the pH adjusted to 2 with HCl 37% to give a white solid that was filtered, washed with water and dried. Yield 91%. 24 g.

Analytical data: m.p. 175° C.-180° C. (lit. 175° C.).

$^1H$ NMR (DMSO-$d_6$) 12.5 (1H, br); 7.31 (1H, br); 6.91 (1H, br); 6.87 (1H, d, J=8.4 Hz); 4.23 (1H, q, J=7.7 Hz); 2.56-2.36 (2H, m); 1.38 (9H, s).

Step 2: N-[(1,1-dimethylethoxycarbonyl)amino]-L-asparagine, benzyl ester

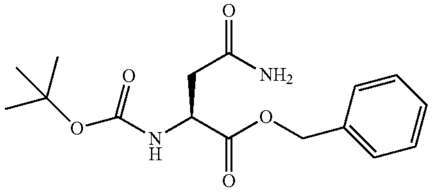 [SMILES: CC(C)(C)OC(=O)N[C@@H](CC(N)=O)C(=O)OCc1ccccc1]

The compound was prepared according to *Bioorg. Med. Chem.*, 6 (1998) 1185-1208. N-[(1,1-dimethylethoxycarbonyl)amino]-L-asparagine (20.7 g, 89.1 mmol, 1 eq.), of Step 1, was dissolved in methanol (500 ml) and cesium carbonate (15.97 g, 49 mmol, 0.55 eq.) was added. The solvent was evaporated to give a white solid that was dissolved in N,N-dimethylformamide (200 ml). To the suspension, benzyl bromide (11.6 ml, 98 mmol, 1.1 eq.) was added dropwise and the mixture was stirred overnight. The solvent was reduced under reduced pressure, water (300 ml) was added and the mixture extracted with ethyl acetate (200 ml), washed with brine (50 ml) and the solvent removed under reduced pressure to give a crude that was suspended in n-hexane (160 ml), filtered and dried under vacuum to give 14.68 g of white solid. Yield 51%.

Analytical data: m.p. 113°-115° C.

$^1H$ NMR (DMSO-$d_6$) 7.35 (6H, m); 7.13 (1H, d, J=7.9 Hz); 6.94 (1H, br s); 5.10 (2H, s); 4.39 (1H, q, J=7.4 Hz); 2.6-2.4 (2H, m); 2.03 (2H, t, J=7.3); 1.37 (9H, s).

Step 3: 3-Amino-2-S-[(1,1-dimethylethoxycarbonyl)amino]-propionic acid, benzyl ester

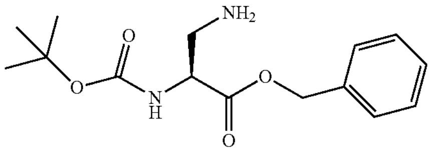 [SMILES: CC(C)(C)OC(=O)N[C@@H](CN)C(=O)OCc1ccccc1]

N-[(1,1-dimethylethoxycarbonyl)amino]-L-asparagine, benzyl ester, (2 g, 6.3 mmol, 1 eq.), of Step 2, was dissolved in acetonitrile (80 ml) and water (80 ml). The solution was cooled to 0°-5° C. and iodobenzene diacetate (3 g, 9.3 mmol, 1.5 eq.) was added portionwise. The mixture was stirred at 0° C. for 30', then at r.t. for 4 h. The organic solvent was removed under vacuum, diethyl ether and HCl 1N were added. The aqueous layer was separated and extracted with dichloromethane (100 ml) and sodium bicarbonate (3.5 g). The organic solvent was dried over sodium sulphate anhydrous, evaporated under reduced pressure to give 0.65 g of colourless oil. Yield 36%

Analytical data:

$^1H$ NMR (DMSO-$d_6$) 7.45-7.20 (7H, m); 7.20 (1H, d, J=7.7 Hz); 5.13 (2H, AB q, J=12.8); 4.01 (1H, m); 2.80 (2H, m); 1.38 (9H, s).

Example G.6

(2S)-2-[(1,1-dimethylethoxycarbonyl)amino]-3-[(4-methylbenzoyl)amino]propanoic acid

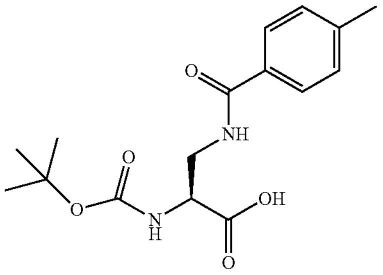 [SMILES: Cc1ccc(C(=O)NC[C@H](NC(=O)OC(C)(C)C)C(=O)O)cc1]

Step 1: 2-S-[(1,1-dimethylethoxycarbonyl)amino]-3-(4-methylbenzoylamino)propionic acid, benzyl ester

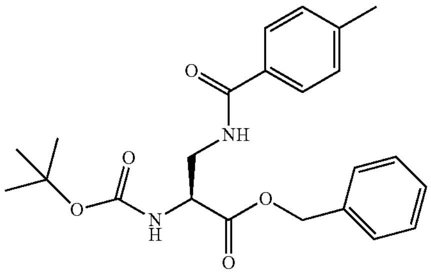 [SMILES: Cc1ccc(C(=O)NC[C@H](NC(=O)OC(C)(C)C)C(=O)OCc2ccccc2)cc1]

3-Amino-2-S-[(1,1-dimethylethoxycarbonyl)amino]-propionic acid, benzyl ester, (690 mg, 2.34 mmol, 1 eq.), of Example G.5, was dissolved in DMF dry (20 ml) and TBTU (900 mg, 2.98 mmol, 1.2 eq.) was added. The mixture was stirred at r.t. for 10', cooled to 0°-5° C. with ice bath and NMM (0.51 ml, 4.68 mmol, 2 eq.) and 4-methyl benzoic acid (380 mg, 2.81 mmol, 1.2 eq.) were added. The mixture was stirred at r.t. for 3 h, poured in water (100 ml) and extracted with ethyl acetate (100 ml). The organic layer was washed with a solution of citric acid 2% (50 ml), sodium bicarbonate 2% (50 ml), NaCl 2% (50 ml), dried over sodium sulphate anhydrous and evaporated at reduced pressure to give 1 g of oil. Yield quantitative.

Analytical data:

$^1$H NMR (DMSO-$d_6$) 8.46 (1H, br t, J=5.7 Hz); 7.70 (2H, d, J=8.0); 7.35-7.2 (8H, m); 5.07 (2H, s); 4.29 (1H, m); 3.67 (1H, m); 3.58 (1H, m); 2.36 (3H, s); 1.37 (9H, s).

Step 2: (2S)-2-[(1,1-dimethylethoxycarbonyl) amino]-3-(4-methylbenzoylamino)propionic acid

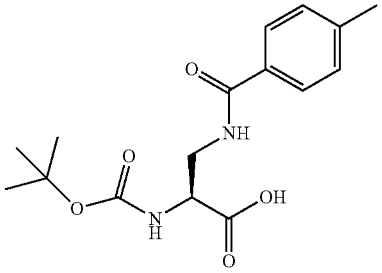 [SMILES: Cc1ccc(C(=O)NC[C@H](NC(=O)OC(C)(C)C)C(=O)O)cc1]

2-S-[(1,1-dimethylethoxycarbonyl)amino]-3-(4-methylbenzoylamino)-propionic acid, benzyl ester, (930 mg, 2.25 mmol), of Step 1, was dissolved in methanol (25 ml) and Pd/C 10% (90 mg) was added. The mixture was hydrogenated at atmospheric pressure for 1 h. Pd/C was filtered and the solution was evaporated under reduced pressure to give 650 mg of white foam. Yield 86%. Analytical data:

$^1$H NMR (DMSO-$d_6$): 12.5 (1H, br); 8.40 (1H, t, J=5.7 Hz); 7.71 (2H, d, J=8.05 Hz), 7.27 (2H, d, J=8.05 Hz); 7.09 (1H, d, J=7.9), 4.17 (1H, m); 3.57 (2H, m); 2.35 (3H, s); 1.37 (9H, m).

Example G.7

2-S-[(1,1-dimethylethoxycarbonyl)amino]-3-(hexanoylamino)propionic acid

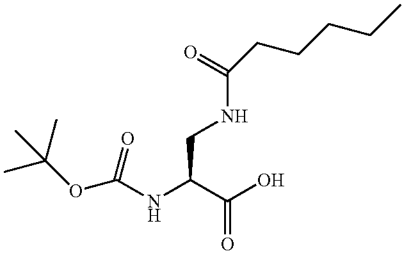 [SMILES: CCCCCC(=O)NC[C@H](NC(=O)OC(C)(C)C)C(=O)O]

Step 1: 2-S-[(1,1-dimethylethoxycarbonyl)amino]-3-(hexanoylamino)propionic acid, benzyl ester

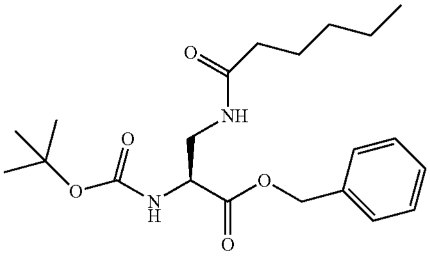 [SMILES: CCCCCC(=O)NC[C@H](NC(=O)OC(C)(C)C)C(=O)OCc1ccccc1]

Hexanoic acid (450 mg, 3.87 mmol, 1.2 eq.) was dissolved in DMF dry (15 ml) and TBTU (1.24 g, 3.87 mmol, 1.2 eq.) was added, the mixture was stirred at r.t. for 20', then was cooled to 0°-5° C. with ice bath. 3-amino-2-S-[(1,1-dimethylethoxycarbonyl)amino]propionic acid, benzyl ester, (950 mg, 3.22 mmol, 1 eq.), of Example G.5, and NMM (1.06 ml, 9.61 mmol, 2.5 eq.) were added. The mixture was stirred at r.t. overnight, poured in water (150 ml) and extracted with ethyl acetate (100 ml). The organic layer was washed with a solution of citric acid 2% (50 ml), sodium bicarbonate 2% (50 ml), NaCl 2% (50 ml), dried over sodium sulphate anhydrous and evaporated at reduced pressure to give a crude that was purified by silica gel column chromatography (eluent: n-hexane/ethyl acetate 2/1, R.f=0.52) 0.5 g of colourless oil.

Yield 40%.

Analytical data:

$^1$H NMR (DMSO-$d_6$).

$\delta_H$, 7.87 (1H, br t, J=6.2 Hz); 7.35 (5H, m); 7.14 (1H, d, J=8.2); 5.07 (2H, s); 4.14 (1H, m); 3.37 (2H, m); 2.00 (2H, t, J=7.1); 1.43 (2H, m); 1.36 (9H, s); 1.3-1.1 (4H, m); 0.83 (3H, t, J=7.1 Hz)

Step 2: 2-S-[(1,1-dimethylethoxycarbonyl)amino]-3-(hexanoylamino)propionic acid

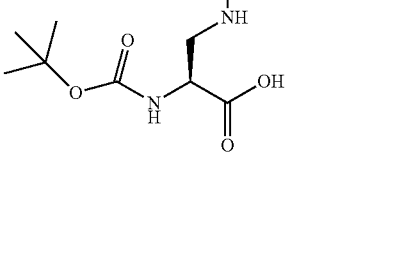

2-S-[(1,1-dimethylethoxycarbonyl)amino]-3-(hexanoylamino)propionic acid, benzyl ester (500 mg, 1.27 mmol), of Step 1, was dissolved in methanol (15 ml) and Pd/C 10% (50 mg) was added. The mixture was hydrogenated at atmospheric pressure for 1 h. Pd/C was filtered and the solution was evaporated under reduced pressure to give 300 mg of white solid. Yield 78%.

Analytical data: m.p. 123°-125° C.

$^1$H NMR (DMSO-$d_6$).

$\delta_H$, 12.6 (1H, br); 7.84 (1H, br t); 6.87 (1H, d, J=7.5 Hz); 4.00 (1H, m); 3.32 (2H, m); 2.04 (2H, t, J=7.5); 1.47 (2H, m); 1.38 (9H, s); 1.3-1.1 (4H, m); 0.85 (3H, t, J=7.1 Hz)

Example G.8

2-S-tert-butoxycarbonylamino-3-(4-fluorosulfonylamino)propionic acid

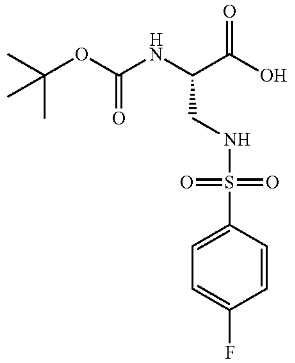 [SMILES: CC(C)(C)OC(=O)N[C@@H](CNS(=O)(=O)c1ccc(F)cc1)C(=O)O]

Step 1: 2-S-[(1,1-dimethylethoxycarbonyl)amino]-3-(4-fluorosulfonylamino)propionic acid, benzyl ester

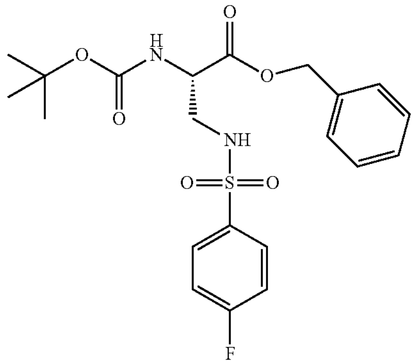 [SMILES: CC(C)(C)OC(=O)N[C@@H](CNS(=O)(=O)c1ccc(F)cc1)C(=O)OCc1ccccc1]

3-Amino-2-S-[(1,1-dimethylethoxycarbonyl)amino]propionic acid, benzyl ester (1.25 g, 4.24 mmol, 1 eq.), of Example G.5, was dissolved in dichloromethane dry (20 ml) and the solution was cooled to 0°-5° C., under nitrogen. TEA (0.65 ml, 4.67 mmol, 1.1 eq.) and 4-fluoro-sulfonylchloride (0.9 g, 4.67 mmol, 1.1 eq.) in dichloromethane dry (10 ml) were added. The mixture was stirred at r.t. for 1 h, evaporated under reduced pressure and diethyl ether (25 ml) was added and a white solid was obtained that was filtered and dried under vacuum to give 1.89 g of product.

Yield 99%.

Analytical data: m.p. 105°-107° C. TLC silica gel (eluent: n-hexane/ethyl acetate 1/1, R.f=0.55).

$^1$H NMR (DMSO-$d_6$).

$\delta_H$: 7.91 (1H, t, J=6.2 Hz); 7.85 (2H, dd, J=5.3, 8.8); 7.43 (2H, t, J=8.8); 7.35 (5H, m); 7.15 (1H, d, J=8.2); 5.09 (2H, s); 4.14 (1H, m); 3.10 (2H, m); 1.36 (9H, s).

Step 2: 2-S-[(1,1-dimethylethoxycarbonyl)amino]-3-(4-fluorosulfonylamino)propionic acid

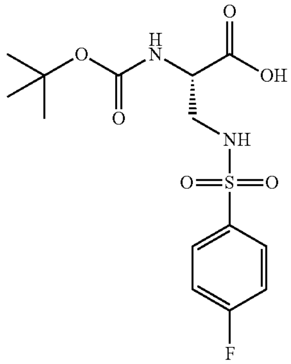 [SMILES: CC(C)(C)OC(=O)N[C@@H](CNS(=O)(=O)c1ccc(F)cc1)C(=O)O]

2-S-[(1,1-dimethylethoxycarbonyl)amino]-3-(4-fluorosulfonylamino)propionic acid, benzyl ester (1.8 g, 3.98 mmol), of Step 1, was dissolved in methanol (30 ml) and Pd/C 10% (180 mg) was added. The mixture was hydrogenated at atmospheric pressure for 1 h. Pd/C was filtered and the solution was evaporated under reduced pressure to give 1.39 g of colourless oil. Yield 97%.

Analytical data:

$^1$H NMR (DMSO-$d_6$).

$\delta_H$: 12.7 (1H, br); 7.83 (2H, dd, J=5.3, 8.8); 7.78 (1H, br t, J=5.5); 7.42 (2H, t, J=8.8); 6.87 (1H, d, J=8.6); 3.99 (1H, m); 3.03 (2H, m); 1.36 (9H, s).

Example G.9

2-S-[(1,1-dimethylethoxycarbonyl)amino]-3-(3,4-dimethoxyphenylacetamido)-propionic acid

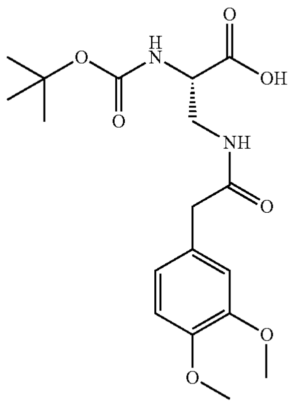 [SMILES: COc1ccc(CC(=O)NC[C@H](NC(=O)OC(C)(C)C)C(=O)O)cc1OC]

Step 1: 2-S-[(1,1-dimethylethoxycarbonyl)amino]-3-(3,4-dimethoxyphenylacetamido)-propionic acid, benzyl ester

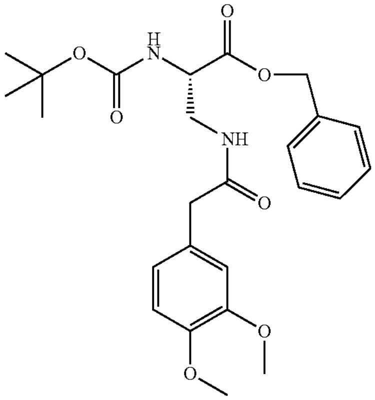 [SMILES: COc1ccc(CC(=O)NC[C@H](NC(=O)OC(C)(C)C)C(=O)OCc2ccccc2)cc1OC]

3,4-Dimethoxy-phenylacetic acid (720 mg, 3.66 mmol, 1.2 eq.) was dissolved in DMF dry (20 ml) and TBTU (1.17 g, 3.66 mmol, 1.2 eq.) was added, the mixture was stirred at r.t. for 20', then was cooled to 0°-5° C. with ice bath. 3-amino-2-S-tert-butoxycarbonylamino-propionic acid, benzyl ester (0.9 g, 3.05 mmol, 1 eq.), of Example G.5, and NMM (1.0 ml, 9.15 mmol, 2.5 eq.) were added. The mixture was stirred at 0° C. for 2 h, then poured in water (200 ml) and extracted with ethyl acetate (100 ml). The organic layer was washed with the following solutions: citric acid 2% (20 ml), sodium bicarbonate 2% (20 ml), NaCl 2% (20 ml), dried over sodium sulphate anhydrous and evaporated at reduced pressure to give a crude that was purified by silica gel chromatography (eluent: n-hexane/ethyl acetate 1/1, R.f=0.57) to give 1 g of colourless oil. Yield 69%.

Analytical data: $^1$H NMR (DMSO-$d_6$). $\delta_H$: 8.02 (1H, t, J=5.7 Hz); 7.34 (5H, m); 7.17 (1H, d, J=7.7); 6.82 (2H, m); 6.71 (1H, dd, J=1.5, 8.2); 5.03 (2H, s); 4.14 (1H, m); 3.71 (3H, s); 3.69 (3H, s); 3.39 (2H, m); 1.36 (9H, s).

Step 2: 2-S-[(1,1-dimethylethoxycarbonyl)amino]-3-(3,4-dimethoxyphenylacetamido)-propionic acid

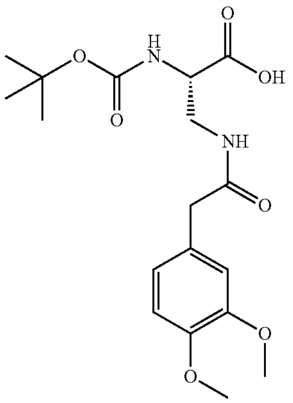 [SMILES: COc1ccc(CC(=O)NC[C@H](NC(=O)OC(C)(C)C)C(=O)O)cc1OC]

2-S-[(1,1-dimethylethoxycarbonyl)amino]-3-(3,4-dimethoxyphenylacetamido)-propionic acid, benzyl ester (1 g, 2.1 mmol), of Step 1, was dissolved in methanol (30 ml) and Pd/C 10% (10 mg) was added. The mixture was hydrogenated at atmospheric pressure for 1 h. Pd/C was filtered and the solution was evaporated under reduced pressure to give 0.73 g of white foam. Yield 91%.

Analytical data: $^1$H NMR (DMSO-$d_6$). $\delta_H$: 12.7 (1H, br); 8.06 (1H, t, J=5.9 Hz); 7.00 (1H, d, J=8.05); 6.91 (2H, m); 6.80 (1H, dd, J=1.5, 8.4); 4.08 (1H, m); 3.80 (3H, s); 3.78 (3H, s); 3.5-3.3 (2H, m); 1.36 (9H, s).

Example G.10

2-[(1,1-dimethylethoxycarbonyl)amino]-3-(3-phenylureido)propionic acid

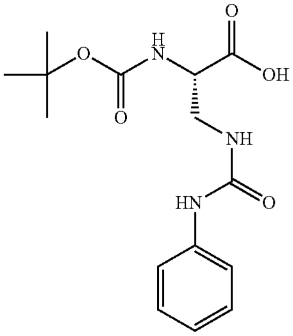 [SMILES: CC(C)(C)OC(=O)N[C@@H](CNC(=O)Nc1ccccc1)C(=O)O]

Step 1: 2-[(1,1-dimethylethoxycarbonyl)amino]-3-(3-phenylureido)propionic acid, benzyl ester

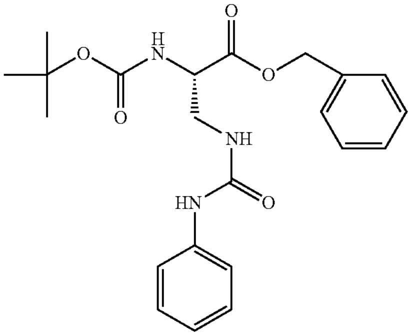 [SMILES: CC(C)(C)OC(=O)N[C@@H](CNC(=O)Nc1ccccc1)C(=O)OCc1ccccc1]

3-Amino-2-S-[(1,1-dimethylethoxycarbonyl)amino]propionic acid, benzyl ester (1.14 g, 3.87 mmol, 1 eq.), of Example G.5, was dissolved in dichloromethane (20 ml) at r.t., The solution was cooled to 0°-5° C. and phenyl isocyanate (0.42 ml, 3.87 mmol, 1 eq.) in dichlorometane (5 ml) was added dropwise. The solution was stirred at r.t. for 1 h, evaporated under reduced pressure and purified by silica gel chromatography (eluent n-hexane/ethyl acetate 1/1) to give 0.71 g of glassy solid that was suspended in diethyl ether to give a white solid. Yield 44%. Analytical data: TLC silica gel (eluent n-hexane/ethyl acetate 1/1 R.f.=0.44), m.p. 48°-50° C.

$^1$H NMR (DMSO-$d_6$). $\delta_H$: 8.68 (1H, s); 7.4-7.27 (8H, m); 7.22 (2H, t, J=8.2 Hz); 6.90 (1H, t, J=7.3); 6.26 (1H, t, J=5.7); 5.11 (2H, s); 4.12 (1H, m); 3.58 (1H, m); 3.28 (1H, m); 1.38 (9H, s).

Step 2: 2-[(1,1-dimethylethoxycarbonyl)amino]-3-(3-phenylureido)propionic acid

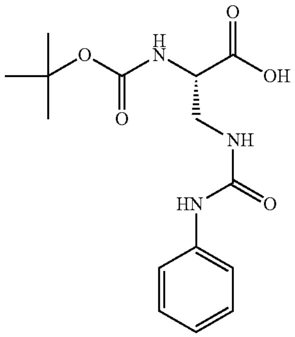 [SMILES: CC(C)(C)OC(=O)N[C@@H](CNC(=O)Nc1ccccc1)C(=O)O]

2-S-[(1,1-dimethylethoxycarbonyl)amino]-3-(3-phenylureido)propionic acid, benzyl ester (0.7 g, 1.7 mmol), of Step 1, was dissolved in methanol (25 ml) and Pd/C 10% (70 mg) was added. The mixture was hydrogenated at atmospheric pressure for 1 h. Pd/C was filtered and the solution was evaporated under reduced pressure to give 0.47 g of desired product. Yield 87%.

Analytical data: $^1H$ NMR (DMSO-$d_6$). $\delta_H$: 12.6 (1H, br); 8.66 (1H, s); 7.37 (2H, d, J=8.1 Hz); 7.21 (2H, t, J=7.50); 7.08 (1H, d, J=7.9); 6.89 (1H, t, J=7.3); 6.21 (1H, t, J=5.9); 3.98 (1H, m); 3.54 (1H, m); 3.22 (1H, m); 1.38 (9H, s).

Example G.11

Synthesis of Further Compounds

The following compounds can be prepared starting from 3-amino-2-S-[(1,1-dimethylethoxycarbonyl)amino]propionic acid, benzyl ester of Example G.5, with the methods described in Step 1 and Step 2 of Examples G.6-G.10.

| | | |
|---|---|---|
| G.11.1 | 2-[(1,1-dimethylethoxycarbonyl) amino]-3-(acetamido) propionic acid. | 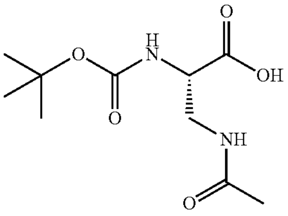 [SMILES: CC(=O)NC[C@H](NC(=O)OC(C)(C)C)C(=O)O] |
| G.11.2 | 2-[(1,1-dimethylethoxycarbonyl) amino]-3-(9-fluorenyl-methyloxycarbamoyl)) propionic acid. | 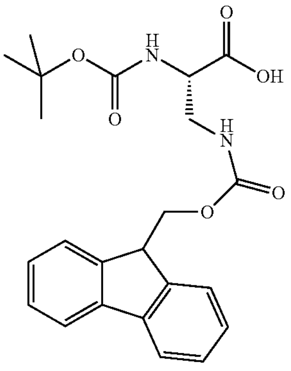 [SMILES: CC(C)(C)OC(=O)N[C@@H](CNC(=O)OCC1c2ccccc2-c2ccccc21)C(=O)O] |

-continued

| | | |
|---|---|---|
| G.11.3 | 2-[(1,1-dimethylethoxycarbonyl) amino]-3-(3-pentylureido) propionic acid. | 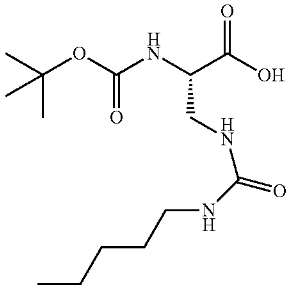 [SMILES: CCCCCNC(=O)NC[C@H](NC(=O)OC(C)(C)C)C(=O)O] |
| G.11.4 | 2-[(1,1-dimethylethoxycarbonyl) amino]-3-(methanesolfonamido) propionic acid. | 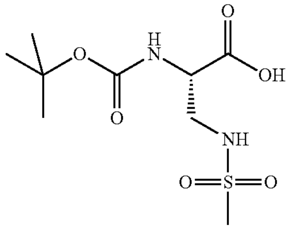 [SMILES: CC(C)(C)OC(=O)N[C@@H](CNS(C)(=O)=O)C(=O)O] |
| G.11.5 | 2-[(1,1-dimethylethoxycarbonyl) amino]-3-[(ethoxycarbonylsuccinyl]-amide)ethyl]-propionic acid. | 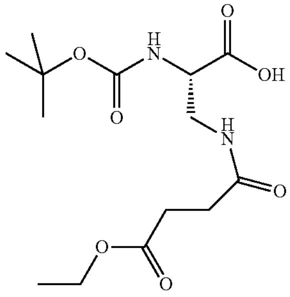 [SMILES: CCOC(=O)CCC(=O)NC[C@H](NC(=O)OC(C)(C)C)C(=O)O] |

Example G.12

2-[(1,1-Dimethylethoxycarbonyl)amino]-3-(3-benzyloxycarbonylamino)propionic acid

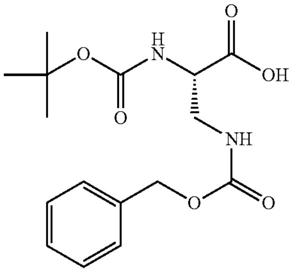 [SMILES: CC(C)(C)OC(=O)N[C@@H](CNC(=O)OCc1ccccc1)C(=O)O]

Step 1: $N^2$-(tert-Butoxycarbonyl)-L-2,3-diaminopropionic acid

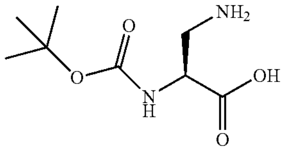

N-tert-butoxycarbonyl-L-asparagine, from step 1 of Example G.5 or commercially available, (8 g, 0.034 mol, 1 eq.) was suspended in ethyl acetate (72 ml), acetonitrile (72 ml) and water (36 ml), and Iodobenzenediacetate (13.3 g, 0.041 mol, 1.2 eq.) was added at 5° C. The mixture was stirred at 10°-25° C. for 3-4-h, then a white solid came off. The solid was filtered, washed with diethyl ether and dried under vacuum to give a white powder. Yield 57%. 4 g.

Analytical data: m.p. 210° C.-211° C. Silica gel (dichloromethane/methanol/acetic acid 5/3/1) Rf 0.5. $^1$H NMR (DMSO-$d_6$) 4.15 (1H, t); 3.15 (2H, m); 1.45 (9H, s);

Step 2: 2-[(1,1-dimethylethoxycarbonyl)amino]-3-(3-benzyloxycarbonylamino)propionic acid

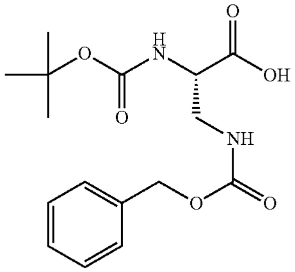 [SMILES: CC(C)(C)OC(=O)N[C@@H](CNC(=O)OCc1ccccc1)C(=O)O]

$N^2$-(tert-Butoxycarbonyl)-L-2,3-diaminopropionic acid, from step 1, (3.8 g, 0.018 mol, 1 eq.) was dissolved in aqueous sodium carbonate 10% (2.2 eq.) at 25° C. and 1,4-dioxane (38 ml). To this solution, benzylchloroformate (3 ml, 0,020 mol, 1.1 eq.) was added dropwise and the solution was stirred at 25° C. for 3 h. At the end of the reaction, the mixture was poured in water (100 ml) and washed with diethyl ether (100 ml). To the aqueous solution, HCl 37% (6 ml) was added till pH 2 and the obtained mixture was extracted with Ethyl Acetate (100 ml). The organic layer was separated, washed with brine and dried over sodium sulfate anhydrous. The solvent was removed under reduced pressure to give a colourless oil that under vacuum gave a white foam.

Yield 93%, 5.9 g.

Analytical data: silica gel (dichloromethane/methanol/acetic acid 5/3/1) Rf 1.

$^1$H NMR (DMSO-$d_6$) 12.6 (1H br s); 7.35 (5H m); 6.94 (1H, d); 5 (2H, s); 4.1 (2H, m); 1.4 (9H, s).

Example G.13

2-(tert-Butoxycarbonilamino)-3-pyrazol-1-yl-propionic acid

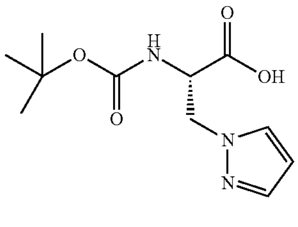 [SMILES: CC(C)(C)OC(=O)N[C@@H](Cn1cccn1)C(=O)O]

The intermediate was prepared according to the procedure described in Vederas, *J. Am. Chem. Soc.,* 1985, 107, 7105-7109.

Example G.14

1-Methanesulfonyl-piperidine 4-carboxylic acid

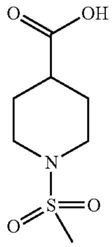

Step 1: 1-[(1,1-Dimethylethoxycarbonyl)amino]-piperidine-4-carboxylic acid

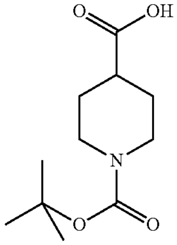 [SMILES: CC(C)(C)OC(=O)N1CCC(C(=O)O)CC1]

Piperidine-4-carboxylic acid (5 g, 38.7 mmol, 1 eq.) was dissolved in sodium carbonate solution (4.5 g, 42.6 mmol, 2.2 eq.), 70 ml, and 1,4-dioxane (30 ml). A solution of di-tert-butyldicarbonate (9.3 g, 42.61 mmol, 1.1 eq.) in 1,4-dioxane (40 ml) was added dropwise and the resulting mixture was stirred overnight at room temperature. The organic solvent was removed under reduced pressure and the resulting solution was acidified with HCl 37% till pH 2. The obtained suspension was filtered, the white solid washed with diethyl ether (5 ml). The mother liquor has been extracted with ethyl acetate (120 ml) and the previous solid was added. The organic solution was dried over anhydrous sodium sulfate, evaporated under reduced pressure to give a white solid that was dried at 80° C. under vacuum to give the title compound. Yield 93%, 8.2 g.

Analytical data: m.p. 133°-135° C.

$^1$H NMR (DMSO-$d_6$) 12.3 (1H br s); 3.85 (2H, d); 2.8 (2H, br); 2.35 (1H, t); 1.8 (2H, d); 1.4 (11H, m).

Step 2: 1-[(1,1-Dimethylethoxycarbonyl)amino]-piperidine-4-carboxylic acid benzyl ester

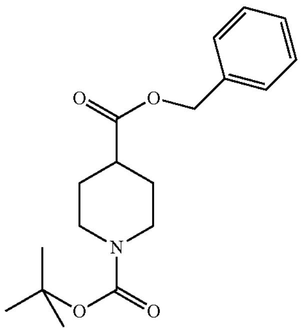 [SMILES: CC(C)(C)OC(=O)N1CCC(C(=O)OCc2ccccc2)CC1]

1-[(1,1-Dimethylethoxycarbonyl)amino]-piperidine-4-carboxylic acid (6 g, 26.16 mmol, 1 eq.), from step 1, was dissolved in methanol (150 ml) and cesium carbonate (4.26 g, 13.08 mmol, 0.5 eq.) was added. The mixture was stirred at room temperature for 2 h, the solvent was removed under reduced pressure. The crude was dissolved in DMF (100 ml) and benzylbromide (5.37 g, 31.39 mmol, 1.2 eq.) was added dropwise. The mixture was stirred overnight at room temperature and poured in water (300 ml), extracted with Ethyl Acetate (900 ml) The organic layer was dried over anhydrous sodium sulfate and evaporated under reduced pressure to give a white solid.

Yield 95%, 7 g.

Analytical data:

$^1$H NMR (DMSO-$d_6$) 7.3 (5H m); 5.1 (2H, s); 3.85 (2H, d); 2.8 (2H, br); 2.65 (1H, t); 1.8 (2H, d); 1.4 (11H, m).

Step 3: Piperidine-4-carboxylic acid benzyl ester, hydrochloride salt

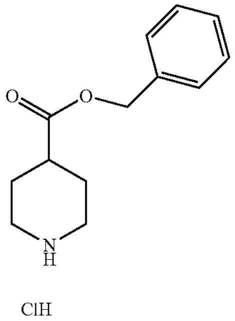 [SMILES: O=C(OCc1ccccc1)C1CCNCC1 ; Cl]

1-[(1,1-Dimethylethoxycarbonyl)amino]-piperidine-4-carboxylic acid benzyl ester (7 g, 21.0 mmol), from step 2, was dissolved in 1,4-dioxane (20 ml). To this solution, HCl 4N in 1,4-dioxane (7.8 ml, 300 ml, 12 eq.) was added and the resulting solution was stirredovernight at room temperature. The solid was filtered, suspended in n-hexane (50 ml), and filtered to give a white solid. Yield 54%, 2.5 g.

Analytical data:

$^1$H NMR (DMSO-$d_6$) 8.9 (2H, br); 7.35 (5H, m); 5.1 (2H, s); 3.25 (2H, d); 2.9 (2H, t); 2.75 (1H, m); 2.0 (2H, m); 1.8 (2H, m).

Step 4: 1-Methanesulfonyl-piperidine-4-carboxylic acid benzyl ester

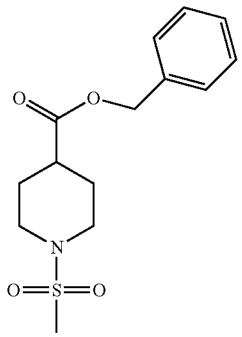 [SMILES: CS(=O)(=O)N1CCC(C(=O)OCc2ccccc2)CC1]

Piperidine-4-carboxylic acid benzyl ester, hydrochloride salt (1 g, 3.9 mmol, 1 e.) from step 3, was dissolved in DMF (15 ml), Triethylamine (0.55 ml, 4 mmol, 1 eq.) and methanesulfonylchloride were added. The mixture was stirred for 1 h at room temperature, then was poured in water (20 ml). The aqueous solution was extracted with Ethyl Acetate (90 ml) and the organic layer was dried over anhydrous sodium sulfate, evaporated under reduced pressure to give a colourless oil. Yield 78%, 0.9 g.

Analytical Data:

$^1$H NMR (DMSO-$d_6$) 7.35 (5H, m); 5.1 (2H, s); 3.5 (2H, d); 2.8 (5H, m); 2.6 (1H, m); 2.0 (2H, m); 1.6 (2H, m).

Step 5: 1-Methanesulfonyl-piperidine 4-carboxylic acid

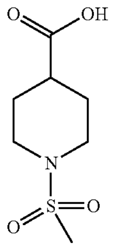

1-Methanesulfonyl-piperidine-4-carboxylic acid benzyl ester (0.8 g, 26.7 mmol) from step 4, was dissolved in ethyl acetate (100 ml) and methanol (10 ml), Pd/C 10% (80 mg) was added and the resulting mixture was hydrogenated at 1 bar. The catalyst was filtered over celite, the solvent was removed under reduced pressure to give a white solid. Yield 73%, 0.4 g Analytical data:

$^1$H NMR (DMSO-$d_6$) 12.4 (1H, br); 3.6 (2H, d); 2.9 (4H, m); 2.4 (1H, m); 2.0 (2H, m); 1.6 (2H, m).

Example G.15

(4-Methylphenyl)-ureido-sulfonylchloride

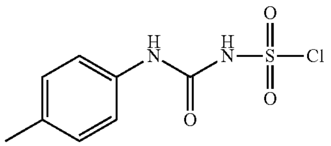

This compound was prepared according to *J. Med. Chem.* 1996, 39, 1243-1252. Briefly, a solution of chlorosulfonyl-isocyanate (1.62 g, 11.5 mmol, 1 eq.) was diluted in dry diethylether and the resulting solution was cooled at −50° C.<T<−40° C. To this solution, p-toluidine (1.23 g, 11.5 mmol, 1 eq.) was added. The solution was stirred at −35° C. for 10' and a suspension was obtained. The solid was filtered and washed with diethyl ether. Yield 80%, 2.3 g.

Analytical data: m.p. 127°-129° C.

$^1$H NMR (DMSO-$d_6$) 9.9 (1H, s); 7.3 (2H, d); 7.1 (2H, d); 2.25 (3H, s);

Example G.16

Isoxazole-5-carboxylic acid

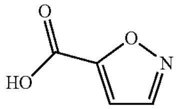

The desired carboxylic acid was prepared according to the procedure by Wolfang et al., *Synthesis,* 1986, 69-70.

Utility

Compound Activity

The present compounds can inhibit proteasome activity. Table F-1 below provides data related to several Example compounds of the invention with respect to, for example, ability to inhibit proteasome activity.

Methods and Compositions

Compounds of the present invention can inhibit the activity of proteasome leading to the inhibition or blocking of a variety of intracellular functions with which the proteasome is directly or indirectly associated. For example, proteasome inhibitors can modulate, such as induce, apoptosis in a cell. In some embodiments, the compounds herein can kill tumor cells by induction of apoptosis. Thus, the present compounds can be used to treat cancer, tumors or other proliferative disorders.

In further embodiments, inhibition of proteasome function by compounds of the invention can inhibit the activation or processing of transcription factor NF-κB. This protein plays a role in the regulation of genes involved in the immune and inflammatory responses as well as in cell viability Inhibition of proteasome function can also inhibit the ubiquitination/proteolysis pathway. This pathway catalyzes, inter alia, selective degradation of highly abnormal proteins and short-lived regulatory proteins. In some embodiments, compounds of the invention can prevent the degradation of p53 which is typically degraded by the ubiquitin-dependent pathway. The ubiquitination/proteolysis pathway also is involved in the processing of internalized cellular or viral antigens into antigenic peptides that bind to MHC-I molecules. Thus, the compounds of the invention can be used to reduce the activity of the cytosolic ATP-ubiquitin-dependent proteolytic system in a number of cell types.

Accordingly, the usefulness of such compounds can include therapeutics, such as the treatment of various diseases or disorders associated with proteasome. The methods include administering a therapeutically effective amount of a compound of the invention, or composition thereof, to a mammal, such as a human having a disease or disorder associated with proteasome. The phrase “therapeutically effective amount” refers to an amount sufficient to prevent, alleviate, or ameliorate any phenomenon, such as a cause or symptom, known in the art to be associated with the disease or disorder.

Treatable diseases or disorders (abnormal physical conditions) can be associated with either normal or abnormal activities of proteasome, such as the regulation of apoptosis. Numerous diseases or disorders that are associated with proteasome, or that are desirably treated by induction of apoptosis, are known and include, for example, various cancers and tumors including those associated with skin, prostate, colorectal, pancreas, kidney, ovary, mammary, liver, tongue, lung, and smooth muscle tissues. Preferred tumors that can be treated with proteasome inhibitors include, but are not limited to hematological tumors, such as, for example, leukemias, lymphomas, non-Hodgkin lymphoma, myeloma, multiple myeloma, as well as solid tumors such as, for example, colorectal, mammary, prostate, lung, and pancreas tumors. In order to elicit therapeutic effects, the proteasome inhibitors can be administered to patients as single agents or in combination with one or more antitumor or anticancer agent and/or radiotherapy. Examples of other anti-tumor or anti-cancer agents which can be advantageously administered concomitantly with a proteasome inhibitor include but are not limited to, adriamycin, daunomycin, methotrexate, vincristin, 6-mercaptopurine, cytosine arabinoside, cyclophosphamide, 5-FU, hexamethylmelamine, carboplatin, cisplatin, idarubycin, paclitaxel, docetaxel, topotecan, irinotecam, gemcitabine, L-PAM, BCNU and VP-16. Methods for determining apoptosis in vitro are well known in the art and kits are available commercially. See for example the Apo-ONE™ Homogeneous Caspase-3/7 Assay from Promega Corporation, Madison Wis., USA (Technical Bulletin No. 295, revised 2/02, Promega Corporation).

Further diseases or disorders associated with the proteasome include accelerated or enhanced proteolysis that occurs in atrophying muscles, such as is often associated with activation of a nonlysomal ATP-requiring process involving ubiquitin. Accelerated or enhanced proteolysis can be the result of any of numerous causes including sepsis, burns, trauma, cancer, infection, neurodegenerative diseases such as muscular dystrophy, acidosis, or spinal/nerve injuries, corticosteroid use, fever, stress, and starvation. Compounds of the invention can be tested for inhibition of muscle wastage by any various procedures known in the art such as by measuring urinary excretion of modified amino acid 3-methylhistidine (see, e.g., Young, et al., *Federation Proc.,* 1978, 37, 229).

Compounds of the present invention can be further used to treat or prevent diseases or disorders associated with activity of NF-κB including for example, human immunodeficiency virus (HIV) infection and inflammatory disorders resulting from, for example, transplantation rejection, arthritis, infection, inflammatory bowel disease, asthma, osteoporosis, osteoarthritis, psoriasis, restenosis, and autoimmune diseases. Accordingly, a process that prevents activation of NF-κB in patients suffering from such a disease would be therapeutically beneficial. Inhibition of the NF-κB activity can be measured by using a DNA binding assay such a described in Palombella, et al., *Cell,* 1994, 78,773.

Those of ordinary skill in the art can readily identify individuals who are prone to or suspected of suffering from such diseases or disorders using standard diagnostic techniques.

Example A

Assay for Chymotrypsin-like Activity of 20S Human Erythrocyte Proteasome (HEP)

Proteasome chymotrypsin-like activity of compounds of the invention was assayed according to the following procedure.

In 96-well microtiter plates, 20S Human Erythrocyte Proteasome (HEP), purchased from Immatics Biotechnologies Inc., Tübingen, Germany was plated at 0.2 μg/mL (about 0.6 nM catalytic sites) in 0.04% SDS 20 mM Tris buffer. A fluorimetric substrate Suc-LLVY-AMC (succinyl-Leu-Leu-Val-Tyr-7-amido-4-methylcoumarin), purchased from Sigma Inc., St. Louis, Mo., USA was added to a final concentration of 100 μM from a stock solution of 10 mM in dimethylsulfoxide. Reaction volumes were 100 μl per well. After incubation for various periods of time at 37° C., the concentration of free AMC (aminomethylcoumarin) was determined on a Perkin Elmer HTS 7000 Plus microplate reader, excitation 370 nM and emission 465 nM. Proteasome activity was determined under conditions in which substrate hydrolysis increased linearly with time and the change in fluorescence signal was proportional to the concentration of free AMC.

Example B

Assay for Activity of α-Chymotrypsin

In 96-well microtiter plates bovine α-chymotrypsin, purchased from Sigma Inc., was plated at 10 ng/mL (about 2 μM catalytic sites) in 0.5 M NaCl 50 mM Hepes buffer. A fluorimetric substrate Suc-AAPF-AMC (succinyl-Ala-Ala-Pro-Phe-7-amido-4-methylcoumarin), purchased from Sigma Inc., St. Louis, Mo., USA was added to a final concentration of 25 μM from a stock solution of 10 mM in dimethylsulfoxide. Reaction volumes were 100 μl per well. After incubation for various periods of time at room temperature, the concentration of free AMC was determined on a Perkin Elmer HTS 7000 Plus microplate reader, excitation 370 nM and emission 465 nM. α-Chymotrypsin activity was determined under conditions in which substrate hydrolysis increased linearly with time and the change in fluorescence signal was proportional to the concentration of free AMC.

Example C

Determination of $IC_{50}$ Values for HEP and α-Chymotrypsin Inhibitors $IC_{50}$ values are typically defined as the concentration of a compound necessary to produce 50% inhibition of the enzyme's activity. $IC_{50}$ values are useful indicators of the activity of a compound for its designated use. The proteasome inhibitors of the invention can be considered active if they have $IC_{50}$ values of less than about 1 micromolar for inhibition of human erythrocyte proteasome (HEP). In some embodiments, the inhibitors show some specificity for HEP and the ratio of the $IC_{50}$ for inhibition of bovine α-chymotrypsin versus the $IC_{50}$ for inhibition of HEP, i.e, $IC_{50}$ (α-Chymotripsin)/$IC_{50}$ (HEP), is greater then about 100.

Inhibition of the chymotrypsin-like activity of HEP and of bovine α-chymotrypsin was determined by incubating the enzyme with various concentrations of putative inhibitors for 15 minutes at 37° C. (or room temperature for α-chymotrypsin) prior to the addition of substrate. Each experimental condition was evaluated in triplicate, and replicate experiments were performed for the inhibitors described herein.

Compounds of the present invention are considered active in the above identified assay if their $IC_{50}$ values for inhibition of HEP are less than 1000 nanoMolar. Preferably compounds of the present invention will have $IC_{50}$ values for inhibition of HEP less than 100 nanoMolar. More preferably compounds of the present invention will have $IC_{50}$ values for inhibition of HEP less than 10 nanoMolar. Compounds of the present invention have demonstrated, in the above identified assay, $IC_{50}$ values for inhibition of HEP less than 1000 nanoMolar.

Example D

Cellular Assay for Chymotrypsin-Like Activity of Proteasome in Molt-4 Cell Line

The chymotrypsin-like activity of proteasome in Molt-4 cells (human leukemia) was assayed according to the following procedure. A brief description of the method was published previously (Harding et al., *J. Immunol.,* 1995, 155, 1767).

Molt-4 cells were washed and resuspended in HEPES-buffered Saline (5.4 mM KCl, 120 mM NaCl, 25 mM Glucose, 1.5 mM $MgSO_4$, 1 mM Na pyruvate, 20 mM Hepes) and plated in 96-well microtiter white plates to a final concentration of $6\times10^6$ cells/mL. Then various 5× proteasome inhibitor concentrations (or diluted DMSO for controls), prepared from 250×DMSO solutions by diluting 50-fold using HEPES-buffered saline, were added to the plate to a final 1× concentration. After 15 minutes incubation at 37° C., a fluorimetric cell permeable substrate (MeOSuc-FLF-AFC) (methoxysuccinyl-Phe-Leu-Phe-7-amido-4-trifluoromethylcoumarin) purchased from Enzyme Systems Products, catalogue number AFC-88, was added to each well at a final concentration of 25 μM from a stock solution of 20 mM in DMSO. Reaction volumes were 100 μl per well.

The concentration of free AFC was monitored every 1.5 min for 30 min (22 cycles) on a Polastar Optima, BMG Labtechnologies microplate reader, using an excitation wavelength of 390 nm and emission wavelength of 520 nm. Proteasome activity was determined under conditions in which substrate hydrolysis increased linearly with time and the change in fluorescent signal was proportional to the concentration of free AFC.

Example E

Determination of $EC_{50}$ Values for Proteasome Inhibitors in MOLT-4 Cell Line $EC_{50}$ values are typically defined as the concentration of a compound required to produce an inhibition of the enzyme's activity halfway between the minimum and the maximum response (0% and 85-90% respectively for this assay). $EC_{50}$ values are useful indicators of the activity of a compound for its designated use. The compounds of the invention can be considered active if they have an $EC_{50}$ of less than about 10 micromolar.

Inhibition of chymotrypsin-like activity of proteasome in Molt-4 cells was determined by incubating cells with various concentrations of putative inhibitors for 15 minutes at 37° C. prior to the addition of substrate. Each experimental condition was evaluated in triplicate, and replicate experiments were performed for the inhibitors described herein.

Compounds of the present invention are considered active in the above identified assay if their $EC_{50}$ values for proteasome inhibition in MOLT-4 are less than 10 microMolar. Preferably compounds of the present invention will have $EC_{50}$ values for proteasome inhibition in MOLT-4 less than 2 microMolar. More preferably compounds of the present invention will have $EC_{50}$ values for proteasome inhibition in MOLT-4 less than 200 nanomolar. Compounds of the present invention have demonstrated, in the above identified assay, $EC_{50}$ values for proteasome inhibition in MOLT-4 cells of less than 10 microMolar.

Example F

Assay for Trypsin-like Activity of the Proteasome

The trypsin-like activity of human proteasome can be assayed as described above with the following modifications. Reactions can be carried out in Tris-glycerol buffer (pH 9.5) supplemented with 1 mM 2-mercaptoethanol, and the substrate can be a fluorogenic substrate such as benzyloxycarbonyl-Phe-Arg-AMC (100 μM).

After incubation for various periods of time at 37° C., the concentration of free AMC can be determined on a Fluoroskan II spectrofluorimeter with an excitation filter of 390 nm and an emission filter of 460 nm. Protease activity can be determined under conditions in which substrate hydrolysis increases linearly with time and the change in fluorescence is proportional to the concentration of free AMC.

Example G

In vivo Inhibition of Cellular Muscle Breakdown

The effect of inhibitors on the unweighting atrophy of the soleus muscle in juvenile rats can be determined by, for example, the procedures described in Tischler, *Metabolism,* 1990, 39, 756. For example, juvenile female Sprague-Dawley rats (80-90 g) can be tail-cast, hind limb suspended as described in Jaspers, et al., *J. Appl. Physiol.,* 1984, 57, 1472. The animal's hind limbs can be elevated above the floor of the cage with each animal housed individually. Animals can have free access to food and water, and can be weighed at the time of suspension and at time of termination. During the suspension period the animals can be checked daily to ensure that their toes are not touching the floor of the cage, and that there is no swelling of the tail due to the cast.

Experimental Design—Part 1

Each experiment can begin with the suspension of 20 rats which are randomly divided into 4 groups of 5 animals each. Group A can be suspended for 2 days, providing baseline data to approximate the soleus muscle size in other animals suspended for longer times. Average body weights for the groups at the outset of the study can be compared and used as a correction factor for body size differences. Group B can be a second control group which has the soleus of one limb treated with an aqueous solution of mersalyl after two days of unweighting, to demonstrate the ability to slow muscle atrophy during unweighting, for each group of animals. At 2 days after unweighting commences, an aqueous solution of mersalyl (200 nM; 4 μL/100 g initial body wt) can be injected into one soleus. The contralateral muscle can be injected with a similar volume of 0.9% saline ("Vehicle"). The animals can be maintained under Innovar-vet (10 μL/100 g body wt) tranquilization during the in situ injection procedure. After the injections, the animals can be suspended for an additional 24 hours and the soleus can be removed. Groups C and D for each experiment can be used for testing each of two different embodiments of the disclosed compounds. Animals can be treated as in group B, except that 1 mM proteasome inhibitor, contained in dimethysulfoxide (DMSO), can be injected into the soleus of one leg and DMSO only into the contralateral soleus. Thus each experiment consists of two control groups and the testing of proteasome inhibitors of the invention. The completion of five such experiments with different pairs of inhibitors provides for an "n" value of 10 for testing each inhibitor and each can be tested in two different shipments of animals.

Processing of the Soleus Muscle—Part 1

After the animal is sacrificed, the soleus can be excised, trimmed of fat and connective tissue, and carefully weighed. The muscle can then homogenized in 10% trichloroacetic acid (TCA) and the precipitated protein pelleted by centrifugation. The pellet can then be washed once with 10% TCA and once with ethanol:ether (1:1). The final pellet can be solubilized in 4 ml of 1N sodium hydroxide. The sample can be then analyzed for protein content by the biuret procedure, using albumin as a standard.

Data Analysis—Part 1

The effect of inhibitors on total muscle protein content can be examined primarily by paired comparison with the untreated contralateral muscle. The ratio of contents can be calculated and then analyzed statistically by analysis of variance ("ANOVA"). The left leg can always be the treated leg so that the protein content ratios can be compared to the non-treated control animals as well. In this way, a significant difference can be shown by comparing the protein content of the two legs, as well as the relative effectiveness of the tested inhibitors. A paired student test can also be performed for the effect of each separate treatment. The non-treated control data also provide an estimate of protein content of day 2. This allows approximation of the protein changes over the 24 hours of treatment for each of the Groups B, C, and D.

Experimental Design—Part 2

Each experiment can consist of 10 animals with groups of 5 animals being tested with one of the inhibitors for its effect on protein synthesis. Control animals are not needed for this aspect of the study as the contralateral DMSO-treated muscle serves as the paired control for the inhibitor-treated muscle. Each group can be injected as described for groups C and D in part 1. Twenty-four hours after the in situ treatment the fractional rate of protein synthesis can be analyzed in both soleus muscles. Each muscle can be injected with a 0.9% saline solution (3.5 μl/100 g final body wt) containing $^3$H-phenylalanine (50 mM; 1 μCi/$^m$l). Fifteen minutes later the middle two-thirds of the muscle can be excised and the muscle can be processed as described below.

Processing of the Soleus Muscle—Part 2

The muscle can be first washed for 10 minutes in 0.84% saline containing 0.5 mM cycloheximide, to terminate protein synthesis, and 20 mM cycloleucine, to trap phenylalanine in the cell. The muscle can then be homogenized in 2.5 mL of ice-cold 2% perchloric acid. The precipitated protein can be pelleted by centrifugation. One aliquot of the supernatant can be taken for liquid scintillation counting and another aliquot can be processed for conversion of phenylalanine to phenethylamine to determine the soluble phenylalanine concentration fluorometrically. See, e.g., Garlick, et al., *Biochem. J.,* 1980, 192, 719. These values can provide the intracellular specific activity. The specific activity of phenylalanine in the muscle protein can be determined after hydrolyzing the protein by heating in 6N HCl. The aminoacids released can be solubilized in buffer. One aliquot can be taken for scintillation counting and another for analysis of phenylalanine as for the supernatant fraction. The fractional rate of protein synthesis can be calculated as: protein specific activity/intracellular specific activity.times.time.

Data Analysis—Part 2

Analyses of protein synthesis can be on a paired basis for each inhibitor. Student paired t test comparisons of the contralateral muscles can determine whether there is any effect of the inhibitor on protein synthesis. Protein breakdown can be calculated approximately as the fractional rate of protein synthesis (from part 2) plus the fractional rate of protein accretion (from part 1), where protein loss yields a negative value for protein accretion.

Qualitatively the ability of inhibitors to slow protein loss without affecting protein synthesis indicates a slowing of protein degradation.

Example H

In vivo Investigation of Anti-Tumor Activity

Materials

The proteasome inhibitors used for in vivo studies can be formulated in an appropriate medium for intravenous (iv) or oral (po) administration. For example, for the iv administration the compounds can be administered dissolved in 0.9% NaCl, or in mixtures of 0.9% NaCl, solutol HS15 and dimethylsulfoxide, for example in the ratio 87:10:3 (v:v:v), respectively.

Cell Lines

The following human and murine tumor cell lines of different histological origine can be used to test the antitumor activity of the compounds of the invention: H460 (human, lung), A2780 (human, ovary), PC-3 (human, prostate), LoVo (human, colon), HCT116 (human, colon), BXPC3 (human, pancreatic), PANC-1 (human, pancreatic), MX-1 (human, mammary), MOLT (human, leukemia), multiple myeloma (human, myeloma), YC8 (murine, lymphoma), L1210 (murine, leukemia), 3LL (murine, lung).

Animal Species 5-6 weeks immunocompetent or immunodeprived mice are purchased from commercial sources, for example from Harlan (Correzzana, Mi Italy). CD1 nu/nu mice are maintained under sterile conditions; sterilized cages, bedding, food and acidified water are used.

Tumor Cell Implantation and Growth

Solid tumor models of different hystotype (lung, ovary, breast, prostate, pancreatic, colon) can be transplanted subcutaneously (sc.) into the axillary region of immunocompetent mice (murine models) or in immunodeprived mice (human models). Human tumor cell lines, originally obtained from ATCC, can be adapted to grow “in vivo” as solid tumor from “in vitro culture”.

Hematological human or murine tumor models can be transplanted into different sites (iv, ip, ic or sc) in immunocompetent mice (murine tumors) or in immunodeprived mice (human leukemia, lymphoma and myeloma models), according to their highest tumor take.

Drug Treatment

Mice bearing solid (staged) or hematological tumors are randomized in experimental groups (10 mice/group). For solid tumors, an average tumor weight of 80-100 mg for each group is considered to start the treatment; mice with the smallest and largest tumors are discarded.

Experimental groups are randomly assigned to the drug treatment and to the control group. Animals can be treated iv or orally, depending on the oral bioavailability with the compounds following different treatment schedules: iv weekly or twice weekly, or by daily oral administration.

On solid tumor models, drug treatment can begin when the tumor size ranges between 80-100 mg after tumor transplantation (Day 0).

The compounds can be administered in a volume of 10 mL/Kg body weight/mouse in the appropriate solvent.

Parameters of Antitumor Activity

The following parameters can be assessed for the evaluation of the antitumor activity:

growth of primary solid tumor; in each mouse is monitored by caliper measurement twice weekly;

survival time of treated mice as compared to control mice twice weekly body weight evaluation of individual mice.

The tumor growth inhibition, TWI % (percentage of primary tumor growth inhibition in comparison with vehicle treated control groups) or the Relative tumor growth inhibition, RTWI % in case of staged tumors, is evaluated one week after the last drug treatment and the Tumor weight (TW) can be calculated as follows:

$$TW=\tfrac{1}{2}ab^2$$

where a and b are long and short diameters of the tumor mass in mm.

The antitumor activity can be determined as tumor weight inhibition (TWI %), which is calculated according to the formula:

$$TWI\ \% = 100 - \frac{\text{mean } TW \text{ treated}}{\text{mean } TW \text{ controls}} \times 100$$

The RTWI % (relative percentage of primary tumor growth inhibition in comparison with vehicle treated control groups) is evaluated one week after the last drug treatment, according to the following formula:

$$RTWI\ \% = 100 - \frac{\text{mean } RV \text{ of treated mice}}{\text{mean } RV \text{ of controls mice}} \times 100$$

where $$RV = \frac{Vt(\text{tumor weight on day } t)}{Vo(\text{initial tumor weight at the outset of treatment})}$$

The Percent of Tumor Regression can be calculated as regressions in terms of relative tumor weight, determined as tumor weight at given day divided by initial tumor weight at the outset the experiment.

On haematological tumour models the antitumor activity can be determined as percentage increase of the median survival time of mice expressed as the ratio (T/C %) of the median survival time of the treated group (T) to that of the control group (C). Animals which are tumour-free at the end of the experiment (60 days after transplantation) are excluded from the calculation and considered as long term survivors (LTS).

Evaluation of Toxicity in Tumor Bearing Mice

Toxicity can be evaluated daily on the basis of the gross autopsy findings and the weight loss. Mice are considered to have died of toxicity when death occurs before the death of vehicle treated control animals, or when significant body weight loss (>20%), and/or spleen and liver size reduction are observed.

The BWC % (Body weight change %) is assessed as follow: 100−(mean body weight of mice at given day/mean body weight at start of treatment)×100. This value is determined one week after the last treatment with the test compound.

Example K

In vitro Viability of Cells

The $IC_{50}$ values measuring in vitro viability of cells in the presence of test compounds can be determined according to the following procedure. Cells can be seeded in 96-well plates at varying densities and then assayed using the Calcein-AM viability assay after 24 hours to determine the optimal final density for each cell type. Cells can then be seeded in 96-well plates at the determined density in 100 μL of an appropriate cell media known to one skilled in the art.

Serial dilutions of test compounds can be made so that the concentrations are twice the desired concentration to be evaluated. When 100 μL of the dilution is then added to the cells plated in 100 μL of media, a final concentration of, for example, 0, 11.7, 46.9, 187.5, 375, and 750 nM can be obtained. Compounds can be added to the plates three to four hours after seeding the cells, then the plates can be incubated at 37° C. for the desired time point (e.g., one, two, or three days).

Calcein-AM viability assays can be conducted at the desired time points as follows. Media can be aspirated using a manifold and metal plate to leave approximately 50 μL/well. The wells can be washed three times with 200 μL DPBS, aspirating each time with the manifold to leave 50 μL/well. A 8 μM solution of Calcein-AM in DPBS can be prepared and 150 μL can be added to each well. The plates can then be incubated at 37° C. for 30 minutes. After incubation, calcein can be aspirated with the manifold and cells can be washed with 200 μL DPBS as before. After final aspiration, fluorescence can be measured using a Cytofluor 2300 fluorescence plate reader. Negative controls can contain media and no cells, and experiments can be conducted in triplicate.

Example L

Kinetic Experiments In vitro

Compounds of the invention can be tested for proteasome inhibitory activity using a protocol described in Rock, et al., *Cell,* 1994, 78, 761. According to this procedure, dissociation constants ($K_i$) for the equilibrium established when proteasome and test compound interact to form a complex. The reactions can be carried out using SDS-activated 20S proteasome from rabbit muscle, and the proteasome substrate can be Suc-LLVY-AMC.

Example M

Inhibition of Activation of NF-κB

Compounds of the invention can be tested for inhibiting the activity of NF-κB by carrying out the assay described in Palombella, et al., *Cell,* 1994, 78, 773). For example, MG63 osteocarcinoma cells can be stimulated by treatment with TNF-α for designated times. Whole cell extracts can be prepared and analyzed by electrophoretic mobility shift assays using the PRDII probe from the human IFN-β gene promoter.

Example N

Compound Activity

Using the assays of Example C and Example E above the following Table F-1 demonstrates the utility of compounds of the invention for proteasome inhibition. In the following Tables, for the inhibition of HEP, Example C, compounds of the present invention with a "+" are less than 1000 nM; compounds of the present invention with a "++" are less than 100 nM; and compounds of the present invention with a "+++" are less than 10 nM in $IC_{50}$ for HEP inhibition. In the following Tables, for the inhibition of MOLT4, Example E, compounds of the present invention with a "+" are less than 10000 nM; compounds of the present invention with a "++" are less than 2000 nM; and compounds of the present invention with a "+++" are less than 200 nM in $EC_{50}$ for HEP inhibition. Where ">+" occurs activity was greater than the limits of the assay. Where no $IC_{50}$ value or $EC_{50}$ value is represented, data has yet to be determined

TABLE F-1

| Example # | HEP ($IC_{50}$) | MOLT4 ($EC_{50}$) |
|---|---|---|
| D.1.1 | +++ | +++ |
| D.1.2 | ++ | ++ |
| D.1.3 | +++ | ++ |
| D.1.4 | +++ | +++ |
| D.1.5 | +++ | ++ |
| D.1.6 | ++ | ++ |
| D.1.7 | ++ | + |
| D.1.8 | +++ | ++ |
| D.1.9 | ++ | |
| D.1.10 | ++ | ++ |
| D.1.11 | ++ | >+ |
| D.1.12 | +++ | ++ |
| D.1.13 | +++ | + |
| D.1.14 | ++ | >+ |
| D.2 | +++ | +++ |
| D.2.1 | +++ | ++ |
| D.2.2 | +++ | >+ |
| D.2.3 | +++ | +++ |
| D.2.4 | +++ | +++ |
| D.2.5 | +++ | ++ |
| D.2.6 | ++ | + |
| D.2.7 | +++ | +++ |
| D.2.8 | ++ | +++ |
| D.2.9 | +++ | +++ |
| D.2.10 | +++ | +++ |
| D.3.1 | +++ | +++ |
| D.3.2 | +++ | +++ |
| D.3.3 | +++ | ++ |
| D.3.7 | +++ | +++ |
| D.3.8 | +++ | +++ |
| D.3.11 | +++ | +++ |
| D.3.12 | +++ | +++ |
| D.3.15 | +++ | +++ |
| D.3.24 | +++ | +++ |
| D.3.26 | +++ | +++ |
| D.3.27 | +++ | +++ |
| D.3.29 | +++ | +++ |
| D.3.31 | ++ | ++ |
| D.3.32 | +++ | +++ |
| D.3.34 | +++ | +++ |
| D.3.36 | +++ | +++ |
| D.3.37 | +++ | +++ |
| D.3.38 | +++ | +++ |
| D.3.39 | +++ | +++ |
| D.3.43 | +++ | +++ |
| D.3.49 | +++ | ++ |
| D.3.50 | +++ | +++ |
| D.3.54 | +++ | +++ |
| D.3.55 | +++ | +++ |
| D.3.57 | +++ | +++ |
| D.3.58 | +++ | +++ |
| D.3.59 | +++ | ++ |
| D.3.62 | +++ | +++ |
| D.3.64 | +++ | +++ |
| D.3.66 | +++ | +++ |
| D.3.67 | +++ | +++ |
| D.3.68 | +++ | |
| D.3.69 | +++ | |
| D.3.70 | +++ | +++ |
| D.3.73 | +++ | +++ |
| D.3.75 | +++ | +++ |
| D.3.76 | +++ | |

TABLE F-1-continued

| Example # | HEP ($IC_{50}$) | MOLT4 ($EC_{50}$) |
|---|---|---|
| D.3.77 | +++ | |
| D.3.78 | +++ | |
| D.3.80 | +++ | |
| D.3.87 | +++ | |
| D.3.89 | +++ | |
| D.3.91 | +++ | +++ |
| D.3.92 | +++ | +++ |
| D.3.93 | +++ | +++ |
| D.3.94 | +++ | +++ |
| D.3.96 | +++ | +++ |
| D.3.97 | +++ | +++ |
| D.3.102 | +++ | ++ |
| D.3.103 | +++ | ++ |
| D.3.104 | +++ | ++ |
| D.3.105 | +++ | ++ |
| D.3.115 | +++ | |
| D.3.117 | +++ | +++ |
| D.3.119 | +++ | +++ |
| D.3.122 | +++ | +++ |
| D.3.124 | +++ | +++ |
| D.3.125 | +++ | +++ |
| D.3.126 | +++ | +++ |
| D.3.128 | +++ | ++ |
| D.3.129 | +++ | +++ |
| D.3.130 | +++ | |
| D.3.131 | +++ | +++ |
| D.3.132 | +++ | +++ |
| D.3.133 | +++ | ++ |
| D.3.136 | +++ | >+ |
| D.3.137 | ++ | + |
| D.3.138 | ++ | ++ |
| D.3.161 | +++ | ++ |
| D.3.174 | ++ | +++ |
| D.3.175 | ++ | ++ |
| D.3.176 | +++ | +++ |
| D.3.177 | +++ | +++ |
| D.3.178 | ++ | +++ |
| D.3.179 | +++ | +++ |
| D.3.180 | +++ | +++ |
| D.3.182 | ++ | ++ |
| D.3.185 | +++ | +++ |
| D.3.186 | +++ | +++ |
| D.3.189 | +++ | +++ |
| D.3.190 | +++ | +++ |
| D.3.191 | +++ | +++ |
| D.3.192 | ++ | + |
| D.4.3 | +++ | +++ |
| D.4.4 | +++ | +++ |
| D.4.6 | ++ | +++ |
| D.4.7 | ++ | +++ |
| D.4.8 | ++ | +++ |
| D.4.9 | ++ | +++ |
| D.6.3 | +++ | +++ |
| D.6.5 | +++ | +++ |
| D.6.8 | ++ | +++ |
| D.6.9 | +++ | +++ |
| D.7.1 | +++ | + |
| D.7.2 | +++ | + |
| D.7.3 | +++ | + |
| D.7.4 | +++ | >+ |
| D.7.5 | +++ | ++ |
| D.7.6 | +++ | >+ |
| D.7.7 | +++ | >+ |
| D.7.8 | +++ | >+ |
| D.7.11 | +++ | + |
| D.7.12 | +++ | >+ |
| D.7.17 | +++ | ++ |
| D.7.19 | +++ | + |
| D.7.20 | +++ | + |
| D.7.21 | +++ | + |
| D.7.23 | +++ | >+ |
| D.7.24 | +++ | ++ |
| D.7.25 | +++ | + |
| D.7.26 | +++ | + |
| D.7.27 | +++ | + |
| D.7.28 | +++ | >+ |
| D.7.30 | ++ | >+ |
| D.7.31 | +++ | >+ |

TABLE F-1-continued

| Example # | HEP ($IC_{50}$) | MOLT4 ($EC_{50}$) |
|---|---|---|
| D.7.32 | +++ | + |
| D.7.33 | +++ | + |
| D.7.35 | +++ | >+ |
| D.7.36 | +++ | + |
| D.7.37 | +++ | >+ |
| D.7.38 | +++ | ++ |
| D.7.39 | +++ | + |
| D.7.41 | +++ | +++ |
| D.7.60 | +++ | + |
| D.7.61 | +++ | >+ |
| D.8 | +++ | +++ |
| D.8.4 | ++ | +++ |
| D.8.5 | +++ | +++ |
| D.8.6 | +++ | +++ |
| D.8.18 | ++ | ++ |
| D.8.19 | +++ | +++ |
| D.8.20 | +++ | +++ |
| D.9 | +++ | +++ |
| D.12 | +++ | +++ |
| D.16.6 | +++ | +++ |
| D.18 | +++ | +++ |
| D.19 | +++ | +++ |
| D.24.3 | +++ | +++ |
| D.24.4 | +++ | +++ |
| D.24.6 | +++ | +++ |
| D.24.8 | +++ | +++ |
| D.24.9 | +++ | +++ |
| D.24.10 | +++ | +++ |
| D.24.11 | +++ | +++ |
| D.24.12 | +++ | +++ |
| D.24.14 | +++ | +++ |
| D.24.15 | +++ | +++ |
| D.24.16 | +++ | +++ |
| E.1.1 | +++ | >+ |
| E.1.2 | +++ | + |
| E.1.3 | +++ | ++ |
| E.1.4 | +++ | ++ |
| E.1.5 | +++ | >+ |
| E.1.6 | ++ | + |
| E.1.7 | +++ | + |
| E.1.8 | +++ | >+ |
| E.1.10 | +++ | |
| E.1.11 | +++ | ++ |
| E.1.12 | +++ | >+ |
| E.1.13 | +++ | + |
| E.1.14 | +++ | |
| E.1.15 | +++ | ++ |
| E.1.16 | +++ | +++ |
| E.1.17 | +++ | +++ |
| E.1.18 | +++ | +++ |
| E.1.19 | +++ | ++ |
| E.1.20 | +++ | +++ |
| E.1.21 | +++ | +++ |
| E.1.22 | +++ | >+ |
| E.1.23 | +++ | +++ |
| E.1.24 | +++ | +++ |
| E.1.25 | +++ | +++ |
| E.1.26 | +++ | +++ |
| E.1.27 | +++ | +++ |
| E.1.28 | +++ | ++ |
| E.1.29 | +++ | ++ |
| E.1.30 | +++ | + |
| E.2.1 | +++ | +++ |
| E.2.2 | +++ | ++ |
| E.2.3 | +++ | + |
| E.2.4 | +++ | >+ |
| E.2.5 | +++ | + |
| E.2.6 | +++ | ++ |
| E.2.7 | +++ | + |
| E.2.8 | +++ | + |
| E.2.9 | +++ | ++ |
| E.2.10 | +++ | >+ |
| E.2.11 | +++ | >+ |
| E.2.12 | +++ | +++ |
| E.2.13 | +++ | + |
| E.2.14 | +++ | >+ |
| E.2.15 | +++ | >+ |
| E.2.16 | +++ | >+ |

TABLE F-1-continued

| Example # | HEP ($IC_{50}$) | MOLT4 ($EC_{50}$) |
|---|---|---|
| E.2.18 | +++ | + |
| E.2.19 | +++ | + |
| E.2.20 | +++ | + |
| E.2.21 | +++ | + |
| E.2.22 | +++ | ++ |
| E.2.23 | +++ | ++ |
| E.2.24 | +++ | >+ |
| E.2.25 | +++ | + |
| E.2.26 | +++ | >+ |
| E.2.27 | +++ | >+ |
| E.2.28 | +++ | >+ |
| E.2.29 | +++ | + |
| E.2.31 | +++ | >+ |
| E.2.32 | +++ | >+ |
| E.2.33 | +++ | + |
| E.2.34 | +++ | + |
| E.2.35 | +++ | >+ |
| E.2.36 | +++ | >+ |
| E.2.37 | +++ | >+ |
| E.2.38 | +++ | + |
| E.2.39 | +++ | ++ |
| E.2.40 | +++ | + |
| E.2.41 | +++ | >+ |
| E.2.42 | +++ | >+ |
| E.2.45 | +++ | +++ |
| E.2.46 | +++ | ++ |
| E.2.47 | +++ | >+ |
| E.2.48 | +++ | ++ |
| E.2.49 | +++ | >+ |
| E.2.50 | +++ | >+ |
| E.2.51 | ++ | >+ |
| E.2.52 | +++ | + |
| E.2.53 | ++ | >+ |
| E.2.54 | +++ | >+ |
| E.2.55 | +++ | + |
| E.2.56 | +++ | + |
| E.2.57 | +++ | + |
| E.2.58 | +++ | + |
| E.2.59 | +++ | + |
| E.2.60 | +++ | + |
| E.2.61 | +++ | + |
| E.2.62 | +++ | >+ |
| E.2.64 | +++ | >+ |
| E.2.65 | ++ | >+ |
| E.2.66 | +++ | >+ |
| E.2.67 | +++ | + |
| E.2.68 | +++ | >+ |
| E.2.69 | +++ | >+ |
| E.2.70 | +++ | >+ |
| E.2.75 | +++ | >+ |
| E.2.76 | +++ | + |
| E.2.77 | +++ | + |
| E.2.78 | +++ | + |
| E.2.79 | +++ | ++ |
| E.2.80 | ++ | + |
| E.2.81 | ++ | + |
| E.3 | +++ | +++ |
| E.3.1 | +++ | +++ |
| E.3.2 | +++ | +++ |
| E.3.3 | +++ | +++ |
| E.3.4 | ++ | +++ |
| E.3.5 | +++ | +++ |
| E.3.6 | +++ | +++ |
| E.3.7 | +++ | +++ |
| E.3.8 | +++ | +++ |
| E.3.9 | +++ | +++ |
| E.3.10 | +++ | +++ |
| E.4 | +++ | +++ |
| E.4.1 | ++ | ++ |
| E.4.2 | ++ | +++ |
| E.4.3 | +++ | +++ |
| E.5 | +++ | +++ |
| E.5.1 | +++ | +++ |
| E.5.2 | +++ | +++ |
| E.5.3 | ++ | ++ |
| E.5.5 | +++ | +++ |
| E.5.6 | +++ | +++ |
| E.5.7 | +++ | +++ |

TABLE F-1-continued

| Example # | HEP ($IC_{50}$) | MOLT4 ($EC_{50}$) |
|---|---|---|
| E.5.8 | +++ | +++ |
| E.5.9 | +++ | +++ |
| E.5.10 | +++ | +++ |
| E.5.11 | +++ | +++ |
| E.5.12 | +++ | +++ |
| E.5.13 | +++ | +++ |
| E.5.16 | +++ | +++ |
| E.5.17 | +++ | ++ |
| E.5.18 | +++ | +++ |
| E.5.19 | +++ | +++ |
| E.5.20 | +++ | +++ |
| E.5.21 | +++ | +++ |
| E.5.22 | +++ | +++ |
| E.5.24 | +++ | ++ |
| E.5.25 | +++ | +++ |
| E.5.26 | +++ | ++ |
| E.5.27 | +++ | +++ |
| E.5.28 | +++ | +++ |
| E.5.29 | +++ | +++ |
| E.5.30 | +++ | ++ |
| E.5.31 | +++ | +++ |
| E.5.32 | +++ | +++ |
| E.5.33 | +++ | ++ |
| E.5.34 | +++ | +++ |
| E.5.35 | +++ | +++ |
| E.5.36 | ++ | ++ |
| E.5.37 | +++ | +++ |
| E.5.40 | +++ | +++ |
| E.5.41 | ++ | +++ |
| F.1 | +++ | |
| F.2.1 | ++ | ++ |

Pharmaceutical Formulations and Dosage Forms

When employed as pharmaceuticals, the compounds of Formula (I) can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of Formula (I) above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. An amount adequate to accomplish this is referred to as "therapeutically effective amount." Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present invention also includes pharmaceutical kits useful, for example, in the treatment or prevention of inflammatory diseases, which comprise one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Various modifications of the invention, in addition to those described herein, will be apparent to those skilled in the art from the foregoing description. Such modifications are also intended to fall within the scope of the appended claims. Each reference cited in the present application, including patents, published patent applications, and journal articles, is incorporated herein by reference in its entirety.

What is claimed is:

1. A method for treating a cancer selected from the group consisting of skin, prostate, colorectal, pancreas, kidney, ovary, mammary, liver, tongue, smooth muscle tissue, leukemia, lymphoma, non-Hodgkin lymphoma, myeloma, and multiple myeloma comprising administering to a mammal having or predisposed to said cancer a therapeutically effective amount of a compound of Formula (I)

(I)

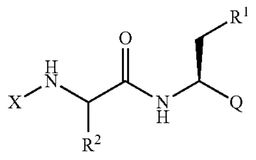

or a pharmaceutically acceptable salt, stereoisomeric or tautomeric form thereof, wherein:

$R^1$ is $C_1$-$C_8$ alkyl, $C_2$-$C_8$ alkenyl, $C_2$-$C_8$ alkynyl, or $C_3$-$C_7$ cycloalkyl;

$R^2$ is H;

Q is —$B(OH)_2$, —$B(OR^{14})_2$, or a cyclic boronic ester wherein said cyclic boronic ester contains from 2 to 20 carbon atoms, and, optionally, a heteroatom which can be N, S, or O;

$R^{14}$ is H, $C_1$-$C_4$ alkyl, cycloalkyl, cycloalkylalkyl, aryl, or aralkyl;

X is $R^AC$(═O)—; $R^ANHC$(═O)—, $R^AS(O)_2$—, $R^ASC$(═O)—, or $R^A$;

$R^A$ is $C_1$-$C_{20}$ alkyl optionally substituted with $R^{20}$;
$C_2$-$C_{20}$ alkenyl optionally substituted with $R^{20}$;
$C_2$-$C_{20}$ alkynyl optionally substituted with $R^{20}$;
carbocyclyl optionally substituted with 1-5 $R^{22}$; or
heterocarbocyclyl optionally substituted with 1-5 $R^{22}$;

$R^{20}$ is selected from the group consisting of:
—$OR^{20a}$, —$SR^{20a}$—S(═O)$R^{20a}$, —S(═O)$_2R^{20a}$, —S(═O)$_2NHR^{20a}$, —SC(═O)$R^{20a}$, —C(═O)$R^{20a}$, —C(═O)$NHR^{20a}$, —C(═O)O—$R^{20a}$, phthalimido, —(O-alkyl), —O-alkyl-OH, —(O-alkyl)$_r$-OH, —$OR^{20c}$, —$SR^{20c}$, —O—alkyl-$R^{20c}$, —S(═O)$_2$—$R^{20c}$, —S(═O)$_2$—$NHR^{20c}$, —SC(═O)$R^{20c}$, —C(═O)$R^{20c}$, —C(═O)$OR^{20c}$, —C(═O)$NHR^{20c}$, carbocyclyl optionally substituted with 1-5 $R^{22}$; and heterocarbocyclyl optionally substituted with 1-5 $R^{22}$;

$R^{20a}$ is $C_1$-$C_{20}$ alkyl, $C_2$-$C_{20}$ alkenyl, or $C_2$-$C_{20}$ alkynyl; wherein said alkyl, alkenyl, or alkynyl is optionally substituted by one or more halo, $C_1$-$C_4$ alkyl, aryl, heteroaryl or —$NHR^{20b}$;

$R^{20c}$ is carbocyclyl optionally substituted with 1-5 $R^{22}$; or heterocarbocyclyl optionally substituted with 1-5 $R^{22}$;

$R^{22}$ is selected from the group consisting of:
$C_1$-$C_{10}$ alkyl, $C_2$-$C_{10}$ alkenyl, $C_2$-$C_{10}$ alkynyl, phenyl, halo, haloalkyl, alkoxy, thialkoxy, amino, alkylamino, dialkylamino, carboxyl, alkyl-OC(═O)—, alkyl-C(═O)—, aryl-OC(═O)—, alkyl-OC(═O)NH—, aryl-OC(═O)NH—, alkyl-C(═O)NH—, alkyl-C(═O)O—, (alkyl-O)$_r$-alkyl, HO-(alkyl-O)$_r$-alkyl-, —OH, —SH, —CN, —$N_3$, —CNO, —CNS, alkyl-S(═O)—, alkyl-S(═O)$_2$—, $H_2NS$(═O)—, and $H_2NS$(═O)$_2$—; and r is 2, 3, 4, 5, 6, 7, 8, 9, or 10.

2. The method of claim 1, wherein X is $R^AC$(═O)—.

3. The method of claim 1, whereinX is $R^AC$(═O)— and $R^A$ is aryl optionally substituted with 1-3 substituents selected from the group consisting of $C_1$-$C_{10}$ alkyl, $C_2$-$C_{10}$ alkenyl, $C_2$-$C_{10}$ alkynyl, halo, haloalkyl, alkoxy, thialkoxy, amino, alkylamino, dialkylamino, alkyl-OC(═O)—, alkyl-C(═O)—, alkyl-OC(═O)NH—, alkyl-C(═O)NH—, —OH, —CN, alkyl-S(═O)—, and alkyl-S(═O)$_2$.

4. The method of claim 1, wherein the cancer is selected from the group consisting of skin, prostate, colorectal, pancreas, kidney, ovary, mammary, liver, tongue, and smooth muscle tissue.

5. The method of claim 1, wherein the cancer is selected from the group consisting of leukemia, lymphoma, non-Hodgkin's lymphoma, myeloma, and multiple myeloma.

6. The method of claim 1, wherein the cancer is multiple myeloma.

7. The method of claim 1, comprising administering the compound in combination with one or more antitumor or anticancer agents and/or radiotherapy.

8. The method of claim 1, wherein the cancer is leukemia.

9. The method of claim 1, wherein the cancer is non-Hodgkin's lymphoma.

10. The method of claim 1, wherein the cancer is lymphoma.

* * * * *